(12) United States Patent
Tsutsumi et al.

(10) Patent No.: US 7,557,113 B2
(45) Date of Patent: Jul. 7, 2009

(54) SUBSTITUTED PYRROLO[3,2-D]PYRIMIDINE DERIVATIVES

(75) Inventors: Takaharu Tsutsumi, Hino (JP); Satoshi Sugiura, Hino (JP); Masahiro Koga, Hino (JP); Yoshiyuki Matsumoto, Hino (JP); Toshihiro Ishii, Hino (JP); Akira Nakano, Hino (JP); Gen Unoki, Hino (JP); Yuri Sakai, Hino (JP); Reiko Takarada, Hino (JP); Hiroko Ogawa, Hino (JP)

(73) Assignee: Teijin Pharma Limited, Tokyo (JP)

( * ) Notice: Subject to any disclaimer, the term of this patent is extended or adjusted under 35 U.S.C. 154(b) by 237 days.

(21) Appl. No.: 10/928,969

(22) Filed: Aug. 26, 2004

(65) Prior Publication Data

US 2006/0160831 A1 Jul. 20, 2006

Related U.S. Application Data

(60) Provisional application No. 60/499,071, filed on Sep. 2, 2003, provisional application No. 60/560,013, filed on Apr. 7, 2004.

(30) Foreign Application Priority Data

Aug. 26, 2003 (JP) ............................. 2003-301022
Mar. 30, 2004 (JP) ............................. 2004-100022

(51) Int. Cl.
C07D 487/04 (2006.01)
A61K 31/519 (2006.01)
A61P 35/04 (2006.01)
A61P 25/18 (2006.01)

(52) U.S. Cl. .................................. 514/265.1; 544/280
(58) Field of Classification Search ................. 544/280; 514/265.1
See application file for complete search history.

(56) References Cited

U.S. PATENT DOCUMENTS

| | | | |
|---|---|---|---|
| 6,458,799 B1 | 10/2002 | Montgomery et al. | |
| 6,900,217 B2 * | 5/2005 | Chen ....................... | 514/259.3 |
| 2003/0096813 A1 * | 5/2003 | Cao et al. ................. | 514/228.5 |
| 2003/0114466 A1 | 6/2003 | Bantia et al. | |
| 2004/0214840 A1 * | 10/2004 | Winslow et al. .......... | 514/265.1 |
| 2005/0137201 A1 * | 6/2005 | Aronov et al. ............. | 514/249 |

FOREIGN PATENT DOCUMENTS

| | | | |
|---|---|---|---|
| JP | 58-26888 A | | 2/1983 |
| JP | 2-204414 A | | 8/1990 |
| JP | 7-507062 A | | 8/1995 |
| JP | 10-506126 A | | 6/1998 |
| JP | 2001-519437 A | | 10/2001 |
| WO | WO 95/01355 | * | 1/1995 |
| WO | WO 95/01355 A1 | | 1/1995 |
| WO | WO 96/35689 | * | 11/1996 |
| WO | WO 97/49706 | * | 12/1997 |
| WO | WO 97-49706 A1 | | 12/1997 |
| WO | WO 02/18371 A1 | | 3/2002 |
| WO | WO 02/085909 A1 | | 10/2002 |
| WO | WO 03/070729 A1 | | 8/2003 |
| WO | WO 03/100009 A2 | | 12/2003 |
| WO | WO 2004/018496 A1 | | 3/2004 |
| WO | WO 2006/002231 A1 * | | 1/2006 |

OTHER PUBLICATIONS

Evans et. al. (J. Med. Chem., 2003, 46(15), 3412-3423).*
Farutin et. al. (J. Med. Chem., 1999, 42(13), 2422-2431).*
Glushkov et. al. (Khimiko-Farmatsebticheskii Zhurnal, 1995, 29(5), 19-21).*
Jukic et. al. (Heterocycles, 2000, 53(4), 805-820).*
Gary B. Evans, et al., "Exploring Structure-Activity Relationships of Transition State Analogues of Human Purine Nucleoside Phosphorylase" *Journal of Medicinal Chemistry*, 2003, vol. 46, No. 15, p. 3412-3423.
Andrzej Lewandowicz, et al. "Achieving the Ultimate Physiological Goal in Transition State Analogue Inhibitors for Purine Nucleoside Phosphorylase", *Journal of Biological Chemistry*, 2003, vol. 278, No. 34, pp. 31465-31468.
Andrzej Lewandowicz, et al. "Over-the-Barrier Transition State Analogues and Crystal Structure with *Mycobacterium tuberculosis* Purine Nucleoside Phosphoryalse", *Biochemistry*, 2003, vol. 42, No. 20, p. 6057-6066.

(Continued)

*Primary Examiner*—Brenda L Coleman
*Assistant Examiner*—Susanna Moore
(74) *Attorney, Agent, or Firm*—Sughrue Mion, PLLC

(57) ABSTRACT

A compound having GSK-3 inhibitory activity.

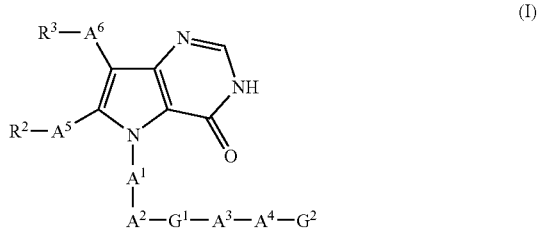

(I)

$A^1$ and $A^3$ are a single bond, an aliphatic hydrocarbon group; $A^2$ and $A^4$ are a single bond, CO, COO, CONR, O, OCO, NR, NRCO, NRCOO, etc.; $G^1$ is a single bond, an aliphatic hydrocarbon, aromatic hydrocarbon, heterocyclic; $G^2$ is H, an aliphatic hydrocarbon, an alicyclic hydrocarbon, an aromatic hydrocarbon, heterocyclic; $A^5$ is a single bond, NR; $R^2$ is H, halogen, an aliphatic hydrocarbon, alicyclic hydrocarbon, aromatic hydrocarbon, heterocyclic; $A^6$ is a single bond, NR, CO, NRCO, NRCONR, CONR, COO, O, etc.; $R^3$ is H, halogen, nitro, saturated aliphatic hydrocarbon, alicyclic hydrocarbon, aromatic hydrocarbon, heterocyclic; and $R^3$ may be a trimethylsilyl, formyl, acyl, carboxyl, alkoxylcarbonyl, carbamoyl, alkylcarbamoyl, or cyano group when $A^6$ is CR=CR or C≡C, wherein R is H or an lower aliphatic hydrocarbon group.

39 Claims, No Drawings

OTHER PUBLICATIONS

Hsiencheng Shih, et al. "Facile Synthesis of 9-substituted 9-Deazapurines as Potential Purine Nucleoside Phosphorylase Inhibitors", *Chem. Pharma Bull.*, 2002, vol. 50, No. 3, p. 364-367.

Byong K. Chun, et al. Stereocontrolled Syntheses of Carbocyclic C-Nucleosides and Related Compounds, *Journal of Organic Chemistry*, 2001, vol. 66, No. 14, p. 4852-4858.

Adriano D. Andricopulo, et al., "Structure-Activity Relationships for a Collection of Structurally Diverse Inhibitors of Purine Nucleoside Phosphorylase", *Chemical &Pharmaceutical Bulletin*, 2001, vol. 49, No. 1, p. 10-17.

Richard H. Furneaux, et al. Improved Syntheses of 3H, 5H-Pyrrolo[3,2-d] pyrimidines, *Journal of Organic Chemistry*, 1999, vol. 64, No. 22, p. 8411-8412.

Victor Farutin, et al. "Structure-Activity Relationships for a Class of Inhibitors of Purine Nucleoside Phosphorylase", *Journal of Medicinal Chemistry*, 1999, vol. 42, No. 13, p. 2422-2431.

Mu-Ill Lim, et al. "Synthesis of 9-Deazaguanosine and other New Pyrollo[3,2-d]pyrimidine C-Nucleosides" , *Journal of Organic Chemistry*, 1983, vol. 48, No. 6, p. 780-788.

Lucija Jukic, et al. "A synthesis and transformations of alkyl 2-[2-cyano-2-(2-pyridinyl)ethenyl]amino-3-dimethylaminopropenoates. A one-pot sunthesis of pyrrolo [3,2-d]pyrimidin-4-ones", *Heterocycles*, 2000, vol. 53, No. 4, p. 805-820.

Brakta et al., "Efficient Synthesis of 3H,5H-Pyrrolo [3,2-d] pyrimidin-4-one", J. Chem. Soc., Perkin Trans. 1, 1992, 1883-1184.

* cited by examiner

SUBSTITUTED PYRROLO[3,2-D]PYRIMIDINE DERIVATIVES

This application claims benefit to Provisional Application No. 60/499,071 filed Sep. 2, 2003 and Provisional App. No. 60/560,013 filed Apr. 7, 2004.

TECHNICAL FIELD

The present invention relates to novel pyrrolopyrimidinone derivatives that have an action inhibiting glycogen synthase kinase-3 (GSK-3). More particularly, the invention relates to novel pyrrolo[3,2-d]pyrimidinone derivatives useful as pharmaceutical agents for treating and/or preventing disorders mediated by GSK-3 activity, particularly, impaired glucose tolerance, type I diabetes, type II diabetes, diabetic complications (retinopathy, nephropathy, neuropathy or great vessel hindrance), Alzheimer's disease, neurodegenerative diseases (AIDS encephalophy, Huntington's disease, Parkinson's disease, amyotrophic lateral sclerosis or multiple sclerosis), bipolar affective disorder (manic depressive psychosis), traumatic cerebrospinal injury, epilepsy, obesity, atherosclerosis, hypertension, polycystic ovary syndrome, syndrome X, alopecia, inflammatory diseases (arthrosis deformans, rheumatism, atopic dermatitis, psoriasis, ulcerative colitis, Crohn's disease, sepsis or systemic inflammatory response syndrome), cancer and immunodeficiency.

BACKGROUND ART

GSK-3 is a serine/threonine protein kinase. Two isoforms, i.e., $\alpha$ and $\beta$, which are encoded by distinct genes, have been identified (see Trends Biochem. Sci., 1991, Vol. 16, p. 177).

Both GSK-3 isoforms have a monomeric structure and are constitutively active in resting cells. GSK-3 was originally identified as a kinase that inhibits glycogen synthase by direct phosphorylation (see Eur. J. Biochem., 1980, Vol. 107, p. 519). Upon insulin activation, GSK-3 is inactivated, thereby allowing the activation of glycogen synthase and possibly other insulin-dependent events, such as glucose transport. Also, it has been known that GSK-3 activity is inactivated by other growth factors, such as IGF-1 or FGF, through signaling from receptor tyrosine kinases (see Biochem. J., UK, 1993, Vol. 294, p. 625; Biochem. J., UK, 1994, Vol. 303, p. 21; Biochem. J., UK, 1994, Vol. 303, p. 27).

GSK-3 inhibitors are useful in the treatment of disorders that are mediated by GSK-3 activity. In addition, inhibition of GSK-3 mimics the activation of growth factor signaling pathways and consequently GSK-3 inhibitors are useful in the treatment of diseases in which such pathways are inactive. Examples of diseases that can be treated with GSK-3 inhibitors are described below.

Type I diabetes is induced due to autoimmune destruction of $\beta$ cells as pancreatic insulin production cells, resulting in deficiency of insulin. From this, it is necessary for a type I diabetic patient to routinely be administered insulin for maintaining life. However, in current insulin therapy, strict control of the blood glucose levels like the ability of normal $\beta$ cells cannot be reproduced. Thus, type I diabetes is liable to induce diabetic complications such as retinopathy, nephropathy, neuropathy, great vessels hindrance or the like.

Type II diabetes is a multifactorial disease. Hyperglycemia is due to insulin resistance in the liver, skeletal muscle and lipid tissues coupled with inadequate or defective secretion of insulin from pancreatic islets. As a result, diabetic complications such as retinopathy, nephropathy, neuropathy, or great vessels hindrance are induced. Skeletal muscle is the major site for insulin-stimulated glucose uptake, and glucose removed from the circulation is either metabolized through glycolysis and the TCA cycle or stored as glycogen. Muscle glycogen deposition plays a very important role in glucose homeostasis, and Type II diabetic subjects have defective muscle glycogen storage. GSK-3, which is known to phosphorylate glycogen synthase, inhibits the accumulation of glycogen in peripheral tissues and lowers the reactivity of insulin, leading to an increase in blood level of glucose.

Recently, it has been reported that the expression of GSK-3 is stimulated in skeletal muscles of type II diabetic patients, and the GSK-3$\alpha$ activity and insulin in skeletal muscles are inversely correlated (see Diabetes, USA, 2000, Vol. 49, p. 263). Where GSK-3$\beta$ and active GSK-3$\beta$ variants (S9A, S9E) are overexpressed in HEK-293 cells, the GSK activity is inhibited (see Proc. Natl. Acad. Sci., USA, 1996, Vol. 93, p. 10228). In CHO cells in which insulin receptor and insulin receptor substrate 1 (IRS-1) are expressed, overexpression of GSK-3$\beta$ brings about a decrease in the insulin activity (see 8: Proc. Natl. Acad. Sci., USA, 1997, Vol. 94, 9660). Recent research carried out using C57BL/6J mice with pyknic type diabetes has clearly shown that GSK-3 activity stimulation and insulin resistance are correlated to the progress of type II diabetes (see Diabetes, USA, 1999, Vol. 48, p. 1662).

Conventionally, lithium salts have been known to have inhibitory effects of GSK-3 activity (see Proc. Natl. Acad. Sci., USA, 1996, Vol. 93, p. 8455). It has been reported that the therapy using the lithium salts lowers glucose levels in both type I and II diabetic patients, thereby alleviating the severity of the disease (see Biol. Trace Elements Res., 1997, Vol. 60, p. 131). However, lithium salts have also been found to exhibit various side effects on molecular targets other than GSK-3.

From the findings described above, it can be concluded that GSK-3 inhibitors are effective therapeutics for the treatment of impaired glucose tolerance, type I diabetes, type II diabetes and complications thereof.

It is also suggested that GSK-3 is associated with progress of Alzheimer's disease. The characteristic pathological features of Alzheimer's disease are senile plaques due to agglomeration of amyloid beta (A$\beta$) peptide and the formation of intracellular neurofibrillary tangles, leading to a large quantity of neuronal cell death, resulting in dementia. It is believed that GSK-3 involves abnormal phosphorylation of tau protein, which causes a neurofibrillary change in the course of progress of Alzheimer's disease (see Acta Neuropathol., 2002, Vol. 103, p. 91). Also, it has been found that GSK-3 inhibitors can prevent neuronal cell death (see J. Neurochem., 2001, Vol. 77, p. 94). Therefore, it is believed that the application of GSK-3 inhibitors to Alzheimer's disease can delay the progress of the disease. To date, therapeutic agents for Alzheimer's disease have mainly been used in conjunction with allopathy (see Expert Opin. Pharmacother., 1999, Vol. 1, p. 121). However, there is no known pharmaceutical agent that is effective in preventing neuronal cell death and delaying the onset or progress of Alzheimer's disease. These findings imply that GSK-3 inhibitors are effective pharmaceutical agents in alleviating the severity of Alzheimer's dementia.

There is a report that GSK-3 inhibitors suppress neuronal cell death, specifically, neuronal cell death due to overexcitement through glutamic acid (see Proc. Natl. Acad. Sci., USA, 1998, Vol. 95, p. 2642; J. Neurochem., 2001, Vol. 77, p. 94). This suggests that GSK-3 inhibitors are possibly useful in the treatment of bipolar affective disorder such as manic depressive psychosis, epilepsy or other degenerative brain injury or neurodegenerative diseases. Examples of the neurodegenerative disease include in addition to the Alzheimer's disease, AIDS encephalopathy, Huntington's disease, Parkinson's disease, amyotrophic lateral sclerosis, multiple sclerosis, Pick's disease, progressive supranuclear palsy and so on. Also, overexcitement through glutamic acid is presumably a principal cause of brain dysfunction in stroke, including cerebral infarction, intracerebral hemorrhage and subarachnoid hemorrhage, traumatic cerebrospinal injury, bacteria/virus infectious disease, and GSK-3 inhibitors are expected to be effectively used in the treatment of these diseases. All of such diseases accompany neuronal death. Currently, no therapeutic agents for effectively suppressing neuronal death are available. Therefore, GSK-3 inhibitors are believed to become potentially effective pharmaceutical agents for the treatment of various kinds of neurodegenerative diseases, dipolar affective disorders (manic-depressive psychosis), epilepsy, stroke, traumatic cerebrospinal injury, and the like.

Several in vitro research results have led to a report that Wint10B potently suppresses the differentiation of preadipocytes to mature fat cells (see Science, 2000, Vol. 289, p. 950). GSK-3 specific inhibitors mimic Wint10B signaling in preadipocytes, that is, GSK-3 specific inhibitors stabilize free β-catenin in cytoplasm and suppress the induction of C/EBPα and PPARγ, thereby suppressing the formation of fat (see J. Biol. Chem, 2002, Vol. 277, p. 30998). GSK-3 inhibitors are therefore potentially useful as effective pharmaceutical compositions for treating obesity.

Also, β-catenin has been known to be a GSK-3 substrate in vivo. After phosphorylation by GSK-3, β-catenin is subjected to proteosome-dependent degradation (see EMBO J., 1998, Vol. 17, p. 1371). Meanwhile, transient β-catenin stabilization may lead to increase hair development (see Cell, 1998, Vol. 95, p. 605). Consequently, GSK-3 inhibitors are believed to be a useful medicament for the treatment of alopecia.

Further, research into GSK-3β knock out mouse-derived fibroblasts implies that GSK-3β regulates the activity of transcription factor NFκB to be at a positive level (see Nature, 2000, Vol. 406, p. 86). NFκB is in charge of cell responsiveness to numerous inflammatory stimuli. Thus, GSK-3 inhibitors may have beneficial effects in the treatment of inflammatory diseases such as arthrosis deformans, rheumatism, atopic dermatitis, psoriasis, ulcerative colitis, Crohn's Disease, sepsis, or systemic inflammatory response syndrome, by adjusting the NFκB activity to be at a negative level.

A transcription factor NF-AT is dephosphorylated by calcineurine and increases immunosuppressive response (see Science, 1997, Vol. 275, p. 1930). Conversely, GSK-3 phosphorylates NF-AT and transports the same from nuclei, thereby suppressing the expression of initial immune response gene. Thus, GSK-3 inhibitors could be useful to immunity activation for cancer immunotherapy.

Examples of materials that have conventionally been known to have GSK-3 inhibiting activity include hymenialdisine derivatives (see Chemistry & Biology, 2000, Vol. 7, p. 51, and WO01/41768 pamphlet), maleiimide derivatives (see Chemistry & Biology, 2000, Vol. 7, p. 793), paullone derivatives (see Eur. J. Biochem., 2000, Vol. 267, p. 5983 and WO01/60374 Pamphlet), purine derivatives (see WO98/16528 Pamphlet), pyrimidine and pyridine derivatives (see WO99/65897 Pamphlet), hydroxyflavone derivatives (see WO00/17184 Pamphlet), pyrimidone derivatives (see WO00/18758, WO01/70683, WO01/70729, WO01/70728, WO01/70727, WO01/70726, and WO01/70725 Pamphlets), pyrrole-2,5-dione derivatives (see WO00/21927 and WO01/74771 Pamphlets), diamino-1,2,4-triazolecarboxylic acid derivatives (see WO01/09106 Pamphlet), pyrazine derivatives (see WO01/44206 Pamphlet), bicyclic inhibitor (see WO01/44246 Pamphlet), indirubine derivatives (see WO01/37819 Pamphlet), carboxamide derivatives (see WO01/42224 Pamphlet), peptide inhibitors (see WO01/49709 Pamphlet), 2,4-diaminothiazole derivatives (see WO01/56567 Pamphlet), thiadiazolidindione derivatives (see WO01/85685 Pamphlet), aromatic amide derivatives (see WO01/81345 Pamphlet), and so on.

Also, the claims of WO02/085909 Pamphlet show a wide variety of compounds including pyrrolopyrimidine derivatives. However, bicyclic pyrrolopyrimidine derivatives actually synthesized are those having cyano groups at the 7-position of pyrrolopyrimidine ring and limited variety of substituents at other substitutable positions. In addition, while it discloses a method for assaying inhibitory activity of GSK-3 etc., it is silent about which compounds have such activities.

DISCLOSURE OF THE INVENTION

An object of the present invention is to provide novel compounds which are specific to and capable of strongly inhibiting the activity of GSK-3 while being clinically applicable, and pharmaceutical compositions as GSK-3 inhibitors using them as effective ingredients.

Also, another object of the present invention is to provide an agent for treating or preventing a GSK-3-mediated disease.

Further, still another object of the present invention is to provide a method for treating a GSK-3-mediated disease.

The present inventors studied the above objects and consequently reached the following inventions.

Namely, the present invention provides a compound represented by the following formula (I) or a pharmaceutically acceptable salt thereof.

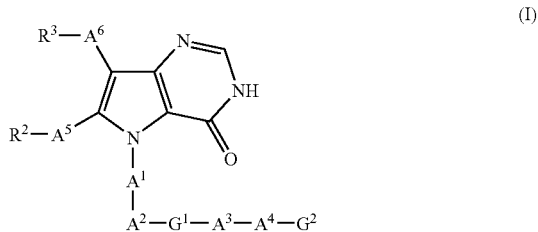

in the formula (I), $A^1$ represents a single bond or represents a divalent acyclic aliphatic hydrocarbon group having 1 to 6 carbon atoms that links a nitrogen atom bonded to $A^1$ with $A^2$ on the same or different carbon atom;

$A^2$ represents a single bond or represents a group that links $A^1$ with $G^1$ in the form of $A^1$—C(=O)-$G^1$,
$A^1$-C(=O)—O-$G^1$,
$A^1$-C(=O)—$NR^{101}$-$G^1$,
$A^1$-C(=S)—$NR^{102}$-$G^1$,
$A^1$-C(=$NR^{103}$)-$G^1$,
$A^1$-O-$G^1$,
$A^1$-OC(=O)-$G^1$,
$A^1$-$NR^{104}$-$G^1$,
$A^1$-$NR^{105}$—C(=O)-$G^1$,
$A^1$-$NR^{106}$—S(=O)$_2$-$G^1$,
$A^1$-$NR^{107}$—C(=O)—O-$G^1$,
$A^1$-$NR^{108}$—C(=O)—$NR^{109}$-$G^1$,
$A^1$-$NR^{110}$C(=S)-$G^1$, $A^1$-$NR^{111}$—C(=S)—$NR^{112}$-$G^1$,
$A^1$-S-$G^1$,
$A^1$-S(=O)-$G^1$,
$A^1$-S(=O)$_2$-$G^1$,
$A^1$-S(=O)$_2$—$NR^{113}$-$G^1$,
$A^1$-$CR^{114}$=CH-$G^1$,
$A^1$-$CR^{115}$=CF-$G^1$,
$A^1$-CH=$CR^{116}$-$G^1$, or
$A^1$-CF=$CR^{117}$-$G^1$;

$G^1$ represents a single bond or represents a divalent group which is obtainable by removing two hydrogen atoms from any one of an optionally substituted alicyclic hydrocarbon group having 3 to 10 carbon atoms, an optionally substituted aromatic hydrocarbon having 6 to 14 carbon atoms, and an optionally substituted heterocyclic compound having 1 to 4 atoms selected from the group consisting of an oxygen atom, a nitrogen atom and a sulfur atom, in the ring.

$A^3$ represents a single bond or represents an optionally substituted aliphatic hydrocarbon group having 1 to 10 carbon atoms that links $G^1$ with $A^4$ on the same or different carbon atom;

$A^4$ represents a single bond or represents a group that links $A^3$ with $G^2$ in the form of
$A^3$—C(=O)-$G^2$,
$A^3$-C(=O)—O-$G^2$,
$A^3$-C(=O)—$NR^{121}$-$G^2$,
$A^3$-C(=S)—$NR^{122}$-$G^2$,
$A^3$-C(=$NR^{123}$)-$G^2$,
$A^3$-O-$G^2$,
$A^3$-O—C(=O)-$G^2$,
$A^3$-$NR^{124}$-$G^2$,
$A^3$-$NR^{125}$—C(=O)-$G^2$,
$A^3$-$NR^{126}$—S(=O)$_2$-$G^2$,
$A^3$-$NR^{127}$—C(=O)—O-$G^2$,
$A^3$-$NR^{128}$—C(=O)—$NR^{129}$-$G^2$,
$A^3$-$NR^{130}$—C(=S)-$G^2$,
$A^3$-$NR^{131}$—C(=S)—$NR^{132}$-$G^2$,
$A^3$-S-$G^2$,
$A^3$-S(=O)-$G^2$,
$A^3$-S(=O)$_2$-$G^2$,
$A^3$-S(=O)$_2$—$NR^{133}$-$G^2$ or
$A^3$-S(=O)$_2$—O-$G^2$;

$G^2$ represents a hydrogen atom, an optionally substituted aliphatic hydrocarbon group having 1 to 10 carbon atoms, an optionally substituted alicyclic hydrocarbon group having 3 to 10 carbon atoms, an optionally substituted aromatic hydrocarbon group having 6 to 14 carbon atoms, or an optionally substituted heterocyclic group having 1 to 4 atoms selected from the group consisting of an oxygen atom, a nitrogen atom and a sulfur atom, in the ring;

$A^5$ represents a single bond or —$NR^{201}$—;

$R^2$ represents a hydrogen atom, a fluorine atom, a chlorine atom, a bromine atom, an iodine atom, an optionally substituted aliphatic hydrocarbon group having 1 to 10 carbon atoms, an optionally substituted alicyclic hydrocarbon group having 3 to 8 carbon atoms, an optionally substituted aromatic hydrocarbon group having 6 to 14 carbon atoms, or an optionally substituted heterocyclic group having 1 to 4 atoms selected from the group consisting of an oxygen atom, a nitrogen atom and a sulfur atom, in the ring;

$A^6$ represents a single bond or represents a group that links $R^3$ with a carbon atom of a pyrrole ring to which $A^6$ is bonded, in the form of
$R^3$—$NR^{301}$-pyrrole ring,
$R^3$—C(=O)-pyrrole ring,
$R^3$—$NR^{302}$—C(=O)-pyrrole ring,
$R^3$—$NR^{303}$—C(=S)-pyrrole ring,
$R^3$—$NR^{304}$—C(=O)—$NR^{305}$-pyrrole ring,
$R^3$—C(=O)—$NR^{306}$-pyrrole ring,
$R^3$—$NR^{307}$—CH=N-pyrrole ring,
$R^3$—C(=O)—O-pyrrole ring,
$R^3$—O—C(=O)-pyrrole ring,
$R^3$—O-pyrrole ring,
$R^3$—S-pyrrole ring,
$R^3$—S(=O)-pyrrole ring,
$R^3$—S(=O)$_2$-pyrrole ring,
$R^3$—$CR^{308}$=$CR^{309}$-pyrrole ring,
$R^3$—C≡C-pyrrole ring, or
$R^3$—S(=O)$_2$—C≡C-pyrrole ring;

$R^3$ is a hydrogen atom, a fluorine atom, a chlorine atom, a bromine atom, an iodine atom, a nitro group, an optionally substituted saturated aliphatic hydrocarbon group having 1 to 10 carbon atoms, an optionally substituted alicyclic hydrocarbon group having 3 to 8 carbon atoms, an optionally substituted aromatic hydrocarbon group having 6 to 14 carbon atoms, or an optionally substituted heterocyclic group having 1 to 4 atoms selected from the group consisting of an oxygen atom, a nitrogen atom and a sulfur atom, in the ring;

$A^6$-$R^3$ may be a combination wherein $A^6$ represents a group that links a carbon atom of a pyrrole ring to which $A^6$ is bonded, with $R^3$ in the form of $R^3$—$CR^{308}$=$CR^{309}$-pyrrole ring or $R^3$—C≡C-pyrrole ring, and $R^3$ represents a trimethylsilyl group, a formyl group, an optionally substituted $C_2$-$C_7$ acyl group, a carboxyl group, a $C_2$-$C_7$ alkoxycarbonyl group, a carbamoyl group, an optionally substituted $C_2$-$C_7$ alkylcarbamoyl group, or a cyano group;

$R^{101}$~$R^{117}$, $R^{121}$~$R^{133}$, $R^{201}$ and $R^{301}$~$R^{309}$ are each independently a hydrogen atom or an aliphatic hydrocarbon group having 1 to 4 carbon atoms.

However, when both $A^1$ and $A^3$ represent acyclic aliphatic hydrocarbon groups, at least one of $A^2$ or $G^1$ is not a single bond.

In addition, the present invention provides a pharmaceutical composition comprising the compound or a pharmaceutically acceptable salt thereof represented by the formula (I); and a pharmaceutically acceptable carrier.

Further, the present invention provides a GSK-3 inhibitor comprising the compound or a pharmaceutically acceptable salt thereof represented by the formula (I) as an effective ingredient.

Furthermore, the present invention provides an agent for treating or preventing a GSK-3-mediated disease, comprising the compound or a pharmaceutically acceptable salt thereof represented by the formula (I) as an effective ingredient.

Furthermore, the present invention provides a method for treating a GSK-3-mediated disease, comprising a step of injecting the compound or a pharmaceutically acceptable salt thereof represented by the formula (I) in treatment valid amount to a patient.

Note that, in $A^1$-$G^2$ portion in the formula (1), there also exists a case where different combinations consequently represent the same substituent according to the combination of $A^1$, $A^2$, $G^1$, $A^3$, $A^4$, and $G^2$, and combinations containing also substituents of them where they may have substituents. However, the scope of the present invention will not become clear due to this.

Note that the corresponding pyrimidine-thione derivative can be derived from the compound represented by the formula (I) of the present invention through the pyrrolopyrimidine derivative represented by the following formula (II).

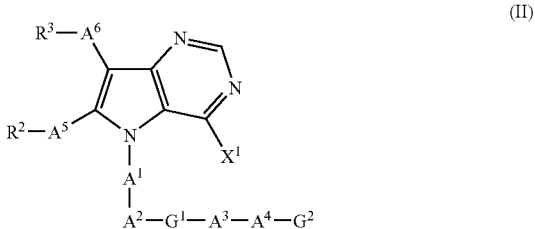

(II)

in formula (I), $A^1$, $A^2$, $A^3$, $A^4$, $A^5$, $A^6$, $G^1$, $G^2$, $R^2$ and $R^3$ are as defined in the formula (I); and $X^1$ is a chlorine atom, a bromine atom, an iodine atom, a $C_2$-$C_{10}$ acylthio group, a $C_2$-$C_8$ alkoxymethylthio group, a $C_1$-$C_8$ alkyl group, or a $C_1$-$C_8$ arylsulfonyloxy group).

Still further, the present invention is a compound represented by the following formula (Ic) which can be used as the manufacture intermediate of the pyrrolopyrimidinone derivative represented by the formula (I).

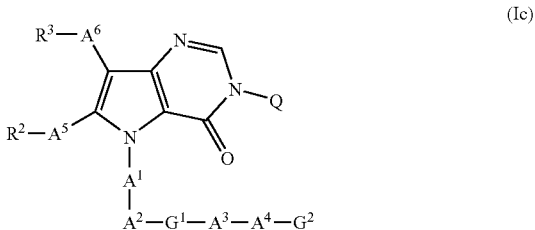

(Ic)

in formula (Ic), $A^1$, $A^2$, $A^3$, $A^4$, $A^5$, $A^6$, $G^1$, $G^2$, $R^2$, and $R^3$ are as defined in the formula (I); and Q represents an optionally substituted a $C_2$-$C_{10}$ acyl group, an optionally substituted $C_2$-$C_{10}$ alkoxymethyl group or an optionally substituted benzyl group.

BEST MODE FOR WORKING THE INVENTION

The "acyclic aliphatic hydrocarbon group" in the present description contains a straight or branched acyclic aliphatic hydrocarbon group. It may be saturated so far as it is the acyclic aliphatic hydrocarbon group as well and may have one or more double bonds or triple bonds in a chemically possible range.

The "alkyl group" in the present description represents a straight or branched saturated acyclic aliphatic hydrocarbon group, for example methyl, ethyl, propyl, butyl, pentyl, hexyl, heptyl, octyl, isopropyl, isobutyl, s-butyl, t-butyl, isopentyl, neopentyl, t-pentyl, or isohexyl.

The "pyridyl group" in the present description contains N-oxide thereof as well.

The term "cycloalkyl group" in the present description means a saturated alicyclic hydrocarbon group, for example cyclopropyl, cyclobutyl, or cyclohexyl.

The term "heterocyclic" in the present description is not particularly limited so far as it can chemically stably exist if it is monocyclic to tricyclic having 1 to 4 atoms selected from among a group consisting of an oxygen atom, a nitrogen atom, and a sulfur atom, in the ring, but preferably monocyclic or bicyclic having carbon atoms not more than 9 containing 1 to 3, preferably 1 or 2 atoms selected from among a group consisting of an oxygen atom, a nitrogen atom, and a sulfur atom, in the ring.

In the formula (I), $A^1$ represents a single bond or represents a divalent acyclic aliphatic hydrocarbon group having 1 to 6 carbon atoms that links a nitrogen atom bonded to $A^1$ with $A^2$ on the same or different carbon atoms.

Examples of the acyclic aliphatic hydrocarbon group having 1 to 6 carbon atoms in $A^1$ include divalent groups obtainable by removing two hydrogen atoms from methane, ethane, propane, butane, 2-methylpropane, pentane, 2-methylbutane, 2,2-dimethylpropane, hexane, 2-methylpentane, 3-methylpentane, 2,2-dimethylbutane, 2,3-dimethylbutane and 2,2,3-trimethylpropane.

Examples of suitable $A^1$ include —$CH_2$—, —$(CH_2)_2$—, —$(CH_2)_3$—, —$(CH_2)_4$—, —$(CH_2$—$)_5$—, —$(CH_2)_6$—, —$CH(CH_3)$—, —$CH(CH_3)CH_2$—, —$CH(CH_3)CH(CH_3)$—, —$C(CH_3)_2CH_2$—, —$CH(CH_3)(CH_2)_2$—, —$CH_2CH(CH_3)CH_2$—, —$CH(CH_3)CH(CH_3)CH_2$—, —$CH(CH_3)CH_2CH(CH_3)$—, —$CH_2C(CH_3)_2CH_2$—, —$CH(CH_3)C(CH_3)_2CH_2$—, —$CH(CH_2CH_3)(CH_2)_2$—, —$CH_2CH(CH_2CH_3)CH_2$—, —$CH(CH_2CH_3)CH(CH_3)CH_2$—, —$CH(CH_3)CH(CH_2CH_3)CH_2$—, —$CH(CH_2CH_3)CH_2CH(CH_3)$—, —$CH(CH_3)(CH_2)_3$—, —$CH_2CH(CH_3)(CH_2)_2$—, —$CH(CH_3)CH(CH_3)(CH_2)_2$—, —$CH(CH_3)CH_2CH(CH_3)CH_2$—, —$CH_2CH(CH_3)CH(CH_3)CH_2$—, —$CH_2C(CH_3)_2(CH_2)_2$—, —$CH(CH_3)C(CH_3)_2CH_2$—, —$CH(CH_2CH_3)(CH_2)_3$—, —$CH_2CH(CH_2CH_3)(CH_2)_2$—, —$CH(CH_3)(CH_2)_4$—, —$CH_2CH(CH_3)(CH_2)_3$—, and —$(CH_2)_2CH(CH_3)(CH_2)_2$—. Examples of preferred $A^1$ include —$CH_2$—, —$(CH_2)_2$—, —$(CH_2)_3$—, —$(CH_2)_4$—, —$CH(CH_3)CH_2$—, —$CH(CH_3)CH(CH_3)$—, —$CH(CH_3)(CH_2)_2$—, —$CH_2CH(CH_3)CH_2$—, and —$CH(CH_3)CH(CH_3)CH_2$—. More preferred examples of $A^1$ include —$CH_2$—, —$(CH_2)_2$—, and —$(CH_2)_3$—. As more preferable examples of $A^1$, —$(CH_2)_2$— may be mentioned.

In the formula (I), $A^2$ represents a single bond or represents a group that links $A^1$ and $G^1$ in the form of $A^1$-C(=O)-$G^1$, $A^1$-C(=O)—O-$G^1$, $A^1$-C(=O)—$NR^{101}$-$G^1$, $A^1$-C(=S)—$NR^{102}$-$G^1$, $A^1$-C(=$NR^{103}$)-$G^1$, $A^1$-O-$G^1$, $A^1$-O—C(=O)-$G^1$, $A^1$-$NR^{104}$-$G^1$, $A^1$-$NR^{105}$—C(=O)-$G^1$, $A^1$-$NR^{106}$—S(=O)$_2$-$G^1$, $A^1$-$NR^{107}$—C(=O)—O-$G^1$, $A^1$-$NR^{108}$—C(=O)—$NR^{109}$-$G^1$, $A^1$-$NR^{110}$—C(=S)-$G^1$, $A^1$-$NR^{111}$—C(=S)—$NR^{112}$-$G^1$, $A^1$—S-$G^1$, $A^1$-S(=O)-$G^1$, $A^1$-S(=O)$_2$-$G^1$, $A^1$-S(=O)$_2$—$NR^{113}$-$G^1$, $A^1$-$CR^{114}$=CH-$G^1$, $A^1$-$CR^{115}$=CF-$G^1$, $A^1$-CH=$CR^{116}$-$G^1$ or $A^1$-CF=$CR^{117}$-$G^1$ ($R^{101}$~$R^{117}$ are independently a hydrogen atom or a acyclic aliphatic hydrocarbon group having 1 to 4 carbon atoms).

When $A^1$ and $G^1$ are linked to each other in the form of $A^1$-C(=O)—$NR^{101}$-$G^1$, examples of the $C_1$-$C_4$ aliphatic hydrocarbon group of $R^{101}$ include methyl, ethyl, propyl, isopropyl, butyl, isobutyl, s-butyl, t-butyl, cyclopropylmethyl, 2-propenyl, 2-butenyl, 3-butenyl, 2-propynyl, 2-butynyl and 3-butynyl group. The $C_1$-$C_4$ acyclic aliphatic hydrocarbon group may also be substituted with one or more substituents selected from the group consisting of a fluorine atom, a chlorine atom, a bromine atom, an iodine atom, a hydroxy group, a methoxy group, an ethoxy group, an oxo group, a cyano group, a carboxyl group, a carbamoyl group, an amino group, a sulfo group, and a phenyl group. Examples of preferred $R^{101}$ include a hydrogen atom, methyl, ethyl, and propyl group. Particularly, a hydrogen atom is preferred.

When $A^1$ and $G^1$ are linked to each other in the form of $A^1$-C(=S)—$NR^{102}$-$G^1$, examples of the $C_1$-$C_4$ aliphatic hydrocarbon group of $R^{102}$ include the same as those selected as the examples of $R^{101}$. Examples of preferred $R^{102}$ include a hydrogen atom, methyl, ethyl, and propyl group. Particularly, a hydrogen atom is preferred.

When $A^1$ and $G^1$ are linked to each other in the form of $A^1$-C(=$NR^{103}$)-$G^1$, examples of the $C_1$-$C_4$ aliphatic hydrocarbon group of $R^{103}$ include the same as those selected as the examples of $R^{101}$. Examples of preferred $R^{103}$ include a hydrogen atom, methyl, ethyl, and propyl group. Particularly, a hydrogen atom is preferred.

When $A^1$ and $G^1$ are linked to each other in the form of $A^1$-$NR^{104}$-$G^1$, examples of the $C_1$-$C_4$ aliphatic hydrocarbon group of $R^{104}$ include the same as those selected as the examples of $R^{101}$. Examples of preferred $R^{104}$ include a hydrogen atom, methyl, ethyl, and propyl group. Particularly, a hydrogen atom is preferred.

When $A^1$ and $G^1$ are linked to each other in the form of $A^1$-$NR^{105}$—C(=O)-$G^1$, examples of the $C_1$-$C_4$ acyclic aliphatic hydrocarbon group of $R^{105}$ include the same as those selected as the examples of $R^{101}$. Examples of preferred $R^{105}$ include a hydrogen atom, methyl, ethyl, and propyl group. Particularly, a hydrogen atom is preferred.

When $A^1$ and $G^1$ are linked to each other in the form of $A^1$-$NR^{106}$—S(=O)$_2$-$G^1$, examples of the $C_1$-$C_4$ aliphatic hydrocarbon group of $R^{106}$ include the same as those selected as the examples of $R^{101}$. Examples of preferred $R^{106}$ include a hydrogen atom, methyl, ethyl, and propyl group. Particularly, a hydrogen atom is preferred.

When $A^1$ and $G^1$ are linked to each other in the form of $A^1$-$NR^{107}$—C(=O)—O-$G^1$, examples of the $C_1$-$C_4$ aliphatic hydrocarbon group of $R^{107}$ include the same as those selected as the examples of $R^{101}$. Examples of preferred $R^{107}$ include a hydrogen atom, methyl, ethyl, and propyl group. Particularly, a hydrogen atom is preferred.

When $A^1$ and $G^1$ are linked to each other in the form of $A^1$-$NR^{108}$—C(=O)$NR^{109}$-$G^1$, examples of such preferred $C_1$-$C_4$ aliphatic hydrocarbon group of $R^{108}$ and $R^{109}$ include the same as those selected as the examples of $R^{101}$. Examples of preferred $R^{108}$ and $R^{109}$ include a hydrogen atom, methyl, ethyl, and propyl group. Particularly, a hydrogen atom is preferred.

When $A^1$ and $G^1$ are linked to each other in the form of $A^1$-$NR^{110}$—C(=S)-$G^1$, examples of such preferred $C_1$-$C_4$ aliphatic hydrocarbon group of $R^{110}$ include the same as those selected as the examples of $R^{101}$. Examples of preferred $R^{110}$ include a hydrogen atom, methyl, ethyl, and propyl group. Particularly, a hydrogen atom is preferred.

When $A^1$ and $G^1$ are linked to each other in the form of $A^1$-$NR^{111}$—C(=S)—$NR^{112}$-$G^1$, examples of the $C_1$-$C_4$ aliphatic hydrocarbon group of $R^{111}$ and $R^{112}$ include the same as those selected as the examples of $R^{101}$. Examples of preferred $R^{111}$ and $R^{112}$ include a hydrogen atom, methyl, ethyl, and propyl group. Particularly, a hydrogen atom is preferred.

When $A^1$ and $G^1$ are linked to each other in the form of $A^1$-S(=O)$_2$—$NR^{113}$-$G^1$, examples of the $C_1$-$C_4$ aliphatic hydrocarbon group of $R^{113}$ include the same as those selected as the examples of $R^{101}$. Examples of preferred $R^{113}$ include a hydrogen atom, methyl, ethyl, and propyl group. Particularly, a hydrogen atom is preferred.

When $A^1$ and $G^1$ are linked to each other in the form of $A^1$-$CR^{114}$=$CR^{115}$-$G^1$, examples of the $C_1$-$C_4$ aliphatic hydrocarbon group of $R^{114}$ and $R^{115}$ include the same as those selected as the examples of $R^{101}$. Examples of preferred $R^{114}$ and $R^{115}$ include a hydrogen atom, methyl, ethyl, and propyl group. Particularly, a hydrogen atom is preferred.

When $A^1$ and $G^1$ are linked to each other in the form of $A^1$-CF=$CR^{117}$-$G^1$, examples of the $C_1$-$C_4$ aliphatic hydrocarbon group of $R^{117}$ include the same as those selected as the examples of $R^{101}$. Examples of preferred $R^{117}$ include a hydrogen atom, methyl, ethyl, and propyl group. Particularly, a hydrogen atom is preferred.

When $A^1$ and $G^1$ are linked to each other in the form of $A^1$-CF=$CR^{117}$-$G^1$, examples of the $C_1$-$C_4$ aliphatic hydrocarbon group of $R^{117}$ include the same as those selected as the examples of $R^{101}$. Examples of preferred $R^{117}$ include a hydrogen atom, methyl, ethyl, and propyl group. Particularly, a hydrogen atom is preferred.

Examples of preferred $A^2$ include groups that link $A^1$ and $G^1$ in the form of $A^1$-C(=O)-$G^1$, $A^1$-C(=O)—$NR^{101}$-$G^1$, $A^1$-O-$G^1$, $A^1$-$NR^{104}$-$G^1$, $A^1$-$NR^{105}$—C(=O)-$G^1$, $A^1$-$NR^{108}$—C(=O)—$NR^{109}$-$G^1$, $A^1$-$NR^{110}$—C(=S)-$G^1$ and $A^1$-$NR^{111}$—C(=S)$NR^{112}$-$G^1$, especially preferably in the form of $A^1$-C(=O)-$G^1$, $A^1$-C(=O)—$NR^{101}$-$G^1$, $A^1$-$NR^{104}$-$G^1$, $A^1$-$NR^{105}$—C(=O)-$G^1$, $A^1$-$NR^{108}$—C(=O)—$NR^{109}$-$G^1$, and $A^1$-$NR^{110}$—C(=S)-$G^1$. Among them, examples of more preferred $A^2$ include groups that link $A^1$ and $G^1$ in the form of $A^1$-C(=O)—$NR^{101}$-$G^1$, $A^1$-$NR^{105}$—C(=O)-$G^1$, and $A^1$-$NR^{108}$—C(=O)—$NR^{109}$-$G^1$. Here, forms of linkage exemplified as preferred and more preferred $A^2$ are preferably combined with structures in which $A^1$ exists in the form of —(CH$_2$)$_2$— or —(CH$_2$)$_3$— in the formula (I).

In the formula (I), $A^3$ represents a single bond or represents an optionally substituted divalent aliphatic hydrocarbon group having 1 to 10 carbon atoms that links $G^1$ and $A^4$ on the same or different carbon atoms.

Examples of the acyclic aliphatic hydrocarbon group having 1 to 10 carbon atoms of $A^3$ include, in addition to the same as those selected as the examples of $A^1$, —CH=CH—, —C(CH$_3$)=CH—, —C(CH$_3$)=C(CH$_3$)—, —C(CH$_2$CH$_3$)=CH—, —C(CH$_2$CH$_3$)=C(CH$_3$)—, —C(CH$_2$CH$_3$)=C(CH$_2$CH$_3$)—, —C(CH$_2$CH$_2$CH$_3$)=CH—, —C(CH$_2$CH$_2$CH$_3$)=C(CH$_3$)—, —CH=CHCH$_2$—, —C(CH$_3$)=CHCH$_2$—, —CH=C(CH$_3$)CH$_2$—, —CH=CHCH(CH$_3$)—, —C(CH$_3$)=C(CH$_3$)CH$_2$—, —C(CH$_3$)=CHCH(CH$_3$)—, —C(CH$_3$)=C(CH$_3$)CH(CH$_3$)—, —C(CH$_3$)=CHC(CH$_3$)$_2$—, —C(CH$_2$CH$_3$)=CHCH$_2$—, —CH=C(CH$_2$CH$_3$)CH$_2$—, —CH=CHCH(CH$_2$CH$_3$)—, —C(CH$_2$CH$_3$)=C(CH$_3$)CH$_2$—, —C(CH$_2$CH$_3$)=CHCH(CH$_3$)—, —C(CH$_3$)=C(CH$_2$CH$_3$)CH$_2$—, —CH=C(CH$_2$CH$_3$)CH(CH$_3$)—, —CH=CHCH(CH$_2$CH$_3$)—, —C(CH$_3$)=CHCH(CH$_2$CH$_3$)—, —CH=C(CH$_3$)CH(CH$_2$CH$_3$)—, —CH=CH(CH$_2$)$_2$—, —C(CH$_3$)=CH(CH$_2$)$_2$—, —CH=C(CH$_3$)(CH$_2$)$_2$—, —CH=CHC(CH$_3$)CH$_2$—, —C H=CHCH$_2$CH(CH$_3$)—, —C(CH$_3$)=C(CH$_3$)(CH$_2$)$_2$—, —C(CH$_3$)=CHCH(CH$_3$)CH$_2$—, —C(CH$_3$)=CHCH$_2$CH(CH$_3$)—, —H$_2$C=CHCH$_2$—, —CH(CH$_3$)CH=CHCH$_2$—, —CH$_2$C(CH$_3$)=CHCH$_2$—, —CH(CH$_3$)C(CH$_3$)=CHCH$_2$—, —CH(CH$_3$)CH=CHCH(CH$_3$)—, —CH(CH$_3$)CH=C(CH$_3$)CH$_2$—, —CH$_2$C(CH$_3$)= C(CH$_3$)CH$_2$—, —CH(CH$_2$CH$_3$)CH=CHCH$_2$—, and —CH$_2$C(CH$_2$CH$_3$)=CHCH$_2$—.

Substituents of divalent substituted aliphatic hydrocarbon group having 1 to 10 carbon atoms of $A^3$ include a hydrocarbon group having 1 to 6 carbon atoms, an alicyclic hydrocarbon group having 3 to 6 carbon atoms, a halogen atom, an alkoxy group having 1 to 6 carbon atoms, a phenoxy group, an amino group, or an alkyl amino group having 1 to 6 carbon atoms.

Examples of such preferred $A^3$ include a single bond, —CH$_2$—, —(CH$_2$)$_2$—, —(CH$_2$)$_3$—, —(CH$_2$)$_4$—, —CH(CH$_3$)CH$_2$—, —CH(CH$_3$)CH(CH$_3$)—, —CH(CH$_3$)(CH$_2$)$_2$—, —CH=CH— and —CH=CHCH$_2$—. Further, examples of more preferred $A^3$ include a single bond, —CH$_2$—, —(CH$_2$)$_2$— and —(CH$_2$)$_3$—. The same applies when $A^3$ is substituted, but a single bond is excluded.

In the formula (I), $A^4$ represents a single bond or represents a group that links $A^3$ and $G^2$ in the form of $A^3$-C(=O)-$G^2$, $A^3$-C(=O)—O-$G^2$, $A^3$-C(=O)—$NR^{121}$-$G^2$, $A^3$-C(=S)—$NR^{122}$-$G^2$, $A^3$-C(=$NR^{123}$)-$G^2$, $A^3$-O-$G^2$, $A^3$-O—C(=O)-

$G^2$, $A^3$-$NR^{124}$-$G^2$, $A^3$-$NR^{125}$—C(=O)-$G^2$, $A^3$-$NR^{126}$—S(=O)$_2$-$G^2$, $A^3$-$NR^{127}$—C(=O)—O-$G^2$, $A^3$-$NR^{128}$—C(=O)—$NR^{129}$-$G^2$, $A^3$-$NR^{130}$—C(=S)-$G^2$, $A^3$-$NR^{131}$—C(=S)—$NR^{132}$-$G^2$, $A^3$-S-$G^2$, $A^3$-S(=O)-$G^2$, $A^3$-S(=O)$_2$-$G^2$, $A^3$-S(=O)$_2$—$NR^{133}$-$G^2$ or $A^3$-S(=O)$_2$—O-$G^2$ (in which $R^{121}$ through $R^{133}$ are each independently a hydrogen atom or a acyclic aliphatic hydrocarbon group having 1 to 4 carbon atoms).

When $A^3$ and $G^2$ are linked to each other in the form of $A^3$-C(=O)—$NR^{121}$-$G^2$, examples the $C_1$-$C_4$ acyclic aliphatic hydrocarbon group of $R^{121}$ include the same as those selected as the examples of $R^{101}$ in $A^2$. Examples of preferred $R^{121}$ include a hydrogen atom, methyl, ethyl, and propyl group. Particularly, a hydrogen atom is preferred.

When $A^3$ and $G^2$ are linked to each other in the form of $A^3$-C(=S)—$NR^{122}$-$G^2$, examples of the $C_1$-$C_4$ acyclic aliphatic hydrocarbon group of $R^{122}$ include the same as those selected as the examples of $R^{101}$ in $A^2$. Examples of preferred $R^{122}$ include a hydrogen atom, methyl, ethyl, and propyl group. Particularly, a hydrogen atom is preferred.

When $A^3$ and $G^2$ are linked to each other in the form of $A^3$-C(=$NR^{123}$)-$G^2$, examples of the $C_1$-$C_4$ acyclic aliphatic hydrocarbon group of $R^{123}$ include the same as those selected as the examples of $R^{101}$ in $A^2$. Examples of preferred $R^{123}$ include a hydrogen atom, methyl, ethyl, and propyl group. Particularly, a hydrogen atom is preferred.

When $A^3$ and $G^2$ are linked to each other in the form of $A^3$-$NR^{124}$-$G^2$, examples of the $C_1$-$C_4$ acyclic aliphatic hydrocarbon group of $R^{124}$ include the same as those selected as the examples of $R^{101}$ in $A^2$. Examples of preferred $R^{124}$ include a hydrogen atom, methyl, ethyl, and propyl group. Particularly, a hydrogen atom is preferred.

When $A^3$ and $G^2$ are linked to each other in the form of $A^3$-$NR^{125}$—C(=O)-$G^2$, examples of the $C_1$-$C_4$ aliphatic hydrocarbon group of $R^{125}$ include the same as those selected as the examples of $R^{101}$ in $A^2$. Examples of preferred $R^{125}$ include a hydrogen atom, methyl, ethyl, and propyl group. Particularly, a hydrogen atom is preferred.

When $A^3$ and $G^2$ are linked to each other in the form of $A^3$-$NR^{126}$—S(=O)$_2$-$G^2$, examples of the $C_1$-$C_4$ acyclic aliphatic hydrocarbon group of $R^{126}$ include the same as those selected as the examples of $R^{101}$ in $A^2$. Examples of preferred $R^{126}$ include a hydrogen atom, methyl, ethyl, and propyl group. Particularly, a hydrogen atom is preferred.

When $A^3$ and $G^2$ are linked to each other in the form of $A^3$-$NR^{127}$—C(=O)—O-$G^2$, examples of the $C_1$-$C_4$ acyclic aliphatic hydrocarbon group of $R^{127}$ include the same as those selected as the examples of $R^{101}$ in $A^2$. Examples of preferred $R^{127}$ include a hydrogen atom, methyl, ethyl, and propyl group. Particularly, a hydrogen atom is preferred.

When $A^3$ and $G^2$ are linked to each other in the form of $A^3$-$NR^{128}$—C(=O)—$NR^{129}$-$G^2$, examples of the $C_1$-$C_4$ aliphatic hydrocarbon group of $R^{128}$ and $R^{129}$ include the same as those selected as the examples of $R^{101}$ in $A^2$. Examples of preferred $R^{128}$ and $R^{129}$ include a hydrogen atom, methyl, ethyl, and propyl group. Particularly, a hydrogen atom is preferred.

When $A^3$ and $G^2$ are linked to each other in the form of $A^3$-$NR^{130}$—C(=S)-$G^2$, examples of the $C_1$-$C_4$ acyclic aliphatic hydrocarbon group of $R^{130}$ include the same as those selected as the examples of $R^{101}$ in $A^2$. Examples of preferred $R^{130}$ include a hydrogen atom, methyl, ethyl, and propyl group. Particularly, a hydrogen atom is preferred.

When $A^3$ and $G^2$ are linked to each other in the form of $A^3$-$NR^{131}$—C(=S)—$NR^{132}$-$G^2$, examples of the $C_1$-$C_4$ acyclic aliphatic hydrocarbon group of $R^{131}$ and $R^{132}$ include the same as those selected as the examples of $R^{101}$ in $A^2$. Examples of preferred $R^{131}$ and $R^{132}$ include a hydrogen atom, methyl, ethyl, and propyl group. Particularly, a hydrogen atom is preferred.

When $A^3$ and $G^2$ are linked to each other in the form of $A^3$-S(=O)$_2$—$NR^{133}$-$G^2$, examples of the $C_1$-$C_4$ acyclic aliphatic hydrocarbon group of $R^{133}$ include the same as those selected as the examples of $R^{101}$ in $A^2$. Examples of preferred $R^{133}$ include a hydrogen atom, methyl, ethyl, and propyl group. Particularly, a hydrogen atom is preferred.

Examples of such $A^4$ include a single bond and a group that links $A^3$ and $G^2$ in the form of $A^3$-C(=O)-$G^2$, $A^3$-C(=O)—O-$G^2$, $A^3$-C(=O)—$NR^{121}$-$G^2$, $A^3$-O-$G^2$, $A^3$-$NR^{124}$-$G^2$, $A^3$-$NR^{125}$—C(=O)-$G^2$, $A^3$-S(=O)$_2$-$G^2$ or $A^3$-S(=O)$_2$—O-$G^2$.

In the formula (I), $G^1$ represents a single bond or a divalent group obtainable by removing two hydrogen atoms from any of groups consisting of a substituted or unsubstituted alicyclic hydrocarbon group having 3 to 10 carbon atoms, a substituted or unsubstituted aromatic hydrocarbon group having 6 to 14 carbon atoms, and a heterocyclic compound having 1 to 4 atoms selected from the group consisting of an oxygen atom, a nitrogen atom and a sulfur atom on its substituted or unsubstituted ring.

In the formula (I), when $G^1$ represents a substituted or unsubstituted divalent alicyclic hydrocarbon group having 3 to 10 carbon atoms, examples of the alicyclic hydrocarbon group having 3 to 10 carbon atoms include cyclopropane, cyclobutane, cyclopentane, cyclopentene, cyclohexane, cyclohexene, cycloheptane, cycloheptene, cyclooctane, bicyclo[2.2.1]heptane, bicyclo[2.2.1]heptene, bicyclo[3.1.1]heptane and bicyclo[2.2.2]octane. Examples of such preferred $C_3$-$C_{10}$ alicyclic hydrocarbon of $G^1$ include monocyclic alicyclic hydrocarbon group having 3 to 6 carbon atoms such as cyclopropane, cyclopentane, cyclohexane and the like.

Examples of the substituent for the substituted alicyclic hydrocarbon group having 3 to 10 carbon atoms of $G^1$ include: a fluorine atom, a chlorine atom, a bromine atom, an iodine atom, a hydroxy group, methoxy, ethoxy, propoxy, isopropoxy, butoxy, isobutoxy, s-butoxy, t-butoxy, pentyloxy, isopentyloxy, neopentyloxy, t-pentyloxy, hexyloxy, isohexyloxy, 2-methyl-pentyloxy, 1-ethylbutoxy, cyclopropyloxy, cyclobutyloxy, cyclopentyloxy, cyclohexyloxy, cyclopropylmethyloxy, cyclopropylethyloxy, cyclopentylmethyloxy and cyclohexylmethyloxy or another $C_1$-$C_7$ alkoxy group consisting of a straight or branched alkyl, cycloalkyl and oxy group, ethylene dioxy or another $C_1$-$C_4$ alkylenedioxy group, phenoxy, 1-naphthoxy and 2-naphthoxy or another $C_6$-$C_{10}$ aryloxy group, benzyloxy, α-phenethyloxy, β-phenethyloxy and phenylpropyloxy or another $C_7$-$C_9$ aralkoxy group, acetoxy, propionyloxy, butyryloxy, isobutyryloxy, valeryloxy, isovaleryloxy, pivaloyloxy and hexanoyloxy or another $C_2$-$C_7$ acyloxy group, oxo, methylsulfonyloxy, ethylsulfonyloxy, propylsulfonyloxy, butylsulfonyloxy and t-butylsulfonyloxy or another $C_1$-$C_6$ alkylsulfonyloxy group consisting of a straight or branched alkyl and sulfonyloxy, acetyl, propionyl, butyryl, isobutyryl, valeryl, isovaleryl, pivaroyl and hexanoyl or another $C_2$-$C_7$ acyl group, carboxy, methoxycarbonyl, ethoxycarbonyl, propoxycarbonyl, isopropoxycarbonyl, butoxycarbonyl, isobutoxycarbonyl, s-butoxycarbonyl and t-butoxycarbonyl or another $C_2$-$C_7$ alkoxycarbonyl group consisting of a straight or branched alkyl and oxycarbonyl group, carbamoyl, N-methylcarbamoyl, N-ethylcarbamoyl, N-propylcarbamoyl, N-isopropylcarbamoyl, N-butylcarbamoyl, N-isobutylcarbamoyl, N-s-butylcarbamoyl, N-t-butylcarbamoyl, N-pentylcarbamoyl, N-cyclopropylcarbamoyl, N-cyclobutylcarbamoyl, N-cyclopentylcarbamoyl, N-cyclohexylcarbamoyl, N-cycloheptylcarbamoyl, N-cyclopropylmethylcarbamoyl, N,N-dimethylcarbamoyl, N-ethyl-N-methylcarbamoyl, N,N-diethylcarbamoyl and N,N-dipropylcarbamoyl or another $C_2$-$C_7$ alkylcarbamoyl group consisting of a straight or branched alkyl, cycloalkyl and carbamoyl group, amino, methylamino, ethylamino, propylamino, isopropylamino, butylamino, isobutylamino, s-butylamino, t-butylamino, pentylamino, hexylamino, cyclopropylamino, cyclobutylamino, cyclopentylamino, cyclohexylamino, cyclopropylmethylamino, dimethylamino, N-ethylmethylamino, diethylamino, N-methylpropylamino, N-methylisopropylamino, N-methylbutyl-amino, N-methyl-t-butylamino, N-ethylisopropylamino, dipropylamino, diisopropylamino and ethylbutylamino or another $C_1$-$C_6$ alkylamino group consisting of a straight or branched alkyl, cycloalkyl and amino group, acetylamino, propionylamino, butyrylamino, isobutyrylamino, valerylamino and hexanoylamino or another $C_2$-$C_7$ acylamino group, methoxycarbonylamino, ethoxycarbonylamino and t-butoxycarbonylamino or another $C_2$-$C_8$ alkoxycarbonylamino group, methylsulfonylamino, ethylsulfonylamino, butylsulfonylamino and t-butylsulfonylamino or another $C_1$-$C_6$ alkylsulfonylamino group, a cyano group, a nitro group, methylthio, ethylthio, propylthio, isopropylthio, butylthio, isobutylthio, s-butylthio, t-butylthio, pentylthio and hexylthio or another $C_1$-$C_6$ alkylthio group, methylsulfynyl, ethylsulfynyl, propylsulfynyl, isopropylsulfynyl, butylsulfynyl, isobutylsulfynyl, s-butylsulfynyl, t-butylsulfynyl, pentylsulfynyl and cyclopentylsulfynyl or another $C_1$-$C_6$ alkylsulfynyl group consisting of a straight or branched alkyl, cycloalkyl and sulfynyl group, methylsulfonyl, ethylsulfonyl, propylsulfonyl, isopropylsulfonyl, butylsulfonyl, isobutylsulfonyl, s-butylsulfonyl, t-butylsulfonyl, pentylsulfonyl, hexylsulfonyl, cyclopentylsulfonyl and cyclohexylsulfonyl or another $C_1$-$C_6$ alkylsulfonyl group consisting of a straight or branched alkyl, cycloalkyl and sulfonyl group, a sulfo group, a sulfamoyl group, methylaminosulfonyl, ethylaminosulfonyl, propylaminosulfonyl, isopropylaminosulfonyl, butylaminosulfonyl, isobutylaminosulfonyl, s-butylaminosulfonyl, pentylaminosulfonyl, dimethylaminosulfonyl, N-ethyl-N-methylaminosulfonyl, diethylaminosulfonyl, dipropylaminosulfonyl, cyclopropylaminosulfonyl, cyclopentylaminosulfonyl, cyclohexylamino-sulfonyl and cyclopropylmethylaminosulfonyl or another $C_1$-$C_6$ aminosulfonyl group consisting of a straight or branched alkyl, a cycloalkyl and aminosulfonyl group, cyclopropyl, cyclobutyl, cyclopentyl and cyclohexyl or another alicyclic hydrocarbon group having 3 to 6 carbon atoms, methyl, ethyl, vinyl, ethynyl, propyl, 1-propenyl, 2-propenyl, isopropyl, isopropenyl, 1-propynyl, 2-propynyl, butyl, isobutyl, s-butyl, t-butyl, 1-butenyl, 2-butenyl, 3-butenyl, 1-methyl-1-propenyl, 2-methyl-1-propenyl, 1-methyl-2-propenyl, 2-methyl-2-propenyl, 1-butynyl, 2-butynyl, pentyl, isopentyl, neopentyl, t-pentyl, 1-pentenyl, 2-pentenyl, 3-pentenyl, 4-pentenyl, hexyl, 5-hexenyl, 4-methyl-3-pentenyl, isohexyl, 2-methylpentyl and 1-ethylbutyl or another aliphatic hydrocarbon group having 1 to 6 carbon atoms which may contain a straight or branched unsaturated bond.

As the substituent of the substituted alicyclic hydrocarbon group having 3 to 10 carbon atoms as $G^1$, a $C_1$-$C_7$ alkoxy group, a $C_2$-$C_7$ acyl group, a $C_2$-$C_7$ alkylcarbamoyl group, a $C_1$-$C_6$ alkylamino group, a $C_2$-$C_7$ acylamino group, an alicyclic hydrocarbon group having 3 to 6 carbon atoms or an aliphatic hydrocarbon group having 1 to 6 carbon atoms, may further be substituted with (one or more substituents selected from the group consisting of a fluorine atom; a chlorine atom; a bromine atom; an iodine atom; a hydroxy group; a $C_1$-$C_6$ alkoxy group such as methoxy, ethoxy, propoxy, isopropoxy, butoxy, isobutoxy, s-butoxy, t-butoxy, pentyloxy or cyclopropyloxy; a $C_2$-$C_7$ acyl group such as methoxymethyloxy group, 2-methoxyethoxy group, formyl group, trifluoroacetyl group, acetyl, propionyl, butyryl, isobutyryl, valeryl or isovaleryl; an oxo group; a carboxyl group; a $C_2$-$C_7$ alkoxycarbonyl group such as methoxycarbonyl, ethoxycarbonyl, propoxycarbonyl, isopropoxycarbonyl, butoxycarbonyl, isobutoxycarbonyl or t-butoxycarbonyl; a carbamoyl group; a $C_2$-$C_7$ alkylcarbamoyl group such as N-methylcarbamoyl, N,N-dimethylcarbamoyl, N-ethylcarbamoyl, N-ethyl-N-methylcarbamoyl, N,N-diethyl-carbamoyl, N-propylcarbamoyl, N-isopropylcarbamoyl, N-butylcarbambyl, N-cyclopropylcarbamoyl or N-cyclopropyl-methylcarbamoyl; an amino group; a $C_1$-$C_6$ alkylamino group such as methylamino, ethylamino, propylamino, isopropylamino, dimethylamino, N-ethylmethylamino, diethylamino, N-methyl-propylamino, N-methylisopropylamino, cyclopropylamino or cyclopropylmethylamino; a $C_4$-$C_6$ cyclic amino group having 1 or 2 atoms selected from the group consisting of an oxygen atom, a nitrogen atom and a sulfur atom, in the ring, such as 1-pyrrolidinyl, piperazinyl, 4-methylpiperazinyl, piperidino or morpholino; a $C_1$-$C_7$ acylamino group such as trifluoroacetylamino group, formylamino, acetylamino, propionylamino, butyrylamino, isobutyrylamino or valerylamino; a $C_1$-$C_6$ alkylsulfonylamino group such as methylsulfonylamino, ethylsulfonylamino, propylsulfonylamino or butylsulfonylamino; a nitro group; and a cyano group).

In the formula (I), when $G^1$ represents a substituted or unsubstituted divalent aromatic hydrocarbon group having 6 to 14 carbon atoms, examples of the aromatic hydrocarbon group having 6 to 14 carbon atoms include a compound having at least one aromatic ring on its molecule, such as benzene, indene, indane, naphthalene, 1,2-dihydronaphthalene, 1,2,3,4-tetrahydronaphthalene, azulene, acenaphthylene, acenaphthene, fluorene, phenanthrene or anthracene.

Examples of such preferred aromatic hydrocarbon group having 6 to 14 carbon atoms of $G^1$ include benzene, naphthalene and indane. Examples of more preferred aromatic hydrocarbon group having 6 to 14 carbon atoms of $G^1$ include benzene.

Exemplary substituents of the substituted aromatic hydrocarbon group having 6 to 14 carbon atoms of $G^1$ include a fluorine atom, a chlorine atom, a bromine atom, an iodine atom, a hydroxy group, an optionally substituted $C_1$-$C_7$ alkoxy group, a $C_6$-$C_{10}$ aryloxy group, a $C_7$-$C_9$ aralkoxy group, a $C_2$-$C_7$-acyloxy group, an oxo group, a $C_1$-$C_6$ alkylsulfonyloxy group, an optionally substituted $C_2$-$C_7$ acyl group, a carboxyl group, a $C_2$-$C_7$ alkoxycarbonyl group, a carbamoyl group, an optionally substituted $C_2$-$C_7$ alkylcarbamoyl group, an amino group, an optionally substituted $C_1$-$C_6$ alkylamino group, an optionally substituted $C_2$-$C_7$ acylamino group, a $C_2$-$C_8$ alkoxycarbonylamino group, a $C_1$-$C_6$ alkylsulfonylamino group, a cyano group, a nitro group, a $C_1$-$C_6$ alkylthio group, a $C_1$-$C_6$ alkylsulfynyl group, a $C_1$-$C_6$ alkylsulfonyl group, a sulfamoyl group, a $C_1$-$C_6$ alkylaminosulfonyl group, a sulfo group, an optionally substituted alicyclic hydrocarbon group having 3 to 6 carbon atoms and an optionally substituted aliphatic hydrocarbon group having 1 to 6 carbon atoms.

Specific examples of the substituent of the substituted aromatic hydrocarbon group having 6 to 14 carbon atoms of $G^1$ include the same as those specifically exemplified as the substituents of the substituted alicyclic hydrocarbon group having 3 to 10 carbon atoms of $G^1$.

As the substituent of the substituted aromatic hydrocarbon group having 6 to 14 carbon atoms, the $C_1$-$C_7$ alkoxy group, the $C_2$-$C_7$ acyl group, the $C_2$-$C_7$ alkylcarbamoyl group, the $C_1$-$C_6$ alkylamino group, the $C_2$-$C_7$ acylamino group, the alicyclic hydrocarbon group having 3 to 6 carbon atoms or the aliphatic hydrocarbon group having 1 to 6 carbon atoms, may further be substituted with (one or more substituents selected from the group consisting of a fluorine atom; a chlorine atom; a bromine atom; an iodine atom; a hydroxy group; a $C_1$-$C_6$ alkoxy group such as methoxy, ethoxy, propoxy, isopropoxy, butoxy, isobutoxy, s-butoxy, t-butoxy, pentyloxy or cyclopropyloxy; a methoxymethyloxy group; a 2-methoxyethoxy group; a formyl group; a trifluoroacetyl group; a $C_2$-$C_7$ acyl group such as acetyl, propionyl, butyryl, isobutyryl, valeryl or isovaleryl; an oxo group; a carboxyl group; a $C_2$-$C_7$ alkoxycarbonyl group such as methoxycarbonyl, ethoxycarbonyl, propoxycarbonyl, isopropoxycarbonyl, butoxycarbonyl, isobutoxycarbonyl or t-butoxycarbonyl; a carbamoyl group; a $C_2$-$C_7$ alkylcarbamoyl group such as N-methylcarbamoyl, N,N-dimethylcarbamoyl, N-ethylcarbamoyl, N-ethyl-N-methylcarbamoyl, N,N-diethyl-carbamoyl, N-propylcarbamoyl, N-isopropylcarbamoyl, N-butylcarbamoyl, N-cyclopropylcarbamoyl or N-cyclopropylmethylcarbamoyl; an amino group; a $C_1$-$C_6$ alkylamino group such as methylamino, ethylamino, propylamino, isopropylamino, dimethylamino, N-ethylmethylamino, diethylamino, N-methylpropylamino, N-methylisopropylamino, cyclopropylamino or cyclopropylmethylamino; a $C_4$-$C_6$ cyclic amino group having 1 or 2 atoms selected from the group consisting of an oxygen atom, a nitrogen atom and a sulfur atom, in the ring, such as 1-pyrrolidinyl, piperazinyl, 4-methylpiperazinyl, piperidino or morpholino; a trifluoroacetylamino group; a $C_1$-$C_7$ acylamino group such as formylamino, acetylamino, propionylamino, butyrylamino, isobutyrylamino or valerylamino; a $C_1$-$C_6$ alkylsulfonylamino group such as methylsulfonylamino, ethylsulfonylamino, propylsulfonylamino or butylsulfonylamino; a nitro group; and a cyano group).

Preferred examples of the substituents of the substituted aromatic hydrocarbon group having 6 to 14 carbon atoms of $G_1$ include a fluorine atom; a chlorine atom; a bromine atom; a $C_1$-$C_6$ alkoxy group consisting of a straight or branched alkyl and oxy group, including methoxy, ethoxy, propoxy, isopropoxy, butoxy, isobutoxy, s-butoxy, t-butoxy, pentyloxy, isopentyloxy, neopentyloxy, t-pentyloxy and hexyloxy; a cyano group; a nitro group; a carboxyl group; a hydroxy group; an amino group; a $C_1$-$C_6$ mono or dialkylamino group consisting of a straight or branched alkyl and amino group, including methylamino, ethylamino, propylamino, isopropylamino, butylamino, isobutylamino, s-butylamino, t-butylamino, pentylamino, hexylamino, dimethylamino, N-ethylmethylamino, diethylamino, N-methylpropylamino, N-methylisopropylamino, N-methylbutyl-amino, N-methyl-t-butylamino, N-ethylisopropylamino, dipropylamino, diisopropylamino and ethylbutylamino; a carbamoyl group; an aminosulfonyl group; an alicyclic hydrocarbon group having 3 to 6 carbon atoms, including cyclopropyl, cyclobutyl, cyclopentyl and cyclohexyl; a $C_2$-$C_7$ acyl group including acetyl, propionyl, butyryl, isobutyryl, pivaroyl and hexanoyl; a $C_1$-$C_6$ alkylthio group including methylthio, ethylthio, propylthio, isopropylthio, butylthio, isobutylthio, s-butylthio, t-butylthio, pentylthio and hexylthio; a $C_1$-$C_6$ alkylsulfonyl group including methylsulfonyl, ethylsulfonyl, propylsulfonyl, isopropylsulfonyl, butylsulfonyl, isobutylsulfonyl, s-butylsulfonyl, t-butylsulfonyl, pentylsulfonyl and hexylsulfonyl; a $C_2$-$C_7$ alkoxycarbonyl group including acetoxy, propionyloxy, butyryloxy, isobutyryloxy, valeryloxy, isovaleryloxy, pivaloyloxy and hexanoyloxy; a $C_2$-$C_7$ acylamino group including acetylamino, propionylamino, butyrylamino, isobutyrylamino, valerylamino and hexanoylamino; trifluoromethyl group, trifluoromethoxy group, and an aliphatic hydrocarbon group having 1 to 6 carbon atoms which may contain a straight or branched unsaturated bond, including methyl, ethyl, vinyl, ethynyl, propyl, 1-propenyl, 2-propenyl, isopropyl, isopropenyl, 1-propynyl, 2-propynyl, butyl, isobutyl, s-butyl, t-butyl, 1-butenyl, 2-butenyl, 3-butenyl, 1-methyl-1-propenyl, 2-methyl-1-propenyl, 1-methyl-2-propenyl, 2-methyl-2-propenyl, 1-butynyl, 2-butynyl, pentyl, isopentyl, neopentyl, t-pentyl, 1-pentenyl, 2-pentenyl, 3-pentenyl, 4-pentenyl, hexyl, 5-hexenyl, 4-methyl-3-pentenyl, isohexyl, 2-methylpentyl and 1-ethylbutyl.

Specifically, examples of more preferred substituents of the substituted aromatic hydrocarbon group having 6 to 14 carbon atoms include a fluorine atom, a chlorine atom, a bromine atom, $C_1$-$C_6$ alkoxy group, cyano group, a nitro group, a carboxyl group, a hydroxy group, an amino group, a $C_1$-$C_6$ mono or dialkylamino group, a carbamoyl group, an alicyclic hydrocarbon group having 3 to 6 carbon atoms, a $C_2$-$C_7$ acyl group, a $C_1$-$C_6$ alkylsulfonyl group, a $C_2$-$C_7$ alkoxycarboxyl group, trifluoromethyl group, trifluoromethoxy group, and a $C_1$-$C_6$ alkyl group including methyl, ethyl, propyl, isopropyl, butyl, isobutyl, s-butyl, t-butyl, pentyl, isopentyl, neopentyl, t-pentyl, hexyl, isohexyl, 2-methylpentyl and 1-ethylbutyl. Examples of particularly preferred substituents include a fluorine atom, a chlorine atom, a $C_1$-$C_6$ alkoxy group, a cyano group, a nitro group, a carboxyl group, a hydroxy group, an amino group, a $C_1$-$C_6$ mono or dialkylamino group, an alicyclic hydrocarbon group having 3 to 6 carbon atoms, a $C_2$-$C_7$ acyl group, a trifluoromethyl group, a trifluoromethoxy group and a $C_1$-$C_6$ alkyl group.

In the formula (I), when $G^1$ represents a divalent group derived from heterocyclic compounds having 1 to 4 atoms selected from the group consisting of an oxygen atom, a nitrogen atom and a sulfur atom on its substituted or unsubstituted ring, examples of such heterocyclic compounds include monocyclic, bicyclic or tricyclic heterocyclic compounds, such as furan, thiophene, pyrrole, pyrroline, pyrrolidine, oxazole, oxazolidine, isooxazole, isooxazolidine, thiazole, thiazolidine, isothiazole, isothiazolidine, furazan, imidazole, imidazoline, imidazolidine, pyrazole, pyrazoline, pyrazolidine, triazole, thiadiazole, oxadiazole, tetrazole, pyran, tetrahydropyran, thiopyran, tetrahydrothiopyran, tetrahydrofuran, 1,3-dioxolane, 1,4-dioxane, pyridine, pyrazine, pyrimidine, pyridazine, benzofuran, dibenzofuran, 1,4-dioxacycloheptane, benzothiophene, indole, 1,2-methylenedioxybenzene, benzimidazole, benzothiazole, benzooxazole, chroman, isochroman, quinoline, decahydrbquinoline, isoquinoline, phthalazine, cinnoline, 1,8-naphthylidine, 1,2,3,4-tetrahydroisoquinoline, quinazoline, quinoxaline, purine, pteridine, azetidine, morpholine, thiomorpholine, piperidine, homopiperidine, piperazine, homopiperazine, indoline, isoindoline, phenoxazine, phenazine, phenothiazine, pyrrolopyrimidine, pyrazolpyrimidine or quinuclidine.

Preferred examples of the heterocyclic compound having 1 to 4 atoms selected from the group consisting of an oxygen atom, a nitrogen atom and a sulfur atom, in the ring of $G^1$ include monocyclic or bicyclic $C_2$-$C_9$ aromatic heterocyclic compounds having 1 to 3 atoms selected from the group consisting of an oxygen atom, a nitrogen atom and a sulfur atom, in the ring, such as furan, pyrrole, thiophene, pyrazole, oxazole, thiazole, isooxazole, isothiazole, pyrazole, imidazole, pyridine, pyrimidine, pyrazine, pyridazine, benzothiophene, benzofuran, 1,2-methylenedioxybenzene, benzimidazole, indole, quinoline, isoquinoline, quinazoline, phthalazine, cinnoline or 1,8-naphthylidin; or monocyclic $C_2$-$C_9$ heterocyclic compounds having 1 or 2 atoms selected from the group consisting of an oxygen atom, a nitrogen atom and a sulfur atom, in the ring, such as pyrrolidine, piperidine, morpholine, thiomorpholine, homopiperidine, homopiperazine, 1,2,3,6-tetrahydropyridine or piperazine.

The heterocyclic group having 1 to 4 atoms selected from the group consisting of an oxygen atom, a nitrogen atom and a sulfur atom, in the ring of $G^1$ links to $A^2$ on a carbon atom or a nitrogen atom.

More preferred examples of the heterocyclic group linking to $A^2$ on a carbon atom include divalent groups derived from monocyclic or bicyclic $C_3$-$C_9$ aromatic heterocyclic compounds having 1 or 2 atoms selected from the group consisting of an oxygen atom, a nitrogen atom and a sulfur atom, in the ring, such as furan, pyrrole, thiophene, pyrazole, oxazole, thiazole, isooxazole, isothiazole, pyrazole, imidazole, pyridine; pyrimidine, pyrazine, pyridazine, benzothiophene, benzofuran, 1,2-methylenedioxybenzene, benzimidazole, indole, quinoline, isoquinoline or quinazoline.

Meanwhile, preferred examples of the heterocyclic group having 1 to 4 atoms selected from the group consisting of an oxygen atom, a nitrogen atom and a sulfur atom, in the ring, the heterocyclic group linking to $A^2$ on a nitrogen atom, include divalent groups derived from monocyclic or bicyclic $C_2$-$C_9$ heterocyclic compounds having 1 or 2 atoms selected from the group consisting of an oxygen atom, a nitrogen atom and a sulfur atom, in the ring, such as pyrrolidine, piperidine, morpholine, thiomorpholine, homopiperidine, homopiperazine, 1,2,3,6-tetrahydropyridine or piperazine. More preferred examples of the monocyclic $C_2$-$C_9$ heterocyclic compounds having 1 or 2 atoms selected from the group consisting of an oxygen atom, a nitrogen atom and a sulfur atom, in the ring, include piperidine, homopiperidine, morpholine, homopiperazine and piperazine.

Exemplary substituent of the heterocyclic group having 1 to 4 atoms selected from the group consisting of an oxygen atom, a nitrogen atom and a sulfur atom on its substituted ring of $G^1$, include a fluorine atom, a chlorine atom, a bromine atom, an iodine atom, a hydroxy group, an optionally substituted $C_1$-$C_7$ alkoxy group, a $C_6$-$C_{10}$ aryloxy group, a $C_7$-$C_9$ aralkoxy group, a $C_2$-$C_7$ acyloxy group, an oxo group, a $C_1$-$C_6$ alkylsulfonyloxy group, an optionally substituted $C_2$-$C_7$ acyl group, a carboxyl group, a $C_2$-$C_7$ alkoxycarbonyl group, a carbamoyl group, an optionally substituted $C_2$-$C_7$ alkylcarbamoyl group, an amino group, an optionally substituted $C_1$-$C_6$ alkylamino group, an optionally substituted $C_2$-$C_7$ acylamino group, a $C_2$-$C_8$ alkoxycarbonylamino group, a $C_1$-$C_6$ alkylsulfonylamino group, a cyano group, a nitro group, a $C_1$-$C_6$ alkylthio group, a $C_1$-$C_6$ alkylsulfynyl group, a $C_1$-$C_6$ alkylsulfonyl group, a sulfamoyl group, a $C_1$-$C_6$ alkylaminosulfonyl group, a sulfo group, an optionally substituted alicyclic hydrocarbon group having 3 to 6 carbon atoms, and an optionally substituted aliphatic hydrocarbon group having 1 to 6 carbon atoms.

Specific examples of the substituent of the heterocyclic group having 1 to 4 atoms selected from the group consisting of an oxygen atom, a nitrogen atom and a sulfur atom on its substituted ring of $G^1$ include the same as those exemplified in the substituted alicyclic hydrocarbon group having 3 to 10 carbon atoms of $G^1$.

As the substituent of the heterocyclic group having 1 to 4 atoms selected from the group consisting of an oxygen atom, a nitrogen atom and a sulfur atom on its substituted ring of $G^1$, a $C_1$-$C_7$ alkoxy group, a $C_2$-$C_7$ acyl group, a $C_2$-$C_7$ alkylcarbamoyl group, a $C_1$-$C_6$ alkylamino group, a $C_2$-$C_7$ acylamino group, an alicyclic hydrocarbon group having 3 to 6 carbon atoms and aliphatic hydrocarbon group having 1 to 6 carbon atoms may further be substituted with (one or more substituents selected from the group consisting of a fluorine atom; a chlorine atom; a bromine atom; an iodine atom; a hydroxy group; a $C_1$-$C_6$ alkoxy group such as methoxy, ethoxy, propoxy, isopropoxy, butoxy, isobutoxy, s-butoxy, t-butoxy, pentyloxy or cyclopropyloxy; a methoxymethyloxy group; a 2-methoxyethoxy group; a formyl group; a trifluoroacetyl group; a $C_2$-$C_7$ acyl group such as acetyl, propionyl, butyryl, isobutyryl, valeryl or isovaleryl; an oxo group; a carboxyl group; a $C_2$-$C_7$ alkoxycarbonyl group such as methoxycarbonyl, ethoxycarbonyl, propoxycarbonyl, isopropoxycarbonyl, butoxycarbonyl, isobutoxycarbonyl or t-butoxycarbonyl; a carbamoyl group; a $C_2$-$C_7$ alkylcarbamoyl group such as N-methylcarbamoyl, N,N-dimethylcarbamoyl, N-ethylcarbamoyl, N-ethyl-N-methylcarbamoyl, N,N-diethylcarbamoyl, N-propylcarbamoyl, N-isopropyl-carbamoyl, N-butylcarbamoyl, N-cyclopropylcarbamoyl or N-cyclopropylmethylcarbamoyl; an amino group; a $C_1$-$C_6$ alkylamino group such as methylamino, ethylamino, propylamino, isopropylamino, dimethylamino, N-ethylmethylamino, diethylamino, N-methylpropylamino, N-methylisopropylamino, cyclopropylamino or cyclopropylmethylamino; a $C_4$-$C_6$ cyclic amino group having 1 or 2 atoms selected from the group consisting of an oxygen atom, a nitrogen atom and a sulfur atom, in the ring, such as 1-pyrrolidinyl, piperazinyl, 4-methylpiperazinyl, piperidino or morpholino; a trifluoroacetylamino group; a $C_1$-$C_7$ acylamino group such as formylamino, acetylamino, propionylamino, butyrylamino, isobutyrylamino or valerylamino; a $C_1$-$C_6$ alkylsulfonylamino group such as methylsulfonylamino, ethylsulfonylamino, propylsulfonylamino or butylsulfonylamino; a nitro group; and a cyano group).

Preferred examples of the substituent of the heterocyclic group having 1 to 4 atoms selected from the group consisting of an oxygen atom, a nitrogen atom and a sulfur atom on its substituted ring of $G^1$, include a fluorine atom; a chlorine atom; a bromine atom; a $C_1$-$C_6$ alkoxy group consisting of a straight or branched alkyl and oxy group, including methoxy, ethoxy, propoxy, isopropoxy, butoxy, isobutoxy, s-butoxy, t-butoxy, pentyloxy, isopentyloxy, neopentyloxy, t-pentyloxy and hexyloxy; a cyano group; a nitro group; a carboxyl group; a hydroxy group; an amino group; a $C_1$-$C_6$ mono or dialkylamino group consisting of a straight or branched alkyl and amino group, including methylamino, ethylamino, propylamino, isopropylamino, butylamino, isobutylamino, s-butylamino, t-butylamino, pentylamino, hexylamino, dimethylamino, N-ethylmethylamino, diethylamino, N-methylpropylamino, N-methylisopropylamino, N-methylbutylamino, N-methyl-t-butylamino, N-ethylisopropylamino, dipropylamino, diisopropylamino and ethylbutylamino; a carbamoyl group; an aminosulfonyl group; an alicyclic hydrocarbon group having 3 to 6 carbon atoms, including cyclopropyl, cyclobutyl, cyclopentyl and cyclohexyl; a $C_2$-$C_7$ acyl group including acetyl, propionyl butyryl, isobutyryl, pivaroyl and hexanoyl; a $C_1$-$C_6$ alkylthio group including methylthio, ethylthio, propylthio, isopropylthio, butylthio, isobutylthio, s-butylthio, t-butylthio, pentylthio and hexylthio; a $C_1$-$C_6$ alkylsulfonyl group, including methylsulfonyl, ethylsulfonyl, propylsulfonyl, isopropylsulfonyl, butylsulfonyl, isobutylsulfonyl, s-butylsulfonyl, t-butylsulfonyl, pentylsulfonyl and hexylsulfonyl; a $C_2$-$C_7$ alkoxycarbonyl group including acetoxy, propionyloxy, butyryloxy, isobutyryloxy, valeryloxy, isovaleryloxy, pivaloyloxy and hexanoyloxy; a $C_2$-$C_7$ acylamino group including acetylamino, propionylamino, butyrylamino, isobutyrylamino, valerylamino and hexanoylamino; trifluoromethyl, trifluoromethoxy, and an aliphatic hydrocarbon group having 1 to 6 carbon atoms which may contain a straight or branched unsaturated bond, including methyl, ethyl, vinyl, ethynyl, propyl, 1-propenyl, 2-propenyl, isopropyl, isopropenyl, 1-propynyl, 2-propynyl, butyl, isobutyl, s-butyl, t-butyl, 1-butenyl, 2-butenyl, 3-butenyl, 1-methyl-1-propenyl, 2-methyl-1-propenyl, 1-methyl-2-propenyl, 2-methyl-2-propenyl, 1-butynyl, 2-butynyl, pentyl, isopentyl, neopentyl, t-pentyl, 1-pentenyl, 2-pentenyl, 3-pentenyl, 4-pentenyl, hexyl, 5-hexenyl, 4-methyl-3-pentenyl, isohexyl, 2-methylpentyl and 1-ethylbutyl.

Specifically, more preferred examples of the substituent of the heterocyclic group having 1 to 4 atoms selected from the group consisting of an oxygen atom, a nitrogen atom and a sulfur atom on its substituted ring of $G^1$, include a fluorine atom, a chlorine atom, a bromine atom, $C_1$-$C_6$ alkoxy group, cyano group, a nitro group, a carboxyl group, a hydroxy group, an amino group, a $C_1$-$C_6$ mono or dialkylamino group, a carbamoyl group, an alicyclic hydrocarbon group having 3 to 6 carbon atoms, a $C_2$-$C_7$ acyl group, a $C_1$-$C_6$ alkylsulfonyl group, a $C_2$-$C_7$ alkoxycarboxyl group, a trifluoromethyl group, a trifluoromethoxy group, and a $C_1$-$C_6$ alkyl group including methyl, ethyl, propyl, isopropyl, butyl, isobutyl, s-butyl, t-butyl, pentyl, isopentyl, neopentyl, t-pentyl, hexyl, isohexyl, 2-methylpentyl and 1-ethylbutyl. Examples of particularly preferred substituents include a fluorine atom, a chlorine atom, a $C_1$-$C_6$ alkoxy group, a cyano group, a nitro group, a carboxyl group, a hydroxy group, an amino group, a $C_1$-$C_6$ mono or dialkylamino group, an alicyclic hydrocarbon group having 3 to 6 carbon atoms, a $C_2$-$C_7$ acyl group, a trifluoromethyl group, a trifluoromethoxy group and a $C_1$-$C_6$ alkyl group.

In the present invention, $G^1$ in the formula (I) is preferably a single bond, a monocyclic aliphatic hydrocarbon group having 3 to 6 carbon atoms, a phenylene group, a monocyclic or bicyclic aromatic hydrocarbon group having 3 to 9 carbon atoms having 1 or 2 atoms selected from among a group consisting of an oxygen atom, a nitrogen atom, and a sulfur atom, in the ring, or a monocyclic heterocyclic group having 2 to 9 carbon atoms having 1 or 2 atoms selected from among a group consisting of an oxygen atom, a nitrogen atom, and a sulfur atom, in the ring.

In the formula (I), $G^2$ represents a hydrogen atom, a substituted or unsubstituted acyclic aliphatic hydrocarbon group having 1 to 10 carbon atoms, a substituted or unsubstituted alicyclic hydrocarbon group having 3 to 10 carbon atoms, a substituted or unsubstituted aromatic hydrocarbon group having 6 to 14 carbon atoms, or a substituted or unsubstituted heterocyclic group having 1 to 4 atoms selected from among a group consisting of an oxygen atom, a nitrogen atom, and a sulfur atom, in the ring.

In formula (I), when $G^2$ represents a substituted or unsubstituted acyclic aliphatic hydrocarbon group having 1 to 10 carbon atoms, examples of such a acyclic aliphatic hydrocarbon group having 1 to 10 carbon atoms of $G^2$ include an alkyl group such as methyl, ethyl, propyl, isopropyl, butyl, isobutyl, s-butyl, t-butyl, pentyl, isopentyl, neopentyl, t-pentyl, 2-methylpentyl, 4-methylpentyl, 1-ethylbutyl, hexyl, heptyl, 2-methylhexyl, 5-methylhexyl, 1,1-dimethylpentyl, 6-methylheptyl, octyl, nonyl or decyl, an alkenyl group such as vinyl, 1-methylvinyl, 1-ethylvinyl, 1-propenyl, 2-propenyl, 2-methyl-1-propenyl, 1-butenyl, 2-butenyl, 2-methyl-1-butenyl, 1,3-butadienyl, 1-pentenyl, 2-pentenyl, 4-methyl-1-pentenyl, 1-hexenyl, 2-hexenyl, 3-hexenyl, 4-hexenyl, 5-hexenyl, 1,5-hexadienyl, 2-heptenyl, 2-octenyl, 2-nonenyl or 2-decenyl, or an alkynyl group such as ethynyl, 1-propynyl, 2-propynyl, 1-butynyl, 3-methyl-1-butynyl, 3,3-dimethyl-1-butynyl, 1-pentynyl, 2-pentynyl, 3-pentynyl, 1-hexynyl, 2-hexynyl, 3-hexynyl, 4-hexynyl, 1-methyl-3-pentynyl, 1-methyl-3-hexynyl, 2-heptynyl, 2-octynyl, 2-nonynyl or 2-decynyl.

Specifically, more preferred examples of such aliphatic hydrocarbon group having 1 to 10 carbon atoms include a straight or branched $C_1$-$C_6$ alkyl group which may contain a unsaturated bond such as methyl, ethyl, propyl, isopropyl, butyl, pentyl, hexyl, vinyl, 1-prophenyl, 1-butenyl, ethynyl or 1-propynyl. Particularly preferred examples of such a acyclic aliphatic hydrocarbon group having 1 to 10 carbon atoms include a straight or branched $C_1$-$C_6$ alkyl group such as methyl, ethyl, propyl, isopropyl, butyl or hexyl.

Exemplary substituents of the substituted acyclic aliphatic hydrocarbon group having 1 to 10 carbon atoms of $G^2$ include: a fluorine atom; a chlorine atom; a bromine atom; an iodine atom; a hydroxy group; a $C_1$-$C_7$ alkoxy group consisting of a straight or branched alkyl group, cycloalkyl group and oxy group, including methoxy, ethoxy, propoxy, isopropoxy, butoxy, isobutoxy, s-butoxy, t-butoxy, pentyloxy, isopentyloxy, neopentyloxy, t-pentyloxy, hexyloxy, isohexyloxy, 2-methylpentyloxy, 1-ethylbutoxy, cyclopropyloxy, cyclobutyloxy, cyclopentyloxy, cyclohexyloxy, cyclopropylmethyloxy, cyclopropylethyloxy, cyclopentyl methyloxy and cyclohexylmethyloxy; an alkyldioxy group having 1 to 4 carbon atoms such as ethylene dioxy; a $C_6$-$C_{10}$ aryloxy group, including phenoxy, 1-naphthoxy and 2-naphthoxy; a $C_7$-$C_9$ aralkoxy group, including benzyloxy, α-phenethyloxy, β-phenethyloxy and phenylpropyloxy; a $C_2$-$C_7$ acyloxy group including acetoxy, propionyloxy, butyryloxy, isobutyryloxy, valeryloxy, isovaleryloxy, pivaloyloxy and hexanoyloxy; an oxo group; a $C_1$-$C_6$ alkylsulfonyloxy group consisting of a straight or branched alkyl and sulfonyloxy, including oxo, methylsulfonyloxy, ethylsulfonyloxy, propylsulfonyloxy, butylsulfonyloxy and t-butylsulfonyloxy; a $C_2$-$C_7$ acyl group, including acetyl, propionyl, butyryl, isobutyryl, valeryl, isovaleryl, pivaroyl and hexanoyl; a carboxyl group; a $C_2$-$C_7$ alkoxycarbonyl group consisting of a straight or branched alkyl and oxycarbonyl group, including methoxycarbonyl, ethoxycarbonyl, propoxycarbonyl, isopropoxycarbonyl, butoxycarbonyl, isobutoxycarbonyl, s-butoxycarbonyl and t-butoxycarbonyl; a carbamoyl group; a $C_2$-$C_7$ alkylcarbamoyl group consisting of a straight or branched alkyl, cycloalkyl and carbamoyl group, including N-methylcarbamoyl, N-ethylcarbamoyl, N-propylcarbamoyl, N-isopropylcarbamoyl, N-butylcarbamoyl, N-isobutylcarbamoyl, N-s-butylcarbamoyl, N-t-butylcarbamoyl, N-pentylcarbamoyl, N-cyclopropylcarbamoyl, N-cyclobutylcarbamoyl, N-cyclopentylcarbamoyl, N-cyclohexylcarbamoyl, N-cycloheptylcarbamoyl, N-cyclopropylmethylcarbamoyl, N,N-dimethylcarbamoyl, N-ethyl-N-methylcarbamoyl, N,N-diethylcarbamoyl and N,N-dipropylcarbamoyl; an amino group; a $C_1$-$C_6$ alkylamino group consisting of a straight or branched alkyl, cycloalkyl and amino group, including methylamino, ethylamino, propylamino, isopropylamino, butylamino, isobutylamino, s-butylamino, t-butylamino, pentylamino, hexylamino, cyclopropylamino, cyclobutylamino, cyclopentylamino, cyclohexylamino, cyclopropylmethylamino, dimethylamino, N-ethylmethylamino, diethylamino, N-methylpropylamino, N-methylisopropylamino, N-methylbutylamino, N-methyl-t-butylamino, N-methylisopropylamino, dipropylamino, diisopropylamino and ethylbutylamino; a $C_2$-$C_7$ acylamino group including acetylamino, propionylamino, butyrylamino, isobutyrylamino, valerylamino and hexanoylamino; a $C_2$-$C_8$ alkoxycarbonylamino group, including methoxycarbonylamino, ethoxycarbonylamino and t-butoxy-carbonylamino; a $C_1$-$C_6$ alkylsulfonylamino group including methylsulfonylamino, ethylsulfonylamino, butylsulfonylamino and t-butylsulfonylamino; a cyano group; a nitro group; a $C_1$-$C_6$ alkylthio group including methylthio, ethylthio, propylthio, isopropylthio, butylthio, isobutylthio, s-butylthio, t-butylthio, pentylthio and hexylthio; a $C_1$-$C_6$ alkylsulfynyl group consisting of a straight or branched alkyl, cycloalkyl and sulfynyl group, including methylsulfynyl, ethylsulfynyl, propylsulfynyl, isopropylsulfynyl, butylsulfynyl, isobutylsulfynyl, s-butylsulfynyl, t-butylsulfynyl, pentylsulfynyl and cyclopentylsulfynyl; a $C_1$-$C_6$ alkylsulfonyl group consisting of a straight or branched alkyl, cycloalkyl and sulfonyl group, including methylsulfonyl, ethylsulfonyl, propylsulfonyl, isopropylsulfonyl, butylsulfonyl, isobutylsulfonyl, s-butylsulfonyl, t-butylsulfonyl, pentylsulfonyl, hexylsulfonyl, cyclopentylsulfonyl and cyclohexylsulfonyl; a sulfo group; a sulfamoyl group; a $C_1$-$C_6$ aminosulfonyl group consisting of a straight or branched alkyl, cycloalkyl and aminosulfonyl group, including methylaminosulfonyl, ethylaminosulfonyl, propylaminosulfonyl, isopropylaminosulfonyl, butylaminosulfonyl, isobutyl-aminosulfonyl, s-butylaminosulfonyl, pentylaminosulfonyl, dimethylaminosulfonyl, N-ethyl-N-methylaminosulfonyl, diethylaminosulfonyl, dipropylaminosulfonyl, cyclopropylaminosulfonyl, cyclopentylaminosulfonyl, cyclohexylaminosulfonyl and cyclopropylmethylaminosulfonyl; an alicyclic hydrocarbon group having 3 to 6 carbon atoms, including cyclopropyl, cyclobutyl, cyclopentyl and cyclohexyl; and an aliphatic hydrocarbon group having 1 to 6 carbon atoms which may contain a straight or branched unsaturated bond, including methyl, ethyl, vinyl, ethynyl, propyl, 1-propenyl, 2-propenyl, isopropyl, isopropenyl, 1-propynyl, 2-propynyl, butyl, isobutyl, s-butyl, t-butyl, 1-butenyl, 2-butenyl, 3-butenyl, 1-methyl-1-propenyl, 2-methyl-1-propenyl, 1-methyl-2-propenyl, 2-methyl-2-propenyl, 1-butynyl, 2-butynyl, pentyl, isopentyl, neopentyl, t-pentyl, 1-pentenyl, 2-pentenyl, 3-pentenyl, 4-pentenyl, hexyl, 5-hexenyl, 4-methyl-3-pentenyl, isohexyl, 2-methylpentyl and 1-ethylbutyl; an aromatic hydrocarbon group having 6 to 14 carbon atoms which is a monovalent group derived from monocyclic, bicyclic or tricyclic aromatic hydrocarbon group, including benzene, naphthalene, indene, indane, 1,2,3,4-tetrahydronaphthalene, and fluorene; and a monovalent group derived from monocyclic, bicyclic or tricyclic heterocyclic compound, including furan, thiophene, pyrrole, pyrroline, pyrrolidine, oxazole, oxazolidine, isooxazole, isooxazolidine, thiazole, thiazolidine, isothiazole, isothiazolidine, imidazole, imidazoline, imidazolidine, pyrazole, pyrazoline, pyrazolidine, triazole, thiadiazole, oxadiazole, tetrazole, pyran, tetrahydropyran, thiopyran, tetrahydrothiopyran, pyridine, pyrazine, pyrimidine, pyridazine, benzofuran, dibenzofuran, benzothiophene, indole, benzimidazole, benzothiazole, benzooxazole, chroman, isochroman, quinoline, decahydroquinoline, isoquinoline, quinazolin, quinoxaline, purine, pteridine, azetidine, morpholine, thiomorpholine, piperidine, homopiperidine, piperazine, homopiperazine, indoline, isoindoline, phenoxazine, phenazine, phenothiazine and quinuclidine, the heterocyclic compound (having 1 to 4 atoms selected from the group consisting of an oxygen atom, a nitrogen atom and a sulfur atom, in the ring).

Preferred examples of the substituent of the substituted acyclic aliphatic hydrocarbon group having 1 to 10 carbon atoms as $G^2$ include a fluorine atom, a hydroxy group, an optionally substituted $C_1$-$C_7$ alkoxy group, an oxo group, an optionally substituted $C_2$-$C_7$ acyl group, a carboxyl group, a $C_2$-$C_7$ alkoxycarbonyl group, a carbamoyl group, an optionally substituted $C_2$-$C_7$ alkylcarbamoyl group, an amino group, an optionally substituted $C_1$-$C_6$ alkylamino group, an optionally substituted $C_2$-$C_7$ acylamino group, a $C_1$-$C_6$ alkylsulfonylamino group, a cyano group, a $C_1$-$C_6$ alkylsulfonyl group, a sulfamoyl group, an optionally substituted aromatic hydrocarbon group having 6 to 14 carbon atoms and an optionally substituted heterocyclic group (having 1 to 4 atoms selected from the group consisting of an oxygen atom, a nitrogen atom and a sulfur atom, in the ring).

More preferred exemplary substituents of the substituted acyclic aliphatic hydrocarbon group having 1 to 10 carbon atoms as $G^2$ include a fluorine atom, a hydroxy group, an optionally substituted $C_1$-$C_7$ alkoxy group, a carboxyl group, an amino group, an optionally substituted $C_1$-$C_6$ alkylamino group, a cyano group, a benzyl group, and an optionally substituted heterocyclic group (having 1 to 4 atoms selected from the group consisting of an oxygen atom, a nitrogen atom and a sulfur atom, in the ring).

As the substituent of the substituted acyclic aliphatic hydrocarbon group having 1 to 10 carbon atoms as $G^2$, the heterocyclic group (having 1 to 4 atoms selected from the group consisting of an oxygen atom, a nitrogen atom and a sulfur atom, in the ring), links to the aliphatic hydrocarbon group having 1 to 10 carbon atoms as $G^2$ on a carbon atom or a nitrogen atom.

Preferred examples of the heterocyclic group (having 1 to 4 atoms selected from the group consisting of an oxygen atom, a nitrogen atom and a sulfur atom, in the ring), links to the aliphatic hydrocarbon group having 1 to 10 carbon atoms as $G^2$ on a carbon atom, include a monovalent group derived from a monocyclic or bicyclic $C_3$-$C_9$ aromatic heterocyclic compound, including furan, pyrrole, thiophene, pyrazole, oxazole, thiazole, isooxazole, isothiazole, pyrazole, imidazole, pyridine, pyrimidine, pyrazine, pyridazine, benzothiophene, benzofuran, 1,2-methylenedioxybenzene, benzimidazole, indole, quinoline, isoquinoline and quinazolin, the monovalent group having 1 or 2 atoms selected from the group consisting of an oxygen atom, a nitrogen atom and a sulfur atom, in the ring.

Meanwhile, preferred examples of the heterocyclic group (having 1 to 4 atoms selected from the group consisting of an oxygen atom, a nitrogen atom and a sulfur atom, in the ring), links to the acyclic aliphatic hydrocarbon group having 1 to 10 carbon atoms as $G^2$ on a nitrogen atom, include a monovalent group derived from a monocyclic $C_2$-$C_9$ heterocyclic compound, including pyrrolidine, piperidine, morpholine, thiomorpholine, homopiperidine, homopiperazine, 1,2,3,6-tetrahydropyridine and piperazine, the monovalent group having 1 or 2 atoms selected from the group consisting of an oxygen atom, a nitrogen atom and a sulfur atom, in the ring.

As the substituent of the substituted acyclic aliphatic hydrocarbon group having 1 to 10 carbon atoms as $G^2$, a $C_1$-$C_7$ alkoxy group, a $C_2$-$C_7$ acyl group, $C_2$-$C_7$ alkylcarbamoyl, a $C_1$-$C_6$ alkylamino group, a $C_2$-$C_7$ acylamino group, an alicyclic hydrocarbon group having 3 to 6 carbon atoms, an aliphatic hydrocarbon group having 1 to 6 carbon atoms, aromatic hydrocarbon group having 6 to 14 carbon atoms, and heterocyclic group having 1 to 4 atoms selected from the group consisting of an oxygen atom, a nitrogen atom and a sulfur atom, in the ring, may further be substituted with (one or more substituents selected from the group consisting of: a fluorine atom; a chlorine atom; a bromine atom; an iodine atom; a hydroxy group; a $C_1$-$C_6$ alkoxy group such as methoxy, ethoxy, propoxy, isopropoxy, butoxy, isobutoxy, s-butoxy, t-butoxy, pentyloxy or cyclopropyloxy; a methoxymethyloxy group; a 2-methoxyethoxy group; a formyl group; a trifluoroacetyl group; a $C_2$-$C_7$ acyl group such as acetyl, propionyl, butyryl, isobutyryl, valeryl or isovaleryl; an oxo group; a carboxyl group; a $C_2$-$C_7$ alkoxycarbonyl group such as methoxycarbonyl, ethoxycarbonyl, propoxycarbonyl, isopropoxycarbonyl, butoxycarbonyl, isobutoxycarbonyl or t-butoxycarbonyl; a carbamoyl group; a $C_2$-$C_7$ alkylcarbamoyl group such as N-methylcarbamoyl, N,N-dimethylcarbamoyl, N-ethylcarbamoyl, N-ethyl-N-methylcarbamoyl, N,N-diethylcarbamoyl, N-propylcarbamoyl, N-isopropylcarbamoyl, N-butylcarbamoyl, N-cyclopropyl-carbamoyl or N-cyclopropylmethylcarbamoyl; an amino group; a $C_1$-$C_6$ alkylamino group such as methylamino, ethylamino, propylamino, isopropylamino, dimethylamino, N-ethylmethylamino, diethylamino, N-methylpropylamino, N-methylisopropylamino, cyclopropylamino or cyclopropylmethylamino; a $C_4$-$C_6$ cyclic amino group having 1 or 2 atoms selected from the group consisting of an oxygen atom, a nitrogen atom and a sulfur atom, in the ring, such as 1-pyrrolidinyl, piperazinyl, 4-methylpiperazinyl, piperidino or morpholino; a trifluoroacetylamino group; a $C_1$-$C_7$ acylamino group such as formylamino, acetylamino, propionylamino, butyrylamino, isobutyrylamino or valerylamino; a $C_1$-$C_6$ alkylsulfonylamino group such as methylsulfonylamino, ethylsulfonylamino, propylsulfonylamino or butylsulfonylamino; a nitro group; a cyano group; a $C_1$-$C_6$ alkyl group including methyl, ethyl, propyl, isopropyl, butyl, isobutyl, s-butyl, and t-butyl; a trifluoromethyl group; and a trifluoromethoxy group).

In the formula (I), when $G^2$ represents a substituted or unsubstituted alicyclic hydrocarbon group having 3 to 10 carbon atoms, examples of the alicyclic hydrocarbon group having 3 to 10 carbon atoms of $G^2$ include cyclopropyl, cyclobutyl, cyclopentyl, cyclopentenyl, cyclohexyl, cyclohexenyl, cycloheptyl, cycloheptenyl, and cyclooctyl group. Preferred examples of the alicyclic hydrocarbon group having 3 to 10 carbon atoms of $G^2$ include cyclopropyl, cyclobutyl, cyclopentyl, cyclohexyl, 3-cyclopentenyl, 4-cyclopentenyl, 1-cyclohexenyl, 3-cyclohexenyl, 4-cyclohexenyl, and 1-cycloheptenyl.

Exemplary substituents of the substituted alicyclic hydrocarbon group having 3 to 10 carbon atoms of $G^2$ include a fluorine atom, a chlorine atom, a bromine atom, an iodine atom, a hydroxy group, an optionally substituted $C_1$-$C_7$ alkoxy group, $C_1$-$C_4$ alkylenedioxy group, a $C_6$-$C_{10}$ aryloxy group, a $C_7$-$C_9$ aralkoxy group, a $C_2$-$C_7$ acyloxy group, an oxo group, a $C_1$-$C_6$ alkylsulfonyloxy group, an optionally substituted $C_2$-$C_7$ acyl group, a carboxyl group, a $C_2$-$C_7$ alkoxycarbonyl group, a carbamoyl group, an optionally substituted $C_2$-$C_7$ alkylcarbamoyl group, an amino group, an optionally substituted $C_1$-$C_6$ alkylamino group, an optionally substituted $C_2$-$C_7$ acylamino group, a $C_2$-$C_8$ alkoxycarbonylamino group, a $C_1$-$C_6$ alkylsulfonylamino group, a cyano group, a nitro group, a $C_1$-$C_6$ alkylthio group, a $C_1$-$C_6$ alkylsulfynyl group, a $C_1$-$C_6$ alkylsulfonyl group, a sulfamoyl group, a $C_1$-$C_6$ alkylaminosulfonyl group, a sulfo group, an optionally substituted alicyclic hydrocarbon group having 3 to 6 carbon atoms, and an optionally substituted aliphatic hydrocarbon group having 1 to 6 carbon atoms, an optionally substituted aromatic hydrocarbon group having 6 to 14 carbon atoms.

Specific examples of the substituent of the substituted alicyclic hydrocarbon group having 3 to 10 carbon atoms of $G^2$ include the same as those exemplified in the substituted aliphatic hydrocarbon group having 1 to 10 carbon atoms of $G^2$.

As the substituent of the substituted alicyclic hydrocarbon group having 3 to 10 carbon atoms of $G^2$, a $C_1$-$C_7$ alkoxy group, a $C_2$-$C_7$ acyl group, a $C_2$-$C_7$ alkylcarbamoyl group, a $C_1$-$C_6$ alkylamino group, a $C_2$-$C_7$ acylamino group, an alicyclic hydrocarbon group having 3 to 6 carbon atoms, an aliphatic hydrocarbon group having 1 to 6 carbon atoms, and an aromatic hydrocarbon group having 6 to 14 carbon atoms, may further be substituted with (one or more substituents selected from the group consisting of: a fluorine atom; a chlorine atom; a bromine atom; an iodine atom; a hydroxy group; a $C_1$-$C_6$ alkoxy group such as methoxy, ethoxy, propoxy, isopropoxy, butoxy, isobutoxy, s-butoxy, t-butoxy, pentyloxy or cyclopropyloxy; a methoxymethyloxy group; a 2-methoxyethoxy group; a formyl group; a trifluoroacetyl group; a $C_2$-$C_7$ acyl group such as acetyl, propionyl, butyryl, isobutyryl, valeryl or isovaleryl; an oxo group; a carboxyl group; a $C_2$-$C_7$ alkoxycarbonyl group such as methoxycarbonyl, ethoxycarbonyl, propoxycarbonyl, isopropoxycarbonyl, butoxycarbonyl, isobutoxycarbonyl or t-butoxycarbonyl; a carbamoyl group; a $C_2$-$C_7$ alkylcarbamoyl group such as N-methylcarbamoyl, N,N-dimethylcarbamoyl, N-ethylcarbamoyl, N-ethyl-N-methylcarbamoyl, N,N-diethyl-carbamoyl, N-propylcarbamoyl, N-isopropylcarbamoyl, N-butylcarbamoyl, N-cyclopropylcarbamoyl or N-cyclopropylmethylcarbamoyl; an amino group; a $C_1$-$C_6$ alkylamino group such as methylamino, ethylamino, propylamino, isopropylamino, dimethylamino, N-ethylmethylamino, diethylamino, N-methylpropylamino, N-methylisopropylamino, cyclopropylamino or cyclopropylmethylamino; a $C_4$-$C_6$ cyclic amino group having 1 or 2 atoms selected from the group consisting of an oxygen atom, a nitrogen atom and a sulfur atom, in the ring, such as 1-pyrrolidinyl, piperazinyl, 4-methylpiperazinyl, piperidino or morpholino; a trifluoroacetylamino group; a $C_1$-$C_7$ acylamino group such as formylamino, acetylamino, propionylamino, butyrylamino, isobutyrylamino or valerylamino, a $C_1$-$C_6$ alkylsulfonylamino group such as methylsulfonylamino, ethylsulfonylamino, propylsulfonylamino or butylsulfonylamino; a nitro group; a cyano group; a $C_1$-$C_6$ alkyl group including methyl, ethyl, propyl, isopropyl, butyl, isobutyl, s-butyl, and t-butyl; a trifluoromethyl group; and a trifluoromethoxy group).

In the formula (I), when $G^2$ represents a substituted or unsubstituted aromatic hydrocarbon group having 6 to 14 carbon atoms, examples of the aromatic hydrocarbon group having 6 to 14 carbon atoms include a monovalent group having at least one aromatic ring on its molecule, such as benzene, indene, indane, naphthalene, 1,2-dihydronaphthalene, 1,2,3,4-tetrahydronaphthalene, azulene, acenaphthylene, acenaphthene, fluorene, phenanthrene or anthracene. Examples of such preferred aromatic hydrocarbon group having 6 to 14 carbon atoms of $G^2$ include a phenyl group.

Exemplary substituents of the aromatic hydrocarbon group having 6 to 14 carbon atoms of $G^2$ include at least one substituent selected from the group consisting of a fluorine atom, a chlorine atom, a bromine atom, an iodine atom, a hydroxy group, an optionally substituted $C_1$-$C_7$ alkoxy group, a $C_1$-$C_4$ alkylenedioxy group, a $C_6$-$C_{10}$ aryloxy group, a $C_7$-$C_9$ aralkoxy group, a $C_2$-$C_7$ acyloxy group, an oxo group, a $C_1$-$C_6$ alkylsulfonyloxy group, an optionally substituted $C_2$-$C_7$ acyl group, a carboxyl group, a $C_2$-$C_7$ alkoxycarbonyl group, a carbamoyl group, an optionally substituted $C_2$-$C_7$ alkylcarbamoyl group, an amino group, an optionally substituted $C_1$-$C_6$ alkylamino group, an optionally substituted $C_2$-$C_7$ acylamino group, a $C_2$-$C_8$ alkoxycarbonylamino group, a $C_1$-$C_6$ alkylsulfonylamino group, a cyano group, a nitro group, a $C_1$-$C_6$ alkylthio group, a $C_1$-$C_6$ alkylsulfynyl group, a $C_1$-$C_6$ alkylsulfonyl group, a sulfamoyl group, a $C_1$-$C_6$ alkylaminosulfonyl group, a sulfo group, an optionally substituted alicyclic hydrocarbon group having 3 to 6 carbon atoms, an optionally substituted aliphatic hydrocarbon group having 1 to 6 carbon atoms, and an optionally substituted aromatic hydrocarbon group having 6 to 14 carbon atoms.

Specific examples of the substituent of the substituted $C_6$-$C_{14}$ aromatic hydrocarbon group of $G^2$ include the same as those exemplified in the substituent of the substituted aliphatic hydrocarbon group having 1 to 10 carbon atoms of $G^2$.

As the substituents of the aromatic hydrocarbon group having 6 to 14 carbon atoms of $G^2$, a $C_1$-$C_7$ alkoxy group, a $C_2$-$C_7$ acyl group, a $C_2$-$C_7$ alkylcarbamoyl group, a $C_1$-$C_6$ alkylamino group, a $C_2$-$C_7$ acylamino group, an alicyclic hydrocarbon group having 3 to 6 carbon atoms, an aliphatic hydrocarbon group having 1 to 6 carbon atoms, and an aromatic hydrocarbon group having 6 to 14 carbon atoms, may further be substituted with (one or more substituents selected from the group consisting of: a fluorine atom; a chlorine atom; a bromine atom; an iodine atom; a hydroxy group; a $C_1$-$C_6$ alkoxy group such as methoxy, ethoxy, propoxy, isopropoxy, butoxy, isobutoxy, s-butoxy, t-butoxy, pentyloxy or cyclopropyloxy; a methoxymethyloxy group; a 2-methoxyethoxy group; a formyl group; a trifluoroacetyl group; a $C_2$-$C_7$ acyl group such as acetyl, propionyl, butyryl, isobutyryl, valeryl or isovaleryl; an oxo group; a carboxyl group; a $C_2$-$C_7$ alkoxycarbonyl group such as methoxycarbonyl, ethoxycarbonyl, propoxycarbonyl, isopropoxycarbonyl, butoxycarbonyl, isobutoxycarbonyl or t-butoxycarbonyl; a carbamoyl group; a $C_2$-$C_7$ alkylcarbamoyl group such as N-methylcarbamoyl, N,N-dimethylcarbamoyl, N-ethylcarbamoyl, N-ethyl-N-methylcarbamoyl, N,N-diethyl-carbamoyl, N-propylcarbamoyl, N-isopropylcarbamoyl, N-butylcarbamoyl, N-cyclopropylcarbamoyl or N-cyclopropylmethylcarbamoyl; an amino group; a $C_1$-$C_6$ alkylamino group such as methylamino, ethylamino, propylamino, isopropylamino, dimethylamino, N-ethylmethylamino, diethylamino, N-methylpropylamino, N-methylisopropylamino, cyclopropylamino or cyclopropylmethylamino; a $C_4$-$C_6$ cyclic amino group having 1 or 2 atoms selected from the group consisting of an oxygen atom, a nitrogen atom and a sulfur atom, in the ring, such as 1-pyrrolidinyl, piperazinyl, 4-methylpiperazinyl, piperidino or morpholino; a trifluoroacetylamino group; a $C_1$-$C_7$ acylamino group such as formylamino, acetylamino, propionylamino, butyrylamino, isobutyrylamino or valerylamino; a $C_1$-$C_6$ alkylsulfonylamino group such as methylsulfonylamino, ethylsulfonylamino, propylsulfonylamino or butylsulfonylamino; a nitro group; a cyano group; a $C_1$-$C_6$ alkyl group including methyl, ethyl, propyl, isopropyl, butyl, isobutyl, s-butyl, and t-butyl; a trifluoromethyl group; and a trifluoromethoxy group).

In the formula (I), when $G^2$ represents a heterocyclic group having 1 to 4 atoms selected from the group consisting of an oxygen atom, a nitrogen atom and a sulfur atom on its substituted or unsubstituted ring, examples of such heterocyclic group include a monovalent group derived from monocyclic, bicyclic or tricyclic compounds, including furan, thiophene, pyrrole, pyrroline, pyrrolidine, oxazole, oxazolidine, isooxazole, isooxazolidine, thiazole, thiazolidine, isothiazole, isothiazolidine, imidazole, imidazoline, imidazolidine, pyrazole, pyrazoline, pyrazolidine, triazole, thiadiazole, oxadiazole, tetrazole, pyran, tetrahydropyran, thiopyran, tetrahydrothiopyran, pyridine, pyrazine, pyrimidine, pyridazine, benzofuran, dibenzofuran, benzothiophene, indole, 1,2-methylene-dioxybenzene, benzimidazole, benzothiazole, benzooxazole, chroman, isochroman, quinoline, decahydroquinoline, isoquinoline, quinazolin, quinoxaline, purine, pteridine, azetidine, morpholine, thiomorpholine, piperidine, homopiperidine, piperazine, homopiperazine, indoline, isoindoline, phenoxazine, phenazine, phenothiazine and quinuclidine.

Preferred examples of the heterocyclic group having 1 to 4 atoms selected from the group consisting of an oxygen atom, a nitrogen atom and a sulfur atom, in the ring of $G^2$ include 2-pyridyl, 3-pyridyl, 4-pyridyl, piperidino, 2-piperizyl, 3-piperizyl, 4-piperizyl, morpholino, 1-homopiperidinyl, 1-pyrrolidinyl, 2-thiazolyl, 4-thiazolyl, 5-thiazolyl, 2-oxazolyl, 4-oxazolyl, 5-oxazolyl, 1-imidazolyl, 2-imidazolyl, 4-imidazolyl, 5-imidazolyl, 3-pyrazolyl, 2-furyl, 3-furyl, 2-thienyl, 3-thienyl, 2-pyrrolyl, 3-pyrrolyl, 4-isooxazolyl, 2-pyrimidinyl, 4-pyrimidinyl, 2-pyrazinyl, 4-triazolyl, 5-tetrazolyl, 1-piperazinyl, 4-tetrahydropyranyl, 2-1,3,4-oxadiazolyl, 4-1,2,3-thiadiazolyl, 2-benzofuranyl, 2-benzothiazolyl, 2-indolyl, 3-indolyl, 5-benzoimidazolyl and 2-1,2,3,4-tetrahydroisoquinolinyl group.

The heterocyclic group having 1 to 4 atoms selected from the group consisting of an oxygen atom, a nitrogen atom and a sulfur atom, in the ring of $G^2$, links to $A^4$ on a carbon atom or a nitrogen atom.

More preferred examples of the heterocyclic group having 1 to 4 atoms selected from the group consisting of an oxygen atom, a nitrogen atom and a sulfur atom, in the ring of $G^2$, the heterocyclic group linking to $A^4$ on a carbon atom, include a monovalent group derived from a monocyclic or bicyclic $C_3$-$C_9$ aromatic heterocyclic compound having 1 or 2 atoms selected from the group consisting of an oxygen atom, a nitrogen atom and a sulfur atom, in the ring, such as furan, pyrrole, thiophene, pyrazole, oxazole, thiazole, isooxazole, isothiazole, pyrazole, imidazole, pyridine, pyrimidine, pyrazine, pyridazine, benzothiophene, benzofuran, 1,2-methylenedioxy-benzene, benzimidazole, indole, quinoline, isoquinoline or quinazolin.

Meanwhile, preferred examples of the heterocyclic group having 1 to 4 atoms selected from the group consisting of an oxygen atom, a nitrogen atom and a sulfur atom, in the ring of $G^2$, the heterocyclic group linking to $A^4$ on a nitrogen atom, include a monovalent group derived from a monocyclic $C_2$-$C_9$ heterocyclic compound having 1 or 2 atoms selected from the group consisting of an oxygen atom, a nitrogen atom and a sulfur atom, in the ring, such as pyrrolidine, piperidine, morpholine, thiomorpholine, homopiperidine, homopiperazine, 1,2,3,6-tetrahydropyridine or piperazine.

More preferred examples of the heterocyclic group as $G^2$ include a monovalent group derived from a monocyclic $C_4$-$C_6$ heterocyclic compound having 1 or 2 atoms selected from the group consisting of an oxygen atom, a nitrogen atom and a sulfur atom, in the ring, such as piperidine, homopiperidine, morpholine, homopiperazine, or piperazine.

Exemplary substituents of the heterocyclic group having 1 to 4 atoms selected from the group consisting of an oxygen atom, a nitrogen atom and a sulfur atom on its substituted ring of $G^2$ include at least one substituent selected from the group consisting of a fluorine atom, a chlorine atom, a bromine atom, an iodine atom, a hydroxy group, an optionally substituted $C_1$-$C_7$ alkoxy group, a $C_1$-$C_4$ alkylenedioxy group, a $C_6$-$C_{10}$ aryloxy group, a $C_7$-$C_9$ aralkoxy group, a $C_2$-$C_7$ acyloxy group, an oxo group, a $C_1$-$C_6$ alkylsulfonyloxy group, an optionally substituted $C_2$-$C_7$ acyl group, a carboxyl group, a $C_2$-$C_7$ alkoxycarbonyl group, a carbamoyl group, an optionally substituted $C_2$-$C_7$ alkylcarbamoyl group, an amino group, an optionally substituted $C_1$-$C_6$ alkylamino group, an optionally substituted $C_2$-$C_7$ acylamino group, a $C_2$-$C_8$ alkoxycarbonylamino group, a $C_1$-$C_6$ alkylsulfonylamino group, a cyano group, a nitro group, a $C_1$-$C_6$ alkylthio group, a $C_1$-$C_6$ alkylsulfynyl group, a $C_1$-$C_6$ alkylsulfonyl group, a sulfamoyl group, a $C_1$-$C_6$ alkylaminosulfonyl group, a sulfo group, an optionally substituted alicyclic hydrocarbon group having 3 to 6 carbon atoms, an optionally substituted aliphatic hydrocarbon group having 1 to 6 carbon atoms, and an optionally substituted aromatic hydrocarbon group having 6 to 14 carbon atoms and.

The substituents of the heterocyclic group having 1 to 4 atoms selected from the group consisting of an oxygen atom, a nitrogen atom and a sulfur atom, in the ring of $G^2$ are as defined above for the substituent of the substituted aliphatic hydrocarbon group having 1 to 10 carbon atoms of $G^2$.

As the substituent of the heterocyclic group having 1 to 4 atoms selected from the group consisting of an oxygen atom, a nitrogen atom and a sulfur atom on its substituted ring of $G^2$, a $C_1$-$C_7$ alkoxy group, a $C_2$-$C_7$ acyl group, a $C_2$-$C_7$ alkylcarbamoyl group, a $C_1$-$C_6$ alkylamino group, a $C_2$-$C_7$ acylamino group, an alicyclic hydrocarbon group having 3 to 6 carbon atoms, an aliphatic hydrocarbon group having 1 to 6 carbon atoms, and an aromatic hydrocarbon group having 6 to 14 carbon atoms, may further be substituted with (one or more substituents selected from the group consisting of: a fluorine atom; a chlorine atom; a bromine atom; an iodine atom; a hydroxy group; a $C_1$-$C_6$ alkoxy group such as methoxy, ethoxy, propoxy, isopropoxy, butoxy, isobutoxy, s-butoxy, t-butoxy, pentyloxy or cyclopropyloxy; a methoxymethyloxy group; a 2-methoxyethoxy group; a formyl group; a trifluoroacetyl group; a $C_2$-$C_7$ acyl group such as acetyl, propionyl, butyryl, isobutyryl, valeryl or isovaleryl; an oxo group; a carboxyl group; a $C_2$-$C_7$ alkoxycarbonyl group such as methoxycarbonyl, ethoxycarbonyl, propoxycarbonyl, isopropoxycarbonyl, butoxycarbonyl, isobutoxycarbonyl or t-butoxycarbonyl; a carbamoyl group; a $C_2$-$C_7$ alkylcarbamoyl group such as N-methylcarbamoyl, N,N-dimethylcarbamoyl, N-ethylcarbamoyl, N-ethyl-N-methylcarbamoyl, N,N-diethylcarbamoyl, N-propylcarbamoyl, N-isopropyl-carbamoyl, N-butylcarbamoyl, N-cyclopropylcarbamoyl or N-cyclopropylmethylcarbamoyl; an amino group; a $C_1$-$C_6$ alkylamino group such as methylamino, ethylamino, propylamino, isopropylamino, dimethylamino, N-ethylmethylamino, diethylamino, N-methylpropylamino, N-methylisopropylamino, cyclopropylamino or cyclopropylmethylamino; a $C_4$-$C_6$ cyclic amino group having 1 or 2 atoms selected from the group consisting of an oxygen atom, a nitrogen atom and a sulfur atom, in the ring, such as 1-pyrrolidinyl, piperazinyl, 4-methylpiperazinyl, piperidino or morpholino; a trifluoroacetylamino group; a $C_1$-$C_7$ acylamino group such as formylamino, acetylamino, propionylamino, butyrylamino, isobutyrylamino or valerylamino; a $C_1$-$C_6$ alkylsulfonylamino group such as methylsulfonylamino, ethylsulfonylamino, propylsulfonylamino or butylsulfonylamino; a nitro group; a cyano group; a $C_1$-$C_6$ alkyl group including methyl, ethyl, propyl, isopropyl, butyl, isobutyl, s-butyl, and t-butyl; a trifluoromethyl group; and a trifluoromethoxy group).

In the present description, when $G^1$, $G^2$, or the substituent of $G^2$ represents a substituted or unsubstituted aromatic hydrocarbon group, a substituted or unsubstituted alicyclic hydrocarbon group, or a substituted or unsubstituted heterocyclic group, the aromatic hydrocarbon group, alicyclic hydrocarbon group, or heterocyclic group is preferably selected from the group consisting of cyclopropane, cyclopentane, cyclohexane, cyclohexene, cycloheptane, *nolvolnane, adamantine, benzene, naphthalene, indane, indoles, 1,3-benzodioxol, benzoimidazol, benzotriazol, pyrazol, imidazol, pyrazoron, thiazol, tetrazol, 1,2,4-oxadiazol, isooxazol, furan, thiophene, pyridine, pyradine, pyrrole, morpholine, benzofuran, benzothiophene, piperazine, pyrrolidine, homopiperizine, tetrahydroisoquinoline, pyrimidine, and quinazoline.

Next, an explanation will be given of preferred combinations of $A^1$, $A^2$, $G^1$, $A^3$, $A^4$ and $G^2$ in the formula (I).

When both of $A^1$ and $A^3$ represent aliphatic hydrocarbon group, at least one of $A^2$ and $G^1$ is not a single bond.

The preferred combinations of $A^1$, $A^2$, $G^1$, $A^3$, $A^4$ and $G^2$, and preferred combinations including also substituents of them if they have substituents are basically preferably combinations of those preferably selected from among $A^1$, $A^2$, $G^1$, $A^3$, $A^4$ and $G^2$, and substituents of them. Then, more preferred combinations are combinations of more preferred elements.

In the formula (I), $A^1$ represents a divalent acyclic aliphatic hydrocarbon group having 1 to 6 carbon atoms, particularly preferably represents —$(CH_2)_2$— or —$(CH_2)_3$—.

More preferably, $A^2$ simultaneously represents those other than the single bond, and especially preferably $A^2$ represents —C(=O)—, —C(=O)—O—, —C(=O)—NH—, —C(=O)—NMe-, —NH—, —NH—C(=O)—, —NH—C(=O)—O—, —NH—C(=O)—NH—, —NH—C(=O)—NMe-, or —NH—C(=S)—. Specifically preferably $A^2$ represents —C(=O)—NH—, —NH—, —NH—C(=O)—, —NH—C(=O)—O—, or —NH—C(=O)—NH—.

Meanwhile, where $A^1$ represents a single bond, preferably also A represents a single bond.

Preferred combinations of $G^1$, $A^3$, $A^4$ and $G^2$ of $G^1$-$G^2$ portion include combinations of 1 to 10 of the following table.

| Combination | $G^1$ | $A^3$ | $A^4$ | $G^2$ |
|---|---|---|---|---|
| 1 | Group other than single bond | Single bond | Single bond | Hydrogen atom |
| 2 | Single bond | Group other than single bond | Single bond | Hydrogen atom |
| 3 | Group other than single bond | Single bond | Single bond | Group other than a hydrogen atom |
| 4 | Single bond | Group other than single bond | Single bond | Group other than a hydrogen atom |
| 5 | Group other than single bond | Single bond | Group other than single bond | Group other than a hydrogen atom |
| 6 | Single bond | Group other than single bond | Group other than single bond | Group other than a hydrogen atom |
| 7 | Group other than single bond | Group other than single bond | Single bond | Group other than a hydrogen atom |
| 8 | Group other than single bond | Group other than single bond | Group other than single bond | Group other than a hydrogen atom |
| 9 | Group other than single bond | Group other than single bond | Group other than single bond | Hydrogen atom |
| 10 | Single bond | Single bond | Single bond | Hydrogen atom |

In the table, in combinations of numbers 4 to 7, $A^3$ represents an alkylene group having 1 to 3 carbon atoms.

Also, in the combination of number 5, $A^4$ preferably represents —C(=O)—, —C(=O)—NH—, —O—, or —NH—C(=O)—.

Also, in the combination of number 8, $A^4$ preferably represents —O—.

Further, combinations of the following a) to f) are preferable.

a) $A^1$ represents —$(CH_2)_2$— or —$(CH_2)_3$—, $A^2$ represents —NH—(C=O)— or —NH—(C=O)—NH—, $G^1$ represents a single bond, and $A^3$ represents a divalent acyclic aliphatic hydrocarbon group having 1 to 10 carbon atoms.

b) $A^1$ represents $—(CH_2)_2—$ or $—(CH_2)_3—$, $A^2$ represents $—NH—C(=O)—$, $—NH—C(=O)—NH—$, $—NH—$, or $—C(=O)—NH—$, and $G^1$ represents a group other than the single bond.

c) $A^1$ represents a divalent acyclic aliphatic hydrocarbon group having 1 to 6 carbon atoms, specifically $—(CH_2)_2—$ or $—(CH_2)_3—$, $A^2$ represents a single bond, and $G^1$ represents an optionally substituted heterocyclic group (note, where a heterocyclic group of $G^1$ is 5 or 6 membered monocyclic ring, the 5 or 6 membered monocyclic heterocyclic group of $G^1$ is substituted, or $A^3$-$G^2$ portion represents those other than the hydrogen atom).

d) $A^1$ represents a divalent acyclic aliphatic hydrocarbon group having 1 to 6 carbon atoms, specifically $—(CH_2)_2—$ or $—(CH_2)_3—$, $A^2$ represents those other than a single bond, and $G^1$ represents an optionally substituted aromatic hydrocarbon group, an optionally substituted alicyclic hydrocarbon group having 7 to 10 carbon atoms, or an optionally substituted heterocyclic group (note, where the aromatic hydrocarbon group of $G^1$ is a phenyl group, or where the heterocyclic group of $G^1$ is 5 or 6 membered monocyclic ring, the phenyl group or 5 or 6 membered monocyclic heterocyclic group of $G^1$ is substituted, or $A^3$-$G^2$ portion represents those other than the hydrogen atom).

e) $A^1$ represents a divalent acyclic aliphatic hydrocarbon group having 1 to 6 carbon atoms, specifically $—(CH_2)_2—$ or $—(CH_2)_3—$, $A^2$ represents those other than a single bond, $G^1$ and $A^4$ represent the single bond, $A^3$ represents an optionally substituted acyclic aliphatic hydrocarbon group having 1 to 10 carbon atoms, $G^2$ represents an optionally substituted alicyclic hydrocarbon group having 5 to 10 carbon atoms, an optionally substituted aromatic hydrocarbon group, or optionally substituted heterocyclic group.

f) $A^1$ represents a divalent acyclic aliphatic hydrocarbon group having 1 to 6 carbon atoms, specifically $—(CH_2)_2—$ or $—(CH_2)_3—$, $A^2$ represents those other than a single bond, $G^1$ represents the single bond, $A^3$ represents an optionally substituted acyclic aliphatic hydrocarbon group having 1 to 10 carbon atoms, and $A^4$ represents $—C(=O)—$, $—C(=O)—NR^{121}—$, $—C(=S)—NR^{122}—$, $—C(=NR^{123})—$, $—O—C(=O)—$, $—NR^{125}—C(=O)—$, $—NR^{126}—S(=O)_2—$, $—NR^{127}—C(=O)—O—$, $—NR^{128}—C(=O)—NR^{129}—$, $—NR^{130}—C(=S)—$, $—NR^{131}—C(=S)—NR^{132}—$, $—S—$, $—S(=O)—$, $—S(=O)_2—$, $—S(=O)_2—NR^{133}—$ or $—S(=O)_2—O—$.

In the cases of d) to f), $A^2$ preferably represents $—C(=O)—$, $—C(=O)—O—$, $—C(=O)—NH—$, $—C(=O)—NMe-$, $—NH—$, $—NH—C(=O)—$, $—NH—C(=O)—O—$, $—NH—C(=O)—NH—$, $—NH—C(=O)—NMe-$, or $—NH—C(=S)—$, especially preferably represents $—C(=O)—NH—$, $—NH—$, $—NH—C(=O)—$, $—NH—C(=O)—O—$, or $—NH—C(=O)—NH—$.

In the formula (I), $A^5$ represents a single bond or represents a group that links $R^2$ with a carbon atom of a pyrrole ring to which $A^5$ is bonded, in the form of $R^2—NR^{201}$-pyrrole ring ($R^{201}$ represents a hydrogen atom or a acyclic aliphatic hydrocarbon group having 1 to 4 carbon atoms), when $A^5$ bonds $R^2$ and a carbon atom of a pyrrole ring to which $A^5$ is bonded, in the form of $R^2—NR^{201}$-pyrrole ring, examples of the acyclic aliphatic hydrocarbon group having 1 to 4 carbon atoms of $R^{201}$ are the same as exemplified as $R^{101}$ of $A^2$ described above. Preferred examples of $R^{102}$ include a hydrogen atom, methyl, ethyl or propyl group, and specifically preferably hydrogen atom and methyl group.

Preferred examples of $A^5$ include a single bond, $—NH—$, and $N(CH_3)—$, and specifically preferably single bond.

In the formula (I), $R^2$ represents a hydrogen atom, a fluorine atom, a chlorine atom, a bromine atom, an iodine atom, an optionally substituted acyclic aliphatic hydrocarbon group having 1 to 10 carbon atoms, an optionally substituted alicyclic hydrocarbon group having 3 to 8 carbon atoms, an optionally substituted aromatic hydrocarbon group having 6 to 14 carbon atoms, or an optionally substituted heterocyclic group having 1 to 4 atoms selected from the group consisting of an oxygen atom, a nitrogen atom and a sulfur atom, in the ring.

$R^2$ in the formula (I) is preferably a chlorine atom or a bromine atom among a fluorine atom, a chlorine atom, a bromine atom, and an iodine atom.

In the formula (I), when $R^2$ represents an optionally substituted acyclic aliphatic hydrocarbon group having 1 to 10 carbon atoms, examples of acyclic aliphatic hydrocarbon group having 1 to 10 carbon atoms of $R^2$ are the same as those exemplified of the acyclic aliphatic hydrocarbon group having 1 to 10 carbon atoms of $G^2$. Preferred examples of the acyclic aliphatic hydrocarbon group having 1 to 10 carbon atoms of $R^2$ include methyl, ethyl, isopropyl, butyl, isobutyl, t-butyl, t-pentyl, vinyl, 2-propenyl, 2-methyl-1-propenyl, and 2-propenyl.

Substituents for the substituted acyclic aliphatic hydrocarbon group having 1 to 10 carbon atoms of $R^2$ include at least one substituent selected from the group consisting of a fluorine atom, a chlorine atom, a bromine atom, an iodine atom, a hydroxy group, an optionally substituted $C_1$-$C_7$ alkoxy group, a $C_6$-$C_{10}$ aryloxy group, a $C_7$-$C_9$ aralkoxy group, a $C_2$-$C_7$ acyloxy group, an oxo group, a $C_1$-$C_6$ alkylsulfonyloxy group, an optionally substituted $C_2$-$C_7$ acyl group, a carboxyl group, a $C_2$-$C_7$ alkoxycarbonyl group, a carbamoyl group, an optionally substituted $C_2$-$C_7$ alkylcarbamoyl group, an amino group, an optionally substituted $C_1$-$C_6$ alkylamino group, an optionally substituted $C_2$-$C_7$ acylamino group, a $C_2$-$C_8$ alkoxycarbonylamino group, a $C_1$-$C_6$ alkylsulfonylamino group, a cyano group, a nitro group, a $C_1$-$C_6$ alkylthio group, a $C_1$-$C_6$ alkylsulfynyl group, a $C_1$-$C_6$ alkylsulfonyl group, a sulfamoyl group, a $C_1$-$C_6$ alkylaminosulfonyl group, a sulfo group, an optionally substituted alicyclic hydrocarbon group having 1 to 6 carbon atoms, an optionally substituted acyclic aliphatic hydrocarbon group having 1 to 6 carbon atoms, an optionally substituted aromatic hydrocarbon group having 6 to 14 carbon atoms, and an optionally substituted heterocyclic group (having 1 to 4 atoms selected from the group consisting of an oxygen atom, a nitrogen atom and a sulfur atom, in the ring).

Specific examples of the substituent of the substituted acyclic aliphatic hydrocarbon group having 1 to 10 carbon atoms of $R^2$ include the same as those exemplified as the substituents of the substituted acyclic aliphatic hydrocarbon group having 1 to 10 carbon atoms of $G^2$.

As the substituent of substituted acyclic aliphatic hydrocarbon group having 1 to 10 carbon atoms as $R^2$, a $C_1$-$C_7$ alkoxy group, a $C_2$-$C_7$ acyl group, $C_2$-$C_7$ alkylcarbamoyl group, a $C_1$-$C_6$ alkylamino group, a $C_2$-$C_7$-acylamino group, an alicyclic hydrocarbon group having 3 to 6 carbon atoms, a acyclic aliphatic hydrocarbon group having 1 to 6 carbon atoms, aromatic hydrocarbon group having 6 to 14 carbon atoms, and heterocyclic group (having 1 to 4 atoms selected from the group consisting of an oxygen atom, a nitrogen atom and a sulfur atom, in the ring), may further be substituted with (one or more substituents selected from the group consisting of: a fluorine atom; a chlorine atom; a bromine atom; an iodine atom; a hydroxy group; a $C_1$-$C_6$ alkoxy group such as methoxy, ethoxy, propoxy, isopropoxy, butoxy, isobutoxy, s-butoxy, t-butoxy, pentyloxy or cyclopropyloxy; a methoxymethyloxy group; a 2-methoxyethoxy group; a formyl group; a trifluoroacetyl group; a $C_2$-$C_7$ acyl group such as acetyl, propionyl, butyryl, isobutyryl, valeryl or isovaleryl; an oxo group; a carboxyl group; a $C_2$-$C_7$ alkoxycarbonyl group such as methoxycarbonyl, ethoxycarbonyl, propoxycarbonyl, isopropoxycarbonyl, butoxycarbonyl, isobutoxycarbonyl or t-butoxycarbonyl; a carbamoyl group; a $C_2$-$C_7$ alkylcarbamoyl group such as N-methylcarbamoyl, N,N-dimethylcarbamoyl, N-ethylcarbamoyl, N-ethyl-N-methylcarbamoyl, N,N-diethyl-carbamoyl, N-propylcarbamoyl, N-isopropylcarbamoyl, N-butylcarbamoyl, N-cyclopropylcarbamoyl or N-cyclopropyl-methylcarbamoyl; an amino group; a $C_1$-$C_6$ alkylamino group such as methylamino, ethylamino, propylamino, isopropylamino, dimethylamino, N-ethylmethylamino, diethylamino, N-methylpropylamino, N-methylisopropylamino, cyclopropylamino or cyclopropylmethylamino; a $C_4$-$C_6$ cyclic amino group having 1 or 2 atoms selected from the group consisting of an oxygen atom, a nitrogen atom and a sulfur atom, in the ring, such as 1-pyrrolidinyl, piperazinyl, 4-methylpiperazinyl, piperidino or morpholino; a trifluoroacetylamino group; a $C_1$-$C_7$ acylamino group such as formylamino, acetylamino, propionylamino, butyrylamino, isobutyrylamino or valerylamino; a $C_1$-$C_6$ alkylsulfonylamino group such as methylsulfonylamino, ethylsulfonylamino, propylsulfonylamino or butylsulfonylamino; a nitro group; a cyano group; a $C_1$-$C_6$ alkyl group including methyl, ethyl, propyl, isopropyl, butyl, isobutyl, s-butyl, and t-butyl; a trifluoromethyl group; and a trifluoromethoxy group).

In the formula (I), when $R^2$ represents a substituted or unsubstituted alicyclic hydrocarbon group having 3 to 8 carbon atoms, examples of the alicyclic hydrocarbon group having 3 to 8 carbon atoms of $R^2$ the same as defined above for the substituents of the substituted alicyclic hydrocarbon group having 3 to 8 carbon atoms of $G^2$. Preferred examples of the alicyclic hydrocarbon group having 3 to 8 carbon atoms of $R^2$ include cyclopropyl, cyclobutyl, cyclopentyl and cyclohexyl. Among them, the cyclopropyl group is preferred.

Exemplary substituents of the substituted alicyclic hydrocarbon group having 3 to 8 carbon atoms of $R^2$ include at least one substituent selected from the group consisting of a fluorine atom, a chlorine atom, a bromine atom, an iodine atom, a hydroxy group, an optionally substituted $C_1$-$C_7$ alkoxy group, a $C_6$-$C_{10}$ aryloxy group, a $C_7$-$C_9$ aralkoxy group, a $C_2$-$C_7$ acyloxy group, an oxo group, a $C_1$-$C_6$ alkylsulfonyloxy group, an optionally substituted $C_2$-$C_7$ acyl group, a carboxyl group, a $C_2$-$C_7$ alkoxycarbonyl group, a carbamoyl group, an optionally substituted $C_2$-$C_7$ alkylcarbamoyl group, an amino group, an optionally substituted $C_1$-$C_6$ alkylamino group, an optionally substituted $C_2$-$C_7$ acylamino group, a $C_2$-$C_8$ alkoxycarbonylamino group, a $C_1$-$C_6$ alkylsulfonylamino group, a cyano group, a nitro group, a $C_1$-$C_6$ alkylthio group, a $C_1$-$C_6$ alkylsulfynyl group, a $C_1$-$C_6$ alkylsulfonyl group, a sulfamoyl group, a $C_1$-$C_6$ alkylaminosulfonyl group, a sulfo group, an optionally substituted alicyclic hydrocarbon group having 3 to 6 carbon atoms, an optionally substituted aliphatic hydrocarbon group having 1 to 6 carbon atoms, an optionally substituted aromatic hydrocarbon group having 6 to 14 carbon atoms, and an optionally substituted heterocyclic group (having 1 to 4 atoms selected from the group consisting of an oxygen atom, a nitrogen atom and a sulfur atom, in the ring).

Specific examples of the substituent of the substituted alicyclic hydrocarbon group having 3 to 8 carbon atoms of $R^2$ include the same as those exemplified in the substituted alicyclic hydrocarbon group having 1 to 10 carbon atoms of $G^2$.

As the substituent of the substituted alicyclic hydrocarbon group having 3 to 8 carbon atoms of $R^2$, a $C_1$-$C_7$ alkoxy group, a $C_2$-$C_7$ acyl group, a $C_2$-$C_7$ alkylcarbamoyl group, a $C_1$-$C_6$ alkylamino group, a $C_2$-$C_7$ acylamino group, an alicyclic hydrocarbon group having 3 to 6 carbon atoms, an aliphatic hydrocarbon group having 1 to 6 carbon atoms, an aromatic hydrocarbon group having 6 to 14 carbon atoms and a heterocyclic group (having 1 to 4 atoms selected from the group consisting of an oxygen atom, a nitrogen atom and a sulfur atom, in the ring), may further be substituted with (one or more substituents selected from the group consisting of: a fluorine atom; a chlorine atom; a bromine atom; an iodine atom; a hydroxy group; a $C_1$-$C_6$ alkoxy group such as methoxy, ethoxy, propoxy, isopropoxy, butoxy, isobutoxy, s-butoxy, t-butoxy, pentyloxy or cyclopropyloxy; a methoxymethyloxy group; a 2-methoxyethoxy group; a formyl group; a trifluoroacetyl group; a $C_2$-$C_7$ acyl group such as acetyl, propionyl, butyryl, isobutyryl, valeryl or isovaleryl; an oxo group; a carboxyl group; a $C_2$-$C_7$ alkoxycarbonyl group such as methoxycarbonyl, ethoxycarbonyl, propoxycarbonyl, isopropoxycarbonyl, butoxycarbonyl, isobutoxycarbonyl or t-butoxycarbonyl; a carbamoyl group; a $C_2$-$C_7$ alkylcarbamoyl group such as N-methylcarbamoyl, N,N-dimethylcarbamoyl, N-ethylcarbamoyl, N-ethyl-N-methylcarbamoyl, N,N-diethylcarbamoyl, N-propylcarbamoyl, N-isopropylcarbamoyl, N-butylcarbamoyl, N-cyclopropyl-carbamoyl or N-cyclopropylmethylcarbamoyl; an amino group; a $C_1$-$C_6$ alkylamino group such as methylamino, ethylamino, propylamino, isopropylamino, dimethylamino, N-ethylmethylamino, diethylamino, N-methylpropylamino, N-methylisopropyl-amino, cyclopropylamino or cyclopropylmethylamino; a $C_4$-$C_6$ cyclic amino group having 1 or 2 atoms selected from the group consisting of an oxygen atom, a nitrogen atom and a sulfur atom, in the ring, such as 1-pyrrolidinyl, piperazinyl, 4-methylpiperazinyl, piperidino or morpholino; a trifluoroacetylamino group; a $C_1$-$C_7$ acylamino group such as formylamino, acetylamino, propionylamino, butyrylamino, isobutyrylamino or valerylamino; a $C_1$-$C_6$ alkylsulfonylamino group such as methylsulfonylamino, ethylsulfonylamino, propylsulfonylamino or butylsulfonylamino; a nitro group; a cyano group; a $C_1$-$C_6$ alkyl group including methyl, ethyl, propyl, isopropyl, butyl, isobutyl, s-butyl, and t-butyl; a trifluoromethyl group, and a trifluoromethoxy group).

In the formula (I), when $R^2$ is a substituted or unsubstituted aromatic hydrocarbon group having 6 to 14 carbon atoms, examples of the aromatic hydrocarbon group having 6 to 14 carbon atoms of $R^2$ include the same as those exemplified in the aromatic hydrocarbon group having 6 to 14 carbon atoms of $G^2$. Examples of such preferred aromatic hydrocarbon group having 6 to 14 carbon atoms of $R^2$ include a phenyl group.

Exemplary substituents of the substituted aromatic hydrocarbon group having 6 to 14 carbon atoms include at least one substituent selected from the group consisting of a fluorine atom, a chlorine atom, a bromine atom, an iodine atom, a hydroxy group, a $C_1$-$C_6$ alkyl group, an optionally substituted $C_1$-$C_7$ alkoxy group, a $C_6$-$C_{10}$ aryloxy group, a $C_7$-$C_9$ aralkoxy group, a $C_2$-$C_7$ acyloxy group, an oxo group, a $C_1$-$C_6$ alkylsulfonyloxy group, an optionally substituted $C_2$-$C_7$ acyl group, a carboxyl group, a $C_2$-$C_7$ alkoxycarbonyl group, a carbamoyl group, an optionally substituted $C_2$-$C_7$ alkylcarbamoyl group, an amino group, an optionally substituted $C_1$-$C_6$ alkylamino group, an optionally substituted $C_2$-$C_7$ acylamino group, a $C_2$-$C_8$ alkoxycarbonylamino group, a $C_1$-$C_6$ alkylsulfonylamino group, a cyano group, a nitro group, a $C_1$-$C_6$ alkylthio group, a $C_1$-$C_6$ alkylsulfynyl group, a $C_1$-$C_6$ alkylsulfonyl group, a sulfamoyl group, a $C_1$-$C_6$ alkylaminosulfonyl group, a sulfo group, an optionally substituted alicyclic hydrocarbon group having 3 to 6 carbon atoms, an optionally substituted aliphatic hydrocarbon group having 1 to 6 carbon atoms, an optionally substituted aromatic hydrocarbon group having 6 to 14 carbon atoms, and an optionally substituted heterocyclic group (having 1 to 4 atoms selected from the group consisting of an oxygen atom, a nitrogen atom and a sulfur atom, in the ring).

Specific examples of the substituent of the substituted aromatic hydrocarbon group having 6 to 14 carbon atoms $R^2$ include the same as those exemplified for the substituted acyclic aliphatic hydrocarbon group having 1 to 10 carbon atoms of $G^2$.

As the substituent of the aromatic hydrocarbon group having 6 to 14 carbon atoms of $R^2$, a $C_1$-$C_7$ alkoxy group, a $C_2$-$C_7$ acyl group, a $C_2$-$C_7$ alkylcarbamoyl group, a $C_1$-$C_6$ alkylamino group, a $C_2$-$C_7$ acylamino group, an alicyclic hydrocarbon group having 3 to 6 carbon atoms, an aliphatic hydrocarbon group having 1 to 6 carbon atoms, an aromatic hydrocarbon group having 6 to 14 carbon atoms and heterocyclic group (having 1 to 4 atoms selected from the group consisting of an oxygen atom, a nitrogen atom and a sulfur atom, in the ring), may further be substituted with (one or more substituents selected from the group consisting of: a fluorine atom; a chlorine atom; a bromine atom; an iodine atom; a hydroxy group; a $C_1$-$C_6$ alkoxy group such as methoxy, ethoxy, propoxy, isopropoxy, butoxy, isobutoxy, s-butoxy, t-butoxy, pentyloxy or cyclopropyloxy; a methoxymethyloxy group; a 2-methoxyethoxy group; a formyl group; a trifluoroacetyl group; a $C_2$-$C_7$ acyl group such as acetyl, propionyl, butyryl, isobutyryl, valeryl or isovaleryl; an oxo group; a carboxyl group; a $C_2$-$C_7$ alkoxycarbonyl group such as methoxycarbonyl, ethoxycarbonyl, propoxycarbonyl, isopropoxycarbonyl, butoxycarbonyl, isobutoxycarbonyl or t-butoxycarbonyl; a carbamoyl group; a $C_2$-$C_7$ alkylcarbamoyl group such as N-methylcarbamoyl, N,N-dimethylcarbamoyl, N-ethylcarbamoyl, N-ethyl-N-methylcarbamoyl, N,N-diethyl-carbamoyl, N-propylcarbamoyl, N-isopropylcarbamoyl, N-butylcarbamoyl, N-cyclopropylcarbamoyl or N-cyclopropyl-methylcarbamoyl; an amino group; a $C_1$-$C_6$ alkylamino group such as methylamino, ethylamino, propylamino, isopropylamino, dimethylamino, N-ethylmethylamino, diethylamino, N-methylpropylamino, N-methylisopropylamino, cyclopropylamino or cyclopropylmethylamino; a $C_4$-$C_6$ cyclic amino group having 1 or 2 atoms selected from the group consisting of an oxygen atom, a nitrogen atom and a sulfur atom, in the ring, such as 1-pyrrolidinyl, piperazinyl, 4-methylpiperazinyl, piperidino or morpholino; a trifluoroacetylamino group; a $C_1$-$C_7$ acylamino group such as formylamino, acetylamino, propionylamino, butyrylamino, isobutyrylamino or valerylamino; a $C_1$-$C_6$ alkylsulfonylamino group such as methylsulfonylamino, ethylsulfonylamino, propylsulfonylamino or butylsulfonylamino; a nitro group; a cyano group; a $C_1$-$C_6$ alkyl group including methyl, ethyl, propyl, isopropyl, butyl, isobutyl, s-butyl, and t-butyl; a trifluoromethyl group, and a trifluoromethoxy group).

In the formula (I), when $R^2$ represents a heterocyclic group having 1 to 4 atoms selected from the group consisting of an oxygen atom, a nitrogen atom and a sulfur atom on its substituted or unsubstituted ring of $R^2$, examples of heterocyclic group of $R^2$ include the same as those exemplified for the heterocyclic group of $G^2$. The heterocyclic group of $R^2$ links to $A^5$ on a carbon atom or a nitrogen atom.

Examples of preferred heterocyclic group linking to $A^5$ on a carbon atom include a monocyclic or cyclic $C_3$-$C_9$ aromatic heterocyclic group having 1 to 3 atoms selected from the group consisting of an oxygen atom, a nitrogen atom and a sulfur atom, in the ring, such as furyl, thienyl, pyrrolyl, pyrazolyl, oxazolyl, isooxazolyl, thiazolyl, isothiazolyl, imidazolyl, pyridyl, pyrazinyl, pyrimidinyl, pyridazinyl, benzofuranyl, indolyl, benzothienyl, quinolyl, isoquinolyl, quinazolyl, benzoimidazolyl or benzooxazolyl. More preferred example of the heterocyclic group include a monocyclic or bicyclic $C_3$-$C_9$ aromatic heterocyclic compound having 1 or 2 atoms selected from the group consisting of an oxygen atom, a nitrogen atom and a sulfur atom, in the ring, such as 2-furyl, 2-thienyl, 2-pyrrolyl, 2-imidazolyl, 5-imidazolyl, 4-pyrazolyl, 2-oxazolyl, 5-oxazolyl, 5-isooxazolyl, 2-thiazolyl, 5-thiazolyl, 5-isothiazolyl, 3-isothiazolyl, 2-pyridyl, 2-pyrimidinyl, 2-benzofuranyl or 2-benzothiophenyl group. Further, particularly preferable examples of the heterocyclic group include a monocyclic $C_3$-$C_5$ aromatic heterocyclic group having 1 or 2 atoms selected from the group consisting of an oxygen atom, a nitrogen atom and a sulfur atom, in the ring, and most preferably, 2-furyl, 2-thienyl, 2-pyrrolyl, 2-pyridyl or 4-pyrazolyl.

Meanwhile, preferred examples of the heterocyclic group having 1 to 4 atoms selected from the group consisting of an oxygen atom, a nitrogen atom and a sulfur atom, in the ring, links to $A^5$ on a nitrogen atom, include 1-pyrazolyl, 1-imidazolyl, 1-pyrrolidinyl, piperidino, morpholino, 1-homopiperidinyl and 1-piperazinyl. When the heterocyclic group having 1 to 4 atoms selected from the group consisting of an oxygen atom, a nitrogen atom and a sulfur atom on a ring of $R^2$, links to $A^5$ on a nitrogen atom, $A^5$ represents a single bond.

Exemplary substituents of the heterocyclic group having 1 to 4 atoms selected from the group consisting of an oxygen atom, a nitrogen atom and a sulfur atom on the substituted ring of $R^2$ include at least one substituent selected from the group consisting of a fluorine atom, a chlorine atom, a bromine atom, an iodine atom, a hydroxy group, an optionally substituted $C_1$-$C_7$ alkoxy group, a $C_6$-$C_{10}$ aryloxy group, a $C_7$-$C_9$ aralkoxy group, a $C_2$-$C_7$ acyloxy group, an oxo group, a $C_1$-$C_6$ alkylsulfonyloxy group, an optionally substituted $C_2$-$C_7$ acyl group, a carboxyl group, a $C_2$-$C_7$ alkoxycarbonyl group, a carbamoyl group, an optionally substituted $C_2$-$C_7$ alkylcarbamoyl group, an amino group, an optionally substituted $C_1$-$C_6$ alkylamino group, an optionally substituted $C_2$-$C_7$ acylamino group, a $C_2$-$C_8$ alkoxycarbonylamino group, a $C_1$-$C_6$ alkylsulfonylamino group, a cyano group, a nitro group, a $C_1$-$C_6$ alkylthio group, a $C_1$-$C_6$ alkylsulfynyl group, a $C_1$-$C_6$ alkylsulfonyl group, a sulfamoyl group, a $C_1$-$C_6$ alkylaminosulfonyl group, a sulfo group, an optionally substituted alicyclic hydrocarbon group having 3 to 6 carbon atoms, an optionally substituted aliphatic hydrocarbon group having 1 to 6 carbon atoms, an optionally substituted aromatic hydrocarbon group having 6 to 14 carbon atoms, and an optionally substituted heterocyclic group (having 1 to 4 atoms selected from the group consisting of an oxygen atom, a nitrogen atom and a sulfur atom, in the ring).

Specific examples of the substituent of the heterocyclic group having 1 to 4 atoms selected from the group consisting of an oxygen atom, a nitrogen atom and a sulfur atom on its substituted ring of $R^2$ include the same as those exemplified as the substituents of the substituted aliphatic hydrocarbon group having 1 to 10 carbon atoms of $G^2$.

As the substituent of the heterocyclic group having 1 to 4 atoms selected from the group consisting of an oxygen atom, a nitrogen atom and a sulfur atom on its substituted ring of $R^2$, a $C_1$-$C_7$ alkoxy group, a $C_2$-$C_7$ acyl group, a $C_2$-$C_7$ alkylcarbamoyl group, a $C_1$-$C_6$ alkylamino group, a $C_2$-$C_7$ acylamino group, an alicyclic hydrocarbon group having 3 to 6 carbon atoms, aliphatic hydrocarbon group having 1 to 6 carbon atoms, an aromatic hydrocarbon group having 6 to 14 carbon atoms, and a heterocyclic group (having 1 to 4 atoms selected from the group consisting of an oxygen atom, a nitrogen atom and a sulfur atom, in the ring) may further be substituted with (one or more substituents selected from the group consisting of: a fluorine atom; a chlorine atom; a bromine atom; an iodine atom; a hydroxy group; a $C_1$-$C_6$ alkoxy group such as methoxy, ethoxy, propoxy, isopropoxy, butoxy, isobutoxy, s-butoxy, t-butoxy, pentyloxy or cyclopropyloxy; a methoxymethyloxy group; a 2-methoxyethoxy group; a formyl group; a trifluoroacetyl group; a $C_2$-$C_7$ acyl group such as acetyl, propionyl, butyryl, isobutyryl, valeryl or isovaleryl; an oxo group; a carboxyl group; a $C_2$-$C_7$ alkoxycarbonyl group such as methoxycarbonyl, ethoxycarbonyl, propoxycarbonyl, isopropoxycarbonyl, butoxycarbonyl, isobutoxycarbonyl or t-butoxycarbonyl; a carbamoyl group; a $C_2$-$C_7$ alkylcarbamoyl group such as N-methylcarbamoyl, N,N-dimethylcarbamoyl, N-ethylcarbamoyl, N-ethyl-N-methylcarbamoyl, N,N-diethylcarbamoyl, N-propylcarbamoyl, N-isopropylcarbamoyl, N-butylcarbamoyl, N-cyclopropylcarbamoyl or N-cyclopropylmethylcarbamoyl; an amino group; a $C_1$-$C_6$ alkylamino group such as methylamino, ethylamino, propylamino, isopropylamino, dimethylamino, N-ethylmethylamino, diethylamino, N-methylpropylamino, N-methylisopropylamino, cyclopropylamino or cyclopropylmethylamino; a $C_4$-$C_6$ cyclic amino group having 1 or 2 atoms selected from the group consisting of an oxygen atom, a nitrogen atom and a sulfur atom, in the ring, such as 1-pyrrolidinyl, piperazinyl, 4-methylpiperazinyl, piperidino or morpholino; a trifluoroacetylamino group; a $C_1$-$C_7$ acylamino group such as formylamino, acetylamino, propionylamino, butyrylamino, isbbutyrylamino or valerylamino; a $C_1$-$C_6$-alkylsulfonylamino group such as methylsulfonylamino, ethylsulfonylamino, propylsulfonylamino or butylsulfonylamino; a nitro group; a cyano group; a $C_1$-$C_6$ alkyl group including methyl, ethyl, propyl, isopropyl, butyl, isobutyl, s-butyl, and t-butyl; a trifluoromethyl group; and a trifluoromethoxy group).

Among exemplary substituents of the heterocyclic group having 1 to 4 atoms selected from the group consisting of an oxygen atom, a nitrogen atom and a sulfur atom on its substituted ring of $R^2$, preferred examples of the substituent include a fluorine atom, a chlorine atom, a bromine atom, an iodine atom, a hydroxy group, a cyano group, a nitro group, an amino group, a $C_1$-$C_6$ mono or dialkylamino group consisting of a straight or branched alkyl group and an amino group, such as substituted or unsubstituted methylamino, ethylamino, propylamino, isopropylamino, butylamino, isobutylamino, s-butylamino, t-butylamino, pentylamino, hexylamino, dimethylamino, N-ethylmethylamino, diethylamino, N-methylpropylamino, N-methylisopropylamino, N-methylbutylamino, N-methyl-t-butylamino, N-ethylisopropylamino, dipropylamino, diisopropylamino and ethylbutylamino, a carboxyl group, an optionally substituted saturated a $C_1$-$C_6$ alkyl group including a substituted or unsubstituted methyl, ethyl, propyl, isopropyl, butyl, isobutyl, s-butyl, t-butyl, pentyl, isopentyl, neopentyl, t-pentyl, hexyl, isohexyl, 2-methylpentyl and 1-ethylbutyl, an alicyclic hydrocarbon group having 3 to 6 carbon atoms including cyclopropyl, cyclobutyl, cyclo pentyl and cyclohexyl, an optionally substituted $C_1$-$C_6$ alkoxy group consisting of a straight or branched alkyl group and an oxy group, including a substituted or unsubstituted methoxy, ethoxy, propoxy, isopropoxy, butoxy, isobutoxy, s-butoxy, t-butoxy, pentyloxy, isopentyloxy, neopentyloxy, t-pentyloxy and hexyloxy, a $C_2$-$C_7$ acyl group, including a substituted or unsubstituted acetyl, propionyl, butyryl, isobutyryl, pivaroyl and hexanoyl, a $C_1$-$C_6$ alkylthio group, including methylthio, ethylthio, propylthio, isopropylthio, butylthio, isobutylthio, s-butylthio, t-butylthio, pentylthio and hexylthio, trifluoromethyl group, trifluoromethoxy group, a $C_2$-$C_7$ acylamino group, including substituted or unsubstituted acetylamino, propionylamino, butyrylamino, isobutyrylamino, valerylamino and hexanoylamino, and a $C_2$-$C_7$ alkylcarbamoyl group consisting of a straight or branched alkyl group and a carbamoyl group, including a substituted or unsubstituted N-methylcarbamoyl, N-ethylcarbamoyl, N-propylcarbamoyl, N-isopropylcarbamoyl, N-butylcarbamoyl, N-isobutylcarbamoyl, N-s-butylcarbamoyl, N-t-butylcarbamoyl, N-pentylcarbamoyl, N,N-dimethylcarbamoyl, N-ethyl-N-methylcarbamoyl and N,N-diethylcarbamoyl.

More preferred examples of the substituent of the heterocyclic group having 1 to 4 atoms selected from the group consisting of an oxygen atom, a nitrogen atom and a sulfur atom on its substituted ring as $R^2$, include one or more of a fluorine atom, a chlorine atom, a bromine atom, an acyl group having 2 to 4 carbon atoms, a hydroxy group, a carboxyl group, an alkoxycarbonyl group, a substituted or unsubstituted $C_1$-$C_6$ alkyl group, a hydroxy group, and a substituted or unsubstituted $C_1$-$C_6$ alkoxy group.

Here, an explanation will be given of preferred combinations of $R^2$ and $A^5$ of the formula (I).

In combinations of $R^2$ and $A^5$ of the formula (I) in the present invention, when $R^2$ is a fluorine atom, a chlorine atom, a bromine atom, or an iodine atom, $A^5$ represents a single bond.

Preferred examples of the combinations of $R^2$ and $A^5$ of the formula (I) in the present invention include those representing an aliphatic hydrocarbon group having 1 to 10 carbon atoms wherein $A^5$ represents a single bond, and $R^2$ may be substituted, an optionally substituted alicyclic hydrocarbon group having 3 to 8 carbon atoms, an optionally substituted aromatic hydrocarbon group having 6 to 14 carbon atoms, or an optionally substituted heterocyclic group. Specific preferred combinations are combinations representing an aliphatic hydrocarbon group having 1 to 10 carbon atoms wherein $A^5$ represents a single bond, and $R^2$ may be substituted, an optionally substituted alicyclic hydrocarbon group having 3 to 8 carbon atoms, an optionally substituted phenyl group, or an optionally substituted heterocyclic group having 1 or 2 atoms selected from the group consisting of an oxygen atom, a nitrogen atom and a sulfur atom, in the ring. Among them, cases where $R^2$ represents a cyclopropyl group, a cyclobutyl group, a cyclopropylmethyl group, a methyl group, an ethyl group, a vinyl group, an isopropyl group, an isobutyl group or 2-methyl-1-propenyl group are preferred.

Also, combinations of $A^5$ and $R^2$ in which $A^5$ represents a single bond and $R^2$ represents a thienyl group, a pyridyl group, a furyl group, a pyrazolyl group or a phenyl group are preferable, wherein the thienyl group, the pyridyl group, the furyl group, the pyrazolyl group or the phenyl group may be further substituted by one or more of a $C_1$-$C_4$ alkyl group, a $C_1$-$C_4$ alkoxy group, a $C_2$-$C_4$ acyl group, a hydroxy group, a carboxyl group, an alkoxycarbonyl group, a fluorine atom or a chlorine atom.

Also a combination wherein $A^5$ is $NR^{201}$—, and $R^2$ represents a hydrogen atom or an optionally substituted aliphatic hydrocarbon group having 1 to 10 carbon atoms is preferred.

In the formula (I), $A^6$ is a single bond, a group that links a carbon atom of a pyrrole ring in which $R^3$ and $A^6$ are linked to each other in the form of $R^3$—$NR^{301}$-pyrrole ring, $R^3$—C(=O)-pyrrole ring, $R^3$—$NR^{302}$—C(=O)-pyrrole ring, $R^3$—$NR^{303}$—C(=S)-pyrrole ring, $R^3$—$NR^{304}$—C(=O)—$NR^{305}$-pyrrole ring, $R^3$—C(=O)—$NR^{306}$-pyrrole ring, $R^3$—$NR^{307}$—CH=N-pyrrole ring, $R^3$—O—C(=O)-pyrrole ring, $R^3$—C(=O)—O-pyrrole ring, $R^3$—O-pyrrole ring, $R^3$—S-pyrrole ring, $R^3$—S(=O)-pyrrole ring, $R^3$—S(=O)$_2$-pyrrole ring, $R^3$—$CR^{308}$=$CR^{309}$-pyrrole ring, $R^3$—C≡C-pyrrole ring, or $R^3$—S(=O)$_2$—C≡C-pyrrole ring ($R^{301}$ through $R^{309}$ are each independently a hydrogen atom or a $C_1$-$C_4$ aliphatic hydrocarbon group.)

When $R^3$-$A^6$- and a carbon atom of a pyrrole ring are linked to each other in the form of $R^3$—$NR^{301}$-pyrrole ring, examples of such $C_1$-$C_4$ aliphatic hydrocarbon group of $R^{301}$ include the same as those selected as the examples of $R^{101}$ in $A^2$. Examples of such preferred $R^{301}$ include a hydrogen atom, methyl, and ethyl group. Particularly, a hydrogen atom is preferred.

When $R^3$-$A^6$- and a carbon atom of a pyrrole ring are linked to each other in the form of $R^3$—$NR^{302}$—C(=O)-pyrrole ring, examples of such $C_1$-$C_4$ aliphatic hydrocarbon group of $R^{302}$ include the same as those selected as the examples of $R^1$ in $A^2$. Examples of such preferred $R^{302}$ include a hydrogen atom, methyl, and ethyl group. Particularly, a hydrogen atom is preferred.

When $R^3$-$A^6$- and a carbon atom of a pyrrole ring are linked to each other in the form of $R^3$—$NR^{303}$—C(=S)-pyrrole ring, examples of such $C_1$-$C_4$ aliphatic hydrocarbon group of $R^{303}$ include the same as those selected as the examples of $R^{101}$ in $A^2$. Examples of such preferred $R^{303}$ include a hydrogen atom, methyl, and ethyl group. Particularly, a hydrogen atom is preferred.

When $R^3$-$A^6$- and a carbon atom of a pyrrole ring are linked to each other in the form of $R^3$—$NR^{304}$—C(=O)—$NR^{305}$-pyrrole ring, examples of such $C_1$-$C_4$ aliphatic hydrocarbon group of $R^{304}$ and $R^{305}$ include the same as those selected as the examples of $R^{101}$ in $A^2$. Examples of such preferred $R^{304}$ and $R^{305}$ include a hydrogen atom, methyl, and ethyl group. Particularly, a hydrogen atom is preferred.

When $R^3$-$A^6$- and a carbon atom of a pyrrole ring are linked to each other in the form of $R^3$—C(=O)—$NR^{306}$-pyrrole ring, examples of such $C_1$-$C_4$ aliphatic hydrocarbon group of $R^{306}$ include the same as those selected as the examples of $R^{101}$ in $A^2$. Examples of such preferred $R^{306}$ include a hydrogen atom, methyl, and ethyl group. Particularly, a hydrogen atom is preferred.

When $R^3$-$A^6$- and a carbon atom of a pyrrole ring are linked to each other in the form of $R^3$—$NR^{307}$—CH=N-pyrrole ring, examples of such $C_1$-$C_4$ aliphatic hydrocarbon group of $R^{307}$ include the same as those selected as the examples of $R^{101}$ in $A^2$. Examples of such preferred $R^{307}$ include a hydrogen atom, methyl, and ethyl group. Particularly, methyl group is preferred.

When $R^3$-$A^6$- and a carbon atom of a pyrrole ring are linked to each other in the form of $R^3$—$CR^{308}$=$CR^{309}$-pyrrole ring, examples of such $C_1$-$C_4$ aliphatic hydrocarbon group of $R^{308}$ and $R^{308}$ include the same as those selected as the examples of $R^{101}$ in $A^2$.

In the formula (I), $R^3$ represents a hydrogen atom, a fluorine atom, a chlorine atom, a bromine atom, an iodine atom, a nitro group, a substituted or unsubstituted saturated aliphatic hydrocarbon group having 1 to 10 carbon atoms, a substituted or unsubstituted alicyclic hydrocarbon group having 3 to 8 carbon atoms, a substituted or unsubstituted aromatic hydrocarbon group having 6 to 14 carbon atoms, or a heterocyclic group having 1 to 4 atoms selected from the group consisting of an oxygen atom, a nitrogen atom and a sulfur atom.

As $R^3$ in the formula (I), among a fluorine atom, a chlorine atom, a bromine atom, and an iodine atom, a chlorine atom, a bromine atom, and an iodine atom are preferred.

In the formula (I), when $R^3$ represents a substituted or unsubstituted acyclic saturated aliphatic hydrocarbon group having 1 to 10 carbon atoms, examples of the acyclic saturated aliphatic hydrocarbon group having 1 to 10 carbon atoms of $R^3$ include an alkyl group, including methyl, ethyl, propyl, isopropyl, butyl, isobutyl, s-butyl, t-butyl, pentyl, isopentyl, neopentyl, t-pentyl, 2-methylpentyl, 4-methylpentyl, 1-ethylbutyl, hexyl, heptyl, 2-methylhexyl, 5-methylhexyl, 1,1-dimethylpentyl, 6-methylheptyl, octyl, nonyl, and decyl. Preferred examples of the acyclic saturated aliphatic hydrocarbon group having 1 to 10 carbon atoms of $R^3$ include methyl, ethyl, isopropyl, butyl, t-butyl, and t-pentyl group.

As the substituent of the substituted acyclic saturated aliphatic hydrocarbon group having 1 to 10 carbon atoms of $R^3$ include at least one substituent selected from the group consisting of a fluorine atom, a chlorine atom, a bromine atom, an iodine atom, a hydroxy group, an optionally substituted $C_1$-$C_7$ alkoxy group, a $C_6$-$C_{10}$ aryloxy group, a $C_7$-$C_9$ aralkoxy group, a $C_2$-$C_7$ acyloxy group, an oxo group, an optionally substituted $C_2$-$C_7$ acyl group, a carboxyl group, a $C_2$-$C_7$ alkoxycarbonyl group, a carbamoyl group, an optionally substituted $C_2$-$C_7$ alkylcarbamoyl group, an amino group, an optionally substituted $C_1$-$C_6$ alkylamino group, an optionally substituted $C_2$-$C_7$ acylamino group, a $C_2$-$C_8$ alkoxycarbonylamino group, a $C_1$-$C_6$ alkylsulfonylamino group, a cyano group, a nitro group, a $C_1$-$C_6$ alkylthio group, a $C_1$-$C_6$ alkylsulfynyl group, an optionally substituted alicyclic hydrocarbon group having 3 to 6 carbon atoms, an optionally substituted aliphatic hydrocarbon group having 1 to 6 carbon atoms, an optionally substituted aromatic hydrocarbon group having 6 to 14 carbon atoms and an optionally substituted heterocyclic group (having 1 to 4 atoms selected from the group consisting of an oxygen atom, a nitrogen atom and a sulfur atom, in the ring).

Specific examples of the substituent of the substituted acyclic saturated aliphatic hydrocarbon group having 1 to 10 carbon atoms of $R^3$ include the same as those exemplified in the substituted acyclic aliphatic hydrocarbon group having 1 to 10 carbon atoms of $G^2$.

As the substituent of the substituted acyclic saturated aliphatic hydrocarbon group having 1 to 10 carbon atoms of $R^3$, a $C_1$-$C_7$ alkoxy group, a $C_2$-$C_7$ acyl group, a $C_2$-$C_7$ alkylcarbamoyl group, a $C_1$-$C_6$ alkylamino group, a $C_2$-$C_7$ acylamino group, an alicyclic hydrocarbon group having 3 to 6 carbon atoms, an aliphatic hydrocarbon group having 1 to 6 carbon atoms, an aromatic hydrocarbon group having 6 to 14 carbon atoms and a heterocyclic group (having 1 to 4 atoms selected from the group consisting of an oxygen atom, a nitrogen atom and a sulfur atom, in the ring), may further be substituted with (one or more substituents selected from the group consisting of: a fluorine atom; a chlorine atom; a bromine atom; an iodine atom; a hydroxy group; a $C_1$-$C_6$ alkoxy group such as methoxy, ethoxy, propoxy, isopropoxy, butoxy, isobutoxy, s-butoxy, t-butoxy, pentyloxy or cyclopropyloxy; a methoxymethyloxy group; a 2-methoxyethoxy group; a formyl group; a trifluoroacetyl group; a $C_2$-$C_7$ acyl group such as acetyl, propionyl, butyryl, isobutyryl, valeryl or isovaleryl; an oxo group; a carboxyl group; a $C_2$-$C_7$ alkoxycarbonyl group such as methoxycarbonyl, ethoxycarbonyl, propoxycarbonyl, isopropoxycarbonyl, butoxycarbonyl, isobutoxycarbonyl or t-butoxycarbonyl; a carbamoyl group; a $C_2$-$C_7$ alkylcarbamoyl group such as N-methylcarbamoyl, N,N-dimethylcarbamoyl, N-ethylcarbamoyl, N-ethyl-N-methylcarbamoyl, N,N-diethylcarbamoyl, N-propylcarbamoyl, N-isopropylcarbamoyl, N-butylcarbamoyl, N-cyclopropyl-carbamoyl or N-cyclopropylmethylcarbamoyl; an amino group; a $C_1$-$C_6$ alkylamino group such as methylamino, ethylamino, propylamino, isopropylamino, dimethylamino, N-ethylmethyl-amino, diethylamino, N-methylpropylamino, N-methylisopropyl-amino, cyclopropylamino or cyclopropylmethylamino; a $C_4$-$C_6$ cyclic amino group having 1 or 2 atoms selected from the group consisting of an oxygen atom, a nitrogen atom and a sulfur atom, in the ring, such as 1-pyrrolidinyl, piperazinyl, 4-methylpiperazinyl, piperidino or morpholino; a trifluoroacetylamino group; a $C_1$-$C_7$ acylamino group such as formylamino, acetylamino, propionylamino, butyrylamino, isobutyrylamino or valerylamino, a $C_1$-$C_6$ alkylsulfonylamino group such as methylsulfonylamino, ethylsulfonylamino, propylsulfonylamino or butylsulfonylamino; a nitro group; a cyano group; a $C_1$-$C_6$ alkyl group including methyl, ethyl, propyl, isopropyl, butyl, isobutyl, s-butyl, and t-butyl; a trifluoromethyl group; and a trifluoromethoxy group).

In the formula (I), when $R^3$ represents a substituted or unsubstituted alicyclic hydrocarbon group having 3 to 8 carbon atoms, examples of the alicyclic hydrocarbon group having 3 to 8 carbon atoms of $R^2$ include the same as those exemplified in the alicyclic hydrocarbon group having 3 to 10 carbon atoms of $G^2$. Preferred examples of the alicyclic hydrocarbon group having 3 to 8 carbon atoms of $R^2$ include cyclopropyl, cyclobutyl and cyclopentyl, cyclohexyl.

Exemplary substituents of the substituted alicyclic hydrocarbon group having 3 to 8 carbon atoms of $R^3$ include at least one substituent selected from the group consisting of a fluorine atom, a chlorine atom, a bromine atom, an iodine atom, a hydroxy group, an optionally substituted $C_1$-$C_7$ alkoxy group, a $C_6$-$C_{10}$ aryloxy group, a $C_7$-$C_9$ aralkoxy group, a $C_2$-$C_7$ acyloxy group, an optionally substituted $C_2$-$C_7$ acyl group, a carboxyl group, a $C_2$-$C_7$ alkoxycarbonyl group, a carbamoyl group, an optionally substituted $C_2$-$C_7$ alkylcarbamoyl group, an amino group, an optionally substituted $C_1$-$C_6$ alkylamino group, an optionally substituted $C_2$-$C_7$ acylamino group, a $C_2$-$C_8$ alkoxycarbonylamino group, a cyano group, a nitro group, an optionally substituted alicyclic hydrocarbon group having 3 to 6 carbon atoms, an optionally substituted aliphatic hydrocarbon group having 1 to 6 carbon atoms, an optionally substituted aromatic hydrocarbon group having 6 to 14 carbon atoms and an optionally substituted heterocyclic group (having 1 to 4 atoms selected from the group consisting of an oxygen atom, a nitrogen atom and a sulfur atom, in the ring).

Specific examples of the substituent of the substituted alicyclic hydrocarbon group having 3 to 8 carbon atoms of $R^3$ include the same as those exemplified as the substituents of the substituted the substituents of the substituted aliphatic hydrocarbon group having 1 to 10 carbon atoms of $G^2$.

As the substituent of the substituted alicyclic hydrocarbon group having 3 to 8 carbon atoms of $R^3$, a $C_1$-$C_7$ alkoxy group, a $C_2$-$C_7$ acyl group, a $C_2$-$C_7$ alkylcarbamoyl group, a $C_1$-$C_6$ alkylamino group, a $C_2$-$C_7$ acylamino, an alicyclic hydrocarbon group having 3 to 6 carbon atoms, an aliphatic hydrocarbon group having 1 to 6 carbon atoms, an aromatic hydrocarbon group having 6 to 14 carbon atoms, and a heterocyclic group (having 1 to 4 atoms selected from the group consisting of an oxygen atom, a nitrogen atom and a sulfur atom, in the ring), may further be substituted with (one or more substituents selected from the group consisting of: a fluorine atom; a chlorine atom; a bromine atom; an iodine atom; a hydroxy group; a $C_1$-$C_6$ alkoxy group such as methoxy, ethoxy, propoxy, isopropoxy, butoxy, isobutoxy, s-butoxy, t-butoxy, pentyloxy or cyclopropyloxy; a methoxymethyloxy group; a 2-methoxyethoxy group; a formyl group; a trifluoroacetyl group; a $C_2$-$C_7$ acyl group such as acetyl, propionyl, butyryl, isobutyryl, valeryl or isovaleryl; an oxo group; a carboxyl group; a $C_2$-$C_7$ alkoxycarbonyl group such as methoxycarbonyl, ethoxycarbonyl, propoxycarbonyl, isopropoxycarbonyl, butoxycarbonyl, isobutoxycarbonyl or t-butoxycarbonyl; a carbamoyl group; a $C_2$-$C_7$ alkylcarbamoyl group such as N-methylcarbamoyl, N,N-dimethylcarbamoyl, N-ethylcarbamoyl, N-ethyl-N-methylcarbamoyl, N,N-diethyl-carbamoyl, N-propylcarbamoyl, N-isopropylcarbamoyl, N-butylcarbamoyl, N-cyclopropylcarbamoyl or N-cyclopropyl-methylcarbamoyl; an amino group; a $C_1$-$C_6$ alkylamino group such as methylamino, ethylamino, propylamino, isopropylamino, dimethylamino, N-ethylmethylamino, diethylamino, N-methylpropylamino, N-methylisopropylamino, cyclopropylamino or cyclopropylmethylamino; a $C_4$-$C_6$ Cyclic amino group having 1 or 2 atoms selected from the group consisting of an oxygen atom, a nitrogen atom and a sulfur atom, in the ring, such as 1-pyrrolidinyl, piperazinyl, 4-methylpiperazinyl, piperidino or morpholino; a trifluoroacetylamino group; a $C_1$-$C_7$ acylamino group such as formylamino, acetylamino, propionylamino, butyrylamino, isobutyrylamino or valerylamino; a $C_1$-$C_6$ alkylsulfonylamino group such as methylsulfonylamino, ethylsulfonylamino, propylsulfonylamino or butylsulfonylamino; a nitro group; a cyano group; a $C_1$-$C_6$ alkyl group including methyl, ethyl, propyl, isopropyl, butyl, isobutyl, s-butyl, and t-butyl; a trifluoromethyl group; and a trifluoromethoxy group).

In the formula (I), when $R^3$ represents a substituted or unsubstituted aromatic hydrocarbon group having 6 to 14 carbon atoms, examples of the aromatic hydrocarbon group having 6 to 14 carbon atoms of $R^3$ include the same as those exemplified in the aromatic hydrocarbon group having 6 to 14 carbon atoms of $G^2$. Preferred examples of the aromatic hydrocarbon group having 6 to 14 carbon atoms of $R^3$ include a phenyl group.

Exemplary substituents of the substituted aromatic hydrocarbon group having 6 to 14 carbon atoms of $R^3$ include at least one substituent selected from the group consisting of a fluorine atom, a chlorine atom, a bromine atom, an iodine atom, a hydroxy group, an optionally substituted $C_1$-$C_7$ alkoxy group, a $C_6$-$C_{10}$ aryloxy group, a $C_7$-$C_9$ aralkoxy group, a $C_2$-$C_7$ acyloxy group, an oxo group, a $C_1$-$C_6$ alkylsulfonyloxy group, an optionally substituted $C_2$-$C_7$ acyl group, a carboxyl group, a $C_2$-$C_7$ alkoxycarbonyl group, a carbamoyl group, an optionally substituted $C_2$-$C_7$ alkylcarbamoyl group, an amino group, an optionally substituted $C_1$-$C_6$ alkylamino group, an optionally substituted $C_2$-$C_7$ acylamino group, a $C_2$-$C_8$ alkoxycarbonylamino group, a $C_1$-$C_6$ alkylsulfonylamino group, a cyano group, a nitro group, a $C_1$-$C_6$ alkylthio group, a $C_1$-$C_6$ alkylsulfynyl group, a $C_1$-$C_6$ alkylsulfonyl group, a sulfamoyl group, a $C_1$-$C_6$ alkylaminosulfonyl group, a sulfo group, an optionally substituted alicyclic hydrocarbon group having 3 to 6 carbon atoms, an optionally substituted aliphatic hydrocarbon group having 1 to 6 carbon atoms, an optionally substituted aromatic hydrocarbon group having 6 to 14 carbon atoms and an optionally substituted heterocyclic group (having 1 to 4 atoms selected from the group consisting of an oxygen atom, a nitrogen atom and a sulfur atom, in the ring).

Specific examples of the substituent of the substituted aromatic hydrocarbon group having 6 to 14 carbon atoms of $R^3$ include the same as those exemplified in the substituent of the substituted aliphatic hydrocarbon group having 1 to 10 carbon atoms of $G^2$.

As the substituent of the substituted aromatic hydrocarbon group having 6 to 14 carbon atoms of $R^3$, a $C_1$-$C_7$ alkoxy group, a $C_2$-$C_7$ acyl group, a $C_2$-$C_7$ alkylcarbamoyl group, a $C_1$-$C_6$ alkylamino group, a $C_2$-$C_7$ acylamino group, an alicyclic hydrocarbon group having 3 to 6 carbon atoms, an aliphatic hydrocarbon group having 1 to 6 carbon atoms, an aromatic hydrocarbon group having 6 to 14 carbon atoms and a heterocyclic group (having 1 to 4 atoms selected from the group consisting of an oxygen atom, a nitrogen atom and a sulfur atom, in the ring), may further be substituted with (one or more substituents selected from the group consisting of: a fluorine atom; a chlorine atom; a bromine atom; an iodine atom; a hydroxy group; a $C_1$-$C_6$ alkoxy group such as methoxy, ethoxy, propoxy, isopropoxy, butoxy, isobutoxy, s-butoxy, t-butoxy, pentyloxy or cyclopropyloxy; a methoxymethyloxy group; a 2-methoxyethoxy group; a formyl group; a trifluoroacetyl group; a $C_2$-$C_7$ acyl group such as acetyl, propionyl, butyryl, isobutyryl, valeryl or isovaleryl; an oxo group; a carboxyl group; a $C_2$-$C_7$ alkoxycarbonyl group such as methoxycarbonyl, ethoxycarbonyl, propoxycarbonyl, isopropoxycarbonyl, butoxycarbonyl, isobutoxycarbonyl or t-butoxycarbonyl; a carbamoyl group; a $C_2$-$C_7$ alkylcarbamoyl group such as N-methylcarbamoyl, N,N-dimethylcarbamoyl, N-ethylcarbamoyl, N-ethyl-N-methylcarbamoyl, N,N-diethylcarbamoyl, N-propylcarbamoyl, N-isopropylcarbamoyl, N-butylcarbamoyl, N-cyclopropyl-carbamoyl or N-cyclopropylmethylcarbamoyl; an amino group; a $C_1$-$C_6$ alkylamino group such as methylamino, ethylamino, propylamino, isopropylamino, dimethylamino, N-ethylmethylamino, diethylamino, N-methylpropylamino, N-methylisopropyl-amino, cyclopropylamino or cyclopropylmethylamino; a $C_4$-$C_6$ cyclic amino group having 1 or 2 atoms selected from the group consisting of an oxygen atom, a nitrogen atom and a sulfur atom, in the ring, such as 1-pyrrolidinyl, piperazinyl, 4-methylpiperazinyl, piperidino or morpholino; a trifluoroacetylamino group; a $C_1$-$C_7$ acylamino group such as formylamino, acetylamino, propionylamino, butyrylamino, isobutyrylamino or valerylamino; a $C_1$-$C_6$ alkylsulfonylamino group such as methylsulfonylamino, ethylsulfonylamino, propylsulfonylamino or butylsulfonylamino; a nitro group; a cyano group; a $C_1$-$C_6$ alkyl group including methyl, ethyl, propyl, isopropyl, butyl, isobutyl, s-butyl, and t-butyl; a trifluoromethyl group; and a trifluoromethoxy group).

In the formula (I), when $R^3$ represents a heterocyclic group having 1 to 4 atoms selected from the group consisting of an oxygen atom, a nitrogen atom and a sulfur atom on its substituted or unsubstituted ring, examples of such heterocyclic group having 1 to 4 atoms selected from the group consisting of an oxygen atom, a nitrogen atom and a sulfur atom on the ring of $R^3$ include the same as those exemplified in the heterocyclic group having 1 to 4 atoms selected from the group consisting of an oxygen atom, a nitrogen atom and a sulfur atom on the ring of $G^2$.

The heterocyclic group having 1 to 4 atoms selected from the group consisting of an oxygen atom, a nitrogen atom and a sulfur atom on the ring of $R^3$ links to $A^6$ on a carbon atom or a nitrogen atom.

Preferred examples of the heterocyclic group having 1 to 4 atoms selected from the group consisting of an oxygen atom, a nitrogen atom and a sulfur atom on the ring of $R^3$ and linking to $A^6$ on a carbon atom, include a monocyclic or bicyclic $C_3$-$C_9$ aromatic heterocyclic group having 1 to 3 atoms selected from the group consisting of an oxygen atom, a nitrogen atom and a sulfur atom, in the ring, including furyl, thienyl, pyrrolyl, pyrazolyl, oxazolyl, isooxazolyl, thiazolyl, isothiazolyl, imidazolyl, pyridyl, N-oxopyridyl, pyrazinyl, pyrimidinyl, pyridazinyl, benzofuranyl, indolyl, benzothienyl, quinolyl, isoquinolyl, quinazolyl, benzoimidazolyl and benzooxazolyl, preferably 2-furyl, 3-furyl, 2-thienyl, 3-thienyl, 2-pyrrolyl, 2-oxazolyl, 2-thiazolyl, 2-pyridyl, 3-pyridyl, 4-pyridyl, 2-N-oxopyridyl, 3-N-oxopyridyl, 4-N-oxopyridyl, 3-pyrazolyl, 4-pyrazolyl, 4-imidazolyl, 2-pyrimidinyl, or 5-pyrimidinyl.

Meanwhile, preferred examples of the heterocyclic group having 1 to 4 atoms selected from the group consisting of an oxygen atom, a nitrogen atom and a sulfur atom on the ring of $R^3$ and linking to $A^6$ on a nitrogen atom, include 1-imidazolyl, 1-pyrazolyl, 1-pyrrolyl, 1-pyrrolidinyl, piperidino, morpholino, 1-homopiperidinyl and 1-piperazinyl, preferably 1-imidazolyl.

When the heterocyclic group having 1 to 4 atoms selected from the group consisting of an oxygen atom, a nitrogen atom and a sulfur atom on the ring of $R^3$ links to $A^6$ on a nitrogen atom, $A^6$ is a single bond, or a group that links a carbon atom of a pyrrole ring in which $R^3$ and $A^6$ are linked to each other in the form of $R^3$—C(=O)-pyrrole ring.

Exemplary substituents of the heterocyclic group having 1 to 4 atoms selected from the group consisting of an oxygen atom, a nitrogen atom and a sulfur atom on the ring of $R^3$ include at least one substituent selected from the group consisting of a fluorine atom, a chlorine atom, a bromine atom, an iodine atom, a hydroxy group, an optionally substituted $C_1$-$C_7$ alkoxy group, a $C_6$-$C_{10}$ aryloxy group, a $C_7$-$C_9$ aralkoxy group, a $C_2$-$C_7$ acyloxy group, an oxo group, a $C_1$-$C_6$ alkylsulfonyloxy group, an optionally substituted $C_2$-$C_7$ acyl group, a carboxyl group, a $C_2$-$C_7$ alkoxycarbonyl group, a carbamoyl group, an optionally substituted $C_2$-$C_7$ alkylcarbamoyl group, an amino group, an optionally substituted $C_1$-$C_6$ alkylamino group, an optionally substituted $C_2$-$C_7$ acylamino group, a $C_2$-$C_8$ alkoxycarbonylamino group, a $C_1$-$C_6$ alkylsulfonylamino group, a cyano group, a nitro group, a $C_1$-$C_6$ alkylthio group, a $C_1$-$C_6$ alkylsulfynyl group, a $C_1$-$C_6$ alkylsulfonyl group, a sulfamoyl group, a $C_1$-$C_6$ alkylaminosulfonyl group, a sulfo group, an optionally substituted alicyclic hydrocarbon group having 3 to 6 carbon atoms, an optionally substituted aliphatic hydrocarbon group having 1 to 6 carbon atoms, an optionally substituted aromatic hydrocarbon group having 6 to 14 carbon atoms and an optionally substituted heterocyclic group (having 1 to 4 atoms selected from the group consisting of an oxygen atom, a nitrogen atom and a sulfur atom, in the ring).

Specific examples of the substituent of the heterocyclic group having 1 to 4 atoms selected from the group consisting of an oxygen atom, a nitrogen atom and a sulfur atom on its substituted ring of $R^3$ include the same as those exemplified in the substituted aliphatic hydrocarbon group having 1 to 10 carbon atoms of $G^2$.

As the substituent of the heterocyclic group having 1 to 4 atoms selected from the group consisting of an oxygen atom, a nitrogen atom and a sulfur atom on its substituted ring of $R^3$, a $C_1$-$C_7$ alkoxy group, a $C_2$-$C_7$ acyl group, a $C_2$-$C_7$ alkylcarbamoyl group, a $C_1$-$C_6$ alkylamino group, a $C_2$-$C_7$ acylamino group, an alicyclic hydrocarbon group having 3 to 6 carbon atoms and an aliphatic hydrocarbon group having 1 to 6 carbon atoms, an aromatic hydrocarbon group having 6 to 14 carbon atoms, and a heterocyclic group (having 1 to 4 atoms selected from the group consisting of oxygen atom, a nitrogen atom and a sulfur atom in the ring) may further be substituted with (one or more substituents selected from the group consisting of: a fluorine atom; a chlorine atom; a bromine atom; an iodine atom; a hydroxy group; a $C_1$-$C_6$ alkoxy group such as methoxy, ethoxy, propoxy, isopropoxy, butoxy, isobutoxy, s-butoxy, t-butoxy, pentyloxy or cyclopropyloxy; a methoxymethyloxy group; a 2-methoxyethoxy group; a formyl group; a trifluoroacetyl group; a $C_2$-$C_7$ acyl group such as acetyl, propionyl, butyryl, isobutyryl, valeryl or isovaleryl; an oxo group; a carboxyl group; a $C_2$-$C_7$ alkoxycarbonyl group such as methoxycarbonyl, ethoxycarbonyl, propoxycarbonyl, isopropoxycarbonyl, butoxycarbonyl, isobutoxycarbonyl or t-butoxycarbonyl; a carbamoyl group; a $C_2$-$C_7$ alkylcarbamoyl group such as N-methylcarbamoyl, N,N-dimethylcarbamoyl, N-ethylcarbamoyl, N-ethyl-N-methylcarbamoyl, N,N-diethylcarbamoyl, N-propylcarbamoyl, N-isopropylcarbamoyl, N-butylcarbamoyl, N-cyclopropyl-carbamoyl or N-cyclopropylmethylcarbamoyl; an amino group; a $C_1$-$C_6$ alkylamino group such as methylamino, ethylamino, propylamino, isopropylamino, dimethylamino, N-ethylmethylamino, diethylamino, N-methylpropylamino, N-methylisopropylamino, cyclopropylamino or cyclopropylmethylamino; a $C_4$-$C_6$ cyclic amino group having 1 or 2 atoms selected from the group consisting of an oxygen atom, a nitrogen atom and a sulfur atom, in the ring, such as 1-pyrrolidinyl, piperazinyl, 4-methylpiperazinyl, piperidino or morpholino; a trifluoroacetylamino group; a $C_1$-$C_7$ acylamino group such as formylamino, acetylamino, propionylamino, butyrylamino, isobutyrylamino or valerylamino; a $C_1$-$C_6$-alkylsulfonylamino group such as methylsulfonylamino, ethylsulfonylamino, propylsulfonylamino or butylsulfonylamino; a nitro group; a cyano group; a $C_1$-$C_6$ alkyl group including methyl, ethyl, propyl, isopropyl, butyl, isobutyl, s-butyl, and t-butyl; a trifluoromethyl group; and a trifluoromethoxy group).

Among those exemplified as substituents of the heterocyclic group having 1 to 4 atoms selected from the group consisting of an oxygen atom, a nitrogen atom and a sulfur atom on the ring of $R^3$, preferred examples thereof include: a fluorine atom; a chlorine atom; a bromine atom; an iodine atom; a hydroxy group; a cyano group; a nitro group; an amino group; a $C_1$-$C_6$ mono or dialkylamino group consisting of a straight or branched alkyl group and an amino group, including a substituted or unsubstituted methylamino, ethylamino, propylamino, isopropylamino, butylamino, isobutylamino, s-butylamino, t-butylamino, pentylamino, hexylamino, dimethylamino, N-ethylmethylamino, diethylamino, N-methylpropylamino, N-methylisopropylamino, N-methylbutylamino, N-methyl-t-butylamino, N-ethylisopropylamino, dipropylamino, diisopropylamino and ethylbutylamino; a carboxyl group; a saturated a $C_1$-$C_6$ alkyl group including a substituted or unsubstituted methyl, ethyl, propyl, isopropyl, butyl, isobutyl, s-butyl, t-butyl, pentyl, isopentyl, neopentyl, t-pentyl, hexyl, isohexyl, 2-methylpentyl and 1-ethylbutyl; an alicyclic hydrocarbon group having 3 to 6 carbon atoms including cyclopropyl, cyclobutyl, cyclopentyl and cyclohexyl; a $C_1$-$C_6$ alkoxy group consisting of a straight or branched alkyl group and an oxy group, including a substituted or unsubstituted methoxy, ethoxy, propoxy, isopropoxy, butoxy, isobutoxy, s-butoxy, t-butoxy, pentyloxy, isopentyloxy, neopentyloxy, t-pentyloxy and hexyloxy; a $C_2$-$C_7$ acyl group including a substituted or unsubstituted acetyl, propionyl, butyryl, isobutyryl, pivaroyl and hexanoyl; a $C_1$-$C_6$ alkylthio group, including methylthio, ethylthio, propylthio, isopropylthio, butylthio, isobutylthio, s-butylthio, t-butylthio, pentylthio and hexylthio; a trifluoromethyl group; a trifluoromethoxy group; a $C_2$-$C_7$ acylamino group including a substituted or unsubstituted acetylamino, propionylamino, butyrylamino, isobutyrylamino, valerylamino and hexanoylamino; and a $C_2$-$C_7$ alkylcarbamoyl group consisting of a straight or branched alkyl group and a carbamoyl group including a substituted or unsubstituted N-methylcarbamoyl, N-ethylcarbamoyl, N-propylcarbamoyl, N-isopropylcarbamoyl, N-butylcarbamoyl, N-isobutylcarbamoyl, N-s-butylcarbamoyl, N-t-butylcarbamoyl, N-pentylcarbamoyl, N,N-dimethylcarbamoyl, N-ethyl-N-methylcarbamoyl and N,N-diethylcarbamoyl.

More preferred substituents of the heterocyclic group having 1 to 4 atoms selected from the group consisting of an oxygen atom, a nitrogen atom and a sulfur atom on the ring of $R^3$, include a fluorine atom, a chlorine atom, a bromine atom, a substituted or unsubstituted $C_1$-$C_6$ alkyl group, a hydroxy group, and a substituted or unsubstituted $C_1$-$C_6$ alkoxy group. Specifically, a methyl group and an ethyl group are preferred.

In the formula (I), $A^6$ is a group that links $R^3$ and a carbon atom of a pyrrole ring in the form of $R^3$—$CR^{308}$=$CR^{309}$-pyrrole ring or $R^3$—C≡C-pyrrole ring. $R^3$ represents a trimethylsilyl group, a formyl group, an optionally substituted $C_2$-$C_7$ acyl group, a carboxyl group, a $C_2$-$C_7$ alkoxycarbonyl group, a carbamoyl group, an optionally substituted $C_2$-$C_7$ alkylcarbamoyl group or a cyano group, preferred examples thereof include a formyl group, an acetyl group, a carboxyl group, a methoxycarbonyl group, an ethoxycarbonyl group and a cyano group.

Here, an explanation will be given of preferred combinations of $R^3$ and $A^6$ in the formula (I).

As combinations of $R^3$ and $A^6$ of the formula (I) in the present invention, when $R^3$ represents a fluorine atom, a chlorine atom, a bromine atom, or an iodine atom, $A^3$ represents a single bond.

Also, when $R^3$ represents a trimethylsilyl group, a formyl group, an optionally substituted a $C_2$-$C_7$ acyl group, a carboxyl group, a $C_2$-$C_7$ alkoxycarbonyl group, a carbamoyl group, an optionally substituted $C_2$-$C_7$ alkylcarbamoyl group, or a cyano group, A is a group that links a carbon atom of a pyrrole ring in which $R^3$ and $A^6$ are linked to each other in the form of a carbon atom of $R^3$—$CR^{308}$=$CR^{309}$-pyrrole ring or $R^3$—C≡C-pyrrole carbon atom.

Preferred combinations of $R^3$ and $A^6$ of the formula (I) in the present invention include cases where $A^6$ represents a single bond and $R^3$ represents an optionally substituted aromatic hydrocarbon group having 6 to 14 carbon atoms or an optionally substituted heterocyclic group. Among them, a case where $R^3$ represents a thienyl group, a furyl group, a pyrrolyl group, a pyrazolyl group or a phenyl group optionally substituted with one or more alkyl group having 1 to 4 carbon atoms is preferred.

Also a case where $A^6$ represents a single bond, and $R^3$ represents a pyridyl group or 1-oxypyridyl group or pyrazolyl group or N-methylpyrazolyl group optionally substituted by an alkyl group having 1 to 4 carbon atoms or one halogen atom.

In addition, the following combinations can be mentioned: a combination in which $A^6$ represents a single bond, and $R^3$ is a fluorine atom, chlorine atom, bromine atom, or iodine atom, a combination in which $A^6$ represents a single bond, and $R^3$ is a substituted or unsubstituted saturated acyclic saturated aliphatic hydrocarbon group having 1 to 10 carbon atoms; a combination in which $A^6$ represents a single bond, and $R^3$ is a substituted or unsubstituted alicyclic hydrocarbon group having 3 to 8 carbon atoms; a combination in which $A^6$ represents a single bond, and $R^3$ is a substituted or unsubstituted aromatic hydrocarbon group having 6 to 14 carbon atoms; a combination in which $A^6$ represents a single bond, and $R^3$ is a substituted or unsubstituted monocyclic $C_3$-$C_5$ aromatic heterocyclic group having 1 or 2 atoms selected from the group consisting of an oxygen atom, a nitrogen atom and a sulfur atom, in the ring; a combination in which $A^6$ is a group that links $R^3$ and a carbon atom of a pyrrole ring in which $A^6$ is linked in the form of the carbon atom of a $R^3$—NH—C(=O)- pyrrole ring, and $R^3$ is a hydrogen atom; a combination in which $A^6$ is a group that links $R^3$ and a carbon atom of a pyrrole ring in which $A^6$ is linked in the form of the carbon atom of a $R^3$—C(=O)—NH-pyrrole ring, and $R^3$ is a substituted or unsubstituted acyclic saturated aliphatic hydrocarbon group having 1 to 10 carbon atoms; a combination in which $A^6$ is a group that links $R^3$ and a carbon atom of a pyrrole ring in which $A^6$ is linked in the form of the carbon atom of the carbon atom of a $R^3$—C(=O)—NH-pyrrole ring, and $R^3$ is a substituted or unsubstituted alicyclic hydrocarbon group having 3 to 8 carbon atoms; a combination in which $A^6$ is a group that links $R^3$ and a carbon atom of a pyrrole ring in which $A^6$ is linked in the form of the carbon atom of a $R^3$—C(=O)—NH-pyrrole ring, and $R^3$ is a substituted or unsubstituted aromatic hydrocarbon group having 6 to 14 carbon atoms; a combination in which $A^6$ is a group that links $R^3$ and a carbon atom of a pyrrole ring in which $A^6$ is linked in the form of the carbon atom of the $R^3$—C(=O)—NH-pyrrole ring, and $R^3$ is a monocyclic $C_3$-$C_5$ aromatic heterocyclic group having 1 or 2 atoms selected from the group consisting of an oxygen atom, a nitrogen atom and a sulfur atom on the substituted or unsubstituted ring; a combination in which $A^6$ is a group that links $R^3$ and a carbon atom of a pyrrole ring in which $A^6$ is linked in the form of the carbon atom of a $R^3$—NH-pyrrole ring, and $R^3$ is a hydrogen atom; a combination in which $A^6$ is a group that links $R^3$ and a carbon atom of a pyrrole ring in which $A^6$ is linked in the form of the carbon atom of a $R^3$—NH-pyrrole ring, and $R^3$ is a substituted or unsubstituted acyclic saturated aliphatic hydrocarbon group having 1 to 10 carbon atoms; a combination in which $A^6$ is a group that links $R^3$ and a carbon atom of a pyrrole ring in which $A^6$ is linked in the form of the carbon atom of a $R^3$—NH-pyrrole ring, and $R^3$ is a substituted or unsubstituted alicyclic hydrocarbon group having 3 to 8 carbon atoms; a combination in which $A^6$ is a group that links $R^3$ and a carbon atom of a pyrrole ring in which $A^6$ is linked in the form of the carbon atom of a $R^3$—NH-pyrrole ring, and $R^3$ is a substituted or unsubstituted aromatic hydrocarbon group having 6 to 14 carbon atoms; a combination in which $A^6$ is a group that links $R^3$ and a carbon atom of a pyrrole ring in which $A^6$ is linked in the form of the carbon atom of $R^3$—NH-pyrrole ring, and $R^3$ is a monocyclic $C_3$-$C_5$ aromatic heterocyclic group having 1 or 2 atoms selected from the group consisting of an oxygen atom, a nitrogen atom and a sulfur atom on the substituted or unsubstituted ring; a combination in which $A^6$ is a group that links $R^3$ and a carbon atom of a pyrrole ring in which $A^6$ is linked in the form of the carbon atom of a $R^3$—HC=CH-pyrrole ring, and $R^3$ is a hydrogen atom; a combination in which $A^6$ is a group that links $R^3$ and a carbon atom of a pyrrole ring in which $A^6$ is linked to each other in the form of the carbon atom of a $R^3$—HC=CH-pyrrole ring, and $R^3$ is a substituted or unsubstituted acyclic saturated aliphatic hydrocarbon group having 1 to 10 carbon atoms; a combination in which $A^6$ is a group that links a carbon atom of a pyrrole ring in which $R^3$ and $A^6$ are linked to each other in the form of the carbon atom of a $R^3$—HC=CH-pyrrole ring, and $R^3$ is a substituted or unsubstituted alicyclic hydrocarbon group having 3 to 8 carbon atoms; a combination in which $A^6$ is a group that links $R^3$ and a carbon atom of a pyrrole ring in which $A^6$ is linked in the form of the carbon atom of a $R^3$—HC=CH-pyrrole ring, and $R^3$ is a substituted or unsubstituted aromatic hydrocarbon group having 6 to 14 carbon atoms; a combination in which $A^6$ is a group that links $R^3$ and a carbon atom of a pyrrole ring in which $A^6$ is linked in the form of the carbon atom of a $R^3$—HC=CH-pyrrole ring, and $R^3$ is a monocyclic $C_3$-$C_5$- aromatic heterocyclic group having 1 or 2 atoms selected from the group consisting of an oxygen atom, a nitrogen atom and a sulfur atom on the substituted or unsubstituted ring; a combination in which $A^6$ is a group that links $R^3$ and a carbon atom of a pyrrole ring in which $A^6$ is linked in the form of the carbon atom of a $R^3$—C≡C-pyrrole ring, and $R^3$ is a hydrogen atom; a combination in which $A^6$ is a group that links $R^3$ and a carbon atom of a pyrrole ring in which $A^6$ is linked in the form of the carbon atom of a $R^3$—C≡C-pyrrole ring, and $R^3$ is a substituted or unsubstituted acyclic saturated aliphatic hydrocarbon group having 1 to 10 carbon atoms; a combination in which $A^6$ is a group that links $R^3$ and a carbon atom of a pyrrole ring in which $A^6$ is linked in the form of the carbon atom of a $R^3$—C≡C-pyrrole ring, and $R^3$ is a substituted or unsubstituted alicyclic hydrocarbon group having 3 to 8 carbon atoms; a combination in which $A^6$ is a group that links $R^3$ and a carbon atom of a pyrrole ring in which $A^6$ is linked in the form of the carbon atom of a $R^3$—C≡C-pyrrole ring, and $R^3$ is a substituted or unsubstituted aromatic hydrocarbon group having 6 to 14 carbon atoms; a combination in which $A^6$ is a group that links $R^3$ and a carbon atom of a pyrrole ring in which $A^6$ is linked in the form of the carbon atom of a $R^3$—C≡C-pyrrole ring, and $R^3$ is a monocyclic $C_3$-$C_5$ aromatic heterocyclic group having 1 or 2 atoms selected from the group consisting of an oxygen atom, a nitrogen atom and a sulfur atom on the substituted or unsubstituted ring; and a combination in which $A^6$ is a group that links $R^3$ and a carbon atom of a pyrrole ring in which $A^6$ is linked in the form of the carbon atom of a $R^3$—C≡C-pyrrole ring, and $R^3$ is a trimethylsilyl group or cyano group.

Here, an explanation will be given of preferred combinations of $R^2$-$A^5$ portion and $R^3$-$A^6$ portion in the formula (I).

Preferred combinations of $R^2$-$A^5$ portion and $R^3$-$A^6$ portion include cases where both of $A^5$ and $A^6$ represent a single bond. In this case, more preferred combinations include cases where $R^2$ represents a cyclopropyl group, a cyclobutyl group, a cyclopropylmethyl group, a methyl group, an ethyl group, a vinyl group, an isopropyl group, an isobutyl group or 2-methyl-1-propenyl group, and $R^3$ represents a pyridyl group or 1-oxypyridyl group or pyrazolyl group or N-methylpyrazolyl group optionally substituted with one alkyl group having 1 to 4 carbon atoms or one halogen atom.

Also combinations wherein both of $A^5$ and $A^6$ represent a single bond, and $R^2$ represents a $C_1$-$C_4$ alkyl group, a $C_1$-$C_4$ alkoxy group, a $C_2$-$C_4$ acyl group, a hydroxy group, a carboxyl group, an alkoxycarbonyl group, a thienyl group, a pyridyl group, a furyl group, a pyrrolyl group, a pyrazolyl group or phenyl group which may be substituted by one or more of a fluorine atom or a chlorine atom, and $R^3$ represents a pyridyl group or 1-oxypyridyl group or pyrazolyl group or N-methylpyrazolyl group which may be substituted by one alkyl group having 1 to 4 carbon atoms or one halogen atom can be mentioned as preferred examples.

Further, an explanation will be given of preferred combinations of $A^1$-$G^2$ portion, $R^2$-$A^5$ portion and $R^3$-$A^6$ portion in the formula (I). Basically, preferably those mentioned as preferred examples for $A^1$-$G^2$ portion, $R^2$-$A^5$ portion and $R^3$-$A^6$ portion are combined, and more preferably more preferred examples are combined.

More specifically, in the combinations of the following a) to f) mentioned as preferred combinations of the $A^1$-$G^2$ portion, further a case where both of $A^5$ and $A^6$ represent a single bond is preferred.

a) $A^1$ represents —(CH$_2$)$_2$— or —(CH$_2$)$_3$—, $A^2$ represents —NH—(C=O)— or —NH—(C=O)—NH—, $G^1$ represents a single bond, and $A^3$ represents a divalent acyclic aliphatic hydrocarbon group having 1 to 10 carbon atoms.

b) $A^1$ represents —$(CH_2)_2$— or —$(CH_2)_3$—, $A^2$ represents —NH—C(=O)—, —NH—C(=O)—NH—, —NH—, or —C(=O)—NH—, and $G^1$ represents a group other than the single bond.

c) $A^1$ represents a divalent acyclic aliphatic hydrocarbon group having 1 to 6 carbon atoms, specifically —$(CH_2)_2$— or —$(CH_2)_3$—, $A^2$ represents a single bond, and $G^1$ represents an optionally substituted heterocyclic group (note, where a heterocyclic group of $G^1$ is 5 or 6 membered monocyclic ring, 5 or 6 membered monocyclic heterocyclic group of $G^1$ is substituted, or $A^3$-$G^2$ portion represents those other than a hydrogen atom).

d) $A^1$ represents a divalent acyclic aliphatic hydrocarbon group having 1 to 6 carbon atoms, specifically —$(CH_2)_2$— or —$(CH_2)_3$—, $A^2$ represents those other than a single bond, and $G^1$ represents an optionally substituted aromatic hydrocarbon group, an optionally substituted alicyclic hydrocarbon group having 7 to 10 carbon atoms, or an optionally substituted heterocyclic group (note, where the aromatic hydrocarbon group of $G^1$ is a phenyl group, or where the heterocyclic group of $G^1$ is 5 or 6 membered monocyclic ring, the phenyl group of $G^1$ or 5 or 6 membered monocyclic heterocyclic group is substituted, or $A^3$-$G^2$ portion represents those other than a hydrogen atom).

e) $A^1$ represents a divalent acyclic aliphatic hydrocarbon group having 1 to 6 carbon atoms, specifically —$(CH_2)_2$— or —$(CH_2)_3$—, $A^2$ represents those other than a single bond, $G^1$ and $A^4$ represent the single bond, $A^3$ represents an optionally substituted acyclic aliphatic hydrocarbon group having 1 to 10 carbon atoms, $G^2$ represents an optionally substituted alicyclic hydrocarbon group having 5 to 10 carbon atoms, an optionally substituted aromatic hydrocarbon group, or optionally substituted heterocyclic group.

f) $A^1$ represents a divalent acyclic aliphatic hydrocarbon group having 1 to 6 carbon atoms, specifically —$(CH_2)_2$— or —$(CH_2)_3$—, $A^2$ represents those other than a single bond, $G^1$ represents the single bond, $A^3$ represents an optionally substituted acyclic aliphatic hydrocarbon group having 1 to 10 carbon atoms, and $A^4$ represents —C(=O)—, —C(=O)—$NR^{121}$—, —C(=S)—$NR^{122}$—, —C(=$NR^{123}$)—, —O—C(=O)—, —$NR^{125}$—C(=O)—, —$NR^{126}$—S(=O)$_2$—, —$NR^{127}$—C(=O)—O—, —$NR^{128}$—C(=O)—$NR^{129}$—, —$NR^{130}$—C(=S)—, —$NR^{131}$—C(=S)—$NR^{132}$—, —S—, —S(=O)—, —S(=O)$_2$—, —S(=O)$_2$—$NR^{133}$— or —S(=O)$_2$—O—.

In the cases of d) to f), $A^2$ preferably represents —C(=O)—, —C(=O)—O—, —C(=O)—NH—, —C(=O)—NMe-, —NH—, —NH—C(=O)—, —NH—C(=O)—O—, —NH—C(=O)—NH—, —NH—C(=O)—NMe-, or —NH—C(=S)—, especially preferably represents —C(=O)—NH—, —NH—, —NH—C(=O)—, —NH—C(=O)—O—, or —NH—C(=O)—NH—.

In these cases of combinations, further preferably $R^2$ represents an optionally substituted acyclic aliphatic hydrocarbon group having 1 to 10 carbon atoms, an optionally substituted alicyclic hydrocarbon group having 3 to 8 carbon atoms, an optionally substituted aromatic hydrocarbon group having 6 to 14 carbon atoms or an optionally substituted heterocyclic group, and $R^3$ represents an optionally substituted aromatic hydrocarbon group having 6 to 14 carbon atoms or an optionally substituted heterocyclic group.

In further detail, in these cases, combinations wherein $R^2$ represents an aliphatic hydrocarbon group having 1 to 10 carbon atoms, an alicyclic hydrocarbon group having 3 to 8 carbon atoms, an optionally substituted phenyl group, or an optionally substituted heterocyclic group having 1 or 2 atoms selected from the group consisting of an oxygen atom, a nitrogen atom and a sulfur atom, in the ring, and $R^3$ represents a thienyl group, a pyridyl group, a furyl group, a pyrrolyl group, a pyrazolyl group or a phenyl group optionally substituted with one or more alkyl group having 1 to 4 carbon atoms are specifically preferred. Especially, preferred combinations can include cases where $R^2$ represents a cyclopropyl group, a methyl group, an ethyl group, a vinyl group, an isopropyl group, an isobutyl group or 2-methyl-1-propenyl group, and $R^3$ represents a pyridyl group or 1-oxypyridyl group or pyrazolyl group or N-methylpyrazolyl group which may be substituted by an alkyl group having 1 to 4 carbon atoms or one halogen atom, and cases where $R^2$ represents a thienyl group, a pyridyl group, a furyl group, a pyrrolyl group, a pyrazolyl group or phenyl group which may be substituted by one or more of a $C_1$-$C_4$ alkyl group, a $C_1$-$C_4$ alkoxy group, and a chlorine group, and $R^3$ represents a pyridyl group or 1-oxypyridyl group or pyrazolyl group or N-methylpyrazolyl group which may be substituted by an alkyl group having 1 to 4 carbon atoms or one halogen atom.

In the pyrrolo-pyrimidinone derivatives of the formula (I), specific preferred combinations of -$G^1$-$A^3$-$A^4$-$G^2$ portion include groups represented by the following formulae, K001-K431. In the respective chemical formula, symbol "- - -" is used to denote a binding site between $A^2$ and the group -$G^1$-$A^3$-$A^4$-$G^2$.

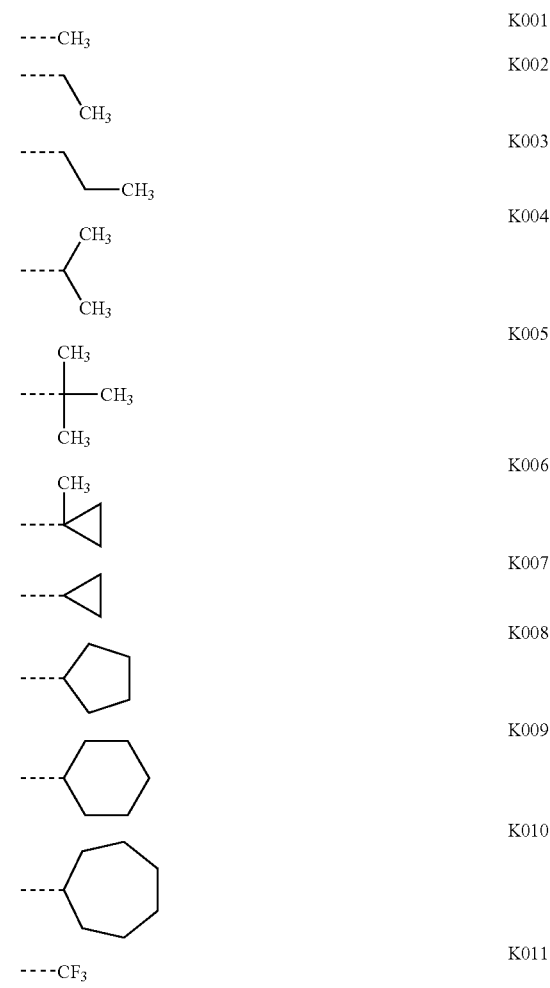

-continued
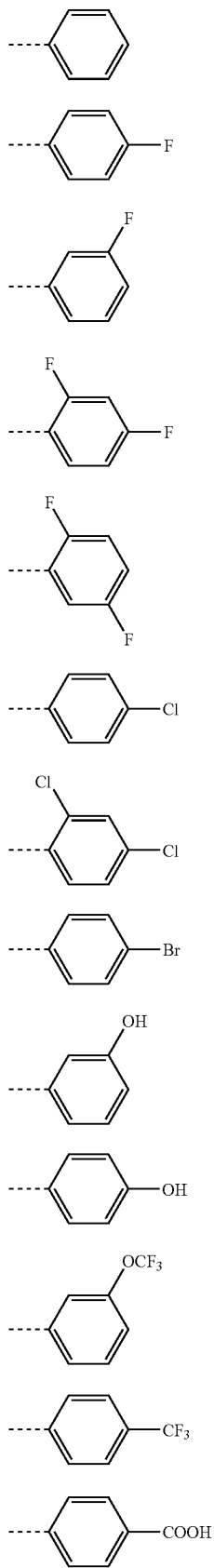
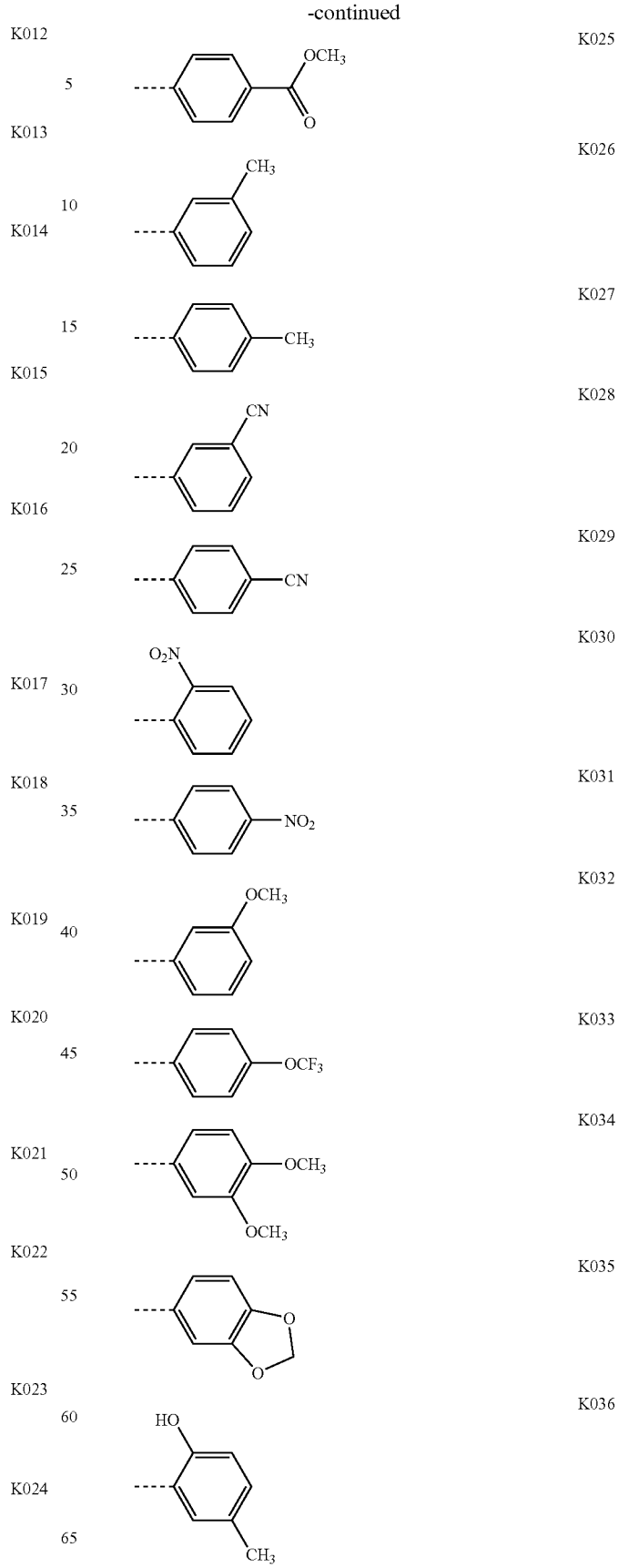

-continued
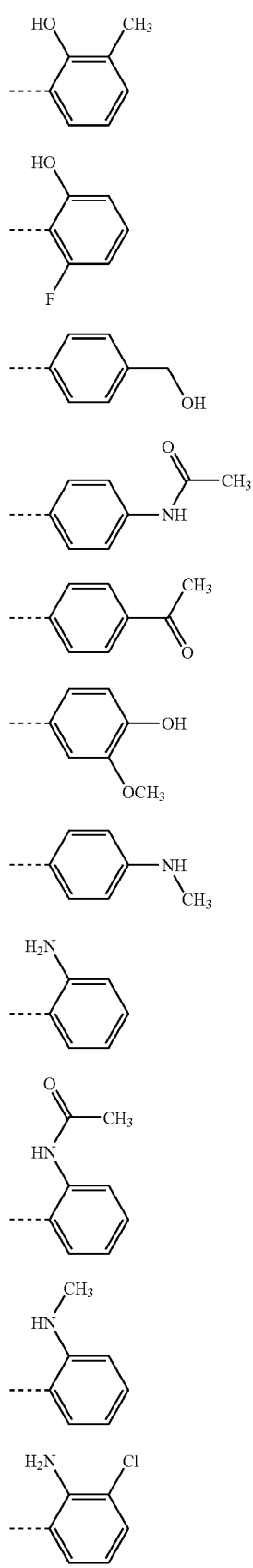
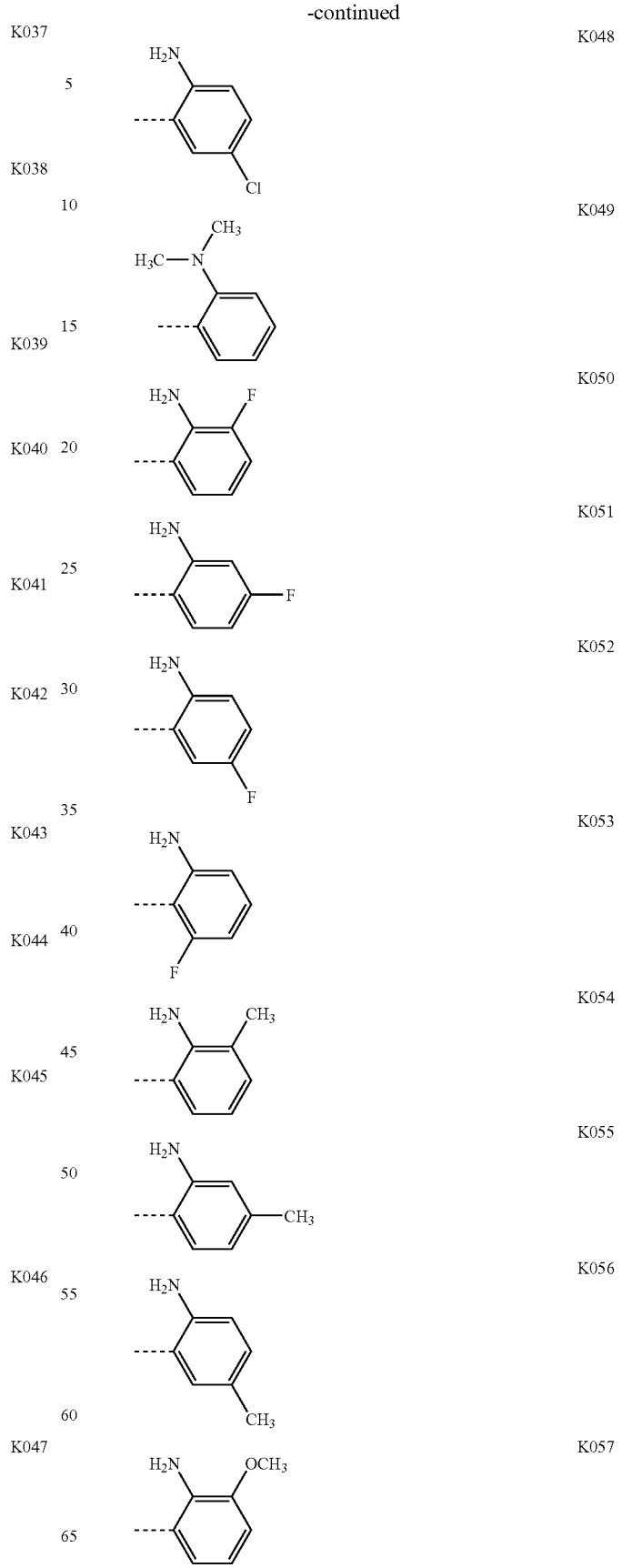

-continued
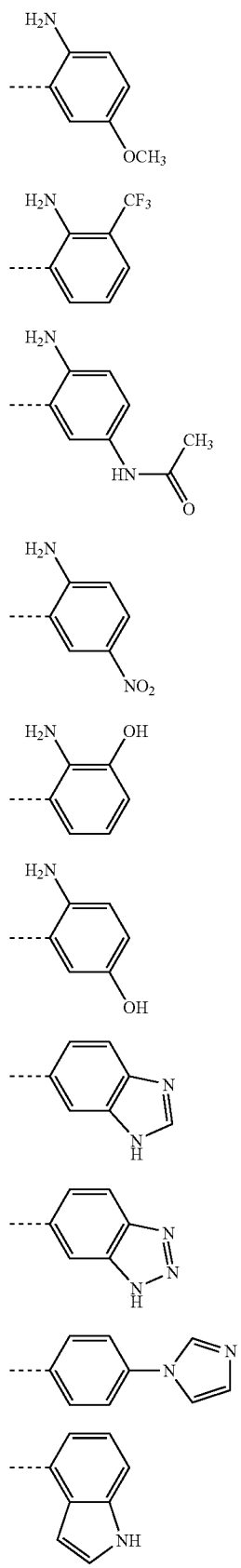
-continued
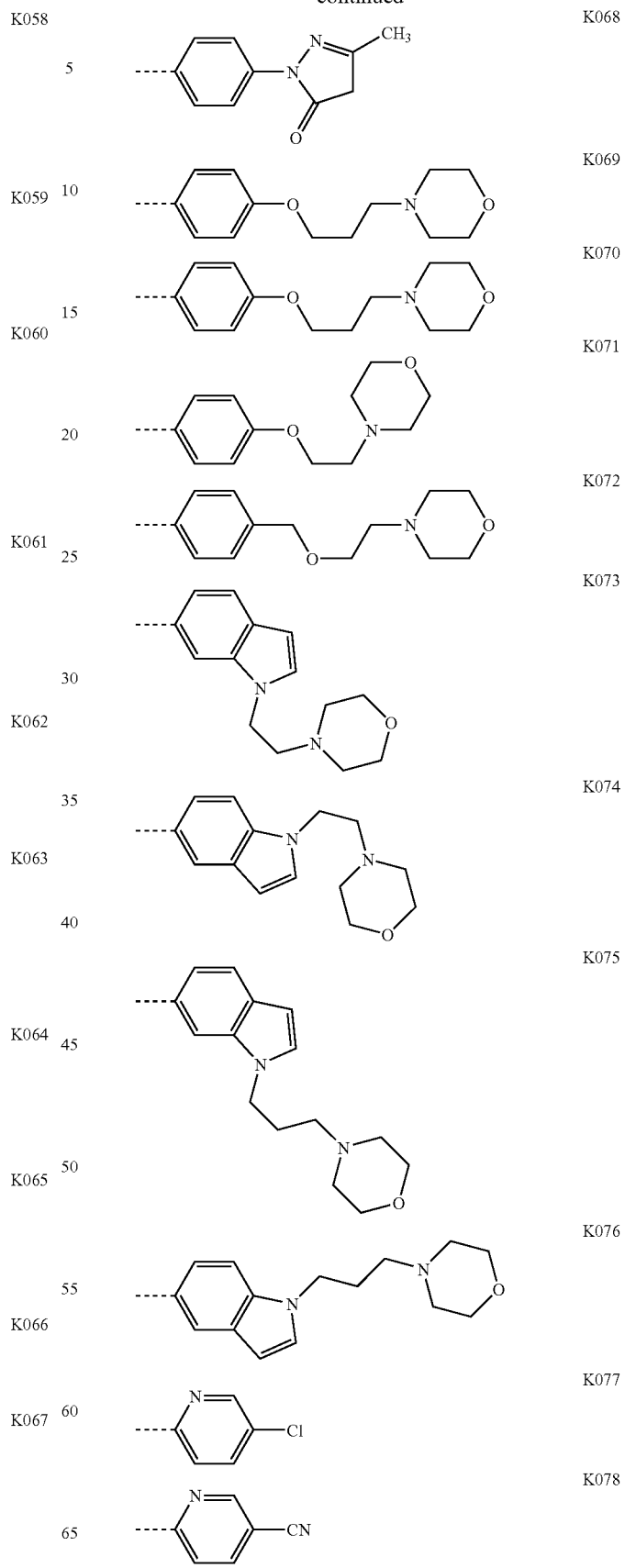

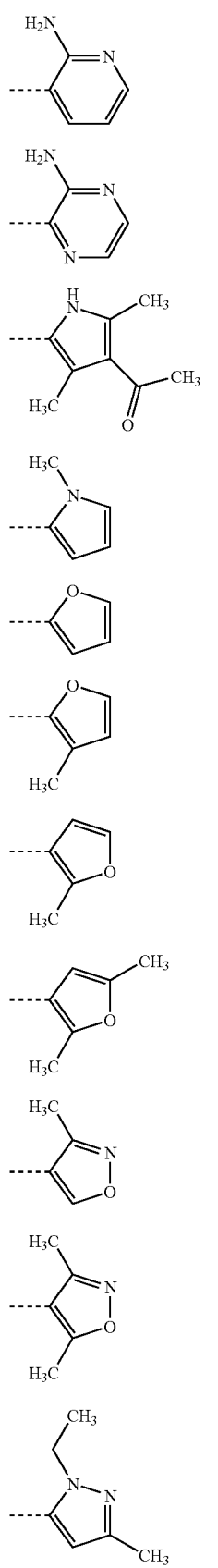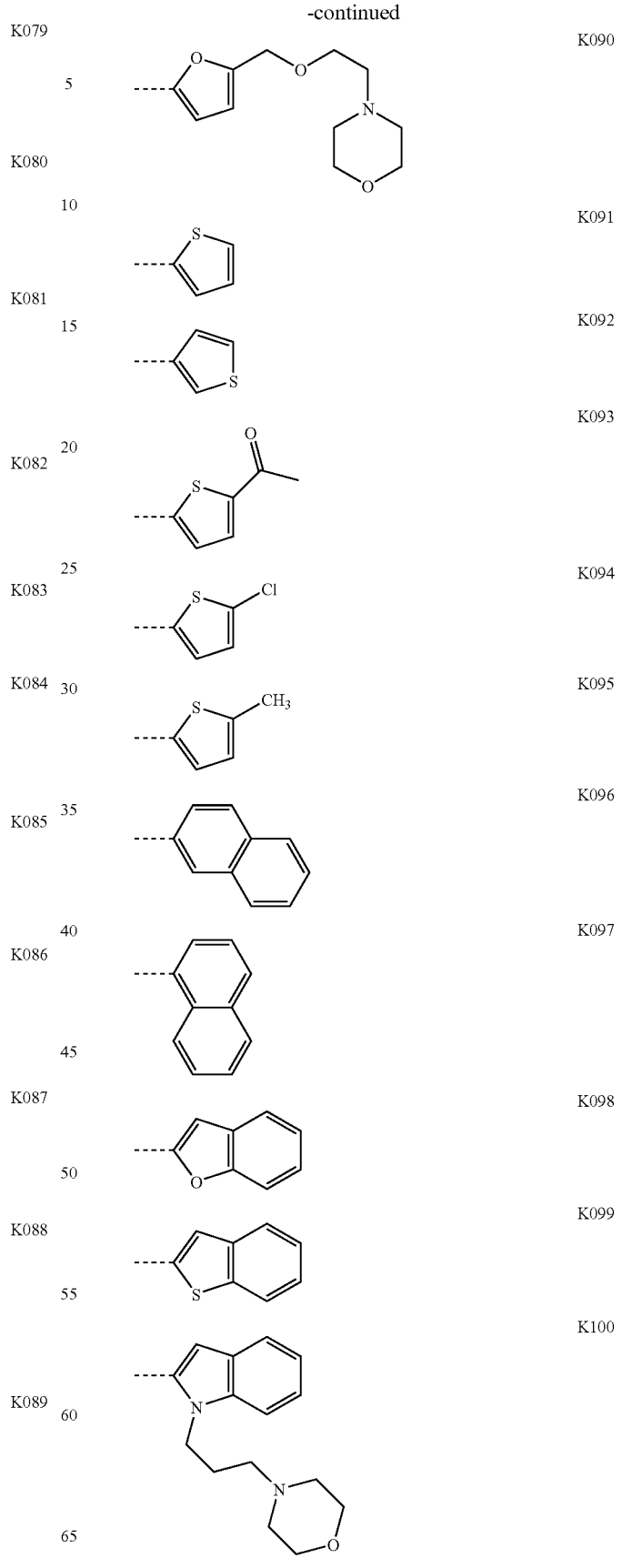

-continued
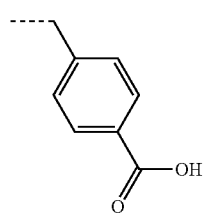
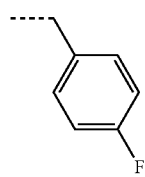
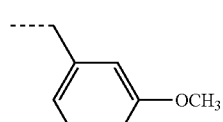
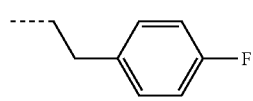
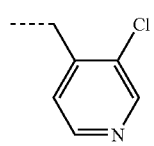
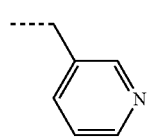
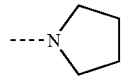
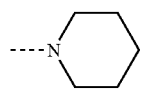
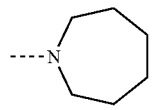
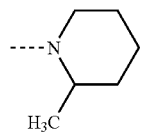
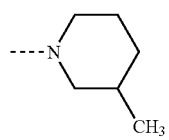
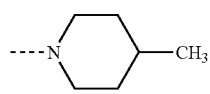
-continued
K101
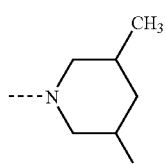
K102
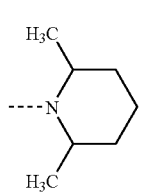
K103
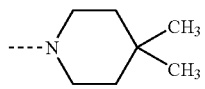
K104
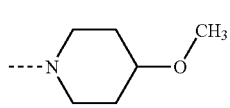
K105
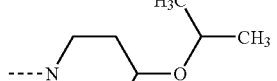
K106
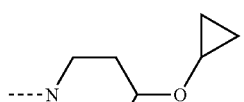
K107
K108
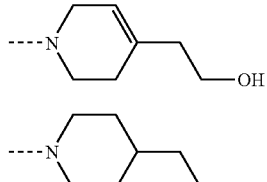
K109
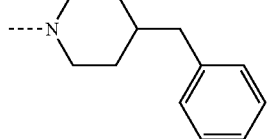
K110
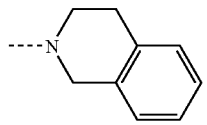
K111
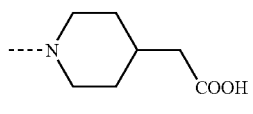
K112
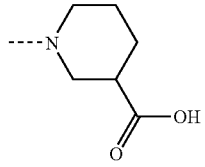
K113
K114
K115
K116
K117
K118
K119
K120
K121
K122
K123
K124

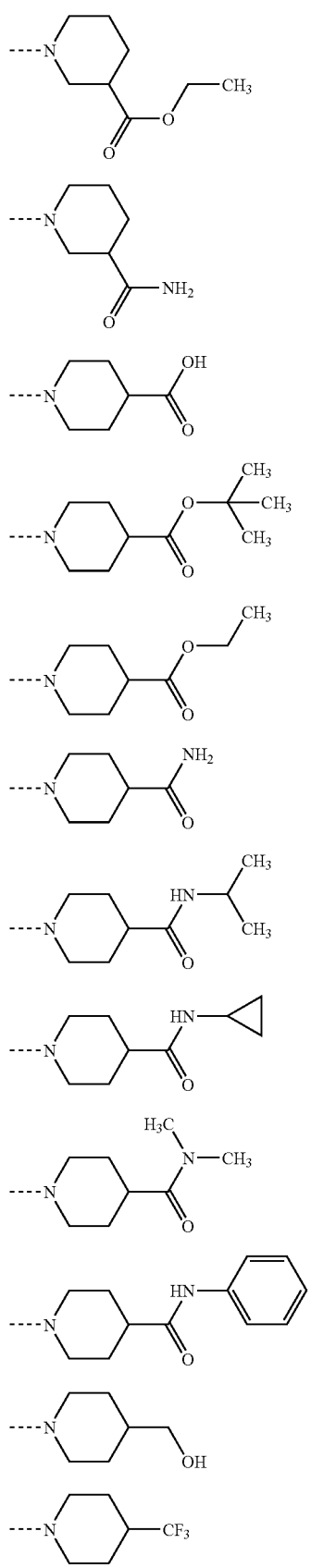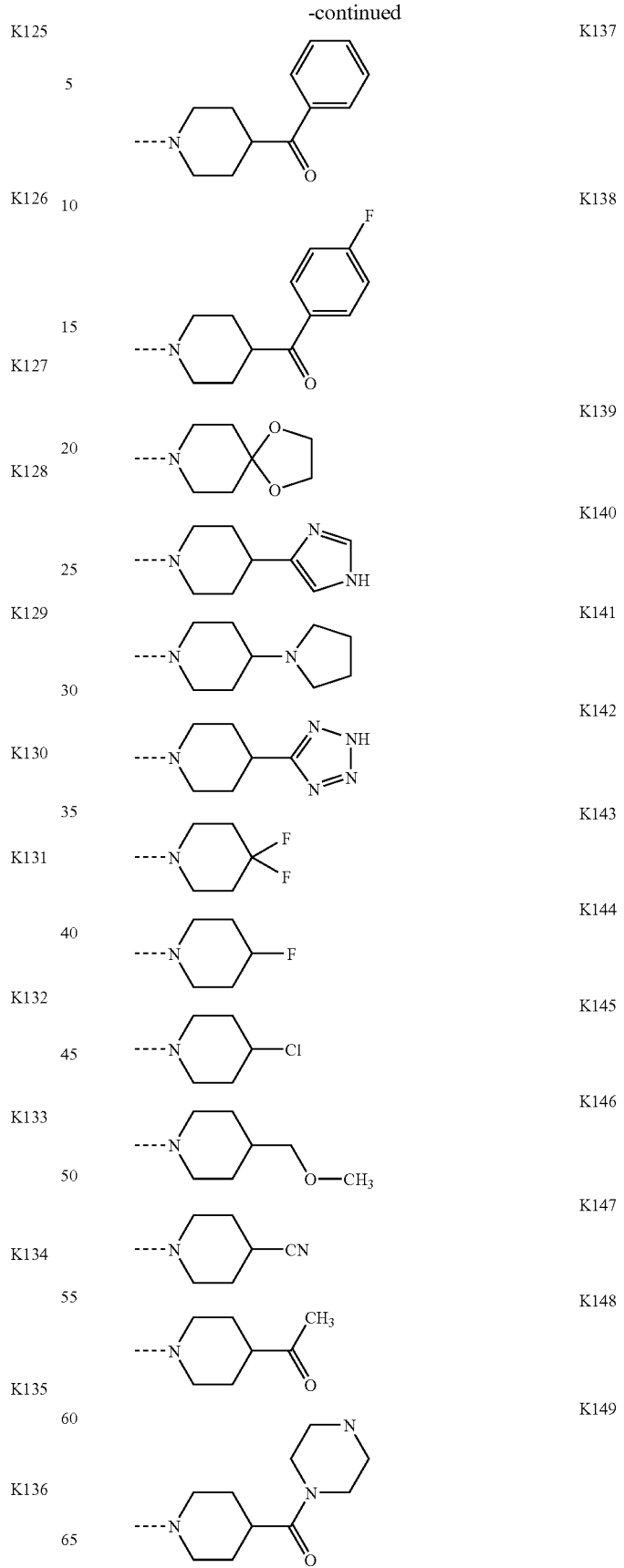

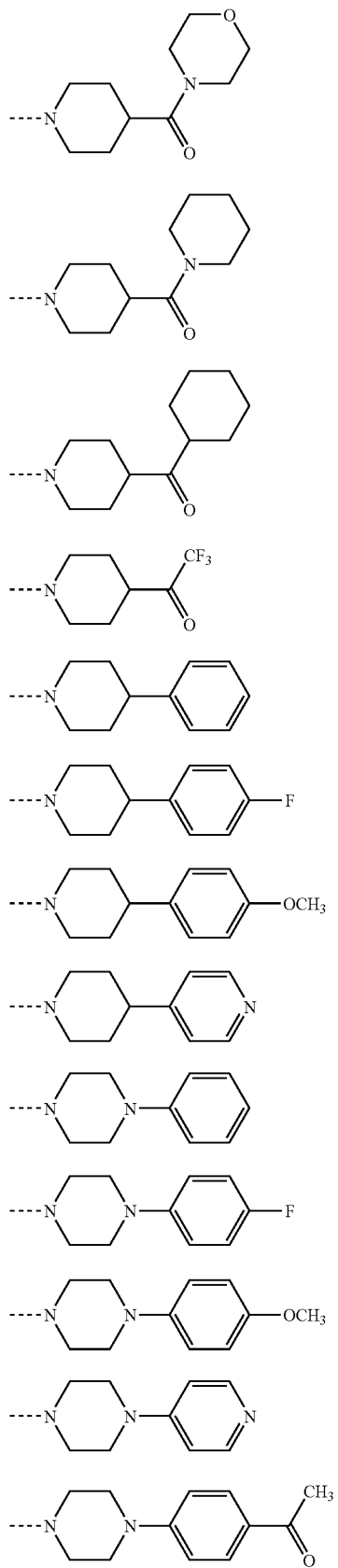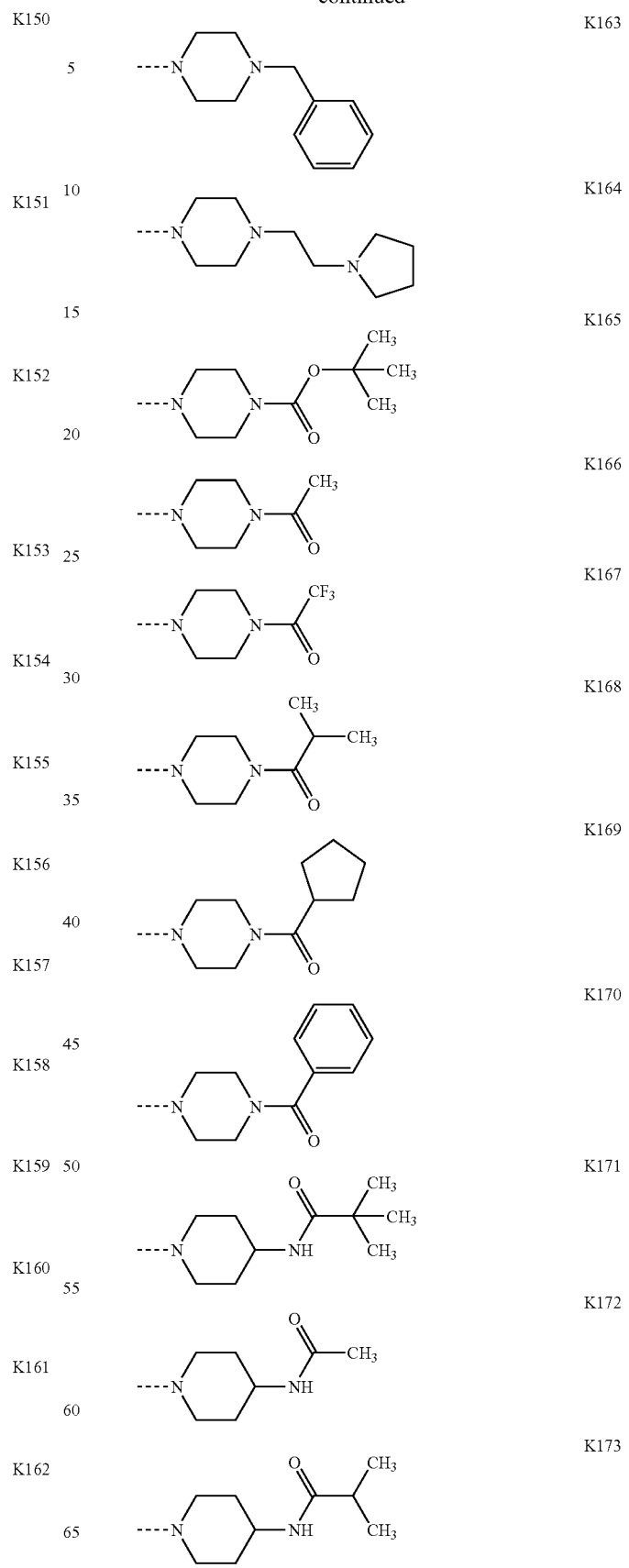

-continued
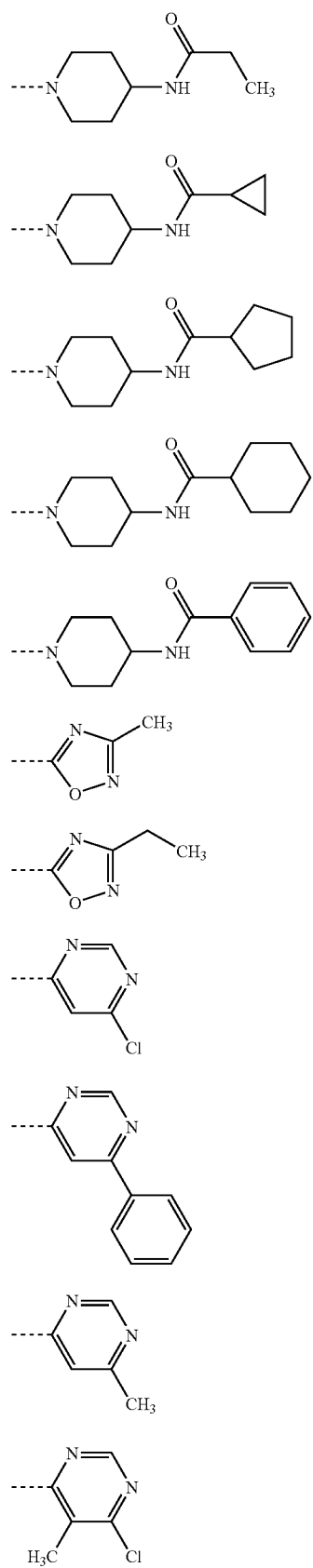
-continued
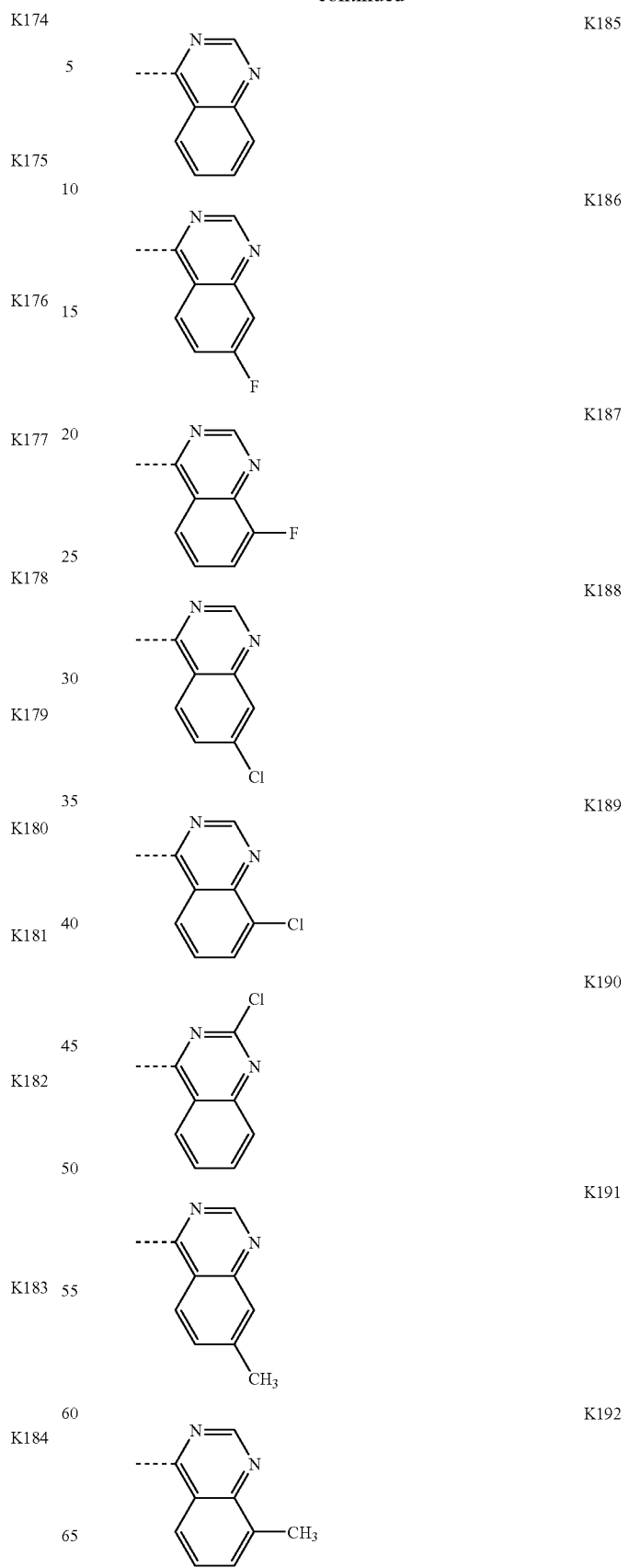

-continued
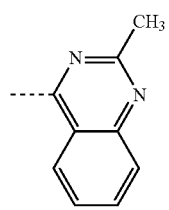 
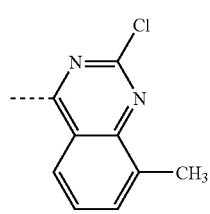
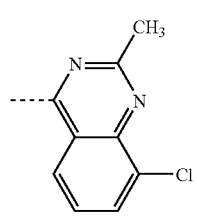
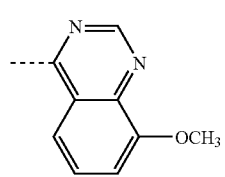
----H
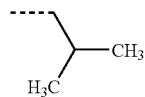
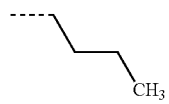
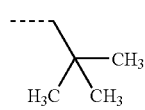
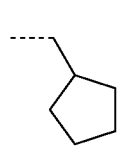
-continued
K193 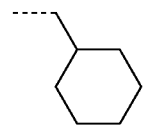 K204
K194 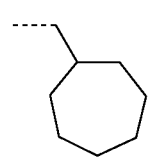 K205
 K206
K195 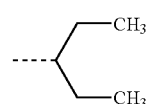 K207
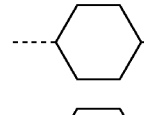 K208
K196 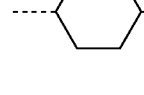 K209
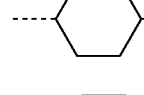 K210
K197 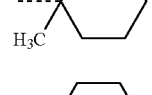 K211
K198 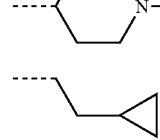 K212
K199  K213
K200 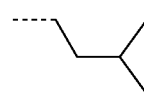 K214
K201 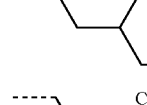 K215
K202 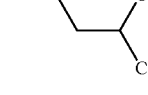 K216
K203 
 K217
 K218

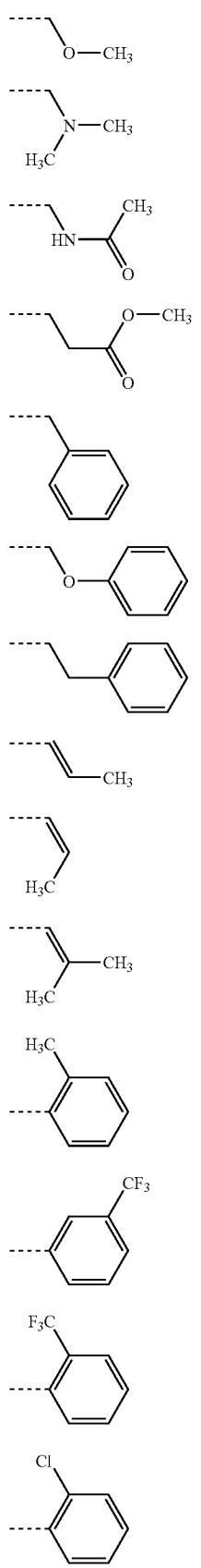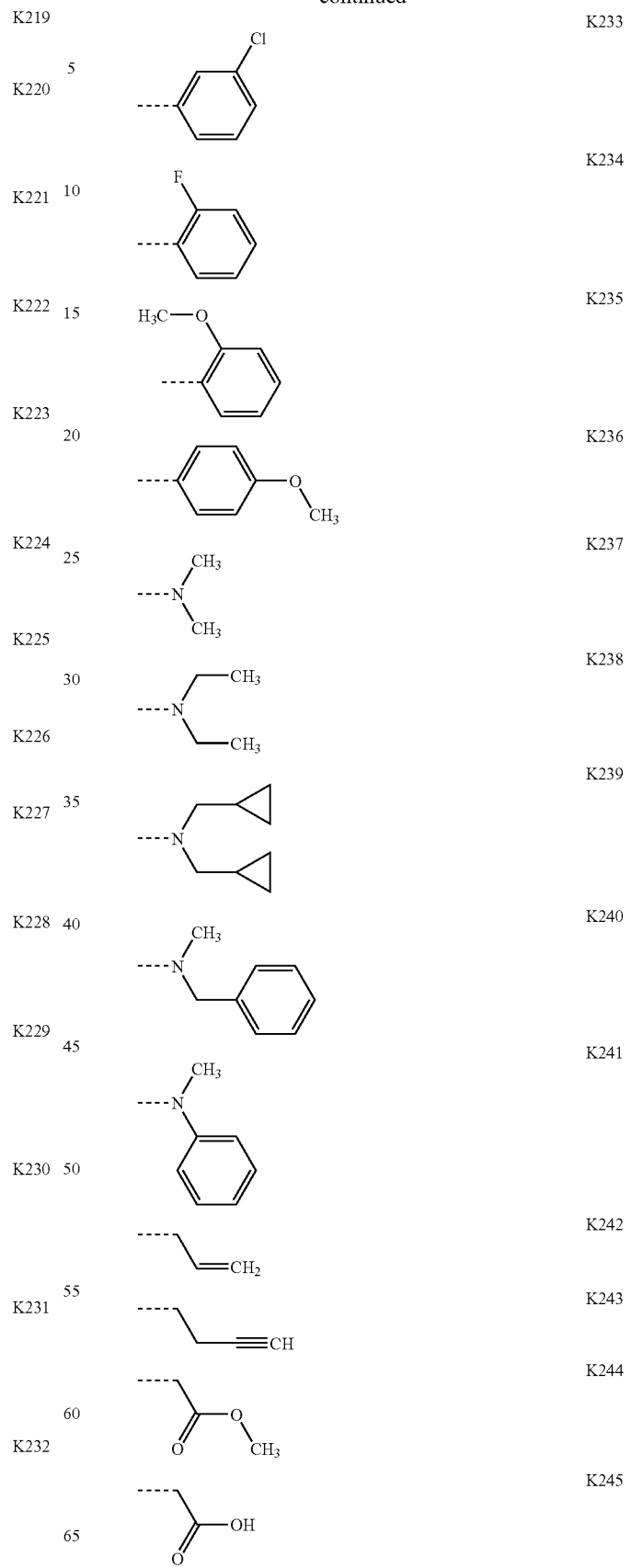

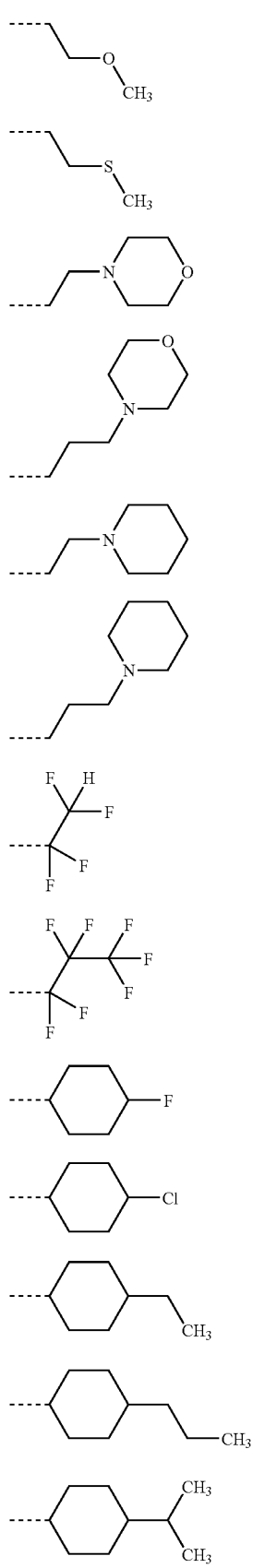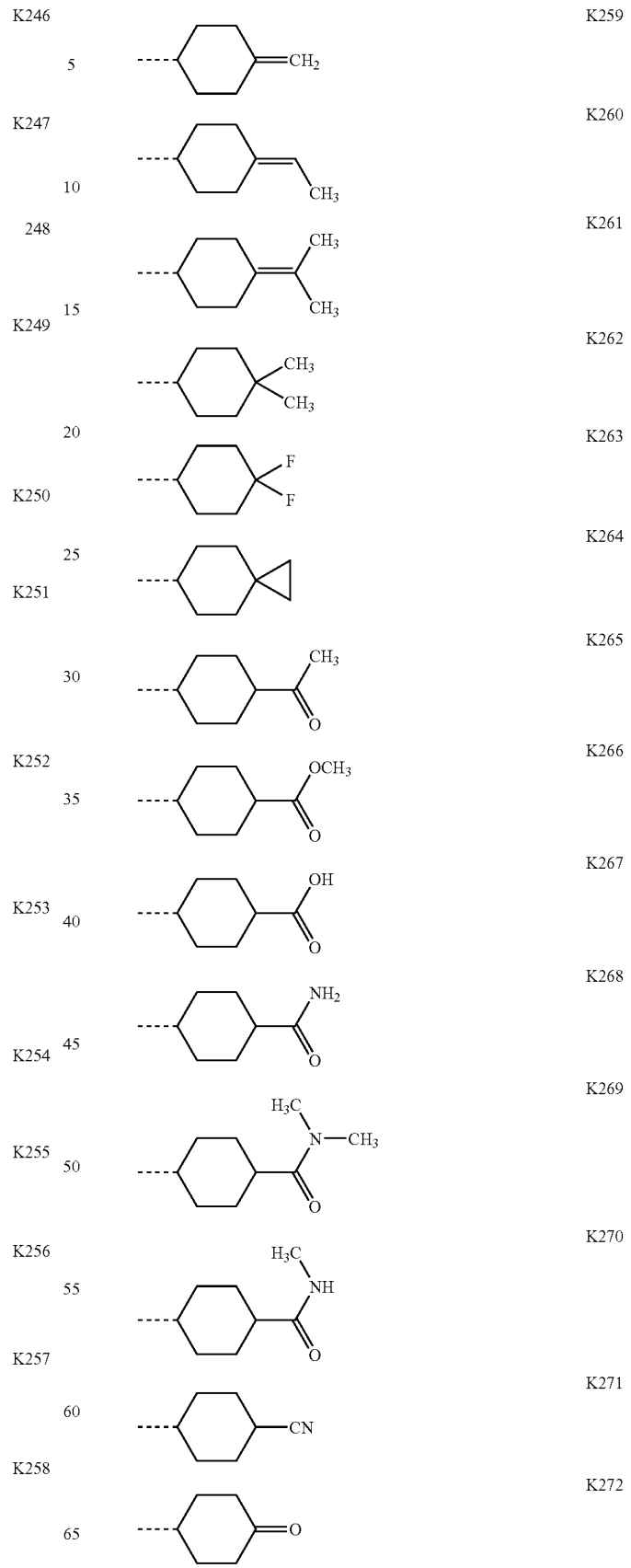

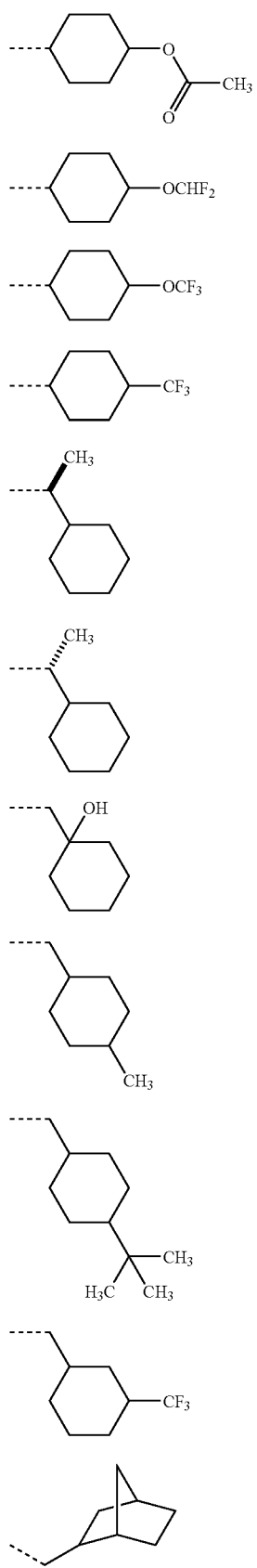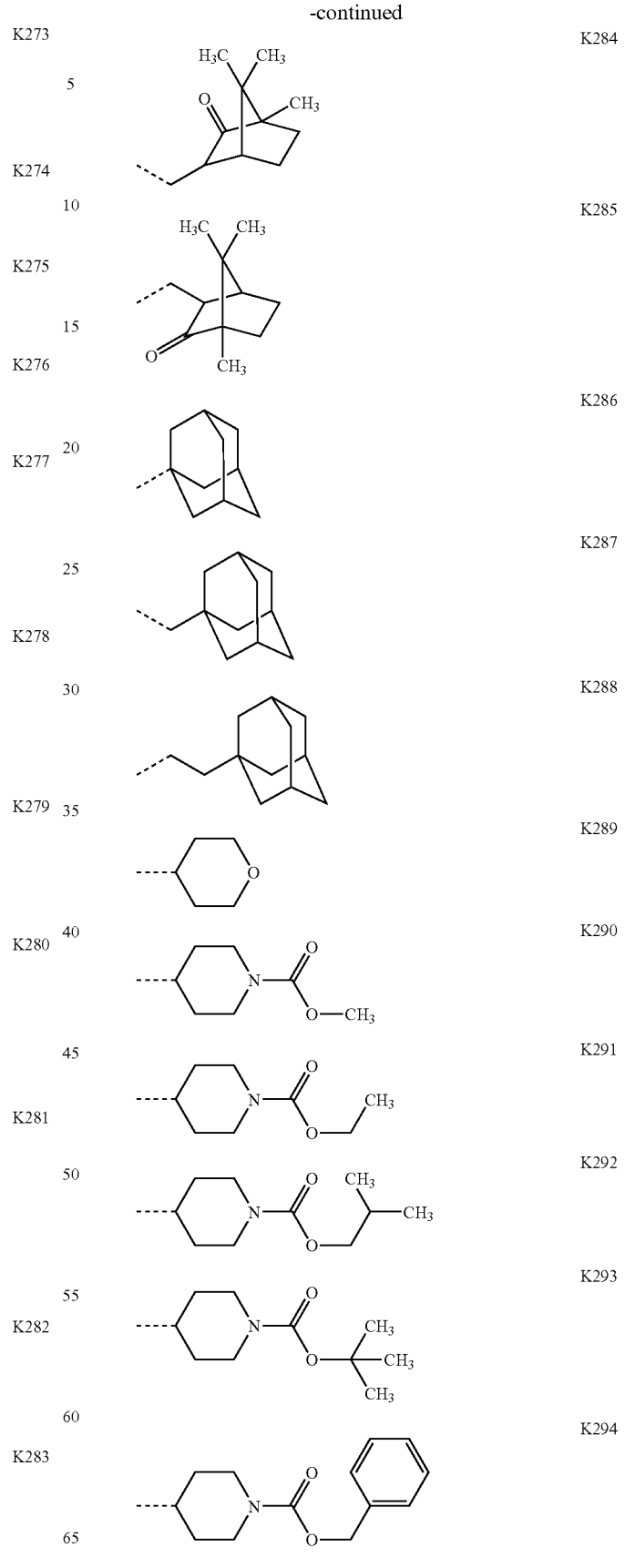

-continued
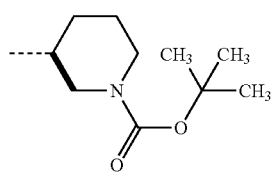
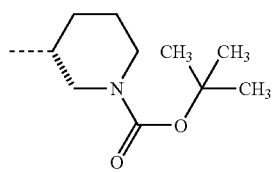
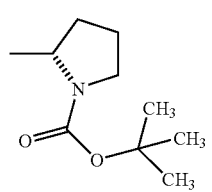
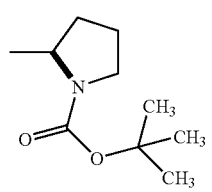
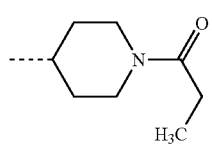
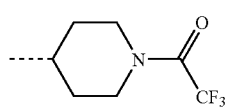
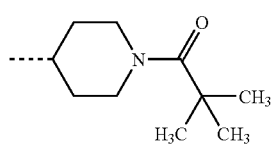
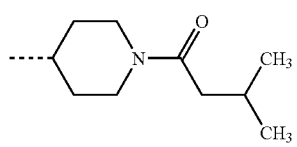
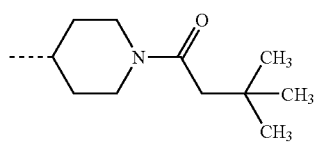
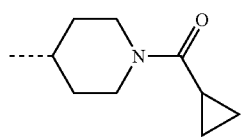
-continued
K295
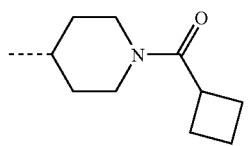 K305
K296
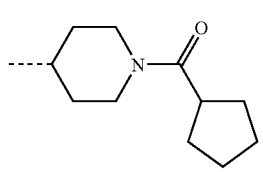 K306
K297
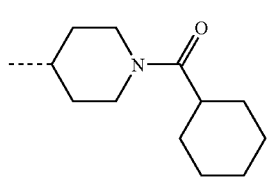 K307
K298
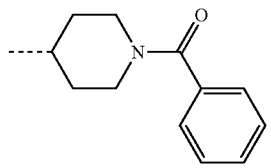 K308
K299
 K309
K300
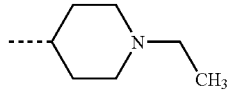 K310
K301
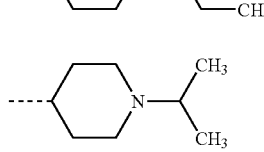 K311
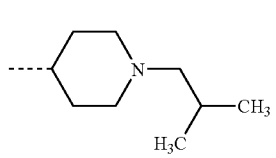 K312
K302
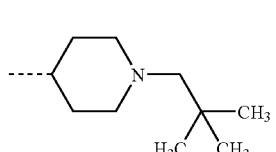 K313
K303
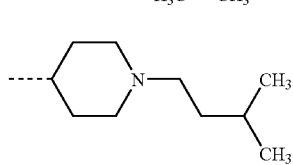 K314
K304
K315

-continued
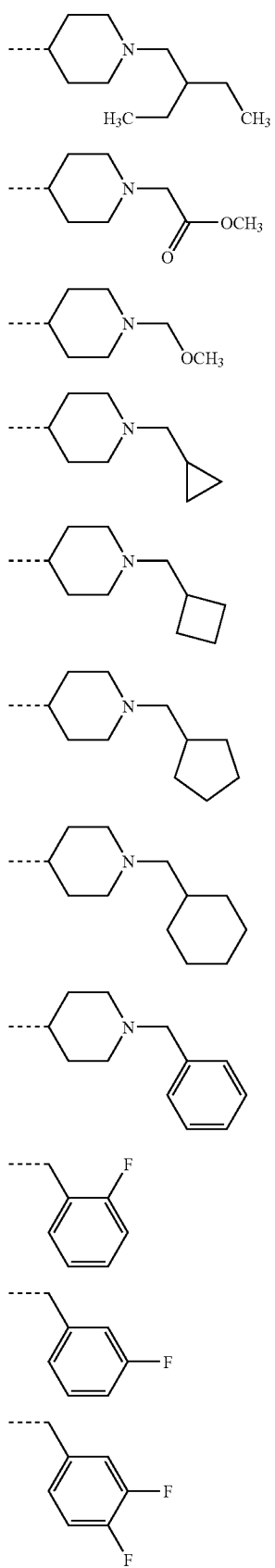
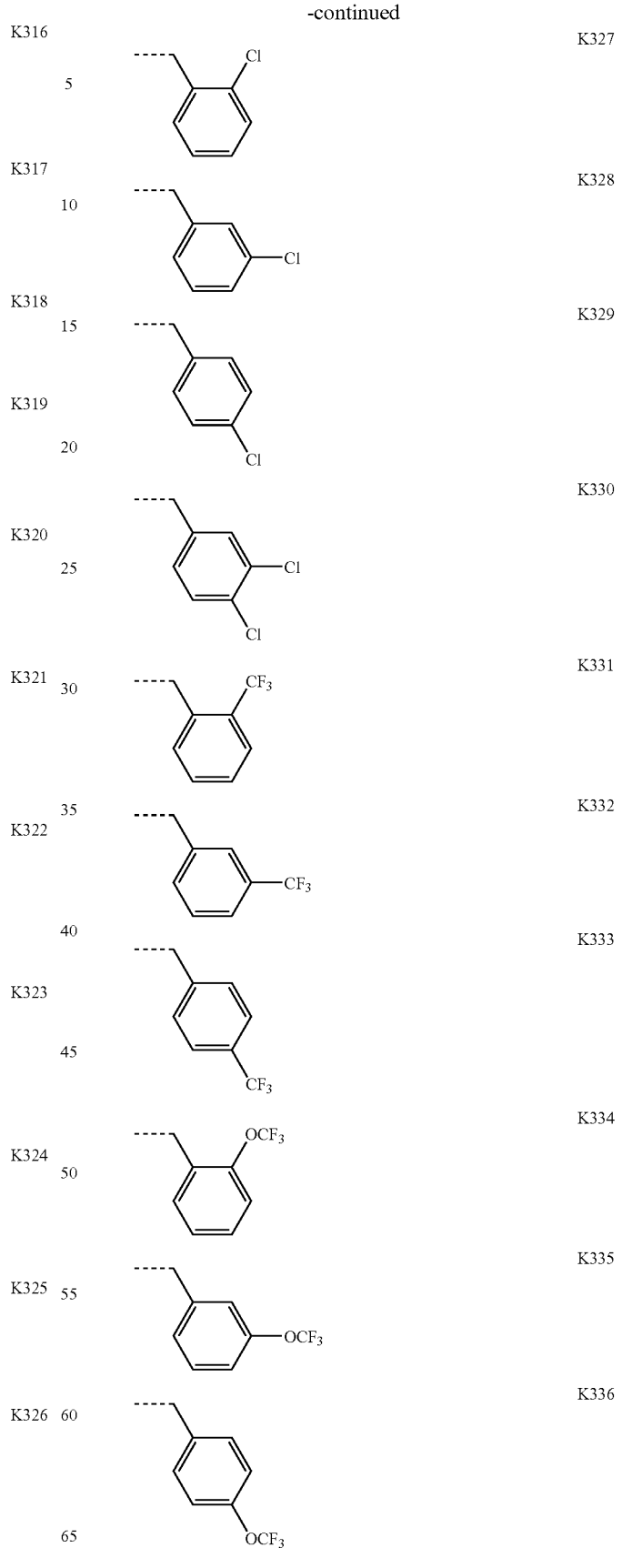

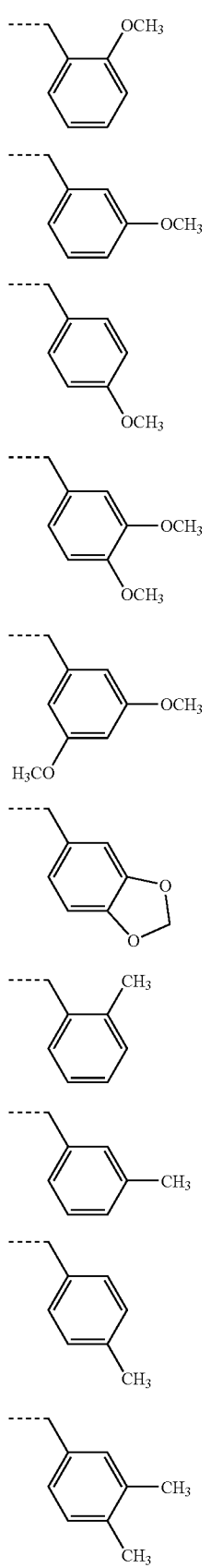
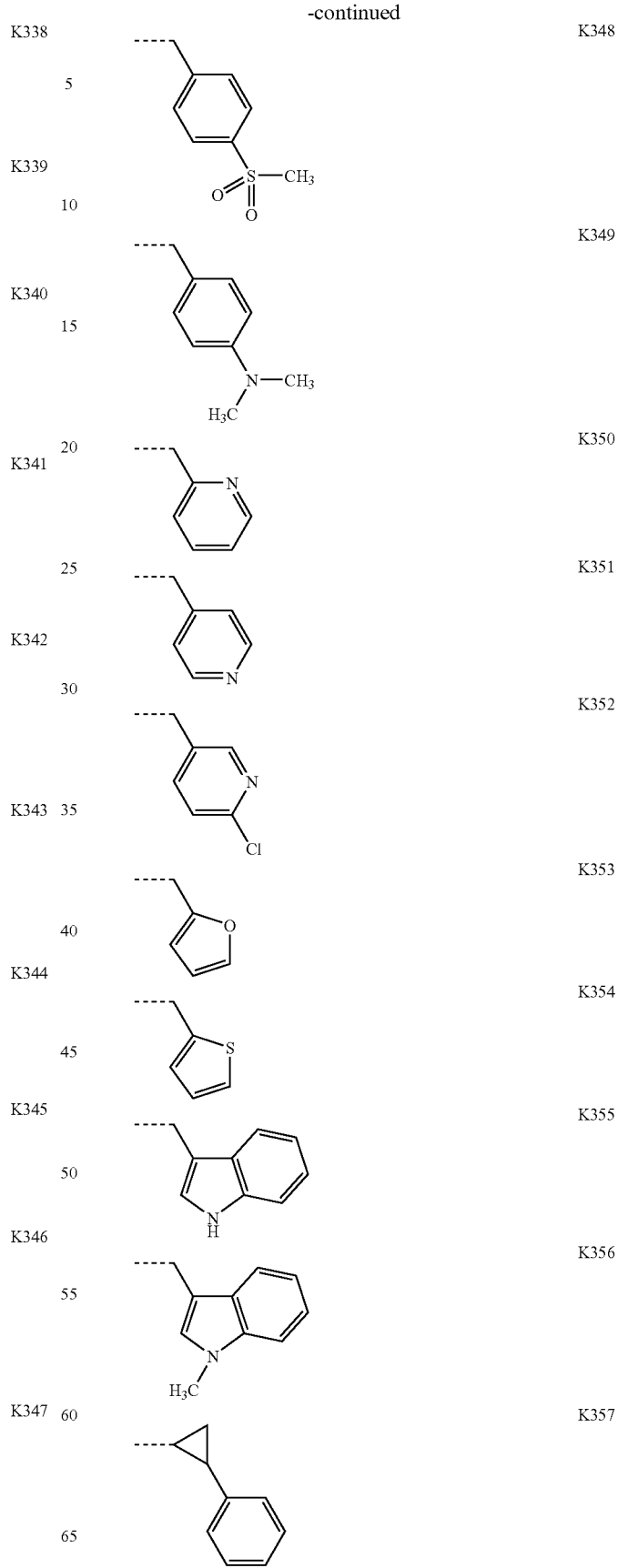

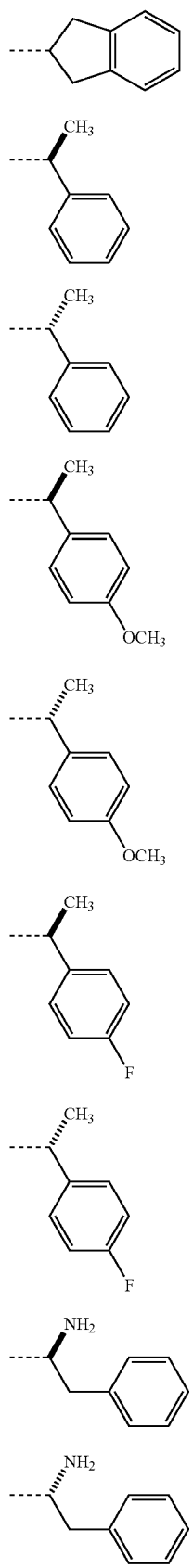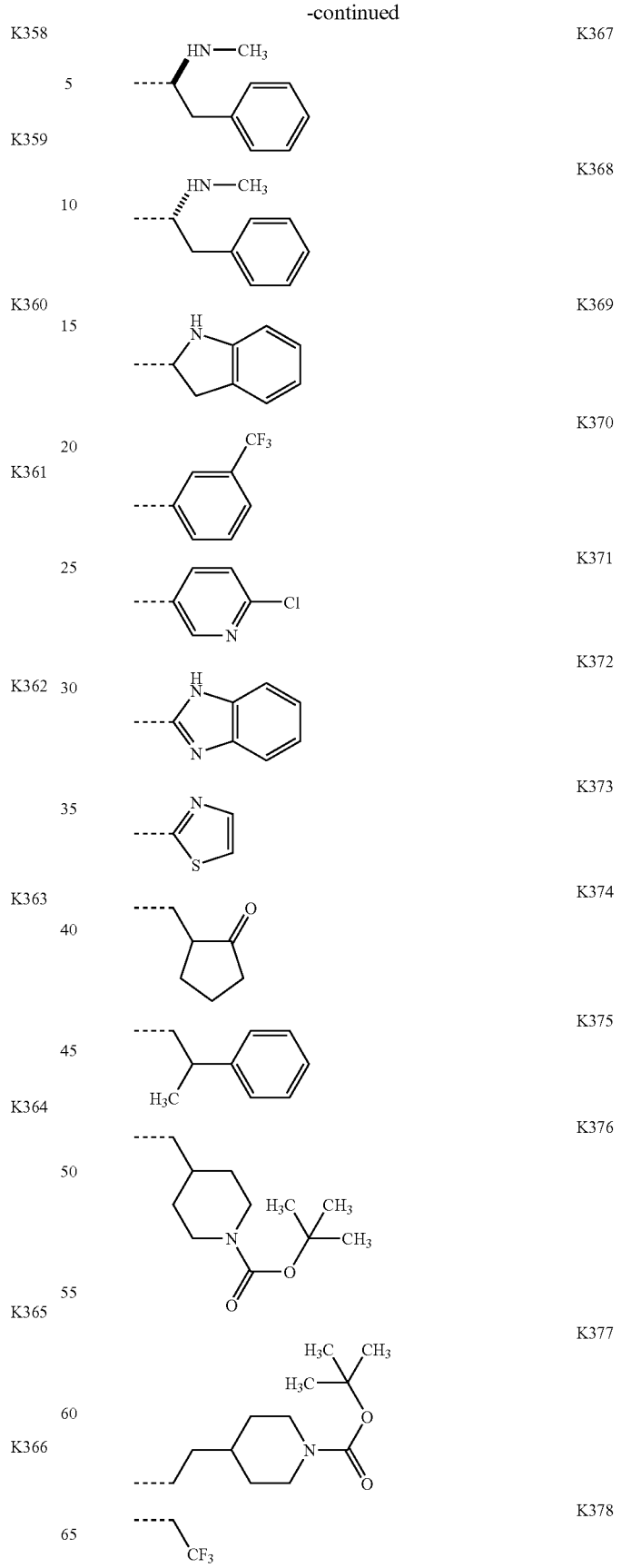

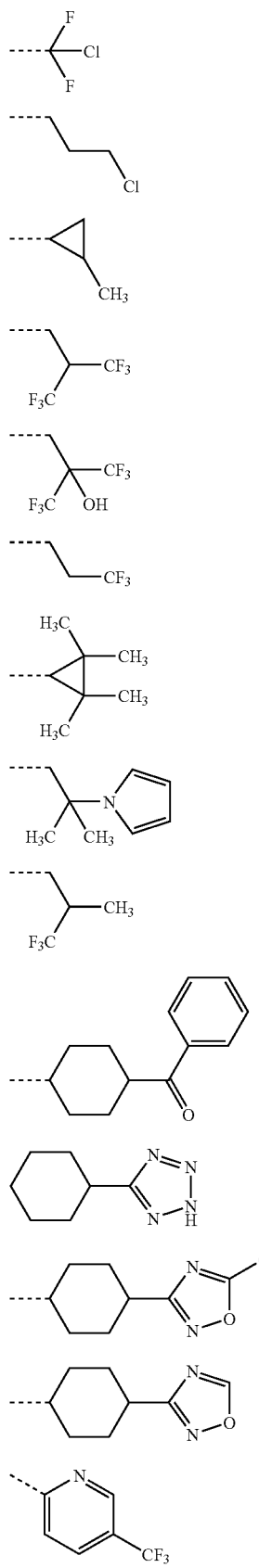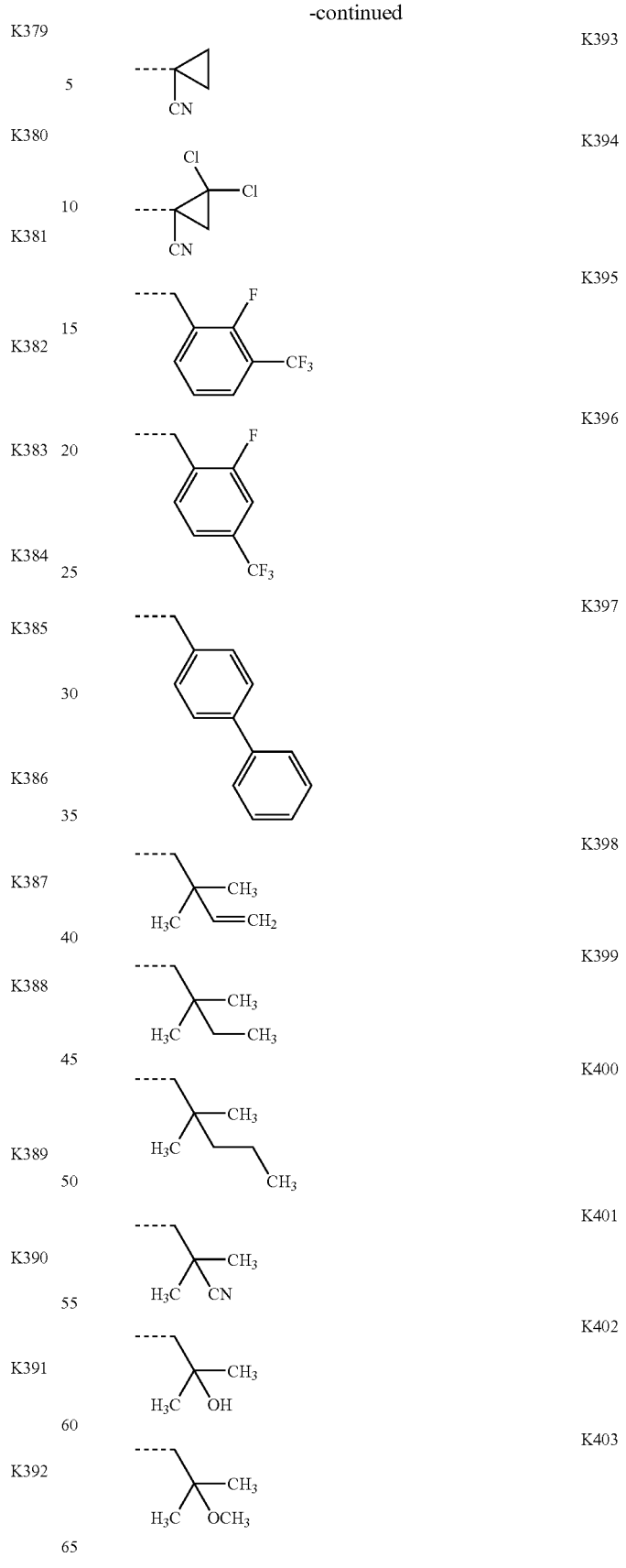

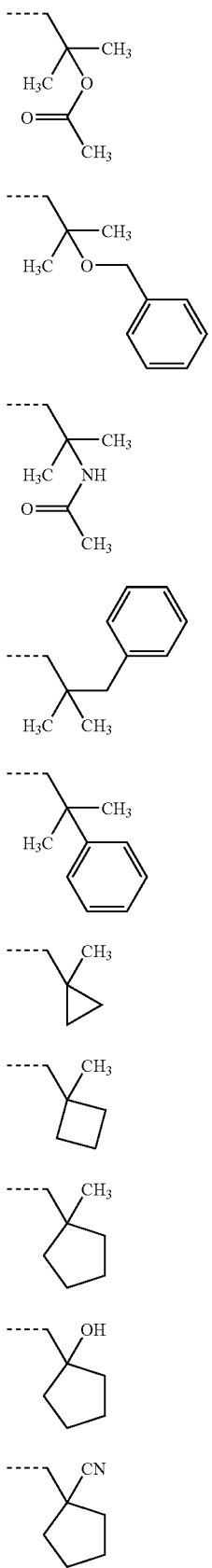
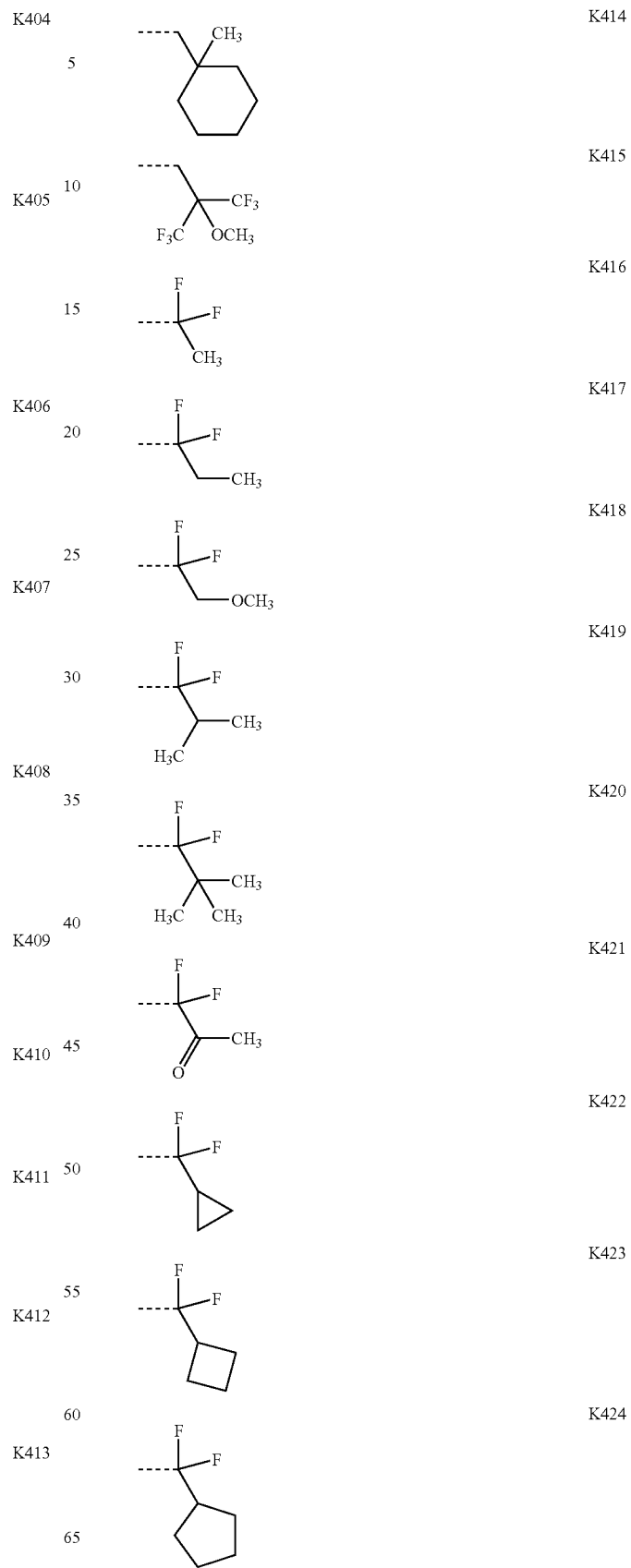

-continued

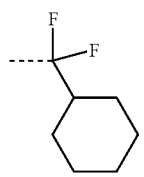 K425

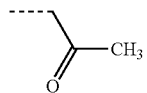 K426

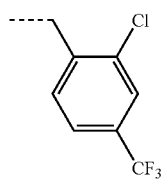 K427

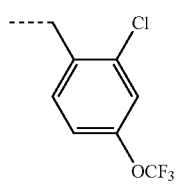 K428

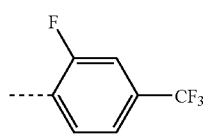 K429

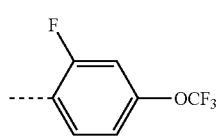 K430

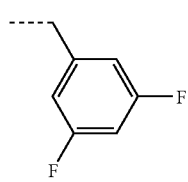 K431

In the pyrrolo-pyrimidinone derivatives of the formula (I), as specific examples of preferred combinations of the -A$^5$-R$^2$ portion, groups represented by the following formulae, J001-J166 may be mentioned. In the respective chemical formulae, symbol "- - -" indicates a binding site between a carbon atom of a pyrrole ring and -A$^5$-R$^2$.

----H        J001
----Cl       J002
----Br       J003
-----I       J004
----CH$_3$   J005
----CF$_3$   J006

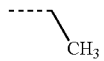 J007

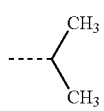 J008

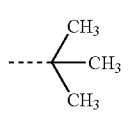 J009

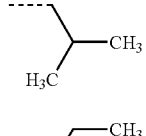 JO10

J011

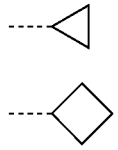 J012

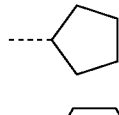 J013

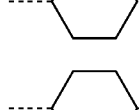 J014

J015

J016

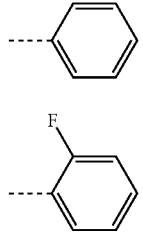 J107

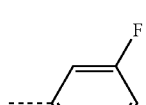 J018

J019

J020

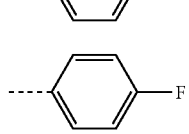 J021

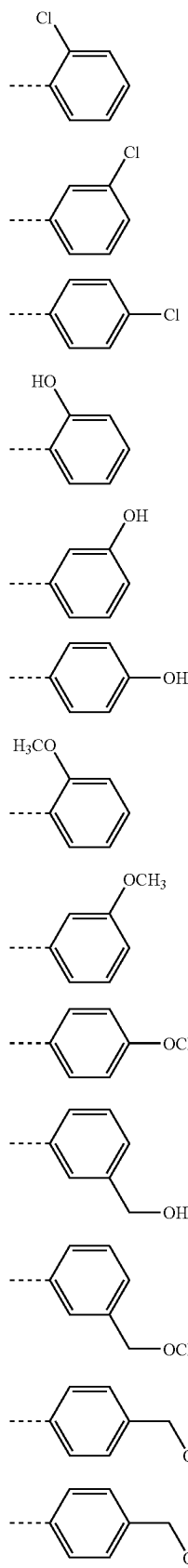
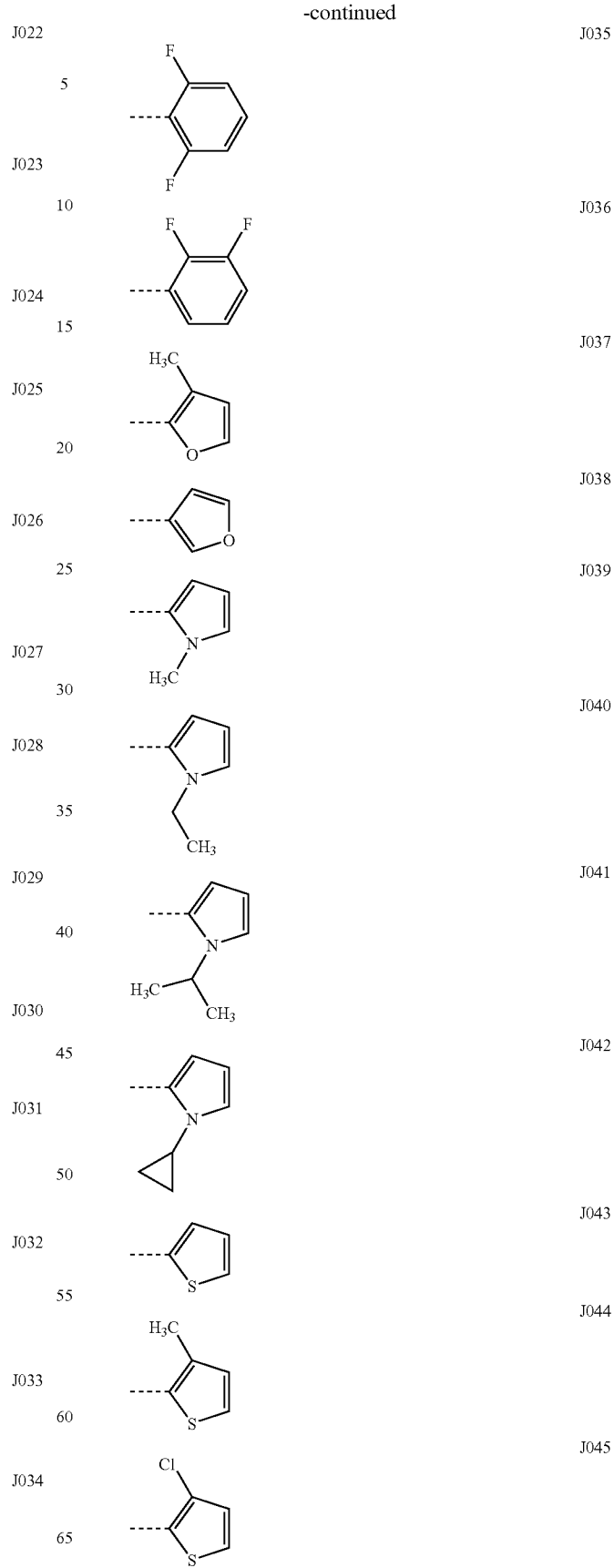

| | | | |
|---|---|---|---|
| | 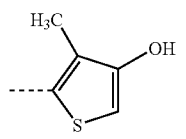 | J046 | 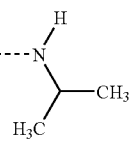 J058 |
| | 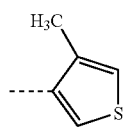 | J047 | 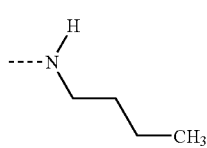 J059 |
| | 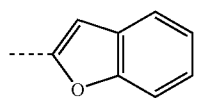 | J048 | 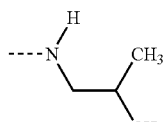 J060 |
| | 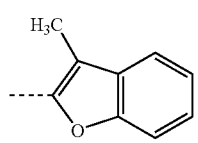 | J049 | 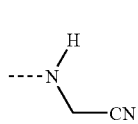 J061 |
| | 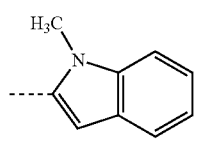 | J050 | 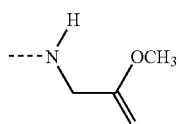 J062 |
| | 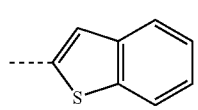 | J051 | 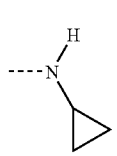 J063 |
| | 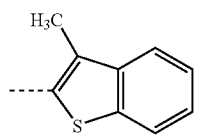 | J052 | 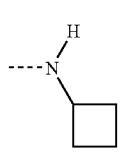 J064 |
| | 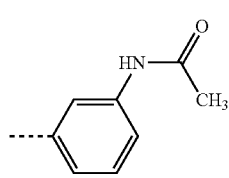 | J053 | 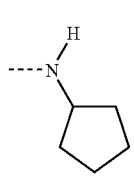 J065 |
| | 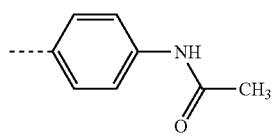 | J054 | 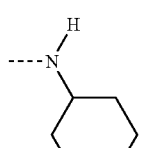 J066 |
| | 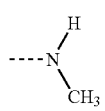 | J055 | 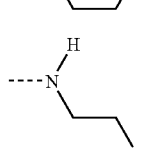 J067 |
| | 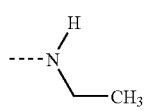 | J056 | 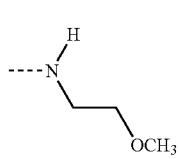 J068 |
| | 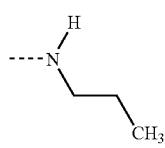 | J057 | |

-continued
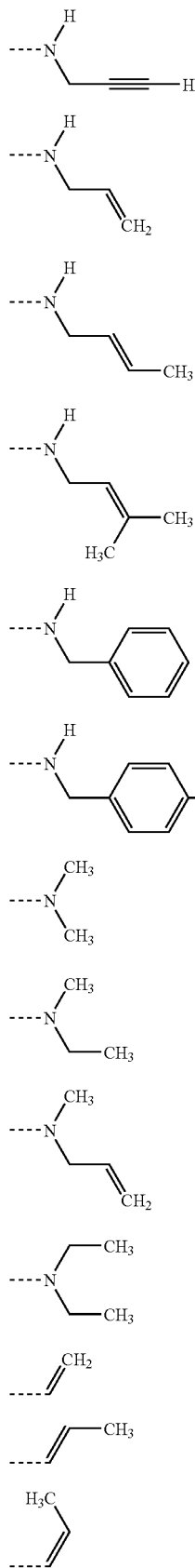
-continued
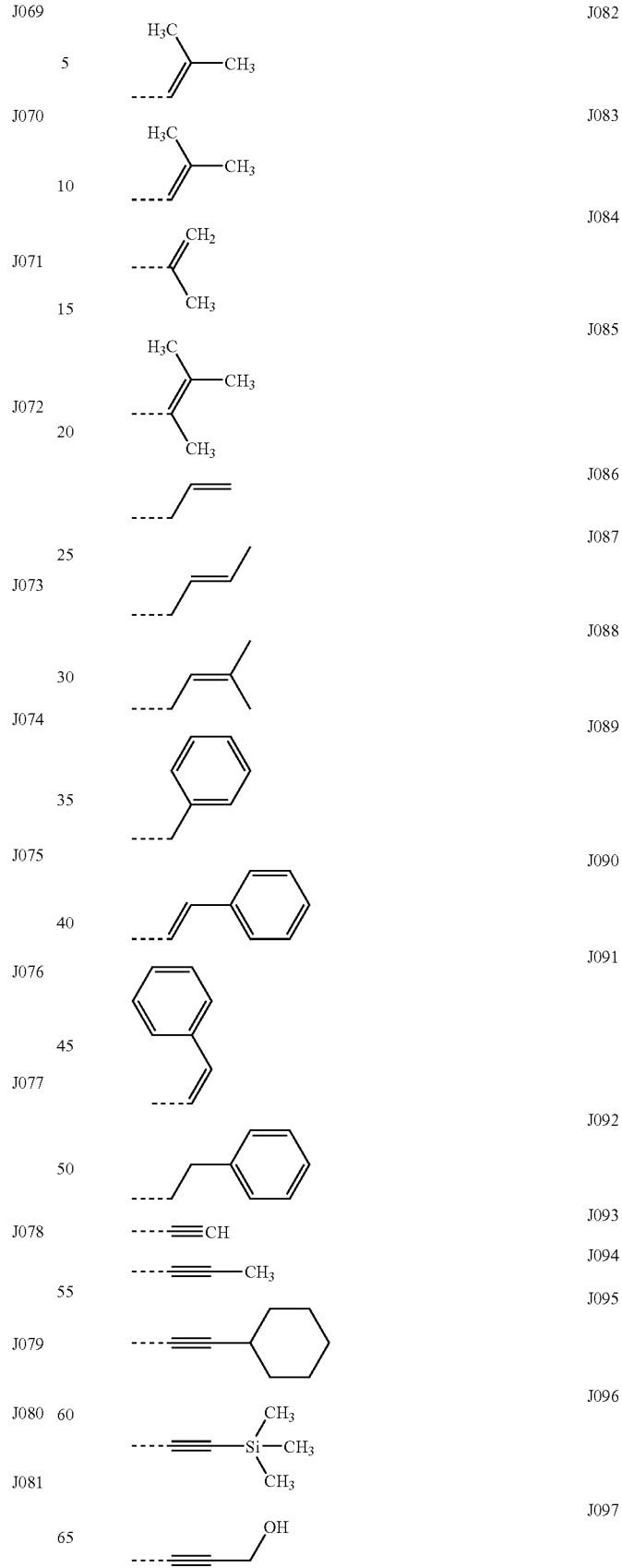

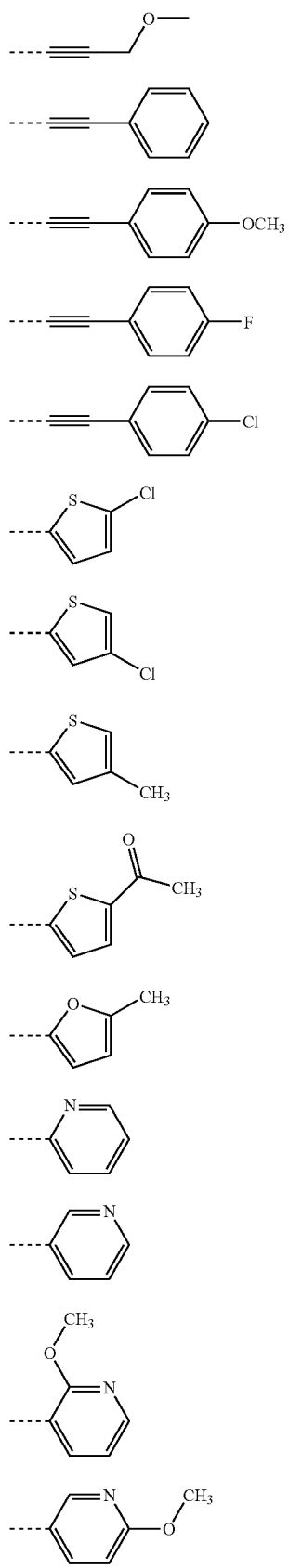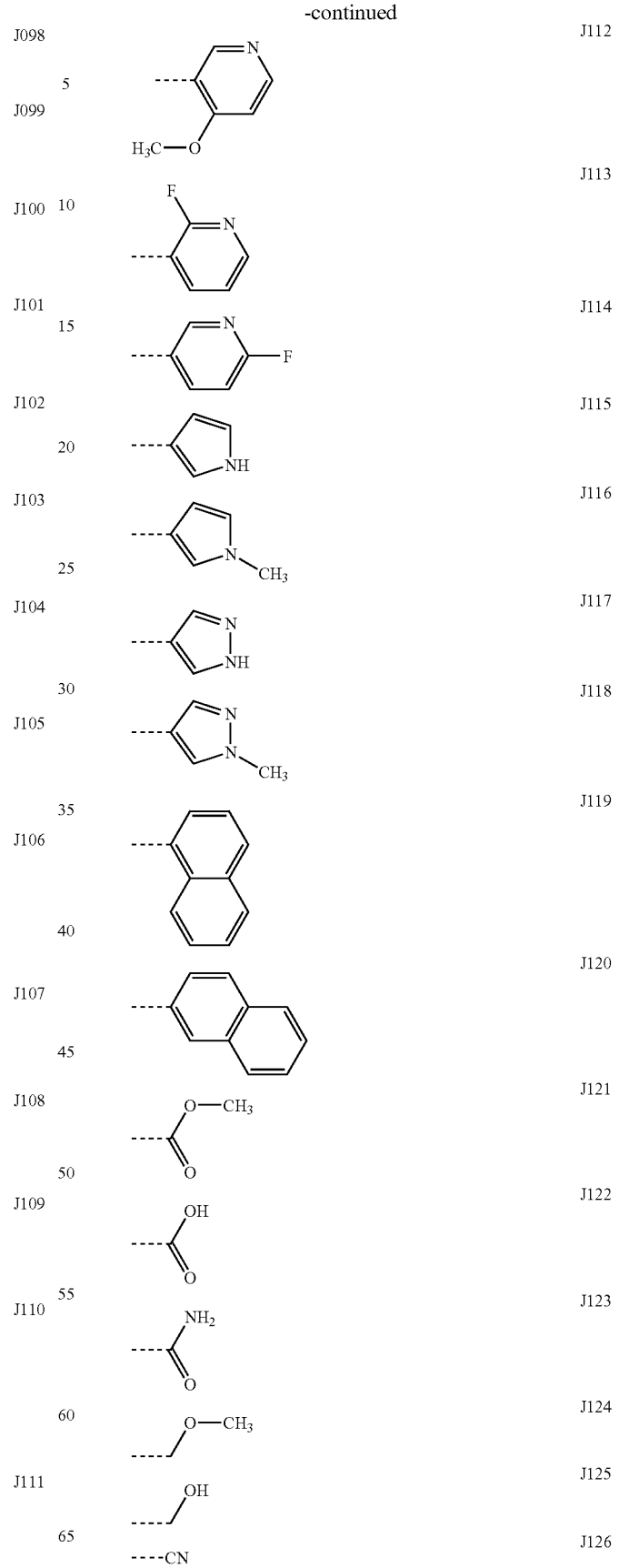

-continued
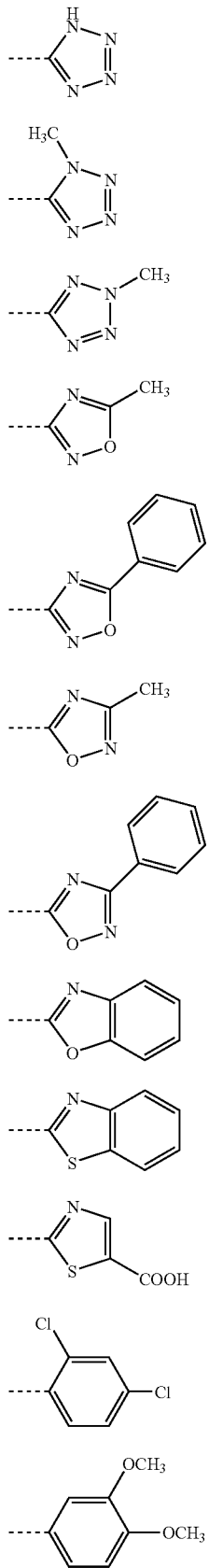
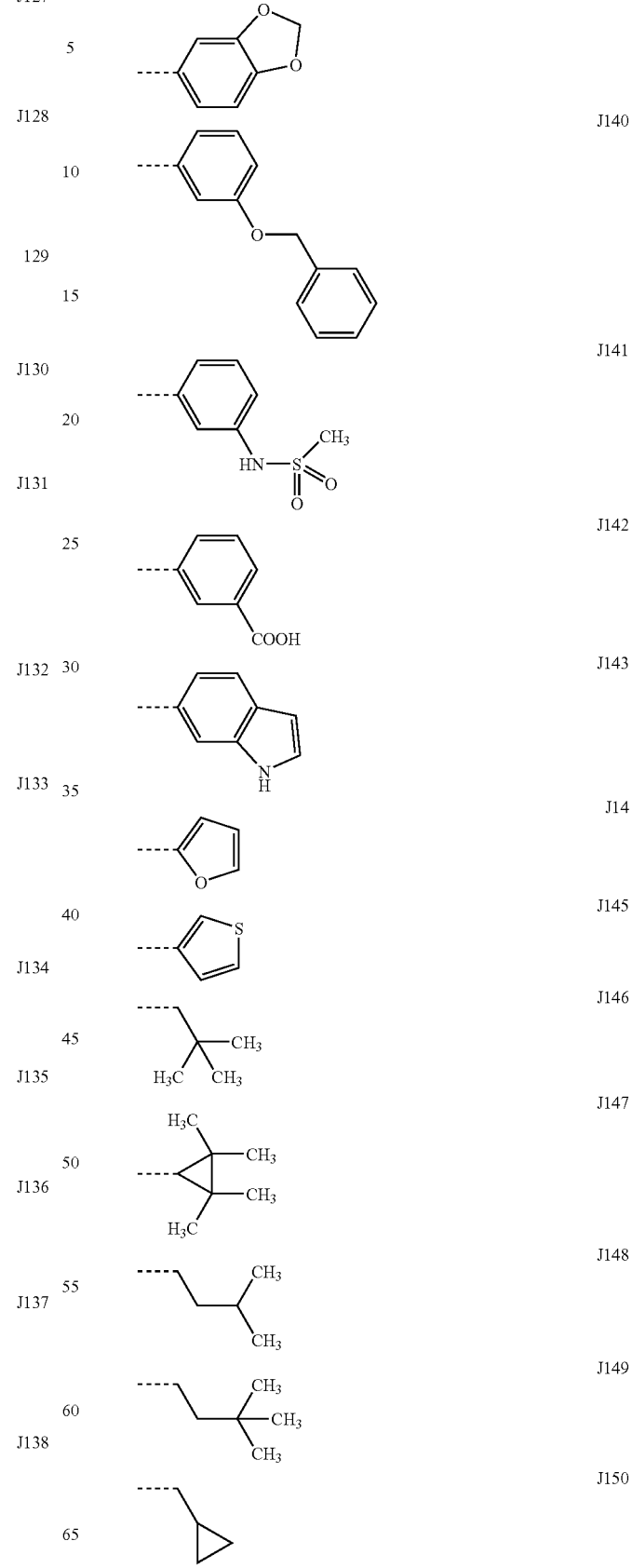

-continued
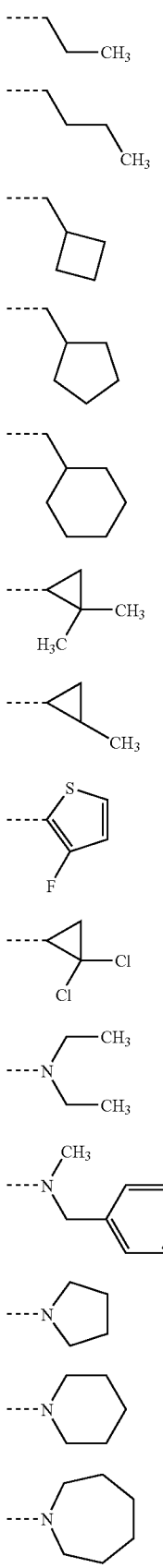
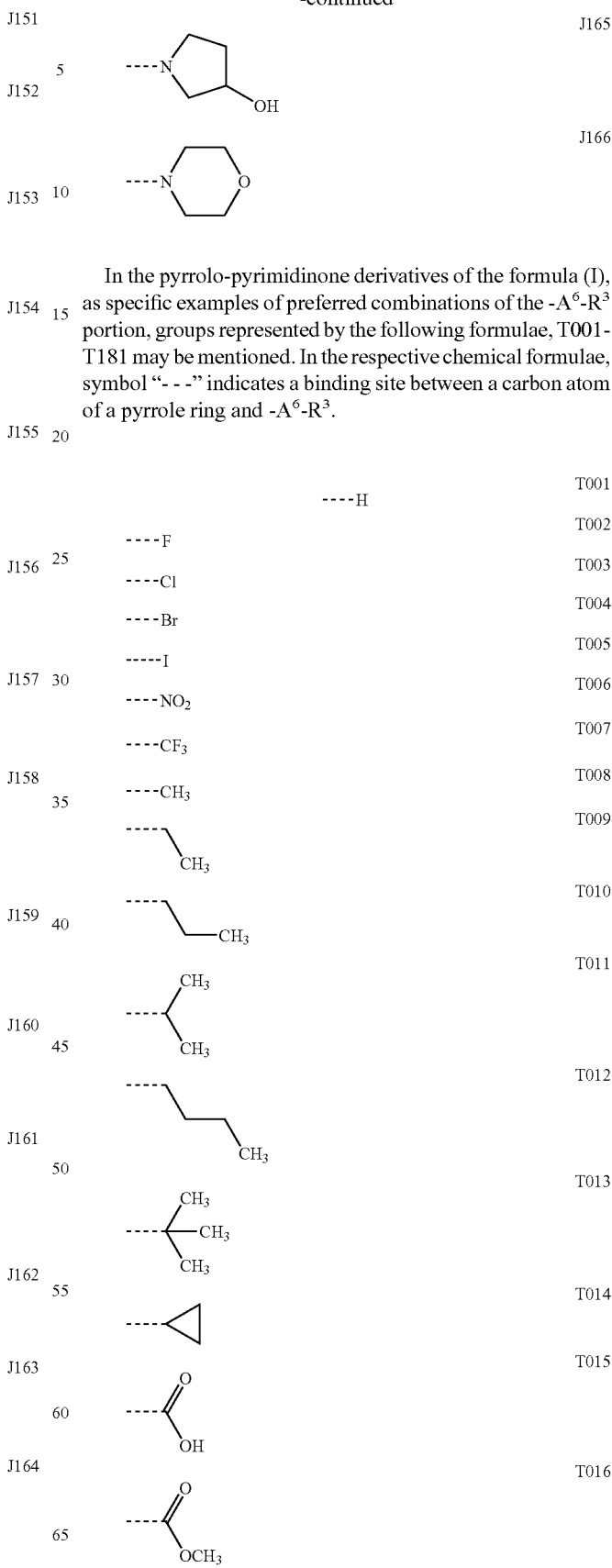
In the pyrrolo-pyrimidinone derivatives of the formula (I), as specific examples of preferred combinations of the -$A^6$-$R^3$ portion, groups represented by the following formulae, T001-T181 may be mentioned. In the respective chemical formulae, symbol "- - -" indicates a binding site between a carbon atom of a pyrrole ring and -$A^6$-$R^3$.

-continued
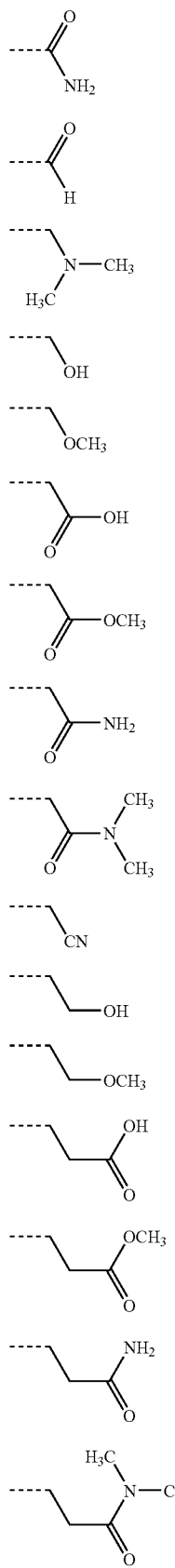
-continued
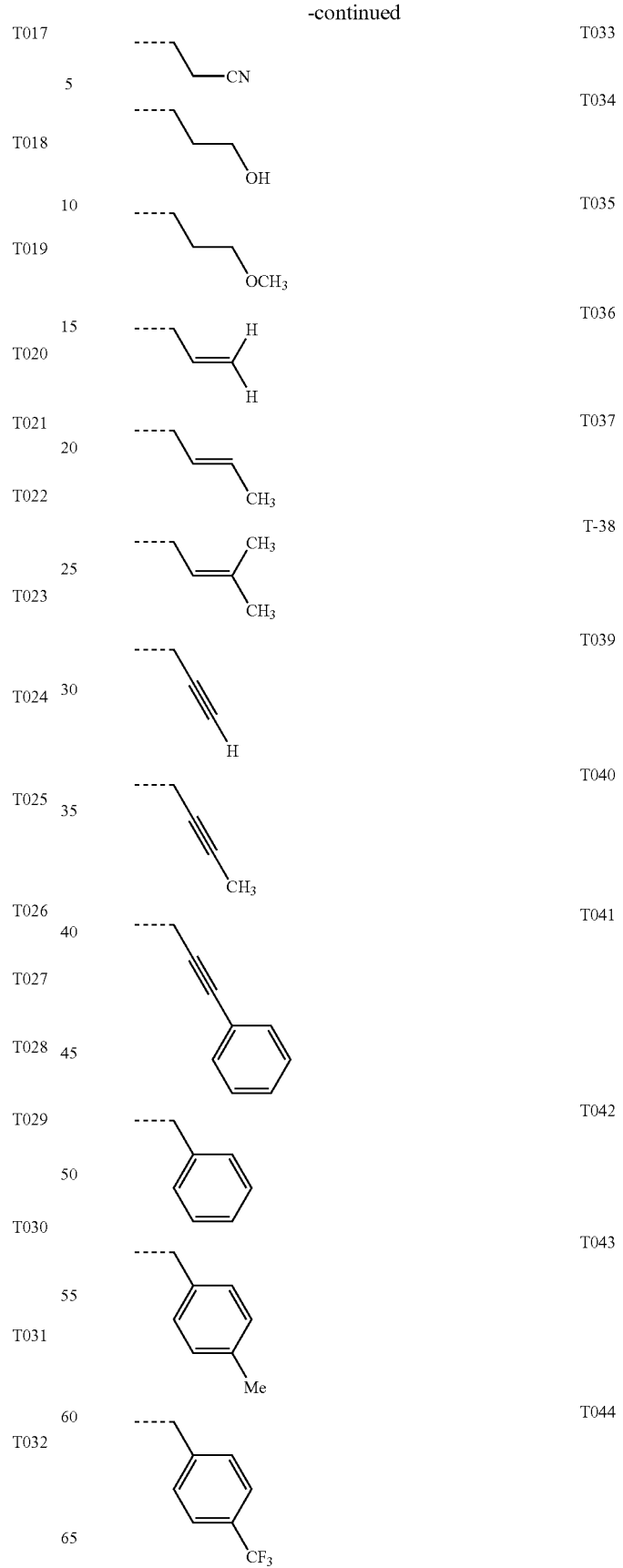

-continued
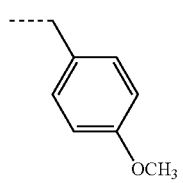 T045
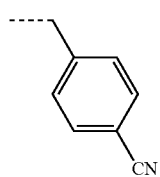 T046
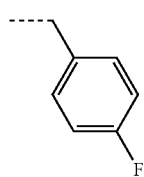 T047
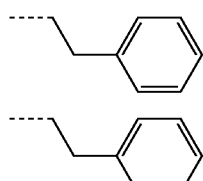 T048
----OH T049
----OCH₃ T050
----SCH₃ T051
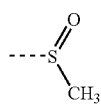 T052
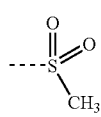 T053
----NH₂ T054
----NHCH₃ T055
----NHCH₂CH₃ T056
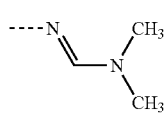 T057
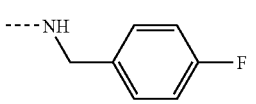 T058
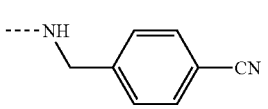 T059
T060
-continued
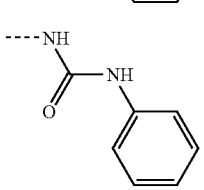 T061
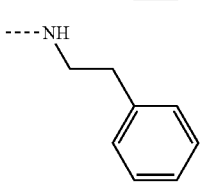 T062
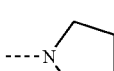 T063
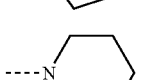 T064
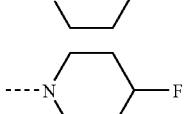 T065
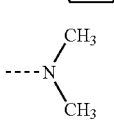 T066
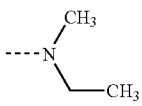 T067
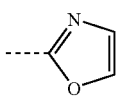 T068
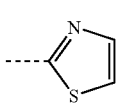 T069
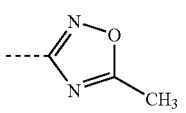 T070
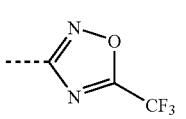 T071
T072
T073
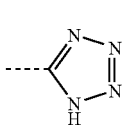 T074

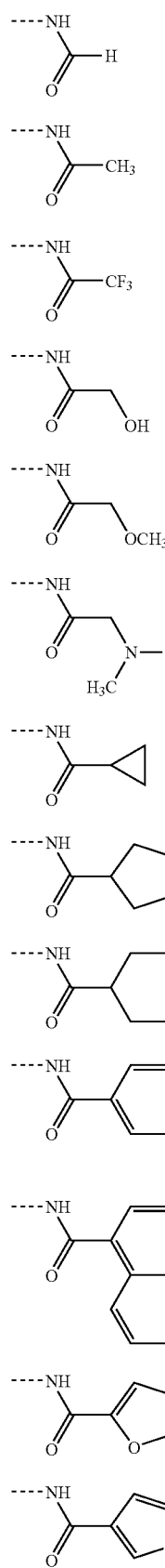
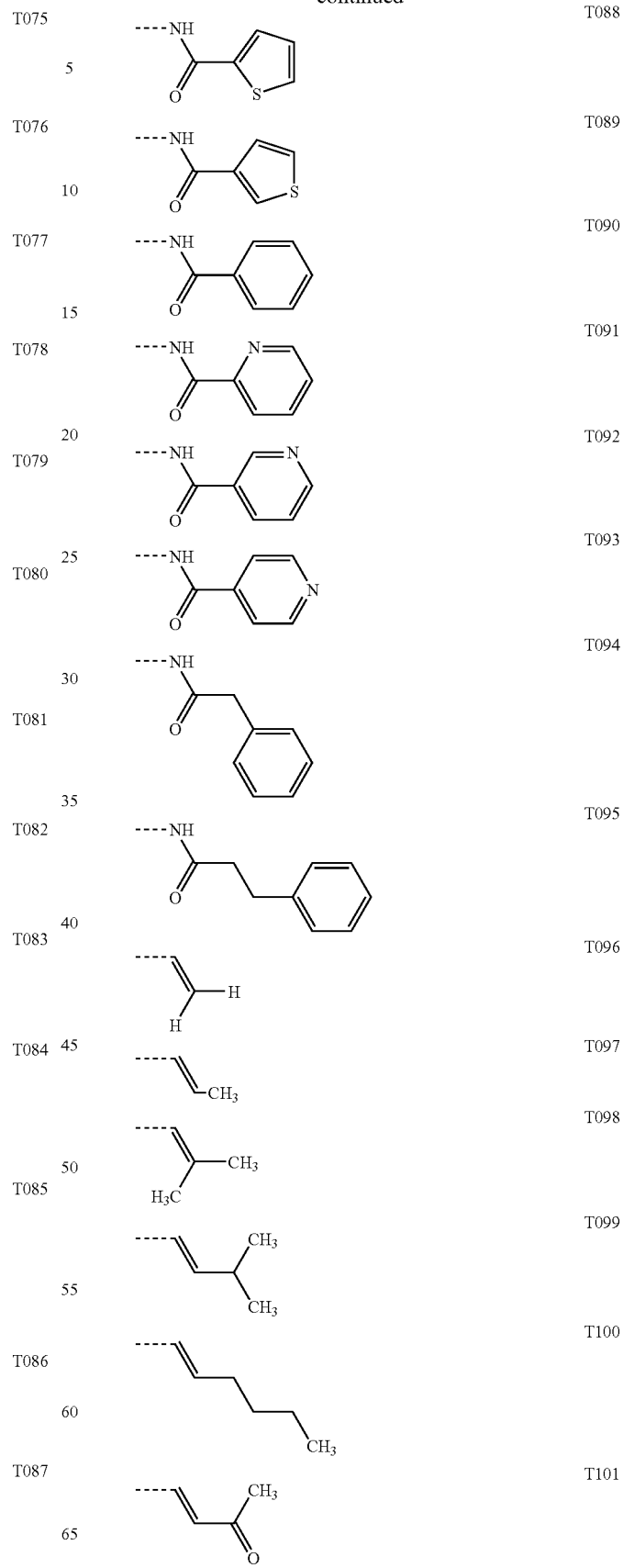

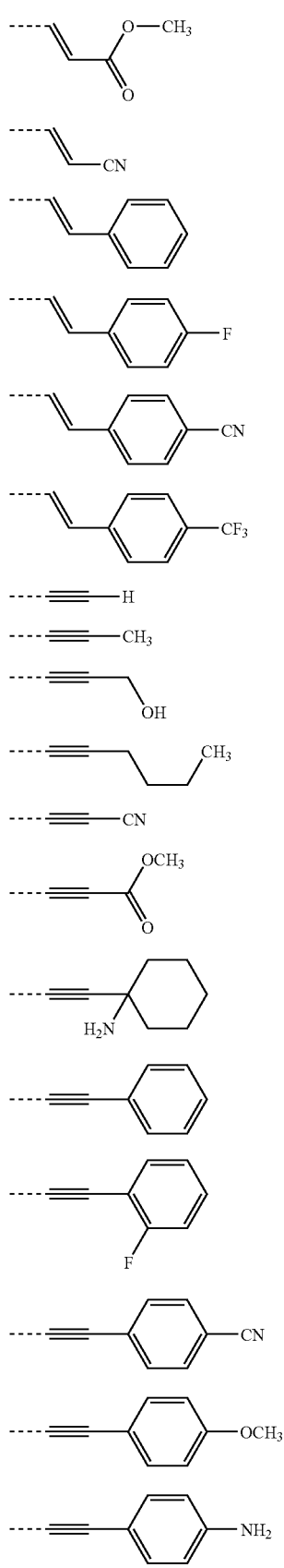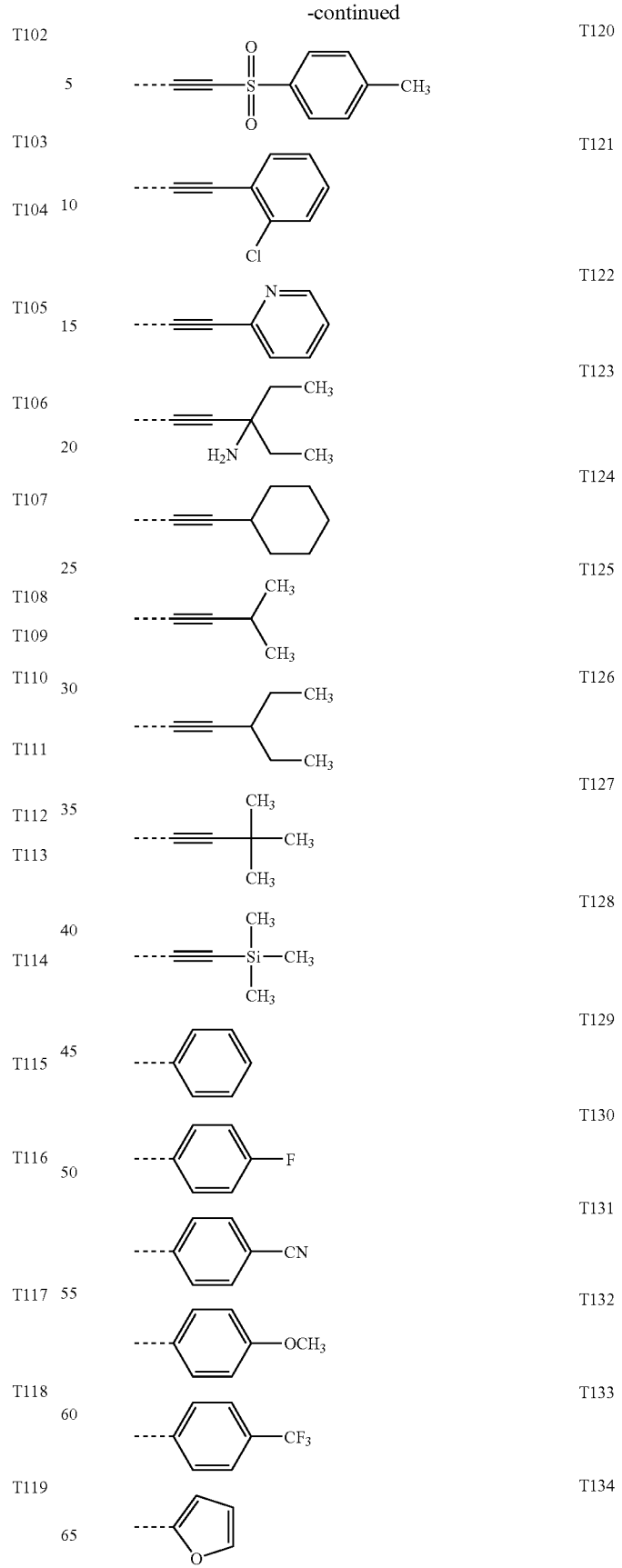

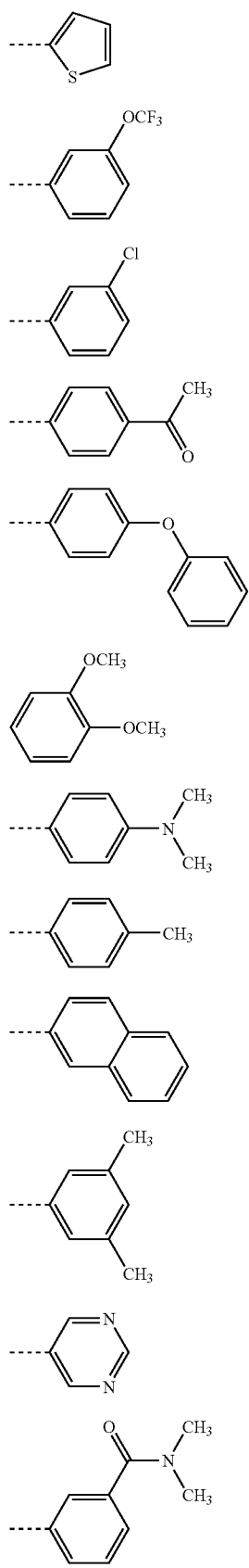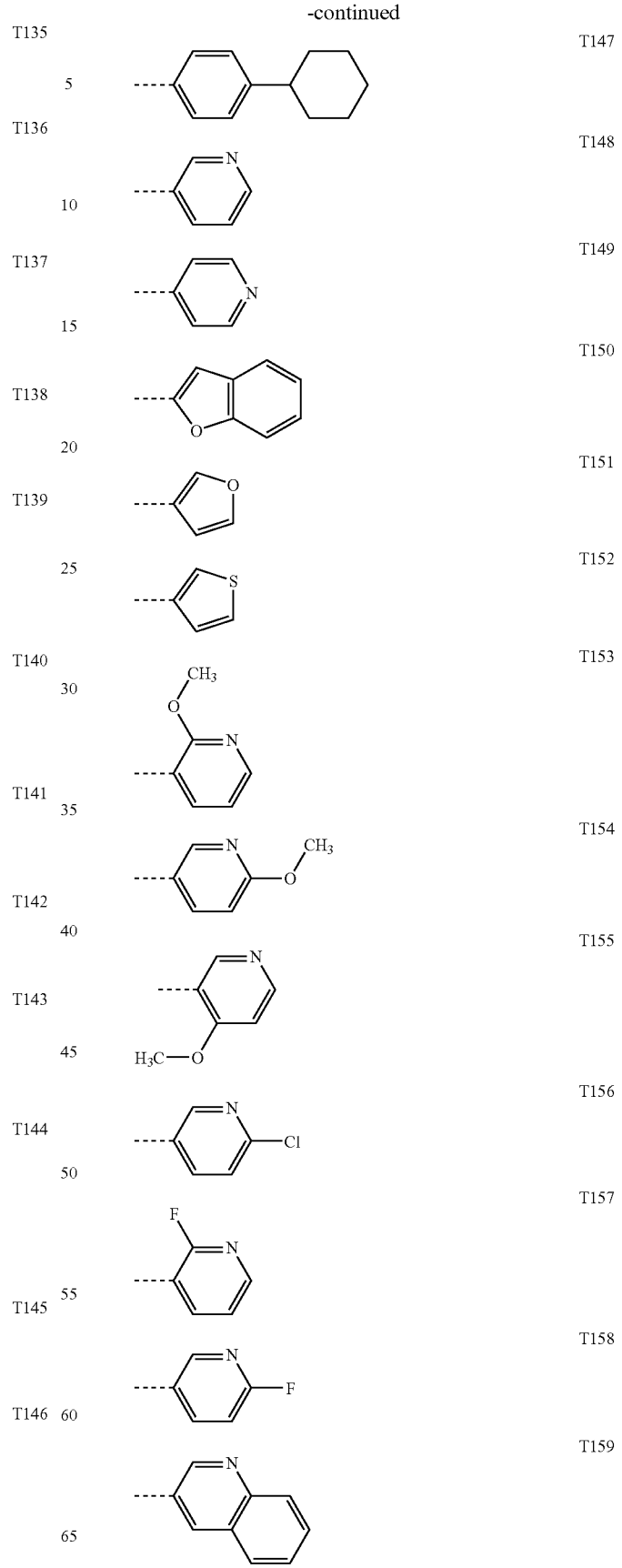

-continued

T160 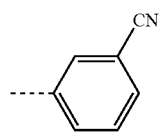

T161 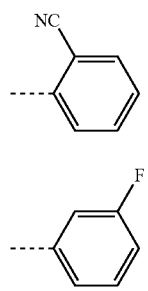

T162

T163

T164

T165

T166

T167

T168

T169

T170

-continued

T171 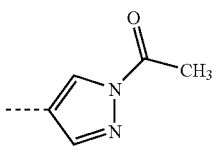

T172 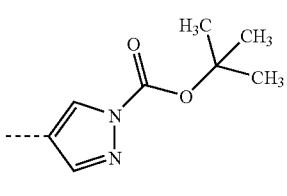

T173 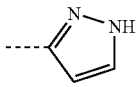

T174 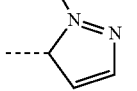

T175 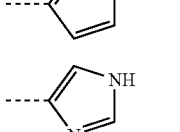

T176 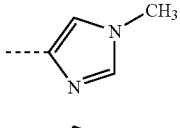

T177 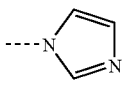

T178 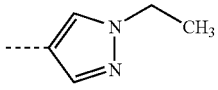

T179

T180 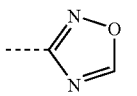

T181

Specific examples of the pyrrolo-pyrimidinone derivatives of formula (I) include the compounds having groups described in the following Table 1 as $A^1$, the compounds having groups described in the following Table 1 as $A^2$, the compounds having groups represented by K001-K431 indicated in the formula as $-G^1-A^3-A^4-G^2$, the compounds having groups represented by J01-J166 indicated in the formula as $-A^5-R^2$, the compounds having groups represented by T001-T181 indicated in the formula as $-A^6-R^3$, and the compounds consisting of any combination of groups mentioned above with regard to each moiety. Preferable examples among such compounds are listed in Tables below.

TABLE 1

| Compound no. | -A$^1$- | -A$^2$- | -G$^1$-A$^3$-A$^4$-G$^2$ | -A$^5$-R$^2$ | -A$^6$-R$^3$ |
|---|---|---|---|---|---|
| 1 | —(CH$_2$)$_2$— | —C(=O)— | K002 | J001 | T148 |
| 2 | —(CH$_2$)$_2$— | —C(=O)— | K002 | J001 | T151 |
| 3 | —(CH$_2$)$_2$— | —C(=O)— | K003 | J001 | T148 |
| 4 | —(CH$_2$)$_2$— | —C(=O)— | K003 | J001 | T151 |
| 5 | —(CH$_2$)$_2$— | —C(=O)— | K004 | J001 | T148 |
| 6 | —(CH$_2$)$_2$— | —C(=O)— | K004 | J001 | T151 |
| 7 | —(CH$_2$)$_2$— | —C(=O)— | K005 | J001 | T148 |
| 8 | —(CH$_2$)$_2$— | —C(=O)— | K005 | J001 | T151 |
| 9 | —(CH$_2$)$_2$— | —C(=O)— | K007 | J001 | T148 |
| 10 | —(CH$_2$)$_2$— | —C(=O)— | K007 | J001 | T152 |
| 11 | —(CH$_2$)$_2$— | —C(=O)— | K008 | J001 | T148 |
| 12 | —(CH$_2$)$_2$— | —C(=O)— | K008 | J001 | T152 |
| 13 | —(CH$_2$)$_2$— | —C(=O)— | K009 | J001 | T148 |
| 14 | —(CH$_2$)$_2$— | —C(=O)— | K009 | J001 | T152 |
| 15 | —(CH$_2$)$_2$— | —C(=O)— | K012 | J001 | T148 |
| 16 | —(CH$_2$)$_2$— | —C(=O)— | K012 | J001 | T152 |
| 17 | —(CH$_2$)$_2$— | —C(=O)— | K107 | J001 | T148 |
| 18 | —(CH$_2$)$_2$— | —C(=O)— | K107 | J001 | T168 |
| 19 | —(CH$_2$)$_2$— | —C(=O)— | K108 | J001 | T148 |
| 20 | —(CH$_2$)$_2$— | —C(=O)— | K108 | J001 | T169 |
| 21 | —(CH$_2$)$_2$— | —C(=O)— | K112 | J001 | T148 |
| 22 | —(CH$_2$)$_2$— | —C(=O)— | K112 | J001 | T170 |
| 23 | —(CH$_2$)$_2$— | —C(=O)— | K129 | J001 | T148 |
| 24 | —(CH$_2$)$_2$— | —C(=O)— | K129 | J001 | T171 |
| 25 | —(CH$_2$)$_2$— | —C(=O)— | K133 | J001 | T148 |
| 26 | —(CH$_2$)$_2$— | —C(=O)— | K133 | J001 | T172 |
| 27 | —(CH$_2$)$_2$— | —C(=O)— | K137 | J001 | T148 |
| 28 | —(CH$_2$)$_2$— | —C(=O)— | K137 | J001 | T173 |
| 29 | —(CH$_2$)$_2$— | —C(=O)—NH— | K007 | J001 | T148 |
| 30 | —(CH$_2$)$_2$— | —C(=O)—NH— | K012 | J001 | T148 |
| 31 | —(CH$_2$)$_2$— | —C(=O)—O— | K001 | J001 | T148 |
| 32 | —(CH$_2$)$_2$— | —C(=O)—O— | K002 | J001 | T151 |
| 33 | —(CH$_2$)$_2$— | —C(=O)—O— | K193 | J001 | T152 |
| 34 | —(CH$_2$)$_2$— | —C(=O)—O— | K227 | J001 | T169 |
| 35 | —(CH$_2$)$_2$— | —C(=O)—O— | K002 | J001 | T148 |
| 36 | —(CH$_2$)$_2$— | —NH— | K181 | J012 | T148 |
| 37 | —(CH$_2$)$_2$— | —NH— | K181 | J012 | T151 |
| 38 | —(CH$_2$)$_2$— | —NH— | K181 | J012 | T152 |
| 39 | —(CH$_2$)$_2$— | —NH— | K181 | J012 | T169 |
| 40 | —(CH$_2$)$_2$— | —NH— | K181 | J045 | T148 |
| 41 | —(CH$_2$)$_2$— | —NH— | K181 | J045 | T151 |
| 42 | —(CH$_2$)$_2$— | —NH— | K181 | J045 | T152 |
| 43 | —(CH$_2$)$_2$— | —NH— | K181 | J045 | T169 |
| 44 | —(CH$_2$)$_2$— | —NH— | K181 | J045 | T170 |
| 45 | —(CH$_2$)$_2$— | —NH— | K181 | J045 | T172 |
| 46 | —(CH$_2$)$_2$— | —NH— | K182 | J012 | T148 |
| 47 | —(CH$_2$)$_2$— | —NH— | K182 | J012 | T151 |
| 48 | —(CH$_2$)$_2$— | —NH— | K182 | J012 | T152 |
| 49 | —(CH$_2$)$_2$— | —NH— | K182 | J012 | T169 |
| 50 | —(CH$_2$)$_2$— | —NH— | K182 | J045 | T148 |
| 51 | —(CH$_2$)$_2$— | —NH— | K182 | J045 | T151 |
| 52 | —(CH$_2$)$_2$— | —NH— | K182 | J045 | T152 |
| 53 | —(CH$_2$)$_2$— | —NH— | K182 | J045 | T169 |
| 54 | —(CH$_2$)$_2$— | —NH— | K182 | J045 | T170 |
| 55 | —(CH$_2$)$_2$— | —NH— | K182 | J045 | T172 |
| 56 | —(CH$_2$)$_2$— | —NH— | K183 | J012 | T148 |
| 57 | —(CH$_2$)$_2$— | —NH— | K183 | J012 | T151 |
| 58 | —(CH$_2$)$_2$— | —NH— | K183 | J012 | T152 |
| 59 | —(CH$_2$)$_2$— | —NH— | K183 | J012 | T169 |
| 60 | —(CH$_2$)$_2$— | —NH— | K183 | J045 | T148 |
| 61 | —(CH$_2$)$_2$— | —NH— | K183 | J045 | T151 |
| 62 | —(CH$_2$)$_2$— | —NH— | K183 | J045 | T152 |
| 63 | —(CH$_2$)$_2$— | —NH— | K183 | J045 | T169 |
| 64 | —(CH$_2$)$_2$— | —NH— | K183 | J045 | T170 |
| 65 | —(CH$_2$)$_2$— | —NH— | K183 | J045 | T172 |
| 66 | —(CH$_2$)$_2$— | —NH— | K184 | J012 | T148 |
| 67 | —(CH$_2$)$_2$— | —NH— | K184 | J012 | T151 |
| 68 | —(CH$_2$)$_2$— | —NH— | K184 | J012 | T152 |
| 69 | —(CH$_2$)$_2$— | —NH— | K184 | J012 | T169 |
| 70 | —(CH$_2$)$_2$— | —NH— | K184 | J045 | T148 |
| 71 | —(CH$_2$)$_2$— | —NH— | K184 | J045 | T151 |
| 72 | —(CH$_2$)$_2$— | —NH— | K184 | J045 | T152 |
| 73 | —(CH$_2$)$_2$— | —NH— | K184 | J045 | T169 |
| 74 | —(CH$_2$)$_2$— | —NH— | K184 | J045 | T170 |
| 75 | —(CH$_2$)$_2$— | —NH— | K184 | J045 | T172 |
| 76 | —(CH$_2$)$_2$— | —NH— | K185 | J012 | T148 |

TABLE 1-continued

| Compound no. | -A¹- | -A²- | -G¹-A³-A⁴-G² | -A⁵-R² | -A⁶-R³ |
|---|---|---|---|---|---|
| 77 | —(CH$_2$)$_2$— | —NH— | K185 | J012 | T151 |
| 78 | —(CH$_2$)$_2$— | —NH— | K185 | J012 | T152 |
| 79 | —(CH$_2$)$_2$— | —NH— | K185 | J012 | T169 |
| 80 | —(CH$_2$)$_2$— | —NH— | K185 | J045 | T004 |
| 81 | —(CH$_2$)$_2$— | —NH— | K185 | J045 | T005 |
| 82 | —(CH$_2$)$_2$— | —NH— | K185 | J045 | T090 |
| 83 | —(CH$_2$)$_2$— | —NH— | K185 | J045 | T129 |
| 84 | —(CH$_2$)$_2$— | —NH— | K185 | J045 | T148 |
| 85 | —(CH$_2$)$_2$— | —NH— | K185 | J045 | T151 |
| 86 | —(CH$_2$)$_2$— | —NH— | K185 | J045 | T152 |
| 87 | —(CH$_2$)$_2$— | —NH— | K185 | J045 | T169 |
| 88 | —(CH$_2$)$_2$— | —NH— | K185 | J045 | T170 |
| 89 | —(CH$_2$)$_2$— | —NH— | K185 | J045 | T172 |
| 90 | —(CH$_2$)$_2$— | —NH— | K186 | J012 | T148 |
| 91 | —(CH$_2$)$_2$— | —NH— | K186 | J012 | T151 |
| 92 | —(CH$_2$)$_2$— | —NH— | K186 | J012 | T152 |
| 93 | —(CH$_2$)$_2$— | —NH— | K186 | J012 | T169 |
| 94 | —(CH$_2$)$_2$— | —NH— | K186 | J045 | T148 |
| 95 | —(CH$_2$)$_2$— | —NH— | K186 | J045 | T151 |
| 96 | —(CH$_2$)$_2$— | —NH— | K186 | J045 | T152 |
| 97 | —(CH$_2$)$_2$— | —NH— | K186 | J045 | T169 |
| 98 | —(CH$_2$)$_2$— | —NH— | K186 | J045 | T170 |
| 99 | —(CH$_2$)$_2$— | —NH— | K186 | J045 | T172 |
| 100 | —(CH$_2$)$_2$— | —NH— | K187 | J012 | T148 |
| 101 | —(CH$_2$)$_2$— | —NH— | K187 | J012 | T151 |
| 102 | —(CH$_2$)$_2$— | —NH— | K187 | J012 | T152 |
| 103 | —(CH$_2$)$_2$— | —NH— | K187 | J012 | T169 |
| 104 | —(CH$_2$)$_2$— | —NH— | K187 | J045 | T148 |
| 105 | —(CH$_2$)$_2$— | —NH— | K187 | J045 | T151 |
| 106 | —(CH$_2$)$_2$— | —NH— | K187 | J045 | T152 |
| 107 | —(CH$_2$)$_2$— | —NH— | K187 | J045 | T169 |
| 108 | —(CH$_2$)$_2$— | —NH— | K187 | J045 | T170 |
| 109 | —(CH$_2$)$_2$— | —NH— | K187 | J045 | T172 |
| 110 | —(CH$_2$)$_2$— | —NH— | K188 | J012 | T148 |
| 111 | —(CH$_2$)$_2$— | —NH— | K188 | J012 | T151 |
| 112 | —(CH$_2$)$_2$— | —NH— | K188 | J012 | T152 |
| 113 | —(CH$_2$)$_2$— | —NH— | K188 | J012 | T169 |
| 114 | —(CH$_2$)$_2$— | —NH— | K188 | J045 | T148 |
| 115 | —(CH$_2$)$_2$— | —NH— | K188 | J045 | T151 |
| 116 | —(CH$_2$)$_2$— | —NH— | K188 | J045 | T152 |
| 117 | —(CH$_2$)$_2$— | —NH— | K188 | J045 | T169 |
| 118 | —(CH$_2$)$_2$— | —NH— | K188 | J045 | T170 |
| 119 | —(CH$_2$)$_2$— | —NH— | K188 | J045 | T172 |
| 120 | —(CH$_2$)$_2$— | —NH— | K189 | J012 | T148 |
| 121 | —(CH$_2$)$_2$— | —NH— | K189 | J012 | T151 |
| 122 | —(CH$_2$)$_2$— | —NH— | K189 | J012 | T152 |
| 123 | —(CH$_2$)$_2$— | —NH— | K189 | J012 | T169 |
| 124 | —(CH$_2$)$_2$— | —NH— | K189 | J045 | T148 |
| 125 | —(CH$_2$)$_2$— | —NH— | K189 | J045 | T151 |
| 126 | —(CH$_2$)$_2$— | —NH— | K189 | J045 | T152 |
| 127 | —(CH$_2$)$_2$— | —NH— | K189 | J045 | T169 |
| 128 | —(CH$_2$)$_2$— | —NH— | K189 | J045 | T170 |
| 129 | —(CH$_2$)$_2$— | —NH— | K189 | J045 | T172 |
| 130 | —(CH$_2$)$_2$— | —NH— | K190 | J012 | T148 |
| 131 | —(CH$_2$)$_2$— | —NH— | K190 | J012 | T151 |
| 132 | —(CH$_2$)$_2$— | —NH— | K190 | J012 | T152 |
| 133 | —(CH$_2$)$_2$— | —NH— | K190 | J012 | T169 |
| 134 | —(CH$_2$)$_2$— | —NH— | K190 | J045 | T148 |
| 135 | —(CH$_2$)$_2$— | —NH— | K190 | J045 | T151 |
| 136 | —(CH$_2$)$_2$— | —NH— | K190 | J045 | T152 |
| 137 | —(CH$_2$)$_2$— | —NH— | K190 | J045 | T169 |
| 138 | —(CH$_2$)$_2$— | —NH— | K190 | J045 | T170 |
| 139 | —(CH$_2$)$_2$— | —NH— | K190 | J045 | T172 |
| 140 | —(CH$_2$)$_2$— | —NH— | K191 | J012 | T148 |
| 141 | —(CH$_2$)$_2$— | —NH— | K191 | J012 | T151 |
| 142 | —(CH$_2$)$_2$— | —NH— | K191 | J012 | T152 |
| 143 | —(CH$_2$)$_2$— | —NH— | K191 | J012 | T169 |
| 144 | —(CH$_2$)$_2$— | —NH— | K191 | J045 | T148 |
| 145 | —(CH$_2$)$_2$— | —NH— | K191 | J045 | T151 |
| 146 | —(CH$_2$)$_2$— | —NH— | K191 | J045 | T152 |
| 147 | —(CH$_2$)$_2$— | —NH— | K191 | J045 | T169 |
| 148 | —(CH$_2$)$_2$— | —NH— | K191 | J045 | T170 |
| 149 | —(CH$_2$)$_2$— | —NH— | K191 | J045 | T172 |
| 150 | —(CH$_2$)$_2$— | —NH— | K192 | J012 | T148 |
| 151 | —(CH$_2$)$_2$— | —NH— | K192 | J012 | T151 |
| 152 | —(CH$_2$)$_2$— | —NH— | K192 | J012 | T152 |

TABLE 1-continued

| Compound no. | -A¹- | -A²- | -G¹-A³-A⁴-G² | -A⁵-R² | -A⁶-R³ |
|---|---|---|---|---|---|
| 153 | —(CH$_2$)$_2$— | —NH— | K192 | J012 | T169 |
| 154 | —(CH$_2$)$_2$— | —NH— | K192 | J045 | T148 |
| 155 | —(CH$_2$)$_2$— | —NH— | K192 | J045 | T151 |
| 156 | —(CH$_2$)$_2$— | —NH— | K192 | J045 | T152 |
| 157 | —(CH$_2$)$_2$— | —NH— | K192 | J045 | T169 |
| 158 | —(CH$_2$)$_2$— | —NH— | K192 | J045 | T170 |
| 159 | —(CH$_2$)$_2$— | —NH— | K192 | J045 | T172 |
| 160 | —(CH$_2$)$_2$— | —NH— | K193 | J012 | T148 |
| 161 | —(CH$_2$)$_2$— | —NH— | K193 | J012 | T151 |
| 162 | —(CH$_2$)$_2$— | —NH— | K193 | J012 | T152 |
| 163 | —(CH$_2$)$_2$— | —NH— | K193 | J012 | T169 |
| 164 | —(CH$_2$)$_2$— | —NH— | K193 | J045 | T148 |
| 165 | —(CH$_2$)$_2$— | —NH— | K193 | J045 | T151 |
| 166 | —(CH$_2$)$_2$— | —NH— | K193 | J045 | T152 |
| 167 | —(CH$_2$)$_2$— | —NH— | K193 | J045 | T169 |
| 168 | —(CH$_2$)$_2$— | —NH— | K193 | J045 | T170 |
| 169 | —(CH$_2$)$_2$— | —NH— | K193 | J045 | T172 |
| 170 | —(CH$_2$)$_2$— | —NH— | K194 | J012 | T148 |
| 171 | —(CH$_2$)$_2$— | —NH— | K194 | J012 | T151 |
| 172 | —(CH$_2$)$_2$— | —NH— | K194 | J012 | T152 |
| 173 | —(CH$_2$)$_2$— | —NH— | K194 | J012 | T169 |
| 174 | —(CH$_2$)$_2$— | —NH— | K194 | J045 | T148 |
| 175 | —(CH$_2$)$_2$— | —NH— | K194 | J045 | T151 |
| 176 | —(CH$_2$)$_2$— | —NH— | K194 | J045 | T152 |
| 177 | —(CH$_2$)$_2$— | —NH— | K194 | J045 | T169 |
| 178 | —(CH$_2$)$_2$— | —NH— | K194 | J045 | T170 |
| 179 | —(CH$_2$)$_2$— | —NH— | K194 | J045 | T172 |
| 180 | —(CH$_2$)$_2$— | —NH— | K195 | J012 | T148 |
| 181 | —(CH$_2$)$_2$— | —NH— | K195 | J012 | T151 |
| 182 | —(CH$_2$)$_2$— | —NH— | K195 | J012 | T152 |
| 183 | —(CH$_2$)$_2$— | —NH— | K195 | J012 | T169 |
| 184 | —(CH$_2$)$_2$— | —NH— | K195 | J045 | T148 |
| 185 | —(CH$_2$)$_2$— | —NH— | K195 | J045 | T151 |
| 186 | —(CH$_2$)$_2$— | —NH— | K195 | J045 | T152 |
| 187 | —(CH$_2$)$_2$— | —NH— | K195 | J045 | T169 |
| 188 | —(CH$_2$)$_2$— | —NH— | K195 | J045 | T170 |
| 189 | —(CH$_2$)$_2$— | —NH— | K195 | J045 | T172 |
| 190 | —(CH$_2$)$_2$— | —NH— | K196 | J012 | T148 |
| 191 | —(CH$_2$)$_2$— | —NH— | K196 | J012 | T151 |
| 192 | —(CH$_2$)$_2$— | —NH— | K196 | J012 | T152 |
| 193 | —(CH$_2$)$_2$— | —NH— | K196 | J012 | T169 |
| 194 | —(CH$_2$)$_2$— | —NH— | K196 | J045 | T148 |
| 195 | —(CH$_2$)$_2$— | —NH— | K196 | J045 | T151 |
| 196 | —(CH$_2$)$_2$— | —NH— | K196 | J045 | T152 |
| 197 | —(CH$_2$)$_2$— | —NH— | K196 | J045 | T169 |
| 198 | —(CH$_2$)$_2$— | —NH— | K196 | J045 | T170 |
| 199 | —(CH$_2$)$_2$— | —NH— | K196 | J045 | T172 |
| 200 | —(CH$_2$)$_2$— | —NH— | K197 | J012 | T148 |
| 201 | —(CH$_2$)$_2$— | —NH— | K197 | J012 | T151 |
| 202 | —(CH$_2$)$_2$— | —NH— | K197 | J012 | T152 |
| 203 | —(CH$_2$)$_2$— | —NH— | K197 | J012 | T169 |
| 204 | —(CH$_2$)$_2$— | —NH— | K197 | J045 | T003 |
| 205 | —(CH$_2$)$_2$— | —NH— | K197 | J045 | T004 |
| 206 | —(CH$_2$)$_2$— | —NH— | K197 | J045 | T005 |
| 207 | —(CH$_2$)$_2$— | —NH— | K197 | J045 | T077 |
| 208 | —(CH$_2$)$_2$— | —NH— | K197 | J045 | T090 |
| 209 | —(CH$_2$)$_2$— | —NH— | K197 | J045 | T148 |
| 210 | —(CH$_2$)$_2$— | —NH— | K197 | J045 | T151 |
| 211 | —(CH$_2$)$_2$— | —NH— | K197 | J045 | T152 |
| 212 | —(CH$_2$)$_2$— | —NH— | K197 | J045 | T161 |
| 213 | —(CH$_2$)$_2$— | —NH— | K197 | J045 | T169 |
| 214 | —(CH$_2$)$_2$— | —NH— | K197 | J045 | T170 |
| 215 | —(CH$_2$)$_2$— | —NH— | K197 | J045 | T172 |
| 216 | —(CH$_2$)$_2$— | —NH—C(=O)— | K001 | J001 | T129 |
| 217 | —(CH$_2$)$_2$— | —NH—C(=O)— | K001 | J045 | T148 |
| 218 | —(CH$_2$)$_2$— | —NH—C(=O)— | K002 | J002 | T130 |
| 219 | —(CH$_2$)$_2$— | —NH—C(=O)— | K002 | J045 | T148 |
| 220 | —(CH$_2$)$_2$— | —NH—C(=O)— | K003 | J001 | T148 |
| 221 | —(CH$_2$)$_2$— | —NH—C(=O)— | K003 | J001 | T169 |
| 222 | —(CH$_2$)$_2$— | —NH—C(=O)— | K003 | J008 | T134 |
| 223 | —(CH$_2$)$_2$— | —NH—C(=O)— | K003 | J008 | T148 |
| 224 | —(CH$_2$)$_2$— | —NH—C(=O)— | K003 | J009 | T148 |
| 225 | —(CH$_2$)$_2$— | —NH—C(=O)— | K003 | J012 | T148 |
| 226 | —(CH$_2$)$_2$— | —NH—C(=O)— | K003 | J018 | T148 |
| 227 | —(CH$_2$)$_2$— | —NH—C(=O)— | K003 | J018 | T152 |
| 228 | —(CH$_2$)$_2$— | —NH—C(=O)— | K003 | J035 | T148 |

TABLE 1-continued

| Compound no. | -A¹- | -A²- | -G¹-A³-A⁴-G² | -A⁵-R² | -A⁶-R³ |
|---|---|---|---|---|---|
| 229 | —(CH$_2$)$_2$— | —NH—C(=O)— | K003 | J035 | T151 |
| 230 | —(CH$_2$)$_2$— | —NH—C(=O)— | K003 | J045 | T148 |
| 231 | —(CH$_2$)$_2$— | —NH—C(=O)— | K003 | J052 | T148 |
| 232 | —(CH$_2$)$_2$— | —NH—C(=O)— | K003 | J052 | T169 |
| 233 | —(CH$_2$)$_2$— | —NH—C(=O)— | K003 | J069 | T148 |
| 234 | —(CH$_2$)$_2$— | —NH—C(=O)— | K003 | J069 | T152 |
| 235 | —(CH$_2$)$_2$— | —NH—C(=O)— | K004 | J003 | T148 |
| 236 | —(CH$_2$)$_2$— | —NH—C(=O)— | K004 | J003 | T152 |
| 237 | —(CH$_2$)$_2$— | —NH—C(=O)— | K004 | J008 | T148 |
| 238 | —(CH$_2$)$_2$— | —NH—C(=O)— | K004 | J009 | T135 |
| 239 | —(CH$_2$)$_2$— | —NH—C(=O)— | K004 | J009 | T148 |
| 240 | —(CH$_2$)$_2$— | —NH—C(=O)— | K004 | J012 | T148 |
| 241 | —(CH$_2$)$_2$— | —NH—C(=O)— | K004 | J020 | T148 |
| 242 | —(CH$_2$)$_2$— | —NH—C(=O)— | K004 | J020 | T151 |
| 243 | —(CH$_2$)$_2$— | —NH—C(=O)— | K004 | J037 | T148 |
| 244 | —(CH$_2$)$_2$— | —NH—C(=O)— | K004 | J037 | T169 |
| 245 | —(CH$_2$)$_2$— | —NH—C(=O)— | K004 | J045 | T148 |
| 246 | —(CH$_2$)$_2$— | —NH—C(=O)— | K004 | J054 | T148 |
| 247 | —(CH$_2$)$_2$— | —NH—C(=O)— | K004 | J054 | T152 |
| 248 | —(CH$_2$)$_2$— | —NH—C(=O)— | K004 | J071 | T148 |
| 249 | —(CH$_2$)$_2$— | —NH—C(=O)— | K004 | J071 | T151 |
| 250 | —(CH$_2$)$_2$— | —NH—C(=O)— | K005 | J008 | T148 |
| 251 | —(CH$_2$)$_2$— | —NH—C(=O)— | K005 | J009 | T148 |
| 252 | —(CH$_2$)$_2$— | —NH—C(=O)— | K005 | J012 | T145 |
| 253 | —(CH$_2$)$_2$— | —NH—C(=O)— | K005 | J012 | T148 |
| 254 | —(CH$_2$)$_2$— | —NH—C(=O)— | K005 | J045 | T148 |
| 255 | —(CH$_2$)$_2$— | —NH—C(=O)— | K006 | J008 | T148 |
| 256 | —(CH$_2$)$_2$— | —NH—C(=O)— | K006 | J009 | T148 |
| 257 | —(CH$_2$)$_2$— | —NH—C(=O)— | K006 | J012 | T148 |
| 258 | —(CH$_2$)$_2$— | —NH—C(=O)— | K006 | J014 | T148 |
| 259 | —(CH$_2$)$_2$— | —NH—C(=O)— | K007 | J004 | T148 |
| 260 | —(CH$_2$)$_2$— | —NH—C(=O)— | K007 | J004 | T169 |
| 261 | —(CH$_2$)$_2$— | —NH—C(=O)— | K007 | J008 | T148 |
| 262 | —(CH$_2$)$_2$— | —NH—C(=O)— | K007 | J009 | T148 |
| 263 | —(CH$_2$)$_2$— | —NH—C(=O)— | K007 | J012 | T148 |
| 264 | —(CH$_2$)$_2$— | —NH—C(=O)— | K007 | J015 | T149 |
| 265 | —(CH$_2$)$_2$— | —NH—C(=O)— | K007 | J021 | T148 |
| 266 | —(CH$_2$)$_2$— | —NH—C(=O)— | K007 | J021 | T152 |
| 267 | —(CH$_2$)$_2$— | —NH—C(=O)— | K007 | J038 | T148 |
| 268 | —(CH$_2$)$_2$— | —NH—C(=O)— | K007 | J038 | T151 |
| 269 | —(CH$_2$)$_2$— | —NH—C(=O)— | K007 | J045 | T148 |
| 270 | —(CH$_2$)$_2$— | —NH—C(=O)— | K007 | J055 | T148 |
| 271 | —(CH$_2$)$_2$— | —NH—C(=O)— | K007 | J055 | T169 |
| 272 | —(CH$_2$)$_2$— | —NH—C(=O)— | K007 | J072 | T148 |
| 273 | —(CH$_2$)$_2$— | —NH—C(=O)— | K007 | J072 | T152 |
| 274 | —(CH$_2$)$_2$— | —NH—C(=O)— | K008 | J005 | T148 |
| 275 | —(CH$_2$)$_2$— | —NH—C(=O)— | K008 | J005 | T151 |
| 276 | —(CH$_2$)$_2$— | —NH—C(=O)— | K008 | J008 | T148 |
| 277 | —(CH$_2$)$_2$— | —NH—C(=O)— | K008 | J008 | T152 |
| 278 | —(CH$_2$)$_2$— | —NH—C(=O)— | K008 | J009 | T148 |
| 279 | —(CH$_2$)$_2$— | —NH—C(=O)— | K008 | J009 | T152 |
| 280 | —(CH$_2$)$_2$— | —NH—C(=O)— | K008 | J012 | T148 |
| 281 | —(CH$_2$)$_2$— | —NH—C(=O)— | K008 | J012 | T152 |
| 282 | —(CH$_2$)$_2$— | —NH—C(=O)— | K008 | J018 | T151 |
| 283 | —(CH$_2$)$_2$— | —NH—C(=O)— | K008 | J022 | T148 |
| 284 | —(CH$_2$)$_2$— | —NH—C(=O)— | K008 | J022 | T169 |
| 285 | —(CH$_2$)$_2$— | —NH—C(=O)— | K008 | J039 | T148 |
| 286 | —(CH$_2$)$_2$— | —NH—C(=O)— | K008 | J039 | T152 |
| 287 | —(CH$_2$)$_2$— | —NH—C(=O)— | K008 | J045 | T148 |
| 288 | —(CH$_2$)$_2$— | —NH—C(=O)— | K008 | J045 | T152 |
| 289 | —(CH$_2$)$_2$— | —NH—C(=O)— | K008 | J056 | T148 |
| 290 | —(CH$_2$)$_2$— | —NH—C(=O)— | K008 | J056 | T151 |
| 291 | —(CH$_2$)$_2$— | —NH—C(=O)— | K008 | J073 | T148 |
| 292 | —(CH$_2$)$_2$— | —NH—C(=O)— | K008 | J073 | T169 |
| 293 | —(CH$_2$)$_2$— | —NH—C(=O)— | K009 | J006 | T148 |
| 294 | —(CH$_2$)$_2$— | —NH—C(=O)— | K009 | J006 | T152 |
| 295 | —(CH$_2$)$_2$— | —NH—C(=O)— | K009 | J008 | T148 |
| 296 | —(CH$_2$)$_2$— | —NH—C(=O)— | K009 | J009 | T148 |
| 297 | —(CH$_2$)$_2$— | —NH—C(=O)— | K009 | J012 | T148 |
| 298 | —(CH$_2$)$_2$— | —NH—C(=O)— | K009 | J023 | T148 |
| 299 | —(CH$_2$)$_2$— | —NH—C(=O)— | K009 | J023 | T151 |
| 300 | —(CH$_2$)$_2$— | —NH—C(=O)— | K009 | J040 | T148 |
| 301 | —(CH$_2$)$_2$— | —NH—C(=O)— | K009 | J040 | T169 |
| 302 | —(CH$_2$)$_2$— | —NH—C(=O)— | K009 | J043 | T152 |
| 303 | —(CH$_2$)$_2$— | —NH—C(=O)— | K009 | J045 | T148 |
| 304 | —(CH$_2$)$_2$— | —NH—C(=O)— | K009 | J057 | T148 |

TABLE 1-continued

| Compound no. | -A$^1$- | -A$^2$- | -G$^1$-A$^3$-A$^4$-G$^2$ | -A$^5$-R$^2$ | -A$^6$-R$^3$ |
|---|---|---|---|---|---|
| 305 | —(CH$_2$)$_2$— | —NH—C(=O)— | K009 | J057 | T152 |
| 306 | —(CH$_2$)$_2$— | —NH—C(=O)— | K009 | J074 | T148 |
| 307 | —(CH$_2$)$_2$— | —NH—C(=O)— | K009 | J074 | T151 |
| 308 | —(CH$_2$)$_2$— | —NH—C(=O)— | K010 | J045 | T157 |
| 309 | —(CH$_2$)$_2$— | —NH—C(=O)— | K011 | J007 | T148 |
| 310 | —(CH$_2$)$_2$— | —NH—C(=O)— | K011 | J007 | T169 |
| 311 | —(CH$_2$)$_2$— | —NH—C(=O)— | K011 | J008 | T148 |
| 312 | —(CH$_2$)$_2$— | —NH—C(=O)— | K011 | J009 | T148 |
| 313 | —(CH$_2$)$_2$— | —NH—C(=O)— | K011 | J012 | T148 |
| 314 | —(CH$_2$)$_2$— | —NH—C(=O)— | K011 | J024 | T148 |
| 315 | —(CH$_2$)$_2$— | —NH—C(=O)— | K011 | J024 | T152 |
| 316 | —(CH$_2$)$_2$— | —NH—C(=O)— | K011 | J041 | T148 |
| 317 | —(CH$_2$)$_2$— | —NH—C(=O)— | K011 | J041 | T151 |
| 318 | —(CH$_2$)$_2$— | —NH—C(=O)— | K011 | J045 | T003 |
| 319 | —(CH$_2$)$_2$— | —NH—C(=O)— | K011 | J045 | T004 |
| 320 | —(CH$_2$)$_2$— | —NH—C(=O)— | K011 | J045 | T005 |
| 321 | —(CH$_2$)$_2$— | —NH—C(=O)— | K011 | J045 | T148 |
| 322 | —(CH$_2$)$_2$— | —NH—C(=O)— | K011 | J058 | T148 |
| 323 | —(CH$_2$)$_2$— | —NH—C(=O)— | K011 | J058 | T169 |
| 324 | —(CH$_2$)$_2$— | —NH—C(=O)— | K011 | J063 | T158 |
| 325 | —(CH$_2$)$_2$— | —NH—C(=O)— | K011 | J075 | T148 |
| 326 | —(CH$_2$)$_2$— | —NH—C(=O)— | K011 | J075 | T152 |
| 327 | —(CH$_2$)$_2$— | —NH—C(=O)— | K012 | J008 | T148 |
| 328 | —(CH$_2$)$_2$— | —NH—C(=O)— | K012 | J008 | T151 |
| 329 | —(CH$_2$)$_2$— | —NH—C(=O)— | K012 | J009 | T148 |
| 330 | —(CH$_2$)$_2$— | —NH—C(=O)— | K012 | J012 | T148 |
| 331 | —(CH$_2$)$_2$— | —NH—C(=O)— | K012 | J025 | T148 |
| 332 | —(CH$_2$)$_2$— | —NH—C(=O)— | K012 | J025 | T169 |
| 333 | —(CH$_2$)$_2$— | —NH—C(=O)— | K012 | J042 | T148 |
| 334 | —(CH$_2$)$_2$— | —NH—C(=O)— | K012 | J042 | T152 |
| 335 | —(CH$_2$)$_2$— | —NH—C(=O)— | K012 | J045 | T148 |
| 336 | —(CH$_2$)$_2$— | —NH—C(=O)— | K012 | J059 | T148 |
| 337 | —(CH$_2$)$_2$— | —NH—C(=O)— | K012 | J059 | T151 |
| 338 | —(CH$_2$)$_2$— | —NH—C(=O)— | K012 | J076 | T148 |
| 339 | —(CH$_2$)$_2$— | —NH—C(=O)— | K012 | J076 | T169 |
| 340 | —(CH$_2$)$_2$— | —NH—C(=O)— | K012 | J081 | T164 |
| 341 | —(CH$_2$)$_2$— | —NH—C(=O)— | K013 | J001 | T168 |
| 342 | —(CH$_2$)$_2$— | —NH—C(=O)— | K013 | J008 | T148 |
| 343 | —(CH$_2$)$_2$— | —NH—C(=O)— | K013 | J012 | T148 |
| 344 | —(CH$_2$)$_2$— | —NH—C(=O)— | K013 | J045 | T005 |
| 345 | —(CH$_2$)$_2$— | —NH—C(=O)— | K013 | J045 | T077 |
| 346 | —(CH$_2$)$_2$— | —NH—C(=O)— | K013 | J045 | T090 |
| 347 | —(CH$_2$)$_2$— | —NH—C(=O)— | K013 | J045 | T129 |
| 348 | —(CH$_2$)$_2$— | —NH—C(=O)— | K013 | J045 | T148 |
| 349 | —(CH$_2$)$_2$— | —NH—C(=O)— | K014 | J002 | T169 |
| 350 | —(CH$_2$)$_2$— | —NH—C(=O)— | K015 | J008 | T170 |
| 351 | —(CH$_2$)$_2$— | —NH—C(=O)— | K016 | J009 | T173 |
| 352 | —(CH$_2$)$_2$— | —NH—C(=O)— | K017 | J012 | T176 |
| 353 | —(CH$_2$)$_2$— | —NH—C(=O)— | K018 | J014 | T178 |
| 354 | —(CH$_2$)$_2$— | —NH—C(=O)— | K019 | J015 | T129 |
| 355 | —(CH$_2$)$_2$— | —NH—C(=O)— | K020 | J018 | T130 |
| 356 | —(CH$_2$)$_2$— | —NH—C(=O)— | K021 | J043 | T134 |
| 357 | —(CH$_2$)$_2$— | —NH—C(=O)— | K022 | J045 | T135 |
| 358 | —(CH$_2$)$_2$— | —NH—C(=O)— | K023 | J063 | T145 |
| 359 | —(CH$_2$)$_2$— | —NH—C(=O)— | K024 | J081 | T148 |
| 360 | —(CH$_2$)$_2$— | —NH—C(=O)— | K025 | J001 | T149 |
| 361 | —(CH$_2$)$_2$— | —NH—C(=O)— | K025 | J045 | T148 |
| 362 | —(CH$_2$)$_2$— | —NH—C(=O)— | K026 | J002 | T151 |
| 363 | —(CH$_2$)$_2$— | —NH—C(=O)— | K027 | J008 | T152 |
| 364 | —(CH$_2$)$_2$— | —NH—C(=O)— | K028 | J009 | T157 |
| 365 | —(CH$_2$)$_2$— | —NH—C(=O)— | K029 | J012 | T158 |
| 366 | —(CH$_2$)$_2$— | —NH—C(=O)— | K030 | J014 | T164 |
| 367 | —(CH$_2$)$_2$— | —NH—C(=O)— | K031 | J015 | T168 |
| 368 | —(CH$_2$)$_2$— | —NH—C(=O)— | K032 | J018 | T169 |
| 369 | —(CH$_2$)$_2$— | —NH—C(=O)— | K033 | J043 | T170 |
| 370 | —(CH$_2$)$_2$— | —NH—C(=O)— | K033 | J045 | T004 |
| 371 | —(CH$_2$)$_2$— | —NH—C(=O)— | K034 | J045 | T173 |
| 372 | —(CH$_2$)$_2$— | —NH—C(=O)— | K035 | J063 | T176 |
| 373 | —(CH$_2$)$_2$— | —NH—C(=O)— | K036 | J081 | T178 |
| 374 | —(CH$_2$)$_2$— | —NH—C(=O)— | K037 | J001 | T129 |
| 375 | —(CH$_2$)$_2$— | —NH—C(=O)— | K038 | J002 | T130 |
| 376 | —(CH$_2$)$_2$— | —NH—C(=O)— | K039 | J008 | T134 |
| 377 | —(CH$_2$)$_2$— | —NH—C(=O)— | K040 | J009 | T135 |
| 378 | —(CH$_2$)$_2$— | —NH—C(=O)— | K041 | J012 | T145 |
| 379 | —(CH$_2$)$_2$— | —NH—C(=O)— | K042 | J014 | T148 |
| 380 | —(CH$_2$)$_2$— | —NH—C(=O)— | K043 | J015 | T149 |

TABLE 1-continued

| Compound no. | -A¹- | -A²- | -G¹-A³-A⁴-G² | -A⁵-R² | -A⁶-R³ |
|---|---|---|---|---|---|
| 381 | —(CH$_2$)$_2$— | —NH—C(=O)— | K044 | J010 | T148 |
| 382 | —(CH$_2$)$_2$— | —NH—C(=O)— | K044 | J010 | T169 |
| 383 | —(CH$_2$)$_2$— | —NH—C(=O)— | K044 | J018 | T151 |
| 384 | —(CH$_2$)$_2$— | —NH—C(=O)— | K044 | J027 | T148 |
| 385 | —(CH$_2$)$_2$— | —NH—C(=O)— | K044 | J027 | T152 |
| 386 | —(CH$_2$)$_2$— | —NH—C(=O)— | K044 | J044 | T148 |
| 387 | —(CH$_2$)$_2$— | —NH—C(=O)— | K044 | J044 | T151 |
| 388 | —(CH$_2$)$_2$— | —NH—C(=O)— | K044 | J061 | T148 |
| 389 | —(CH$_2$)$_2$— | —NH—C(=O)— | K044 | J061 | T169 |
| 390 | —(CH$_2$)$_2$— | —NH—C(=O)— | K044 | J078 | T148 |
| 391 | —(CH$_2$)$_2$— | —NH—C(=O)— | K044 | J078 | T152 |
| 392 | —(CH$_2$)$_2$— | —NH—C(=O)— | K045 | J043 | T152 |
| 393 | —(CH$_2$)$_2$— | —NH—C(=O)— | K046 | J045 | T157 |
| 394 | —(CH$_2$)$_2$— | —NH—C(=O)— | K047 | J063 | T158 |
| 395 | —(CH$_2$)$_2$— | —NH—C(=O)— | K048 | J081 | T164 |
| 396 | —(CH$_2$)$_2$— | —NH—C(=O)— | K049 | J001 | T168 |
| 397 | —(CH$_2$)$_2$— | —NH—C(=O)— | K050 | J002 | T169 |
| 398 | —(CH$_2$)$_2$— | —NH—C(=O)— | K051 | J008 | T170 |
| 399 | —(CH$_2$)$_2$— | —NH—C(=O)— | K052 | J009 | T173 |
| 400 | —(CH$_2$)$_2$— | —NH—C(=O)— | K053 | J012 | T176 |
| 401 | —(CH$_2$)$_2$— | —NH—C(=O)— | K054 | J014 | T178 |
| 402 | —(CH$_2$)$_2$— | —NH—C(=O)— | K055 | J015 | T129 |
| 403 | —(CH$_2$)$_2$— | —NH—C(=O)— | K056 | J018 | T130 |
| 404 | —(CH$_2$)$_2$— | —NH—C(=O)— | K057 | J043 | T134 |
| 405 | —(CH$_2$)$_2$— | —NH—C(=O)— | K058 | J045 | T135 |
| 406 | —(CH$_2$)$_2$— | —NH—C(=O)— | K059 | J063 | T145 |
| 407 | —(CH$_2$)$_2$— | —NH—C(=O)— | K060 | J081 | T148 |
| 408 | —(CH$_2$)$_2$— | —NH—C(=O)— | K061 | J001 | T149 |
| 409 | —(CH$_2$)$_2$— | —NH—C(=O)— | K062 | J002 | T151 |
| 410 | —(CH$_2$)$_2$— | —NH—C(=O)— | K063 | J008 | T152 |
| 411 | —(CH$_2$)$_2$— | —NH—C(=O)— | K064 | J009 | T157 |
| 412 | —(CH$_2$)$_2$— | —NH—C(=O)— | K065 | J012 | T158 |
| 413 | —(CH$_2$)$_2$— | —NH—C(=O)— | K066 | J014 | T164 |
| 414 | —(CH$_2$)$_2$— | —NH—C(=O)— | K067 | J015 | T168 |
| 415 | —(CH$_2$)$_2$— | —NH—C(=O)— | K068 | J018 | T169 |
| 416 | —(CH$_2$)$_2$— | —NH—C(=O)— | K069 | J043 | T170 |
| 417 | —(CH$_2$)$_2$— | —NH—C(=O)— | K070 | J011 | T148 |
| 418 | —(CH$_2$)$_2$— | —NH—C(=O)— | K070 | J011 | T151 |
| 419 | —(CH$_2$)$_2$— | —NH—C(=O)— | K070 | J028 | T148 |
| 420 | —(CH$_2$)$_2$— | —NH—C(=O)— | K070 | J028 | T169 |
| 421 | —(CH$_2$)$_2$— | —NH—C(=O)— | K070 | J045 | T148 |
| 422 | —(CH$_2$)$_2$— | —NH—C(=O)— | K070 | J045 | T152 |
| 423 | —(CH$_2$)$_2$— | —NH—C(=O)— | K070 | J045 | T173 |
| 424 | —(CH$_2$)$_2$— | —NH—C(=O)— | K070 | J062 | T148 |
| 425 | —(CH$_2$)$_2$— | —NH—C(=O)— | K070 | J062 | T151 |
| 426 | —(CH$_2$)$_2$— | —NH—C(=O)— | K070 | J079 | T148 |
| 427 | —(CH$_2$)$_2$— | —NH—C(=O)— | K070 | J079 | T169 |
| 428 | —(CH$_2$)$_2$— | —NH—C(=O)— | K071 | J063 | T176 |
| 429 | —(CH$_2$)$_2$— | —NH—C(=O)— | K072 | J012 | T148 |
| 430 | —(CH$_2$)$_2$— | —NH—C(=O)— | K072 | J012 | T152 |
| 431 | —(CH$_2$)$_2$— | —NH—C(=O)— | K072 | J029 | T148 |
| 432 | —(CH$_2$)$_2$— | —NH—C(=O)— | K072 | J029 | T151 |
| 433 | —(CH$_2$)$_2$— | —NH—C(=O)— | K072 | J046 | T148 |
| 434 | —(CH$_2$)$_2$— | —NH—C(=O)— | K072 | J046 | T169 |
| 435 | —(CH$_2$)$_2$— | —NH—C(=O)— | K072 | J063 | T148 |
| 436 | —(CH$_2$)$_2$— | —NH—C(=O)— | K072 | J063 | T152 |
| 437 | —(CH$_2$)$_2$— | —NH—C(=O)— | K072 | J080 | T148 |
| 438 | —(CH$_2$)$_2$— | —NH—C(=O)— | K072 | J080 | T151 |
| 439 | —(CH$_2$)$_2$— | —NH—C(=O)— | K072 | J081 | T178 |
| 440 | —(CH$_2$)$_2$— | —NH—C(=O)— | K073 | J001 | T129 |
| 441 | —(CH$_2$)$_2$— | —NH—C(=O)— | K074 | J002 | T130 |
| 442 | —(CH$_2$)$_2$— | —NH—C(=O)— | K075 | J008 | T134 |
| 443 | —(CH$_2$)$_2$— | —NH—C(=O)— | K076 | J009 | T135 |
| 444 | —(CH$_2$)$_2$— | —NH—C(=O)— | K077 | J012 | T145 |
| 445 | —(CH$_2$)$_2$— | —NH—C(=O)— | K078 | J014 | T148 |
| 446 | —(CH$_2$)$_2$— | —NH—C(=O)— | K079 | J015 | T149 |
| 447 | —(CH$_2$)$_2$— | —NH—C(=O)— | K080 | J018 | T151 |
| 448 | —(CH$_2$)$_2$— | —NH—C(=O)— | K081 | J043 | T152 |
| 449 | —(CH$_2$)$_2$— | —NH—C(=O)— | K082 | J045 | T157 |
| 450 | —(CH$_2$)$_2$— | —NH—C(=O)— | K083 | J063 | T158 |
| 451 | —(CH$_2$)$_2$— | —NH—C(=O)— | K084 | J081 | T164 |
| 452 | —(CH$_2$)$_2$— | —NH—C(=O)— | K085 | J001 | T168 |
| 453 | —(CH$_2$)$_2$— | —NH—C(=O)— | K086 | J002 | T169 |
| 454 | —(CH$_2$)$_2$— | —NH—C(=O)— | K087 | J008 | T170 |
| 455 | —(CH$_2$)$_2$— | —NH—C(=O)— | K088 | J009 | T173 |
| 456 | —(CH$_2$)$_2$— | —NH—C(=O)— | K089 | J012 | T176 |

TABLE 1-continued

| Compound no. | -A¹- | -A²- | -G¹-A³-A⁴-G² | -A⁵-R² | -A⁶-R³ |
|---|---|---|---|---|---|
| 457 | —(CH₂)₂— | —NH—C(=O)— | K090 | J014 | T178 |
| 458 | —(CH₂)₂— | —NH—C(=O)— | K091 | J015 | T129 |
| 459 | —(CH₂)₂— | —NH—C(=O)— | K092 | J018 | T130 |
| 460 | —(CH₂)₂— | —NH—C(=O)— | K093 | J043 | T134 |
| 461 | —(CH₂)₂— | —NH—C(=O)— | K094 | J045 | T135 |
| 462 | —(CH₂)₂— | —NH—C(=O)— | K095 | J063 | T145 |
| 463 | —(CH₂)₂— | —NH—C(=O)— | K096 | J081 | T148 |
| 464 | —(CH₂)₂— | —NH—C(=O)— | K097 | J001 | T149 |
| 465 | —(CH₂)₂— | —NH—C(=O)— | K098 | J002 | T151 |
| 466 | —(CH₂)₂— | —NH—C(=O)— | K099 | J008 | T152 |
| 467 | —(CH₂)₂— | —NH—C(=O)— | K100 | J009 | T157 |
| 468 | —(CH₂)₂— | —NH—C(=O)— | K101 | J012 | T158 |
| 469 | —(CH₂)₂— | —NH—C(=O)— | K102 | J014 | T164 |
| 470 | —(CH₂)₂— | —NH—C(=O)— | K103 | J015 | T168 |
| 471 | —(CH₂)₂— | —NH—C(=O)— | K104 | J018 | T169 |
| 472 | —(CH₂)₂— | —NH—C(=O)— | K105 | J043 | T170 |
| 473 | —(CH₂)₂— | —NH—C(=O)— | K106 | J045 | T173 |
| 474 | —(CH₂)₂— | —NH—C(=O)— | K107 | J013 | T148 |
| 475 | —(CH₂)₂— | —NH—C(=O)— | K107 | J013 | T169 |
| 476 | —(CH₂)₂— | —NH—C(=O)— | K107 | J030 | T148 |
| 477 | —(CH₂)₂— | —NH—C(=O)— | K107 | J030 | T152 |
| 478 | —(CH₂)₂— | —NH—C(=O)— | K107 | J047 | T148 |
| 479 | —(CH₂)₂— | —NH—C(=O)— | K107 | J047 | T151 |
| 480 | —(CH₂)₂— | —NH—C(=O)— | K107 | J063 | T176 |
| 481 | —(CH₂)₂— | —NH—C(=O)— | K107 | J064 | T148 |
| 482 | —(CH₂)₂— | —NH—C(=O)— | K107 | J064 | T169 |
| 483 | —(CH₂)₂— | —NH—C(=O)— | K107 | J081 | T148 |
| 484 | —(CH₂)₂— | —NH—C(=O)— | K107 | J081 | T152 |
| 485 | —(CH₂)₂— | —NH—C(=O)— | K108 | J008 | T148 |
| 486 | —(CH₂)₂— | —NH—C(=O)— | K108 | J009 | T148 |
| 487 | —(CH₂)₂— | —NH—C(=O)— | K108 | J012 | T148 |
| 488 | —(CH₂)₂— | —NH—C(=O)— | K108 | J014 | T148 |
| 489 | —(CH₂)₂— | —NH—C(=O)— | K108 | J014 | T151 |
| 490 | —(CH₂)₂— | —NH—C(=O)— | K108 | J031 | T148 |
| 491 | —(CH₂)₂— | —NH—C(=O)— | K108 | J031 | T169 |
| 492 | —(CH₂)₂— | —NH—C(=O)— | K108 | J045 | T148 |
| 493 | —(CH₂)₂— | —NH—C(=O)— | K108 | J048 | T148 |
| 494 | —(CH₂)₂— | —NH—C(=O)— | K108 | J048 | T152 |
| 495 | —(CH₂)₂— | —NH—C(=O)— | K108 | J065 | T148 |
| 496 | —(CH₂)₂— | —NH—C(=O)— | K108 | J065 | T151 |
| 497 | —(CH₂)₂— | —NH—C(=O)— | K108 | J081 | T178 |
| 498 | —(CH₂)₂— | —NH—C(=O)— | K108 | J082 | T148 |
| 499 | —(CH₂)₂— | —NH—C(=O)— | K108 | J082 | T169 |
| 500 | —(CH₂)₂— | —NH—C(=O)— | K109 | J001 | T129 |
| 501 | —(CH₂)₂— | —NH—C(=O)— | K109 | J008 | T148 |
| 502 | —(CH₂)₂— | —NH—C(=O)— | K109 | J009 | T148 |
| 503 | —(CH₂)₂— | —NH—C(=O)— | K109 | J012 | T148 |
| 504 | —(CH₂)₂— | —NH—C(=O)— | K109 | J045 | T148 |
| 505 | —(CH₂)₂— | —NH—C(=O)— | K110 | J002 | T130 |
| 506 | —(CH₂)₂— | —NH—C(=O)— | K111 | J008 | T134 |
| 507 | —(CH₂)₂— | —NH—C(=O)— | K112 | J009 | T135 |
| 508 | —(CH₂)₂— | —NH—C(=O)— | K113 | J012 | T145 |
| 509 | —(CH₂)₂— | —NH—C(=O)— | K114 | J014 | T148 |
| 510 | —(CH₂)₂— | —NH—C(=O)— | K115 | J015 | T149 |
| 511 | —(CH₂)₂— | —NH—C(=O)— | K116 | J018 | T151 |
| 512 | —(CH₂)₂— | —NH—C(=O)— | K117 | J043 | T152 |
| 513 | —(CH₂)₂— | —NH—C(=O)— | K118 | J045 | T157 |
| 514 | —(CH₂)₂— | —NH—C(=O)— | K119 | J063 | T158 |
| 515 | —(CH₂)₂— | —NH—C(=O)— | K120 | J081 | T164 |
| 516 | —(CH₂)₂— | —NH—C(=O)— | K121 | J001 | T168 |
| 517 | —(CH₂)₂— | —NH—C(=O)— | K122 | J002 | T169 |
| 518 | —(CH₂)₂— | —NH—C(=O)— | K123 | J008 | T170 |
| 519 | —(CH₂)₂— | —NH—C(=O)— | K124 | J009 | T173 |
| 520 | —(CH₂)₂— | —NH—C(=O)— | K125 | J012 | T176 |
| 521 | —(CH₂)₂— | —NH—C(=O)— | K126 | J014 | T178 |
| 522 | —(CH₂)₂— | —NH—C(=O)— | K127 | J015 | T129 |
| 523 | —(CH₂)₂— | —NH—C(=O)— | K128 | J018 | T130 |
| 524 | —(CH₂)₂— | —NH—C(=O)— | K129 | J043 | T134 |
| 525 | —(CH₂)₂— | —NH—C(=O)— | K130 | J045 | T135 |
| 526 | —(CH₂)₂— | —NH—C(=O)— | K131 | J063 | T145 |
| 527 | —(CH₂)₂— | —NH—C(=O)— | K132 | J081 | T148 |
| 528 | —(CH₂)₂— | —NH—C(=O)— | K133 | J001 | T149 |
| 529 | —(CH₂)₂— | —NH—C(=O)— | K134 | J002 | T151 |
| 530 | —(CH₂)₂— | —NH—C(=O)— | K135 | J008 | T152 |
| 531 | —(CH₂)₂— | —NH—C(=O)— | K136 | J009 | T157 |
| 532 | —(CH₂)₂— | —NH—C(=O)— | K137 | J008 | T148 |

TABLE 1-continued

| Compound no. | -A¹- | -A²- | -G¹-A³-A⁴-G² | -A⁵-R² | -A⁶-R³ |
|---|---|---|---|---|---|
| 533 | —(CH$_2$)$_2$— | —NH—C(=O)— | K137 | J009 | T148 |
| 534 | —(CH$_2$)$_2$— | —NH—C(=O)— | K137 | J012 | T148 |
| 535 | —(CH$_2$)$_2$— | —NH—C(=O)— | K137 | J012 | T158 |
| 536 | —(CH$_2$)$_2$— | —NH—C(=O)— | K137 | J045 | T148 |
| 537 | —(CH$_2$)$_2$— | —NH—C(=O)— | K138 | J014 | T164 |
| 538 | —(CH$_2$)$_2$— | —NH—C(=O)— | K139 | J015 | T168 |
| 539 | —(CH$_2$)$_2$— | —NH—C(=O)— | K140 | J018 | T169 |
| 540 | —(CH$_2$)$_2$— | —NH—C(=O)— | K141 | J043 | T170 |
| 541 | —(CH$_2$)$_2$— | —NH—C(=O)— | K142 | J045 | T173 |
| 542 | —(CH$_2$)$_2$— | —NH—C(=O)— | K143 | J063 | T176 |
| 543 | —(CH$_2$)$_2$— | —NH—C(=O)— | K144 | J008 | T148 |
| 544 | —(CH$_2$)$_2$— | —NH—C(=O)— | K144 | J009 | T148 |
| 545 | —(CH$_2$)$_2$— | —NH—C(=O)— | K144 | J012 | T148 |
| 546 | —(CH$_2$)$_2$— | —NH—C(=O)— | K144 | J015 | T148 |
| 547 | —(CH$_2$)$_2$— | —NH—C(=O)— | K144 | J015 | T152 |
| 548 | —(CH$_2$)$_2$— | —NH—C(=O)— | K144 | J032 | T148 |
| 549 | —(CH$_2$)$_2$— | —NH—C(=O)— | K144 | J032 | T151 |
| 550 | —(CH$_2$)$_2$— | —NH—C(=O)— | K144 | J045 | T148 |
| 551 | —(CH$_2$)$_2$— | —NH—C(=O)— | K144 | J049 | T148 |
| 552 | —(CH$_2$)$_2$— | —NH—C(=O)— | K144 | J049 | T169 |
| 553 | —(CH$_2$)$_2$— | —NH—C(=O)— | K144 | J066 | T148 |
| 554 | —(CH$_2$)$_2$— | —NH—C(=O)— | K144 | J066 | T152 |
| 555 | —(CH$_2$)$_2$— | —NH—C(=O)— | K144 | J081 | T178 |
| 556 | —(CH$_2$)$_2$— | —NH—C(=O)— | K144 | J083 | T148 |
| 557 | —(CH$_2$)$_2$— | —NH—C(=O)— | K144 | J083 | T151 |
| 558 | —(CH$_2$)$_2$— | —NH—C(=O)— | K145 | J001 | T129 |
| 559 | —(CH$_2$)$_2$— | —NH—C(=O)— | K146 | J002 | T130 |
| 560 | —(CH$_2$)$_2$— | —NH—C(=O)— | K147 | J008 | T134 |
| 561 | —(CH$_2$)$_2$— | —NH—C(=O)— | K148 | J009 | T135 |
| 562 | —(CH$_2$)$_2$— | —NH—C(=O)— | K149 | J012 | T145 |
| 563 | —(CH$_2$)$_2$— | —NH—C(=O)— | K150 | J014 | T148 |
| 564 | —(CH$_2$)$_2$— | —NH—C(=O)— | K151 | J015 | T149 |
| 565 | —(CH$_2$)$_2$— | —NH—C(=O)— | K152 | J018 | T151 |
| 566 | —(CH$_2$)$_2$— | —NH—C(=O)— | K153 | J043 | T152 |
| 567 | —(CH$_2$)$_2$— | —NH—C(=O)— | K154 | J045 | T157 |
| 568 | —(CH$_2$)$_2$— | —NH—C(=O)— | K155 | J063 | T158 |
| 569 | —(CH$_2$)$_2$— | —NH—C(=O)— | K156 | J081 | T164 |
| 570 | —(CH$_2$)$_2$— | —NH—C(=O)— | K157 | J001 | T168 |
| 571 | —(CH$_2$)$_2$— | —NH—C(=O)— | K158 | J002 | T169 |
| 572 | —(CH$_2$)$_2$— | —NH—C(=O)— | K159 | J008 | T170 |
| 573 | —(CH$_2$)$_2$— | —NH—C(=O)— | K160 | J009 | T173 |
| 574 | —(CH$_2$)$_2$— | —NH—C(=O)— | K161 | J012 | T176 |
| 575 | —(CH$_2$)$_2$— | —NH—C(=O)— | K162 | J014 | T178 |
| 576 | —(CH$_2$)$_2$— | —NH—C(=O)— | K163 | J015 | T129 |
| 577 | —(CH$_2$)$_2$— | —NH—C(=O)— | K164 | J018 | T130 |
| 578 | —(CH$_2$)$_2$— | —NH—C(=O)— | K165 | J043 | T134 |
| 579 | —(CH$_2$)$_2$— | —NH—C(=O)— | K166 | J045 | T135 |
| 580 | —(CH$_2$)$_2$— | —NH—C(=O)— | K167 | J063 | T145 |
| 581 | —(CH$_2$)$_2$— | —NH—C(=O)— | K168 | J081 | T148 |
| 582 | —(CH$_2$)$_2$— | —NH—C(=O)— | K169 | J001 | T149 |
| 583 | —(CH$_2$)$_2$— | —NH—C(=O)— | K170 | J002 | T151 |
| 584 | —(CH$_2$)$_2$— | —NH—C(=O)— | K171 | J008 | T152 |
| 585 | —(CH$_2$)$_2$— | —NH—C(=O)— | K172 | J009 | T157 |
| 586 | —(CH$_2$)$_2$— | —NH—C(=O)— | K173 | J012 | T158 |
| 587 | —(CH$_2$)$_2$— | —NH—C(=O)— | K174 | J014 | T164 |
| 588 | —(CH$_2$)$_2$— | —NH—C(=O)— | K175 | J015 | T168 |
| 589 | —(CH$_2$)$_2$— | —NH—C(=O)— | K176 | J018 | T169 |
| 590 | —(CH$_2$)$_2$— | —NH—C(=O)— | K177 | J043 | T170 |
| 591 | —(CH$_2$)$_2$— | —NH—C(=O)— | K178 | J045 | T173 |
| 592 | —(CH$_2$)$_2$— | —NH—C(=O)— | K197 | J063 | T176 |
| 593 | —(CH$_2$)$_2$— | —NH—C(=O)— | K198 | J008 | T148 |
| 594 | —(CH$_2$)$_2$— | —NH—C(=O)— | K198 | J009 | T148 |
| 595 | —(CH$_2$)$_2$— | —NH—C(=O)— | K198 | J012 | T148 |
| 596 | —(CH$_2$)$_2$— | —NH—C(=O)— | K198 | J045 | T148 |
| 597 | —(CH$_2$)$_2$— | —NH—C(=O)— | K198 | J081 | T178 |
| 598 | —(CH$_2$)$_2$— | —NH—C(=O)— | K199 | J001 | T129 |
| 599 | —(CH$_2$)$_2$— | —NH—C(=O)— | K199 | J008 | T148 |
| 600 | —(CH$_2$)$_2$— | —NH—C(=O)— | K199 | J009 | T148 |
| 601 | —(CH$_2$)$_2$— | —NH—C(=O)— | K199 | J012 | T148 |
| 602 | —(CH$_2$)$_2$— | —NH—C(=O)— | K199 | J045 | T148 |
| 603 | —(CH$_2$)$_2$— | —NH—C(=O)— | K200 | J002 | T130 |
| 604 | —(CH$_2$)$_2$— | —NH—C(=O)— | K200 | J008 | T005 |
| 605 | —(CH$_2$)$_2$— | —NH—C(=O)— | K200 | J008 | T148 |
| 606 | —(CH$_2$)$_2$— | —NH—C(=O)— | K200 | J008 | T151 |
| 607 | —(CH$_2$)$_2$— | —NH—C(=O)— | K200 | J008 | T152 |
| 608 | —(CH$_2$)$_2$— | —NH—C(=O)— | K200 | J008 | T169 |

TABLE 1-continued

| Compound no. | -A¹- | -A²- | -G¹-A³-A⁴-G² | -A⁵-R² | -A⁶-R³ |
|---|---|---|---|---|---|
| 609 | —(CH₂)₂— | —NH—C(=O)— | K200 | J009 | T005 |
| 610 | —(CH₂)₂— | —NH—C(=O)— | K200 | J009 | T148 |
| 611 | —(CH₂)₂— | —NH—C(=O)— | K200 | J009 | T151 |
| 612 | —(CH₂)₂— | —NH—C(=O)— | K200 | J009 | T152 |
| 613 | —(CH₂)₂— | —NH—C(=O)— | K200 | J009 | T169 |
| 614 | —(CH₂)₂— | —NH—C(=O)— | K200 | J012 | T005 |
| 615 | —(CH₂)₂— | —NH—C(=O)— | K200 | J012 | T148 |
| 616 | —(CH₂)₂— | —NH—C(=O)— | K200 | J012 | T151 |
| 617 | —(CH₂)₂— | —NH—C(=O)— | K200 | J012 | T152 |
| 618 | —(CH₂)₂— | —NH—C(=O)— | K200 | J012 | T169 |
| 619 | —(CH₂)₂— | —NH—C(=O)— | K200 | J016 | T005 |
| 620 | —(CH₂)₂— | —NH—C(=O)— | K200 | J016 | T148 |
| 621 | —(CH₂)₂— | —NH—C(=O)— | K200 | J016 | T169 |
| 622 | —(CH₂)₂— | —NH—C(=O)— | K200 | J033 | T005 |
| 623 | —(CH₂)₂— | —NH—C(=O)— | K200 | J033 | T148 |
| 624 | —(CH₂)₂— | —NH—C(=O)— | K200 | J033 | T152 |
| 625 | —(CH₂)₂— | —NH—C(=O)— | K200 | J045 | T005 |
| 626 | —(CH₂)₂— | —NH—C(=O)— | K200 | J045 | T148 |
| 627 | —(CH₂)₂— | —NH—C(=O)— | K200 | J045 | T151 |
| 628 | —(CH₂)₂— | —NH—C(=O)— | K200 | J045 | T152 |
| 629 | —(CH₂)₂— | —NH—C(=O)— | K200 | J045 | T169 |
| 630 | —(CH₂)₂— | —NH—C(=O)— | K200 | J050 | T148 |
| 631 | —(CH₂)₂— | —NH—C(=O)— | K200 | J050 | T151 |
| 632 | —(CH₂)₂— | —NH—C(=O)— | K200 | J067 | T148 |
| 633 | —(CH₂)₂— | —NH—C(=O)— | K200 | J067 | T169 |
| 634 | —(CH₂)₂— | —NH—C(=O)— | K200 | J084 | T148 |
| 635 | —(CH₂)₂— | —NH—C(=O)— | K200 | J084 | T152 |
| 636 | —(CH₂)₂— | —NH—C(=O)— | K201 | J008 | T134 |
| 637 | —(CH₂)₂— | —NH—C(=O)— | K202 | J009 | T135 |
| 638 | —(CH₂)₂— | —NH—C(=O)— | K203 | J008 | T148 |
| 639 | —(CH₂)₂— | —NH—C(=O)— | K203 | J009 | T148 |
| 640 | —(CH₂)₂— | —NH—C(=O)— | K203 | J012 | T145 |
| 641 | —(CH₂)₂— | —NH—C(=O)— | K203 | J012 | T148 |
| 642 | —(CH₂)₂— | —NH—C(=O)— | K203 | J017 | T148 |
| 643 | —(CH₂)₂— | —NH—C(=O)— | K203 | J017 | T151 |
| 644 | —(CH₂)₂— | —NH—C(=O)— | K203 | J034 | T148 |
| 645 | —(CH₂)₂— | —NH—C(=O)— | K203 | J034 | T169 |
| 646 | —(CH₂)₂— | —NH—C(=O)— | K203 | J045 | T148 |
| 647 | —(CH₂)₂— | —NH—C(=O)— | K203 | J051 | T148 |
| 648 | —(CH₂)₂— | —NH—C(=O)— | K203 | J051 | T152 |
| 649 | —(CH₂)₂— | —NH—C(=O)— | K203 | J068 | T148 |
| 650 | —(CH₂)₂— | —NH—C(=O)— | K203 | J068 | T151 |
| 651 | —(CH₂)₂— | —NH—C(=O)— | K203 | J085 | T148 |
| 652 | —(CH₂)₂— | —NH—C(=O)— | K203 | J085 | T169 |
| 653 | —(CH₂)₂— | —NH—C(=O)— | K204 | J014 | T148 |
| 654 | —(CH₂)₂— | —NH—C(=O)— | K205 | J015 | T149 |
| 655 | —(CH₂)₂— | —NH—C(=O)— | K206 | J008 | T148 |
| 656 | —(CH₂)₂— | —NH—C(=O)— | K206 | J009 | T148 |
| 657 | —(CH₂)₂— | —NH—C(=O)— | K206 | J012 | T148 |
| 658 | —(CH₂)₂— | —NH—C(=O)— | K206 | J018 | T151 |
| 659 | —(CH₂)₂— | —NH—C(=O)— | K206 | J045 | T148 |
| 660 | —(CH₂)₂— | —NH—C(=O)— | K207 | J008 | T148 |
| 661 | —(CH₂)₂— | —NH—C(=O)— | K207 | J009 | T148 |
| 662 | —(CH₂)₂— | —NH—C(=O)— | K207 | J012 | T148 |
| 663 | —(CH₂)₂— | —NH—C(=O)— | K207 | J043 | T152 |
| 664 | —(CH₂)₂— | —NH—C(=O)— | K207 | J045 | T148 |
| 665 | —(CH₂)₂— | —NH—C(=O)— | K208 | J008 | T148 |
| 666 | —(CH₂)₂— | —NH—C(=O)— | K208 | J009 | T148 |
| 667 | —(CH₂)₂— | —NH—C(=O)— | K208 | J012 | T148 |
| 668 | —(CH₂)₂— | —NH—C(=O)— | K208 | J045 | T148 |
| 669 | —(CH₂)₂— | —NH—C(=O)— | K208 | J045 | T157 |
| 670 | —(CH₂)₂— | —NH—C(=O)— | K209 | J008 | T148 |
| 671 | —(CH₂)₂— | —NH—C(=O)— | K209 | J009 | T148 |
| 672 | —(CH₂)₂— | —NH—C(=O)— | K209 | J012 | T148 |
| 673 | —(CH₂)₂— | —NH—C(=O)— | K209 | J045 | T148 |
| 674 | —(CH₂)₂— | —NH—C(=O)— | K209 | J063 | T158 |
| 675 | —(CH₂)₂— | —NH—C(=O)— | K210 | J008 | T148 |
| 676 | —(CH₂)₂— | —NH—C(=O)— | K210 | J009 | T148 |
| 677 | —(CH₂)₂— | —NH—C(=O)— | K270 | J012 | T148 |
| 678 | —(CH₂)₂— | —NH—C(=O)— | K210 | J045 | T148 |
| 679 | —(CH₂)₂— | —NH—C(=O)— | K210 | J081 | T164 |
| 680 | —(CH₂)₂— | —NH—C(=O)— | K211 | J001 | T168 |
| 681 | —(CH₂)₂— | —NH—C(=O)— | K211 | J008 | T148 |
| 682 | —(CH₂)₂— | —NH—C(=O)— | K211 | J009 | T148 |
| 683 | —(CH₂)₂— | —NH—C(=O)— | K211 | J012 | T148 |
| 684 | —(CH₂)₂— | —NH—C(=O)— | K211 | J045 | T148 |

TABLE 1-continued

| Compound no. | -A¹- | -A²- | -G¹-A³-A⁴-G² | -A⁵-R² | -A⁶-R³ |
|---|---|---|---|---|---|
| 685 | —(CH₂)₂— | —NH—C(=O)— | K212 | J002 | T169 |
| 686 | —(CH₂)₂— | —NH—C(=O)— | K212 | J008 | T148 |
| 687 | —(CH₂)₂— | —NH—C(=O)— | K212 | J009 | T148 |
| 688 | —(CH₂)₂— | —NH—C(=O)— | K212 | J012 | T148 |
| 689 | —(CH₂)₂— | —NH—C(=O)— | K212 | J045 | T148 |
| 690 | —(CH₂)₂— | —NH—C(=O)— | K213 | J008 | T170 |
| 691 | —(CH₂)₂— | —NH—C(=O)— | K214 | J009 | T173 |
| 692 | —(CH₂)₂— | —NH—C(=O)— | K215 | J008 | T148 |
| 693 | —(CH₂)₂— | —NH—C(=O)— | K215 | J009 | T148 |
| 694 | —(CH₂)₂— | —NH—C(=O)— | K215 | J012 | T148 |
| 695 | —(CH₂)₂— | —NH—C(=O)— | K215 | J012 | T176 |
| 696 | —(CH₂)₂— | —NH—C(=O)— | K215 | J045 | T148 |
| 697 | —(CH₂)₂— | —NH—C(=O)— | K216 | J014 | T178 |
| 698 | —(CH₂)₂— | —NH—C(=O)— | K217 | J015 | T129 |
| 699 | —(CH₂)₂— | —NH—C(=O)— | K218 | J018 | T130 |
| 700 | —(CH₂)₂— | —NH—C(=O)— | K219 | J008 | T148 |
| 701 | —(CH₂)₂— | —NH—C(=O)— | K219 | J009 | T148 |
| 702 | —(CH₂)₂— | —NH—C(=O)— | K219 | J012 | T148 |
| 703 | —(CH₂)₂— | —NH—C(=O)— | K219 | J043 | T134 |
| 704 | —(CH₂)₂— | —NH—C(=O)— | K219 | J045 | T148 |
| 705 | —(CH₂)₂— | —NH—C(=O)— | K220 | J008 | T148 |
| 706 | —(CH₂)₂— | —NH—C(=O)— | K220 | J009 | T148 |
| 707 | —(CH₂)₂— | —NH—C(=O)— | K220 | J012 | T148 |
| 708 | —(CH₂)₂— | —NH—C(=O)— | K220 | J045 | T135 |
| 709 | —(CH₂)₂— | —NH—C(=O)— | K220 | J045 | T148 |
| 710 | —(CH₂)₂— | —NH—C(=O)— | K221 | J008 | T148 |
| 711 | —(CH₂)₂— | —NH—C(=O)— | K221 | J009 | T148 |
| 712 | —(CH₂)₂— | —NH—C(=O)— | K221 | J012 | T148 |
| 713 | —(CH₂)₂— | —NH—C(=O)— | K221 | J045 | T148 |
| 714 | —(CH₂)₂— | —NH—C(=O)— | K221 | J063 | T145 |
| 715 | —(CH₂)₂— | —NH—C(=O)— | K222 | J008 | T148 |
| 716 | —(CH₂)₂— | —NH—C(=O)— | K222 | J009 | T148 |
| 717 | —(CH₂)₂— | —NH—C(=O)— | K222 | J012 | T148 |
| 718 | —(CH₂)₂— | —NH—C(=O)— | K222 | J045 | T148 |
| 719 | —(CH₂)₂— | —NH—C(=O)— | K222 | J081 | T148 |
| 720 | —(CH₂)₂— | —NH—C(=O)— | K223 | J001 | T149 |
| 721 | —(CH₂)₂— | —NH—C(=O)— | K223 | J008 | T148 |
| 722 | —(CH₂)₂— | —NH—C(=O)— | K223 | J009 | T148 |
| 723 | —(CH₂)₂— | —NH—C(=O)— | K223 | J012 | T148 |
| 724 | —(CH₂)₂— | —NH—C(=O)— | K223 | J045 | T148 |
| 725 | —(CH₂)₂— | —NH—C(=O)— | K224 | J002 | T151 |
| 726 | —(CH₂)₂— | —NH—C(=O)— | K224 | J008 | T148 |
| 727 | —(CH₂)₂— | —NH—C(=O)— | K224 | J009 | T148 |
| 728 | —(CH₂)₂— | —NH—C(=O)— | K224 | J012 | T148 |
| 729 | —(CH₂)₂— | —NH—C(=O)— | K224 | J045 | T148 |
| 730 | —(CH₂)₂— | —NH—C(=O)— | K225 | J008 | T148 |
| 731 | —(CH₂)₂— | —NH—C(=O)— | K225 | J008 | T152 |
| 732 | —(CH₂)₂— | —NH—C(=O)— | K225 | J009 | T148 |
| 733 | —(CH₂)₂— | —NH—C(=O)— | K225 | J012 | T148 |
| 734 | —(CH₂)₂— | —NH—C(=O)— | K225 | J045 | T148 |
| 735 | —(CH₂)₂— | —NH—C(=O)— | K226 | J009 | T157 |
| 736 | —(CH₂)₂— | —NH—C(=O)— | K227 | J012 | T158 |
| 737 | —(CH₂)₂— | —NH—C(=O)— | K228 | J008 | T148 |
| 738 | —(CH₂)₂— | —NH—C(=O)— | K228 | J009 | T148 |
| 739 | —(CH₂)₂— | —NH—C(=O)— | K228 | J012 | T148 |
| 740 | —(CH₂)₂— | —NH—C(=O)— | K228 | J014 | T164 |
| 741 | —(CH₂)₂— | —NH—C(=O)— | K228 | J045 | T148 |
| 742 | —(CH₂)₂— | —NH—C(=O)— | K229 | J015 | T168 |
| 743 | —(CH₂)₂— | —NH—C(=O)— | K230 | J018 | T169 |
| 744 | —(CH₂)₂— | —NH—C(=O)— | K231 | J043 | T170 |
| 745 | —(CH₂)₂— | —NH—C(=O)— | K232 | J045 | T173 |
| 746 | —(CH₂)₂— | —NH—C(=O)— | K233 | J063 | T176 |
| 747 | —(CH₂)₂— | —NH—C(=O)— | K234 | J081 | T178 |
| 748 | —(CH₂)₂— | —NH—C(=O)— | K235 | J012 | T148 |
| 749 | —(CH₂)₂— | —NH—C(=O)— | K236 | J045 | T148 |
| 750 | —(CH₂)₂— | —NH—C(=O)—NH— | K003 | J002 | T148 |
| 751 | —(CH₂)₂— | —NH—C(=O)—NH— | K003 | J002 | T151 |
| 752 | —(CH₂)₂— | —NH—C(=O)—NH— | K003 | J008 | T148 |
| 753 | —(CH₂)₂— | —NH—C(=O)—NH— | K003 | J008 | T151 |
| 754 | —(CH₂)₂— | —NH—C(=O)—NH— | K003 | J008 | T152 |
| 755 | —(CH₂)₂— | —NH—C(=O)—NH— | K003 | J008 | T169 |
| 756 | —(CH₂)₂— | —NH—C(=O)—NH— | K003 | J009 | T148 |
| 757 | —(CH₂)₂— | —NH—C(=O)—NH— | K003 | J009 | T151 |
| 758 | —(CH₂)₂— | —NH—C(=O)—NH— | K003 | J009 | T152 |
| 759 | —(CH₂)₂— | —NH—C(=O)—NH— | K003 | J009 | T169 |
| 760 | —(CH₂)₂— | —NH—C(=O)—NH— | K003 | J012 | T148 |

TABLE 1-continued

| Compound no. | -A$^1$- | -A$^2$- | -G$^1$-A$^3$-A$^4$-G$^2$ | -A$^5$-R$^2$ | -A$^6$-R$^3$ |
|---|---|---|---|---|---|
| 761 | —(CH$_2$)$_2$— | —NH—C(=O)—NH— | K003 | J012 | T151 |
| 762 | —(CH$_2$)$_2$— | —NH—C(=O)—NH— | K003 | J012 | T152 |
| 763 | —(CH$_2$)$_2$— | —NH—C(=O)—NH— | K003 | J012 | T169 |
| 764 | —(CH$_2$)$_2$— | —NH—C(=O)—NH— | K003 | J019 | T148 |
| 765 | —(CH$_2$)$_2$— | —NH—C(=O)—NH— | K003 | J019 | T169 |
| 766 | —(CH$_2$)$_2$— | —NH—C(=O)—NH— | K003 | J036 | T148 |
| 767 | —(CH$_2$)$_2$— | —NH—C(=O)—NH— | K003 | J036 | T152 |
| 768 | —(CH$_2$)$_2$— | —NH—C(=O)—NH— | K003 | J045 | T148 |
| 769 | —(CH$_2$)$_2$— | —NH—C(=O)—NH— | K003 | J045 | T151 |
| 770 | —(CH$_2$)$_2$— | —NH—C(=O)—NH— | K003 | J045 | T152 |
| 771 | —(CH$_2$)$_2$— | —NH—C(=O)—NH— | K003 | J045 | T169 |
| 772 | —(CH$_2$)$_2$— | —NH—C(=O)—NH— | K003 | J053 | T148 |
| 773 | —(CH$_2$)$_2$— | —NH—C(=O)—NH— | K003 | J053 | T151 |
| 774 | —(CH$_2$)$_2$— | —NH—C(=O)—NH— | K003 | J070 | T148 |
| 775 | —(CH$_2$)$_2$— | —NH—C(=O)—NH— | K003 | J070 | T169 |
| 776 | —(CH$_2$)$_2$— | —NH—C(=O)—NH— | K009 | J045 | T148 |
| 777 | —(CH$_2$)$_2$— | —NH—C(=O)—NH— | K012 | J008 | T148 |
| 778 | —(CH$_2$)$_2$— | —NH—C(=O)—NH— | K012 | J008 | T151 |
| 779 | —(CH$_2$)$_2$— | —NH—C(=O)—NH— | K012 | J008 | T152 |
| 780 | —(CH$_2$)$_2$— | —NH—C(=O)—NH— | K012 | J008 | T169 |
| 781 | —(CH$_2$)$_2$— | —NH—C(=O)—NH— | K012 | J009 | T148 |
| 782 | —(CH$_2$)$_2$— | —NH—C(=O)—NH— | K012 | J009 | T151 |
| 783 | —(CH$_2$)$_2$— | —NH—C(=O)—NH— | K012 | J009 | T152 |
| 784 | —(CH$_2$)$_2$— | —NH—C(=O)—NH— | K012 | J009 | T169 |
| 785 | —(CH$_2$)$_2$— | —NH—C(=O)—NH— | K012 | J012 | T148 |
| 786 | —(CH$_2$)$_2$— | —NH—C(=O)—NH— | K012 | J012 | T151 |
| 787 | —(CH$_2$)$_2$— | —NH—C(=O)—NH— | K012 | J012 | T152 |
| 788 | —(CH$_2$)$_2$— | —NH—C(=O)—NH— | K012 | J012 | T169 |
| 789 | —(CH$_2$)$_2$— | —NH—C(=O)—NH— | K012 | J026 | T148 |
| 790 | —(CH$_2$)$_2$— | —NH—C(=O)—NH— | K012 | J026 | T151 |
| 791 | —(CH$_2$)$_2$— | —NH—C(=O)—NH— | K012 | J043 | T148 |
| 792 | —(CH$_2$)$_2$— | —NH—C(=O)—NH— | K012 | J043 | T169 |
| 793 | —(CH$_2$)$_2$— | —NH—C(=O)—NH— | K012 | J045 | T148 |
| 794 | —(CH$_2$)$_2$— | —NH—C(=O)—NH— | K012 | J045 | T151 |
| 795 | —(CH$_2$)$_2$— | —NH—C(=O)—NH— | K012 | J045 | T152 |
| 796 | —(CH$_2$)$_2$— | —NH—C(=O)—NH— | K012 | J045 | T169 |
| 797 | —(CH$_2$)$_2$— | —NH—C(=O)—NH— | K012 | J060 | T148 |
| 798 | —(CH$_2$)$_2$— | —NH—C(=O)—NH— | K012 | J060 | T152 |
| 799 | —(CH$_2$)$_2$— | —NH—C(=O)—NH— | K012 | J077 | T148 |
| 800 | —(CH$_2$)$_2$— | —NH—C(=O)—NH— | K012 | J077 | T151 |
| 801 | —(CH$_2$)$_2$— | —NH—C(=O)—NH— | K013 | J045 | T148 |
| 802 | —(CH$_2$)$_2$— | —NH—C(=O)—NH— | K014 | J045 | T148 |
| 803 | —(CH$_2$)$_2$— | —NH—C(=O)—NH— | K017 | J045 | T148 |
| 804 | —(CH$_2$)$_2$— | —NH—C(=O)—NH— | K032 | J045 | T148 |
| 805 | —(CH$_2$)$_2$— | —NH—C(=O)—NH— | K229 | J045 | T148 |
| 806 | —(CH$_2$)$_2$— | —NH—C(=O)—NH— | K230 | J045 | T148 |
| 807 | —(CH$_2$)$_2$— | —NH—C(=O)—NH— | K231 | J045 | T148 |
| 808 | —(CH$_2$)$_2$— | —NH—C(=O)—NH— | K232 | J045 | T148 |
| 809 | —(CH$_2$)$_2$— | —NH—C(=O)—NH— | K233 | J045 | T148 |
| 810 | —(CH$_2$)$_2$— | —NH—C(=O)—NH— | K234 | J045 | T148 |
| 811 | —(CH$_2$)$_2$— | —NH—C(=O)—NH— | K235 | J045 | T148 |
| 812 | —(CH$_2$)$_2$— | —NH—C(=O)—NH— | K236 | J045 | T148 |
| 813 | —(CH$_2$)$_2$— | —NH—C(=O)—O— | K005 | J001 | T001 |
| 814 | —(CH$_2$)$_2$— | —NH—C(=O)—O— | K005 | J001 | T005 |
| 815 | —(CH$_2$)$_2$— | —NH—C(=O)—O— | K005 | J001 | T010 |
| 816 | —(CH$_2$)$_2$— | —NH—C(=O)—O— | K005 | J001 | T019 |
| 817 | —(CH$_2$)$_2$— | —NH—C(=O)—O— | K005 | J001 | T028 |
| 818 | —(CH$_2$)$_2$— | —NH—C(=O)—O— | K005 | J001 | T037 |
| 819 | —(CH$_2$)$_2$— | —NH—C(=O)—O— | K005 | J001 | T046 |
| 820 | —(CH$_2$)$_2$— | —NH—C(=O)—O— | K005 | J001 | T055 |
| 821 | —(CH$_2$)$_2$— | —NH—C(=O)—O— | K005 | J001 | T064 |
| 822 | —(CH$_2$)$_2$— | —NH—C(=O)—O— | K005 | J001 | T073 |
| 823 | —(CH$_2$)$_2$— | —NH—C(=O)—O— | K005 | J001 | T082 |
| 824 | —(CH$_2$)$_2$— | —NH—C(=O)—O— | K005 | J001 | T091 |
| 825 | —(CH$_2$)$_2$— | —NH—C(=O)—O— | K005 | J001 | T100 |
| 826 | —(CH$_2$)$_2$— | —NH—C(=O)—O— | K005 | J001 | T109 |
| 827 | —(CH$_2$)$_2$— | —NH—C(=O)—O— | K005 | J001 | T118 |
| 828 | —(CH$_2$)$_2$— | —NH—C(=O)—O— | K005 | J001 | T127 |
| 829 | —(CH$_2$)$_2$— | —NH—C(=O)—O— | K005 | J001 | T136 |
| 830 | —(CH$_2$)$_2$— | —NH—C(=O)—O— | K005 | J001 | T145 |
| 831 | —(CH$_2$)$_2$— | —NH—C(=O)—O— | K005 | J001 | T154 |
| 832 | —(CH$_2$)$_2$— | —NH—C(=O)—O— | K005 | J001 | T163 |
| 833 | —(CH$_2$)$_2$— | —NH—C(=O)—O— | K005 | J001 | T172 |
| 834 | —(CH$_2$)$_2$— | —NH—C(=O)—O— | K005 | J002 | T002 |
| 835 | —(CH$_2$)$_2$— | —NH—C(=O)—O— | K005 | J002 | T011 |
| 836 | —(CH$_2$)$_2$— | —NH—C(=O)—O— | K005 | J002 | T020 |

TABLE 1-continued

| Compound no. | -A¹- | -A²- | -G¹-A³-A⁴-G² | -A⁵-R² | -A⁶-R³ |
|---|---|---|---|---|---|
| 837 | —(CH$_2$)$_2$— | —NH—C(=O)—O— | K005 | J002 | T029 |
| 838 | —(CH$_2$)$_2$— | —NH—C(=O)—O— | K005 | J002 | T038 |
| 839 | —(CH$_2$)$_2$— | —NH—C(=O)—O— | K005 | J002 | T047 |
| 840 | —(CH$_2$)$_2$— | —NH—C(=O)—O— | K005 | J002 | T056 |
| 841 | —(CH$_2$)$_2$— | —NH—C(=O)—O— | K005 | J002 | T065 |
| 842 | —(CH$_2$)$_2$— | —NH—C(=O)—O— | K005 | J002 | T074 |
| 843 | —(CH$_2$)$_2$— | —NH—C(=O)—O— | K005 | J002 | T083 |
| 844 | —(CH$_2$)$_2$— | —NH—C(=O)—O— | K005 | J002 | T092 |
| 845 | —(CH$_2$)$_2$— | —NH—C(=O)—O— | K005 | J002 | T101 |
| 846 | —(CH$_2$)$_2$— | —NH—C(=O)—O— | K005 | J002 | T110 |
| 847 | —(CH$_2$)$_2$— | —NH—C(=O)—O— | K005 | J002 | T119 |
| 848 | —(CH$_2$)$_2$— | —NH—C(=O)—O— | K005 | J002 | T128 |
| 849 | —(CH$_2$)$_2$— | —NH—C(=O)—O— | K005 | J002 | T137 |
| 850 | —(CH$_2$)$_2$— | —NH—C(=O)—O— | K005 | J002 | T146 |
| 851 | —(CH$_2$)$_2$— | —NH—C(=O)—O— | K005 | J002 | T155 |
| 852 | —(CH$_2$)$_2$— | —NH—C(=O)—O— | K005 | J002 | T164 |
| 853 | —(CH$_2$)$_2$— | —NH—C(=O)—O— | K005 | J002 | T173 |
| 854 | —(CH$_2$)$_2$— | —NH—C(=O)—O— | K005 | J008 | T003 |
| 855 | —(CH$_2$)$_2$— | —NH—C(=O)—O— | K005 | J008 | T005 |
| 856 | —(CH$_2$)$_2$— | —NH—C(=O)—O— | K005 | J008 | T012 |
| 857 | —(CH$_2$)$_2$— | —NH—C(=O)—O— | K005 | J008 | T021 |
| 858 | —(CH$_2$)$_2$— | —NH—C(=O)—O— | K005 | J008 | T030 |
| 859 | —(CH$_2$)$_2$— | —NH—C(=O)—O— | K005 | J008 | T039 |
| 860 | —(CH$_2$)$_2$— | —NH—C(=O)—O— | K005 | J008 | T048 |
| 861 | —(CH$_2$)$_2$— | —NH—C(=O)—O— | K005 | J008 | T057 |
| 862 | —(CH$_2$)$_2$— | —NH—C(=O)—O— | K005 | J008 | T066 |
| 863 | —(CH$_2$)$_2$— | —NH—C(=O)—O— | K005 | J008 | T075 |
| 864 | —(CH$_2$)$_2$— | —NH—C(=O)—O— | K005 | J008 | T084 |
| 865 | —(CH$_2$)$_2$— | —NH—C(=O)—O— | K005 | J008 | T093 |
| 866 | —(CH$_2$)$_2$— | —NH—C(=O)—O— | K005 | J008 | T102 |
| 867 | —(CH$_2$)$_2$— | —NH—C(=O)—O— | K005 | J008 | T111 |
| 868 | —(CH$_2$)$_2$— | —NH—C(=O)—O— | K005 | J008 | T120 |
| 869 | —(CH$_2$)$_2$— | —NH—C(=O)—O— | K005 | J008 | T129 |
| 870 | —(CH$_2$)$_2$— | —NH—C(=O)—O— | K005 | J008 | T138 |
| 871 | —(CH$_2$)$_2$— | —NH—C(=O)—O— | K005 | J008 | T147 |
| 872 | —(CH$_2$)$_2$— | —NH—C(=O)—O— | K005 | J008 | T156 |
| 873 | —(CH$_2$)$_2$— | —NH—C(=O)—O— | K005 | J008 | T165 |
| 874 | —(CH$_2$)$_2$— | —NH—C(=O)—O— | K005 | J008 | T174 |
| 875 | —(CH$_2$)$_2$— | —NH—C(=O)—O— | K005 | J009 | T004 |
| 876 | —(CH$_2$)$_2$— | —NH—C(=O)—O— | K005 | J009 | T005 |
| 877 | —(CH$_2$)$_2$— | —NH—C(=O)—O— | K005 | J009 | T013 |
| 878 | —(CH$_2$)$_2$— | —NH—C(=O)—O— | K005 | J009 | T022 |
| 879 | —(CH$_2$)$_2$— | —NH—C(=O)—O— | K005 | J009 | T031 |
| 880 | —(CH$_2$)$_2$— | —NH—C(=O)—O— | K005 | J009 | T040 |
| 881 | —(CH$_2$)$_2$— | —NH—C(=O)—O— | K005 | J009 | T049 |
| 882 | —(CH$_2$)$_2$— | —NH—C(=O)—O— | K005 | J009 | T058 |
| 883 | —(CH$_2$)$_2$— | —NH—C(=O)—O— | K005 | J009 | T067 |
| 884 | —(CH$_2$)$_2$— | —NH—C(=O)—O— | K005 | J009 | T076 |
| 885 | —(CH$_2$)$_2$— | —NH—C(=O)—O— | K005 | J009 | T085 |
| 886 | —(CH$_2$)$_2$— | —NH—C(=O)—O— | K005 | J009 | T094 |
| 887 | —(CH$_2$)$_2$— | —NH—C(=O)—O— | K005 | J009 | T103 |
| 888 | —(CH$_2$)$_2$— | —NH—C(=O)—O— | K005 | J009 | T112 |
| 889 | —(CH$_2$)$_2$— | —NH—C(=O)—O— | K005 | J009 | T121 |
| 890 | —(CH$_2$)$_2$— | —NH—C(=O)—O— | K005 | J009 | T130 |
| 891 | —(CH$_2$)$_2$— | —NH—C(=O)—O— | K005 | J009 | T139 |
| 892 | —(CH$_2$)$_2$— | —NH—C(=O)—O— | K005 | J009 | T148 |
| 893 | —(CH$_2$)$_2$— | —NH—C(=O)—O— | K005 | J009 | T157 |
| 894 | —(CH$_2$)$_2$— | —NH—C(=O)—O— | K005 | J009 | T166 |
| 895 | —(CH$_2$)$_2$— | —NH—C(=O)—O— | K005 | J009 | T175 |
| 896 | —(CH$_2$)$_2$— | —NH—C(=O)—O— | K005 | J012 | T005 |
| 897 | —(CH$_2$)$_2$— | —NH—C(=O)—O— | K005 | J012 | T014 |
| 898 | —(CH$_2$)$_2$— | —NH—C(=O)—O— | K005 | J012 | T017 |
| 899 | —(CH$_2$)$_2$— | —NH—C(=O)—O— | K005 | J012 | T023 |
| 900 | —(CH$_2$)$_2$— | —NH—C(=O)—O— | K005 | J012 | T032 |
| 901 | —(CH$_2$)$_2$— | —NH—C(=O)—O— | K005 | J012 | T041 |
| 902 | —(CH$_2$)$_2$— | —NH—C(=O)—O— | K005 | J012 | T050 |
| 903 | —(CH$_2$)$_2$— | —NH—C(=O)—O— | K005 | J012 | T055 |
| 904 | —(CH$_2$)$_2$— | —NH—C(=O)—O— | K005 | J012 | T059 |
| 905 | —(CH$_2$)$_2$— | —NH—C(=O)—O— | K005 | J012 | T068 |
| 906 | —(CH$_2$)$_2$— | —NH—C(=O)—O— | K005 | J012 | T077 |
| 907 | —(CH$_2$)$_2$— | —NH—C(=O)—O— | K005 | J012 | T086 |
| 908 | —(CH$_2$)$_2$— | —NH—C(=O)—O— | K005 | J012 | T095 |
| 909 | —(CH$_2$)$_2$— | —NH—C(=O)—O— | K005 | J012 | T104 |
| 910 | —(CH$_2$)$_2$— | —NH—C(=O)—O— | K005 | J012 | T113 |
| 911 | —(CH$_2$)$_2$— | —NH—C(=O)—O— | K005 | J012 | T122 |
| 912 | —(CH$_2$)$_2$— | —NH—C(=O)—O— | K005 | J012 | T129 |

TABLE 1-continued

| Compound no. | -A¹- | -A²- | -G¹-A³-A⁴-G² | -A⁵-R² | -A⁶-R³ |
|---|---|---|---|---|---|
| 913 | —(CH$_2$)$_2$— | —NH—C(=O)—O— | K005 | J012 | T131 |
| 914 | —(CH$_2$)$_2$— | —NH—C(=O)—O— | K005 | J012 | T140 |
| 915 | —(CH$_2$)$_2$— | —NH—C(=O)—O— | K005 | J012 | T148 |
| 916 | —(CH$_2$)$_2$— | —NH—C(=O)—O— | K005 | J012 | T149 |
| 917 | —(CH$_2$)$_2$— | —NH—C(=O)—O— | K005 | J012 | T151 |
| 918 | —(CH$_2$)$_2$— | —NH—C(=O)—O— | K005 | J012 | T152 |
| 919 | —(CH$_2$)$_2$— | —NH—C(=O)—O— | K005 | J012 | T158 |
| 920 | —(CH$_2$)$_2$— | —NH—C(=O)—O— | K005 | J012 | T167 |
| 921 | —(CH$_2$)$_2$— | —NH—C(=O)—O— | K005 | J012 | T176 |
| 922 | —(CH$_2$)$_2$— | —NH—C(=O)—O— | K005 | J043 | T005 |
| 923 | —(CH$_2$)$_2$— | —NH—C(=O)—O— | K005 | J043 | T006 |
| 924 | —(CH$_2$)$_2$— | —NH—C(=O)—O— | K005 | J043 | T015 |
| 925 | —(CH$_2$)$_2$— | —NH—C(=O)—O— | K005 | J043 | T024 |
| 926 | —(CH$_2$)$_2$— | —NH—C(=O)—O— | K005 | J043 | T033 |
| 927 | —(CH$_2$)$_2$— | —NH—C(=O)—O— | K005 | J043 | T042 |
| 928 | —(CH$_2$)$_2$— | —NH—C(=O)—O— | K005 | J043 | T051 |
| 929 | —(CH$_2$)$_2$— | —NH—C(=O)—O— | K005 | J043 | T060 |
| 930 | —(CH$_2$)$_2$— | —NH—C(=O)—O— | K005 | J043 | T069 |
| 931 | —(CH$_2$)$_2$— | —NH—C(=O)—O— | K005 | J043 | T078 |
| 932 | —(CH$_2$)$_2$— | —NH—C(=O)—O— | K005 | J043 | T087 |
| 933 | —(CH$_2$)$_2$— | —NH—C(=O)—O— | K005 | J043 | T096 |
| 934 | —(CH$_2$)$_2$— | —NH—C(=O)—O— | K005 | J043 | T105 |
| 935 | —(CH$_2$)$_2$— | —NH—C(=O)—O— | K005 | J043 | T114 |
| 936 | —(CH$_2$)$_2$— | —NH—C(=O)—O— | K005 | J043 | T123 |
| 937 | —(CH$_2$)$_2$— | —NH—C(=O)—O— | K005 | J043 | T132 |
| 938 | —(CH$_2$)$_2$— | —NH—C(=O)—O— | K005 | J043 | T141 |
| 939 | —(CH$_2$)$_2$— | —NH—C(=O)—O— | K005 | J043 | T150 |
| 940 | —(CH$_2$)$_2$— | —NH—C(=O)—O— | K005 | J043 | T159 |
| 941 | —(CH$_2$)$_2$— | —NH—C(=O)—O— | K005 | J043 | T168 |
| 942 | —(CH$_2$)$_2$— | —NH—C(=O)—O— | K005 | J043 | T177 |
| 943 | —(CH$_2$)$_2$— | —NH—C(=O)—O— | K005 | J045 | T001 |
| 944 | —(CH$_2$)$_2$— | —NH—C(=O)—O— | K005 | J045 | T003 |
| 945 | —(CH$_2$)$_2$— | —NH—C(=O)—O— | K005 | J045 | T004 |
| 946 | —(CH$_2$)$_2$— | —NH—C(=O)—O— | K005 | J045 | T005 |
| 947 | —(CH$_2$)$_2$— | —NH—C(=O)—O— | K005 | J045 | T007 |
| 948 | —(CH$_2$)$_2$— | —NH—C(=O)—O— | K005 | J045 | T008 |
| 949 | —(CH$_2$)$_2$— | —NH—C(=O)—O— | K005 | J045 | T016 |
| 950 | —(CH$_2$)$_2$— | —NH—C(=O)—O— | K005 | J045 | T017 |
| 951 | —(CH$_2$)$_2$— | —NH—C(=O)—O— | K005 | J045 | T018 |
| 952 | —(CH$_2$)$_2$— | —NH—C(=O)—O— | K005 | J045 | T019 |
| 953 | —(CH$_2$)$_2$— | —NH—C(=O)—O— | K005 | J045 | T020 |
| 954 | —(CH$_2$)$_2$— | —NH—C(=O)—O— | K005 | J045 | T025 |
| 955 | —(CH$_2$)$_2$— | —NH—C(=O)—O— | K005 | J045 | T034 |
| 956 | —(CH$_2$)$_2$— | —NH—C(=O)—O— | K005 | J045 | T042 |
| 957 | —(CH$_2$)$_2$— | —NH—C(=O)—O— | K005 | J045 | T043 |
| 958 | —(CH$_2$)$_2$— | —NH—C(=O)—O— | K005 | J045 | T052 |
| 959 | —(CH$_2$)$_2$— | —NH—C(=O)—O— | K005 | J045 | T055 |
| 960 | —(CH$_2$)$_2$— | —NH—C(=O)—O— | K005 | J045 | T061 |
| 961 | —(CH$_2$)$_2$— | —NH—C(=O)—O— | K005 | J045 | T070 |
| 962 | —(CH$_2$)$_2$— | —NH—C(=O)—O— | K005 | J045 | T077 |
| 963 | —(CH$_2$)$_2$— | —NH—C(=O)—O— | K005 | J045 | T079 |
| 964 | —(CH$_2$)$_2$— | —NH—C(=O)—O— | K005 | J045 | T088 |
| 965 | —(CH$_2$)$_2$— | —NH—C(=O)—O— | K005 | J045 | T090 |
| 966 | —(CH$_2$)$_2$— | —NH—C(=O)—O— | K005 | J045 | T096 |
| 967 | —(CH$_2$)$_2$— | —NH—C(=O)—O— | K005 | J045 | T097 |
| 968 | —(CH$_2$)$_2$— | —NH—C(=O)—O— | K005 | J045 | T100 |
| 969 | —(CH$_2$)$_2$— | —NH—C(=O)—O— | K005 | J045 | T106 |
| 970 | —(CH$_2$)$_2$— | —NH—C(=O)—O— | K005 | J045 | T108 |
| 971 | —(CH$_2$)$_2$— | —NH—C(=O)—O— | K005 | J045 | T110 |
| 972 | —(CH$_2$)$_2$— | —NH—C(=O)—O— | K005 | J045 | T111 |
| 973 | —(CH$_2$)$_2$— | —NH—C(=O)—O— | K005 | J045 | T114 |
| 974 | —(CH$_2$)$_2$— | —NH—C(=O)—O— | K005 | J045 | T115 |
| 975 | —(CH$_2$)$_2$— | —NH—C(=O)—O— | K005 | J045 | T116 |
| 976 | —(CH$_2$)$_2$— | —NH—C(=O)—O— | K005 | J045 | T118 |
| 977 | —(CH$_2$)$_2$— | —NH—C(=O)—O— | K005 | J045 | T119 |
| 978 | —(CH$_2$)$_2$— | —NH—C(=O)—O— | K005 | J045 | T121 |
| 979 | —(CH$_2$)$_2$— | —NH—C(=O)—O— | K005 | J045 | T122 |
| 980 | —(CH$_2$)$_2$— | —NH—C(=O)—O— | K005 | J045 | T123 |
| 981 | —(CH$_2$)$_2$— | —NH—C(=O)—O— | K005 | J045 | T124 |
| 982 | —(CH$_2$)$_2$— | —NH—C(=O)—O— | K005 | J045 | T128 |
| 983 | —(CH$_2$)$_2$— | —NH—C(=O)—O— | K005 | J045 | T129 |
| 984 | —(CH$_2$)$_2$— | —NH—C(=O)—O— | K005 | J045 | T130 |
| 985 | —(CH$_2$)$_2$— | —NH—C(=O)—O— | K005 | J045 | T133 |
| 986 | —(CH$_2$)$_2$— | —NH—C(=O)—O— | K005 | J045 | T136 |
| 987 | —(CH$_2$)$_2$— | —NH—C(=O)—O— | K005 | J045 | T137 |
| 988 | —(CH$_2$)$_2$— | —NH—C(=O)—O— | K005 | J045 | T138 |

TABLE 1-continued

| Compound no. | -A¹- | -A²- | -G¹-A³-A⁴-G² | -A⁵-R² | -A⁶-R³ |
|---|---|---|---|---|---|
| 989 | —(CH₂)₂— | —NH—C(=O)—O— | K005 | J045 | T139 |
| 990 | —(CH₂)₂— | —NH—C(=O)—O— | K005 | J045 | T140 |
| 991 | —(CH₂)₂— | —NH—C(=O)—O— | K005 | J045 | T141 |
| 992 | —(CH₂)₂— | —NH—C(=O)—O— | K005 | J045 | T142 |
| 993 | —(CH₂)₂— | —NH—C(=O)—O— | K005 | J045 | T143 |
| 994 | —(CH₂)₂— | —NH—C(=O)—O— | K005 | J045 | T144 |
| 995 | —(CH₂)₂— | —NH—C(=O)—O— | K005 | J045 | T145 |
| 996 | —(CH₂)₂— | —NH—C(=O)—O— | K005 | J045 | T146 |
| 997 | —(CH₂)₂— | —NH—C(=O)—O— | K005 | J045 | T147 |
| 998 | —(CH₂)₂— | —NH—C(=O)—O— | K005 | J045 | T148 |
| 999 | —(CH₂)₂— | —NH—C(=O)—O— | K005 | J045 | T149 |
| 1000 | —(CH₂)₂— | —NH—C(=O)—O— | K005 | J045 | T150 |
| 1001 | —(CH₂)₂— | —NH—C(=O)—O— | K005 | J045 | T151 |
| 1002 | —(CH₂)₂— | —NH—C(=O)—O— | K005 | J045 | T152 |
| 1003 | —(CH₂)₂— | —NH—C(=O)—O— | K005 | J045 | T153 |
| 1004 | —(CH₂)₂— | —NH—C(=O)—O— | K005 | J045 | T154 |
| 1005 | —(CH₂)₂— | —NH—C(=O)—O— | K005 | J045 | T155 |
| 1006 | —(CH₂)₂— | —NH—C(=O)—O— | K005 | J045 | T156 |
| 1007 | —(CH₂)₂— | —NH—C(=O)—O— | K005 | J045 | T157 |
| 1008 | —(CH₂)₂— | —NH—C(=O)—O— | K005 | J045 | T158 |
| 1009 | —(CH₂)₂— | —NH—C(=O)—O— | K005 | J045 | T159 |
| 1010 | —(CH₂)₂— | —NH—C(=O)—O— | K005 | J045 | T160 |
| 1011 | —(CH₂)₂— | —NH—C(=O)—O— | K005 | J045 | T162 |
| 1012 | —(CH₂)₂— | —NH—C(=O)—O— | K005 | J045 | T163 |
| 1013 | —(CH₂)₂— | —NH—C(=O)—O— | K005 | J045 | T167 |
| 1014 | —(CH₂)₂— | —NH—C(=O)—O— | K005 | J045 | T169 |
| 1015 | —(CH₂)₂— | —NH—C(=O)—O— | K005 | J045 | T178 |
| 1016 | —(CH₂)₂— | —NH—C(=O)—O— | K005 | J063 | T008 |
| 1017 | —(CH₂)₂— | —NH—C(=O)—O— | K005 | J063 | T017 |
| 1018 | —(CH₂)₂— | —NH—C(=O)—O— | K005 | J063 | T026 |
| 1019 | —(CH₂)₂— | —NH—C(=O)—O— | K005 | J063 | T035 |
| 1020 | —(CH₂)₂— | —NH—C(=O)—O— | K005 | J063 | T044 |
| 1021 | —(CH₂)₂— | —NH—C(=O)—O— | K005 | J063 | T053 |
| 1022 | —(CH₂)₂— | —NH—C(=O)—O— | K005 | J063 | T062 |
| 1023 | —(CH₂)₂— | —NH—C(=O)—O— | K005 | J063 | T071 |
| 1024 | —(CH₂)₂— | —NH—C(=O)—O— | K005 | J063 | T080 |
| 1025 | —(CH₂)₂— | —NH—C(=O)—O— | K005 | J063 | T089 |
| 1026 | —(CH₂)₂— | —NH—C(=O)—O— | K005 | J063 | T098 |
| 1027 | —(CH₂)₂— | —NH—C(=O)—O— | K005 | J063 | T107 |
| 1028 | —(CH₂)₂— | —NH—C(=O)—O— | K005 | J063 | T116 |
| 1029 | —(CH₂)₂— | —NH—C(=O)—O— | K005 | J063 | T125 |
| 1030 | —(CH₂)₂— | —NH—C(=O)—O— | K005 | J063 | T134 |
| 1031 | —(CH₂)₂— | —NH—C(=O)—O— | K005 | J063 | T143 |
| 1032 | —(CH₂)₂— | —NH—C(=O)—O— | K005 | J063 | T152 |
| 1033 | —(CH₂)₂— | —NH—C(=O)—O— | K005 | J063 | T161 |
| 1034 | —(CH₂)₂— | —NH—C(=O)—O— | K005 | J063 | T170 |
| 1035 | —(CH₂)₂— | —NH—C(=O)—O— | K005 | J063 | T179 |
| 1036 | —(CH₂)₂— | —NH—C(=O)—O— | K005 | J081 | T009 |
| 1037 | —(CH₂)₂— | —NH—C(=O)—O— | K005 | J081 | T018 |
| 1038 | —(CH₂)₂— | —NH—C(=O)—O— | K005 | J081 | T027 |
| 1039 | —(CH₂)₂— | —NH—C(=O)—O— | K005 | J081 | T036 |
| 1040 | —(CH₂)₂— | —NH—C(=O)—O— | K005 | J081 | T045 |
| 1041 | —(CH₂)₂— | —NH—C(=O)—O— | K005 | J081 | T054 |
| 1042 | —(CH₂)₂— | —NH—C(=O)—O— | K005 | J081 | T063 |
| 1043 | —(CH₂)₂— | —NH—C(=O)—O— | K005 | J081 | T072 |
| 1044 | —(CH₂)₂— | —NH—C(=O)—O— | K005 | J081 | T081 |
| 1045 | —(CH₂)₂— | —NH—C(=O)—O— | K005 | J081 | T090 |
| 1046 | —(CH₂)₂— | —NH—C(=O)—O— | K005 | J081 | T099 |
| 1047 | —(CH₂)₂— | —NH—C(=O)—O— | K005 | J081 | T108 |
| 1048 | —(CH₂)₂— | —NH—C(=O)—O— | K005 | J081 | T117 |
| 1049 | —(CH₂)₂— | —NH—C(=O)—O— | K005 | J081 | T126 |
| 1050 | —(CH₂)₂— | —NH—C(=O)—O— | K005 | J081 | T135 |
| 1051 | —(CH₂)₂— | —NH—C(=O)—O— | K005 | J081 | T144 |
| 1052 | —(CH₂)₂— | —NH—C(=O)—O— | K005 | J081 | T153 |
| 1053 | —(CH₂)₂— | —NH—C(=O)—O— | K005 | J081 | T162 |
| 1054 | —(CH₂)₂— | —NH—C(=O)—O— | K005 | J081 | T171 |
| 1055 | —(CH₂)₂— | Single bond | K179 | J045 | T148 |
| 1056 | —(CH₂)₂— | Single bond | K180 | J045 | T148 |
| 1057 | —(CH₂)₂— | Single bond | K239 | J045 | T148 |
| 1058 | —(CH₂)₃— | —C(=O)— | K002 | J001 | T151 |
| 1059 | —(CH₂)₃— | —C(=O)— | K002 | J012 | T151 |
| 1060 | —(CH₂)₃— | —C(=O)— | K003 | J001 | T151 |
| 1061 | —(CH₂)₃— | —C(=O)— | K003 | J012 | T151 |
| 1062 | —(CH₂)₃— | —C(=O)— | K004 | J001 | T151 |
| 1063 | —(CH₂)₃— | —C(=O)— | K004 | J012 | T151 |
| 1064 | —(CH₂)₃— | —C(=O)— | K005 | J001 | T151 |

TABLE 1-continued

| Compound no. | -A$^1$- | -A$^2$- | -G$^1$-A$^3$-A$^4$-G$^2$ | -A$^5$-R$^2$ | -A$^6$-R$^3$ |
|---|---|---|---|---|---|
| 1065 | —(CH$_2$)$_3$— | —C(=O)— | K005 | J012 | T151 |
| 1066 | —(CH$_2$)$_3$— | —C(=O)— | K007 | J001 | T152 |
| 1067 | —(CH$_2$)$_3$— | —C(=O)— | K007 | J012 | T152 |
| 1068 | —(CH$_2$)$_3$— | —C(=O)— | K008 | J001 | T152 |
| 1069 | —(CH$_2$)$_3$— | —C(=O)— | K008 | J012 | T152 |
| 1070 | —(CH$_2$)$_3$— | —C(=O)— | K009 | J001 | T152 |
| 1071 | —(CH$_2$)$_3$— | —C(=O)— | K009 | J012 | T152 |
| 1072 | —(CH$_2$)$_3$— | —C(=O)— | K012 | J001 | T152 |
| 1073 | —(CH$_2$)$_3$— | —C(=O)— | K012 | J012 | T152 |
| 1074 | —(CH$_2$)$_3$— | —C(=O)— | K107 | J001 | T168 |
| 1075 | —(CH$_2$)$_3$— | —C(=O)— | K107 | J012 | T169 |
| 1076 | —(CH$_2$)$_3$— | —C(=O)— | K108 | J001 | T169 |
| 1077 | —(CH$_2$)$_3$— | —C(=O)— | K108 | J012 | T169 |
| 1078 | —(CH$_2$)$_3$— | —C(=O)— | K112 | J001 | T170 |
| 1079 | —(CH$_2$)$_3$— | —C(=O)— | K112 | J012 | T169 |
| 1080 | —(CH$_2$)$_3$— | —C(=O)— | K129 | J001 | T171 |
| 1081 | —(CH$_2$)$_3$— | —C(=O)— | K129 | J012 | T169 |
| 1082 | —(CH$_2$)$_3$— | —C(=O)— | K133 | J001 | T172 |
| 1083 | —(CH$_2$)$_3$— | —C(=O)— | K133 | J012 | T169 |
| 1084 | —(CH$_2$)$_3$— | —C(=O)— | K137 | J001 | T173 |
| 1085 | —(CH$_2$)$_3$— | —C(=O)— | K137 | J012 | T169 |
| 1086 | —(CH$_2$)$_3$— | —C(=O)—O— | K001 | J001 | T148 |
| 1087 | —(CH$_2$)$_3$— | —C(=O)—O— | K002 | J001 | T151 |
| 1088 | —(CH$_2$)$_3$— | —C(=O)—O— | K193 | J001 | T152 |
| 1089 | —(CH$_2$)$_3$— | —C(=O)—O— | K227 | J045 | T169 |
| 1090 | —(CH$_2$)$_3$— | —NH— | K185 | J045 | T151 |
| 1091 | —(CH$_2$)$_3$— | —NH— | K185 | J045 | T169 |
| 1092 | —(CH$_2$)$_3$— | —NH—C(=O)— | K008 | J012 | T151 |
| 1093 | —(CH$_2$)$_3$— | —NH—C(=O)— | K008 | J012 | T169 |
| 1094 | —(CH$_2$)$_3$— | —NH—C(=O)— | K013 | J001 | T151 |
| 1095 | —(CH$_2$)$_3$— | —NH—C(=O)— | K013 | J001 | T169 |
| 1096 | —(CH$_2$)$_3$— | —NH—C(=O)— | K200 | J045 | T148 |
| 1097 | —(CH$_2$)$_3$— | —NH—C(=O)— | K200 | J045 | T152 |
| 1098 | —(CH$_2$)$_3$— | —NH—C(=O)—NH— | K003 | J012 | T148 |
| 1099 | —(CH$_2$)$_3$— | —NH—C(=O)—NH— | K003 | J012 | T152 |
| 1100 | —(CH$_2$)$_3$— | —NH—C(=O)—O— | K005 | J001 | T148 |
| 1101 | —(CH$_2$)$_3$— | —NH—C(=O)—O— | K005 | J001 | T152 |
| 1102 | —CH$_2$— | —C(=O)— | K107 | J001 | T148 |
| 1103 | —CH$_2$— | —C(=O)— | K107 | J012 | T148 |
| 1104 | —CH$_2$— | —C(=O)— | K107 | J018 | T148 |
| 1105 | —CH$_2$— | —C(=O)— | K108 | J001 | T129 |
| 1106 | —CH$_2$— | —C(=O)— | K108 | J001 | T148 |
| 1107 | —CH$_2$— | —C(=O)— | K108 | J001 | T151 |
| 1108 | —CH$_2$— | —C(=O)— | K108 | J001 | T152 |
| 1109 | —CH$_2$— | —C(=O)— | K108 | J001 | T164 |
| 1110 | —CH$_2$— | —C(=O)— | K108 | J001 | T170 |
| 1111 | —CH$_2$— | —C(=O)— | K108 | J001 | T171 |
| 1112 | —CH$_2$— | —C(=O)— | K108 | J012 | T148 |
| 1113 | —CH$_2$— | —C(=O)— | K108 | J022 | T148 |
| 1114 | —CH$_2$— | —C(=O)— | K112 | J001 | T148 |
| 1115 | —CH$_2$— | —C(=O)— | K112 | J012 | T148 |
| 1116 | —CH$_2$— | —C(=O)— | K129 | J001 | T148 |
| 1117 | —CH$_2$— | —C(=O)— | K129 | J012 | T148 |
| 1118 | —CH$_2$— | —C(=O)— | K129 | J014 | T148 |
| 1119 | —CH$_2$— | —C(=O)— | K133 | J001 | T148 |
| 1120 | —CH$_2$— | —C(=O)— | K133 | J008 | T148 |
| 1121 | —CH$_2$— | —C(=O)— | K133 | J012 | T148 |
| 1122 | —CH$_2$— | —C(=O)— | K137 | J001 | T129 |
| 1123 | —CH$_2$— | —C(=O)— | K137 | J001 | T148 |
| 1124 | —CH$_2$— | —C(=O)— | K137 | J001 | T151 |
| 1125 | —CH$_2$— | —C(=O)— | K137 | J001 | T152 |
| 1126 | —CH$_2$— | —C(=O)— | K137 | J001 | T164 |
| 1127 | —CH$_2$— | —C(=O)— | K137 | J001 | T170 |
| 1128 | —CH$_2$— | —C(=O)— | K137 | J001 | T172 |
| 1129 | —CH$_2$— | —C(=O)— | K137 | J009 | T148 |
| 1130 | —CH$_2$— | —C(=O)— | K137 | J012 | T148 |
| 1131 | —CH$_2$— | —C(=O)— | K237 | J001 | T148 |
| 1132 | —CH$_2$— | —C(=O)—NH— | K001 | J001 | T148 |
| 1133 | —CH$_2$— | —C(=O)—NH— | K002 | J001 | T148 |
| 1134 | —CH$_2$— | —C(=O)—NH— | K002 | J012 | T148 |
| 1135 | —CH$_2$— | —C(=O)—NH— | K002 | J063 | T148 |
| 1136 | —CH$_2$— | —C(=O)—NH— | K003 | J001 | T148 |
| 1137 | —CH$_2$— | —C(=O)—NH— | K003 | J012 | T148 |
| 1138 | —CH$_2$— | —C(=O)—NH— | K003 | J065 | T148 |
| 1139 | —CH$_2$— | —C(=O)—NH— | K004 | J001 | T148 |
| 1140 | —CH$_2$— | —C(=O)—NH— | K004 | J012 | T148 |

TABLE 1-continued

| Compound no. | -A¹- | -A²- | -G¹-A³-A⁴-G² | -A⁵-R² | -A⁶-R³ |
|---|---|---|---|---|---|
| 1141 | —CH₂— | —C(=O)—NH— | K004 | J070 | T148 |
| 1142 | —CH₂— | —C(=O)—NH— | K005 | J001 | T148 |
| 1143 | —CH₂— | —C(=O)—NH— | K005 | J012 | T148 |
| 1144 | —CH₂— | —C(=O)—NH— | K005 | J075 | T148 |
| 1145 | —CH₂— | —C(=O)—NH— | K007 | J001 | T129 |
| 1146 | —CH₂— | —C(=O)—NH— | K007 | J001 | T148 |
| 1147 | —CH₂— | —C(=O)—NH— | K007 | J001 | T151 |
| 1148 | —CH₂— | —C(=O)—NH— | K007 | J001 | T152 |
| 1149 | —CH₂— | —C(=O)—NH— | K007 | J001 | T164 |
| 1150 | —CH₂— | —C(=O)—NH— | K007 | J001 | T169 |
| 1151 | —CH₂— | —C(=O)—NH— | K007 | J001 | T170 |
| 1152 | —CH₂— | —C(=O)—NH— | K007 | J012 | T148 |
| 1153 | —CH₂— | —C(=O)—NH— | K007 | J081 | T148 |
| 1154 | —CH₂— | —C(=O)—NH— | K008 | J001 | T148 |
| 1155 | —CH₂— | —C(=O)—NH— | K008 | J012 | T148 |
| 1156 | —CH₂— | —C(=O)—NH— | K008 | J085 | T148 |
| 1157 | —CH₂— | —C(=O)—NH— | K009 | J001 | T148 |
| 1158 | —CH₂— | —C(=O)—NH— | K009 | J012 | T148 |
| 1159 | —CH₂— | —C(=O)—NH— | K009 | J043 | T148 |
| 1160 | —CH₂— | —C(=O)—NH— | K012 | J001 | T129 |
| 1161 | —CH₂— | —C(=O)—NH— | K012 | J001 | T148 |
| 1162 | —CH₂— | —C(=O)—NH— | K012 | J001 | T151 |
| 1163 | —CH₂— | —C(=O)—NH— | K012 | J001 | T152 |
| 1164 | —CH₂— | —C(=O)—NH— | K012 | J001 | T164 |
| 1165 | —CH₂— | —C(=O)—NH— | K012 | J001 | T170 |
| 1166 | —CH₂— | —C(=O)—NH— | K012 | J012 | T148 |
| 1167 | —CH₂— | —C(=O)—NH— | K012 | J045 | T148 |
| 1168 | —CH₂— | —C(=O)—NH— | K218 | J001 | T148 |
| 1169 | —CH₂— | —C(=O)—O— | K001 | J001 | T148 |
| 1170 | —CH₂— | —C(=O)—O— | K002 | J001 | T148 |
| 1171 | —CH₂— | —C(=O)—O— | K002 | J001 | T151 |
| 1172 | —CH₂— | —C(=O)—O— | K193 | J001 | T152 |
| 1173 | —CH₂— | —C(=O)—O— | K227 | J001 | T169 |
| 1174 | Single bond | Single bond | K001 | J001 | T148 |
| 1175 | Single bond | Single bond | K001 | J002 | T148 |
| 1176 | Single bond | Single bond | K197 | J001 | T005 |
| 1177 | Single bond | Single bond | K197 | J001 | T148 |
| 1178 | Single bond | Single bond | K197 | J012 | T148 |
| 1179 | Single bond | Single bond | K223 | J001 | T148 |
| 1180 | Single bond | Single bond | K223 | J002 | T148 |
| 1181 | —(CH₂)₂— | —NH— | K078 | J001 | T148 |
| 1182 | —(CH₂)₂— | —NH— | K078 | J045 | T148 |
| 1183 | —(CH₂)₂— | —NH— | K078 | J045 | T170 |
| 1184 | —(CH₂)₂— | —NH— | K182 | J001 | T148 |
| 1185 | —(CH₂)₂— | —NH— | K372 | J045 | T148 |
| 1186 | —(CH₂)₂— | —NH— | K392 | J045 | T170 |
| 1187 | —(CH₂)₂— | —NH—C(=O)— | K003 | J044 | T170 |
| 1188 | —(CH₂)₂— | —NH—C(=O)— | K004 | J007 | T148 |
| 1189 | —(CH₂)₂— | —NH—C(=O)— | K004 | J010 | T148 |
| 1190 | —(CH₂)₂— | —NH—C(=O)— | K004 | J013 | T148 |
| 1191 | —(CH₂)₂— | —NH—C(=O)— | K004 | J014 | T148 |
| 1192 | —(CH₂)₂— | —NH—C(=O)— | K004 | J044 | T148 |
| 1193 | —(CH₂)₂— | —NH—C(=O)— | K004 | J044 | T170 |
| 1194 | —(CH₂)₂— | —NH—C(=O)— | K006 | J007 | T148 |
| 1195 | —(CH₂)₂— | —NH—C(=O)— | K006 | J010 | T148 |
| 1196 | —(CH₂)₂— | —NH—C(=O)— | K006 | J013 | T148 |
| 1197 | —(CH₂)₂— | —NH—C(=O)— | K007 | J007 | T148 |
| 1198 | —(CH₂)₂— | —NH—C(=O)— | K007 | J010 | T148 |
| 1199 | —(CH₂)₂— | —NH—C(=O)— | K007 | J013 | T148 |
| 1200 | —(CH₂)₂— | —NH—C(=O)— | K007 | J014 | T148 |
| 1201 | —(CH₂)₂— | —NH—C(=O)— | K007 | J039 | T170 |
| 1202 | —(CH₂)₂— | —NH—C(=O)— | K007 | J044 | T148 |
| 1203 | —(CH₂)₂— | —NH—C(=O)— | K007 | J044 | T169 |
| 1204 | —(CH₂)₂— | —NH—C(=O)— | K007 | J044 | T170 |
| 1205 | —(CH₂)₂— | —NH—C(=O)— | K007 | J045 | T151 |
| 1206 | —(CH₂)₂— | —NH—C(=O)— | K007 | J045 | T170 |
| 1207 | —(CH₂)₂— | —NH—C(=O)— | K008 | J007 | T148 |
| 1208 | —(CH₂)₂— | —NH—C(=O)— | K008 | J010 | T148 |
| 1209 | —(CH₂)₂— | —NH—C(=O)— | K008 | J013 | T148 |
| 1210 | —(CH₂)₂— | —NH—C(=O)— | K008 | J014 | T148 |
| 1211 | —(CH₂)₂— | —NH—C(=O)— | K008 | J039 | T170 |
| 1212 | —(CH₂)₂— | —NH—C(=O)— | K008 | J044 | T148 |
| 1213 | —(CH₂)₂— | —NH—C(=O)— | K008 | J044 | T169 |
| 1214 | —(CH₂)₂— | —NH—C(=O)— | K008 | J044 | T170 |
| 1215 | —(CH₂)₂— | —NH—C(=O)— | K008 | J045 | T151 |
| 1216 | —(CH₂)₂— | —NH—C(=O)— | K008 | J045 | T169 |

TABLE 1-continued

| Compound no. | -A$^1$- | -A$^2$- | -G$^1$-A$^3$-A$^4$-G$^2$ | -A$^5$-R$^2$ | -A$^6$-R$^3$ |
|---|---|---|---|---|---|
| 1217 | —(CH$_2$)$_2$— | —NH—C(=O)— | K008 | J045 | T170 |
| 1218 | —(CH$_2$)$_2$— | —NH—C(=O)— | K009 | J007 | T148 |
| 1219 | —(CH$_2$)$_2$— | —NH—C(=O)— | K009 | J010 | T148 |
| 1220 | —(CH$_2$)$_2$— | —NH—C(=O)— | K009 | J013 | T148 |
| 1221 | —(CH$_2$)$_2$— | —NH—C(=O)— | K009 | J014 | T148 |
| 1222 | —(CH$_2$)$_2$— | —NH—C(=O)— | K009 | J037 | T170 |
| 1223 | —(CH$_2$)$_2$— | —NH—C(=O)— | K009 | J039 | T170 |
| 1224 | —(CH$_2$)$_2$— | —NH—C(=O)— | K009 | J043 | T170 |
| 1225 | —(CH$_2$)$_2$— | —NH—C(=O)— | K009 | J044 | T148 |
| 1226 | —(CH$_2$)$_2$— | —NH—C(=O)— | K009 | J044 | T170 |
| 1227 | —(CH$_2$)$_2$— | —NH—C(=O)— | K009 | J045 | T152 |
| 1228 | —(CH$_2$)$_2$— | —NH—C(=O)— | K009 | J045 | T170 |
| 1229 | —(CH$_2$)$_2$— | —NH—C(=O)— | K009 | J047 | T170 |
| 1230 | —(CH$_2$)$_2$— | —NH—C(=O)— | K009 | J145 | T148 |
| 1231 | —(CH$_2$)$_2$— | —NH—C(=O)— | K009 | J147 | T148 |
| 1232 | —(CH$_2$)$_2$— | —NH—C(=O)— | K010 | J012 | T148 |
| 1233 | —(CH$_2$)$_2$— | —NH—C(=O)— | K010 | J012 | T164 |
| 1234 | —(CH$_2$)$_2$— | —NH—C(=O)— | K010 | J013 | T148 |
| 1235 | —(CH$_2$)$_2$— | —NH—C(=O)— | K010 | J013 | T170 |
| 1236 | —(CH$_2$)$_2$— | —NH—C(=O)— | K010 | J045 | T148 |
| 1237 | —(CH$_2$)$_2$— | —NH—C(=O)— | K010 | J045 | T170 |
| 1238 | —(CH$_2$)$_2$— | —NH—C(=O)— | K010 | J045 | T178 |
| 1239 | —(CH$_2$)$_2$— | —NH—C(=O)— | K010 | J045 | T179 |
| 1240 | —(CH$_2$)$_2$— | —NH—C(=O)— | K011 | J044 | T170 |
| 1241 | —(CH$_2$)$_2$— | —NH—C(=O)— | K023 | J045 | T170 |
| 1242 | —(CH$_2$)$_2$— | —NH—C(=O)— | K033 | J045 | T170 |
| 1243 | —(CH$_2$)$_2$— | —NH—C(=O)— | K104 | J045 | T170 |
| 1244 | —(CH$_2$)$_2$— | —NH—C(=O)— | K198 | J007 | T148 |
| 1245 | —(CH$_2$)$_2$— | —NH—C(=O)— | K198 | J010 | T148 |
| 1246 | —(CH$_2$)$_2$— | —NH—C(=O)— | K198 | J013 | T148 |
| 1247 | —(CH$_2$)$_2$— | —NH—C(=O)— | K198 | J014 | T148 |
| 1248 | —(CH$_2$)$_2$— | —NH—C(=O)— | K198 | J039 | T170 |
| 1249 | —(CH$_2$)$_2$— | —NH—C(=O)— | K198 | J044 | T170 |
| 1250 | —(CH$_2$)$_2$— | —NH—C(=O)— | K198 | J045 | T170 |
| 1251 | —(CH$_2$)$_2$— | —NH—C(=O)— | K199 | J007 | T148 |
| 1252 | —(CH$_2$)$_2$— | —NH—C(=O)— | K199 | J010 | T148 |
| 1253 | —(CH$_2$)$_2$— | —NH—C(=O)— | K199 | J013 | T148 |
| 1254 | —(CH$_2$)$_2$— | —NH—C(=O)— | K199 | J014 | T148 |
| 1255 | —(CH$_2$)$_2$— | —NH—C(=O)— | K199 | J039 | T170 |
| 1256 | —(CH$_2$)$_2$— | —NH—C(=O)— | K199 | J044 | T170 |
| 1257 | —(CH$_2$)$_2$— | —NH—C(=O)— | K199 | J045 | T170 |
| 1258 | —(CH$_2$)$_2$— | —NH—C(=O)— | K200 | J001 | T170 |
| 1259 | —(CH$_2$)$_2$— | —NH—C(=O)— | K200 | J002 | T170 |
| 1260 | —(CH$_2$)$_2$— | —NH—C(=O)— | K200 | J007 | T148 |
| 1261 | —(CH$_2$)$_2$— | —NH—C(=O)— | K200 | J007 | T170 |
| 1262 | —(CH$_2$)$_2$— | —NH—C(=O)— | K200 | J008 | T170 |
| 1263 | —(CH$_2$)$_2$— | —NH—C(=O)— | K200 | J009 | T164 |
| 1264 | —(CH$_2$)$_2$— | —NH—C(=O)— | K200 | J009 | T170 |
| 1265 | —(CH$_2$)$_2$— | —NH—C(=O)— | K200 | J010 | T148 |
| 1266 | —(CH$_2$)$_2$— | —NH—C(=O)— | K200 | J010 | T170 |
| 1267 | —(CH$_2$)$_2$— | —NH—C(=O)— | K200 | J011 | T148 |
| 1268 | —(CH$_2$)$_2$— | —NH—C(=O)— | K200 | J011 | T164 |
| 1269 | —(CH$_2$)$_2$— | —NH—C(=O)— | K200 | J011 | T170 |
| 1270 | —(CH$_2$)$_2$— | —NH—C(=O)— | K200 | J012 | T164 |
| 1271 | —(CH$_2$)$_2$— | —NH—C(=O)— | K200 | J012 | T170 |
| 1272 | —(CH$_2$)$_2$— | —NH—C(=O)— | K200 | J013 | T148 |
| 1273 | —(CH$_2$)$_2$— | —NH—C(=O)— | K200 | J013 | T170 |
| 1274 | —(CH$_2$)$_2$— | —NH—C(=O)— | K200 | J014 | T148 |
| 1275 | —(CH$_2$)$_2$— | —NH—C(=O)— | K200 | J037 | T148 |
| 1276 | —(CH$_2$)$_2$— | —NH—C(=O)— | K200 | J037 | T169 |
| 1277 | —(CH$_2$)$_2$— | —NH—C(=O)— | K200 | J037 | T170 |
| 1278 | —(CH$_2$)$_2$— | —NH—C(=O)— | K200 | J038 | T170 |
| 1279 | —(CH$_2$)$_2$— | —NH—C(=O)— | K200 | J039 | T148 |
| 1280 | —(CH$_2$)$_2$— | —NH—C(=O)— | K200 | J039 | T164 |
| 1281 | —(CH$_2$)$_2$— | —NH—C(=O)— | K200 | J039 | T170 |
| 1282 | —(CH$_2$)$_2$— | —NH—C(=O)— | K200 | J043 | T148 |
| 1283 | —(CH$_2$)$_2$— | —NH—C(=O)— | K200 | J043 | T169 |
| 1284 | —(CH$_2$)$_2$— | —NH—C(=O)— | K200 | J043 | T170 |
| 1285 | —(CH$_2$)$_2$— | —NH—C(=O)— | K200 | J044 | T148 |
| 1286 | —(CH$_2$)$_2$— | —NH—C(=O)— | K200 | J044 | T170 |
| 1287 | —(CH$_2$)$_2$— | —NH—C(=O)— | K200 | J045 | T164 |
| 1288 | —(CH$_2$)$_2$— | —NH—C(=O)— | K200 | J045 | T170 |
| 1289 | —(CH$_2$)$_2$— | —NH—C(=O)— | K200 | J045 | T171 |
| 1290 | —(CH$_2$)$_2$— | —NH—C(=O)— | K200 | J045 | T177 |
| 1291 | —(CH$_2$)$_2$— | —NH—C(=O)— | K200 | J045 | T178 |
| 1292 | —(CH$_2$)$_2$— | —NH—C(=O)— | K200 | J045 | T179 |

TABLE 1-continued

| Compound no. | -A¹- | -A²- | -G¹-A³-A⁴-G² | -A⁵-R² | -A⁶-R³ |
|---|---|---|---|---|---|
| 1293 | —(CH₂)₂— | —NH—C(═O)— | K200 | J045 | T180 |
| 1294 | —(CH₂)₂— | —NH—C(═O)— | K200 | J047 | T148 |
| 1295 | —(CH₂)₂— | —NH—C(═O)— | K200 | J047 | T169 |
| 1296 | —(CH₂)₂— | —NH—C(═O)— | K200 | J047 | T170 |
| 1297 | —(CH₂)₂— | —NH—C(═O)— | K200 | J079 | T148 |
| 1298 | —(CH₂)₂— | —NH—C(═O)— | K200 | J079 | T169 |
| 1299 | —(CH₂)₂— | —NH—C(═O)— | K200 | J079 | T170 |
| 1300 | —(CH₂)₂— | —NH—C(═O)— | K200 | J080 | T148 |
| 1301 | —(CH₂)₂— | —NH—C(═O)— | K200 | J080 | T169 |
| 1302 | —(CH₂)₂— | —NH—C(═O)— | K200 | J080 | T170 |
| 1303 | —(CH₂)₂— | —NH—C(═O)— | K200 | J081 | T148 |
| 1304 | —(CH₂)₂— | —NH—C(═O)— | K200 | J081 | T164 |
| 1305 | —(CH₂)₂— | —NH—C(═O)— | K200 | J081 | T170 |
| 1306 | —(CH₂)₂— | —NH—C(═O)— | K200 | J082 | T148 |
| 1307 | —(CH₂)₂— | —NH—C(═O)— | K200 | J082 | T169 |
| 1308 | —(CH₂)₂— | —NH—C(═O)— | K200 | J082 | T170 |
| 1309 | —(CH₂)₂— | —NH—C(═O)— | K200 | J090 | T148 |
| 1310 | —(CH₂)₂— | —NH—C(═O)— | K200 | J090 | T169 |
| 1311 | —(CH₂)₂— | —NH—C(═O)— | K200 | J090 | T170 |
| 1312 | —(CH₂)₂— | —NH—C(═O)— | K200 | J092 | T148 |
| 1313 | —(CH₂)₂— | —NH—C(═O)— | K200 | J092 | T164 |
| 1314 | —(CH₂)₂— | —NH—C(═O)— | K200 | J092 | T170 |
| 1315 | —(CH₂)₂— | —NH—C(═O)— | K200 | J093 | T148 |
| 1316 | —(CH₂)₂— | —NH—C(═O)— | K200 | J103 | T148 |
| 1317 | —(CH₂)₂— | —NH—C(═O)— | K200 | J103 | T164 |
| 1318 | —(CH₂)₂— | —NH—C(═O)— | K200 | J103 | T170 |
| 1319 | —(CH₂)₂— | —NH—C(═O)— | K200 | J104 | T148 |
| 1320 | —(CH₂)₂— | —NH—C(═O)— | K200 | J104 | T164 |
| 1321 | —(CH₂)₂— | —NH—C(═O)— | K200 | J104 | T170 |
| 1322 | —(CH₂)₂— | —NH—C(═O)— | K200 | J105 | T148 |
| 1323 | —(CH₂)₂— | —NH—C(═O)— | K200 | J105 | T164 |
| 1324 | —(CH₂)₂— | —NH—C(═O)— | K200 | J105 | T169 |
| 1325 | —(CH₂)₂— | —NH—C(═O)— | K200 | J106 | T148 |
| 1326 | —(CH₂)₂— | —NH—C(═O)— | K200 | J106 | T164 |
| 1327 | —(CH₂)₂— | —NH—C(═O)— | K200 | J106 | T170 |
| 1328 | —(CH₂)₂— | —NH—C(═O)— | K200 | J107 | T148 |
| 1329 | —(CH₂)₂— | —NH—C(═O)— | K200 | J107 | T164 |
| 1330 | —(CH₂)₂— | —NH—C(═O)— | K200 | J107 | T170 |
| 1331 | —(CH₂)₂— | —NH—C(═O)— | K200 | J109 | T170 |
| 1332 | —(CH₂)₂— | —NH—C(═O)— | K200 | J118 | T170 |
| 1333 | —(CH₂)₂— | —NH—C(═O)— | K200 | J138 | T170 |
| 1334 | —(CH₂)₂— | —NH—C(═O)— | K200 | J139 | T170 |
| 1335 | —(CH₂)₂— | —NH—C(═O)— | K200 | J144 | T148 |
| 1336 | —(CH₂)₂— | —NH—C(═O)— | K200 | J144 | T169 |
| 1337 | —(CH₂)₂— | —NH—C(═O)— | K200 | J144 | T170 |
| 1338 | —(CH₂)₂— | —NH—C(═O)— | K200 | J145 | T170 |
| 1339 | —(CH₂)₂— | —NH—C(═O)— | K200 | J146 | T148 |
| 1340 | —(CH₂)₂— | —NH—C(═O)— | K200 | J146 | T164 |
| 1341 | —(CH₂)₂— | —NH—C(═O)— | K200 | J105 | T170 |
| 1342 | —(CH₂)₂— | —NH—C(═O)— | K200 | J147 | T148 |
| 1343 | —(CH₂)₂— | —NH—C(═O)— | K200 | J147 | T170 |
| 1344 | —(CH₂)₂— | —NH—C(═O)— | K200 | J148 | T148 |
| 1345 | —(CH₂)₂— | —NH—C(═O)— | K200 | J149 | T148 |
| 1346 | —(CH₂)₂— | —NH—C(═O)— | K200 | J149 | T170 |
| 1347 | —(CH₂)₂— | —NH—C(═O)— | K200 | J150 | T148 |
| 1348 | —(CH₂)₂— | —NH—C(═O)— | K200 | J150 | T170 |
| 1349 | —(CH₂)₂— | —NH—C(═O)— | K200 | J151 | T148 |
| 1350 | —(CH₂)₂— | —NH—C(═O)— | K200 | J151 | T170 |
| 1351 | —(CH₂)₂— | —NH—C(═O)— | K200 | J152 | T148 |
| 1352 | —(CH₂)₂— | —NH—C(═O)— | K200 | J153 | T148 |
| 1353 | —(CH₂)₂— | —NH—C(═O)— | K200 | J154 | T148 |
| 1354 | —(CH₂)₂— | —NH—C(═O)— | K200 | J155 | T148 |
| 1355 | —(CH₂)₂— | —NH—C(═O)— | K200 | J156 | T148 |
| 1356 | —(CH₂)₂— | —NH—C(═O)— | K200 | J157 | T148 |
| 1357 | —(CH₂)₂— | —NH—C(═O)— | K200 | J158 | T148 |
| 1358 | —(CH₂)₂— | —NH—C(═O)— | K200 | J158 | T170 |
| 1359 | —(CH₂)₂— | —NH—C(═O)— | K200 | J159 | T148 |
| 1360 | —(CH₂)₂— | —NH—C(═O)— | K200 | J159 | T170 |
| 1361 | —(CH₂)₂— | —NH—C(═O)— | K201 | J007 | T148 |
| 1362 | —(CH₂)₂— | —NH—C(═O)— | K201 | J008 | T148 |
| 1363 | —(CH₂)₂— | —NH—C(═O)— | K201 | J010 | T148 |
| 1364 | —(CH₂)₂— | —NH—C(═O)— | K201 | J012 | T148 |
| 1365 | —(CH₂)₂— | —NH—C(═O)— | K201 | J013 | T148 |
| 1366 | —(CH₂)₂— | —NH—C(═O)— | K201 | J014 | T148 |
| 1367 | —(CH₂)₂— | —NH—C(═O)— | K201 | J037 | T170 |
| 1368 | —(CH₂)₂— | —NH—C(═O)— | K201 | J039 | T170 |

TABLE 1-continued

| Compound no. | -A¹- | -A²- | -G¹-A³-A⁴-G² | -A⁵-R² | -A⁶-R³ |
|---|---|---|---|---|---|
| 1369 | —(CH₂)₂— | —NH—C(=O)— | K201 | J043 | T170 |
| 1370 | —(CH₂)₂— | —NH—C(=O)— | K201 | J044 | T148 |
| 1371 | —(CH₂)₂— | —NH—C(=O)— | K201 | J044 | T170 |
| 1372 | —(CH₂)₂— | —NH—C(=O)— | K201 | J045 | T148 |
| 1373 | —(CH₂)₂— | —NH—C(=O)— | K201 | J045 | T152 |
| 1374 | —(CH₂)₂— | —NH—C(=O)— | K201 | J045 | T170 |
| 1375 | —(CH₂)₂— | —NH—C(=O)— | K201 | J047 | T170 |
| 1376 | —(CH₂)₂— | —NH—C(=O)— | K201 | J145 | T148 |
| 1377 | —(CH₂)₂— | —NH—C(=O)— | K201 | J147 | T148 |
| 1378 | —(CH₂)₂— | —NH—C(=O)— | K202 | J007 | T148 |
| 1379 | —(CH₂)₂— | —NH—C(=O)— | K202 | J008 | T148 |
| 1380 | —(CH₂)₂— | —NH—C(=O)— | K202 | J010 | T148 |
| 1381 | —(CH₂)₂— | —NH—C(=O)— | K202 | J012 | T148 |
| 1382 | —(CH₂)₂— | —NH—C(=O)— | K202 | J013 | T148 |
| 1383 | —(CH₂)₂— | —NH—C(=O)— | K202 | J014 | T148 |
| 1384 | —(CH₂)₂— | —NH—C(=O)— | K202 | J039 | T170 |
| 1385 | —(CH₂)₂— | —NH—C(=O)— | K202 | J044 | T148 |
| 1386 | —(CH₂)₂— | —NH—C(=O)— | K202 | J044 | T164 |
| 1387 | —(CH₂)₂— | —NH—C(=O)— | K202 | J044 | T170 |
| 1388 | —(CH₂)₂— | —NH—C(=O)— | K202 | J045 | T148 |
| 1389 | —(CH₂)₂— | —NH—C(=O)— | K202 | J045 | T164 |
| 1390 | —(CH₂)₂— | —NH—C(=O)— | K203 | J007 | T148 |
| 1391 | —(CH₂)₂— | —NH—C(=O)— | K203 | J010 | T148 |
| 1392 | —(CH₂)₂— | —NH—C(=O)— | K203 | J013 | T148 |
| 1393 | —(CH₂)₂— | —NH—C(=O)— | K203 | J014 | T148 |
| 1394 | —(CH₂)₂— | —NH—C(=O)— | K203 | J039 | T170 |
| 1395 | —(CH₂)₂— | —NH—C(=O)— | K203 | J044 | T148 |
| 1396 | —(CH₂)₂— | —NH—C(=O)— | K203 | J044 | T164 |
| 1397 | —(CH₂)₂— | —NH—C(=O)— | K203 | J044 | T170 |
| 1398 | —(CH₂)₂— | —NH—C(=O)— | K203 | J045 | T164 |
| 1399 | —(CH₂)₂— | —NH—C(=O)— | K203 | J045 | T170 |
| 1400 | —(CH₂)₂— | —NH—C(=O)— | K204 | J007 | T148 |
| 1401 | —(CH₂)₂— | —NH—C(=O)— | K204 | J008 | T148 |
| 1402 | —(CH₂)₂— | —NH—C(=O)— | K204 | J009 | T170 |
| 1403 | —(CH₂)₂— | —NH—C(=O)— | K204 | J010 | T148 |
| 1404 | —(CH₂)₂— | —NH—C(=O)— | K204 | J011 | T170 |
| 1405 | —(CH₂)₂— | —NH—C(=O)— | K204 | J012 | T148 |
| 1406 | —(CH₂)₂— | —NH—C(=O)— | K204 | J013 | T148 |
| 1407 | —(CH₂)₂— | —NH—C(=O)— | K204 | J037 | T170 |
| 1408 | —(CH₂)₂— | —NH—C(=O)— | K204 | J039 | T170 |
| 1409 | —(CH₂)₂— | —NH—C(=O)— | K204 | J043 | T170 |
| 1410 | —(CH₂)₂— | —NH—C(=O)— | K204 | J044 | T148 |
| 1411 | —(CH₂)₂— | —NH—C(=O)— | K204 | J044 | T169 |
| 1412 | —(CH₂)₂— | —NH—C(=O)— | K204 | J044 | T170 |
| 1413 | —(CH₂)₂— | —NH—C(=O)— | K204 | J045 | T148 |
| 1414 | —(CH₂)₂— | —NH—C(=O)— | K204 | J045 | T169 |
| 1415 | —(CH₂)₂— | —NH—C(=O)— | K204 | J045 | T170 |
| 1416 | —(CH₂)₂— | —NH—C(=O)— | K204 | J047 | T170 |
| 1417 | —(CH₂)₂— | —NH—C(=O)— | K204 | J079 | T170 |
| 1418 | —(CH₂)₂— | —NH—C(=O)— | K204 | J145 | T148 |
| 1419 | —(CH₂)₂— | —NH—C(=O)— | K204 | J147 | T148 |
| 1420 | —(CH₂)₂— | —NH—C(=O)— | K205 | J007 | T148 |
| 1421 | —(CH₂)₂— | —NH—C(=O)— | K205 | J008 | T148 |
| 1422 | —(CH₂)₂— | —NH—C(=O)— | K205 | J010 | T148 |
| 1423 | —(CH₂)₂— | —NH—C(=O)— | K205 | J012 | T148 |
| 1424 | —(CH₂)₂— | —NH—C(=O)— | K205 | J013 | T148 |
| 1425 | —(CH₂)₂— | —NH—C(=O)— | K205 | J014 | T148 |
| 1426 | —(CH₂)₂— | —NH—C(=O)— | K205 | J044 | T170 |
| 1427 | —(CH₂)₂— | —NH—C(=O)— | K205 | J045 | T170 |
| 1428 | —(CH₂)₂— | —NH—C(=O)— | K206 | J039 | T170 |
| 1429 | —(CH₂)₂— | —NH—C(=O)— | K206 | J044 | T170 |
| 1430 | —(CH₂)₂— | —NH—C(=O)— | K206 | J045 | T170 |
| 1431 | —(CH₂)₂— | —NH—C(=O)— | K207 | J044 | T170 |
| 1432 | —(CH₂)₂— | —NH—C(=O)— | K208 | J007 | T148 |
| 1433 | —(CH₂)₂— | —NH—C(=O)— | K208 | J009 | T170 |
| 1434 | —(CH₂)₂— | —NH—C(=O)— | K208 | J010 | T148 |
| 1435 | —(CH₂)₂— | —NH—C(=O)— | K208 | J011 | T170 |
| 1436 | —(CH₂)₂— | —NH—C(=O)— | K208 | J013 | T148 |
| 1437 | —(CH₂)₂— | —NH—C(=O)— | K208 | J014 | T148 |
| 1438 | —(CH₂)₂— | —NH—C(=O)— | K208 | J037 | T170 |
| 1439 | —(CH₂)₂— | —NH—C(=O)— | K208 | J039 | T170 |
| 1440 | —(CH₂)₂— | —NH—C(=O)— | K208 | J043 | T170 |
| 1441 | —(CH₂)₂— | —NH—C(=O)— | K208 | J044 | T148 |
| 1442 | —(CH₂)₂— | —NH—C(=O)— | K208 | J044 | T169 |
| 1443 | —(CH₂)₂— | —NH—C(=O)— | K208 | J044 | T170 |
| 1444 | —(CH₂)₂— | —NH—C(=O)— | K208 | J045 | T169 |

TABLE 1-continued

| Compound no. | -A$^1$- | -A$^2$- | -G$^1$-A$^3$-A$^4$-G$^2$ | -A$^5$-R$^2$ | -A$^6$-R$^3$ |
|---|---|---|---|---|---|
| 1445 | —(CH$_2$)$_2$— | —NH—C(=O)— | K208 | J045 | T170 |
| 1446 | —(CH$_2$)$_2$— | —NH—C(=O)— | K208 | J047 | T170 |
| 1447 | —(CH$_2$)$_2$— | —NH—C(=O)— | K208 | J079 | T170 |
| 1448 | —(CH$_2$)$_2$— | —NH—C(=O)— | K208 | J145 | T148 |
| 1449 | —(CH$_2$)$_2$— | —NH—C(=O)— | K208 | J147 | T148 |
| 1450 | —(CH$_2$)$_2$— | —NH—C(=O)— | K209 | J007 | T148 |
| 1451 | —(CH$_2$)$_2$— | —NH—C(=O)— | K209 | J010 | T148 |
| 1452 | —(CH$_2$)$_2$— | —NH—C(=O)— | K209 | J013 | T148 |
| 1453 | —(CH$_2$)$_2$— | —NH—C(=O)— | K209 | J014 | T148 |
| 1454 | —(CH$_2$)$_2$— | —NH—C(=O)— | K209 | J044 | T170 |
| 1455 | —(CH$_2$)$_2$— | —NH—C(=O)— | K210 | J007 | T148 |
| 1456 | —(CH$_2$)$_2$— | —NH—C(=O)— | K210 | J010 | T148 |
| 1457 | —(CH$_2$)$_2$— | —NH—C(=O)— | K210 | J013 | T148 |
| 1458 | —(CH$_2$)$_2$— | —NH—C(=O)— | K210 | J014 | T148 |
| 1459 | —(CH$_2$)$_2$— | —NH—C(=O)— | K210 | J044 | T170 |
| 1460 | —(CH$_2$)$_2$— | —NH—C(=O)— | K213 | J007 | T148 |
| 1461 | —(CH$_2$)$_2$— | —NH—C(=O)— | K213 | J008 | T148 |
| 1462 | —(CH$_2$)$_2$— | —NH—C(=O)— | K213 | J010 | T148 |
| 1463 | —(CH$_2$)$_2$— | —NH—C(=O)— | K213 | J012 | T148 |
| 1464 | —(CH$_2$)$_2$— | —NH—C(=O)— | K213 | J013 | T148 |
| 1465 | —(CH$_2$)$_2$— | —NH—C(=O)— | K213 | J014 | T148 |
| 1466 | —(CH$_2$)$_2$— | —NH—C(=O)— | K213 | J044 | T170 |
| 1467 | —(CH$_2$)$_2$— | —NH—C(=O)— | K214 | J007 | T148 |
| 1468 | —(CH$_2$)$_2$— | —NH—C(=O)— | K214 | J008 | T148 |
| 1469 | —(CH$_2$)$_2$— | —NH—C(=O)— | K214 | J010 | T148 |
| 1470 | —(CH$_2$)$_2$— | —NH—C(=O)— | K214 | J012 | T148 |
| 1471 | —(CH$_2$)$_2$— | —NH—C(=O)— | K214 | J013 | T148 |
| 1472 | —(CH$_2$)$_2$— | —NH—C(=O)— | K214 | J014 | T148 |
| 1473 | —(CH$_2$)$_2$— | —NH—C(=O)— | K214 | J044 | T170 |
| 1474 | —(CH$_2$)$_2$— | —NH—C(=O)— | K215 | J007 | T148 |
| 1475 | —(CH$_2$)$_2$— | —NH—C(=O)— | K215 | J010 | T148 |
| 1476 | —(CH$_2$)$_2$— | —NH—C(=O)— | K215 | J013 | T148 |
| 1477 | —(CH$_2$)$_2$— | —NH—C(=O)— | K215 | J014 | T148 |
| 1478 | —(CH$_2$)$_2$— | —NH—C(=O)— | K215 | J044 | T170 |
| 1479 | —(CH$_2$)$_2$— | —NH—C(=O)— | K216 | J007 | T148 |
| 1480 | —(CH$_2$)$_2$— | —NH—C(=O)— | K216 | J008 | T148 |
| 1481 | —(CH$_2$)$_2$— | —NH—C(=O)— | K216 | J010 | T148 |
| 1482 | —(CH$_2$)$_2$— | —NH—C(=O)— | K216 | J012 | T148 |
| 1483 | —(CH$_2$)$_2$— | —NH—C(=O)— | K216 | J013 | T148 |
| 1484 | —(CH$_2$)$_2$— | —NH—C(=O)— | K216 | J014 | T148 |
| 1485 | —(CH$_2$)$_2$— | —NH—C(=O)— | K216 | J044 | T170 |
| 1486 | —(CH$_2$)$_2$— | —NH—C(=O)— | K216 | J045 | T170 |
| 1487 | —(CH$_2$)$_2$— | —NH—C(=O)— | K217 | J007 | T148 |
| 1488 | —(CH$_2$)$_2$— | —NH—C(=O)— | K217 | J008 | T148 |
| 1489 | —(CH$_2$)$_2$— | —NH—C(=O)— | K217 | J010 | T148 |
| 1490 | —(CH$_2$)$_2$— | —NH—C(=O)— | K217 | J012 | T148 |
| 1491 | —(CH$_2$)$_2$— | —NH—C(=O)— | K217 | J013 | T148 |
| 1492 | —(CH$_2$)$_2$— | —NH—C(=O)— | K217 | J014 | T148 |
| 1493 | —(CH$_2$)$_2$— | —NH—C(=O)— | K217 | J044 | T170 |
| 1494 | —(CH$_2$)$_2$— | —NH—C(=O)— | K217 | J045 | T170 |
| 1495 | —(CH$_2$)$_2$— | —NH—C(=O)— | K218 | J007 | T148 |
| 1496 | —(CH$_2$)$_2$— | —NH—C(=O)— | K218 | J008 | T148 |
| 1497 | —(CH$_2$)$_2$— | —NH—C(=O)— | K218 | J010 | T148 |
| 1498 | —(CH$_2$)$_2$— | —NH—C(=O)— | K218 | J012 | T148 |
| 1499 | —(CH$_2$)$_2$— | —NH—C(=O)— | K218 | J012 | T164 |
| 1500 | —(CH$_2$)$_2$— | —NH—C(=O)— | K218 | J013 | T148 |
| 1501 | —(CH$_2$)$_2$— | —NH—C(=O)— | K218 | J013 | T170 |
| 1502 | —(CH$_2$)$_2$— | —NH—C(=O)— | K218 | J014 | T148 |
| 1503 | —(CH$_2$)$_2$— | —NH—C(=O)— | K218 | J044 | T170 |
| 1504 | —(CH$_2$)$_2$— | —NH—C(=O)— | K218 | J045 | T170 |
| 1505 | —(CH$_2$)$_2$— | —NH—C(=O)— | K218 | J045 | T178 |
| 1506 | —(CH$_2$)$_2$— | —NH—C(=O)— | K218 | J045 | T179 |
| 1507 | —(CH$_2$)$_2$— | —NH—C(=O)— | K222 | J007 | T148 |
| 1508 | —(CH$_2$)$_2$— | —NH—C(=O)— | K222 | J010 | T148 |
| 1509 | —(CH$_2$)$_2$— | —NH—C(=O)— | K222 | J013 | T148 |
| 1510 | —(CH$_2$)$_2$— | —NH—C(=O)— | K222 | J014 | T148 |
| 1511 | —(CH$_2$)$_2$— | —NH—C(=O)— | K240 | J045 | T148 |
| 1512 | —(CH$_2$)$_2$— | —NH—C(=O)— | K242 | J045 | T169 |
| 1513 | —(CH$_2$)$_2$— | —NH—C(=O)— | K242 | J045 | T170 |
| 1514 | —(CH$_2$)$_2$— | —NH—C(=O)— | K243 | J045 | T170 |
| 1515 | —(CH$_2$)$_2$— | —NH—C(=O)— | K244 | J045 | T169 |
| 1516 | —(CH$_2$)$_2$— | —NH—C(=O)— | K244 | J045 | T170 |
| 1517 | —(CH$_2$)$_2$— | —NH—C(=O)— | K245 | J045 | T170 |
| 1518 | —(CH$_2$)$_2$— | —NH—C(=O)— | K246 | J045 | T170 |
| 1519 | —(CH$_2$)$_2$— | —NH—C(=O)— | K247 | J012 | T148 |
| 1520 | —(CH$_2$)$_2$— | —NH—C(=O)— | K247 | J045 | T148 |

TABLE 1-continued

| Compound no. | -A¹- | -A²- | -G¹-A³-A⁴-G² | -A⁵-R² | -A⁶-R³ |
|---|---|---|---|---|---|
| 1521 | —(CH$_2$)$_2$— | —NH—C(=O)— | K247 | J045 | T170 |
| 1522 | —(CH$_2$)$_2$— | —NH—C(=O)— | K248 | J045 | T148 |
| 1523 | —(CH$_2$)$_2$— | —NH—C(=O)— | K248 | J045 | T170 |
| 1524 | —(CH$_2$)$_2$— | —NH—C(=O)— | K249 | J007 | T148 |
| 1525 | —(CH$_2$)$_2$— | —NH—C(=O)— | K249 | J008 | T148 |
| 1526 | —(CH$_2$)$_2$— | —NH—C(=O)— | K249 | J010 | T148 |
| 1527 | —(CH$_2$)$_2$— | —NH—C(=O)— | K249 | J013 | T148 |
| 1528 | —(CH$_2$)$_2$— | —NH—C(=O)— | K249 | J014 | T148 |
| 1529 | —(CH$_2$)$_2$— | —NH—C(=O)— | K249 | J045 | T170 |
| 1530 | —(CH$_2$)$_2$— | —NH—C(=O)— | K250 | J045 | T148 |
| 1531 | —(CH$_2$)$_2$— | —NH—C(=O)— | K250 | J045 | T170 |
| 1532 | —(CH$_2$)$_2$— | —NH—C(=O)— | K251 | J045 | T170 |
| 1533 | —(CH$_2$)$_2$— | —NH—C(=O)— | K252 | J045 | T148 |
| 1534 | —(CH$_2$)$_2$— | —NH—C(=O)— | K252 | J045 | T170 |
| 1535 | —(CH$_2$)$_2$— | —NH—C(=O)— | K253 | J045 | T148 |
| 1536 | —(CH$_2$)$_2$— | —NH—C(=O)— | K253 | J045 | T170 |
| 1537 | —(CH$_2$)$_2$— | —NH—C(=O)— | K254 | J007 | T148 |
| 1538 | —(CH$_2$)$_2$— | —NH—C(=O)— | K254 | J008 | T148 |
| 1539 | —(CH$_2$)$_2$— | —NH—C(=O)— | K254 | J010 | T148 |
| 1540 | —(CH$_2$)$_2$— | —NH—C(=O)— | K254 | J012 | T148 |
| 1541 | —(CH$_2$)$_2$— | —NH—C(=O)— | K254 | J013 | T148 |
| 1542 | —(CH$_2$)$_2$— | —NH—C(=O)— | K254 | J014 | T148 |
| 1543 | —(CH$_2$)$_2$— | —NH—C(=O)— | K254 | J044 | T170 |
| 1544 | —(CH$_2$)$_2$— | —NH—C(=O)— | K254 | J045 | T169 |
| 1545 | —(CH$_2$)$_2$— | —NH—C(=O)— | K254 | J045 | T170 |
| 1546 | —(CH$_2$)$_2$— | —NH—C(=O)— | K255 | J012 | T148 |
| 1547 | —(CH$_2$)$_2$— | —NH—C(=O)— | K255 | J045 | T169 |
| 1548 | —(CH$_2$)$_2$— | —NH—C(=O)— | K255 | J045 | T170 |
| 1549 | —(CH$_2$)$_2$— | —NH—C(=O)— | K256 | J012 | T148 |
| 1550 | —(CH$_2$)$_2$— | —NH—C(=O)— | K256 | J039 | T170 |
| 1551 | —(CH$_2$)$_2$— | —NH—C(=O)— | K256 | J044 | T170 |
| 1552 | —(CH$_2$)$_2$— | —NH—C(=O)— | K256 | J045 | T169 |
| 1553 | —(CH$_2$)$_2$— | —NH—C(=O)— | K256 | J045 | T170 |
| 1554 | —(CH$_2$)$_2$— | —NH—C(=O)— | K257 | J012 | T148 |
| 1555 | —(CH$_2$)$_2$— | —NH—C(=O)— | K257 | J039 | T170 |
| 1556 | —(CH$_2$)$_2$— | —NH—C(=O)— | K257 | J044 | T170 |
| 1557 | —(CH$_2$)$_2$— | —NH—C(=O)— | K257 | J045 | T169 |
| 1558 | —(CH$_2$)$_2$— | —NH—C(=O)— | K257 | J045 | T170 |
| 1559 | —(CH$_2$)$_2$— | —NH—C(=O)— | K258 | J012 | T148 |
| 1560 | —(CH$_2$)$_2$— | —NH—C(=O)— | K258 | J045 | T169 |
| 1561 | —(CH$_2$)$_2$— | —NH—C(=O)— | K258 | J045 | T170 |
| 1562 | —(CH$_2$)$_2$— | —NH—C(=O)— | K259 | J012 | T148 |
| 1563 | —(CH$_2$)$_2$— | —NH—C(=O)— | K259 | J039 | T170 |
| 1564 | —(CH$_2$)$_2$— | —NH—C(=O)— | K259 | J044 | T170 |
| 1565 | —(CH$_2$)$_2$— | —NH—C(=O)— | K259 | J045 | T169 |
| 1566 | —(CH$_2$)$_2$— | —NH—C(=O)— | K259 | J045 | T170 |
| 1567 | —(CH$_2$)$_2$— | —NH—C(=O)— | K260 | J012 | T148 |
| 1568 | —(CH$_2$)$_2$— | —NH—C(=O)— | K260 | J045 | T169 |
| 1569 | —(CH$_2$)$_2$— | —NH—C(=O)— | K260 | J045 | T170 |
| 1570 | —(CH$_2$)$_2$— | —NH—C(=O)— | K261 | J012 | T148 |
| 1571 | —(CH$_2$)$_2$— | —NH—C(=O)— | K261 | J045 | T169 |
| 1572 | —(CH$_2$)$_2$— | —NH—C(=O)— | K261 | J045 | T170 |
| 1573 | —(CH$_2$)$_2$— | —NH—C(=O)— | K262 | J007 | T148 |
| 1574 | —(CH$_2$)$_2$— | —NH—C(=O)— | K262 | J008 | T148 |
| 1575 | —(CH$_2$)$_2$— | —NH—C(=O)— | K262 | J010 | T148 |
| 1576 | —(CH$_2$)$_2$— | —NH—C(=O)— | K262 | J012 | T148 |
| 1577 | —(CH$_2$)$_2$— | —NH—C(=O)— | K262 | J013 | T148 |
| 1578 | —(CH$_2$)$_2$— | —NH—C(=O)— | K262 | J014 | T148 |
| 1579 | —(CH$_2$)$_2$— | —NH—C(=O)— | K262 | J044 | T148 |
| 1580 | —(CH$_2$)$_2$— | —NH—C(=O)— | K262 | J044 | T170 |
| 1581 | —(CH$_2$)$_2$— | —NH—C(=O)— | K262 | J044 | T178 |
| 1582 | —(CH$_2$)$_2$— | —NH—C(=O)— | K262 | J045 | T148 |
| 1583 | —(CH$_2$)$_2$— | —NH—C(=O)— | K262 | J045 | T169 |
| 1584 | —(CH$_2$)$_2$— | —NH—C(=O)— | K262 | J045 | T170 |
| 1585 | —(CH$_2$)$_2$— | —NH—C(=O)— | K262 | J045 | T178 |
| 1586 | —(CH$_2$)$_2$— | —NH—C(=O)— | K263 | J007 | T148 |
| 1587 | —(CH$_2$)$_2$— | —NH—C(=O)— | K263 | J008 | T148 |
| 1588 | —(CH$_2$)$_2$— | —NH—C(=O)— | K263 | J010 | T148 |
| 1589 | —(CH$_2$)$_2$— | —NH—C(=O)— | K263 | J012 | T148 |
| 1590 | —(CH$_2$)$_2$— | —NH—C(=O)— | K263 | J012 | T164 |
| 1591 | —(CH$_2$)$_2$— | —NH—C(=O)— | K263 | J013 | T148 |
| 1592 | —(CH$_2$)$_2$— | —NH—C(=O)— | K263 | J013 | T170 |
| 1593 | —(CH$_2$)$_2$— | —NH—C(=O)— | K263 | J014 | T148 |
| 1594 | —(CH$_2$)$_2$— | —NH—C(=O)— | K263 | J039 | T170 |
| 1595 | —(CH$_2$)$_2$— | —NH—C(=O)— | K263 | J044 | T148 |
| 1596 | —(CH$_2$)$_2$— | —NH—C(=O)— | K263 | J044 | T170 |

TABLE 1-continued

| Compound no. | -A¹- | -A²- | -G¹-A³-A⁴-G² | -A⁵-R² | -A⁶-R³ |
|---|---|---|---|---|---|
| 1597 | —(CH₂)₂— | —NH—C(=O)— | K263 | J044 | T179 |
| 1598 | —(CH₂)₂— | —NH—C(=O)— | K263 | J045 | T148 |
| 1599 | —(CH₂)₂— | —NH—C(=O)— | K263 | J045 | T169 |
| 1600 | —(CH₂)₂— | —NH—C(=O)— | K263 | J045 | T170 |
| 1601 | —(CH₂)₂— | —NH—C(=O)— | K263 | J045 | T178 |
| 1602 | —(CH₂)₂— | —NH—C(=O)— | K263 | J045 | T179 |
| 1603 | —(CH₂)₂— | —NH—C(=O)— | K264 | J012 | T148 |
| 1604 | —(CH₂)₂— | —NH—C(=O)— | K264 | J045 | T169 |
| 1605 | —(CH₂)₂— | —NH—C(=O)— | K264 | J045 | T170 |
| 1606 | —(CH₂)₂— | —NH—C(=O)— | K265 | J012 | T148 |
| 1607 | —(CH₂)₂— | —NH—C(=O)— | K265 | J044 | T148 |
| 1608 | —(CH₂)₂— | —NH—C(=O)— | K265 | J044 | T180 |
| 1609 | —(CH₂)₂— | —NH—C(=O)— | K265 | J045 | T148 |
| 1610 | —(CH₂)₂— | —NH—C(=O)— | K265 | J045 | T169 |
| 1611 | —(CH₂)₂— | —NH—C(=O)— | K265 | J045 | T170 |
| 1612 | —(CH₂)₂— | —NH—C(=O)— | K265 | J045 | T180 |
| 1613 | —(CH₂)₂— | —NH—C(=O)— | K266 | J012 | T148 |
| 1614 | —(CH₂)₂— | —NH—C(=O)— | K266 | J045 | T169 |
| 1615 | —(CH₂)₂— | —NH—C(=O)— | K266 | J045 | T170 |
| 1616 | —(CH₂)₂— | —NH—C(=O)— | K267 | J012 | T148 |
| 1617 | —(CH₂)₂— | —NH—C(=O)— | K267 | J045 | T169 |
| 1618 | —(CH₂)₂— | —NH—C(=O)— | K267 | J045 | T170 |
| 1619 | —(CH₂)₂— | —NH—C(=O)— | K268 | J012 | T148 |
| 1620 | —(CH₂)₂— | —NH—C(=O)— | K268 | J045 | T170 |
| 1621 | —(CH₂)₂— | —NH—C(=O)— | K269 | J012 | T148 |
| 1622 | —(CH₂)₂— | —NH—C(=O)— | K269 | J045 | T170 |
| 1623 | —(CH₂)₂— | —NH—C(=O)— | K210 | J012 | T148 |
| 1624 | —(CH₂)₂— | —NH—C(=O)— | K270 | J045 | T170 |
| 1625 | —(CH₂)₂— | —NH—C(=O)— | K271 | J012 | T148 |
| 1626 | —(CH₂)₂— | —NH—C(=O)— | K271 | J045 | T169 |
| 1627 | —(CH₂)₂— | —NH—C(=O)— | K271 | J045 | T170 |
| 1628 | —(CH₂)₂— | —NH—C(=O)— | K272 | J012 | T148 |
| 1629 | —(CH₂)₂— | —NH—C(=O)— | K272 | J045 | T169 |
| 1630 | —(CH₂)₂— | —NH—C(=O)— | K272 | J045 | T170 |
| 1631 | —(CH₂)₂— | —NH—C(=O)— | K273 | J012 | T148 |
| 1632 | —(CH₂)₂— | —NH—C(=O)— | K273 | J045 | T170 |
| 1633 | —(CH₂)₂— | —NH—C(=O)— | K274 | J012 | T148 |
| 1634 | —(CH₂)₂— | —NH—C(=O)— | K274 | J045 | T170 |
| 1635 | —(CH₂)₂— | —NH—C(=O)— | K275 | J007 | T148 |
| 1636 | —(CH₂)₂— | —NH—C(=O)— | K275 | J008 | T148 |
| 1637 | —(CH₂)₂— | —NH—C(=O)— | K275 | J010 | T148 |
| 1638 | —(CH₂)₂— | —NH—C(=O)— | K275 | J012 | T148 |
| 1639 | —(CH₂)₂— | —NH—C(=O)— | K275 | J013 | T148 |
| 1640 | —(CH₂)₂— | —NH—C(=O)— | K275 | J014 | T148 |
| 1641 | —(CH₂)₂— | —NH—C(=O)— | K275 | J044 | T170 |
| 1642 | —(CH₂)₂— | —NH—C(=O)— | K275 | J045 | T169 |
| 1643 | —(CH₂)₂— | —NH—C(=O)— | K275 | J045 | T170 |
| 1644 | —(CH₂)₂— | —NH—C(=O)— | K276 | J007 | T148 |
| 1645 | —(CH₂)₂— | —NH—C(=O)— | K276 | J008 | T148 |
| 1646 | —(CH₂)₂— | —NH—C(=O)— | K276 | J010 | T148 |
| 1647 | —(CH₂)₂— | —NH—C(=O)— | K276 | J012 | T148 |
| 1648 | —(CH₂)₂— | —NH—C(=O)— | K276 | J012 | T164 |
| 1649 | —(CH₂)₂— | —NH—C(=O)— | K276 | J013 | T148 |
| 1650 | —(CH₂)₂— | —NH—C(=O)— | K276 | J013 | T170 |
| 1651 | —(CH₂)₂— | —NH—C(=O)— | K276 | J014 | T148 |
| 1652 | —(CH₂)₂— | —NH—C(=O)— | K276 | J044 | T170 |
| 1653 | —(CH₂)₂— | —NH—C(=O)— | K276 | J045 | T169 |
| 1654 | —(CH₂)₂— | —NH—C(=O)— | K276 | J045 | T170 |
| 1655 | —(CH₂)₂— | —NH—C(=O)— | K276 | J045 | T178 |
| 1656 | —(CH₂)₂— | —NH—C(=O)— | K276 | J045 | T179 |
| 1657 | —(CH₂)₂— | —NH—C(=O)— | K277 | J045 | T170 |
| 1658 | —(CH₂)₂— | —NH—C(=O)— | K278 | J045 | T170 |
| 1659 | —(CH₂)₂— | —NH—C(=O)— | K279 | J045 | T170 |
| 1660 | —(CH₂)₂— | —NH—C(=O)— | K280 | J012 | T148 |
| 1661 | —(CH₂)₂— | —NH—C(=O)— | K280 | J045 | T170 |
| 1662 | —(CH₂)₂— | —NH—C(=O)— | K281 | J045 | T170 |
| 1663 | —(CH₂)₂— | —NH—C(=O)— | K282 | J045 | T170 |
| 1664 | —(CH₂)₂— | —NH—C(=O)— | K283 | J045 | T170 |
| 1665 | —(CH₂)₂— | —NH—C(=O)— | K284 | J045 | T170 |
| 1666 | —(CH₂)₂— | —NH—C(=O)— | K285 | J045 | T170 |
| 1667 | —(CH₂)₂— | —NH—C(=O)— | K286 | J045 | T170 |
| 1668 | —(CH₂)₂— | —NH—C(=O)— | K287 | J045 | T170 |
| 1669 | —(CH₂)₂— | —NH—C(=O)— | K288 | J045 | T170 |
| 1670 | —(CH₂)₂— | —NH—C(=O)— | K289 | J007 | T148 |
| 1671 | —(CH₂)₂— | —NH—C(=O)— | K289 | J008 | T148 |
| 1672 | —(CH₂)₂— | —NH—C(=O)— | K289 | J010 | T148 |

TABLE 1-continued

| Compound no. | -A¹- | -A²- | -G¹-A³-A⁴-G² | -A⁵-R² | -A⁶-R³ |
|---|---|---|---|---|---|
| 1673 | —(CH$_2$)$_2$— | —NH—C(=O)— | K289 | J012 | T148 |
| 1674 | —(CH$_2$)$_2$— | —NH—C(=O)— | K289 | J013 | T148 |
| 1675 | —(CH$_2$)$_2$— | —NH—C(=O)— | K289 | J014 | T148 |
| 1676 | —(CH$_2$)$_2$— | —NH—C(=O)— | K289 | J044 | T169 |
| 1677 | —(CH$_2$)$_2$— | —NH—C(=O)— | K289 | J044 | T170 |
| 1678 | —(CH$_2$)$_2$— | —NH—C(=O)— | K289 | J045 | T169 |
| 1679 | —(CH$_2$)$_2$— | —NH—C(=O)— | K289 | J045 | T170 |
| 1680 | —(CH$_2$)$_2$— | —NH—C(=O)— | K290 | J045 | T170 |
| 1681 | —(CH$_2$)$_2$— | —NH—C(=O)— | K291 | J045 | T170 |
| 1682 | —(CH$_2$)$_2$— | —NH—C(=O)— | K292 | J045 | T148 |
| 1683 | —(CH$_2$)$_2$— | —NH—C(=O)— | K292 | J045 | T170 |
| 1684 | —(CH$_2$)$_2$— | —NH—C(=O)— | K293 | J007 | T148 |
| 1685 | —(CH$_2$)$_2$— | —NH—C(=O)— | K293 | J008 | T148 |
| 1686 | —(CH$_2$)$_2$— | —NH—C(=O)— | K293 | J010 | T148 |
| 1687 | —(CH$_2$)$_2$— | —NH—C(=O)— | K293 | J012 | T148 |
| 1688 | —(CH$_2$)$_2$— | —NH—C(=O)— | K293 | J013 | T148 |
| 1689 | —(CH$_2$)$_2$— | —NH—C(=O)— | K293 | J014 | T148 |
| 1690 | —(CH$_2$)$_2$— | —NH—C(=O)— | K293 | J044 | T170 |
| 1691 | —(CH$_2$)$_2$— | —NH—C(=O)— | K293 | J045 | T148 |
| 1692 | —(CH$_2$)$_2$— | —NH—C(=O)— | K293 | J045 | T169 |
| 1693 | —(CH$_2$)$_2$— | —NH—C(=O)— | K293 | J045 | T170 |
| 1694 | —(CH$_2$)$_2$— | —NH—C(=O)— | K294 | J045 | T170 |
| 1695 | —(CH$_2$)$_2$— | —NH—C(=O)— | K295 | J045 | T170 |
| 1696 | —(CH$_2$)$_2$— | —NH—C(=O)— | K295/K296 | J045 | T148 |
| 1697 | —(CH$_2$)$_2$— | —NH—C(=O)— | K296 | J045 | T170 |
| 1698 | —(CH$_2$)$_2$— | —NH—C(=O)— | K297 | J045 | T170 |
| 1699 | —(CH$_2$)$_2$— | —NH—C(=O)— | K298 | J045 | T148 |
| 1700 | —(CH$_2$)$_2$— | —NH—C(=O)— | K298 | J045 | T170 |
| 1701 | —(CH$_2$)$_2$— | —NH—C(=O)— | K299 | J045 | T170 |
| 1702 | —(CH$_2$)$_2$— | —NH—C(=O)— | K300 | J045 | T170 |
| 1703 | —(CH$_2$)$_2$— | —NH—C(=O)— | K301 | J044 | T170 |
| 1704 | —(CH$_2$)$_2$— | —NH—C(=O)— | K301 | J045 | T169 |
| 1705 | —(CH$_2$)$_2$— | —NH—C(=O)— | K301 | J045 | T170 |
| 1706 | —(CH$_2$)$_2$— | —NH—C(=O)— | K302 | J012 | T148 |
| 1707 | —(CH$_2$)$_2$— | —NH—C(=O)— | K302 | J044 | T170 |
| 1708 | —(CH$_2$)$_2$— | —NH—C(=O)— | K302 | J045 | T170 |
| 1709 | —(CH$_2$)$_2$— | —NH—C(=O)— | K303 | J007 | T148 |
| 1710 | —(CH$_2$)$_2$— | —NH—C(=O)— | K303 | J008 | T148 |
| 1711 | —(CH$_2$)$_2$— | —NH—C(=O)— | K303 | J010 | T148 |
| 1712 | —(CH$_2$)$_2$— | —NH—C(=O)— | K303 | J013 | T148 |
| 1713 | —(CH$_2$)$_2$— | —NH—C(=O)— | K303 | J014 | T148 |
| 1714 | —(CH$_2$)$_2$— | —NH—C(=O)— | K303 | J044 | T170 |
| 1715 | —(CH$_2$)$_2$— | —NH—C(=O)— | K303 | J045 | T148 |
| 1716 | —(CH$_2$)$_2$— | —NH—C(=O)— | K303 | J045 | T169 |
| 1717 | —(CH$_2$)$_2$— | —NH—C(=O)— | K303 | J045 | T170 |
| 1718 | —(CH$_2$)$_2$— | —NH—C(=O)— | K304 | J012 | T148 |
| 1719 | —(CH$_2$)$_2$— | —NH—C(=O)— | K304 | J045 | T148 |
| 1720 | —(CH$_2$)$_2$— | —NH—C(=O)— | K304 | J045 | T170 |
| 1721 | —(CH$_2$)$_2$— | —NH—C(=O)— | K305 | J045 | T148 |
| 1722 | —(CH$_2$)$_2$— | —NH—C(=O)— | K305 | J045 | T170 |
| 1723 | —(CH$_2$)$_2$— | —NH—C(=O)— | K306 | J044 | T170 |
| 1724 | —(CH$_2$)$_2$— | —NH—C(=O)— | K306 | J045 | T170 |
| 1725 | —(CH$_2$)$_2$— | —NH—C(=O)— | K307 | J045 | T170 |
| 1726 | —(CH$_2$)$_2$— | —NH—C(=O)— | K308 | J007 | T148 |
| 1727 | —(CH$_2$)$_2$— | —NH—C(=O)— | K308 | J008 | T148 |
| 1728 | —(CH$_2$)$_2$— | —NH—C(=O)— | K308 | J010 | T148 |
| 1729 | —(CH$_2$)$_2$— | —NH—C(=O)— | K308 | J012 | T148 |
| 1730 | —(CH$_2$)$_2$— | —NH—C(=O)— | K308 | J013 | T148 |
| 1731 | —(CH$_2$)$_2$— | —NH—C(=O)— | K308 | J014 | T148 |
| 1732 | —(CH$_2$)$_2$— | —NH—C(=O)— | K308 | J045 | T170 |
| 1733 | —(CH$_2$)$_2$— | —NH—C(=O)— | K309 | J045 | T170 |
| 1734 | —(CH$_2$)$_2$— | —NH—C(=O)— | K310 | J045 | T170 |
| 1735 | —(CH$_2$)$_2$— | —NH—C(=O)— | K311 | J045 | T170 |
| 1736 | —(CH$_2$)$_2$— | —NH—C(=O)— | K312 | J012 | T148 |
| 1737 | —(CH$_2$)$_2$— | —NH—C(=O)— | K312 | J045 | T170 |
| 1738 | —(CH$_2$)$_2$— | —NH—C(=O)— | K313 | J012 | T148 |
| 1739 | —(CH$_2$)$_2$— | —NH—C(=O)— | K313 | J045 | T148 |
| 1740 | —(CH$_2$)$_2$— | —NH—C(=O)— | K313 | J045 | T170 |
| 1741 | —(CH$_2$)$_2$— | —NH—C(=O)— | K314 | J007 | T148 |
| 1742 | —(CH$_2$)$_2$— | —NH—C(=O)— | K314 | J008 | T148 |
| 1743 | —(CH$_2$)$_2$— | —NH—C(=O)— | K314 | J010 | T148 |
| 1744 | —(CH$_2$)$_2$— | —NH—C(=O)— | K314 | J012 | T148 |
| 1745 | —(CH$_2$)$_2$— | —NH—C(=O)— | K314 | J013 | T148 |
| 1746 | —(CH$_2$)$_2$— | —NH—C(=O)— | K314 | J014 | T148 |
| 1747 | —(CH$_2$)$_2$— | —NH—C(=O)— | K314 | J044 | T170 |
| 1748 | —(CH$_2$)$_2$— | —NH—C(=O)— | K314 | J045 | T148 |

TABLE 1-continued

| Compound no. | -A¹- | -A²- | -G¹-A³-A⁴-G² | -A⁵-R² | -A⁶-R³ |
|---|---|---|---|---|---|
| 1749 | —(CH₂)₂— | —NH—C(=O)— | K314 | J045 | T169 |
| 1750 | —(CH₂)₂— | —NH—C(=O)— | K314 | J045 | T170 |
| 1751 | —(CH₂)₂— | —NH—C(=O)— | K315 | J045 | T148 |
| 1752 | —(CH₂)₂— | —NH—C(=O)— | K315 | J045 | T170 |
| 1753 | —(CH₂)₂— | —NH—C(=O)— | K316 | J045 | T148 |
| 1754 | —(CH₂)₂— | —NH—C(=O)— | K316 | J045 | T170 |
| 1755 | —(CH₂)₂— | —NH—C(=O)— | K317 | J012 | T148 |
| 1756 | —(CH₂)₂— | —NH—C(=O)— | K317 | J045 | T170 |
| 1757 | —(CH₂)₂— | —NH—C(=O)— | K318 | J045 | T170 |
| 1758 | —(CH₂)₂— | —NH—C(=O)— | K319 | J045 | T148 |
| 1759 | —(CH₂)₂— | —NH—C(=O)— | K319 | J045 | T170 |
| 1760 | —(CH₂)₂— | —NH—C(=O)— | K320 | J045 | T170 |
| 1761 | —(CH₂)₂— | —NH—C(=O)— | K321 | J045 | T170 |
| 1762 | —(CH₂)₂— | —NH—C(=O)— | K322 | J045 | T170 |
| 1763 | —(CH₂)₂— | —NH—C(=O)— | K323 | J007 | T148 |
| 1764 | —(CH₂)₂— | —NH—C(=O)— | K323 | J008 | T148 |
| 1765 | —(CH₂)₂— | —NH—C(=O)— | K323 | J010 | T148 |
| 1766 | —(CH₂)₂— | —NH—C(=O)— | K323 | J013 | T148 |
| 1767 | —(CH₂)₂— | —NH—C(=O)— | K323 | J014 | T148 |
| 1768 | —(CH₂)₂— | —NH—C(=O)— | K323 | J045 | T169 |
| 1769 | —(CH₂)₂— | —NH—C(=O)— | K323 | J045 | T170 |
| 1770 | —(CH₂)₂— | —NH—C(=O)— | K326 | J045 | T170 |
| 1771 | —(CH₂)₂— | —NH—C(=O)— | K332 | J012 | T148 |
| 1772 | —(CH₂)₂— | —NH—C(=O)— | K332 | J012 | T164 |
| 1773 | —(CH₂)₂— | —NH—C(=O)— | K332 | J013 | T148 |
| 1774 | —(CH₂)₂— | —NH—C(=O)— | K332 | J013 | T170 |
| 1775 | —(CH₂)₂— | —NH—C(=O)— | K332 | J045 | T170 |
| 1776 | —(CH₂)₂— | —NH—C(=O)— | K332 | J045 | T178 |
| 1777 | —(CH₂)₂— | —NH—C(=O)— | K332 | J045 | T179 |
| 1778 | —(CH₂)₂— | —NH—C(=O)— | K333 | J012 | T148 |
| 1779 | —(CH₂)₂— | —NH—C(=O)— | K333 | J012 | T164 |
| 1780 | —(CH₂)₂— | —NH—C(=O)— | K333 | J013 | T148 |
| 1781 | —(CH₂)₂— | —NH—C(=O)— | K333 | J013 | T170 |
| 1782 | —(CH₂)₂— | —NH—C(=O)— | K333 | J045 | T170 |
| 1783 | —(CH₂)₂— | —NH—C(=O)— | K333 | J045 | T178 |
| 1784 | —(CH₂)₂— | —NH—C(=O)— | K333 | J045 | T179 |
| 1785 | —(CH₂)₂— | —NH—C(=O)— | K335 | J012 | T148 |
| 1786 | —(CH₂)₂— | —NH—C(=O)— | K335 | J012 | T164 |
| 1787 | —(CH₂)₂— | —NH—C(=O)— | K335 | J013 | T148 |
| 1788 | —(CH₂)₂— | —NH—C(=O)— | K335 | J013 | T170 |
| 1789 | —(CH₂)₂— | —NH—C(=O)— | K335 | J045 | T170 |
| 1790 | —(CH₂)₂— | —NH—C(=O)— | K335 | J045 | T178 |
| 1791 | —(CH₂)₂— | —NH—C(=O)— | K335 | J045 | T179 |
| 1792 | —(CH₂)₂— | —NH—C(=O)— | K336 | J012 | T148 |
| 1793 | —(CH₂)₂— | —NH—C(=O)— | K336 | J012 | T164 |
| 1794 | —(CH₂)₂— | —NH—C(=O)— | K336 | J013 | T148 |
| 1795 | —(CH₂)₂— | —NH—C(=O)— | K336 | J013 | T170 |
| 1796 | —(CH₂)₂— | —NH—C(=O)— | K336 | J045 | T170 |
| 1797 | —(CH₂)₂— | —NH—C(=O)— | K336 | J045 | T178 |
| 1798 | —(CH₂)₂— | —NH—C(=O)— | K336 | J045 | T179 |
| 1799 | —(CH₂)₂— | —NH—C(=O)— | K340 | J045 | T170 |
| 1800 | —(CH₂)₂— | —NH—C(=O)— | K343 | J045 | T170 |
| 1801 | —(CH₂)₂— | —NH—C(=O)— | K345 | J045 | T169 |
| 1802 | —(CH₂)₂— | —NH—C(=O)— | K346 | J045 | T169 |
| 1803 | —(CH₂)₂— | —NH—C(=O)— | K346 | J045 | T170 |
| 1804 | —(CH₂)₂— | —NH—C(=O)— | K355 | J045 | T148 |
| 1805 | —(CH₂)₂— | —NH—C(=O)— | K356 | J045 | T148 |
| 1806 | —(CH₂)₂— | —NH—C(=O)— | K357 | J045 | T148 |
| 1807 | —(CH₂)₂— | —NH—C(=O)— | K357 | J045 | T170 |
| 1808 | —(CH₂)₂— | —NH—C(=O)— | K358 | J045 | T148 |
| 1809 | —(CH₂)₂— | —NH—C(=O)— | K358 | J045 | T170 |
| 1810 | —(CH₂)₂— | —NH—C(=O)— | K359 | J012 | T170 |
| 1811 | —(CH₂)₂— | —NH—C(=O)— | K359 | J045 | T170 |
| 1812 | —(CH₂)₂— | —NH—C(=O)— | K360 | J012 | T170 |
| 1813 | —(CH₂)₂— | —NH—C(=O)— | K360 | J045 | T170 |
| 1814 | —(CH₂)₂— | —NH—C(=O)— | K361 | J012 | T170 |
| 1815 | —(CH₂)₂— | —NH—C(=O)— | K361 | J045 | T170 |
| 1816 | —(CH₂)₂— | —NH—C(=O)— | K362 | J012 | T170 |
| 1817 | —(CH₂)₂— | —NH—C(=O)— | K362 | J045 | T170 |
| 1818 | —(CH₂)₂— | —NH—C(=O)— | K363 | J012 | T170 |
| 1819 | —(CH₂)₂— | —NH—C(=O)— | K363 | J045 | T170 |
| 1820 | —(CH₂)₂— | —NH—C(=O)— | K364 | J012 | T170 |
| 1821 | —(CH₂)₂— | —NH—C(=O)— | K364 | J045 | T170 |
| 1822 | —(CH₂)₂— | —NH—C(=O)— | K365 | J012 | T170 |
| 1823 | —(CH₂)₂— | —NH—C(=O)— | K365 | J045 | T148 |
| 1824 | —(CH₂)₂— | —NH—C(=O)— | K365 | J045 | T170 |

TABLE 1-continued

| Compound no. | -A¹- | -A²- | -G¹-A³-A⁴-G² | -A⁵-R² | -A⁶-R³ |
|---|---|---|---|---|---|
| 1825 | —(CH$_2$)$_2$— | —NH—C(=O)— | K366 | J012 | T170 |
| 1826 | —(CH$_2$)$_2$— | —NH—C(=O)— | K366 | J045 | T170 |
| 1827 | —(CH$_2$)$_2$— | —NH—C(=O)— | K367 | J012 | T170 |
| 1828 | —(CH$_2$)$_2$— | —NH—C(=O)— | K367 | J045 | T148 |
| 1829 | —(CH$_2$)$_2$— | —NH—C(=O)— | K367 | J045 | T170 |
| 1830 | —(CH$_2$)$_2$— | —NH—C(=O)— | K368 | J012 | T170 |
| 1831 | —(CH$_2$)$_2$— | —NH—C(=O)— | K368 | J045 | T170 |
| 1832 | —(CH$_2$)$_2$— | —NH—C(=O)— | K369 | J012 | T170 |
| 1833 | —(CH$_2$)$_2$— | —NH—C(=O)— | K369 | J045 | T148 |
| 1834 | —(CH$_2$)$_2$— | —NH—C(=O)— | K369 | J045 | T170 |
| 1835 | —(CH$_2$)$_2$— | —NH—C(=O)— | K370 | J012 | T170 |
| 1836 | —(CH$_2$)$_2$— | —NH—C(=O)— | K370 | J045 | T170 |
| 1837 | —(CH$_2$)$_2$— | —NH—C(=O)— | K371 | J012 | T170 |
| 1838 | —(CH$_2$)$_2$— | —NH—C(=O)— | K371 | J045 | T170 |
| 1839 | —(CH$_2$)$_2$— | —NH—C(=O)— | K372 | J012 | T170 |
| 1840 | —(CH$_2$)$_2$— | —NH—C(=O)— | K372 | J045 | T170 |
| 1841 | —(CH$_2$)$_2$— | —NH—C(=O)— | K373 | J012 | T170 |
| 1842 | —(CH$_2$)$_2$— | —NH—C(=O)— | K373 | J045 | T170 |
| 1843 | —(CH$_2$)$_2$— | —NH—C(=O)— | K374 | J012 | T148 |
| 1844 | —(CH$_2$)$_2$— | —NH—C(=O)— | K374 | J012 | T170 |
| 1845 | —(CH$_2$)$_2$— | —NH—C(=O)— | K374 | J045 | T170 |
| 1846 | —(CH$_2$)$_2$— | —NH—C(=O)— | K375 | J012 | T148 |
| 1847 | —(CH$_2$)$_2$— | —NH—C(=O)— | K375 | J012 | T170 |
| 1848 | —(CH$_2$)$_2$— | —NH—C(=O)— | K375 | J045 | T170 |
| 1849 | —(CH$_2$)$_2$— | —NH—C(=O)— | K376 | J012 | T148 |
| 1850 | —(CH$_2$)$_2$— | —NH—C(=O)— | K376 | J012 | T170 |
| 1851 | —(CH$_2$)$_2$— | —NH—C(=O)— | K376 | J045 | T170 |
| 1852 | —(CH$_2$)$_2$— | —NH—C(=O)— | K377 | J012 | T148 |
| 1853 | —(CH$_2$)$_2$— | —NH—C(=O)— | K377 | J012 | T170 |
| 1854 | —(CH$_2$)$_2$— | —NH—C(=O)— | K377 | J045 | T170 |
| 1855 | —(CH$_2$)$_2$— | —NH—C(=O)— | K378 | J012 | T148 |
| 1856 | —(CH$_2$)$_2$— | —NH—C(=O)— | K378 | J012 | T170 |
| 1857 | —(CH$_2$)$_2$— | —NH—C(=O)— | K378 | J039 | T170 |
| 1858 | —(CH$_2$)$_2$— | —NH—C(=O)— | K378 | J044 | T170 |
| 1859 | —(CH$_2$)$_2$— | —NH—C(=O)— | K378 | J045 | T169 |
| 1860 | —(CH$_2$)$_2$— | —NH—C(=O)— | K378 | J045 | T170 |
| 1861 | —(CH$_2$)$_2$— | —NH—C(=O)— | K379 | J012 | T148 |
| 1862 | —(CH$_2$)$_2$— | —NH—C(=O)— | K379 | J012 | T170 |
| 1863 | —(CH$_2$)$_2$— | —NH—C(=O)— | K379 | J045 | T169 |
| 1864 | —(CH$_2$)$_2$— | —NH—C(=O)— | K379 | J045 | T170 |
| 1865 | —(CH$_2$)$_2$— | —NH—C(=O)— | K380 | J012 | T148 |
| 1866 | —(CH$_2$)$_2$— | —NH—C(=O)— | K380 | J012 | T170 |
| 1867 | —(CH$_2$)$_2$— | —NH—C(=O)— | K380 | J045 | T170 |
| 1868 | —(CH$_2$)$_2$— | —NH—C(=O)— | K381 | J012 | T148 |
| 1869 | —(CH$_2$)$_2$— | —NH—C(=O)— | K381 | J012 | T170 |
| 1870 | —(CH$_2$)$_2$— | —NH—C(=O)— | K381 | J045 | T169 |
| 1871 | —(CH$_2$)$_2$— | —NH—C(=O)— | K381 | J045 | T170 |
| 1872 | —(CH$_2$)$_2$— | —NH—C(=O)— | K382 | J007 | T148 |
| 1873 | —(CH$_2$)$_2$— | —NH—C(=O)— | K382 | J008 | T148 |
| 1874 | —(CH$_2$)$_2$— | —NH—C(=O)— | K382 | J010 | T148 |
| 1875 | —(CH$_2$)$_2$— | —NH—C(=O)— | K382 | J012 | T148 |
| 1876 | —(CH$_2$)$_2$— | —NH—C(=O)— | K382 | J012 | T170 |
| 1877 | —(CH$_2$)$_2$— | —NH—C(=O)— | K382 | J013 | T148 |
| 1878 | —(CH$_2$)$_2$— | —NH—C(=O)— | K382 | J014 | T148 |
| 1879 | —(CH$_2$)$_2$— | —NH—C(=O)— | K382 | J039 | T170 |
| 1880 | —(CH$_2$)$_2$— | —NH—C(=O)— | K382 | J044 | T170 |
| 1881 | —(CH$_2$)$_2$— | —NH—C(=O)— | K382 | J045 | T169 |
| 1882 | —(CH$_2$)$_2$— | —NH—C(=O)— | K382 | J045 | T170 |
| 1883 | —(CH$_2$)$_2$— | —NH—C(=O)— | K383 | J012 | T170 |
| 1884 | —(CH$_2$)$_2$— | —NH—C(=O)— | K383 | J045 | T170 |
| 1885 | —(CH$_2$)$_2$— | —NH—C(=O)— | K384 | J012 | T148 |
| 1886 | —(CH$_2$)$_2$— | —NH—C(=O)— | K384 | J012 | T170 |
| 1887 | —(CH$_2$)$_2$— | —NH—C(=O)— | K384 | J039 | T170 |
| 1888 | —(CH$_2$)$_2$— | —NH—C(=O)— | K384 | J044 | T170 |
| 1889 | —(CH$_2$)$_2$— | —NH—C(=O)— | K384 | J045 | T169 |
| 1890 | —(CH$_2$)$_2$— | —NH—C(=O)— | K384 | J045 | T170 |
| 1891 | —(CH$_2$)$_2$— | —NH—C(=O)— | K385 | J012 | T148 |
| 1892 | —(CH$_2$)$_2$— | —NH—C(=O)— | K385 | J012 | T170 |
| 1893 | —(CH$_2$)$_2$— | —NH—C(=O)— | K385 | J045 | T169 |
| 1894 | —(CH$_2$)$_2$— | —NH—C(=O)— | K385 | J045 | T170 |
| 1895 | —(CH$_2$)$_2$— | —NH—C(=O)— | K386 | J012 | T148 |
| 1896 | —(CH$_2$)$_2$— | —NH—C(=O)— | K386 | J039 | T170 |
| 1897 | —(CH$_2$)$_2$— | —NH—C(=O)— | K386 | J044 | T170 |
| 1898 | —(CH$_2$)$_2$— | —NH—C(=O)— | K386 | J045 | T170 |
| 1899 | —(CH$_2$)$_2$— | —NH—C(=O)— | K387 | J012 | T148 |
| 1900 | —(CH$_2$)$_2$— | —NH—C(=O)— | K387 | J045 | T170 |

TABLE 1-continued

| Compound no. | -A¹- | -A²- | -G¹-A³-A⁴-G² | -A⁵-R² | -A⁶-R³ |
|---|---|---|---|---|---|
| 1901 | —(CH₂)₂— | —NH—C(=O)— | K388 | J012 | T148 |
| 1902 | —(CH₂)₂— | —NH—C(=O)— | K388 | J039 | T170 |
| 1903 | —(CH₂)₂— | —NH—C(=O)— | K388 | J044 | T170 |
| 1904 | —(CH₂)₂— | —NH—C(=O)— | K388 | J045 | T170 |
| 1905 | —(CH₂)₂— | —NH—C(=O)— | K389 | J012 | T148 |
| 1906 | —(CH₂)₂— | —NH—C(=O)— | K389 | J045 | T170 |
| 1907 | —(CH₂)₂— | —NH—C(=O)— | K390 | J012 | T148 |
| 1908 | —(CH₂)₂— | —NH—C(=O)— | K390 | J045 | T170 |
| 1909 | —(CH₂)₂— | —NH—C(=O)— | K391 | J012 | T148 |
| 1910 | —(CH₂)₂— | —NH—C(=O)— | K391 | J045 | T170 |
| 1911 | —(CH₂)₂— | —NH—C(=O)— | K392 | J012 | T148 |
| 1912 | —(CH₂)₂— | —NH—C(=O)— | K392 | J045 | T170 |
| 1913 | —(CH₂)₂— | —NH—C(=O)— | K393 | J012 | T148 |
| 1914 | —(CH₂)₂— | —NH—C(=O)— | K393 | J045 | T170 |
| 1915 | —(CH₂)₂— | —NH—C(=O)— | K394 | J012 | T148 |
| 1916 | —(CH₂)₂— | —NH—C(=O)— | K394 | J045 | T170 |
| 1917 | —(CH₂)₂— | —NH—C(=O)— | K398 | J012 | T148 |
| 1918 | —(CH₂)₂— | —NH—C(=O)— | K399 | J010 | T148 |
| 1919 | —(CH₂)₂— | —NH—C(=O)— | K399 | J010 | T170 |
| 1920 | —(CH₂)₂— | —NH—C(=O)— | K399 | J012 | T148 |
| 1921 | —(CH₂)₂— | —NH—C(=O)— | K399 | J013 | T148 |
| 1922 | —(CH₂)₂— | —NH—C(=O)— | K399 | J013 | T170 |
| 1923 | —(CH₂)₂— | —NH—C(=O)— | K399 | J044 | T170 |
| 1924 | —(CH₂)₂— | —NH—C(=O)— | K399 | J045 | T170 |
| 1925 | —(CH₂)₂— | —NH—C(=O)— | K399 | J146 | T148 |
| 1926 | —(CH₂)₂— | —NH—C(=O)— | K399 | J147 | T148 |
| 1927 | —(CH₂)₂— | —NH—C(=O)— | K399 | J150 | T148 |
| 1928 | —(CH₂)₂— | —NH—C(=O)— | K399 | J150 | T170 |
| 1929 | —(CH₂)₂— | —NH—C(=O)— | K399 | J151 | T148 |
| 1930 | —(CH₂)₂— | —NH—C(=O)— | K399 | J159 | T148 |
| 1931 | —(CH₂)₂— | —NH—C(=O)— | K399 | J159 | T170 |
| 1932 | —(CH₂)₂— | —NH—C(=O)— | K400 | J012 | T148 |
| 1933 | —(CH₂)₂— | —NH—C(=O)— | K400 | J013 | T170 |
| 1934 | —(CH₂)₂— | —NH—C(=O)— | K400 | J045 | T170 |
| 1935 | —(CH₂)₂— | —NH—C(=O)— | K400 | J151 | T148 |
| 1936 | —(CH₂)₂— | —NH—C(=O)— | K400 | J151 | T170 |
| 1937 | —(CH₂)₂— | —NH—C(=O)— | K401 | J012 | T148 |
| 1938 | —(CH₂)₂— | —NH—C(=O)— | K401 | J045 | T170 |
| 1939 | —(CH₂)₂— | —NH—C(=O)— | K402 | J012 | T148 |
| 1940 | —(CH₂)₂— | —NH—C(=O)— | K402 | J045 | T170 |
| 1941 | —(CH₂)₂— | —NH—C(=O)— | K402 | J151 | T170 |
| 1942 | —(CH₂)₂— | —NH—C(=O)— | K402 | J159 | T148 |
| 1943 | —(CH₂)₂— | —NH—C(=O)— | K402 | J159 | T170 |
| 1944 | —(CH₂)₂— | —NH—C(=O)— | K403 | J012 | T148 |
| 1945 | —(CH₂)₂— | —NH—C(=O)— | K403 | J013 | T148 |
| 1946 | —(CH₂)₂— | —NH—C(=O)— | K403 | J013 | T170 |
| 1947 | —(CH₂)₂— | —NH—C(=O)— | K403 | J044 | T170 |
| 1948 | —(CH₂)₂— | —NH—C(=O)— | K403 | J045 | T170 |
| 1949 | —(CH₂)₂— | —NH—C(=O)— | K403 | J151 | T148 |
| 1950 | —(CH₂)₂— | —NH—C(=O)— | K403 | J151 | T170 |
| 1951 | —(CH₂)₂— | —NH—C(=O)— | K403 | J158 | T170 |
| 1952 | —(CH₂)₂— | —NH—C(=O)— | K404 | J012 | T148 |
| 1953 | —(CH₂)₂— | —NH—C(=O)— | K405 | J012 | T148 |
| 1954 | —(CH₂)₂— | —NH—C(=O)— | K406 | J012 | T148 |
| 1955 | —(CH₂)₂— | —NH—C(=O)— | K406 | J045 | T170 |
| 1956 | —(CH₂)₂— | —NH—C(=O)— | K407 | J012 | T148 |
| 1957 | —(CH₂)₂— | —NH—C(=O)— | K407 | J013 | T148 |
| 1958 | —(CH₂)₂— | —NH—C(=O)— | K407 | J013 | T170 |
| 1959 | —(CH₂)₂— | —NH—C(=O)— | K407 | J044 | T170 |
| 1960 | —(CH₂)₂— | —NH—C(=O)— | K407 | J045 | T170 |
| 1961 | —(CH₂)₂— | —NH—C(=O)— | K408 | J012 | T148 |
| 1962 | —(CH₂)₂— | —NH—C(=O)— | K409 | J012 | T148 |
| 1963 | —(CH₂)₂— | —NH—C(=O)— | K409 | J045 | T170 |
| 1964 | —(CH₂)₂— | —NH—C(=O)— | K410 | J012 | T148 |
| 1965 | —(CH₂)₂— | —NH—C(=O)— | K411 | J012 | T148 |
| 1966 | —(CH₂)₂— | —NH—C(=O)— | K411 | J045 | T170 |
| 1967 | —(CH₂)₂— | —NH—C(=O)— | K412 | J012 | T148 |
| 1968 | —(CH₂)₂— | —NH—C(=O)— | K413 | J012 | T148 |
| 1969 | —(CH₂)₂— | —NH—C(=O)— | K414 | J012 | T148 |
| 1970 | —(CH₂)₂— | —NH—C(=O)— | K414 | J044 | T170 |
| 1971 | —(CH₂)₂— | —NH—C(=O)— | K414 | J045 | T170 |
| 1972 | —(CH₂)₂— | —NH—C(=O)— | K415 | J012 | T148 |
| 1973 | —(CH₂)₂— | —NH—C(=O)— | K415 | J013 | T148 |
| 1974 | —(CH₂)₂— | —NH—C(=O)— | K415 | J013 | T170 |
| 1975 | —(CH₂)₂— | —NH—C(=O)— | K415 | J044 | T170 |
| 1976 | —(CH₂)₂— | —NH—C(=O)— | K415 | J045 | T170 |

TABLE 1-continued

| Compound no. | -A¹- | -A²- | -G¹-A³-A⁴-G² | -A⁵-R² | -A⁶-R³ |
|---|---|---|---|---|---|
| 1977 | —(CH₂)₂— | —NH—C(=O)— | K415 | J151 | T148 |
| 1978 | —(CH₂)₂— | —NH—C(=O)— | K415 | J151 | T170 |
| 1979 | —(CH₂)₂— | —NH—C(=O)— | K415 | J158 | T170 |
| 1980 | —(CH₂)₂— | —NH—C(=O)— | K416 | J012 | T148 |
| 1981 | —(CH₂)₂— | —NH—C(=O)— | K417 | J012 | T148 |
| 1982 | —(CH₂)₂— | —NH—C(=O)— | K418 | J012 | T148 |
| 1983 | —(CH₂)₂— | —NH—C(=O)— | K419 | J012 | T148 |
| 1984 | —(CH₂)₂— | —NH—C(=O)— | K419 | J045 | T170 |
| 1985 | —(CH₂)₂— | —NH—C(=O)— | K420 | J012 | T148 |
| 1986 | —(CH₂)₂— | —NH—C(=O)— | K420 | J013 | T148 |
| 1987 | —(CH₂)₂— | —NH—C(=O)— | K420 | J013 | T170 |
| 1988 | —(CH₂)₂— | —NH—C(=O)— | K420 | J044 | T170 |
| 1989 | —(CH₂)₂— | —NH—C(=O)— | K420 | J045 | T148 |
| 1990 | —(CH₂)₂— | —NH—C(=O)— | K420 | J045 | T170 |
| 1991 | —(CH₂)₂— | —NH—C(=O)— | K420 | J149 | T148 |
| 1992 | —(CH₂)₂— | —NH—C(=O)— | K420 | J150 | T148 |
| 1993 | —(CH₂)₂— | —NH—C(=O)— | K420 | J150 | T170 |
| 1994 | —(CH₂)₂— | —NH—C(=O)— | K420 | J151 | T148 |
| 1995 | —(CH₂)₂— | —NH—C(=O)— | K420 | J151 | T170 |
| 1996 | —(CH₂)₂— | —NH—C(=O)— | K420 | J158 | T170 |
| 1997 | —(CH₂)₂— | —NH—C(=O)— | K421 | J012 | T148 |
| 1998 | —(CH₂)₂— | —NH—C(=O)— | K422 | J012 | T148 |
| 1999 | —(CH₂)₂— | —NH—C(=O)— | K423 | J012 | T148 |
| 2000 | —(CH₂)₂— | —NH—C(=O)— | K424 | J012 | T148 |
| 2001 | —(CH₂)₂— | —NH—C(=O)— | K425 | J012 | T148 |
| 2002 | —(CH₂)₂— | —NH—C(=O)— | K426 | J012 | T148 |
| 2003 | —(CH₂)₂— | —NH—C(=O)— | K200 | J022 | T170 |
| 2004 | —(CH₂)₂— | —NH—C(=O)— | K357 | J012 | T148 |
| 2005 | —(CH₂)₂— | —NH—C(=O)—NH— | K005 | J045 | T148 |
| 2006 | —(CH₂)₂— | —NH—C(=O)—NH— | K008 | J045 | T148 |
| 2007 | —(CH₂)₂— | —NH—C(=O)—NH— | K023 | J012 | T148 |
| 2008 | —(CH₂)₂— | —NH—C(=O)—NH— | K033 | J012 | T148 |
| 2009 | —(CH₂)₂— | —NH—C(=O)—NH— | K077 | J045 | T148 |
| 2010 | —(CH₂)₂— | —NH—C(=O)—NH— | K102 | J045 | T148 |
| 2011 | —(CH₂)₂— | —NH—C(=O)—NH— | K102 | J045 | T170 |
| 2012 | —(CH₂)₂— | —NH—C(=O)—NH— | K106 | J045 | T148 |
| 2013 | —(CH₂)₂— | —NH—C(=O)—NH— | K336 | J012 | T148 |
| 2014 | —(CH₂)₂— | —NH—C(=O)—NH— | K204 | J045 | T148 |
| 2015 | —(CH₂)₂— | —NH—C(=O)—NH— | K204 | J045 | T170 |
| 2016 | —(CH₂)₂— | —NH—C(=O)—NH— | K223 | J045 | T148 |
| 2017 | —(CH₂)₂— | —NH—C(=O)—NH— | K230 | J012 | T148 |
| 2018 | —(CH₂)₂— | —NH—C(=O)—NH— | K231 | J012 | T148 |
| 2019 | —(CH₂)₂— | —NH—C(=O)—NH— | K248 | J045 | T148 |
| 2020 | —(CH₂)₂— | —NH—C(=O)—NH— | K249 | J045 | T148 |
| 2021 | —(CH₂)₂— | —NH—C(=O)—NH— | K250 | J045 | T148 |
| 2022 | —(CH₂)₂— | —NH—C(=O)—NH— | K278 | J012 | T148 |
| 2023 | —(CH₂)₂— | —NH—C(=O)—NH— | K277 | J045 | T148 |
| 2024 | —(CH₂)₂— | —NH—C(=O)—NH— | K277 | J045 | T170 |
| 2025 | —(CH₂)₂— | —NH—C(=O)—NH— | K278 | J045 | T148 |
| 2026 | —(CH₂)₂— | —NH—C(=O)—NH— | K278 | J045 | T170 |
| 2027 | —(CH₂)₂— | —NH—C(=O)—NH— | K279 | J045 | T148 |
| 2028 | —(CH₂)₂— | —NH—C(=O)—NH— | K286 | J045 | T148 |
| 2029 | —(CH₂)₂— | —NH—C(=O)—NH— | K324 | J045 | T148 |
| 2030 | —(CH₂)₂— | —NH—C(=O)—NH— | K324 | J045 | T170 |
| 2031 | —(CH₂)₂— | —NH—C(=O)—NH— | K325 | J012 | T148 |
| 2032 | —(CH₂)₂— | —NH—C(=O)—NH— | K325 | J045 | T148 |
| 2033 | —(CH₂)₂— | —NH—C(=O)—NH— | K325 | J045 | T170 |
| 2034 | —(CH₂)₂— | —NH—C(=O)—NH— | K326 | J045 | T148 |
| 2035 | —(CH₂)₂— | —NH—C(=O)—NH— | K326 | J045 | T169 |
| 2036 | —(CH₂)₂— | —NH—C(=O)—NH— | K326 | J045 | T170 |
| 2037 | —(CH₂)₂— | —NH—C(=O)—NH— | K327 | J045 | T170 |
| 2038 | —(CH₂)₂— | —NH—C(=O)—NH— | K328 | J045 | T170 |
| 2039 | —(CH₂)₂— | —NH—C(=O)—NH— | K329 | J045 | T170 |
| 2040 | —(CH₂)₂— | —NH—C(=O)—NH— | K330 | J012 | T148 |
| 2041 | —(CH₂)₂— | —NH—C(=O)—NH— | K330 | J045 | T170 |
| 2042 | —(CH₂)₂— | —NH—C(=O)—NH— | K331 | J012 | T148 |
| 2043 | —(CH₂)₂— | —NH—C(=O)—NH— | K331 | J045 | T170 |
| 2044 | —(CH₂)₂— | —NH—C(=O)—NH— | K332 | J045 | T169 |
| 2045 | —(CH₂)₂— | —NH—C(=O)—NH— | K332 | J045 | T170 |
| 2046 | —(CH₂)₂— | —NH—C(=O)—NH— | K333 | J012 | T148 |
| 2047 | —(CH₂)₂— | —NH—C(=O)—NH— | K333 | J044 | T170 |
| 2048 | —(CH₂)₂— | —NH—C(=O)—NH— | K333 | J045 | T169 |
| 2049 | —(CH₂)₂— | —NH—C(=O)—NH— | K333 | J045 | T170 |
| 2050 | —(CH₂)₂— | —NH—C(=O)—NH— | K334 | J045 | T170 |
| 2051 | —(CH₂)₂— | —NH—C(=O)—NH— | K335 | J044 | T170 |
| 2052 | —(CH₂)₂— | —NH—C(=O)—NH— | K335 | J045 | T148 |

TABLE 1-continued

| Compound no. | -A¹- | -A²- | -G¹-A³-A⁴-G² | -A⁵-R² | -A⁶-R³ |
|---|---|---|---|---|---|
| 2053 | —(CH$_2$)$_2$— | —NH—C(=O)—NH— | K335 | J045 | T170 |
| 2054 | —(CH$_2$)$_2$— | —NH—C(=O)—NH— | K336 | J012 | T170 |
| 2055 | —(CH$_2$)$_2$— | —NH—C(=O)—NH— | K336 | J044 | T170 |
| 2056 | —(CH$_2$)$_2$— | —NH—C(=O)—NH— | K336 | J045 | T148 |
| 2057 | —(CH$_2$)$_2$— | —NH—C(=O)—NH— | K336 | J045 | T169 |
| 2058 | —(CH$_2$)$_2$— | —NH—C(=O)—NH— | K336 | J045 | T170 |
| 2059 | —(CH$_2$)$_2$— | —NH—C(=O)—NH— | K337 | J045 | T170 |
| 2060 | —(CH$_2$)$_2$— | —NH—C(=O)—NH— | K338 | J045 | T148 |
| 2061 | —(CH$_2$)$_2$— | —NH—C(=O)—NH— | K338 | J045 | T170 |
| 2062 | —(CH$_2$)$_2$— | —NH—C(=O)—NH— | K339 | J045 | T148 |
| 2063 | —(CH$_2$)$_2$— | —NH—C(=O)—NH— | K339 | J045 | T170 |
| 2064 | —(CH$_2$)$_2$— | —NH—C(=O)—NH— | K340 | J012 | T148 |
| 2065 | —(CH$_2$)$_2$— | —NH—C(=O)—NH— | K340 | J045 | T148 |
| 2066 | —(CH$_2$)$_2$— | —NH—C(=O)—NH— | K340 | J045 | T169 |
| 2067 | —(CH$_2$)$_2$— | —NH—C(=O)—NH— | K340 | J045 | T170 |
| 2068 | —(CH$_2$)$_2$— | —NH—C(=O)—NH— | K341 | J045 | T148 |
| 2069 | —(CH$_2$)$_2$— | —NH—C(=O)—NH— | K341 | J045 | T170 |
| 2070 | —(CH$_2$)$_2$— | —NH—C(=O)—NH— | K342 | J045 | T148 |
| 2071 | —(CH$_2$)$_2$— | —NH—C(=O)—NH— | K342 | J045 | T170 |
| 2072 | —(CH$_2$)$_2$— | —NH—C(=O)—NH— | K343 | J045 | T148 |
| 2073 | —(CH$_2$)$_2$— | —NH—C(=O)—NH— | K343 | J045 | T170 |
| 2074 | —(CH$_2$)$_2$— | —NH—C(=O)—NH— | K344 | J045 | T170 |
| 2075 | —(CH$_2$)$_2$— | —NH—C(=O)—NH— | K345 | J045 | T170 |
| 2076 | —(CH$_2$)$_2$— | —NH—C(=O)—NH— | K346 | J045 | T170 |
| 2077 | —(CH$_2$)$_2$— | —NH—C(=O)—NH— | K347 | J045 | T170 |
| 2078 | —(CH$_2$)$_2$— | —NH—C(=O)—NH— | K348 | J045 | T148 |
| 2079 | —(CH$_2$)$_2$— | —NH—C(=O)—NH— | K348 | J045 | T170 |
| 2080 | —(CH$_2$)$_2$— | —NH—C(=O)—NH— | K349 | J045 | T170 |
| 2081 | —(CH$_2$)$_2$— | —NH—C(=O)—NH— | K350 | J045 | T148 |
| 2082 | —(CH$_2$)$_2$— | —NH—C(=O)—NH— | K350 | J045 | T170 |
| 2083 | —(CH$_2$)$_2$— | —NH—C(=O)—NH— | K351 | J045 | T148 |
| 2084 | —(CH$_2$)$_2$— | —NH—C(=O)—NH— | K351 | J045 | T170 |
| 2085 | —(CH$_2$)$_2$— | —NH—C(=O)—NH— | K352 | J045 | T148 |
| 2086 | —(CH$_2$)$_2$— | —NH—C(=O)—NH— | K352 | J045 | T170 |
| 2087 | —(CH$_2$)$_2$— | —NH—C(=O)—NH— | K353 | J045 | T148 |
| 2088 | —(CH$_2$)$_2$— | —NH—C(=O)—NH— | K353 | J045 | T170 |
| 2089 | —(CH$_2$)$_2$— | —NH—C(=O)—NH— | K354 | J045 | T148 |
| 2090 | —(CH$_2$)$_2$— | —NH—C(=O)—NH— | K354 | J045 | T170 |
| 2091 | —(CH$_2$)$_2$— | —NH—C(=O)—NH— | K355 | J045 | T170 |
| 2092 | —(CH$_2$)$_2$— | —NH—C(=O)—NH— | K356 | J045 | T170 |
| 2093 | —(CH$_2$)$_2$— | —NH—C(=O)—NH— | K359 | J045 | T148 |
| 2094 | —(CH$_2$)$_2$— | —NH—C(=O)—NH— | K360 | J045 | T148 |
| 2095 | —(CH$_2$)$_2$— | —NH—C(=O)—NH— | K362 | J045 | T148 |
| 2096 | —(CH$_2$)$_2$— | —NH—C(=O)—NH— | K361 | J045 | T148 |
| 2097 | —(CH$_2$)$_2$— | —NH—C(=O)—NH— | K362 | J045 | T170 |
| 2098 | —(CH$_2$)$_2$— | —NH—C(=O)—NH— | K364 | J045 | T170 |
| 2099 | —(CH$_2$)$_2$— | —NH—C(=O)—NH— | K370 | J045 | T148 |
| 2100 | —(CH$_2$)$_2$— | —NH—C(=O)—NH— | K371 | J045 | T148 |
| 2101 | —(CH$_2$)$_2$— | —NH—C(=O)—NH— | K373 | J045 | T148 |
| 2102 | —(CH$_2$)$_2$— | —NH—C(=O)—NH— | K431 | J045 | T170 |
| 2103 | —(CH$_2$)$_2$— | —NH—C(=O)—NH— | K395 | J012 | T148 |
| 2104 | —(CH$_2$)$_2$— | —NH—C(=O)—NH— | K395 | J045 | T170 |
| 2105 | —(CH$_2$)$_2$— | —NH—C(=O)—NH— | K396 | J012 | T148 |
| 2106 | —(CH$_2$)$_2$— | —NH—C(=O)—NH— | K396 | J045 | T170 |
| 2107 | —(CH$_2$)$_2$— | —NH—C(=O)—NH— | K397 | J012 | T148 |
| 2108 | —(CH$_2$)$_2$— | —NH—C(=O)—NH— | K397 | J045 | T170 |
| 2109 | —(CH$_2$)$_2$— | —NH—C(=O)— | K241 | J045 | T148 |
| 2110 | —(CH$_2$)$_2$— | —NH—C(=O)—O— | K005 | J001 | T148 |
| 2111 | —(CH$_2$)$_2$— | —NH—C(=O)—O— | K005 | J007 | T148 |
| 2112 | —(CH$_2$)$_2$— | —NH—C(=O)—O— | K005 | J008 | T148 |
| 2113 | —(CH$_2$)$_2$— | —NH—C(=O)—O— | K005 | J009 | T170 |
| 2114 | —(CH$_2$)$_2$— | —NH—C(=O)—O— | K005 | J010 | T148 |
| 2115 | —(CH$_2$)$_2$— | —NH—C(=O)—O— | K005 | J011 | T170 |
| 2116 | —(CH$_2$)$_2$— | —NH—C(=O)—O— | K005 | J012 | T170 |
| 2117 | —(CH$_2$)$_2$— | —NH—C(=O)—O— | K005 | J013 | T148 |
| 2118 | —(CH$_2$)$_2$— | —NH—C(=O)—O— | K005 | J014 | T148 |
| 2119 | —(CH$_2$)$_2$— | —NH—C(=O)—O— | K005 | J015 | T170 |
| 2120 | —(CH$_2$)$_2$— | —NH—C(=O)—O— | K005 | J026 | T001 |
| 2121 | —(CH$_2$)$_2$— | —NH—C(=O)—O— | K005 | J026 | T148 |
| 2122 | —(CH$_2$)$_2$— | —NH—C(=O)—O— | K005 | J026 | T170 |
| 2123 | —(CH$_2$)$_2$— | —NH—C(=O)—O— | K005 | J037 | T170 |
| 2124 | —(CH$_2$)$_2$— | —NH—C(=O)—O— | K005 | J039 | T170 |
| 2125 | —(CH$_2$)$_2$— | —NH—C(=O)—O— | K005 | J043 | T170 |
| 2126 | —(CH$_2$)$_2$— | —NH—C(=O)—O— | K005 | J045 | T072 |
| 2127 | —(CH$_2$)$_2$— | —NH—C(=O)—O— | K005 | J045 | T074 |
| 2128 | —(CH$_2$)$_2$— | —NH—C(=O)—O— | K005 | J045 | T180 |

TABLE 1-continued

| Compound no. | -A¹- | -A²- | -G¹-A³-A⁴-G² | -A⁵-R² | -A⁶-R³ |
|---|---|---|---|---|---|
| 2129 | —(CH$_2$)$_2$— | —NH—C(=O)—O— | K005 | J047 | T170 |
| 2130 | —(CH$_2$)$_2$— | —NH—C(=O)—O— | K005 | J079 | T170 |
| 2131 | —(CH$_2$)$_2$— | —NH—C(=O)—O— | K005 | J080 | T148 |
| 2132 | —(CH$_2$)$_2$— | —NH—C(=O)—O— | K005 | J081 | T148 |
| 2133 | —(CH$_2$)$_2$— | —NH—C(=O)—O— | K005 | J082 | T148 |
| 2134 | —(CH$_2$)$_2$— | —NH—C(=O)—O— | K005 | J090 | T148 |
| 2135 | —(CH$_2$)$_2$— | —NH—C(=O)—O— | K005 | J092 | T148 |
| 2136 | —(CH$_2$)$_2$— | —NH—C(=O)—O— | K005 | J103 | T170 |
| 2137 | —(CH$_2$)$_2$— | —NH—C(=O)—O— | K005 | J104 | T170 |
| 2138 | —(CH$_2$)$_2$— | —NH—C(=O)—O— | K005 | J105 | T170 |
| 2139 | —(CH$_2$)$_2$— | —NH—C(=O)—O— | K005 | J106 | T170 |
| 2140 | —(CH$_2$)$_2$— | —NH—C(=O)—O— | K005 | J107 | T170 |
| 2141 | —(CH$_2$)$_2$— | —NH—C(=O)—O— | K005 | J140 | T001 |
| 2142 | —(CH$_2$)$_2$— | —NH—C(=O)—O— | K005 | J140 | T148 |
| 2143 | —(CH$_2$)$_2$— | —NH—C(=O)—O— | K005 | J140 | T170 |
| 2144 | —(CH$_2$)$_2$— | —NH—C(=O)—O— | K005 | J144 | T148 |
| 2145 | —(CH$_2$)$_2$— | —NH—C(=O)—O— | K005 | J146 | T148 |
| 2146 | —(CH$_2$)$_2$— | —NH—C(=O)—O— | K199 | J045 | T148 |
| 2147 | —(CH$_2$)$_2$— | —NH—C(=O)—O— | K223 | J045 | T148 |
| 2148 | —(CH$_2$)$_2$— | —NH—C(=O)—O— | K198 | J045 | T148 |
| 2149 | —(CH$_2$)$_2$— | —NH—S(=O)$_2$— | K200 | J012 | T148 |
| 2150 | —(CH$_2$)$_2$— | —NH—S(=O)$_2$— | K200 | J044 | T170 |
| 2151 | —(CH$_2$)$_2$— | —NH—S(=O)$_2$— | K200 | J045 | T170 |
| 2152 | —(CH$_2$)$_2$— | —NH—S(=O)$_2$— | K223 | J012 | T148 |
| 2153 | —(CH$_2$)$_2$— | —NH—S(=O)$_2$— | K223 | J044 | T170 |
| 2154 | —(CH$_2$)$_2$— | —NH—S(=O)$_2$— | K230 | J044 | T170 |
| 2155 | —(CH$_2$)$_2$— | —NH—S(=O)$_2$— | K230 | J045 | T170 |
| 2156 | —(CH$_2$)$_2$— | —NH—S(=O)$_2$— | K231 | J044 | T170 |
| 2157 | —(CH$_2$)$_2$— | —NH—S(=O)$_2$— | K231 | J045 | T170 |
| 2158 | —(CH$_2$)$_3$— | —C(=O)— | K108 | J001 | T148 |
| 2159 | —(CH$_2$)$_3$— | —C(=O)— | K108 | J022 | T170 |
| 2160 | —(CH$_2$)$_3$— | —C(=O)— | K109 | J029 | T170 |
| 2161 | —(CH$_2$)$_3$— | —C(=O)— | K112 | J012 | T148 |
| 2162 | —(CH$_2$)$_3$— | —C(=O)— | K112 | J012 | T170 |
| 2163 | —(CH$_2$)$_3$— | —C(=O)— | K112 | J037 | T170 |
| 2164 | —(CH$_2$)$_3$— | —C(=O)— | K112 | J043 | T170 |
| 2165 | —(CH$_2$)$_3$— | —C(=O)— | K112 | J138 | T148 |
| 2166 | —(CH$_2$)$_3$— | —C(=O)— | K112 | J138 | T170 |
| 2167 | —(CH$_2$)$_3$— | —C(=O)— | K112 | J144 | T148 |
| 2168 | —(CH$_2$)$_3$— | —C(=O)— | K112 | J144 | T164 |
| 2169 | —(CH$_2$)$_3$— | —C(=O)— | K112 | J144 | T169 |
| 2170 | —(CH$_2$)$_3$— | —C(=O)— | K112 | J144 | T170 |
| 2171 | —(CH$_2$)$_3$— | —C(=O)— | K116 | J012 | T148 |
| 2172 | —(CH$_2$)$_3$— | —C(=O)— | K121 | J043 | T170 |
| 2173 | —(CH$_2$)$_3$— | —C(=O)— | K129 | J012 | T148 |
| 2174 | —(CH$_2$)$_3$— | —C(=O)— | K136 | J044 | T170 |
| 2175 | —(CH$_2$)$_3$— | —C(=O)— | K137 | J012 | T148 |
| 2176 | —(CH$_2$)$_3$— | —C(=O)— | K137 | J012 | T170 |
| 2177 | —(CH$_2$)$_3$— | —C(=O)— | K137 | J045 | T170 |
| 2178 | —(CH$_2$)$_3$— | —C(=O)— | K138 | J079 | T170 |
| 2179 | —(CH$_2$)$_3$— | —C(=O)— | K139 | J012 | T148 |
| 2180 | —(CH$_2$)$_3$— | —C(=O)— | K142 | J012 | T148 |
| 2181 | —(CH$_2$)$_3$— | —C(=O)— | K143 | J012 | T148 |
| 2182 | —(CH$_2$)$_3$— | —C(=O)— | K144 | J012 | T148 |
| 2183 | —(CH$_2$)$_3$— | —C(=O)— | K144 | J043 | T148 |
| 2184 | —(CH$_2$)$_3$— | —C(=O)— | K144 | J043 | T170 |
| 2185 | —(CH$_2$)$_3$— | —C(=O)— | K144 | J138 | T148 |
| 2186 | —(CH$_2$)$_3$— | —C(=O)— | K144 | J138 | T170 |
| 2187 | —(CH$_2$)$_3$— | —C(=O)— | K144 | J144 | T148 |
| 2188 | —(CH$_2$)$_3$— | —C(=O)— | K144 | J144 | T170 |
| 2189 | —(CH$_2$)$_3$— | —C(=O)— | K147 | J012 | T148 |
| 2190 | —(CH$_2$)$_3$— | —C(=O)— | K147 | J138 | T170 |
| 2191 | —(CH$_2$)$_3$— | —C(=O)— | K148 | J012 | T148 |
| 2192 | —(CH$_2$)$_3$— | —C(=O)— | K148 | J139 | T170 |
| 2193 | —(CH$_2$)$_3$— | —C(=O)— | K150 | J012 | T148 |
| 2194 | —(CH$_2$)$_3$— | —C(=O)— | K154 | J012 | T148 |
| 2195 | —(CH$_2$)$_3$— | —C(=O)— | K166 | J012 | T148 |
| 2196 | —(CH$_2$)$_3$— | —C(=O)— | K166 | J144 | T170 |
| 2197 | —(CH$_2$)$_3$— | —C(=O)— | K170 | J007 | T170 |
| 2198 | —(CH$_2$)$_3$— | —C(=O)— | K172 | J012 | T170 |
| 2199 | —(CH$_2$)$_3$— | —C(=O)— | K237 | J012 | T148 |
| 2200 | —(CH$_2$)$_3$— | —C(=O)— | K391 | J144 | T170 |
| 2201 | —(CH$_2$)$_3$— | —C(=O)—NH— | K004 | J012 | T148 |
| 2202 | —(CH$_2$)$_3$— | —C(=O)—NH— | K009 | J001 | T148 |
| 2203 | —(CH$_2$)$_3$— | —C(=O)—NH— | K009 | J007 | T148 |
| 2204 | —(CH$_2$)$_3$— | —C(=O)—NH— | K009 | J007 | T164 |

TABLE 1-continued

| Compound no. | -A¹- | -A²- | -G¹-A³-A⁴-G² | -A⁵-R² | -A⁶-R³ |
|---|---|---|---|---|---|
| 2205 | —(CH₂)₃— | —C(=O)—NH— | K009 | J007 | T169 |
| 2206 | —(CH₂)₃— | —C(=O)—NH— | K009 | J007 | T170 |
| 2207 | —(CH₂)₃— | —C(=O)—NH— | K009 | J012 | T148 |
| 2208 | —(CH₂)₃— | —C(=O)—NH— | K009 | J037 | T170 |
| 2209 | —(CH₂)₃— | —C(=O)—NH— | K012 | J001 | T148 |
| 2210 | —(CH₂)₃— | —C(=O)—NH— | K013 | J012 | T148 |
| 2211 | —(CH₂)₃— | —C(=O)—NH— | K013 | J012 | T170 |
| 2212 | —(CH₂)₃— | —C(=O)—NH— | K023 | J012 | T148 |
| 2213 | —(CH₂)₃— | —C(=O)—NH— | K023 | J029 | T148 |
| 2214 | —(CH₂)₃— | —C(=O)—NH— | K023 | J029 | T164 |
| 2215 | —(CH₂)₃— | —C(=O)—NH— | K023 | J029 | T169 |
| 2216 | —(CH₂)₃— | —C(=O)—NH— | K023 | J029 | T170 |
| 2217 | —(CH₂)₃— | —C(=O)—NH— | K023 | J043 | T170 |
| 2218 | —(CH₂)₃— | —C(=O)—NH— | K029 | J012 | T148 |
| 2219 | —(CH₂)₃— | —C(=O)—NH— | K029 | J044 | T148 |
| 2220 | —(CH₂)₃— | —C(=O)—NH— | K029 | J044 | T164 |
| 2221 | —(CH₂)₃— | —C(=O)—NH— | K029 | J044 | T169 |
| 2222 | —(CH₂)₃— | —C(=O)—NH— | K029 | J044 | T170 |
| 2223 | —(CH₂)₃— | —C(=O)—NH— | K029 | J045 | T170 |
| 2224 | —(CH₂)₃— | —C(=O)—NH— | K033 | J012 | T148 |
| 2225 | —(CH₂)₃— | —C(=O)—NH— | K033 | J043 | T148 |
| 2226 | —(CH₂)₃— | —C(=O)—NH— | K033 | J043 | T164 |
| 2227 | —(CH₂)₃— | —C(=O)—NH— | K033 | J043 | T169 |
| 2228 | —(CH₂)₃— | —C(=O)—NH— | K033 | J043 | T170 |
| 2229 | —(CH₂)₃— | —C(=O)—NH— | K033 | J044 | T170 |
| 2230 | —(CH₂)₃— | —C(=O)—NH— | K034 | J012 | T148 |
| 2231 | —(CH₂)₃— | —C(=O)—NH— | K034 | J045 | T148 |
| 2232 | —(CH₂)₃— | —C(=O)—NH— | K034 | J045 | T164 |
| 2233 | —(CH₂)₃— | —C(=O)—NH— | K034 | J045 | T169 |
| 2234 | —(CH₂)₃— | —C(=O)—NH— | K034 | J045 | T170 |
| 2235 | —(CH₂)₃— | —C(=O)—NH— | K034 | J079 | T170 |
| 2236 | —(CH₂)₃— | —C(=O)—NH— | K077 | J138 | T170 |
| 2237 | —(CH₂)₃— | —C(=O)—NH— | K078 | J139 | T170 |
| 2238 | —(CH₂)₃— | —C(=O)—NH— | K101 | J144 | T170 |
| 2239 | —(CH₂)₃— | —C(=O)—NH— | K102 | J007 | T170 |
| 2240 | —(CH₂)₃— | —C(=O)—NH— | K102 | J012 | T148 |
| 2241 | —(CH₂)₃— | —C(=O)—NH— | K102 | J012 | T170 |
| 2242 | —(CH₂)₃— | —C(=O)—NH— | K102 | J079 | T148 |
| 2243 | —(CH₂)₃— | —C(=O)—NH— | K102 | J079 | T164 |
| 2244 | —(CH₂)₃— | —C(=O)—NH— | K102 | J079 | T169 |
| 2245 | —(CH₂)₃— | —C(=O)—NH— | K102 | J079 | T170 |
| 2246 | —(CH₂)₃— | —C(=O)—NH— | K103 | J012 | T148 |
| 2247 | —(CH₂)₃— | —C(=O)—NH— | K103 | J138 | T148 |
| 2248 | —(CH₂)₃— | —C(=O)—NH— | K103 | J138 | T164 |
| 2249 | —(CH₂)₃— | —C(=O)—NH— | K103 | J138 | T169 |
| 2250 | —(CH₂)₃— | —C(=O)—NH— | K103 | J138 | T170 |
| 2251 | —(CH₂)₃— | —C(=O)—NH— | K104 | J012 | T148 |
| 2252 | —(CH₂)₃— | —C(=O)—NH— | K104 | J012 | T170 |
| 2253 | —(CH₂)₃— | —C(=O)—NH— | K104 | J139 | T148 |
| 2254 | —(CH₂)₃— | —C(=O)—NH— | K104 | J139 | T164 |
| 2255 | —(CH₂)₃— | —C(=O)—NH— | K104 | J139 | T169 |
| 2256 | —(CH₂)₃— | —C(=O)—NH— | K104 | J139 | T170 |
| 2257 | —(CH₂)₃— | —C(=O)—NH— | K108 | J012 | T148 |
| 2258 | —(CH₂)₃— | —C(=O)—NH— | K198 | J012 | T148 |
| 2259 | —(CH₂)₃— | —C(=O)—NH— | K198 | J022 | T170 |
| 2260 | —(CH₂)₃— | —C(=O)—NH— | K200 | J012 | T148 |
| 2261 | —(CH₂)₃— | —C(=O)—NH— | K200 | J029 | T170 |
| 2262 | —(CH₂)₃— | —C(=O)—NH— | K201 | J012 | T148 |
| 2263 | —(CH₂)₃— | —C(=O)—NH— | K201 | J037 | T170 |
| 2264 | —(CH₂)₃— | —C(=O)—NH— | K204 | J002 | T148 |
| 2265 | —(CH₂)₃— | —C(=O)—NH— | K204 | J012 | T148 |
| 2266 | —(CH₂)₃— | —C(=O)—NH— | K204 | J012 | T170 |
| 2267 | —(CH₂)₃— | —C(=O)—NH— | K204 | J043 | T148 |
| 2268 | —(CH₂)₃— | —C(=O)—NH— | K204 | J043 | T170 |
| 2269 | —(CH₂)₃— | —C(=O)—NH— | K204 | J138 | T170 |
| 2270 | —(CH₂)₃— | —C(=O)—NH— | K204 | J139 | T148 |
| 2271 | —(CH₂)₃— | —C(=O)—NH— | K204 | J144 | T148 |
| 2272 | —(CH₂)₃— | —C(=O)—NH— | K204 | J144 | T170 |
| 2273 | —(CH₂)₃— | —C(=O)—NH— | K215 | J012 | T148 |
| 2274 | —(CH₂)₃— | —C(=O)—NH— | K216 | J007 | T170 |
| 2275 | —(CH₂)₃— | —C(=O)—NH— | K216 | J012 | T148 |
| 2276 | —(CH₂)₃— | —C(=O)—NH— | K216 | J012 | T164 |
| 2277 | —(CH₂)₃— | —C(=O)—NH— | K216 | J012 | T170 |
| 2278 | —(CH₂)₃— | —C(=O)—NH— | K216 | J022 | T170 |
| 2279 | —(CH₂)₃— | —C(=O)—NH— | K216 | J029 | T170 |
| 2280 | —(CH₂)₃— | —C(=O)—NH— | K216 | J037 | T170 |

TABLE 1-continued

| Compound no. | -A¹- | -A²- | -G¹-A³-A⁴-G² | -A⁵-R² | -A⁶-R³ |
|---|---|---|---|---|---|
| 2281 | —(CH₂)₃— | —C(=O)—NH— | K216 | J043 | T148 |
| 2282 | —(CH₂)₃— | —C(=O)—NH— | K216 | J043 | T170 |
| 2283 | —(CH₂)₃— | —C(=O)—NH— | K216 | J044 | T169 |
| 2284 | —(CH₂)₃— | —C(=O)—NH— | K216 | J044 | T170 |
| 2285 | —(CH₂)₃— | —C(=O)—NH— | K216 | J045 | T170 |
| 2286 | —(CH₂)₃— | —C(=O)—NH— | K216 | J079 | T170 |
| 2287 | —(CH₂)₃— | —C(=O)—NH— | K216 | J138 | T148 |
| 2288 | —(CH₂)₃— | —C(=O)—NH— | K216 | J138 | T170 |
| 2289 | —(CH₂)₃— | —C(=O)—NH— | K216 | J139 | T170 |
| 2290 | —(CH₂)₃— | —C(=O)—NH— | K216 | J144 | T148 |
| 2291 | —(CH₂)₃— | —C(=O)—NH— | K216 | J144 | T170 |
| 2292 | —(CH₂)₃— | —C(=O)—NH— | K223 | J001 | T148 |
| 2293 | —(CH₂)₃— | —C(=O)—NH— | K223 | J045 | T170 |
| 2294 | —(CH₂)₃— | —C(=O)—NH— | K224 | J079 | T170 |
| 2295 | —(CH₂)₃— | —C(=O)—NH— | K225 | J138 | T170 |
| 2296 | —(CH₂)₃— | —C(=O)—NH— | K229 | J012 | T148 |
| 2297 | —(CH₂)₃— | —C(=O)—NH— | K229 | J139 | T170 |
| 2298 | —(CH₂)₃— | —C(=O)—NH— | K234 | J012 | T148 |
| 2299 | —(CH₂)₃— | —C(=O)—NH— | K198 | J001 | T148 |
| 2300 | —(CH₂)₃— | —C(=O)—NH— | K244 | J001 | T148 |
| 2301 | —(CH₂)₃— | —C(=O)—NH— | K246 | J001 | T148 |
| 2302 | —(CH₂)₃— | —C(=O)—NH— | K280 | J012 | T148 |
| 2303 | —(CH₂)₃— | —C(=O)—NH— | K293 | J144 | T170 |
| 2304 | —(CH₂)₃— | —C(=O)—NH— | K323 | J007 | T170 |
| 2305 | —(CH₂)₃— | —C(=O)—NH— | K324 | J012 | T148 |
| 2306 | —(CH₂)₃— | —C(=O)—NH— | K324 | J012 | T170 |
| 2307 | —(CH₂)₃— | —C(=O)—NH— | K325 | J022 | T170 |
| 2308 | —(CH₂)₃— | —C(=O)—NH— | K326 | J029 | T170 |
| 2309 | —(CH₂)₃— | —C(=O)—NH— | K327 | J037 | T170 |
| 2310 | —(CH₂)₃— | —C(=O)—NH— | K333 | J007 | T170 |
| 2311 | —(CH₂)₃— | —C(=O)—NH— | K333 | J012 | T148 |
| 2312 | —(CH₂)₃— | —C(=O)—NH— | K333 | J012 | T170 |
| 2313 | —(CH₂)₃— | —C(=O)—NH— | K333 | J022 | T170 |
| 2314 | —(CH₂)₃— | —C(=O)—NH— | K333 | J029 | T170 |
| 2315 | —(CH₂)₃— | —C(=O)—NH— | K333 | J037 | T170 |
| 2316 | —(CH₂)₃— | —C(=O)—NH— | K333 | J043 | T170 |
| 2317 | —(CH₂)₃— | —C(=O)—NH— | K333 | J044 | T170 |
| 2318 | —(CH₂)₃— | —C(=O)—NH— | K333 | J045 | T170 |
| 2319 | —(CH₂)₃— | —C(=O)—NH— | K333 | J079 | T170 |
| 2320 | —(CH₂)₃— | —C(=O)—NH— | K333 | J138 | T170 |
| 2321 | —(CH₂)₃— | —C(=O)—NH— | K333 | J139 | T170 |
| 2322 | —(CH₂)₃— | —C(=O)—NH— | K333 | J144 | T170 |
| 2323 | —(CH₂)₃— | —C(=O)—NH— | K334 | J043 | T170 |
| 2324 | —(CH₂)₃— | —C(=O)—NH— | K335 | J044 | T170 |
| 2325 | —(CH₂)₃— | —C(=O)—NH— | K336 | J012 | T148 |
| 2326 | —(CH₂)₃— | —C(=O)—NH— | K340 | J045 | T170 |
| 2327 | —(CH₂)₃— | —C(=O)—NH— | K343 | J012 | T148 |
| 2328 | —(CH₂)₃— | —C(=O)—NH— | K343 | J079 | T170 |
| 2329 | —(CH₂)₃— | —C(=O)—NH— | K344 | J012 | T148 |
| 2330 | —(CH₂)₃— | —C(=O)—NH— | K346 | J007 | T170 |
| 2331 | —(CH₂)₃— | —C(=O)—NH— | K346 | J012 | T148 |
| 2332 | —(CH₂)₃— | —C(=O)—NH— | K346 | J012 | T170 |
| 2333 | —(CH₂)₃— | —C(=O)—NH— | K346 | J022 | T170 |
| 2334 | —(CH₂)₃— | —C(=O)—NH— | K346 | J029 | T170 |
| 2335 | —(CH₂)₃— | —C(=O)—NH— | K346 | J037 | T170 |
| 2336 | —(CH₂)₃— | —C(=O)—NH— | K346 | J043 | T148 |
| 2337 | —(CH₂)₃— | —C(=O)—NH— | K346 | J043 | T170 |
| 2338 | —(CH₂)₃— | —C(=O)—NH— | K346 | J044 | T170 |
| 2339 | —(CH₂)₃— | —C(=O)—NH— | K346 | J045 | T170 |
| 2340 | —(CH₂)₃— | —C(=O)—NH— | K346 | J079 | T170 |
| 2341 | —(CH₂)₃— | —C(=O)—NH— | K346 | J080/J081 | T148 |
| 2342 | —(CH₂)₃— | —C(=O)—NH— | K346 | J090 | T148 |
| 2343 | —(CH₂)₃— | —C(=O)—NH— | K346 | J100 | T148 |
| 2344 | —(CH₂)₃— | —C(=O)—NH— | K346 | J138 | T148 |
| 2345 | —(CH₂)₃— | —C(=O)—NH— | K346 | J138 | T170 |
| 2346 | —(CH₂)₃— | —C(=O)—NH— | K346 | J139 | T170 |
| 2347 | —(CH₂)₃— | —C(=O)—NH— | K346 | J144 | T148 |
| 2348 | —(CH₂)₃— | —C(=O)—NH— | K346 | J144 | T170 |
| 2349 | —(CH₂)₃— | —C(=O)—NH— | K347 | J138 | T170 |
| 2350 | —(CH₂)₃— | —C(=O)—NH— | K353 | J012 | T148 |
| 2351 | —(CH₂)₃— | —C(=O)—NH— | K370 | J139 | T170 |
| 2352 | —(CH₂)₃— | —C(=O)—NH— | K427 | J012 | T148 |
| 2353 | —(CH₂)₃— | —C(=O)—NH— | K428 | J045 | T170 |
| 2354 | —(CH₂)₃— | —C(=O)—NH— | K429 | J012 | T148 |
| 2355 | —(CH₂)₃— | —C(=O)—NH— | K430 | J045 | T170 |
| 2356 | —(CH₂)₃— | —C(=O)— | K240 | J012 | T148 |

TABLE 1-continued

| Compound no. | -A$^1$- | -A$^2$- | -G$^1$-A$^3$-A$^4$-G$^2$ | -A$^5$-R$^2$ | -A$^6$-R$^3$ |
|---|---|---|---|---|---|
| 2357 | —(CH$_2$)$_3$— | —C(=O)— | K240 | J012 | T170 |
| 2358 | —(CH$_2$)$_3$— | —C(=O)—O— | K001 | J002 | T148 |
| 2359 | —(CH$_2$)$_3$— | —C(=O)—O— | K001 | J007 | T170 |
| 2360 | —(CH$_2$)$_3$— | —C(=O)—O— | K001 | J012 | T148 |
| 2361 | —(CH$_2$)$_3$— | —C(=O)—O— | K002 | J044 | T170 |
| 2362 | —(CH$_2$)$_3$— | —C(=O)—O— | K197 | J002 | T148 |
| 2363 | —(CH$_2$)$_3$— | —C(=O)—O— | K197 | J012 | T148 |
| 2364 | —(CH$_2$)$_3$— | —C(=O)—O— | K197 | J012 | T170 |
| 2365 | —(CH$_2$)$_3$— | —C(=O)—O— | K197 | J045 | T170 |
| 2366 | —(CH$_2$)$_3$— | —NH— | K185 | J007 | T148 |
| 2367 | —(CH$_2$)$_3$— | —NH— | K185 | J044 | T170 |
| 2368 | —(CH$_2$)$_3$— | —NH—C(=O)— | K005 | J007 | T148 |
| 2369 | —(CH$_2$)$_3$— | —NH—C(=O)— | K005 | J044 | T170 |
| 2370 | —(CH$_2$)$_3$— | —NH—C(=O)— | K007 | J012 | T148 |
| 2371 | —(CH$_2$)$_3$— | —NH—C(=O)— | K007 | J045 | T170 |
| 2372 | —(CH$_2$)$_3$— | —NH—C(=O)— | K008 | J012 | T148 |
| 2373 | —(CH$_2$)$_3$— | —NH—C(=O)— | K008 | J045 | T170 |
| 2374 | —(CH$_2$)$_3$— | —NH—C(=O)— | K009 | J007 | T148 |
| 2375 | —(CH$_2$)$_3$— | —NH—C(=O)— | K009 | J044 | T170 |
| 2376 | —(CH$_2$)$_3$— | —NH—C(=O)— | K011 | J007 | T148 |
| 2377 | —(CH$_2$)$_3$— | —NH—C(=O)— | K011 | J044 | T170 |
| 2378 | —(CH$_2$)$_3$— | —NH—C(=O)— | K013 | J007 | T148 |
| 2379 | —(CH$_2$)$_3$— | —NH—C(=O)— | K013 | J044 | T170 |
| 2380 | —(CH$_2$)$_3$— | —NH—C(=O)— | K051 | J012 | T148 |
| 2381 | —(CH$_2$)$_3$— | —NH—C(=O)— | K051 | J045 | T170 |
| 2382 | —(CH$_2$)$_3$— | —NH—C(=O)— | K200 | J012 | T148 |
| 2383 | —(CH$_2$)$_3$— | —NH—C(=O)— | K200 | J045 | T170 |
| 2384 | —(CH$_2$)$_3$— | —NH—C(=O)— | K204 | J007 | T148 |
| 2385 | —(CH$_2$)$_3$— | —NH—C(=O)— | K204 | J044 | T170 |
| 2386 | —(CH$_2$)$_3$— | —NH—C(=O)— | K208 | J012 | T148 |
| 2387 | —(CH$_2$)$_3$— | —NH—C(=O)— | K208 | J045 | T170 |
| 2388 | —(CH$_2$)$_3$— | —NH—C(=O)— | K212 | J012 | T148 |
| 2389 | —(CH$_2$)$_3$— | —NH—C(=O)— | K212 | J045 | T170 |
| 2390 | —(CH$_2$)$_3$— | —NH—C(=O)— | K262 | J012 | T148 |
| 2391 | —(CH$_2$)$_3$— | —NH—C(=O)— | K262 | J045 | T170 |
| 2392 | —(CH$_2$)$_3$— | —NH—C(=O)— | K263 | J007 | T148 |
| 2393 | —(CH$_2$)$_3$— | —NH—C(=O)— | K263 | J044 | T170 |
| 2394 | —(CH$_2$)$_3$— | —NH—C(=O)— | K266 | J007 | T148 |
| 2395 | —(CH$_2$)$_3$— | —NH—C(=O)— | K266 | J044 | T170 |
| 2396 | —(CH$_2$)$_3$— | —NH—C(=O)— | K272 | J012 | T148 |
| 2397 | —(CH$_2$)$_3$— | —NH—C(=O)— | K272 | J045 | T170 |
| 2398 | —(CH$_2$)$_3$— | —NH—C(=O)— | K293 | J007 | T148 |
| 2399 | —(CH$_2$)$_3$— | —NH—C(=O)— | K293 | J044 | T170 |
| 2400 | —(CH$_2$)$_3$— | —NH—C(=O)—NH— | K033 | J012 | T148 |
| 2401 | —(CH$_2$)$_3$— | —NH—C(=O)—NH— | K033 | J045 | T170 |
| 2402 | —(CH$_2$)$_3$— | —NH—C(=O)—NH— | K333 | J007 | T148 |
| 2403 | —(CH$_2$)$_3$— | —NH—C(=O)—NH— | K333 | J044 | T170 |
| 2404 | —(CH$_2$)$_3$— | —NH—C(=O)—NH— | K336 | J012 | T148 |
| 2405 | —(CH$_2$)$_3$— | —NH—C(=O)—NH— | K336 | J045 | T170 |
| 2406 | Single bond | Single bond | K001 | J002 | T170 |
| 2407 | Single bond | Single bond | K001 | J007 | T148 |
| 2408 | Single bond | Single bond | K001 | J007 | T170 |
| 2409 | Single bond | Single bond | K001 | J012 | T148 |
| 2410 | Single bond | Single bond | K001 | J012 | T170 |
| 2411 | Single bond | Single bond | K001 | J029 | T148 |
| 2412 | Single bond | Single bond | K001 | J029 | T170 |
| 2413 | Single bond | Single bond | K001 | J037 | T148 |
| 2414 | Single bond | Single bond | K001 | J037 | T170 |
| 2415 | Single bond | Single bond | K001 | J043 | T148 |
| 2416 | Single bond | Single bond | K001 | J043 | T170 |
| 2417 | Single bond | Single bond | K001 | J044 | T148 |
| 2418 | Single bond | Single bond | K001 | J044 | T170 |
| 2419 | Single bond | Single bond | K001 | J045 | T148 |
| 2420 | Single bond | Single bond | K001 | J045 | T170 |
| 2421 | Single bond | Single bond | K001 | J138 | T148 |
| 2422 | Single bond | Single bond | K001 | J138 | T170 |
| 2423 | Single bond | Single bond | K001 | J144 | T148 |
| 2424 | Single bond | Single bond | K001 | J144 | T170 |
| 2425 | Single bond | Single bond | K002 | J012 | T148 |
| 2426 | Single bond | Single bond | K002 | J012 | T170 |
| 2427 | Single bond | Single bond | K002 | J044 | T148 |
| 2428 | Single bond | Single bond | K002 | J044 | T170 |
| 2429 | Single bond | Single bond | K002 | J045 | T170 |
| 2430 | Single bond | Single bond | K002 | J139 | T148 |
| 2431 | Single bond | Single bond | K002 | J139 | T170 |
| 2432 | Single bond | Single bond | K197 | J002 | T148 |

TABLE 1-continued

| Compound no. | -A$^1$- | -A$^2$- | -G$^1$-A$^3$-A$^4$-G$^2$ | -A$^5$-R$^2$ | -A$^6$-R$^3$ |
|---|---|---|---|---|---|
| 2433 | Single bond | Single bond | K197 | J002 | T170 |
| 2434 | Single bond | Single bond | K197 | J007 | T148 |
| 2435 | Single bond | Single bond | K197 | J007 | T170 |
| 2436 | Single bond | Single bond | K197 | J008 | T148 |
| 2437 | Single bond | Single bond | K197 | J008 | T170 |
| 2438 | Single bond | Single bond | K197 | J010 | T148 |
| 2439 | Single bond | Single bond | K197 | J010 | T170 |
| 2440 | Single bond | Single bond | K197 | J012 | T170 |
| 2441 | Single bond | Single bond | K197 | J013 | T148 |
| 2442 | Single bond | Single bond | K197 | J013 | T170 |
| 2443 | Single bond | Single bond | K197 | J014 | T148 |
| 2444 | Single bond | Single bond | K197 | J014 | T170 |
| 2445 | Single bond | Single bond | K197 | J018 | T148 |
| 2446 | Single bond | Single bond | K197 | J022 | T148 |
| 2447 | Single bond | Single bond | K197 | J022 | T170 |
| 2448 | Single bond | Single bond | K197 | J026 | T148 |
| 2449 | Single bond | Single bond | K197 | J026 | T170 |
| 2450 | Single bond | Single bond | K197 | J027 | T148 |
| 2451 | Single bond | Single bond | K197 | J027 | T170 |
| 2452 | Single bond | Single bond | K197 | J028 | T148 |
| 2453 | Single bond | Single bond | K197 | J028 | T170 |
| 2454 | Single bond | Single bond | K197 | J029 | T148 |
| 2455 | Single bond | Single bond | K197 | J029 | T169 |
| 2456 | Single bond | Single bond | K197 | J029 | T170 |
| 2457 | Single bond | Single bond | K197 | J030 | T148 |
| 2458 | Single bond | Single bond | K197 | J030 | T170 |
| 2459 | Single bond | Single bond | K197 | J031 | T148 |
| 2460 | Single bond | Single bond | K197 | J031 | T170 |
| 2461 | Single bond | Single bond | K197 | J032 | T148 |
| 2462 | Single bond | Single bond | K197 | J032 | T170 |
| 2463 | Single bond | Single bond | K197 | J034 | T148 |
| 2464 | Single bond | Single bond | K197 | J034 | T170 |
| 2465 | Single bond | Single bond | K197 | J036 | T148 |
| 2466 | Single bond | Single bond | K197 | J036 | T170 |
| 2467 | Single bond | Single bond | K197 | J037 | T148 |
| 2468 | Single bond | Single bond | K197 | J037 | T170 |
| 2469 | Single bond | Single bond | K197 | J039 | T148 |
| 2470 | Single bond | Single bond | K197 | J039 | T170 |
| 2471 | Single bond | Single bond | K197 | J043 | T148 |
| 2472 | Single bond | Single bond | K197 | J043 | T170 |
| 2473 | Single bond | Single bond | K197 | J044 | T148 |
| 2474 | Single bond | Single bond | K197 | J044 | T170 |
| 2475 | Single bond | Single bond | K197 | J045 | T148 |
| 2476 | Single bond | Single bond | K197 | J045 | T170 |
| 2477 | Single bond | Single bond | K197 | J090 | T148 |
| 2478 | Single bond | Single bond | K197 | J090 | T170 |
| 2479 | Single bond | Single bond | K197 | J092 | T148 |
| 2480 | Single bond | Single bond | K197 | J092 | T170 |
| 2481 | Single bond | Single bond | K197 | J144 | T148 |
| 2482 | Single bond | Single bond | K197 | J121 | T148 |
| 2483 | Single bond | Single bond | K197 | J121 | T170 |
| 2484 | Single bond | Single bond | K197 | J137 | T148 |
| 2485 | Single bond | Single bond | K197 | J137 | T170 |
| 2486 | Single bond | Single bond | K197 | J138 | T148 |
| 2487 | Single bond | Single bond | K197 | J138 | T170 |
| 2488 | Single bond | Single bond | K197 | J139 | T148 |
| 2489 | Single bond | Single bond | K197 | J139 | T170 |
| 2490 | Single bond | Single bond | K197 | J141 | T148 |
| 2491 | Single bond | Single bond | K197 | J141 | T170 |
| 2492 | Single bond | Single bond | K197 | J142 | T148 |
| 2493 | Single bond | Single bond | K197 | J142 | T169 |
| 2494 | Single bond | Single bond | K197 | J142 | T170 |
| 2495 | Single bond | Single bond | K197 | J143 | T148 |
| 2496 | Single bond | Single bond | K197 | J143 | T170 |
| 2497 | Single bond | Single bond | K197 | J107 | T148 |
| 2498 | Single bond | Single bond | K197 | J144 | T170 |
| 2499 | Single bond | Single bond | K223 | J001 | T164 |
| 2500 | Single bond | Single bond | K223 | J138 | T148 |
| 2501 | —(CH$_2$)$_3$— | —C(=O)—O— | K002 | J001 | T001 |
| 2502 | —(CH$_2$)$_3$— | —C(=O)—O— | K002 | J001 | T005 |
| 2503 | —(CH$_2$)$_3$— | —C(=O)—O— | K197 | J001 | T148 |
| 2504 | —(CH$_2$)$_3$— | —C(=O)—O— | K002 | J002 | T148 |
| 2505 | —(CH$_2$)$_3$— | —C(=O)—O— | K002 | J002 | T170 |
| 2506 | —(CH$_2$)$_3$— | —C(=O)—NH— | K346 | J002 | T170 |
| 2507 | —(CH$_2$)$_3$— | —C(=O)—O— | K002 | J012 | T001 |
| 2508 | —(CH$_2$)$_3$— | —C(=O)—O— | K002 | J012 | T005 |

TABLE 1-continued

| Compound no. | -A¹- | -A²- | -G¹-A³-A⁴-G² | -A⁵-R² | -A⁶-R³ |
|---|---|---|---|---|---|
| 2509 | —(CH$_2$)$_3$— | —C(=O)—O— | K002 | J012 | T148 |
| 2510 | —(CH$_2$)$_3$— | —C(=O)—O— | K002 | J012 | T170 |
| 2511 | —(CH$_2$)$_2$— | —NH—C(=O)— | K005 | J012 | T004 |
| 2512 | —(CH$_2$)$_3$— | —C(=O)—O— | K002 | J001 | T148 |
| 2513 | —(CH$_2$)$_2$— | —NH—C(=O)—O— | K005 | J045 | T181 |
| 2514 | —(CH$_2$)$_2$— | —NH—C(=O)— | K338 | J012 | T148 |

Also, among compounds described in Table 1, compounds of the following numbers are more preferred.

Compound numbers 19, 20, 22, 27, 29, 30, 34, 36, 37, 38, 39, 40, 41, 42, 43, 44, 46, 47, 48, 49, 50, 51, 52, 53, 54, 56, 57, 58, 59, 60, 61, 62, 63, 64, 66, 67, 68, 69, 70, 71, 72, 73, 74, 76, 77, 78, 79, 81, 84, 85, 86, 87, 88, 90, 91, 92, 93, 94, 95, 96, 97, 98, 100, 101, 102, 103, 104, 105, 106, 107, 108, 110, 111, 112, 113, 114, 115, 116, 117, 118, 120, 121, 122, 123, 124, 125, 126, 127, 128, 130, 131, 132, 133, 134, 135, 136, 137, 138, 140, 141, 142, 143, 144, 145, 146, 147, 148, 150, 151, 152, 153, 154, 155, 156, 157, 158, 160, 161, 162, 163, 164, 165, 166, 167, 168, 170, 171, 172, 173, 174, 175, 176, 177, 178, 180, 181, 182, 183, 184, 185, 186, 187, 188, 190, 191, 192, 193, 194, 195, 196, 197, 198, 200, 201, 202, 203, 206, 210, 211, 213, 214, 217, 219, 221, 223, 225, 226, 227, 228, 229, 230, 231, 232, 237, 240, 241, 242, 243, 244, 245, 250, 253, 254, 255, 257, 258, 260, 261, 262, 263, 265, 266, 267, 268, 269, 275, 276, 277, 278, 279, 280, 281, 282, 283, 284, 285, 286, 287, 288, 294, 295, 296, 297, 298, 299, 300, 301, 302, 303, 308, 309, 310, 311, 312, 313, 314, 315, 316, 317, 320, 321, 327, 328, 330, 331, 332, 333, 334, 335, 340, 342, 343, 348, 349, 350, 351, 352, 353, 359, 361, 362, 363, 364, 365, 366, 368, 369, 371, 373, 379, 381, 382, 383, 384, 385, 386, 387, 392, 393, 395, 397, 398, 399, 400, 401, 407, 409, 410, 411, 412, 413, 415, 416, 417, 418, 419, 420, 421, 422, 423, 426, 427, 429, 430, 431, 432, 433, 434, 437, 438, 439, 445, 447, 448, 449, 451, 453, 454, 455, 456, 457, 463, 465, 466, 467, 468, 469, 471, 472, 473, 474, 475, 476, 477, 478, 479, 483, 484, 485, 486, 487, 488, 489, 490, 491, 492, 493, 494, 497, 498, 499, 501, 502, 503, 504, 509, 511, 512, 513, 515, 517, 518, 519, 520, 521, 527, 529, 530, 531, 532, 533, 534, 535, 536, 537, 539, 540, 541, 543, 544, 545, 546, 547, 548, 549, 550, 551, 552, 555, 556, 557, 563, 565, 566, 567, 569, 571, 572, 573, 574, 575, 581, 583, 584, 585, 586, 587, 589, 590, 591, 593, 594, 595, 596, 597, 599, 600, 601, 602, 605, 606, 607, 608, 610, 611, 612, 613, 615, 616, 617, 618, 620, 621, 623, 624, 625, 626, 627, 628, 629, 630, 631, 634, 635, 638, 639, 641, 642, 643, 644, 645, 646, 647, 648, 651, 652, 653, 655, 656, 657, 658, 659, 660, 661, 662, 663, 664, 665, 666, 667, 668, 669, 670, 671, 672, 673, 675, 676, 677, 678, 679, 681, 682, 683, 684, 685, 686, 687, 688, 689, 690, 691, 692, 693, 694, 695, 696, 697, 700, 701, 702, 704, 705, 706, 707, 709, 710, 711, 712, 713, 715, 716, 717, 718, 719, 721, 722, 723, 724, 725, 726, 727, 728, 729, 730, 731, 732, 733, 734, 735, 736, 737, 738, 739, 740, 741, 743, 744, 745, 747, 748, 749, 750, 751, 752, 753, 754, 755, 756, 757, 758, 759, 760, 761, 762, 763, 764, 765, 766, 767, 768, 769, 770, 771, 773, 776, 777, 778, 779, 780, 781, 782, 783, 784, 785, 786, 787, 788, 789, 790, 791, 792, 793, 794, 795, 796, 801, 802, 803, 804, 805, 806, 807, 808, 809, 810, 811, 812, 852, 853, 874, 892, 893, 915, 917, 918, 919, 921, 939, 946, 998, 1000, 1001, 1002, 1007, 1008, 1014, 1015, 1054, 1055, 1056, 1059, 1061, 1063, 1065, 1067, 1069, 1071, 1073, 1075, 1076, 1077, 1078, 1079, 1080, 1081, 1083, 1085, 1089, 1090, 1091, 1092, 1093, 1095, 1096, 1097, 1098, 1099, 1103, 1104, 1106, 1110, 1112, 1113, 1115, 1117, 1118, 1120, 1121, 1127, 1129, 1130, 1131, 1132, 1134, 1137, 1140, 1143, 1146, 1151, 1152, 1153, 1155, 1156, 1158, 1159, 1161, 1165, 1166, 1167, 1168, 1170, 1178, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, 1567, 1568, 1569, 1570, 1571, 1572, 1573, 1574, 1575, 1576, 1577, 1578, 1579, 1580, 1581, 1582, 1583, 1584, 1585, 1586, 1587, 1588, 1589, 1590, 1591, 1592, 1593, 1594, 1595, 1596, 1597, 1598, 1599, 1600, 1601, 1602, 1603, 1604, 1605, 1606, 1607, 1608, 1609, 1610, 1611, 1612, 1613, 1614, 1615, 1616, 1617, 1618, 1619, 1620, 1621, 1622, 1623, 1624, 1625, 1626, 1627, 1628, 1629, 1630, 1631, 1632, 1633, 1634, 1635, 1636, 1637, 1638, 1639, 1640, 1641, 1642, 1643, 1644, 1645, 1646, 1647, 1648, 1649, 1650, 1651, 1652, 1653, 1654, 1655, 1656, 1657, 1658, 1659, 1660, 1661, 1662, 1663, 1664, 1665, 1666, 1667, 1668, 1669, 1670, 1671, 1672, 1673, 1674, 1675, 1676, 1677, 1678, 1679, 1680, 1681, 1682, 1683, 1684, 1685, 1686, 1687, 1688, 1689, 1690, 1691, 1692, 1693, 1694, 1695, 1696, 1697, 1698, 1700, 1701, 1702, 1703, 1704, 1705, 1706, 1707, 1708, 1709, 1710, 1711, 1712, 1713, 1714, 1715, 1716, 1717, 1718, 1719, 1720, 1721, 1722, 1723, 1724, 1725, 1726, 1727, 1728, 1729, 1730, 1731, 1732, 1733, 1734, 1735, 1736, 1737, 1738, 1739, 1740, 1741, 1742, 1743, 1744, 1745, 1746, 1747, 1748, 1749, 1750, 1751, 1752, 1753, 1754, 1755, 1756, 1757, 1758, 1759, 1760, 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 1788, 1789, 1790, 1791, 1792, 1793, 1794, 1795, 1796, 1797, 1798, 1799, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1829, 1830, 1831, 1832, 1833, 1834, 1835, 1836, 1837, 1838, 1839, 1840, 1841, 1842, 1843, 1844, 1845, 1846, 1847, 1848, 1849, 1850, 1851, 1852, 1853, 1854, 1855, 1856, 1857, 1858, 1859, 1860, 1861, 1862, 1863, 1864, 1865, 1866, 1867, 1868, 1869, 1870, 1871, 1872, 1873, 1874, 1875, 1876, 1877, 1878, 1879, 1880, 1881, 1882, 1883, 1884, 1885, 1886, 1887, 1888, 1889, 1890, 1891, 1892, 1893, 1894, 1895, 1896, 1897, 1898, 1899, 1900, 1901, 1902, 1903, 1904, 1905, 1906, 1907, 1908, 1909, 1910, 1911, 1912, 1913, 1914, 1915, 1916, 1917, 1918, 1919, 1920, 1921, 1922, 1923, 1924, 1925, 1926, 1927, 1928, 1929, 1930, 1931, 1932, 1933, 1934, 1935, 1936, 1937, 1938, 1939, 1940, 1941, 1942, 1943, 1944, 1945, 1946, 1947, 1948, 1949, 1950, 1951, 1952, 1953, 1954, 1955, 1956, 1957, 1958, 1959, 1960, 1961, 1962, 1963, 1964, 1965, 1966, 1967, 1968, 1969, 1970, 1971, 1972, 1973, 1974, 1975, 1976, 1977, 1978, 1979, 1980, 1981, 1982, 1983, 1984, 1985, 1986, 1987, 1988, 1989, 1990, 1991, 1992, 1993, 1994, 1995, 1996, 1997, 1998, 1999, 2000, 2001, 2002, 2003, 2004, 2005, 2006, 2007, 2008, 2010, 2011, 2012, 2013, 2014, 2015, 2016, 2017, 2018, 2019, 2020, 2021, 2022, 2023, 2024, 2025, 2026, 2027, 2028, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2068, 2069, 2070, 2071, 2072, 2073, 2074, 2075, 2076, 2077, 2078, 2079, 2080, 2081, 2082, 2083, 2084, 2085, 2086, 2087, 2088, 2089, 2090, 2091, 2092, 2093, 2094, 2095, 2096, 2097, 2098, 2099, 2100, 2101, 2102, 2103, 2104, 2105, 2106, 2107, 2108, 2109, 2111, 2112, 2113, 2114, 2115, 2116, 2117, 2118, 2119, 2121, 2122, 2123, 2124, 2125, 2128, 2129, 2130, 2131, 2132, 2133, 2134, 2135, 2136, 2137, 2138, 2139, 2140, 2143, 2144, 2145, 2146, 2147, 2148, 2149, 2150, 2151, 2152, 2153, 2154, 2155, 2156, 2157, 2158, 2159, 2160, 2161, 2162, 2163, 2164, 2166, 2167, 2168, 2169, 2170, 2171, 2172, 2173, 2174, 2175, 2176, 2177, 2178, 2179, 2180, 2181, 2182, 2183, 2184, 2185, 2186, 2187, 2188, 2189, 2190, 2191, 2192, 2193, 2194, 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2261, 2262, 2263, 2264, 2265, 2266, 2267, 2268, 2269, 2270, 2271, 2272, 2273, 2274, 2275, 2276, 2277, 2278, 2279, 2280, 2281, 2282, 2283, 2284, 2285, 2286, 2288, 2289, 2290, 2291, 2292, 2293, 2294, 2295, 2296, 2297, 2298, 2299, 2300, 2302, 2303, 2304, 2305, 2306, 2307, 2308, 2309, 2310, 2311, 2312, 2313, 2314, 2315, 2316, 2317, 2318, 2319, 2320, 2321, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2349, 2350, 2351, 2352, 2353, 2354, 2355, 2356, 2357, 2358, 2359, 2360, 2361, 2363, 2364, 2365, 2366, 2367, 2368, 2369, 2370, 2371, 2372, 2373, 2374, 2375, 2376, 2377, 2378, 2379, 2380, 2381, 2382, 2383, 2384, 2385, 2386, 2387, 2388, 2389, 2390, 2391, 2392, 2393, 2394, 2395, 2396, 2397, 2398, 2399, 2400, 2401, 2402, 2403, 2404, 2405, 2406, 2407, 2408, 2409, 2410, 2411, 2412, 2413, 2414, 2415, 2416, 2417, 2418, 2419, 2420, 2421, 2422, 2423, 2424, 2425, 2426, 2427, 2428, 2429, 2430, 2431, 2433, 2434, 2435, 2436, 2437, 2438, 2439, 2440, 2441, 2442, 2443, 2444, 2445, 2446, 2447, 2448, 2449, 2450, 2451, 2452, 2453, 2454, 2455, 2456, 2457, 2458, 2459, 2460, 2461, 2462, 2463, 2464, 2465, 2466, 2467, 2468, 2469, 2470, 2471, 2472, 2473, 2474, 2475, 2476, 2477, 2478, 2479, 2480, 2481, 2482, 2483, 2484, 2485, 2486, 2487, 2488, 2489, 2490, 2491, 2492, 2493, 2494, 2495, 2496, 2497, 2498, 2505, 2506, 2509, 2510, 2514.

Preferred combinations of $A^1$, $A^2$, $G^1$, $A^3$, $A^4$ and $G^2$ in the formula (I) were explained above. As another method of arrangement, they can be summarized also as the following combinations 1) through 41). Not only do these combinations indicate preferred relationships among $A^1$, $A^2$, $G^1$, $A^3$, $A^4$ and $G^2$, but also the partial structures per se comprised of these as a whole are preferred substituents in the pyrrolopyrimidinone derivatives of the present invention.

1) In the formula (I), when $A^1$ is —$(CH_2)_2$—, $A^1$-$A^2$-$G^1$ links in the form of $A^1$-NH—C(=O)-$G^1$, and $G^1$ is a phenylene group, the phenylene group as $G^1$ is preferably substituted with one or more substituents selected from those exemplified for the preferred substituents of the substituted aromatic hydrocarbon group having 6 to 14 carbon atoms of $G^1$.

2) In the formula (I), when $A^1$ is —$(CH_2)_2$—, $A^1$-$A^2$-$G^1$ links in the form of $A^1$-NH—C(=O)-$G^1$, $G^1$ is a phenylene group, and the phenylene group as $G^1$ is not substituted, it is preferable that $A^3$-$A^4$-$G^2$ as a whole is a group other than a hydrogen atom.

3) In the formula (I), when $A^1$ is —$(CH_2)_2$—, $A^1$-$A^2$-$G^1$ links in the form of $A^1$-NH—C(=O)-$G^1$, $G^1$ is preferably a divalent group derived from a monocyclic or bicyclic $C_3$-$C_9$ aromatic heterocyclic compound having 1 to 3, preferably 1 or 2, atoms selected from the group consisting of an oxygen atom, a nitrogen atom and a sulfur atom, in the ring.

4) In the formula (I), when $A^1$ is —$(CH_2)_2$— and $A^1$-$A^2$-$G^1$ links in the form of $A^1$-NH—C(=O)-$G^1$, $G^1$ is preferably a divalent group derived from a monocyclic or bicyclic $C_2$-$C_9$ aromatic heterocyclic compound having 1 to 3, preferably 1 or 2 atoms selected from the group consisting of an oxygen atom, a nitrogen atom and a sulfur atom, in the ring. However, the divalent group derived from the aromatic heterocyclic compound as $G^1$ is more preferably substituted with one or more substituents selected from the group consisting of substituents defined as preferred examples for the heterocyclic compound having 1 to 4 atoms selected from the group consisting of an oxygen atom, a nitrogen atom and a sulfur atom, in the ring.

5) In the formula (I), when $A^1$ is —$(CH_2)_2$— and $A^1$-$A^2$-$G^1$ links in the form of $A^1$-NH—C(=O)-$G^1$, $G^1$ is preferably a divalent group derived from a monocyclic or bicyclic $C_2$-$C_9$ aromatic heterocyclic compound having 1 to 3, preferably 1 or 2 atoms selected from the group consisting of an oxygen atom, a nitrogen atom and a sulfur atom, in the ring. However, when the divalent group derived from the aromatic heterocyclic compound as $G^1$ is not substituted, it is more preferable that $A^3$-$A^4$-$G^2$ as a whole is a group other than a hydrogen atom.

6) In the formula (I), when $A^1$ is —$(CH_2)_2$—, $A^1$-$A^2$-$G^1$ links in the form of $A^1$-NH—C(=O)-$G^1$, and $G^1$ represents a single bond, it is more preferable that $A^3$-$A^4$-$G^2$ as a whole is a acyclic aliphatic hydrocarbon group having 1 to 6 carbon atoms or a cycloalkylalkyl group consisting of a acyclic aliphatic hydrocarbon group having 1 to 6 carbon atoms and an alicyclic hydrocarbon group having 3 to 8 carbon atoms.

7) In the formula (I), when $A^1$ is —$(CH_2)_2$—, $A^1$-$A^2$-$G^1$ links in the form of $A^1$-NH—C(=O)-$G^1$, and $G^1$ represents a single bond, $A^3$-$A^4$-$G^2$ is preferably a acyclic aliphatic hydrocarbon group having 1 to 6 carbon atoms or a cycloalkylalkyl group consisting of a acyclic aliphatic hydrocarbon group having 1 to 6 carbon atoms and an alicyclic hydrocarbon group having 3 to 8 carbon atoms as a whole, but a acyclic aliphatic hydrocarbon group having 1 to 6 carbon atoms as $A^3$-$A^4$-$G^2$ is more preferably substituted with one or more substituents selected from those exemplified for the preferred substituents of the substituted acyclic aliphatic hydrocarbon group having 1 to 10 carbon atoms of $A^3$. Also, in a cycloalkylalkyl group consisting of a acyclic aliphatic hydrocarbon group having 1 to 6 carbon atoms and an alicyclic hydrocarbon group having 3 to 8 carbon atoms as $A^3$-$A^4$-$G^2$, a acyclic aliphatic hydrocarbon group portion having 1 to 6 carbon atoms is further preferably substituted with one or more substituents selected from those exemplified for the preferred substituents of the substituted aliphatic hydrocarbon group having 1 to 10 carbon atoms of $A^3$, or an alicyclic hydrocarbon group portion having 3 to 8 carbon atoms is further preferably substituted with one or more substituents selected from those exemplified for the preferred substituents of the substituted alicyclic hydrocarbon group having 3 to 10 carbon atoms of $G^2$ (including a case where both are substituted).

8) In the formula (I), when $A^1$ is —$(CH_2)_2$—, $A^1$-$A^2$-$G^1$ links in the form of $A^1$-NH—C(=O)-$G^1$, and $G^1$ represents a single bond, $A^3$-$A^4$-$G^2$ is preferably an aralkyl group consisting of a acyclic aliphatic hydrocarbon group having 1 to 6 carbon atoms and an aromatic hydrocarbon group having 6 to 10 carbon atoms as a whole.

9) In the formula (I), when $A^1$ is —$(CH_2)_2$—, $A^1$-$A^2$-$G^1$ links in the form of $A^1$-NH—C(=O)-$G^1$, and $G^1$ represents a single bond, $A^3$-$A^4$-$G^2$ is preferably an aralkyl group consisting of a acyclic aliphatic hydrocarbon group having 1 to 6 carbon atoms and an aromatic hydrocarbon group having 6 to 10 carbon atoms as a whole, but in an aralkyl group as $A^3$-$A^4$-$G^2$, a acyclic aliphatic hydrocarbon group portion having 1 to 6 carbon atoms is further preferably substituted with one or more substituents selected from those exemplified for the preferred substituents of the substituted acyclic aliphatic hydrocarbon group having 1 to 10 carbon atoms of $A^3$, or an aromatic hydrocarbon group portion having 6 to 10 carbon atoms is further preferably substituted with one or more substituents selected from those exemplified for the preferred substituents of the substituted aromatic hydrocarbon group having 6 to 14 carbon atoms of $G^2$ (including a case where both are substituted).

10) In the formula (I), when $A^1$ is —$(CH_2)_2$—, $A^1$-$A^2$-$G^1$ links in the form of $A^1$-NH—C(=O)-$G^1$, and $G^1$ represents a single bond, $A^3$-$A^4$-$G^2$ is preferably a heterocyclic substituted alkyl group consisting of a acyclic aliphatic hydrocarbon group having 1 to 6 carbon atoms and a heterocyclic group having 1 to 4 atoms selected from the group consisting of an oxygen atom, a nitrogen atom and a sulfur atom, in the ring as a whole.

11) In the formula (I), when $A^1$ is —$(CH_2)_2$—, $A^1$-$A^2$-$G^1$ links in the form of $A^1$-NH—C(=O)-$G^1$, and $G^1$ represents a single bond, $A^3$-$A^4$-$G^2$ is preferably a heterocyclic substituted alkyl group consisting of a acyclic aliphatic hydrocarbon group having 1 to 6 carbon atoms and a heterocyclic group having 1 to 4 atoms selected from the group consisting of an oxygen atom, a nitrogen atom and a sulfur atom, in the ring as a whole. However, in the heterocyclic substituted alkyl group as $A^3$-$A^4$-$G^2$, a acyclic aliphatic hydrocarbon group portion having 1 to 6 carbon atoms is further preferably substituted with one or more substituents selected from those exemplified for the preferred substituents of the substituted acyclic aliphatic hydrocarbon group having 1 to 10 carbon atoms of $A^3$, or a heterocyclic portion is further preferably substituted with one or more substituents selected from those exemplified for the preferred substituents of the heterocyclic group having 1 to 4 atoms selected from the group consisting of an oxygen atom, a nitrogen atom and a sulfur atom, in the ring, of $G^2$ (including a case where both are substituted).

12) In the formula (I), when $A^1$ is —$(CH_2)_2$—, $A^1$-$A^2$-$G^1$ links in the form of $A^1$-NH—C(=O)-$G^1$, and $G^1$ is a phenylene group, the phenylene group as $G^1$ is preferably substituted with one or more substituents selected from those exemplified for the preferred substituents of the substituted aromatic hydrocarbon group having 6 to 14 carbon atoms of $G^1$.

13) In the formula (I), when $A^1$ is —$(CH_2)_2$—, $A^1$-$A^2$-$G^1$ links in the form of $A^1$-NH—C(=O)—NH-$G^1$, $G^1$ is a phenylene group, and the phenylene group as $G^1$ is not substituted, it is preferable that $A^3$-$A^4$-$G^2$ as a whole is a group other than a hydrogen atom.

14) In the formula (I), when $A^1$ is —$(CH_2)$— and $A^1$-$A^2$-$G^1$ links in the form of $A^1$-NH—C(=O)—NH-$G^1$, $G^1$ is preferably a divalent group derived from a monocyclic or bicyclic $C_3$-$C_9$ aromatic heterocyclic compound having 1 to 3, preferably 1 or 2, atoms selected from the group consisting of an oxygen atom, a nitrogen atom and a sulfur atom, in the ring.

15) In the formula (I), when $A^1$ is —$(CH_2)$— and $A^1$-$A^2$-$G^1$ links in the form of $A^1$-NH—C(=O)—NH-$G^1$, $G^1$ is preferably a divalent group derived from a monocyclic or bicyclic $C_2$-$C_9$ aromatic heterocyclic compound having 1 to 3, preferably 1 or 2 atoms selected from the group consisting of an oxygen atom, a nitrogen atom and a sulfur atom, in the ring. However, the divalent group derived from the aromatic heterocyclic compound as $G^1$ is more preferably substituted with one or more substituents selected from the group consisting of substituents defined as preferred examples for the heterocyclic compound having 1 to 4 atoms selected from the group consisting of an oxygen atom, a nitrogen atom and a sulfur atom, in the ring.

16) In the formula (I), when $A^1$ is —$(CH_2)_2$— and $A^1$-$A^2$-$G^1$ links in the form of $A^1$-NH—C(=O)—NH-$G^1$, $G^1$ is preferably a divalent group derived from a monocyclic or bicyclic $C_2$-$C_9$ aromatic heterocyclic compound having 1 to 3, preferably 1 or 2 atoms selected from the group consisting of an oxygen atom, a nitrogen atom and a sulfur atom, in the ring. However, when the divalent group derived from the aromatic heterocyclic compound as $G^1$ is not substituted, it is more preferable that $A^3$-$A^4$-$G^2$ as a whole is a group other than a hydrogen atom.

17) In the formula (I), when $A^1$ is —$(CH_2)_2$—, $A^1$-$A^2$-$G^1$ links in the form of $A^1$-NH—C(=O)—NH-$G^1$, and $G^1$ represents a single bond, it is more preferable that $A^3$-$A^4$-$G^2$ as a whole is a cycloalkylalkyl group consisting of a acyclic aliphatic hydrocarbon group having 1 to 6 carbon atoms and an alicyclic hydrocarbon group having 3 to 8 carbon atoms.

18) In the formula (I), when $A^1$ is —$(CH_2)_2$—, $A^1$-$A^2$-$G^1$ links in the form of $A^1$-NH—C(=O)—NH-$G^1$, and $G^1$ represents a single bond, it is more preferable that $A^3$-$A^4$-$G^2$ as a whole is a cycloalkylalkyl group consisting of a acyclic aliphatic hydrocarbon group having 1 to 6 carbon atoms and an alicyclic hydrocarbon group having 3 to 8 carbon atoms. However, in the cycloalkylalkyl group as $A^3$-$A^4$-$G^2$, a acyclic aliphatic hydrocarbon group portion having 1 to 6 carbon atoms is more preferably substituted with one or more substituents selected from those exemplified for the preferred substituents of the substituted acyclic aliphatic hydrocarbon group having 1 to 10 carbon atoms of $A^3$, or an alicyclic hydrocarbon group portion having 3 to 8 carbon atoms is further preferably substituted with one or more substituents selected from those exemplified for the preferred substituents of the substituted alicyclic hydrocarbon group having 3 to 10 carbon atoms of $G^2$ (including a case where both are substituted).

19) In the formula (I), when $A^1$ is —$(CH_2)_2$—, $A^1$-$A^2$-$G^1$ links in the form of $A^1$-NH—C(=O)—NH-$G^1$, and $G^1$ represents a single bond, it is more preferable that $A^3$-$A^4$-$G^2$ as a whole is an aralkyl group consisting of a acyclic aliphatic hydrocarbon group having 1 to 6 carbon atoms and an aromatic hydrocarbon group having 6 to 10 carbon atoms.

20) In the formula (I), when $A^1$ is —$(CH_2)_2$—, $A^1$-$A^2$-$G^1$ links in the form of $A^1$-NH—C(=O)—NH-$G^1$, and $G^1$ represents a single bond, it is more preferable that $A^3$-$A^4$-$G^2$ as a whole is an aralkyl group consisting of a acyclic aliphatic hydrocarbon group having 1 to 6 carbon atoms and an aromatic hydrocarbon group having 6 to 14 carbon atoms. However, in the aralkyl group as $A^3$-$A^4$-$G^2$, a acyclic aliphatic hydrocarbon group portion having 1 to 6 carbon atoms is more preferably substituted with one or more substituents selected from those exemplified for the preferred substituents of the substituted acyclic aliphatic hydrocarbon group having 1 to 10 carbon atoms of $A^3$, or an aromatic hydrocarbon group portion having 6 to 10 carbon atoms is further preferably substituted with one or more substituents selected from those exemplified for the preferred substituents of the substituted aromatic hydrocarbon group having 6 to 14 carbon atoms of $G^2$ (including a case where both are substituted).

21) In the formula (I), when $A^1$ is —$(CH_2)_2$—, $A^1$-$A^2$-$G^1$ links in the form of $A^1$-NH—C(=O)—NH-$G^1$, and $G^1$ represents a single bond, it is preferable that $A^3$-$A^4$-$G^2$ as a whole is a heterocyclic substituted alkyl group consisting of a acyclic aliphatic hydrocarbon group having 1 to 6 carbon atoms and a heterocyclic group having 1 to 4 atoms selected from the group consisting of an oxygen atom, a nitrogen atom and a sulfur atom, in the ring.

22) In the formula (I), when $A^1$ is —$(CH_2)_2$—, $A^1$-$A^2$-$G^1$ links in the form of $A^1$-NH—C(=O)—NH-$G^1$, and $G^1$ represents a single bond, it is preferable that $A^3$-$A^4$-$G^2$ as a whole is a heterocyclic substituted alkyl group consisting of a acyclic aliphatic hydrocarbon group having 1 to 6 carbon atoms and a heterocyclic group having 1 to 4 atoms selected from the group consisting of an oxygen atom, a nitrogen atom and a sulfur atom, in the ring. However, in the heterocyclic substituted alkyl group as $A^3$-$A^4$-$G^2$, a acyclic aliphatic hydrocarbon group portion having 1 to 6 carbon atoms is further preferably substituted with one or more substituents selected from those exemplified for the preferred substituents of the substituted acyclic aliphatic hydrocarbon group having 1 to 10 carbon atoms of $A^3$, or a heterocyclic group portion is further preferably substituted with one or more substituents selected from those exemplified for the preferred substituents of the heterocyclic group having 1 to 4 atoms selected from the group consisting of an oxygen atom, a nitrogen atom and a sulfur atom, in the ring, of $G^2$ (including a case where both are substituted).

23) In the formula (I), when $A^1$ is —$(CH_2)_2$—, $A^1$-$A^2$-$G^1$ links in the form of $A^1$-NH-$G^1$, and $G^1$ is a phenylene group, the phenylene group as $G^1$ is preferably substituted with one or more substituents selected from those exemplified for the preferred substituents of the substituted aromatic hydrocarbon group having 6 to 14 carbon atoms of $G^1$.

24) In the formula (I), when $A^1$ is —$(CH_2)_2$—, $A^1$-$A^2$-$G^1$ links in the form of $A^1$-NH-$G^1$, $G^1$ is a phenylene group, and the phenylene group as $G^1$ is not substituted, it is preferable that $A^3$-$A^4$-$G^2$ as a whole is a group other than a hydrogen atom.

25) In the formula (I), when $A^1$ is —$(CH_2)_2$—, $A^1$-$A^2$-$G^1$ links in the form of $A^1$-NH-$G^1$, and $G^1$ is a divalent group derived from a monocyclic or bicyclic $C_2$-$C_9$ aromatic heterocyclic compound having 1 to 3 atoms selected from the group consisting of an oxygen atom, a nitrogen atom and a sulfur atom, in the ring, the aromatic heterocyclic group is preferably substituted with one or more substituents selected from the group consisting of substituents defined as preferred examples for the heterocyclic group having 1 to 4 atoms selected from the group consisting of an oxygen atom, a nitrogen atom and a sulfur atom, in the ring.

26) In the formula (I), when $A^1$ is —$(CH_2)_2$—, $A^1$-$A^2$-$G^1$ links in the form of $A^1$-NH-$G^1$, $G^1$ is a divalent group derived from a monocyclic or bicyclic $C_2$-$C_9$ aromatic heterocyclic compound having 1 to 3 atoms selected from the group consisting of an oxygen atom, a nitrogen atom and a sulfur atom, in the ring, and the aromatic heterocyclic compound is not substituted, it is more preferable that $A^3$-$A^4$-$G^2$ as a whole is a group other than a hydrogen atom.

27) In the formula (I), when $A^1$ is —$(CH_2)_2$— and $A^1$-$A^2$-$G^1$ links in the form of $A^1$-C(=O)-$G^1$, $G^1$ is preferably a divalent group derived from a monocyclic $C_2$-$C_9$ heterocyclic compound having 1 or 2 atoms selected from the group consisting of an oxygen atom, a nitrogen atom and a sulfur atom, in the ring, such as pyrrolidine, piperidine, morpholine, thiomorpholine, homopiperidine, homopiperazine, 1,2,3,6-tetrahydropyridine or piperazine, and $G^1$ is bonded with $A^1$-C(=O)— through a nitrogen atom.

28) In the formula (I), when $A^1$ is —$(CH_2)_2$— and $A^1$-$A^2$-$G^1$ links in the form of $A^1$-C(=O)-$G^1$, $G^1$ is a preferably divalent group derived from a monocyclic $C_2$-$C_9$ heterocyclic compound having 1 or 2 atoms selected from an oxygen atom, a nitrogen atom and a sulfur atom, in the ring, such as pyrrolidine, piperidine, morpholine, thiomorpholine, homopiperidine, homopiperazine, 1,2,3,6-tetrahydropyridine or piperazine, and $G^1$ is preferably bonded with $A^1$-C(=O)— through a nitrogen atom. However, the divalent group derived from the monocyclic $C_2$-$C_9$ heterocyclic compound having 1 or 2 atoms selected from an oxygen atom, a nitrogen atom and a sulfur atom, in the ring as $G^1$ is more preferably substituted with one or more substituents selected from the group consisting of substituents defined as proffered examples for the heterocyclic group having 1 to 4 atoms selected from the group consisting of an oxygen atom, a nitrogen atom and a sulfur atom on the substituted ring of $G^1$.

29) In the formula (I), when $A^1$ is —$(CH_2)_2$— and $A^1$-$A^2$-$G^1$ links in the form of $A^1$-C(=O)-$G^1$, $G^1$ is a preferably divalent group derived from a monocyclic $C_2$-$C_9$ heterocyclic compound having 1 or 2 atoms selected from an oxygen atom, a nitrogen atom and a sulfur atom, in the ring, such as pyrrolidine, piperidine, morpholine, thiomorpholine, homopiperidine, homopiperazine, 1,2,3,6-tetrahydropyridine or piperazine, and $G^1$ is preferably bonded with $A^1$-C(=O)— through a nitrogen atom. However, when the divalent group derived from the monocyclic $C_2$-$C_9$ heterocyclic compound having 1 or 2 atoms selected from an oxygen atom, a nitrogen atom and a sulfur atom, in the ring as $G^1$ is not substituted, it is more preferable that $A^3$-$A^4$-$G^2$ as a whole is a group other than a hydrogen atom.

30) In the formula (I), when $A^1$ is —$(CH_2)_3$—, $A^1$-$A^2$-$G^1$ links in the form of $A^1$-C(=O)—NH-$G^1$, and $G^1$ is a phenylene group, the phenylene group as $G^1$ is preferably substituted with one or more substituents selected from those exemplified for the preferred substituents of the substituted aromatic hydrocarbon group having 6 to 14 carbon atoms of $G^1$.

31) In the formula (I), when $A^1$ is —$(CH_2)_2$—, $A^1$-$A^2$-$G^1$ links in the form of $A^1$-C(=O)—NH-$G^1$, $G^1$ is a phenylene group, and the phenylene group as $G^1$ is not substituted, it is preferable that $A^3$-$A^4$-$G^2$ as a whole is a group other than a hydrogen atom.

32) In the formula (I), when $A^1$ is —$(CH_2)_3$— and $A^1$-$A^2$-$G^1$ links in the form of $A^1$-C(=O)—NH-$G^1$, $G^1$ is preferably a divalent group derived from a monocyclic or bicyclic $C_3$-$C_9$ aromatic heterocyclic compound having 1 to 3, preferably 1 or 2, atoms selected from the group consisting of an oxygen atom, a nitrogen atom and a sulfur atom, in the ring.

33) In the formula (I), when $A^1$ is —$(CH_2)_3$— and $A^1$-$A^2$-$G^1$ links in the form of $A^1$-C(=O)—NH-$G^1$, $G^1$ is preferably a divalent group derived from a monocyclic or bicyclic $C_2$-$C_9$ aromatic heterocyclic compound having 1 to 3, preferably 1 or 2 atoms selected from the group consisting of an oxygen atom, a nitrogen atom and a sulfur atom, in the ring. However, the divalent group derived from the aromatic heterocyclic compound as $G^1$ is more preferably substituted with one or more substituents selected from the group consisting of substituents defined as preferred examples for the heterocyclic compound having 1 to 4 atoms selected from the group consisting of an oxygen atom, a nitrogen atom and a sulfur atom, in the ring.

34) In the formula (I), when $A^1$ is —$(CH_2)_3$— and $A^1$-$A^2$-$G^1$ links in the form of $A^1$-C(=O)—NH-$G^1$, $G^1$ is preferably a divalent group derived from a monocyclic or bicyclic $C_2$-$C_9$ aromatic heterocyclic compound having 1 to 3, preferably 1 or 2 atoms selected from the group consisting of an oxygen atom, a nitrogen atom and a sulfur atom, in the ring. However, when the divalent group derived from the aromatic heterocyclic compound as $G^1$ is not substituted, it is more preferable that $A^3$-$A^4$-$G^2$ as a whole is a group other than a hydrogen atom.

35) In the formula (I), when $A^1$ is —$(CH_2)_3$—, $A^1$-$A^2$-$G^1$ links in the form of $A^1$-C(=O)—NH-$G^1$, and $G^1$ represents a single bond, it is more preferable that $A^3$-$A^4$-$G^2$ as a whole is a cycloalkylalkyl group consisting of a acyclic aliphatic hydrocarbon group having 1 to 6 carbon atoms and an alicyclic hydrocarbon group having 3 to 8 carbon atoms.

36) In the formula (I), when $A^1$ is —$(CH_2)_3$—, $A^1$-$A^2$-$G^1$ links in the form of $A^1$-C(=O)—NH-$G^1$, and $G^1$ represents a single bond, it is more preferable that $A^3$-$A^4$-$G^2$ as a whole is a cycloalkylalkyl group consisting of a acyclic aliphatic hydrocarbon group having 1 to 6 carbon atoms and an alicyclic hydrocarbon group having 3 to 8 carbon atoms. However, in the cycloalkylalkyl group as $A^3$-$A^4$-$G^2$, a acyclic aliphatic hydrocarbon group portion having 1 to 6 carbon atoms is more preferably substituted with one or more substituents selected from those exemplified for the preferred substituents of the substituted acyclic aliphatic hydrocarbon group having 1 to 10 carbon atoms of $A^3$, or an alicyclic hydrocarbon group portion having 3 to 8 carbon atoms is further preferably substituted with one or more substituents selected from those exemplified for the preferred substituents of the substituted alicyclic hydrocarbon group having 3 to 10 carbon atoms of $G^2$ (including a case where the both are substituted).

37) In the formula (I), when $A^1$ is —$(CH_2)_3$—, $A^1$-$A^2$-$G^1$ links in the form of $A^1$-C(=O)—NH-$G^1$, and $G^1$ represents a single bond, it is more preferable that $A^3$-$A^4$-$G^2$ as a whole is an aralkyl group consisting of a acyclic aliphatic hydrocarbon group having 1 to 6 carbon atoms and an aromatic hydrocarbon group having 6 to 14 carbon atoms.

38) In the formula (I), when $A^1$ is —$(CH_2)_3$—, $A^1$-$A^2$-$G^1$ links in the form of $A^1$-C(=O)—NH-$G^1$, and $G^1$ represents a single bond, it is more preferable that $A^3$-$A^4$-$G^2$ as a whole is an aralkyl group consisting of a acyclic aliphatic hydrocarbon group having 1 to 6 carbon atoms and an aromatic hydrocarbon group having 6 to 10 carbon atoms. However, in the aralkyl group as $A^3$-$A^4$-$G^2$, a acyclic aliphatic hydrocarbon group portion having 1 to 6 carbon atoms is more preferably substituted with one or more substituents selected from those exemplified for the preferred substituents of the substituted acyclic aliphatic hydrocarbon group having 1 to 10 carbon atoms of $A^3$, or an aromatic hydrocarbon group portion having 6 to 10 carbon atoms is further preferably substituted with one or more substituents selected from those exemplified for the preferred substituents of the substituted aromatic hydrocarbon group having 6 to 14 carbon atoms of $G^2$ (including a case where both are substituted).

39) In the formula (I), when $A^1$ is —$(CH_2)_3$—, $A^1$-$A^2$-$G^1$ links in the form of $A^1$-C(=O)—NH-$G^1$, and $G^1$ represents a single bond, it is preferable that $A^3$-$A^4$-$G^2$ as a whole is a heterocyclic substituted alkyl group consisting of a acyclic aliphatic hydrocarbon group having 1 to 6 carbon atoms and a heterocyclic group having 1 to 4 atoms selected from the group consisting of an oxygen atom, a nitrogen atom and a sulfur atom, in the ring.

40) In the formula (I), when $A^1$ is —$(CH_2)_3$—, $A^1$-$A^2$-$G^1$ links in the form of $A^1$-C(=O)—NH-$G^1$, and $G^1$ represents a single bond, it is preferable that $A^3$-$A^4$-$G^2$ as a whole is a heterocyclic substituted alkyl group consisting of a acyclic aliphatic hydrocarbon group having 1 to 6 carbon atoms and a heterocyclic group having 1 to 4 atoms selected from the group consisting of an oxygen atom, a nitrogen atom and a sulfur atom, in the ring. However, in the heterocyclic substituted alkyl group as $A^3$-$A^4$-$G^2$, a acyclic aliphatic hydrocarbon group portion having 1 to 6 carbon atoms is further preferably substituted with one or more substituents selected from those exemplified for the preferred substituents of the substituted acyclic aliphatic hydrocarbon group having 1 to 10 carbon atoms of $A^3$, or a heterocyclic group portion is further preferably substituted with one or more substituents selected from those exemplified for the preferred substituents of the heterocyclic group having 1 to 4 atoms selected from the group consisting of an oxygen atom, a nitrogen atom and a sulfur atom, in the ring, of $G^2$ (including a case where both are substituted).

41) In the formula (I), when all of $A^1$, $A^2$, $G^1$, $A^3$, and $A^4$ represent a single bond, $G^2$ is preferably a hydrogen atom or a acyclic aliphatic hydrocarbon group having 1 to 6 carbon atoms.

Also, the preferred combinations of X, $A^1$, $A^2$, $G^1$, $A^3$, $A^4$ and $G^2$ in formula (I) as described in above 1) through 41) are more preferably combined with a preferred group represented by $R^2$-$A^5$-, exemplified as preferred combinations of R and $A^5$, that is $R^2$-$A^5$- group in which $A^5$ is a single bond and $R^2$ is a substituted or unsubstituted monocyclic $C_3$-$C_5$ aromatic heterocyclic group having 1 or 2 atoms selected from the group consisting of an oxygen atom, a nitrogen atom and a sulfur atom, in the ring, or $R^2$-$A^5$- group in which $R^2$ is a substituted or unsubstituted aliphatic hydrocarbon group, and with a preferred group represented by $R^3$-$A^6$-, exemplified as preferred combinations of $R^3$ and $A^6$.

The pyrrolopyrimidinone derivative of the formula (I) has tautomeric forms represented by the following formula (III):

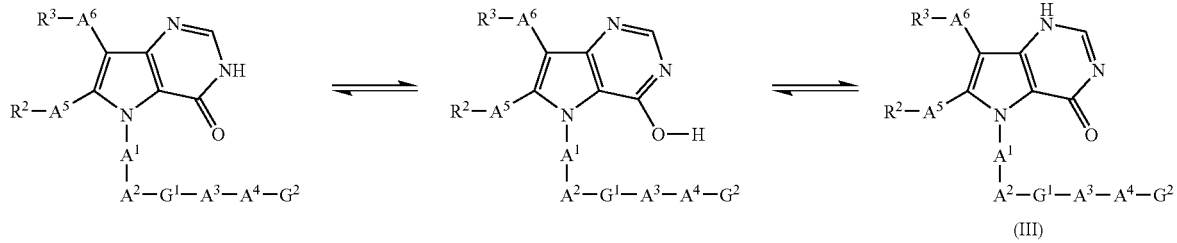

[wherein $A^1$, $A^2$, $A^3$, $A^4$, $A^5$, $A^6$, $G^1$, $G^2$, $R^2$, and $R^3$ are the same as those defined above in the formula (I).]

However, needless to say all such tautomeric forms are within the scope of the present invention.

When one or more asymmetric structures exist on atoms constituting molecules of the pyrrolopyrimidinone derivative formula (I), optically active forms of the respective asymmetric structures and their mixtures combined in an arbitrary ratio are also within the scope of the present invention.

When there exist stereochemical isomers of molecules of the pyrrolopyrimidinone derivative of formula (I), the stereochemical isomers and their combinations in any are also within the scope of the present invention.

The pyrrolopyrimidinone derivative of the formula (I) may have a basic group in its molecules. In this case, if necessary, it can be converted into pharmaceutically acceptable acid addition salts. Such acids include inorganic acids such as hydrochloric acid, hydrobromic acid, sulfuric acid, phosphoric acid, and carbonic acid; or organic acids such as acetic acid, citric acid, malic acid, oxalic acid, tartaric acid, lactic acid, maleic acid, fumaric acid, and methanesulfonic acid.

The pyrrolopyrimidinone derivative of formula (I) may have an acidic group in its molecules. In this case, when required, the acidic group may be converted into pharmaceutically acceptable salts, including non-toxic cation salts, exemplified by alkali metal ions such as $Na^+$ or $K^+$, alkaline earth metal ions such as $Mg^{2+}$ or $Ca^{2+}$, metal ions such as $Al^{3+}$ or $Zn^{2+}$, ammonia, and salts with an organic base such as triethylamine, ethylenediamine, propanediamine, pyrrolidine, piperidine, piperazine, pyridine, lysine, choline, ethanolamine, N,N-dimethylethanolamine, 4-hydroxypiperidine, glucosamine, or N-methylglucamine.

In the formula (II), $A^1$, $A^2$, $A^3$, $A^4$, $A^5$, $A^6$, $G^1$, $G^2$, $R^2$, and $R^3$ are the same as those defined above in the formula (I), and examples thereof include the same as those exemplified in the formula (I), respectively. Also preferred examples of $A^1$, $A^2$, $A^3$, $A^4$, $A^5$, $A^6$, $G^1$, $G^2$, $R^2$ and $R^3$ and preferred combinations of them are the same as those described for the pyrrolopyrimidinone derivative of the present invention represented in the formula (I) except those being obstacle on the chemical reaction in both of the reaction from the pyrrolopyrimidine derivative of the present invention represented by the formula (I) to the pyrrolopyrimidinone derivative of the present invention represented by the formula (I), and the reaction from the pyrrolopyrimidine derivative represented by the formula (II) to the pyrrolopyrimidinone derivative of the present invention represented by the formula (I).

In the formula (II), $X^1$ represents a chlorine atom, a bromine atom, an iodine atom, a $C_2$-$C_{10}$ acylthio group, a $C_2$-$C_8$ alkoxymethylthio group, a $C_1$-$C_8$ alkyl group or a $C_1$-$C_8$ arylsulfonyloxy group, but an explanation will be given below of the case where $X^1$ represents a chlorine atom, a bromine atom, an iodine atom, or a $C_1$-$C_8$ alkyl or arylsulfonyloxy group. When $X^1$ represents a $C_1$-$C_8$ alkyl or arylsulfonyloxy group, examples of the $C_1$-$C_8$ alkyl or arylsulfonyloxy group include sulfonyloxy group consisting optionally substituted $C_1$-$C_8$ alkyl or aryl group and sulfonyl group, such as methylsulfonyloxy, trifluoromethylsulfonyloxy, ethylsulfonyloxy, propylsulfonyloxy, butylsulfonyloxy, t-butylsulfonyloxy, nonafluorobutylsulfonyloxy, phenylsulfonyloxy, p-bromophenylsulfonyloxy, p-toluylsulfonyloxy, benzylsulfonyloxy, α-phenethylsulfonyloxy and β-phenethylsulfonyloxy. Examples of such preferred $X^1$ include a chlorine atom, a bromine atom, an iodine atom and a trifluoromethylsulfonyloxy group. Particularly, a chlorine atom or a trifluoromethylsulfonyloxy group is more preferred.

From the compounds represented by the formula (Ic), the pyrrolopyrimidinone derivative of formula (I) of the present invention can be easily manufactured based on the technical common sense of the person skilled in the art.

In the formula (Ic), $A^1$, $A^2$, $A^3$, $A^4$, $A^5$, $A^6$, $G^1$, $G^2$, $R^2$, and $R^3$ are the same as those defined above in formula (I), and examples thereof include the same as those exemplified in formula (I), respectively.

In the formula (Ic), Q represents a $C_2$-$C_{10}$ acyl group, a $C_2$-$C_{10}$ alkoxymethyl group, or a substituted or unsubstituted benzyl group. When Q represents a $C_2$-$C_{10}$ acyl group, examples of the $C_2$-$C_{10}$ acyl group include acetyl, trifluoroacetyl, propionyl, butyryl, isobutyryl, valeryl, isovaleryl, pivaloyl, hexanoyl, benzoyl, phenylacetyl, phenylpropionyl, cinnamoyl. When Q represents a $C_2$-$C_{10}$ alkoxymethyl, examples of the $C_2$-$C_{10}$ alkoxymethyl group include methoxymethyl, methoxyethoxymethyl, t-butoxymethyl, 2-(trimethylsilyl)ethoxymethyl, benzyloxymethyl, p-methoxybenzyloxymethyl, p-nitrobenzyl-oxymethyl, o-nitrobenzyloxymethyl and 4-methoxyphenoxymethyl. When Q represents a substituted or unsubstituted benzyl group, examples of the substituted or unsubstituted benzyl group include benzyl, p-methoxybenzyl, 3,4-dimethoxybenzyl, o-nitrobenzyl, p-nitrobenzyl and p-cyanobenzyl. Examples of such preferred Q include 2-(trimethylsilyl)ethoxymethyl.

The pyrrolopyrimidinone derivative of the formula (I) can be prepared from pyrrolo[3,2-d]pyrimidine derivative of the formula (II) by the following synthesis (A).

Note that, the pyrrolopyrimidinone derivative represented by the formula (I) is described as (Ia) in the following synthesis and is sometimes expressed as a pyrrolo[3,2-d]pyrimidine derivative.

[Synthesis (A)]

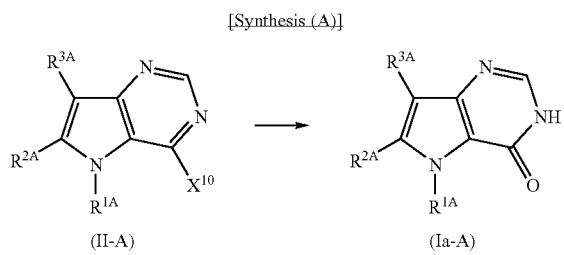

(II-A) → (Ia-A)

[wherein $R^{1A}$ represents a group capable of withstanding a conversion reaction among groups defined to be represented by $A^1$-$A^2$-$G^1$-$A^3$-$A^4$-$G^2$ in formula (I). $R^{2A}$ represents a group capable of withstanding a conversion reaction among groups defined to be represented by $R^2$-$A^5$ in formula (I). $R^{3A}$ represents a group capable of withstanding a conversion reaction among groups defined to be represented by $R^3$-$A^6$ in formula (I). $X^{10}$ represents a chlorine atom, a bromine atom, an iodine atom, or an optionally substituted $C_1$-$C_8$ alkyl or arylsulfonyloxy group.]

In other words, the pyrrolopyrimidinone derivative Ia-A) of the present invention can be synthesized by hydrolysis of the pyrrolo[3,2-d]pyrimidine derivative (II-A). In this hydrolysis reaction, the reaction is performed by using a base such as a sodium hydroxide or a lithium hydroxide and using a solvent such as dioxane, ethanol, 2-propanol, or dimethyl sulfoxide at a temperature in a range of 0° C. to 150° C.

Among the pyrrolo[3,2-d]pyrimidine derivatives of formula (II), a pyrrolo[3,2-d]pyrimidine derivative of formula (II-B) can be synthesized from the pyrrolo[3,2-d]pyrimidine derivative of formula (Ia) by the following synthesis.

[Synthesis (B)]

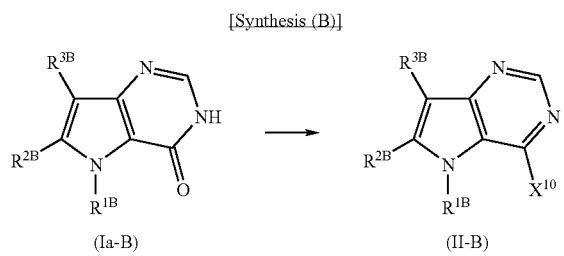

(Ia-B) → (II-B)

[wherein $R^{1B}$ represents a group capable of withstanding a conversion reaction among groups defined to be represented by $A^1$-$A^2$-$G^1$-$A^3$-$A^4$-$G^2$ in formula (I). $R^{2B}$ represents a group capable of withstanding a conversion reaction among groups defined to be represented by $R^2$-$A^5$ in formula (I). $R^{3B}$ represents a group capable of withstanding a conversion reaction among groups defined to be represented by $R^3$-$A^6$ in formula (I). $X^{10}$ has the same meaning as defined above.]

In other words, when $X^{10}$ is a chlorine atom, the pyrrolopyrimidinone derivative (II-B) of the present invention can be synthesized by reacting the pyrrolopyrimidinone derivative (Ia-B) of the present invention with phosphorus oxychloride. In the chlorination using phosphorus oxychloride, the reaction is carried out in a solvent such as acetonitrile under general chlorination reaction conditions, for example, in the presence or absence of a solvent such as triethylamine, 4-dimethylaminopyridine or dimethyl type aniline, at a temperature in a range of 0° C. to 150° C.

Also, when $X^{10}$ is a trifluoromethanesulfonyloxy group, the pyrrolopyrimidinone derivative (II-B) of the present invention can be synthesized by reacting the pyrrolopyrimidinone derivative (Ia-B) of the present invention with trifluoromethanesulfonic anhydride. In trifluoromethane sulfonyloxylation using trifluoromethane sulfonic anhydride, the reaction can be carried out together with pyridine or amines such as triethylamine in the presence or absence of a solvent such as dichloromethane at a temperature in a range of 0° C. to 100° C.

Among the pyrrolo[3,2-d]pyrimidine derivatives of formula (Ia-B), the pyrrolo[3,2-d]pyrimidine derivative of formula (Ia-B1) can be synthesized from the 7-cyanopyrrolo[3,2-d]pyrimidine derivative of the formula (Ia-CN) by the following synthesis (B1).

[Synthesis (B1)]

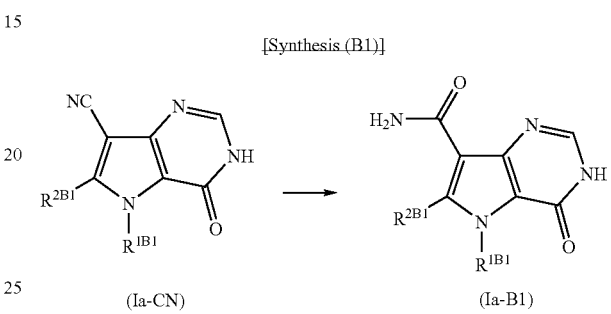

(Ia-CN) → (Ia-B1)

[wherein $R^{1B1}$ represents a group capable of withstanding a conversion reaction among groups defined to be represented by $A^1$-$A^2$-$G^1$-$A^3$-$A^4$-$G^2$ in the formula (I). $R^{2B1}$ represents a group capable of withstanding a conversion reaction among groups defined to be represented by $R^2$-$A^5$ in the formula (I).]

In other words, the pyrrolopyrimidinone derivative (Ia-B1) of the present invention can be synthesized by the hydrolyzing pyrrolo[3,2-d]pyrimidine derivative (Ia-CN). The hydrolysis reaction is carried out using a base such as sodium hydroxide or lithium hydroxide in a solvent such as ethanol, 2-propanol or dimethylsulfoxide in the presence or absence of hydrogen peroxide at a temperature in a range of 0° C. to 100° C.

Among the pyrrolo[3,2-d]pyrimidine derivatives of the formula (Ia-B), a pyrrolo[3,2-d]pyrimidine derivative of the formula (Ia-B2) can be synthesized from the pyrrolo[3,2-d]pyrimidine derivative of the formula (Ia-B1) by the following synthesis (B2).

[Synthesis (B2)]

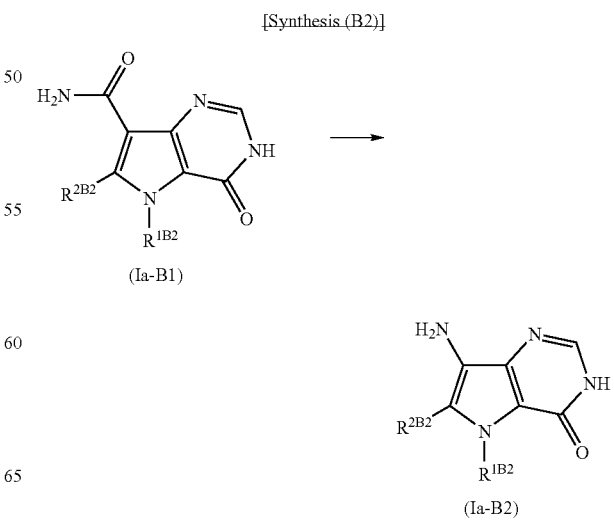

(Ia-B1) → (Ia-B2)

[wherein $R^{1B2}$ represents a group capable of withstanding a conversion reaction among groups defined to be represented by $A^1$-$A^2$-$G^1$-$A^3$-$A^4$-$G^2$ in formula (I). $R^{2B2}$ represents a group capable of withstanding a conversion reaction among groups defined to be represented by $R^2$-$A^5$ in formula (I).]

In other words, the pyrrolopyrimidinone derivative (Ia-B2) of the present invention can be synthesized by performing a Hoffmann rearrangement on the pyrrolopyrimidinone derivative (Ia-B1) of the present invention. The Hoffmann rearrangement is carried out in a solvent such as ethanol, 2-propanol, acetonitrile or water, using a reagent such as sodium hypochlorite, bromine, or benzyltrimethyl ammonium tribromide in the presence or absence of a base such as sodium hydroxide at a temperature of 0° C. to 150° C.

Among the pyrrolo[3,2-d]pyrimidine derivatives of formula (Ia-B), a pyrrolo[3,2-d]pyrimidine derivative of formula (Ia-B3) can be synthesized from the pyrrolo[3,2-d]pyrimidine derivative of formula (Ia-B2) by the following synthesis (B3).

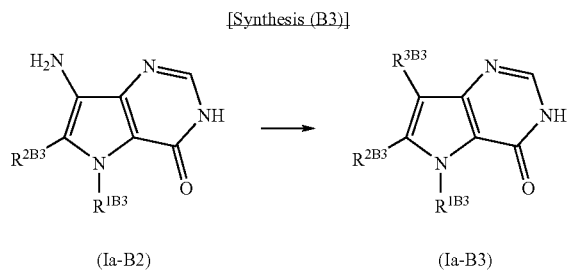

[wherein $R^{1B3}$ represents a group capable of withstanding a conversion reaction among groups defined to be represented by $A^1$-$A^2$-$G^1$-$A^3$-$A^4$-$G^2$ in the formula (I). $R^{2B3}$ represents a group capable of withstanding a conversion reaction among groups defined to be represented by $R^2$-$A^5$ in the formula (I). $R^{3B3}$ represents a fluorine atom, a chlorine atom, a bromine atom or an iodine atom.]

In other words, the pyrrolopyrimidinone derivative (Ia-B3) of the present invention can be synthesized by reacting the pyrrolopyrimidinone derivative (Is-B2) of the present invention with nitrous acid or nitrite ester and performing a Sandmayer reaction. In the Sandmayer reaction using nitrous acid or nitrite ester, reagents, for example, nitrous acid, sodium nitrite, isoamyl nitrite, or t-butyl nitrite is used, and the reaction can be performed in the presence of halogenation reagents, for example hydrofluoric acid or fluoroboric acid for fluorination, for example copper chloride or carbon tetrachloride for chlorination, for example carbon tetrabromide or bromoform for bromination, and diiodomethane or iodine for iodination, in the presence or absence of an acid such as sulfuric acid or hydrochloric acid, in the presence or absence of an acid such as sulfuric acid or hydrochloric acid, by using or without using a solvent such as ethanol, acetonitrile or water, at a temperature in a range of 0° C. to 150° C.

Among the pyrrolo[3,2-d]pyrimidine derivatives of formula (Ia-B), a pyrrolo[3,2-d]pyrimidine derivative of formula (Ia-B4) can be synthesized from the pyrrolo[3,2-d]pyrimidine derivative of formula (Ia-B2) by the following synthesis (B4).

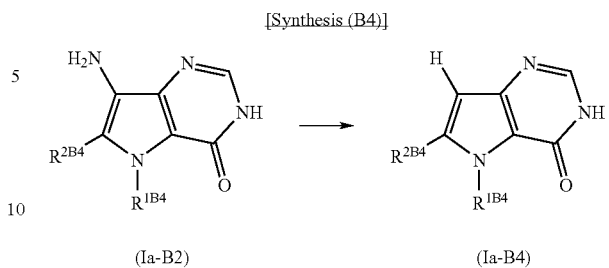

[wherein $R^{1B4}$ represents a group capable of withstanding a conversion reaction among groups defined to be represented by $A^1$-$A^2$-$G^1$-$A^3$-$A^4$-$G^2$ in the formula (I). $R^{2B4}$ represents a group capable of withstanding a conversion reaction among groups defined to be represented by $R^2$-$A^5$ in the formula (I).]

In other words, the pyrrolopyrimidinone derivative (Ia-B4) of the present invention can be synthesized by reacting the pyrrolopyrimidinone derivative (Ia-B2) of the present invention with nitrous acid or nitrite ester. The reaction using nitrous acid or nitrite ester can be performed by using nitrous acid, sodium nitrite, isoamyl nitrite, or t-butyl nitrite as a reagent, in the presence of or in the absence of an acid such as sulfuric acid or hydrochloric acid in the presence of dimethylformamide, tetrahydrofuran, ethanol or water as a solvent, at a temperature in a range of 0° C. to 150° C.

Among the pyrrolo[3,2-d]pyrimidine derivatives of formula (Ia-B), a pyrrolo[3,2-d]pyrimidine derivative of formula (Ia-B5) can be synthesized from the pyrrolo[3,2-d]pyrimidine derivative of formula (Ia-B4) by the following synthesis (B5).

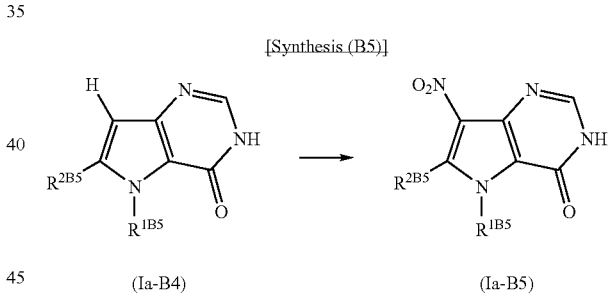

[wherein $R^{1B5}$ represents a group capable of withstanding a conversion reaction among groups defined to be represented by $A^1$-$A^2$-$G^1$-$A^3$-$A^4$-$G^2$ in the formula (I). $R^{2B5}$ represents a group capable of withstanding a conversion reaction among groups defined to be represented by $R^2$-$A^5$ in the formula (I).]

In other words, the pyrrolopyrimidinone derivative (Ia-B5) of the present invention can be synthesized by reacting nitric acid or nitrogen dioxide with the pyrrolopyrimidinone derivative (Ia-B4) of the present invention. The reaction using nitric acid or nitrogen dioxide can be performed by using nitric acid, nitrogen dioxide, cerium ammonium nitrate or sodium nitrite as a reagent, in the presence or absence of sulfuric acid, hydrochloric acid, acetic acid or ozone, in the presence of dichloroethane, dichloromethane, acetonitrile or water as a solvent, at a temperature in a range of 0° C. to 100° C.

Among the pyrrolo[3,2-d]pyrimidine derivatives of formula (Ia-B), a pyrrolo[3,2-d]pyrimidine derivative of formula (Ia-B6) can be synthesized from the pyrrolo[3,2-d]pyrimidine derivative of formula (Ia-B6a) by the following synthesis (B6).

[Synthesis (B6)]

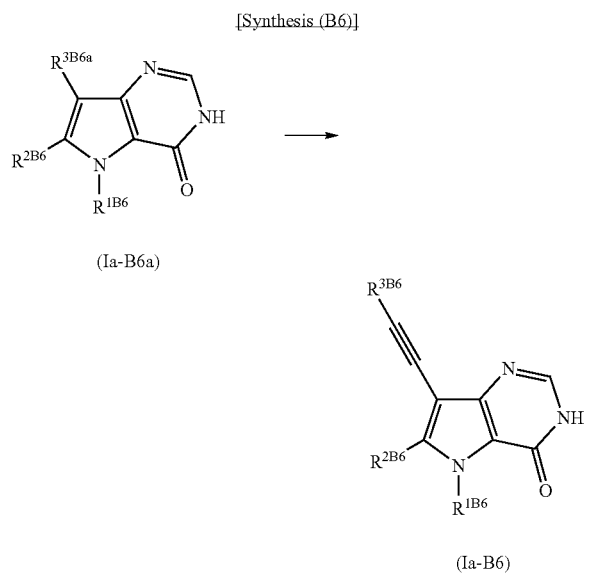

(Ia-B6a)

(Ia-B6)

[wherein $R^{1B6}$ represents a group capable of withstanding a conversion reaction among groups defined to be represented by $A^1$-$A^2$-$G^1$-$A^3$-$A^4$-$G^2$ in the formula (I). $R^{2B6}$ represents a group capable of withstanding a conversion reaction among groups defined to be represented by $R^2$-$A^5$ in the formula (I). $R^{3B6a}$ is a bromine atom or iodine atom, and among groups defined as $R^3$ in the formula (I), $R^{3B6}$ is a substituted or unsubstituted saturated aliphatic hydrocarbon group having 1 to 10 carbon atoms, a substituted or unsubstituted alicyclic hydrocarbon group having 3 to 8 carbon atoms, a substituted or unsubstituted aromatic hydrocarbon group having 6 to 14 carbon atoms, a monocyclic $C_3$-$C_5$ aromatic heterocyclic group having 1 or 2 atoms selected from the group consisting of an oxygen atom, a nitrogen atom and a sulfur atom on the substituted or unsubstituted ring, or a trimethylsilyl.]

In other words, the pyrrolopyrimidinone derivative (Ia-B6) of the present invention can be synthesized by reacting the pyrrolopyrimidinone derivative (Ia-B6a) of the present invention with a terminal alkyne derivative represented by formula $R^{3B6}$—C≡C—H in the presence of a catalytic amount of palladium. The reaction with the terminal alkyne derivative using the catalytic amount of palladium is carried out using the terminal alkyne derivative together with a palladium catalyst, e.g., tetrakis(triphenylphosphine)palladium, chlorobis(triphenylphosphine)palladium, or palladium acetate, in the presence or absence of a ligand, such as triphenylphosphine, tri(o-tolyl)phosphine, or 1,1'-bis(diphenylphosphino)ferrocene, in the presence or absence of a catalytic amount of copper salts, e.g., copper iodide or copper bromide, in the presence of a base such as triethylamine, diethylamine, piperizine or pyrrolidine, using solvents such as tetrahydrofuran, dimethylformamide, and toluene, at a temperature in a range of 0° C. to 150° C.

Among the pyrrolo[3,2-d]pyrimidine derivatives of the formula (Ia-B), a pyrrolo[3,2-d]pyrimidine derivative of formula (Ia-B7) can be prepared from the pyrrolo[3,2-d]pyrimidine derivative of formula (Ia-B7a) by the following synthesis (B7).

[Synthesis (B7)]

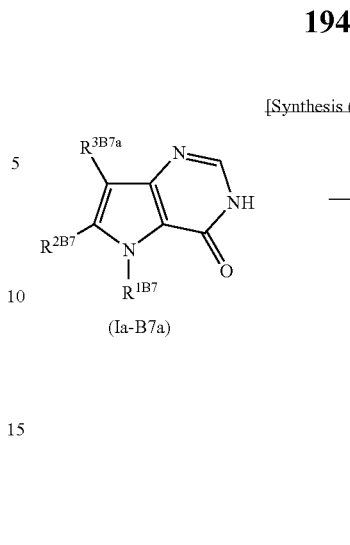

(Ia-B7a)

(Ia-B7)

[wherein $R^{1B7}$ represents a group capable of withstanding a conversion reaction among groups defined to be represented by $A^1$-$A^2$-$G^1$-$A^3$-$A^4$-$G^2$ in the formula (I). $R^{2B7}$ represents a group capable of withstanding a conversion reaction among groups defined to be represented by $R^2$-$A^5$ in the formula (I). $R^{3B7a}$ is a bromine atom or an iodine atom. $R^{3B7}$ is a substituted or unsubstituted aromatic hydrocarbon group having 6 to 14 carbon atoms, or an aromatic heterocyclic group having 1 or 2 atoms selected from the group consisting of an oxygen atom, a nitrogen atom and a sulfur atom on the substituted or unsubstituted ring among groups defined as $R^3$ in the formula (I).]

In other words, the pyrrolopyrimidinone derivative (Ia-B7) of the present invention can be synthesized, in the presence of a catalytic amount of palladium, by adding a boric acid derivative [$R^{3B7}$—B(OR)$_2$, wherein $R^{3B7}$ is the same as defined above in the synthesis (B7), and R represents a hydrogen atom or an alkyl group] to the pyrrolopyrimidinone derivative (Ia-B7a) of the present invention. That is, in the reaction with the boric acid derivative using the catalytic amount of palladium, the reaction can be performed by using, together with the boric acid derivative, a palladium catalyst, for example, chlorobis(triphenylphosphine)palladium, palladium acetate, and tris(dibenzylideneacetone)dipalladiumuchloroform adduct in the presence or absence of a ligand, such as triphenylphosphine, tri(o-tolyl)phosphine, or 1,1'-bis(diphenylphosphino)ferrocene, in the presence of base such as potassium phosphate, sodium carbonate, potassium hydroxide, or sodium ethoxide, using a solvent such as tetrahydrofuran, dimethylformamide, 2-propanol and water, at a temperature in a range of 0° C. to 150° C.

Among the pyrrolo[3,2-d]pyrimidine derivatives of formula (Ia-B), a pyrrolo[3,2-d]pyrimidine derivative of formula (Ia-B8) can be synthesized from the pyrrolo[3,2-d]pyrimidine derivative of formula (Ib-B8a) by the following synthesis (B8).

[Synthesis (B8)]

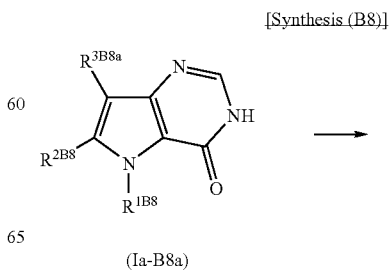

(Ia-B8a)

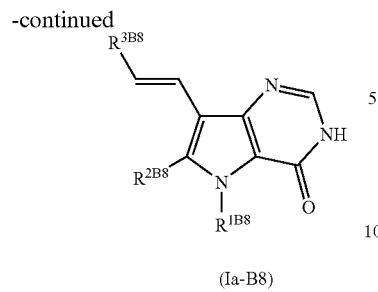

(Ia-B8)

[wherein $R^{1B8}$ represents a group capable of withstanding a conversion reaction among groups defined to be represented by $A^1$-$A^2$-$G^1$-$A^3$-$A^4$-$G^2$ in the formula (I). $R^{2B8}$ represents a group capable of withstanding a conversion reaction among groups defined to be represented by $R^2$-$A^5$ in the formula (I). $R^{3B8a}$ is a bromine atom or an iodine atom, and $R^{3B8}$ is a group defined as $R^3$ in the formula (I).]

In other words, the pyrrolopyrimidinone derivative (Ia-B8) of the present invention can be synthesized by reacting a terminal alkene derivative upon the pyrrolopyrimidinone derivative (Ia-B8a) of the present invention in the presence of a catalytic amount of palladium. That is, in the reaction with a terminal alkene derivative using the catalytic amount of palladium, the reaction can be performed by using, together with the terminal alkene derivative, a palladium catalyst, for example, palladium chloride, palladium acetate, or tris (dibenzylideneacetone)dipalladium-chloroform adduct in the presence or absence of a ligand, such as triphenylphosphine, tri(o-tolyl)phosphine, or 1,1'-bis(diphenylphosphino) ferrocene, in the presence of a base such as a potassium phosphate, potassium carbonate or triethylamine, and using a solvent such as tetrahydrofuran, dimethylformamide or water, at a temperature in a range of 0° C. to 150° C.

Alternatively, the pyrrolopyrimidinone derivative (Ia-B8) of the present invention can also be synthesized by performing a catalytic semi-reduction or hydroboration-protonation on the pyrrolo[3,2-d]pyrimidine derivative (Ia-B6) having an alkynyl group prepared by the Synthesis (B6). For example, the catalytic semi-reduction is performed using a solvent such as methanol, ethanol or tetrahydrofuran, in the presence of a palladium catalyst, e.g., palladium-barium sulfate-quinoline, palladium-activated carbon-quinoline, under a hydrogen atmosphere, at a temperature in a range of 0° C. to 100° C. The hydroboration-protonation is performed such that hydroboratino is performed using a hydroborating reagent, e.g., 9-borabicyclo[3.3.1]nonane or dicyclohexylborane, and protonation is then performed using acetic acid. The reaction can be performed using a solvent such as tetrahydrofuran, diethylether, methylenedichloride, or toluene, at a temperature in a range of 0° C. to 100° C.

Among the pyrrolo[3,2-d]pyrimidine derivatives of formula (Ia-B), a pyrrolo[3,2-d]pyrimidine derivative of formula (Ia-B9) can be synthesized from the pyrrolo[3,2-d]pyrimidine derivative of formula (Ia-B9a) by the following synthesis (B9).

[Synthesis (B9)]

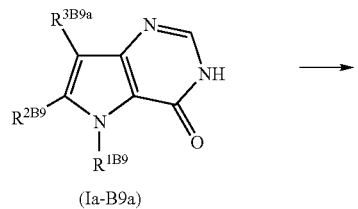

(Ia-B9a)

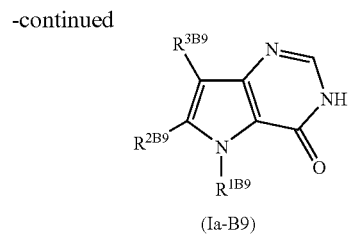

(Ia-B9)

[wherein $R^{1B9}$ represents a group capable of withstanding a conversion reaction among groups defined to be represented by $A^1$-$A^2$-$G^1$-$A^3$-$A^4$-$G^2$ in formula (I). $R^{2B9}$ represents a group capable of withstanding a conversion reaction among groups defined to be represented by $R^2$-$A^5$ in formula (I). $R^{3B9a}$ is a bromine atom or an iodine atom. $R^{3B9}$ is a substituted or unsubstituted saturated aliphatic hydrocarbon group having 1 to 10 carbon atoms, substituted or unsubstituted $C_1$-$C_{10}$ alicyclic hydrocarbon group, or a vinyl group.]

In other words, the pyrrolopyrimidinone derivative (Ia-B9) of the present invention can be synthesized by reacting an organometallic reagent to the pyrrolopyrimidinone derivative (Ia-B9a) of the present invention using a catalytic amount of palladium or nickel. For example, in the reaction with the organometallic reagent using the catalytic amount of palladium or nickel, an organozinc reagent, e.g., phenylzinc chloride or an organozinc compound prepared from a Grignard reagent and zinc chloride, an organotin reagent, e.g., phenyltrimethyltin or tetramethyltin can be used. As the Grignard reagent, organometallic reagents, such as phenylbromomagnesium or n-butylbromomagnesium, can be used. Useful examples of the palladium catalyst include tetrakis(triphenylphosphine)palladium, tris(dibenzylidene-acetone)dipalladium-chloroform adduct, chloro{1,1'-bis(diphenylphosphino)ferrocene}palladium, and the like. Useful examples of the nickel catalyst include chloro{1,3-bis(diphenylphosphino)propane}nickel or nickel bromide. The reaction can be performed using a solvent such as diethylether, tetrahydrofuran or dimethylformamide, in the presence or absence of a ligand, such as triphenylphosphine, tri(o-tolyl)phosphine, or 1,1'-bis(diphenylphosphino)ferrocene, at a temperature in a range of 0° C. to 150° C.

The pyrrolopyrimidinone derivative (Ia-B9) can also be synthesized through hydrogen reduction of the pyrrolo[3,2-d]pyrimidine derivative (Ia-B6) having an alkynyl group prepared by the synthesis (B6) or the pyrrolo[3,2-d]pyrimidine derivative (Ia-B8) having an alkenyl group prepared by the synthesis (B8). The hydrogen reduction is performed using a solvent such as methanol, ethanol or tetrahydrofuran in the presence of a catalytic amount of palladium-activated carbon under a hydrogen atmosphere at a temperature in a range of 0° C. to 100° C.

Among the pyrrolo[3,2-d]pyrimidine derivatives of formula (Ia-B), a pyrrolo[3,2-d]pyrimidine derivative of formula (Ia-B10) can be synthesized from the pyrrolo[3,2-d]pyrimidine derivative of formula (Iz-10a) by the following synthesis (B10).

[Synthesis (B10)]

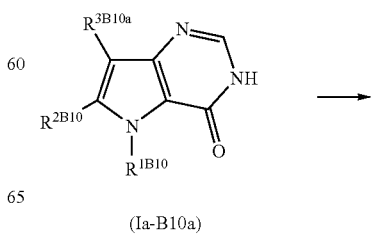

(Ia-B10a)

-continued

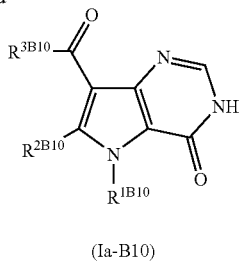

(Ia-B10)

[wherein $R^{1B10}$ represents a group capable of withstanding a conversion reaction among groups defined to be represented by $A^1$-$A^2$-$G^1$-$A^3$-$A^4$-$G^2$ in the formula (I) $R^{2B10}$ represents a group capable of withstanding a conversion reaction among groups defined to be represented by $R^2$-$A^5$ in the formula (I). $R^{3B10a}$ is a bromine atom or an iodine atom. $R^{3B10}$ is a $C_2$-$C_{10}$ hydroxyl, alkoxy, N-substituted amino or N,N-disubstituted amino group.

In other words, the pyrrolopyrimidinone derivative (Ia-B10) of the present invention can be synthesized by reacting the pyrrolopyrimidinone derivative (Ia-B10a) of the present invention with carbon monoxide in the presence of a catalytic amount of palladium. For example, the carbonyl insertion reaction using a catalytic amount of palladium is performed under a carbon monoxide atmosphere, using a palladium catalyst, e.g., tetrakis(triphenylphosphine)palladium, palladium acetate, or tris(dibenzylideneacetone)dipalladium-chloroform adduct, in the presence or absence of a ligand, e.g., triphenylphosphine, tri(o-tolyl)phosphine, or 1,1'-bis(diphenylphosphino)ferrocene, in the presence or absence of a base, e.g., potassium carbonate, or triethylamine. A solvent such as acetonitrile, tetrahydrofuran, or dimethylformamide is used, and the reaction is carried out at a temperature ranging between 0° C. and 150° C. In this case, addition of water as a reacting agent gives a compound with a carboxy group, and addition of an alcohol gives a compound with an alkoxycarbonyl group. Addition of a primary or secondary amine gives a compound with N-substituted or N,N-disubstituted aminocarbonyl group.

Among the pyrrolo[3,2-d]pyrimidine derivatives of formula (Ia-B), a pyrrolo[3,2-d]pyrimidine derivative of formula (Ia-B11) can be synthesized from the pyrrolo[3,2-d]pyrimidine derivative of formula (Ia-B11a) by the following synthesis (B11).

[Synthesis (B11)]

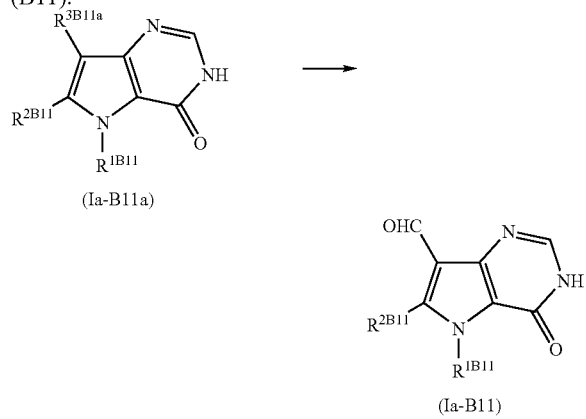

(Ia-B11a)

(Ia-B11)

[wherein $R^{1B11}$ represents a group capable of withstanding a conversion reaction among groups defined to be represented by $A^1$-$A^2$-$G^1$-$A^3$-$A^4$-$G^2$ in the formula (I). $R^{2B11}$ represents a group capable of withstanding a conversion reaction among groups defined to be represented by $R^2$-$A^5$ in the formula (I). $R^{2B11a}$ is a bromine atom or an iodine atom.]

In other words, the pyrrolopyrimidinone derivative (Ia-B11) of the present invention can be synthesized by reacting the pyrrolo[3,2-d]pyrimidine derivative (Ia-B11a) of the present invention under a carbon monoxide atmosphere in the presence of a reducing agent and a catalytic amount of palladium. For example, the formylation reaction using a catalytic amount of palladium is performed under the carbon monoxide atmosphere. Useful examples of the palladium catalyst include tetrakis(triphenylphosphine)palladium, palladium acetate, tris(dibenzylideneacetone)dipalladium-chloroform adduct. The reaction is performed using a solvent such as acetonitrile, tetrahydrofuran, or dimethylformamide in the presence or absence of a ligand such as triphenylphosphine or tri(o-tolyl)phosphine or 1,1'-bis(diphenylphosphino)ferrocene in a temperature range of 0° C. to 150° C. The reaction is performed in the presence of or in the absence of a base such as potassium carbonate or triethylamine. Addition of a reducing agent such as tributyltin hydride or triethylsilane gives a compound with a formyl group, and addition of an organometallic agent such as alkyl zinc, alkyl boron or an organotin reagent give a compound with an alkylcarbonyl group.

Among the pyrrolo[3,2-d]pyrimidine derivatives of formula (Ia-B), a pyrrolo[3,2-d]pyrimidine derivative of formula (Ia-B12) can be synthesized from the pyrrolo[3,2-d]pyrimidine derivative of formula (Ia-B12a) by the following synthesis (B12).

[Synthesis (B12)]

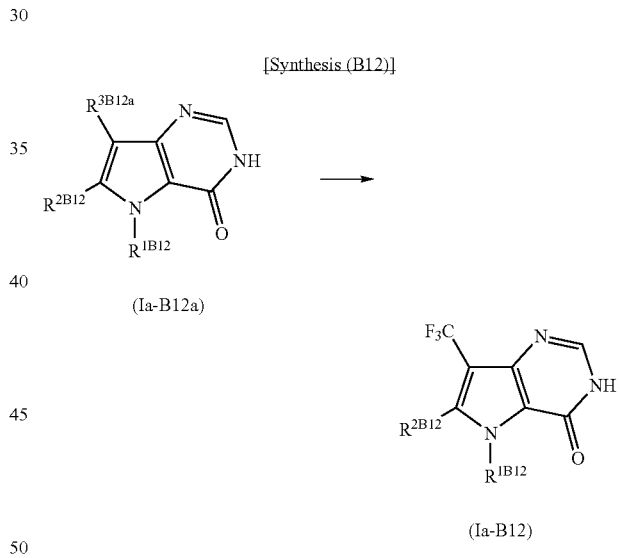

(Ia-B12a)

(Ia-B12)

[wherein $R^{1B12}$ represents a group capable of withstanding a conversion reaction among groups defined to be represented by $A^1$-$A^2$-$G^1$-$A^3$-$A^4$-$G^2$ in the formula (I). $R^{2B12}$ represents a group capable of withstanding a conversion reaction among groups defined to be represented by $R^2$-$A^5$ in the formula (I). $R^{3B12a}$ is a bromine atom or an iodine atom.]

In other words, the pyrrolopyrimidinone derivative (Ia-B12) of the present invention can be synthesized by reacting the pyrrolopyrimidinone derivative (Ia-B12a) of the present invention with a trifluoromethyl donating reagent. That is, in the trifluoromethylation reaction, the reaction can be performed by utilizing various methods, for example, a method using copper (I) iodide or cesium fluoride together with a trifluoromethyl donator such as sodium trifluoroacetate or trifluoromethyl acetate, a method for preparing a trifluoromethyl copper compound from a trifluoromethyl zinc compound or a trifluoromethyl cadmium compound and copper (I) bromide, or a method for preparing a trifluoromethyl copper compound from a trifluoromethyl iodide and copper powder, by using a solvent such as dimethylformamide, N-methylpyrrolidinone, hexamethylphosphoramide, acetonitrile, or pyridine, at a temperature in a range of 0° C. to 150° C.

Among the pyrrolo[3,2-d]pyrimidine derivatives of formula (Ia-B), a pyrrolo[3,2-d]pyrimidine derivative of Formula (Ia-B13) can be synthesized from the pyrrolo[3,2-d]pyrimidine derivative of Formula (Ia-B13a) by the following synthesis (B13).

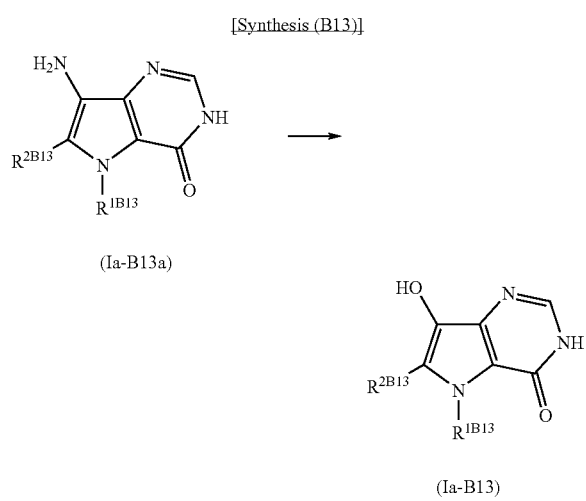

[wherein $R^{1B13}$ represents a group capable of withstanding a conversion reaction among groups defined to be represented by $A^1$-$A^2$-$G^1$-$A^3$-$A^4$-$G^2$ in the formula (I). $R^{2B13}$ represents a group capable of withstanding a conversion reaction among groups defined to be represented by $R^2$-$A^5$ in the formula (I).]

The pyrrolopyrimidinone derivative (Ia-B13) of the present invention can be synthesized by reacting the pyrrolopyrimidinone derivative (Ia-B13a) of the present invention with water in the presence of nitrous acid. That is, the hydroxylation reaction in the presence of nitrous acid is performed using sodium nitrite or isoamyl nitrite in the presence of trifluoroacetic acid or sulfuric acid. The reaction can be performed using water as a solvent in the presence or absence of a cosolvent such as acetonitrile or dimethylformamide, at a temperature in a range of 0° C. to 150° C.

Among the pyrrolo[3,2-d]pyrimidine derivatives of formula (Ia-B), a pyrrolo[3,2-d]pyrimidine derivative of formula (Ia-B14) can be synthesized from the pyrrolo[3,2-d]pyrimidine derivative of formula (Ia-B14a) by the following synthesis (B14).

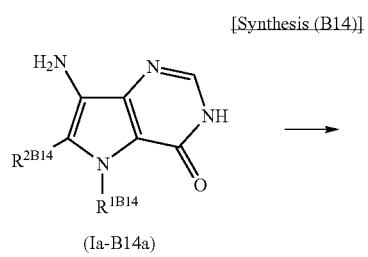

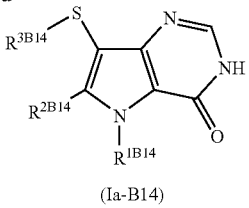

[wherein $R^{1B14}$ represents a group capable of withstanding a conversion reaction among groups defined to be represented by $A^1$-$A^2$-$G^1$-$A^3$-$A^4$-$G^2$ in the formula (I). $R^{2B14}$ represents a group capable of withstanding a conversion reaction among groups defined to be represented by $R^2$-$A^5$ in the formula (I). $R^{3B14}$ is a $C_1$-$C_6$ aliphatic hydrocarbon group.]

In other words, the pyrrolopyrimidinone derivative (Ia-B14) of the present invention can be synthesized by reacting the pyrrolopyrimidinone derivative (Ia-B14a) of the present invention with water in the presence of nitrous acid. That is, the alkylthioration reaction in the presence of nitrous acid is performed using sodium nitrite or isoamyl nitrite in the presence or absence of acids such as hydrochloric acid or sulfuric acid. The reaction is carried out using dialkyldisulfide or alkanethiol as a reagent in a solvent such as acetonitrile or dimethylformamide at a temperature in a range of 0° C. to 150° C.

Among the pyrrolo[3,2-d]pyrimidine derivatives represented by (Ia-B) of the synthesis (B) or (Ib-CN) of the synthesis (B1), a pyrrolo[3,2-d]pyrimidine derivative of formula (Ia-C2) can be synthesized from the pyrrolo[3,2-d]pyrimidine derivative of formula (Ia-C1) by the following synthesis (C).

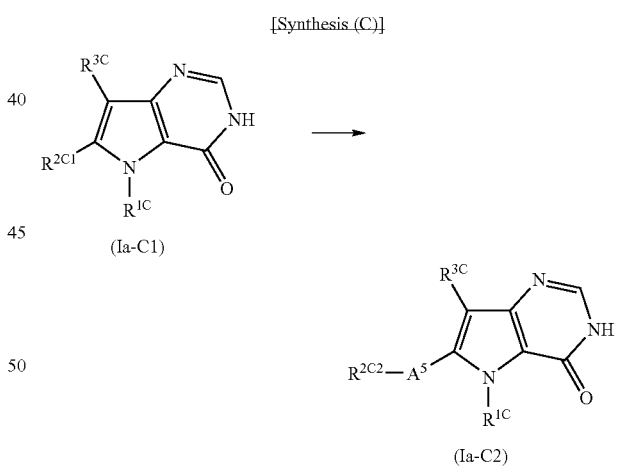

[wherein $R^{1C}$ represents a group capable of withstanding a conversion reaction among groups defined to be represented by $A^1$-$A^2$-$G^1$-$A^3$-$A^4$-$G^2$ in the formula (I). $R^{2C1}$ is a chlorine atom or a bromine atom. $R^{3C}$ represents a cyano group or a group capable of withstanding a conversion reaction among groups defined to be represented by $R^2$-$A^5$ in the formula (I). When $A^5$ is —$NR^{201}$— ($R^{201}$ is the same as defined above for $R^{201}$ in the formula (1)), $R^{2C2}$ is as defined to exclude a fluorine atom, a chlorine atom, a bromine atom and an iodine atom from groups defined for $R^2$ in formula (I). Also, when $A^5$ is a single bond, $R^{2C2}$ is a heterocyclic group having 1 to 4 atoms selected from the group consisting of an oxygen atom, a nitrogen atom and a sulfur atom on the substituted or unsubstituted ring in which $R^{2C2}$ is linked to $A^5$ on a nitrogen atom.

In other words, the pyrrolopyrimidinone derivatives (Ia-C2) can be synthesized by reacting the pyrrolopyrimidinone derivatives (Ia-C1) of the present invention with a primary or secondary amine. Amination using the primary or secondary amine is performed without the use of a solvent or with the use of a solvent such as dimethylsulfoxide, dimethylformamide, dioxane, tetrahydrofuran or toluene in the presence or absence of a base such as pyridine, triethylamine, diisopropylethyl-amine, 4-dimethylaminopyridine or sodium carbonate. The reaction is performed in the presence or absence of a transition metal complex catalyst prepared by mixing a palladium salt such as palladium acetate with a phosphorus ligand such as triphenylphosphine, at a temperature in a range of 0° C. to 150° C.

Among the pyrrolo[3,2-d]pyrimidine derivatives represented by the formula (Ia) or (Ia-CN) of the synthesis (B1), a pyrrolo[3,2-d]pyrimidine derivative of formula (Ia-D2) can be synthesized from the pyrrolo[3,2-d]pyrimidine derivative of formula (Ia-D1) by the following synthesis (D).

[Synthesis (D)]

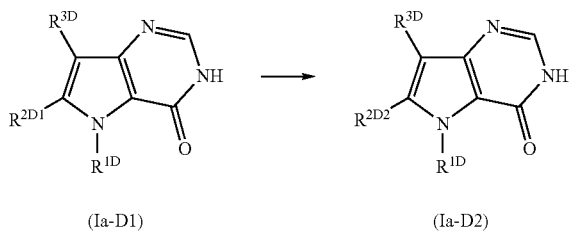

(Ia-D1)　　　　　　　　(Ia-D2)

[wherein $R^{1D}$ represents a group capable of withstanding a conversion reaction among groups defined to be represented by $A^1$-$A^2$-$G^1$-$A^3$-$A^4$-$G^2$ in the formula (I). $R^{2D1}$ is a chlorine atom or a bromine atom. $R^{2D2}$ is a substituted or unsubstituted aromatic hydrocarbon group having 6 to 14 carbon atoms, or an aromatic heterocyclic group having 1 or 2 atoms selected from the group consisting of an oxygen atom, a nitrogen atom and a sulfur atom on the substituted or unsubstituted ring. $R^{3D}$ is a cyano group or a group capable of withstanding a conversion reaction among groups defined to be represented $A^6$-$R^3$ in the formula (I).]

In other words, the pyrrolopyrimidinone derivative (Ia-D2) of the present invention can be synthesized by reacting the pyrrolopyrimidinone derivative (Ia-D1) of the present invention with, for example, a boric acid derivative represented by $R^{2D2}$—$B(OR)_2$ [in which $R^{2D2}$ is as defined above in the synthesis (D), and R is a hydrogen atom or an alkyl group]. The reaction with the boric acid derivative is performed under general Suzuki reaction conditions, for example, at a temperature in a range of 0° C. to 150° C. using a solvent such as 2-propanol and/or water in the presence of an inorganic base such as sodium carbonate, by using a catalyst such as palladium acetate, and adding a ligand such as triphenylphosphine.

Among the pyrrolo[3,2-d]pyrimidine derivatives of Formula (Ia) or (Ia-CN) prepared in the synthesis (B1), a pyrrolo[3,2-d]pyrimidine derivative of formula (Ia-E2) can be synthesized from the pyrrolo[3,2-d]pyrimidine derivative of formula (Ia-E1) in the following manner shown in Synthesis (E):

[Synthesis (E)]

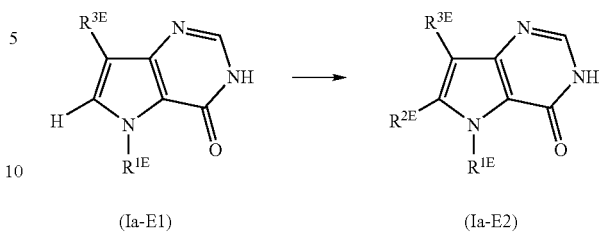

(Ia-E1)　　　　　　　　(Ia-E2)

[wherein $R^{1E}$ represents a group capable of withstanding a conversion reaction among groups defined to be represented by $A^1$-$A^2$-$G^1$-$A^3$-$A^4$-$G^2$ in the formula (I). $R^{2E}$ is a chlorine atom, a bromine atom or an iodine atom. $R^{3E}$ is a cyano group or a group capable of withstanding a conversion reaction among groups defined to be represented by $A^6$-$R^3$.]

In other words, the pyrrolopyrimidinone derivative (Ia-E2) of the present invention can be synthesized by halogenation of the pyrrolopyrimidinone derivative (Ia-E1) of the present invention. The halogenation is performed using a halogenation reagent such as N-chlorosuccinic imide or N-bromosuccinic imide in the presence of a solvent such as dimethylformamide, dioxane or tetrahydrofuran at a temperature in a range of −20° C. to 150° C.

Among the pyrrolo[3,2-d]pyrimidine derivatives of Formula (Ia) or (Ia-CN) prepared in the synthesis (B1), a pyrrolo[3,2-d]pyrimidine derivative of formula (1a-F) given below can be synthesized from the pyrrol derivative of formula (IV-F) in the following manner shown in Synthesis (F):

[Synthesis (F)]

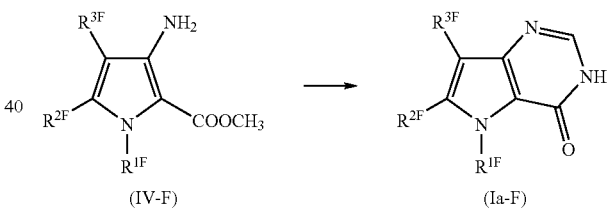

(IV-F)　　　　　　　　(Ia-F)

[wherein $R^{1F}$ represents a group capable of withstanding a conversion reaction among groups defined to be represented by $A^1$-$A^2$-$G^1$-$A^3$-$A^4$-$G^2$ in the formula (I). $R^{2F}$ represents, among the groups defined for $R^2$ in the formula (I), groups excluding a fluorine atom, a chlorine atom, a bromine atom, an iodine atom, and a substituted or unsubstituted heterocyclic group that is bonded with a carbon atom and a nitrogen atom of a pyrrole ring to which $R^{2F}$ is bonded, and having 1 to 4 atoms selected from the group consisting of an oxygen atom, a nitrogen atom and a sulfur atom, in the ring. $R^{3F}$ is a cyano group or a group capable of withstanding a conversion reaction among groups defined to be represented by $A^6$-$R^3$ in formula (I).]

In other words, the pyrrolo[3,2-d]pyrimidine derivative of the formula (Ia-F) of the present invention can be synthesized by performing a cyclization reaction using formamidine or formamide on the pyrrole derivative of formula (IV-F). The cyclization reaction using formamidine can be performed by using formamidine acetate, for example, in a solvent such as 2-propanol at a temperature in a range of 0° C. to 150° C. The cyclization reaction using formamide can be performed smoothly by using a base such as formamide or sodiummethoxide, in the presence or absence of a solvent such as dimethylsulfoxide or dimethoxyethane at a temperature in a range of 0° C. to 150° C.

The pyrrolo[3,2-d]pyrimidine derivatives of the formula (Ia) or the synthesis (B1) can be synthesized from the pyrrolo [3,2-d]pyrimidine derivative of the Formula (I-G) by the following synthesis (G).

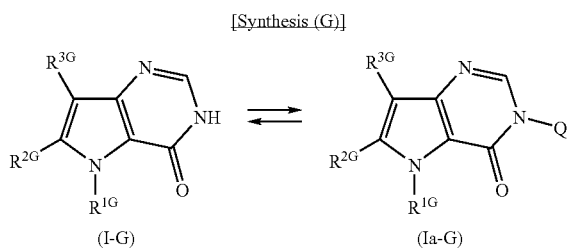

[wherein $R^{1G}$ represents a group capable of withstanding a conversion reaction among groups defined to be represented by $A^1$-$A^2$-$G^1$-$A^3$-$A^4$-$G^2$ in the formula (I). $R^{2G}$ represents a group capable of withstanding a conversion reaction among groups defined to be represented by $R^2$-$A^5$ in the formula (I). $R^{3G}$ is a cyano group or a group capable of withstanding a conversion reaction among groups defined to be represented by $A^6$-$R^3$ in formula (I). Q is an optionally substituted $C_2$-$C_{10}$ acyl group, an optionally substituted a $C_2$-$C_8$ alkoxymethyl group, or substituted or unsubstituted benzy group.]

In other words, when for example Q is an acyl group, the pyrrolopyrimidinone derivative (Ib-G) of the present invention can be synthesized by reacting the pyrrolopyrimidinone derivative (I-G) of the present invention with an acyl halide. The acylation reaction using the acyl halide is performed under conventional acylation reaction conditions, for example, in the presence of triethylamine or pyridine, at a temperature in a range of 0° C. to 100° C.

Also, when Q is for example an alkoxymethyl or benzyl group, the pyrrolopyrimidinone derivative (I-G) of the present invention can be synthesized by reacting the pyrrolo [3,2-d]pyrimidine derivative (I-G) of the present invention with an alkoxymethyl halide or a benzyl halide. The reaction using the alkoxymethyl halide or the benzyl halide can be performed in the presence of for example sodium hydride in a temperature range of 0° C. to 100° C.

In the thus obtained pyrrolopyrimidinone derivatives (Ib-G) according to the present invention, conversion reactions known to one skilled in the art can be performed for $A^1$, $A^2$, $A^3$, $A^4$, $A^5$, $A^6$, $G^1$, $G^2$, $R^2$ and/or $R^3$. Such pyrrolo[3,2-d] pyrimidine derivatives (Ib-G) can be converted into the pyrrolopyrimidinone derivatives (I-G) of the present invention by performing hydrolysis under a neutral or alkaline condition when Q is an acyl group, or under an acidic condition using, for example, trifluoroacetic acid, when Q is an alkoxymethyl group, or by performing a hydrogen addition reaction when $R^3$ is a benzyl group.

The pyrrolopyrimidinone derivatives or the present invention synthesized by the syntheses (A), (B), (C), (D), (E), (F), and (G) have easily convertible substituents, such as an alkoxycarbonyl group, an acyloxy group, or an aromatic nitro group, they can be easily converted into pyrrolopyrimidinone derivatives or the present invention respectively having a carboxy group, a hydroxy group, and an amino group by performing reactions known to one skilled in the art.

When the pyrrolopyrimidinone derivatives of the present invention synthesized by the synthesis (A), (B), (C), (D), (E), (F), and (G) have a carboxy group, they can be converted into pyrrolopyrimidinone derivatives of the present invention having an alkoxycarbonyl group, a carbamoyl group, and an N-alkylcarbamoyl group by a condensation reaction known to one skilled in the art.

When the pyrrolopyrimidinone derivatives of the synthesized by the synthesis (A), (B), (C), (D), (E), (F), and (G) have an amino group, they can be converted into pyrrolopyrimidinone derivatives of the present invention having an acylamino group or an alkylsulfonylamino group by a condensation reaction well known to one skilled in the art.

Also, when they have an amino group, they can also be converted into pyrrolopyrimidinone derivatives of the present invention having a monoalkylamino or a dialkylamino group by a reductive alkylation reaction known to one skilled in the art.

When the pyrrolopyrimidinone derivatives of the present invention synthesized by the synthesis (A), (B), (C), (D), (E), (F), and (G) have a hydroxy group, they can be converted into pyrrolopyrimidinone derivatives of the present invention having an acyloxy group by a condensation reaction known to one skilled in the art.

When the pyrrolopyrimidinone derivatives of the present invention synthesized by the synthesis (A), (B), (C), (D), (E), (F), and (G) have a formyl group, they can be converted into pyrrolopyrimidinone derivatives of the present invention having an alkylaminomethyl group by a reductive alkylation reaction known to one skilled in the art.

In the synthesis of the pyrrolopyrimidinone derivative of the formula (I), the pyrrole derivatives of formula (IV-F) used as starting materials can be prepared from a 3-alkoxypropene nitrile derivative of formula (VI-H) by the following synthesis (H).

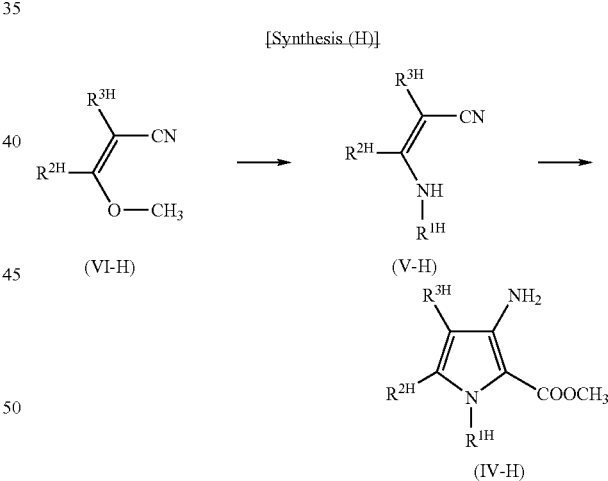

[wherein $R^{1H}$ represents a group capable of withstanding a conversion reaction among groups defined to be represented by $A^1$-$A^2$-$G^1$-$A^3$-$A^4$-$G^2$ in the formula (I). $R^{2H}$ represents, among the groups defined for $R^2$-$A^5$ in the formula (I), groups excluding a fluorine atom, a chlorine atom, a bromine atom, an iodine atom, and a substituted or unsubstituted heterocyclic group that is bonded with a carbon atom and a nitrogen atom of a pyrrole ring to which $R^{2H}$ is bonded, and having 1 to 4 atoms selected from the group consisting of an oxygen atom, a nitrogen atom and a sulfur atom, in the ring. $R^{3H}$ is a cyano group or a group capable of withstanding a conversion reaction among groups defined to be represented by $A^6$-$R^3$ in formula (I).]

In other words, aminopropenitrile derivatives (V-H) can by synthesized by reacting alkoxypropene nitriles (VI-H) with a primary amine (represented by $R^1$—$NH_2$ in which $R^1$ is as defined above for $R^1$ prepared by the synthesis (H)). The pyrrole derivatives (IV-H) can be synthesized through a reaction between the aminopropenenitrile derivatives (V-H) and methyl bromoacetate in the presence of a base, or through a cyclization reaction.

The reaction between the alkoxypropene nitrile derivatives (V-H) and the primary amine is performed using a solvent such as methanol, ethanol or 2-propanol at a temperature in a range of 0° C. to 100° C.

The reaction between the alkoxypropenenitrile derivatives (VI-H) and methyl bromoacetate is performed in the presence of a base such as sodium carbonate using a solvent such as acetonitrile at a temperature in a range of 0° C. to 150° C.

In the synthesis of the pyrrolopyrimidinone derivative of the formula (I), among the pyrrole derivatives of the formula (IV-F) used as starting materials, a pyrrole derivative having a hydrogen atom as $R^{2F}$ can be prepared from 3-oxopropanenitrile derivatives of formula (VII-J) by the following synthesis (J)

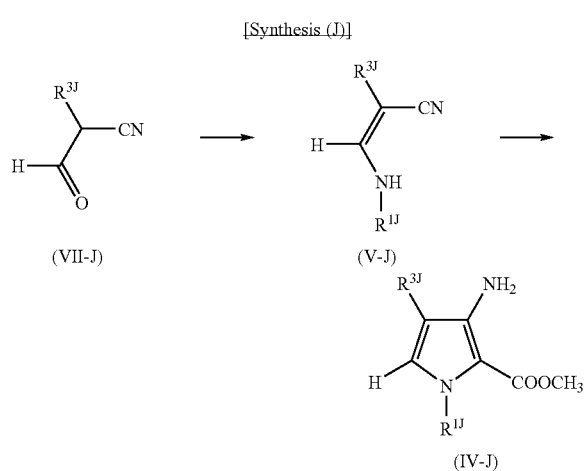

[wherein $R^{1J}$ represents a group which can be converted to $A^1$-$A^2$-$G^1$-$A^3$-$A^4$-$G^2$ in the formula (I), and a group capable of withstanding a conversion reaction. $R^{3J}$ is a cyano group or a group capable of withstanding a conversion reaction among groups defined to be represented by $A^6$-$R^3$ in the formula (I).]

In other words, the aminopropenenitrile derivative (V-J) can be synthesized by reacting the 3-oxopropanenitrile derivative (VII-J) with a primary amine ($R^1$—$NH_2$ in which $R^1$ is as defined above for $R^1$ prepared by the synthesis (J)). The pyrrole derivatives (IV-J) can be synthesized through a reaction between the aminopropenitrile derivatives (V-J) and methyl bromoacetate in the presence of a base, or through a cyclization reaction.

The reaction between 3-oxopropanenitrile derivative (VII-J) and the primary amine is performed using a solvent such as methanol, ethanol or 2-propanol at a temperature in a range of 0° C. to 100° C.

The reaction between the aminopropenitrile derivative (VI-J) and methyl bromoacetate is performed in the presence of a base such as sodium carbonate using a solvent such as acetonitrile in a temperature range of 0° C. to 150° C.

Alternatively, in the syntheses of the pyrrolopyrimidinone derivative of the formula (I), among the pyrrole derivatives of formula (IV-F) used as starting materials, a pyrrole derivative of formula (IV-F) having a hydrogen atom as $R^2F$ can also be prepared by the following synthesis (K):

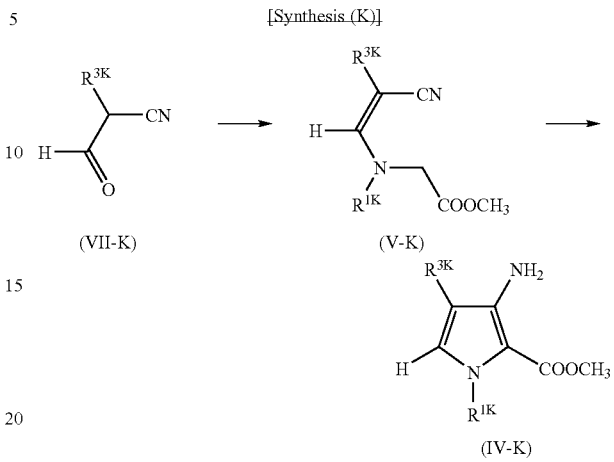

[wherein $R^{1K}$ represents a group which can be converted to $A^1$-$A^2$-$G^1$-$A^3$-$A^4$-$G^2$ in the formula (I), and a group capable of withstanding a conversion reaction. $R^{3K}$ is a cyano or a group capable of withstanding a conversion reaction among groups defined to be represented by $A^6$-$R^3$ in formula (I).]

In other words, the aminopropenitrile derivative (V-K) can by synthesized by reacting the 3-oxopropanenitrile derivative (VII-K) and a glycinemethylester derivative ($R^1$—NH—$CH_2$—$COOCH_3$ having $R^1$ on a nitrogen atom in which $R^1$ is as defined above for $R^1$ prepared by the synthesis (K)) The pyrrole derivative (IV-L) can be synthesized by performing cyclization of the aminopropenitrile derivative (V-K) in the presence of a base.

The reaction between the 3-oxopropanenitrile derivative (VII-K) and the glycinemethylester derivative is performed using a solvent such as acetic acid at a temperature in a range of 0° C. to 150° C.

The cyclization reaction of the aminopropenitrile derivative (V-K) is performed using a solvent such as acetonitrile or ethylene glycol dimethyl ether in the presence of a base such as 1,8-diazabicyclo[5,4,0]-7-undecene or cesium carbonate at a temperature in a range of 0° C. to 150° C.

The thus obtained pyrrolopyrimidinone derivatives of formula (I) have an inhibitory effect of GSK-3 activity, and can be advantageously used as preventive and/or therapeutic agents which are clinically applicable GSK-3 inhibitors. Diseases that can be treated by the GSK-3 activity inhibitor include diabetes, diabetic complications, atherosclerosis, hypertension, obesity, syndrome X, Alzheimer's disease, neurodegenerative diseases (AIDS encephalopy, Huntington's disease, Parkinson's disease, or ischemic attack), manic depressive psychosis, traumatic cerebrospinal injury, alopecia, inflammatory response syndrome, cancer and immunodeficiency.

Also, the pyrrolopyrimidinone derivatives of formula (I) and its pharmaceutically acceptable salts may be formed as pharmaceutical compositions together with pharmacologically acceptable carriers and/or diluents. The compositions of the present invention may be formed as various kinds of formulations to be administered orally or parenterally. The term "parenteral" as used herein includes intravenous, subcutaneous, intramuscular, percutaneous, and rectal injection or infusion techniques.

For oral administration, examples of the formulation include tablets, pills, granules, powder, solutions, suspensions, syrups, and so on.

Here, the tablet formulations can be formed by conventional methods using a pharmaceutically acceptable carrier such as a vehicle, a binding agent, a disintegrating agent, and the like. The pills, granules and powder can also be formed by conventional methods using a vehicle or the like, like the tablets. The formulations in the form of solutions, suspensions and syrups can be prepared by general methods using glycerine esters, alcohols, water, vegetable oils, and so on. The capsule formulations can be formed by filling capsules of gelatin with granules, powder or solutions.

Among formulations for parenteral administration, intravenous, subcutaneous, and intramuscular administration can take forms of injectable formulations. For injection, the compounds of the invention may be formulated in aqueous solutions such as physiological saline or in nonaqueous solutions including organic esters such as propylene glycol, polyethylene glycol, or vegetable oils.

For transdermal administration, formulations can be used in the form of ointment or cream. Ointments can be used in combination with oils or vaselin, for example. Creams can be prepared in combination with emulsifying agents, for example.

When required, these formulations can be further provided with pharmaceutically acceptable carriers such as an isotonic, a preservative, an antiseptic, a wetting agent, a buffering agent, an emulsifying agent, a dispersing agent, or a stabilizer.

Also, such a variety of formulations can be sterilized through appropriate treatments, for example, filtration using a bacteria retaining filter or combination of disinfectants.

The amount of the pyrrolopyrimidinone derivative of formula (I) and its pharmaceutically acceptable salt that may be administered may vary depending upon the kind of a disease, administration route, symptom, age, sex, body weight, and so on of the patient. Generally, a dosage for oral administration is between 0.1 and 500 mg/day/patient. A dosage for parenteral application, including intravenous, subcutaneous, intramuscular, and percutaneous injection is between 0.1 and 100 mg/day/patient.

EXAMPLES

The present invention will now be described in more detail through the following examples. However, the present invention is not limited to these examples. In the following examples, compound numbers labeled for the respective compounds correspond to the compound numbers labeled for the compounds listed in the above tables as specific examples.

Note that, with regard to data for compounds synthesized in the following examples, the term "HPLC retention time" refers to a retention time (unit: min) associated with a particular compound in HPLC analysis performed under the following analysis condition. HPLC (High performance liquid chromatography) Analysis Condition
System: Hewlett-Packard 1100 HPLC
Column: Cadenza CD-C18 (manufactured by Imtakt Co.) 100 mm×4.6 mmφ

Solvent A:
  $H_2O$/acetonitrile=95/5 (0.05% trifluoroacetic acid)

Solvent B:
  $H_2O$/acetonitrile=5/95 (0.05% trifluoroacetic acid)

Flow rate: 1.0 mL/min

Gradient:
  0 to 1 min Solvent B: 10%, Solvent A: 90%
  1 to 14 min Solvent B: 10% →100%, Solvent A: 90% → 0%
  14 to 16 min Solvent B: 100%, Solvent A: 0% Calculation of the purity: Area percentage at UV absorption (254 nm)

Reference Example 1

Synthesis of (cyclopropylhydroxy-methylene)methane-1,1-dicarbonitrile

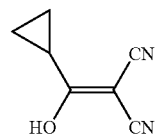

A tetrahydrofuran (150 mL) suspension of sodium hydride (11.49 g) was cooled to 0° C. To the cooled suspension was added dropwise a tetrahydrofuran (50 mL) solution of malononitrile (15.8 g) over an hour. The reaction mixture was stirred at room temperature for 1 hour and cooled to 0° C. To the reaction mixture was added dropwise over 80 minutes a tetrahydrofuran (50 mL) solution of cyclopropylcarbonyl chloride (25.0 g). The reaction mixture was stirred at room temperature for 49 hours, followed by adding water (50 mL) to the reaction solution. The solvent was distilled off under reduced pressure. To the residue were added ethyl acetate (200 mL) and hydrochloric acid (270 mL, 1 mol/L), which was extracted with ethyl acetate. The organic layer was washed with saturated brine and dried over anhydrous sodium sulfate, and then the solvent was distilled off under reduced pressure to obtain a crude product (40.9 g) of the title compound. The NMR data of the compound is given below.

$^1$H-NMR (400 MHz, $CDCl_3$)δ(ppm): 1.10-1.22 (m, 4H), 2.10-2.22 (m, 1H), 4.27 (s, 3H).

In a similar manner as described above, [(3-chloro(2-thienyl))hydroxymethylene]methane-1,1-dicarbonitrile was prepared from malononitrile and 3-chlorothiophene-2-carbonylchloride. The NMR data and ESI/MS data of the compound are given below.

$^1$H-NMR (400 MHz, $CD_3OD$) δ(ppm): 6.92 (d, J=5.1, 1H) 7.51 (d, J=5.4, 1H) ESI/MS m/e: ($M^+$+H, $C_8H_3ClN_2OS$).

Reference Example 2

Synthesis of (cyclopropylmethoxy-methylene)methane-1,1-dicarbonitrile

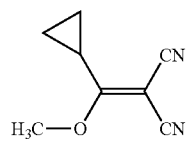

A tetrahydrofuran (100 mL) suspension of sodium hydride (2.6 g) was cooled to 0° C. To the cooled suspension was added dropwise a tetrahydrofuran (60 mL) solution of crude (1-hydroxy-2-phenylmethylidene)methane-1,1-dicarbonitrile (14.5 g) over 30 minutes. The reaction mixture was stirred at room temperature for 20 minutes and cooled to 0° C.

To the reaction mixture was added dropwise a tetrahydrofuran solution (40 mL) of dimethyl sulfate (13.7 g) over 1 hour. After heating for 21 hours to reflux, the reaction mixture was cooled to room temperature, and the solvent was distilled off under reduced pressure. To the residue were added ethyl acetate (100 mL) and saturated sodium hydrogen carbonate solution (100 mL), and extraction with ethyl acetate was performed. The organic layer was washed with saturated brine and dried over anhydrous sodium sulfate, and then the solvent was distilled off under reduced pressure. The obtained crude product was purified by column chromatography on silica gel using hexane/ethyl acetate=1/3 as an eluent to obtain the title compound (6.8 g, 54%) as a light yellow solid. NMR data of the compound is given below.

$^1$H-NMR (400 MHz, CDCl$_3$)δ(ppm): 1.10-1.22 (m, 4H), 2.10-2.22 (m, 1H), 4.27 (s, 3H).

Reference Example 3

Synthesis of methyl 3-amino-1-{2-[(t-butoxy)carbonylamino]ethyl}-4-cyano-5-cyclopropylpyrrole-2-carboxylate

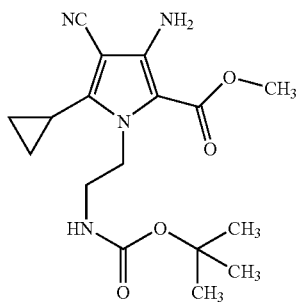

To an acetonitrile (150 mL) solution of (methoxycyclopropylmethylene)methane-1,1-dicarbonitrile (8.7 g) was added N-(2-aminoethyl) t-butyl carbaminic acid (16.3 g) and stirred at room temperature for 10 minutes. To the resultant product were added anhydrous cesium carbonate (38.5 g) and methyl bromoacetate (11.2 mL), followed by heating for 6 hours to reflux. The reaction product was cooled to room temperature and allowed to stand. Then, the supernatant was separated by decantation and the solvent was distilled off under reduced pressure. The concentrated residue and a solid remaining after decantation were collected and ethyl acetate and water were added thereto, followed by extracting 3 times with ethyl acetate. The organic phase was washed with water and saturated brine, and dried over anhydrous magnesium sulfate. After magnesium sulfate was removed by filtration, the solvent was distilled off under reduced pressure. The residue was purified by column chromatography on silica gel (hexane/ethyl acetate=2/1) to obtain the title compound (17.5 g, yield 85%). The ESI/MS data of the compound are given below.

ESI/MS m/e: 349.1 (M$^+$+H, C$_{17}$H$_{24}$N$_4$O$_4$)

Methyl 3-amino-1-{2-[(t-butoxy)carbonylamino}ethyl}-5-(3-chloro(2-thienyl))-4-cyanopyrrole-2-carboxylate was synthesized from [(3-chloro(2-thienyl))hydroxymethylene]methane-1,1-dicarbonitrile used as a starting material in a similar manner to that in Reference Examples 2 and 3. The ESI/MS data of the compound are given below.

ESI/MS m/e: 425.2 (M$^+$+H, C$_{18}$H$_{21}$ClN$_4$O$_4$S)

Reference Example 4

Synthesis of (t-butoxy)-N-[2-(7-cyano-4-oxo-6-cyclopropyl(3-hydropyrrolo[3,2-d]pyrimidin-5-yl))ethyl]carboxyamide

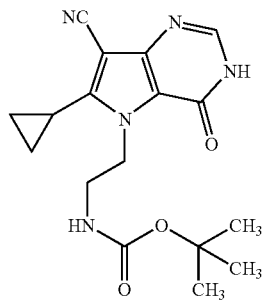

Methyl 3-amino-1-{2-[(t-butoxy)carbonylamino]ethyl}-4-cyano-5-cyclopropylpyrrole-2-carboxylate (17.4 g) and formamidine acetate (104.1 g) were added to 2-propanol (360 mL) and heated for 45 hours to reflux. The reaction mixture was cooled to room temperature, and the solvent was distilled off under reduced pressure. To the residue was added water, and the obtained solid was isolated by filtration and sufficiently washed with water. The resulting solid was recrystallized (ethanol/ethyl acetate/hexane=1/2/1) to obtain the title compound (9.8 g, yield 57%). The ESI/MS data of the compound are given below.

ESI/MS m/e: 362.1 (M$^+$+H, C$_{17}$H$_{21}$N$_5$O$_3$)

(t-butoxy)-N-{2-[6-(3-chloro(2-thienyl))-7-cyano-4-oxo(3-hydropyrrolo[3,2-d]pyrimidin-5-yl)]ethyl}carboxyamide was prepared from methyl-3-amino-1-{2-[(t-butoxy)carbonyl-amino]ethyl}-5-(3-chloro(2-thienyl))-4-cyanopyrrole-2-carboxylate in a similar manner to that described above. ESI/MS data of the compound are given below.

ESI/MS m/e: 420.2 (M$^+$+H, C$_{18}$H$_{18}$ClN$_5$O$_3$S)

Reference Example 5

Synthesis of 3-oxo-2-(3-pyridyl)propanenitrile hydrochloride

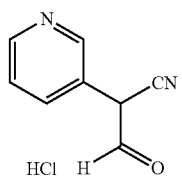

To a toluene solution (100 mL) of 3-pyridylacetonitrile (40.86 g) was added dimethylformamidedimethylacetal (123.6 g) and the mixture was heated for 4 hours to reflux. The reaction solution was cooled to room temperature, and the solvent was distilled off under reduced pressure. The residue was purified by column chromatography on silica gel (ethyl acetate) to obtain a brown solid. The obtained brown solid was washed with ethyl acetate, yielding 46.93 g of a colorless solid. To a tetrahydrofuran (300 mL) suspension of the reaction product (20.37 g) were added water (40 mL) and concentrated hydrochloric acid (24.50 mL) and the mixture was stirred at 50° C. for 4 hours. The reaction solution was cooled to room temperature, and the solvent was distilled off under reduced pressure. The residue was dried in vacuo to obtain a crude product (30.12 g) of the title compound, which was used for the subsequent reaction without further purification. ESI/MS data of the compound are given below.

ESI/MS m/e: 147.1 ($M^++H$, $C_8H_6N_2O$ HCl)

Reference Example 6

Synthesis of ethyl 3-{((1Z)-2-cyano-2-(3-pyridyl)vinyl)[(methoxycarbonyl)methyl]amino}propanate

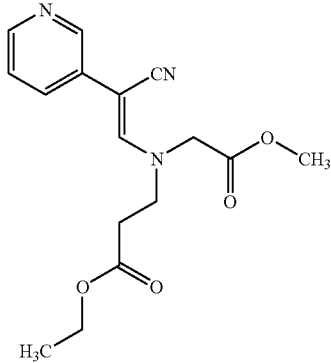

To an acetic acid (30 mL) solution of ethyl 3-{[(methoxycarbonyl)methyl]amino}propanate (6.720 g) was added a crude product of 3-oxo-2-(3-pyridyl)propanenitrile (7.826 g), and the mixture was stirred at 80° C. for 2 days. The reaction solution was cooled to room temperature, and the solvent was distilled off under reduced pressure. The residue was diluted with water, and sodium carbonate was added thereto for neutralization, followed by extracting the solution with ethyl acetate. The organic layer was washed with saturated brine, and dried over sodium sulfate, which was then filtered for separation. Thereafter, the solvent was distilled off under reduced pressure. The residue was purified by column chromatography on silica gel (hexane/ethyl acetate=1/3), to obtain the title compound (7.521 g, yield 83%). The ESI/MS data of the compound are given below.

ESI/MS m/e: 318.2 ($M^++H$, $C_{16}H_{19}N_3O_4$)

Reference Example 7

Synthesis of ethyl 3-[3-amino-2-(methoxycarbonyl)-4-(3-pyridyl)pyrrolyl]propanate

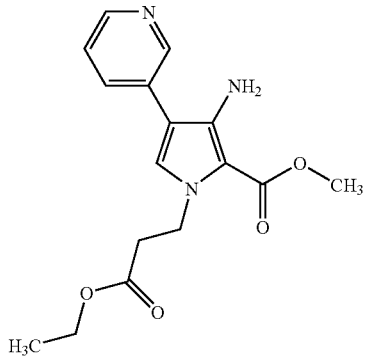

To an ethylene glycol dimethyl ether (50 mL) solution of ethyl 3-{((1Z)-2-cyano-2-(3-pyridyl)vinyl)[(methoxycarbonyl)methyl]amino}propanate (6.236 g) was added 1,8-diazabicyclo[5,4,0]-7-undecene (3.590 g), and the mixture was stirred at 60° C. overnight. The reaction solution was cooled to room temperature and neutralized with acetic acid, and the solvent was distilled off under reduced pressure. The residue was purified by column chromatography on silica gel (hexane/ethyl acetate=1/5), to obtain the title compound (4.380 g, yield 70%). The NMR data and ESI/MS data of the compound are given below.

$^1$H-NMR (400 MHz, DMSO-$d_6$) δ(ppm): 1.10-1.18 (m, 3H), 2.74 (t, J=6.82, 2H), 3.77 (s, 3H), 3.99-4.07 (m, 2H), 4.38 (t, J=6.84, 2H), 7.46 (s, 1H), 7.85 (dd, J=5.74, J=7.94, 1H), 8.36 (d, J=8.08, 1H), 8.60 (d, J=5.40, 1H), 8.84 (s, 1H). ESI/MS m/e: 318.2 ($M^++H$, $C_{16}H_{19}N_3O_4$)

Reference Example 8

Synthesis of (cyclopropylhydroxy-methylene)methane-1-(3-pyridyl)-1-carbonitrile

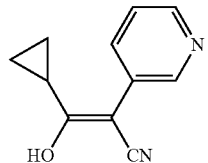

To a 500 mL branched flask was added 13.0 g of 3-pyridinacetonitrile (110 mmol) and 150 mL of tetrahydrofuran, and 44 mL of "BuLi (2.6 M solution) (114 mmol) was added dropwise thereto using a syringe with stirring at 0° C., followed by stirring at 0° C. for 30 minutes and at 40° C. for 30 minutes. While the reaction product was cooled at 0° C. with stirring, a tetrahydrofuran solution (30 mL) of 10.45 g of cyclopropanecarbonyl chloride (100 mmol) was added dropwise, and stirred at room temperature for 1 hour, followed by adding to the reaction solution 300 mL of a saturated ammonium chloride solution and separated. The aqueous layer was extracted with 100 mL of ethyl acetate. The organic layer was washed twice with 300 mL of saturated brine. The organic layer was dehydrated and dried over magnesium sulfate, filtered and concentrated to obtain 18.25 g of concentrated residue. To the concentrated residue was added 30 mL of acetonitrile and an insoluble portion was filtered off, followed by washing with 20 mL of acetonitrile to obtain a crude product of the title compound (5.17 g, 28%). The NMR data and ESI/MS data of the compound are given below.

$^1$H-NMR (400 MHz, DMSO-$d_6$)δ(ppm): 0.64 (m, 4H), 2.24 (m, 1H) 2.50 (brds, 1H), 7.70 (dd, J=5.4 Hz, J=8.6 Hz, 1H), 8.11 (d, J=5.4 Hz, 1H), 8.21 (d, J=8.6 Hz, 1H), 9.12 (brds, 1H). ESI/MS m/e: 187.1 ($M^++H$, $C_{11}H_{10}N_2O$).

Reference Example 9

Synthesis of (cyclopropyl-p-toluene-sulfonyloxymethylene)methane-1-(3-pyridyl)-1-carbonitrile

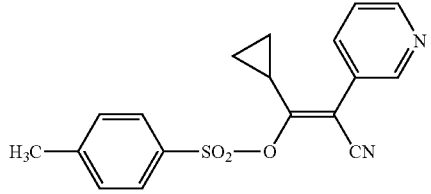

A 200 mL branched flask were charged with 4.51 g of (cyclopropylhydroxymethylene)methane-1-(3-pyridyl)-1- carbonitrile (24.3 mmol) and 9.14 g of p-toluene sulfonic anhydride (28 mmol), and 100 mL of dichloromethane was added thereto, followed by adding 4.8 mL of triethylamine (34.5 mmol) dropwise with stirring the reaction mixture at room temperature, and stirring at room temperature for 2 hours. After the completion of the reaction, 50 mL of water was added to the reaction solution and separated. The aqueous layer was extracted with 20 mL of dichloromethane. The organic layer was washed once with 50 mL of saturated sodium hydrogen carbonate solution and twice with 50 mL of water. The organic layer was dehydrated and dried over magnesium sulfate, filtered and concentrated to obtain a crude product (8.47 g, 100%) of the title compound. The NMR data and ESI/MS data of the compound are given below.

$^1$H-NMR (270 MHz, CDCl$_3$)δ(ppm): 1.10-1.32 (m, 4H), 2.40 (s, 3H) 2.15-2.42 (m, 1H), 7.05 (m, 3H), 7.40 (m, 2H), 7.60 (m, 1H), 8.40 (m, 2H). ESI/MS m/e: 341.0 (M$^+$+H, C$_{18}$H$_{16}$N$_2$O$_3$S).

Reference Example 10

Synthesis of ethyl 3-amino-4-(3-pyridyl)-5-cyclopropylpyrrole-2-carboxylate

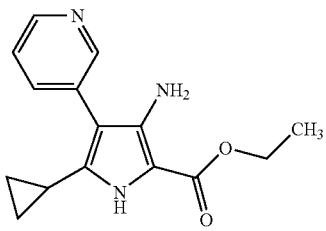

A 200 mL branched flask was charged with 7.764 g of (cyclopropyl-p-toluenesulfonyloxymethylene)methane-1-(3-pyridyl)-1-carbonitrile (22.8 mmol), and 70 mL of ethanol and 35 mL of tetrahydrofuran were added thereto, followed by adding 5.08 g of diethylaminomalonate hydrochloric acid (24 mmol) with stirring the reaction mixture at 0° C., and stirring at 0° C. for 1 hour. Subsequently, 35 mL of an ethanol solution of sodium ethoxide (5.43 g, 80 mmol) was added dropwise to the reaction solution and stirred at 0° C. for 1 hour. After the completion of the reaction, the solvent was concentrated under reduced pressure and concentrated. To the residue were added 150 mL of water and ethyl 100 mL of acetate for extraction. The aqueous layer was extracted with 50 mL of ethyl acetate. The organic layer was washed once with 100 mL of water and three times with 50 mL of saturated brine solution. The organic layer was dehydrated and dried over magnesium sulfate, filtered and concentrated to obtain 3.90 g of a crude product, which was then purified by column chromatography (silica gel 100 g; using 4:1 to 0:1 hexane/ethyl acetate as an eluent) to obtain the title compound (1.074 g, yield 17%). The NMR data and ESI/MS data of the compound are given below.

$^1$H-NMR (270 MHz, CDCl$_3$) δ(ppm): 0.60-0.95 (m, 4H) 1.30 (m, 1H), 1.36 (t, J=7.0 Hz, 3H), 4.15 (q, J=7.0 Hz, 2H), 4.35 (brds, 2H), 7.15 (m, 1H), 7.75 (m, 1H), 8.50 (m, 1H), 8.75 (s, 1H). ESI/MS m/e: 272.1 (M$^+$+H, C$_{15}$H$_{17}$N$_3$O$_2$).

Reference Example 11

Synthesis of N-{2-[4-chloro-6-(3-chloro(2-thienyl))-7-iodopyrrolo[3,2-d]pyrimidin-5-yl]ethyl}-2,2,2-trifluoroacetamide

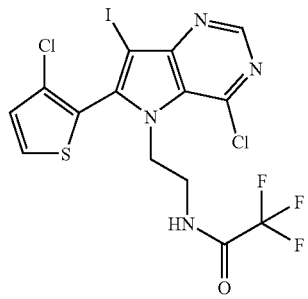

A 3.0 mL phosphorus oxychloride solution of N-{2-[6-(3-chloro(2-thienyl))-7-iodo-4-oxo(3-hydropyrrolo[3,2-d]pyrimidin-5-yl)]ethyl}-2,2,2-trifluoroacetamide (333 mg) was stirred at 110° C. for 2 hours. The reaction mixture was cooled to room temperature, and excess phosphorus oxychloride was distilled off under reduced pressure. The residue was dried in vacuo to obtain a crude product of the title compound, which was used for the subsequent reaction without further purification. The ESI/MS data of the compound are given below.

ESI/MS m/e: 535.2 (M$^+$+H, C$_{14}$H$_8$Cl$_2$F$_3$IN$_4$OS)

Reference Example 12

Synthesis of N-{2-[7-bromo-4-chloro-6-(3-chloro(2-thienyl))pyrrolo[3,2-d]pyrimidin-5-yl]ethyl}-2,2,2-trifluoroacetamide

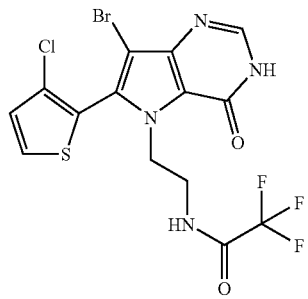

A crude product of the title compound was prepared from N-{2-[7-bromo-6-(3-chloro(2-thienyl))-4-oxo(3-hydropyrrolo[3,2-d]pyrimidin-5-yl)]ethyl}-2,2,2-trifluoroacetamide in a similar manner to that described in Reference Example 11. The ESI/MS data of the compound are given below.

ESI/MS m/e: 489.0 (M$^+$+H, C$_{14}$H$_8$BrCl$_2$F$_3$N$_4$OS)

Reference Example 13

Synthesis of N-{2-[4,7-dichloro-6-(3-chloro(2-thienyl))pyrrolo[3,2-d]pyrimidin-5-yl]ethyl}-2,2,2-trifluoroacetamide

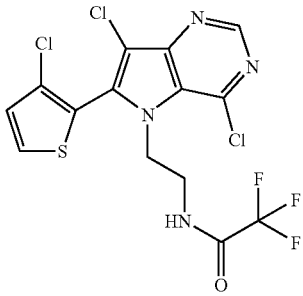

A crude product of the title compound was prepared from N-{2-[7-chloro-6-(3-chloro(2-thienyl))-4-oxo(3-hydropyrrolo[3,2-d]pyrimidin-5-yl)]ethyl}-2,2,2-trifluoroacetamide in a similar manner to that described in Reference Example 11. The ESI/MS data of the compound are given below.

ESI/MS m/e: 443.4 (M$^+$+H, C$_{14}$H$_8$Cl$_3$F$_3$N$_4$OS)

Reference Example 14

Synthesis of N-(2-{7-[(1E)-1-aza-2-(dimethylamino)vinyl]-4-chloro-6-(3-chloro(2-thienyl))pyrrolo[3,2-d]pyrimidin-5-yl}ethyl)(4-fluorophenyl)carboxyamide

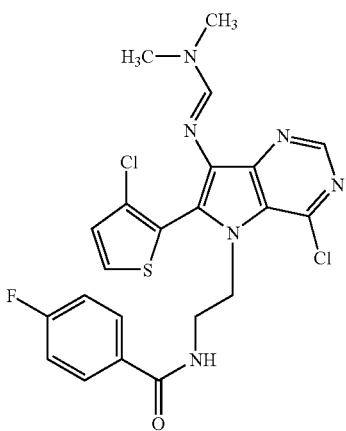

N-(6-(3-chloro(2-thienyl))-5-{2-[(4-fluorophenyl)carbonylamino]ethyl}-4-oxo(3-hydropyrrolo[3,2-d]pyrimidin-7-yl))-2,2,2-trifluoroacetamide (1.09 g) was used to obtain a crude product (0.87 g) of the title compound in the same way as Reference Example 11. NMR data and ESI/MS data of the compound are given below.

$^1$H-NMR (400 MHz, DMSO-d$_6$)δ(ppm): 2.81 (brs, 1H), 2.97 (brs, 1H), 3.28 (s, 2H), 3.37-3.45 (m, 2H), 7.17-7.27 (m, 3H), 7.55-7.68 (m, 2H), 7.86 (d, J=5.4, 1H), 8.31-8.38 (m, 1H), 8.61 (s, 1H), 8.75 (s, 1H). ESI/MS m/e: 505.4 (M$^+$+H, C$_{22}$H$_{19}$Cl$_2$FN$_6$OS)

Example 1

Synthesis of 5-{2-[(t-butoxy)carbonylamino]ethyl}-6-{3-chloro(2-thienyl)}-4-oxo-3-hydropyrrolo[3,2-d]pyrimidin-7-carboxyamide (Compound No: 950)

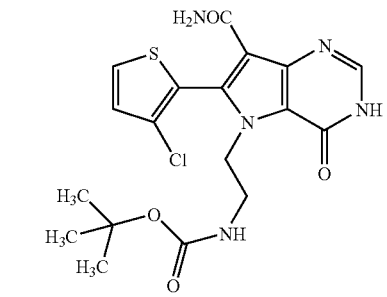

(t-butoxy)-N-{2-[6-{3-chloro(2-thienyl)}-7-cyano-4-oxo(3-hydropyrrolo[3,2-d]pyrimidin-5-yl)]ethyl}carboxyamide (3.0 g) was dissolved in ethanol (100 mL), and a 5M aqueous sodium hydroxide solution (20 mL) was added thereto. A 30% hydrogen peroxide solution (30 mL) was added to the reaction mixture over 20 minutes with stirring. After stirring at 45 to 50° C. for 24 hours, 30% hydrogen peroxide solution (20 mL) was added to the reaction solution, stirred at 45 to 50° C. for 24 hours, concentrated and neutralized with 1 M hydrochloric acid, to obtain a white precipitate. The precipitate was filtered, washed, and dried under reduced pressure to obtain the title compound (2.68 g, yield 86%). The HPLC retention time, NMR data and ESI/MS data of the compound are given below.

HPLC retention time=7.2 (min) $^1$H-NMR (270 MHz, DMSO-d$_6$)δ(ppm): 1.26 (s, 9H), 3.2-3.5 (m, 2H), 3.8-4.0 (m, 1H), 4.4-4.6 (m, 2H), 6.5-6.6 (m, 1H), 7.17 (d, 1H, J=4.6 Hz), 7.2-7.3 (m, 1H), 7.91 (d, 1H, J=5.4 Hz), 8.0-8.1 (m, 1H), 12.4-12.5 (m, 1H). ESI/MS m/e: 438.3 (M$^+$+H, C$_{18}$H$_{20}$ClN$_5$O$_4$S

Example 2

Synthesis of 5-{2-[(t-butoxy)carbonylamino]ethyl}-6-cyclopropyl-4-oxo-3-hydropyrrolo[3,2-d]pyrimidin-7-carboxyamide (Compound No: 898)

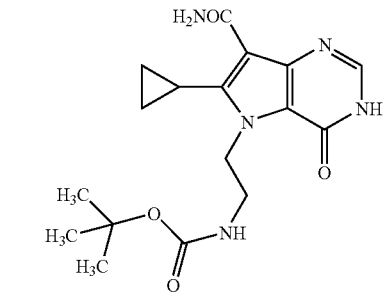

The title compound was prepared from (t-butoxy)-N-{2-[6-cyclopropyl-7-cyano-4-oxo(3-hydropyrrolo[3,2-d]pyrimidin-5-yl)]ethyl}carboxyamide in a similar manner to that described in Example 1. The ESI/MS data of the compound are given below.

ESI/MS:m/e 362.1 (M$^+$+H, C$_{17}$H$_{23}$N$_5$O$_4$)

Example 3

Synthesis of N-{2-[7-amino-6-(3-chloro(2-thienyl))-4-oxo(3-hydropyrrolo[3,2-d]pyrimidin-5-yl)]ethyl}(t-butoxy)carboxyamide (Compound No: 959)

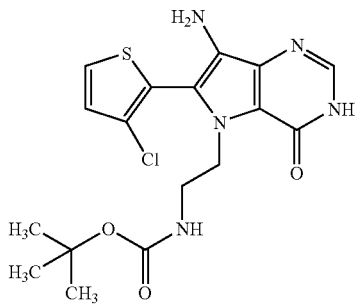

5-{2-[(t-butoxy)carbonylamino]ethyl}-6-(3-chloro(2-thienyl))₄-oxo-3-hydropyrrolo[3,2-d]pyrimidine-7-carboxyamide (110 mg) was suspended in a 1 M aqueous sodium hydroxide solution (7.5 mL), and benzyltrimethylammonium tribromide (135 mg) was added thereto and the mixture was stirred for 1.5 hours. 1 M hydrochloric acid was added to the reaction mixture to acidify the reaction system, and then washed with ethyl acetate. The aqueous layer was made alkaline with sodium hydrogen carbonate and extracted with ethyl acetate. The organic layer was washed with saturated brine, dried over anhydrous sodium sulfate, filtered, concentrated, and purified by column chromatography on silica gel (15 g) using 1:1 to 0:1 hexane:ethyl acetate as an eluent to obtain the title compound (72 mg, yield 70%). The NMR data and ESI/MS data of the compound are given below.

HPLC retention time=6.4 (min) $^1$H-NMR (270 MHz, CDCl$_3$)δ(ppm): 1.32 (s, 9H), 3.3-3.5 (m, 2H), 4.3-4.5 (m, 2H), 4.9-5.0 (m, 1H), 7.11 (d, 1H, J=5.4 Hz), 7.54 (d, 1H, J=5.4 Hz), 7.79 (brs, 1H), 10.0-10.1 (m, 1H). ESI/MS m/e: 410.3 (M$^+$+H, C$_{17}$H$_{20}$ClN$_5$O$_3$S)

Example 4

Synthesis of N-{2-[7-amino-6-cyclopropyl-4-oxo(3-hydropyrrolo[3,2-d]pyrimidin-5-yl)]ethyl}(t-butoxy)carboxyamide (Compound No: 903)

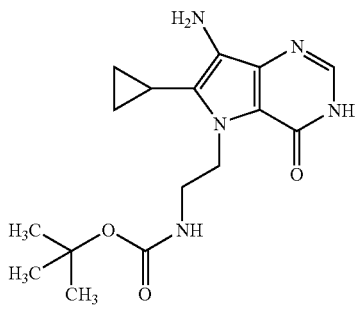

The title compound was prepared from 5-{2-[(t-butoxy)carbonylamino]ethyl}-6-cyclopropyl-4-oxo-3-hydropyrrolo[3,2-d]pyrimidin-7-carboxyamide in a similar manner to that described in Example 3. The NMR data and ESI/MS data of the compound are given below.

$^1$H-NMR (270 MHz, CDCl$_3$)δ(ppm): 1.34 (s, 9H), 0.8-1.2 (m, 5H), 3.4 (brs, 2H), 3.5-3.6 (m, 3H), 4.5-4.6 (m, 2H), 5.6 (brs, 1H), 7.8 (brs, 1H) ESI/MS m/e: 334.1 (M$^+$+H, C$_{16}$H$_{23}$N$_5$O$_3$)

Example 5

Synthesis of (t-butoxy)-N-{2-[7-bromo-6-(3-chloro(2-thienyl))-4-oxo(3-hydropyrrolo[3,2-d]pyrimidin-5-yl)]ethyl}carboxyamide (Compound No: 945)

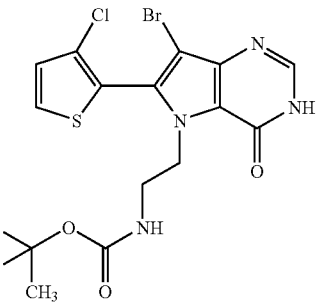

To 30 mg of N-{2-[7-amino-6-(3-chloro(2-thienyl))-4-oxo(3-hydropyrrolo[3,2-d]pyrimidin-5-yl)]ethyl}(t-butoxy)carboxyamide, 1 ml of bromoform was added, followed by adding 50 μl of isoamyl nitrite. After stirring at 70° C. for 4 hours, saturated brine was added to the reaction solution, which was extracted with ethyl acetate. The organic layer was dried over anhydrous sodium sulfate, filtered, and concentrated, followed by subjecting to thin layer chromatography on silica gel using ethyl acetate as a developing solvent to obtain the title compound (15 mg, yield 43%). The HPLC retention time, NMR data and ESI/MS data of the compound are given below.

HPLC retention time=9.5 (min) $^1$H-NMR (270 MHz, CDCl$_3$)δ(ppm): 1.31 (s, 9H), 3.3-3.5 (m, 2H) 4.2-4.3 (m, 1H), 4.5-4.7 (m, 1H), 4.7-4.9 (m, 1H), 7.13 (d, 1H, J=5.7 Hz), 7.60 (d, 1H, J=5.4 Hz), 7.94 (d, 1H, J=3.0 Hz). ESI/MS m/e 475.2 (M$^+$+H, C$_{17}$H$_{18}$BrClN$_4$O$_3$S)

Example 6

Synthesis of (t-butoxy)-N-{2-[7-bromo-6-cyclopropyl-4-oxo(3-hydropyrrolo[3,2-d]pyrimidin-5-yl)]ethyl}carboxyamide (Compound No: 2511)

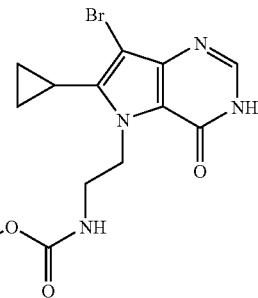

The title compound was prepared from N-{2-[7-amino-6-cyclopropyl-4-oxo(3-hydropyrrolo[3,2-d]pyrimidin-5-yl)]ethyl}(t-butoxy)carboxyamide in a similar manner to that described in Example 5. The HPLC retention time, NMR data and ESI/MS data of the compound are given below.

HPLC retention time=8.5 (min) 1H-NMR (270 MHz, CDCl$_3$)δ(ppm): 1.31 (s, 9H), 1.1-1.3 (m, 5H), 3.5-3.9 (m, 3H), 4.5-4.9 (m, 2H), 5.1-5.3 (brs, 1H), 7.9 (s, 1H) ESI/MS m/e: 397.1 (M$^+$+H, C$_{16}$H$_{21}$BrN$_4$O$_2$S)

Example 7

Synthesis of (t-butoxy)-N-{2-[6-(3-chloro(2-thienyl))-7-iodo-4-oxo(3-hydropyrrolo[3,2-d]pyrimidin-5-yl)]ethyl}carboxyamide (Compound No: 946)

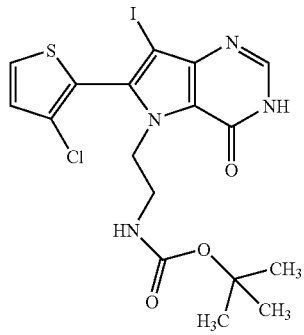

To 1 g of N-{2-[7-amino-6-(3-chloro(2-thienyl))-4-oxo(3-hydropyrrolo[3,2-d]pyrimidin-5-yl)]ethyl}(t-butoxy)carboxyamide, 7 mL of diiodomethane was added, followed by adding 822 µl of isoamyl nitrite. After stirring at 70° C. for 4 hours, saturated brine was added to the reaction solution, which was extracted with ethyl acetate. The organic layer was dried over anhydrous sodium sulfate, filtered, and concentrated, followed by subjecting to chromatography on silica gel (using 5:1 to 0:1 hexane/ethyl acetate as an eluent), to yield the title compound (694 g, yield: 55%). NMR data and ESI/MS data of the compound are given below.

HPLC retention time=9.6 (min) $^1$H-NMR (270 MHz, CDCl$_3$)δ(ppm): 1.32 (s, 9H), 3.3-3.5 (m, 2H), 4.2-4.35 (m, 1H), 4.6-4.75 (m, 1H), 4.8-5.0 (m, 1H), 7.14 (d, 1H, J=5.4 Hz), 7.59 (d, 1H, J=5.7 Hz), 7.95-8.05 (m, 1H). ESI/MS m/e 521.3 (M$^+$+H, C$_{17}$H$_{18}$ClIN$_4$O$_3$S Example 8

Synthesis of (t-butoxy-N-{2-[7-iodo-6-cyclopropyl]-4-oxo(3-hydropyrrolo[3,2-d]pyrimidin-5-yl)}Ethyl)carboxyamide (Compound No: 896)

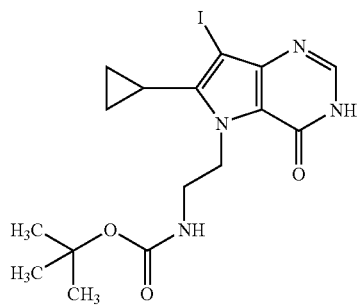

The title compound was prepared from N-{2-[7-amino-6-cyclopropyl-4-oxo(3-hydropyrrolo[3,2-d]pyrimidin-5-yl)]ethyl}(t-butoxy)carboxyamide in a similar manner to that described in Example 7. The HPLC retention time, NMR data and ESI/MS data of the compound are given below.

HPLC retention time=8.7 (min) $^1$H-NMR (270 MHz, CDCl$_3$)δ(ppm): 1.31 (s, 9H), 1.0-1.3 (m, 5H), 3.5-3.8 (m, 3H), 4.7-4.9 (m, 2H), 5.2-5.3 (brs, 1H), 7.9 (s, 1H) ESI/MS m/e: 445.4 (M$^+$+H, C$_{16}$H$_{21}$IN$_4$O$_3$)

Example 9

Synthesis of (t-butoxy)-N-{2-[7-chloro-6-(3-chloro(2-thienyl))-4-oxo(3-hydropyrrolo[3,2-d]pyrimidin-5-yl)]ethyl}carboxyamide (Compound No: 944)

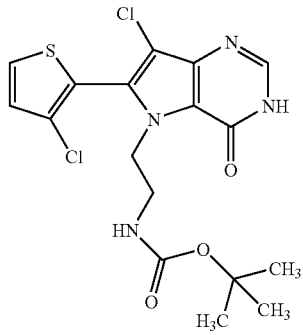

To 20 mg of N-{2-[7-amino-6-(3-chloro(2-thienyl))-4-oxo(3-hydropyrrolo[3,2-d]pyrimidin-5-yl)]ethyl}(t-butoxy)carboxyamide, 2 ml of carbon tetrachloride was added, followed by adding 34 µl of isoamyl nitrite. After refluxing for 40 hours, saturated brine was added to the reaction solution, which was extracted with ethyl acetate. The organic layer was dried over anhydrous sodium sulfate, filtered, and concentrated, followed by subjecting to thin layer chromatography on silica gel (using ethyl acetate as a developing solvent) to obtain the title compound (5 mg, yield: 24%). The HPLC retention time, NMR data and ESI/MS data of the compound are given below.

HPLC retention time=9.4 (min) $^1$H-NMR (270 MHz, CDCl$_3$)δ(ppm): 1.32 (s, 9H), 3.3-3.5 (m, 2H), 4.15-4.4 (m, 1H), 4.6-4.75 (m, 1H), 4.8-4.95 (m, 1H), 7.13 (d, 1H, J=5.4 Hz), 7.60 (d, 1H, J=5.4 Hz), 7.98 (brs, 1H). ESI/MS m/e 429.4 (M$^+$+H, C$_{17}$H$_{18}$Cl$_2$N$_4$O$_3$S)

Example 10

Synthesis of (t-butoxy)-N-{2-[6-(3-chloro(2-thienyl))-4-oxo(3-hydropyrrolo[3,2-d]pyrimidin-5-yl)]ethyl}carboxyamide (Compound No. 943)

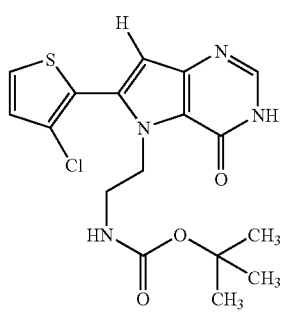

To 15 mg of N-{2-[7-amino-6-(3-chloro(2-thienyl))-4-oxo(3-hydropyrrolo[3,2-d]pyrimidin-5-yl)]ethyl}(t-butoxy)carboxyamide, 2 mL of tetrahydrofuran was added, followed by adding 50 µl of isoamyl nitrite. After stirring at 50° C. for 3

Example 11

Synthesis of 5-(2-aminoethyl)-6-(3-chloro(2-thienyl))-7-iodo-3-hydropyrrolo[3,2-d]pyrimidin-4-one hydrochloride (Compound No. 206)

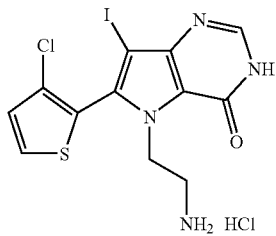

hours, saturated brine was added to the reaction solution, which was extracted with ethyl acetate. The organic layer was dried over anhydrous sodium sulfate, filtered, and concentrated, followed by subjecting to thin layer chromatography on silica gel (developing solvent: ethyl acetate) to obtain the title compound (8 mg, yield 55%). The NMR data and ESI/MS data of the compound are given below.

HPLC retention time=8.4 (min) $^1$H-NMR (270 MHz, CDCl$_3$) δ(ppm): 1.31 (s, 9H), 3.3-3.5 (m, 2H) 4.4-4.6 (m, 2H), 5.01 (brs, 1H), 6.66 (s, 1H), 7.07 (d, 1H, J=5.4 Hz), 7.49 (d, 1H, J=5.1 Hz), 7.93 (brs, 1H), 11.2-11.3 (m, 1H). ESI/MS m/e 395.2 ($M^+$+H, $C_{17}H_{19}ClN_4O_3S$)

(t-butoxy)-N-{2-[6-(3-chloro(2-thienyl))-7-iodo-4-oxo(3-hydropyrrolo[3,2-d]pyrimidin-5-yl)]ethyl}carboxyamide (331 mg) was dissolved in a mixed solution of methanol (0.5 mL) and 1,4-dioxane (5.0 mL), and hydrochloric acid/1,4-dioxane solution (4 mol/L, 0.64 mL) was added and the mixture was stirred at 60° C. for 2 hours. The reaction mixture was cooled to room temperature, and the solvent was distilled off under reduced pressure. The residue was dried under reduced pressure to obtain the title compound (334 mg in a quantitative yield). The ESI/MS data of the compound are given below.

ESI/MS m/e: 421.2 ($M^+$+H, $C_{12}H_{10}ClN_4OS$ HCl)

Example 12

Synthesis of 5-(2-aminoethyl)-7-bromo-6-(3-chloro(2-thienyl))-3-hydropyrrolo[3,2-d]pyrimidin-4-one hydrochloride (Compound No. 205)

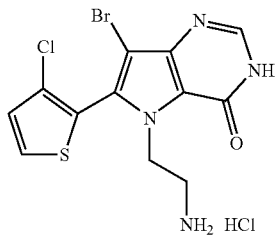

The title compound was prepared from (t-butoxy)-N-{2-[7-bromo-6-(3-chloro(2-thienyl))-4-oxo(3-hydropyrrolo[3,2-d]pyrimidin-5-yl)]ethyl}carboxyamide in a similar manner to that described in Example 11. The ESI/MS data of the compound are given below.

ESI/MS m/e: 375.0 ($M^+$+H, $C_{12}H_{10}BrClN_4OS$ HCl)

Example 13

Synthesis of 5-(2-aminoethyl)-7-chloro-6-(3-chloro(2-thienyl))-3-hydropyrrolo[3,2-d]pyrimidin-4-one hydrochloride (Compound No. 204)

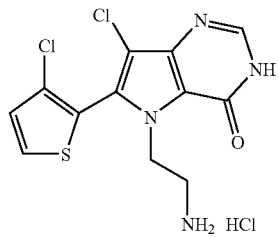

The title compound was prepared from (t-butoxy)-N-{2-[7-chloro-6-(3-chloro(2-thienyl))-4-oxo(3-hydropyrrolo[3,2-d]pyrimidin-5-yl)]ethyl}carboxyamide in a similar manner to that described in Example 11. The ESI/MS data of the compound are given below.

ESI/MS m/e: 329.4 ($M^+$+H, $C_{12}H_{10}Cl_2N_4OS$ HCl)

Example 14

Synthesis of N-{2-[6-(3-chloro(2-thienyl))-7-iodo-4-oxo(3-hydropyrrolo[3,2-d]pyrimidin-5-yl)]ethyl}-2,2,2-trifluoroacetamide (Compound No. 320)

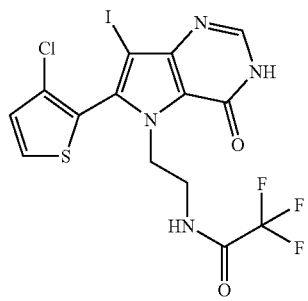

To a tetrahydrofuran (5.0 mL) solution of 5-(2-aminoethyl)-6-(3-chloro(2-thienyl))-7-iodo-3-hydropyrrolo[3,2-d]pyrimidin-4-one hydrochloride (259 mg) was added trifluoroacetic anhydride (595 mg), and triethylamine (1.2 mL) was added slowly dropwise. The reaction mixture was stirred at room temperature for 2 hours, and methanol was added to stop the reaction. The solvent was distilled off under reduced pressure. To the residue were added water and ethyl acetate, which was extracted 3 times with ethyl acetate. The organic layer was washed with saturated brine, and dried over anhydrous magnesium sulfate. After anhydrous magnesium sulfate was filtered off, the solvent was distilled off under reduced pressure. The residue was dried under reduced to obtain a crude product (365 mg) of the title compound. The HPLC retention time, NMR data and ESI/MS data of the compound are given below.

HPLC retention time=9.1 (min) $^1$H-NMR (400 MHz, DMSO-d$_6$)δ(ppm): 3.45 (m, 2H), 4.16 (m, 1H) 4.61 (m, 1H), 7.30 (m, 1H), 7.93 (m, 1H), 8.02 (m, 1H), 9.37 (m, 1H), 12.29 (brs, 1H). ESI/MS m/e: 517.2 ($M^+$+H, $C_{14}H_9ClF_{31}N_4O_2S$)

Example 15

Synthesis of N-{2-[7-bromo-6-(3-chloro(2-thienyl))-4-oxo(3-hydropyrrolo[3,2-d]pyrimidin-5-yl)]ethyl}-2,2,2-trifluoroacetamide (Compound No. 319)

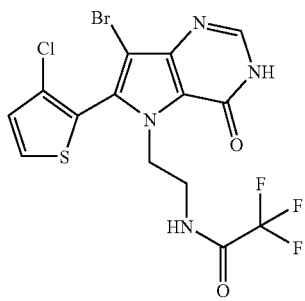

The title compound was prepared from 5-(2-aminoethyl)-7-bromo-6-(3-chloro(2-thienyl))-3-hydropyrrolo[3,2-d]pyrimidin-4-one hydrochloride in a similar manner to that described in Example 14. The ESI/MS data of the compound are given below.

ESI/MS m/e: 471.1 (M$^+$+H, C$_{14}$H$_9$BrClF$_3$N$_4$O$_2$S)

Example 16

Synthesis of N-{2-[7-chloro-6-(3-chloro(2-thienyl))-4-oxo(3-hydropyrrolo[3,2-d]pyrimidin-5-yl)]ethyl}-2,2,2-trifluoroacetamide (Compound No. 318)

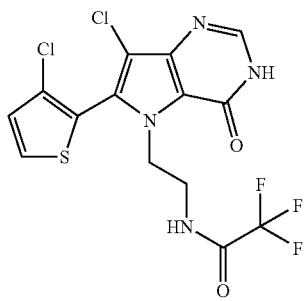

The title compound was prepared from 5-(2-aminoethyl)-7-chloro-6-(3-chloro(2-thienyl))-3-hydropyrrolo[3,2-d]pyrimidin-4-one hydrochloride in a similar manner to that described in Example 14. The ESI/MS data of the compound are given below.

ESI/MS m/e: 425.4 (M$^+$+H, C$_{14}$H$_9$Cl$_2$F$_3$N$_4$O$_2$S)

Example 17

Synthesis of N-{2-[6-(3-chloro(2-thienyl))-7-iodo-4-oxo(3-hydropyrrolo[3,2-d]pyrimidin-5-yl)]ethyl}(4-fluorophenyl)carboxyamide (Compound No. 344)

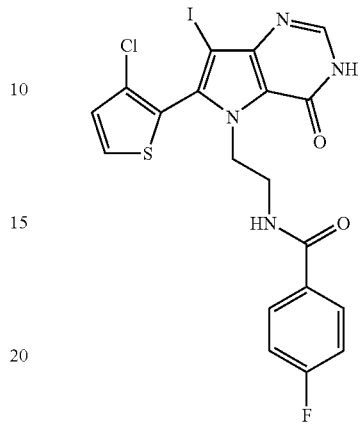

To an N,N-dimethylacetamide (2.0 mL) solution of 5-(2-aminoethyl)-6-(3-chloro(2-thienyl))-7-iodo-3-hydropyrrolo[3,2-d]pyrimidin-4-one hydrochloride (33 mg) was added 4-fluorobenzoylchloride (23 mg), and the mixture was stirred at room temperature for a short time, followed by adding triethylamine (0.2 mL) and stirring at room temperature for 2 hours. To the reaction solution was added water (0.2 mL), and the solution was stirred again at room temperature overnight. The solvent was distilled off under reduced pressure, and the residue was purified by fraction HPLC to obtain the title compound (22 mg, yield 55%). The HPLC retention time, NMR data and ESI/MS data of the compound are given below.

HPLC retention time=9.1 (min) $^1$H-NMR (400 MHz, DMSO-d$_6$) δ(ppm): 3.52 (m, 2H), 4.24 (m, 1H), 4.63 (m, 1H), 7.19-7.26 (m, 3H), 7.70-7.74 (m, 2H), 7.88-7.92 (m, 2H), 8.45 (m, 1H), 12.24 (brs, 1H). ESI/MS m/e: 543.4 (M$^+$+H, C$_{19}$H$_{13}$ClFIN$_4$O$_2$S)

Example 18

Synthesis of 6-(3-chloro(2-thienyl))-7-iodo-5-[2-(quinazolin-4-ylamino)ethyl]-3-hydropyrrolo[3,2-d]pyrimidin-4-one (Compound No. 81)

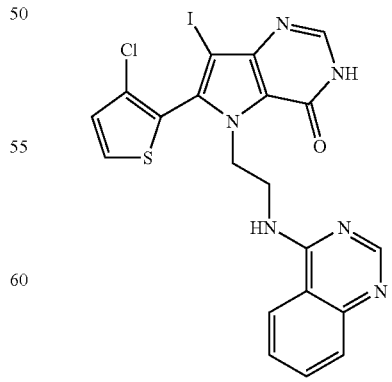

To an N,N-dimethylacetamide (2.0 mL) solution of 5-(2-aminoethyl)-6-(3-chloro(2-thienyl))-7-iodo-3-hydropyrrolo

[3,2-d]pyrimidin-4-one hydrochloride (36 mg) and 4-chloroquinazoline (10 mg), was added triethylamine (16 mg) and the mixture was stirred at 70° C. for 2 hours. Triethylamine (32 mg) was further added to the reaction mixture and stirred at 70° C. for 2 hours. The reaction mixture was cooled to room temperature and purified by fraction HPLC to obtain the title compound (21 mg, yield 49%). The HPLC retention time, NMR data and ESI/MS data of the compound are given below.

HPLC retention time: 6.9 (min) $^1$H-NMR (400 MHz, DMSO-$d_6$)δ(ppm): 3.95 (m, 2H), 4.48 (m, 1H) 4.87 (m, 1H), 7.12 (m, 1H), 7.71-7.82 (m, 3H), 7.87 (brs, 1H), 8.00 (t, J=7.7, 1H), 8.18 (d, J=8.3, 1H), 8.60 (s, 1H), 9.91 (brs, 1H), 12.24 (brs, 1H). ESI/MS m/e: 549.4 (M$^+$+H, $C_{20}H_{14}ClIN_6OS$)

Example 19

Synthesis of N-(5-{2-[(t-butoxy)carbonylamino]ethyl}-6-(3-chloro(2-thienyl))-4-oxo(3-hydropyrrolo[3,2-d]pyrimidin-7-yl))-2,2,2-trifluoroacetamide (Compound No. 962)

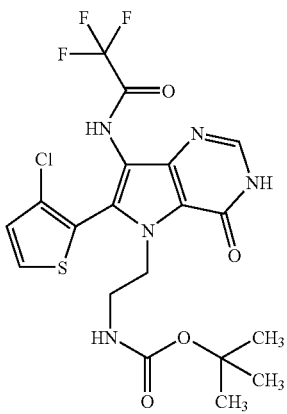

To a tetrahydrofuran solution (39 mL) of N-{2-[7-amino-6-(3-chloro(2-thienyl))-4-oxo(3-hydropyrrolo[3,2-d]pyrimidin-5-yl)]ethyl}(t-butoxy)carboxyamide (1.60 g) was added triethylamine (2.7 mL), and cooled to 0° C., followed by adding trifluoroacetic anhydride (1.35 mL) slowly dropwise. The reaction mixture was stirred at room temperature for 1 hour, and saturated brine was added dropwise to stop the reaction. Ethyl acetate was added to the reaction solution for extraction. The organic layer was washed with saturated brine, dried over anhydrous magnesium sulfate and filtered. The solvent was distilled off under reduced pressure to obtain the title compound (1.97 g, a quantitative yield) as a light yellow solid. The HPLC retention time, NMR data and ESI/MS data of the compound are given below.

HPLC retention time=8.7 (min) $^1$H-NMR (400 MHz, DMSO-$d_6$)δ(ppm): 1.26 (s, 9H), 3.13-3.26 (m, 2H), 4.11 (brs, 1H), 4.49 (brs, 1H), 6.60-6.73 (m, 1H), 7.23 (d, J=5.4, 1H), 7.88 (s, 1H), 7.95 (d, J=5.4, 1H), 10.86 (s, 1H), 12.21 (brs, 1H). ESI/MS m/e: 506.4 (M$^+$+H, $C_{19}H_{19}ClF_3N_5O_4S$)

Example 20

Synthesis of N-[5-(2-aminoethyl)-6-(3-chloro(2-thienyl))-4-oxo(3-hydropyrrolo[3,2-d]pyrimidin-7-yl)]-2,2,2-trifluoroacetamide hydrochloride (Compound No. 207)

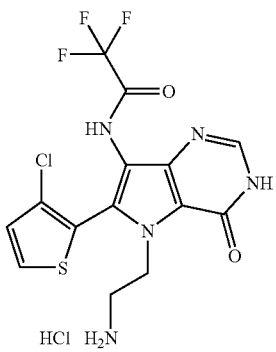

A methanol solution (13 mL) of N-(5-{2-[(t-butoxy)carbonylamino]ethyl}-6-(3-chloro(2-thienyl))-4-oxo(3-hydropyrrolo[3,2-d]pyrimidin-7-yl))-2,2,2-trifluoroacetamide (1.97 g) was cooled to 0° C. and added was 4 mol/L hydrochloric acid/1,4-dioxane solution (26 mL), followed by stirring at room temperature for 4 hours. The solvent was distilled off under reduced pressure, yielding a crude product (1.73 g) of the title compound. The ESI/MS data of the compound are given below.

ESI/MS m/e: 406.3 (M$^+$+H, $C_{14}H_{11}F_3N_5O_2S$.HCl)

Example 21

Synthesis of N-(6-(3-chloro(2-thienyl))-5-{2-[(4-fluorophenyl)carbonylamino]ethyl}-4-oxo(3-hydropyrrolo[3,2-d]pyrimidin-7-yl))-2,2,2-trifluoroacetamide (Compound No. 345)

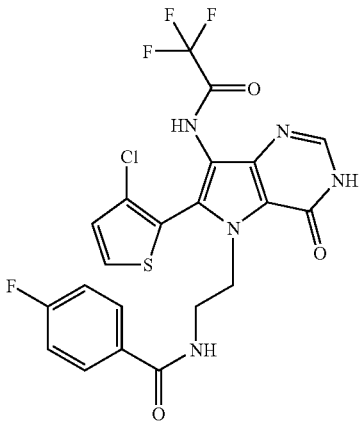

N-[5-(2-aminoethyl)-6-(3-chloro(2-thienyl))-4-oxo(3-hydropyrrolo[3,2-d]pyrimidin-7-yl)]-2,2,2-trifluoro-acetamide crude product (1.73 g) in pyridine (39 mL) was cooled to 0° C., and 4-fluorobenzoylchloride (0.92 mL) was added thereto, followed by stirring at room temperature for 1 hour. To the reaction solution was added water (40 mL), stirred at room temperature for 1 hour, and to stop the reaction. Brine was added until the reaction solution was saturated, and extraction with ethyl acetate was performed. The organic layer was washed with a mixed solution of saturated brine and 1 mol/L of hydrochloric acid (9:1), dried over anhydrous sodium sulfate and filtered. The solvent was distilled off under reduced pressure and purified by column chromatography on silica gel using 1/2 hexane/ethyl acetate and then using ethyl acetate only as eluents to obtain the title compound (1.60 g, 78% yield for 2 steps). The HPLC retention time, NMR data and ESI/MS data of the compound are given below.

HPLC retention time=8.3 (min) $^1$H-NMR (400 MHz, DMSO-d$_6$)δ(PPM): 3.49-3.58 (m, 2H) 4.34 (brs, 1H), 4.66 (brs, 1H), 7.16 (d, J=5.4, 1H), 7.19 (t, J=7.1, 2H), 7.65-7.75 (m, 2H), 7.83 (d, J=5.4, 1H), 7.88 (s, 1H), 8.40-8.50 (m, 1H), 10.85 (s, 1H), 12.25 (brs, 1H). ESI/MS m/e: 528.4 (M$^+$+H, $C_{21}H_{14}ClF_4N_5O_3S$)

Example 22

Synthesis of (t-butoxy)-N-{2-[6-(3-chloro(2-thienyl))-4-oxo-7-(phenylcarbonylamino)(3-hydropyrrolo[3,2-d]pyrimidin-5-yl)]ethyl}carboxyamide (Compound No. 965)

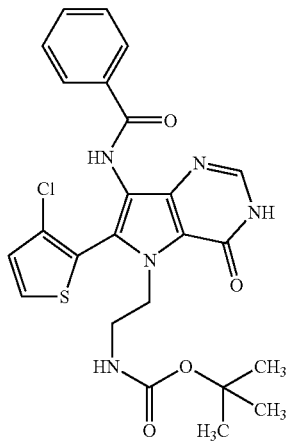

To a tetrahydrofuran solution (10 mL) of N-{2-[7-amino-6-(3-chloro(2-thienyl))-4-oxo(3-hydropyrrolo[3,2-d]pyrimidin-5-yl)]ethyl}(t-butoxy)carboxyamide (0.41 g) was added triethylamine (0.69 mL), and the reaction mixture was cooled to 0° C. and benzoylchloride (0.29 mL) was added slowly dropwise. The reaction mixture was stirred at room temperature for 1 hour, and an aqueous sodium hydroxide solution (2 mol/L, 2.0 mL) was added dropwise and stirred for 18 hours to stop the reaction. Hydrochloric acid (1 mol/L, 4.0 mL) was added to the reaction solution for neutralization, brine was added thereto until the reaction solution was saturated, and extraction with ethyl acetate was performed. The organic layer was washed with saturated brine, dried over anhydrous sodium sulfate and filtered. The solvent was distilled off under reduced pressure, and purified by column chromatography was performed on silica gel using ethyl acetate only to obtain the title compound (0.51 g, a quantitative yield). The ESI/MS data of the compound are given below.

ESI/MS m/e: 514.4 (M$^+$+H, $C_{24}H_{24}ClN_5O_4S$)

Example 23

Synthesis of N-[5-(2-aminoethyl)-6-(3-chloro(2-thienyl))-4-oxo(3-hydropyrrolo[3,2-d]pyrimidin-7-yl)]benzamide hydrochloride (Compound No. 208)

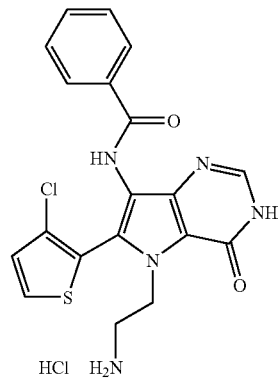

To a methanol solution (3.3 mL) of (t-butoxy)-N-{2-[6-(3-chloro(2-thienyl))-4-oxo-7-(phenylcarbonylamino)(3-hydropyrrolo[3,2-d]pyrimidin-5-yl)]ethyl}carboxyamide (0.51 g) was added 4 mol/L hydrochloric acid/1,4-dioxane solution (6.6 mL) and the mixture was stirred at room temperature for 5 hours. The solvent was distilled off under reduced pressure, yielding a crude product (0.47 g) of the title compound. The ESI/MS data of the compound are given below.

ESI/MS m/e: 414.3 (M$^+$+H, $C_{19}H_{16}ClN_5O_2$.HCl)

Example 24

Synthesis of N-{2-[6-(3-chloro(2-thienyl))-4-oxo-7-(phenylcarbonylamino)(3-hydropyrrolo[3,2-d]pyrimidin-5-yl)]ethyl}(4-fluorophenyl)carboxyamide (Compound No. 346)

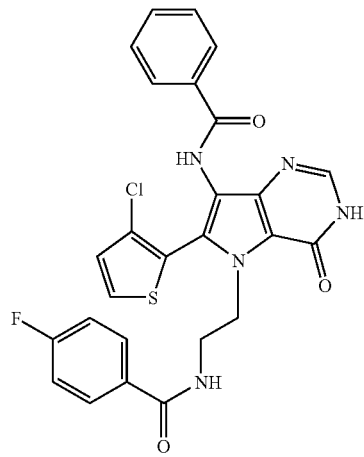

To a dimethylacetamide solution (1.0 mL) of N-[5-(aminoethyl)-6-(3-chloro(2-thienyl))-4-oxo(3-hydropyrrolo[3,2-d]pyrimidin-7-yl)]benzamide (45 mg), were added 4-fluorobenzoylchloride (23.6 μL) and triethylamine (55 μL) and the mixture was stirred at room temperature for 1 hour. 2 mol/L of an aqueous sodium hydroxide solution (1.0 mL) was added dropwise, and the solution was stirred for 1 hour and stopped the reaction. 1 mol/L of hydrochloric acid (2.0 mL) was added to the reaction solution for neutralization, brine was added thereto until the reaction solution was saturated, and extraction with ethyl acetate was performed. The organic layer was washed with saturated brine, dried over anhydrous sodium sulfate and filtered. The solvent was distilled off under reduced pressure, and purified by fraction HPLC to obtain the title compound (25.5 mg, yield 48%). The HPLC retention time, NMR data and ESI/MS data of the compound are given below.

HPLC retention time=8.2 (min) $^1$H-NMR (400 MHz, DMSO-$d_6$) δ(ppm): 3.50-3.70 (m, 2H), 4.35 (brs, 1H), 4.68 (brs, 1H), 7.12 (d, J=5.4, 1H), 7.22 (t, J=8.8, 2H), 7.44 (t, J=7.3, 2H), 7.47-7.56 (m, 1H), 7.69-7.78 (m, 3H), 7.84 (d, J=7.6, 2H), 7.89 (s, 1H), 8.47 (t, J=5.4, 1H), 9.72 (s, 1H), 12.22 (brs, 1H). ESI/MS m/e: 536.4 (M$^+$+H, $C_{26}H_{19}ClFN_5O_3S$)

Example 25

Synthesis of N-{6-(3-chloro(2-thienyl))-4-oxo-5-[2-(quinazolin-4-ylamino)ethyl](3-hydropyrrolo[3,2-d]pyrimidin-7-yl)}benzamide (Compound No. 82)

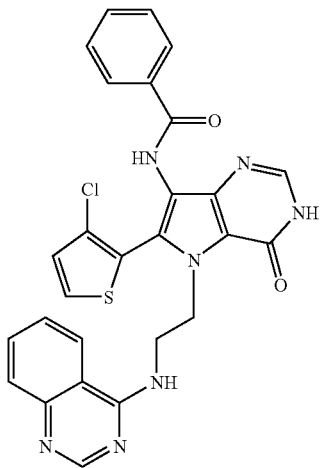

N-[5-(aminoethyl)-6-(3-chloro(2-thienyl))-4-oxo(3-hydropyrrolo[3,2-d]pyrimidin-7-yl)]benzamide (45 mg) and 4-chloroquinazoline (16.5 mg) were dissolved in dimethylacetamide (2.9 mL), and triethylamine (27.7 µL) was added thereto and the mixture was stirred at 70° C. for 3 hours. Triethylamine (13.9 µL) was further added to the reaction mixture and the solution was stirred at 70° C. for 5 hours. The reaction solution was cooled to room temperature and purified by fraction HPLC, to obtain the title compound (44.3 mg, 82%). The HPLC retention time, NMR data and ESI/MS data of the compound are given below.

HPLC retention time=6.4 (min) $^1$H-NMR (400 MHz, DMSO-$d_6$)δ(ppm): 3.95-4.05 (m , 2H), 4.52 (brs, 1H), 5.00 (brs, 1H), 7.05 (d, J=5.4, 1H), 7.43 (t, J=7.6, 2H), 7.52 (t, J=7.3, 1H), 7.65 (d, J=5.4, 1H), 7.70-7.85 (m, 5H), 8.02 (t, J=7.8, 1H), 8.23 (d, J=8.5, 1H), 8.61 (s, 1H), 9.66 (s, 1H), 10.17 (m, 1H), 12.10 (brs, 1H). ESI/MS m/e: 542.4 (M$^+$+H, $C_{27}H_{20}ClN_7O_2S$)

Example 26

Synthesis of (t-butoxy)-N-{2-[6-(3-chloro(2-thienyl))-4-oxo-7-vinyl(3-hydropyrrolo[3,2-d]pyrimidin-5-yl)]ethyl}carboxyamide (Compound No. 966)

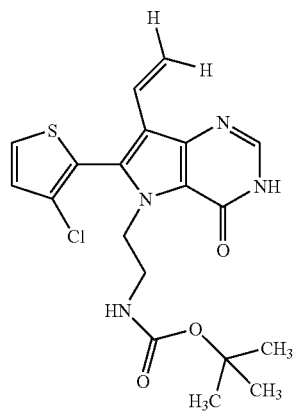

A nitrogen flushed flask was charged with a 0.5 M zinc chloride/tetrahydrofuran solution, and 1.0 mL of a 1.0 M vinyl magnesium bromide/tetrahydrofuran solution was added thereto with stirring, the mixture solution was stirred for 30 minutes, to obtain a suspension which was used in a subsequent reaction. To a round-bottom flask, were transferred 26 mg of (t-butoxy)-N-{2-[6-(3-chloro(2-thienyl))-4-oxo-7-iodo(3-hydropyrrolo[3,2-d]pyrimidin-5-yl)]ethyl}carboxyamide and 12 mg of tetrakistriphenylphosphine palladium (O), followed by flushing with nitrogen and adding 2 mL dry tetrahydrofuran thereto. 600 µl of the suspension was added to the reaction mixture and the mixture was stirred at 50° C. for 8 hours, and saturated brine was added thereto and extracted with ethyl acetate. The organic layer was dried over anhydrous sodium sulfate, filtered and concentrated. The obtained crude product was subjected to chromatography on silica gel (eluent: 5:1 to 0:1 hexane:ethyl acetate), to obtain the title compound (5.5 mg, yield 26%). The HPLC retention time and ESI/MS data of the compound are given below.

HPLC retention time=9.6 (min) EMS/MS m/e 421.2 (M$^+$+H, $C_{19}H_{21}ClN_4O_3S$)

Example 27

Synthesis of (t-butoxy)-N-{2-[6-(3-chloro(2-thienyl))-7-(3-hydroxy-1-prop-1-ynyl)-4-oxo(3-hydropyrrolo[3,2-d]pyrimidin-5-yl)]ethyl}carboxyamide (Compound No. 971)

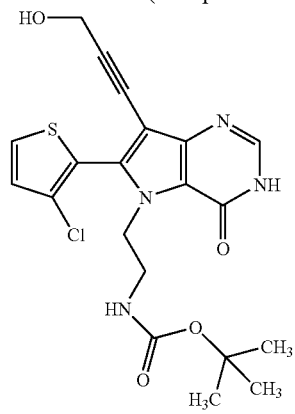

A round-bottom flask was charged with 26 mg of (t-butoxy)-N-{2-[6-(3-chloro(2-thienyl))-4-oxo-7-iodo(3-hydropyrrolo[3,2-d]pyrimidin-5-yl)]ethyl}carboxyamide, 12 mg of tetrakistriphenylphosphine palladium, 3.8 mg of copper (I) iodide and 15 μl of propargyl alcohol, followed by flushing with nitrogen, and 1 mL of dry tetrahydrofuran and 209 μl of triethylamine were added thereto. The reaction mixture was stirred at 50° C. for 5 hours, and saturated brine was added thereto and extracted with ethyl acetate. The organic layer was concentrated and subjected to column chromatography on silica gel, (developing solvent: 10 mL of toluene to 8 mL of ethyl acetate:methanol=2:1). A portion eluted by ethyl acetate/methanol was concentrated and subjected to fraction HPLC to obtain the title compound. The HPLC retention time and ESI/MS data of the compound are given below.

HPLC retention time=9.0 (min) EMS/MS m/e 448.9 (M+H$^+$, $C_{20}H_{21}ClN_4O_4S$)

Example 28

Synthesis of N-{2-[7-benzo[d]furan-2-yl-6-(3-chloro (2-thienyl))-4-oxo(3-hydropyrrolo[3,2-d]pyrimidin-5-yl)]ethyl}(t-butoxy)carboxyamide (Compound No. 1000)

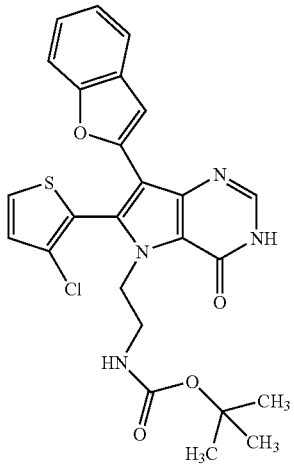

A round-bottom flask was charged with 26 mg of (t-butoxy)-N-{2-[6-(3-chloro(2-thienyl))-4-oxo-7-iodo(3-hydropyrrolo[3,2-d]pyrimidin-5-yl)]ethyl}carboxyamide, 2.2 mg of palladium acetate, triphenylphosphine, 26 mg of sodium carbonate and 16.2 mg of 2-benzofuranyl boric acid and flushed with nitrogen. 1 mL of a solution containing dimethylformamide and water mixed in a ratio of 2:1 was added to the reaction mixture and the mixture was stirred at 80° C. for 24 hours, and saturated brine was added thereto and extracted with ethyl acetate. The organic layer was concentrated and subjected to chromatography on silica gel, (developing solvent: 10 mL of toluene to 8 mL of ethyl acetate/methanol=2: 1). A portion eluted by ethyl acetate/methanol was concentrated and subjected to fraction HPLC to obtain the title compound. The HPLC retention time and ESI/MS data of the compound are given below.

HPLC retention time=11.6 (min) EMS/MS m/e 511.3 (M+H$^+$, $C_{25}H_{23}ClN_4O_4S$)

Example 29

Synthesis of N-{2-[6-(3-chloro-thiophen-2-yl)-7-iodo-4-oxo-3-hydropyrrolo[3,2-d]pyrimidin-5-yl] ethyl}-t-butylacetylamide (Compound No. 625)<

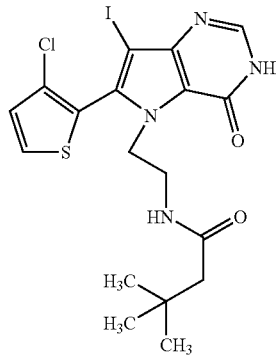

To an N,N-dimethylacetamide solution (5.0 mL) of 5-(2-aminoethyl)-6-(3-chloro-thiophen-2-yl)-7-iodo-3-hydropyrrolo[3,2-d]pyrimidin-4-one hydrochloride (173 mg) was added t-butylacetyl chloride (95 mg) and the mixture was stirred at room temperature for a short time, followed by adding triethylamine (1.0 mL) and stirring at room temperature for 2 hours. To the reaction solution was added water (1.0 mL) and further the solution was stirred at room temperature overnight. The obtained solution was extracted with ethyl acetate (10 mL×2). The organic layer was washed with saturated brine, and the solvent was distilled off under reduced pressure. The obtained crude product was purified by column chromatography on silica gel (using ethyl acetate only) to obtain the title compound (160 mg, yield: 88%). The NMR data and ESI/MS data of the compound are given below.

$^1$H-NMR (400 MHz, DMSO-d$_6$) δ(ppm): 0.84 (s, 9H), 1.81 (d, J=3.67, 2H), 3.25-3.34 (m, 2H), 4.05-4.12 (m, 1H), 4.44-4.50 (m, 1H), 7.28 (d, J=5.36, 1H), 7.69 (t, J=5.86, 1H), 7.92 (d, J=3.67, 1H), 8.00 (d, J=5.36, 1H), 12.25 (brs, 1H). ESI/MS m/e: 519.1 (M$^+$+H, $C_{18}H_{20}ClN_4O_2S$)

Example 30

Synthesis of N-{2-[7-(1H-pyrazol-4-yl)-6-(3-chloro-thiophen-2-yl)-4-oxo-3-hydropyrrolo[3,2-d]pyrimidin-5-yl]ethyl}-t-butylacetylamide (Compound No. 629)

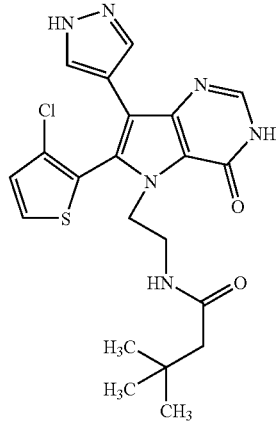

To a screw-cap vial were transferred N-{2-[6-(3-chloro-thiophen-2-yl)-4-oxo-7-iodo-3-hydropyrrolo[3,2-d]pyrimidin-5-yl]ethyl}-t-butylacetylamide (26 mg), palladium acetate (2.2 mg), triphenylphosphine (5.2 mg), sodium carbonate (26 mg) and 4-(4,4,5,5,-tetramethyl-[1,3,2]-dioxaborolan-2-yl)-1H-pyrazole (19.4 mg), and flushed with nitrogen. A 2:1 dimethylformamide:water solution (1 mL) was added to the reaction mixture and the mixture was stirred at 80° C. for 12 hours. Saturated brine was added to the obtained solution and extracted with ethyl acetate. The organic layer was concentrated and purified by fraction HPLC to obtain the title compound (5.2 mg, yield 23%). The HPLC retention time, NMR data and ESI/MS data of the compound are given below.

HPLC retention time=10.9 (min) $^1$H-NMR (400 MHz, DMSO-$d_6$) δ(ppm): 0.85 (s, 9H), 1.84 (d, J=1.68, 2H), 3.30-3.38 (m, 2H), 4.04-4.11 (m, 1H), 4.35-4.40 (m, 1H), 7.34 (d, J=5.38, 1H), 7.44 (brs, 2H), 7.76 (t, J=5.60, 1H), 7.93 (s, 1H), 8.05 (d, J=5.38, 1H), 12.17 (brs, 1H). EMS/MS m/e 459.3 ($M+H^+$, $C_{21}H_{23}ClN_6O_2S$

Example 31

Synthesis of 5-(2-aminoethyl)-6-(3-chloro-thiophen-2-yl)-7-pyridin-3-yl-3-hydropyrrolo[3,2-d]pyrimidin-4-one (Compound No. 209) dihydrochloride

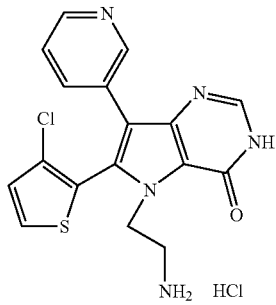

(t-butoxy)-N-{2-[6-(3-chloro-thiophen-2-yl)-7-pyridin-3-yl-4-oxo-3-hydropyrrolo[3,2-d]pyrimidin-5-yl]-ethyl}carboxyamide (1.68 g) was dissolved in methanol (10.0 mL), followed by adding 4 mol/L hydrochloric acid/1,4-dioxane solution (2.0 mL) thereto and stirring at 60° C. for 12 hours. The reaction mixture was cooled to room temperature, and the solvent was distilled off under reduced pressure. The residue was dried under reduced pressure to obtain the title compound (1.64 g, a quantitative yield). The ESI/MS data of the compound are given below.

ESI/MS m/e: 371.9 ($M^++H$, $C_{17}H_{14}ClN_5OS$ 2HCl)

Example 32

Synthesis of 1-{2-[6-(3-chloro-thiophen-2-yl)-4-oxo-7-pyridin-3-yl-3-hydropyrrolo[3,2-d]pyrimidin-5-yl]ethyl}-3-phenylurea (Compound No. 793)

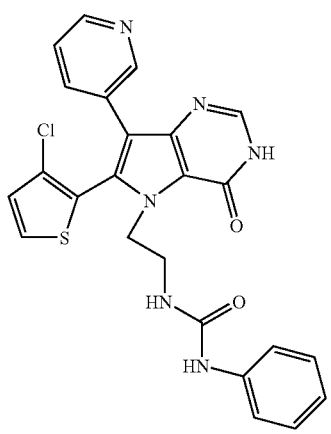

To an N,N-dimethylformamide (1.0 mL) solution of 5-(2-aminoethyl)-6-(3-chloro-thiophen-2-yl)-7-pyridin-3-yl-3-hydropyrrolo[3,2-d]pyrimidin-4-one dihydrochloride (25 mg) was added phenylisocyanate (20 mg) and the mixture was stirred at room temperature for a short time, followed by adding triethylamine (0.2 mL) and stirring at room temperature for 2 hours. Saturated brine was added to the obtained solution and extracted with ethyl acetate. The reaction solution was distilled off under reduced pressure, and the residue was purified by fraction HPLC to obtain the title compound (8 mg, yield 29%). The HPLC retention time and ESI/MS data of the compound are given below.

HPLC retention time=6.6 (min) ESI/MS m/e: 491.04 ($M^++H$, $C_{24}H_{19}ClN_6O_2S$

Example 33

Synthesis of 4-fluoropiperidine-1-{2-[6-(3-chloro-thiophen-2-yl)-4-oxo-7-pyridin-3-yl-3-hydropyrrolo[3,2-d]pyrimidin-5-yl]-ethyl}-carboxyamide (Compound No. 550)

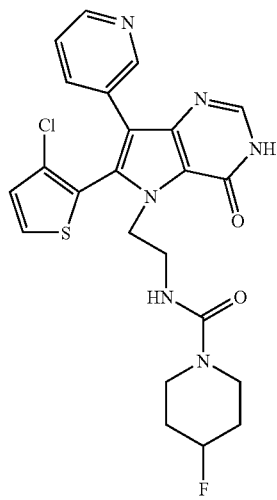

To a chloroform (1.0 mL) solution of 5-(2-aminoethyl)-6-(3-chloro-thiophen-2-yl)-7-pyridin-3-yl-3-hydropyrrolo[3,2-d]pyrimidin-4-one dihydrochloride (25 mg) were added triethylamine (0.078 mL) and triphosgene (17 mg) and the mixture was stirred at room temperature for a short time, and 4-fluoropiperidine (12 mg) was added thereto followed by stirring at room temperature for 3 hours. Saturated brine was added to the obtained solution and extracted with ethyl acetate. The reaction solution was distilled off under reduced pressure, and the residue was purified by fraction HPLC to obtain the title compound (1.2 mg, yield 5%). The HPLC retention time and ESI/MS data of the compound are given below.

HPLC retention time=6.9 (min) ESI/MS m/e: 501.41 ($M^++H$, $C_{23}H_{22}ClFN_6O_2S$)

Example 34

Synthesis of 5-[2-(bis(cyclopropylmethyl)amino) ethyl]-6-(3-chloro-thiophen-2-yl)-7-pyridin-3-yl-3-hydropyrrolo[3,2-d]pyrimidin-4-one (Compound No. 1057)

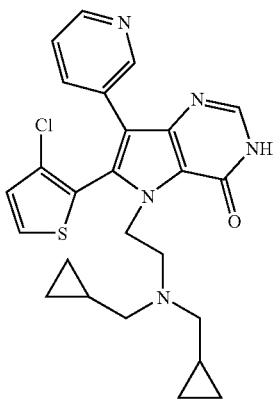

To an N,N-dimethylformamide (1.0 mL) solution of 5-(2-aminoethyl)-6-(3-chloro-thiophen-2-yl)-7-pyridin-3-yl-3-hydropyrrolo[3,2-d]pyrimidin-4-one dihydrochloride (25 mg) were added cyclopropyl aldehyde (5 mg), sodium triacetoxy borohydride (24 mg) and acetic acid (0.1 mL) and the mixture was stirred at room temperature for 10 hours. Saturated brine was added to the obtained solution and extracted with ethyl acetate. The reaction solution was distilled off under reduced pressure, and the residue was purified by fraction HPLC to obtain the title compound (10 mg, yield 36%). The HPLC retention time and ESI/MS data of the compound are given below.

HPLC retention time=5.4 (min) ESI/MS m/e: 482.0 ($M^+$+H, $C_{25}H_{26}ClFN_5OS$)

Example 35

Synthesis of N-{2-[6-(3-chloro-thiophen-2-yl)-4-oxo-7-pyridin-3-yl-3-hydropyrrolo[3,2-d]pyrimidin-5-yl]ethyl}-t-butylacetylamide (Compound No. 626)

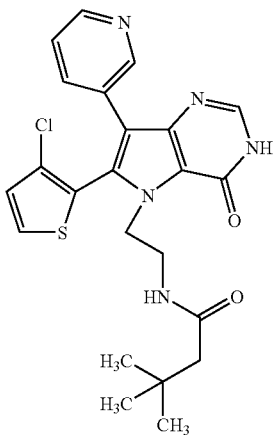

To an N,N-dimethylacetamide (1.0 mL) solution of 5-(2-aminoethyl)-6-(3-chloro-thiophen-2-yl)-7-pyridin-3-yl-3-hydropyrrolo[3,2-d]pyrimidin-4-one dihydrochloride (25 mg) was added t-butylacetyl chloride (23 mg) and the mixture was stirred at room temperature for a short time, followed by adding triethylamine (0.2 mL) and stirring at room temperature for 2 hours. Water (0.2 mL) was added to the reaction solution and the solution was stirred again at room temperature overnight. Saturated brine was added to the obtained solution and extracted with ethyl acetate. The reaction solution was distilled off under reduced pressure, and the residue was purified by fraction HPLC to obtain the title compound (19 mg, yield 72%). The HPLC retention time and ESI/MS data of the compound are given below.

HPLC retention time=7.6 (min) ESI/MS m/e: 470.1 ($M^+$+H, $C_{23}H_{24}ClN_5O_2S$)

Example 36

Synthesis of 1-methyl-cyclohexane-{2-[6-(3-chloro-thiophen-2-yl)-4-oxo-7-pyridin-3-yl-3-hydropyrrolo[3,2-d]pyrimidin-5-yl]-ethyl}-carboxyamide (Compound No. 684)

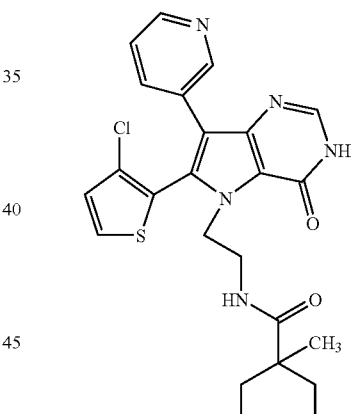

To an N,N-dimethylformamide (1.0 mL) solution of 5-(2-aminoethyl)-6-(3-chlorothiophen-2-yl)-7-pyridin-3-yl-3-hydropyrrolo[3,2-d]pyrimidin-4-one dihydrochloride (25 mg) were added 1-methyl-cyclohexanecarboxylic acid (24 mg), 1-ethyl-3-(3'-dimethylaminopropyl)carboxyamide hydrochloride (43 mg), N-hydroxybenzotriazole (8 mg) and triethylamine (0.2 mL) and the mixture was stirred at room temperature for 10 hours. Saturated brine was added to the obtained solution and extracted with ethyl acetate. The reaction solution was distilled off under reduced pressure, and the residue was purified by fraction HPLC to obtain the title compound (11 mg, yield 41%). The HPLC retention time and ESI/MS data of the compound are given below.

HPLC retention time=8.2 (min) ESI/MS m/e: 496.0 ($M^+$+H, $C_{25}H_{26}ClN_5O_2S$)

Example 37

Synthesis of N-{2-[6-(3-chloro(2-thienyl))-4-oxo-7-(3-pyridyl)-3-hydropyrrolo[3,2-d]pyrimidin-5-yl]ethyl}acetamide (Compound No. 217)

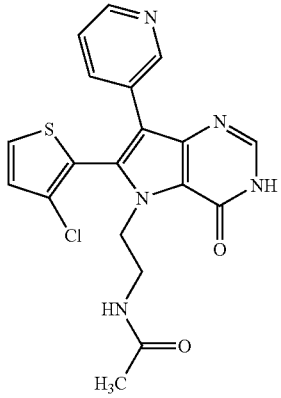

To a 1,4-dioxane (6.0 mL) and methanol (1.0 mL) solution of (t-butoxy)-N-{2-[6-(3-chloro(2-thienyl))-4-oxo-7-(3-pyridyl)(3-hydropyrrolo[3,2-d]pyrimidin-5-yl)]ethyl}carboxamide (356 mg) was added 4 mol/L hydrochloric acid/dioxane solution (0.75 mL) and the mixture was stirred 60° C. for 1 hour. The reaction solution was cooled to room temperature, and the solvent was distilled off under reduced pressure. The residue was dried under reduced pressure to obtain crude product (370 mg). To a dimethylacetamide solution (2.0 mL) of the reaction product (26 mg) were added chloroacetyl (10 mg) and triethylamine (0.2 mL) and the mixture was stirred at room temperature for 1 hour, followed by adding water (0.2 mL) and further stirring at room temperature for 1 hour. Purification by fraction HPLC was performed to obtain the title compound (15 mg, yield 57%). The HPLC retention time, NMR data and ESI/MS data of the compound are given below.

HPLC retention time=5.7 (min) $^1$H-NMR (400 MHz, DMSO-$d_6$) δ(ppm): 1.65 (s, 3H), 3.31-3.41 (m, 2H), 4.16 (m, 1H), 4.50 (m, 1H), 7.29 (m, 1H), 7.61 (dd, J=5.12, J=8.08, 1H), 7.86 (m, 1H), 7.92 (m, 1H), 8.01 (m, 2H), 8.54 (d, J=5.12, 1H), 8.64 (s, 1H), 12.38 (brs, 1H). ESI/MS m/e: 414.4 (M$^+$+H, $C_{19}H_{16}ClN_5O_2S$)

Example 38

Synthesis of 6-(3-chloro(2-thienyl))-7-(3-pyridyl)-5-[2-quinazolin-4-ylamino]ethyl]-3-hydropyrrolo[3,2-d]pyrimidin-4-one (Compound No. 84)

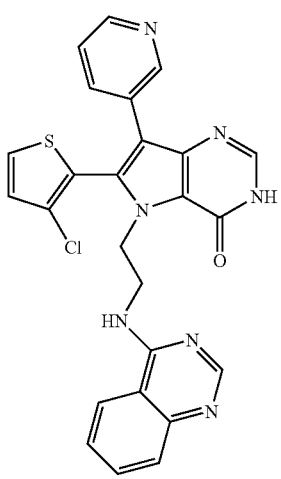

A 4 mol/L hydrochloric acid/dioxane solution (0.75 mL) was added to a 1,4-dioxane (6.0 mL) and methanol (1.0 mL) solution of (t-butoxy)-N-{2-[6-(3-chloro(2-thienyl))-4-oxo-7-(3-pyridyl)(3-hydropyrrolo[3,2-d]pyrimidin-5-yl)]ethyl}carboxyamide (356 mg) and the mixture was stirred at 60° C. for 1 hour. The reaction solution was cooled to room temperature, and the solvent was distilled off under reduced pressure. The residue was dried under reduced pressure to obtain a crude product (370 mg). To a dimethylacetamide (2.0 mL) solution of the reaction product (32 mg) were added 4-chloroquinazoline (13 mg) and triethylamine (16 mg) and the solution was stirred at 70° C. for 2 hours. The reaction solution was cooled to room temperature, and purification by fraction HPLC was performed to obtain the title compound (21 mg, yield 54%). The HPLC retention time, NMR data and ESI/MS data of the compound are given below.

HPLC retention time=5.6 (min) $^1$H-NMR (400 MHz, DMSO-$d_6$) δ(ppm): 4.01-4.06 (m, 2H), 4.55 (m, 1H), 4.96 (m, 1H), 7.08 (m, 1H), 7.47 (dd, J=4.88, J=8.04, 1H), 7.72-7.78 (m, 3H), 7.83 (m, 1H), 7.90 (s, 1H), 8.02 (t, J=7.68, 1H), 8.23 (d, J=8.52, 1H), 8.46 (d, J=5.12, 1H), 8.52 (s, 1H), 8.67 (s, 1H), 10.18 (m, 1H), 12.30 (brs, 1H). ESI/MS m/e: 500.4 (M$^+$+H, $C_{25}H_{18}ClN_7OS$)

Example 39

Synthesis of ethyl 3-(4-oxo-7-(3-pyridyl)-3-hydropyrrolo[3,2-d]pyrimidin-5-yl)propanate (Compound No. 35)

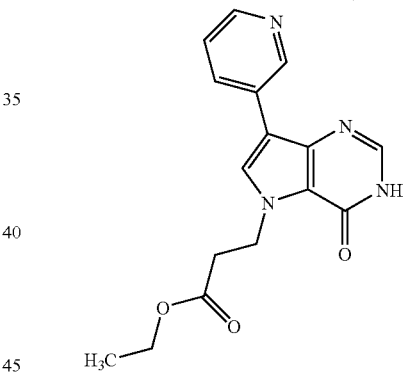

To an isopropyl alcohol (80 mL) solution of ethyl 3-[3-amino-2-(methoxycarbonyl)-4-(3-pyridyl)pyrrolyl]propanate (4.380 g) was added formamidine acetate (7.184 g) and the mixture was stirred at 90° C. for 10 hours. The reaction solution was cooled to room temperature, and the solid was subjected to fractional filtration. The extractant was distilled off under reduced pressure. To the residue was added water and extracted with ethyl acetate. The organic layer was washed with saturated brine and dried with sodium sulfate, which was then subjected to fractional filtration. Then, the solvent was distilled off under reduced pressure. The residue was purified by column chromatography on silica gel (ethyl acetate:ethanol=7:1), to obtain the title compound (0.747 g, yield 17%). The HPLC retention time, NMR data and ESI/MS data of the compound are given below.

HPLC retention time=5.6 (min) $^1$H-NMR (400 MHz, DMSO-$d_6$) δ(ppm): 1.11 (t, J=7.08, 3H), 2.95 (t, J=6.96, 2H), 4.03 (dd, J=6.96, J=14.28, 2H), 4.63 (t, J=6.84, 2H), 7.81 (dd, J=5.12, J=8.04, 1H), 7.99 (s, 1H), 8.22 (s, 1H), 8.60 (d, J=5.12, 1H), 8.81 (d, J=8.04, 1H), 9.38 (s, 1H), 12.29 (s, 1H). ESI/MS m/e: 313.2 (M$^+$+H, $C_{16}H_{16}N_4O_3$)

Example 40

Synthesis of 3-(4-oxo-7-(3-pyridyl)(3-hydropyrrolo[3,2-d]pyrimidin-5-yl))-N-phenylpropaneamide (Compound No. 30)

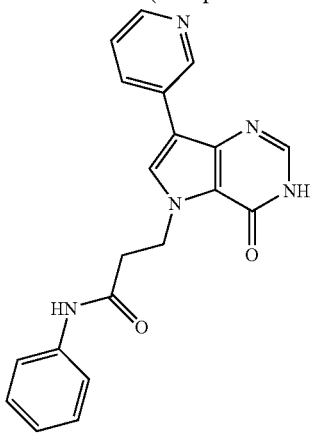

Water (0.40 mL) and a 5 M aqueous sodium hydroxide solution (0.18 mL) were added to a 1,4-dioxane (3.0 mL) solution of ethyl 3-(4-oxo-7-(3-pyridyl)-3-hydropyrrolo[3,2-d]pyrimidin-5-yl)propanate (91 mg) and the mixture was stirred at room temperature for 2 hours. The reaction solution was neutralized with acetic acid, and the resulting solid was filtered and washed with water and ethyl acetate to obtain a crude product (78 mg). 1-ethyl-3-(3'-dimethylaminopropyl)carbodiimide hydrochloride (41 mg) and pyridine (0.2 mL) were added to a mixed solution of dichloromethane (1.0 mL) and dimethylacetamide (1.0 mL) of the reaction product (20 mg) and the mixture was stirred at room temperature for 1 hour. To the reaction solution was added aniline (20 mg) and the solution was stirred at 40° C. overnight. Methanol was added to stop the reaction, and the solvent was distilled off under reduced pressure. The residue was purified by fraction HPLC to obtain the title compound (19 mg, yield 76%). The HPLC retention time, NMR data and ESI/MS data of the compound are given below.

HPLC retention time=6.1 (min) $^1$H-NMR (400 MHz, DMSO-$d_6$) δ(ppm): 2.97 (t, J=6.58, 2H) 4.69 (t, J=6.48, 2H), 6.99 (t, J=7.46, 1H), 7.24 (t, J=7.92, 2H), 7.51 (d, J=8.56, 2H), 7.78 (dd, J=5.50, J=7.94, 1H), 7.99 (s, 1H), 8.18 (s, 1H), 8.57 (d, J=5.40, 1H), 8.78 (d, J=8.04, 1H), 9.36 (s, 1H), 9.96 (s, 1H), 12.30 (brs, 1H). ESI/MS m/e: 360.2 (M$^+$+H, $C_{20}H_{17}N_5O_2$)

Example 41

Synthesis of 6-chloro-5-benzyl-7-(3-pyridyl)-3-hydropyrrolo[3,2-d]pyrimidin-4-one (Compound No. 1180)

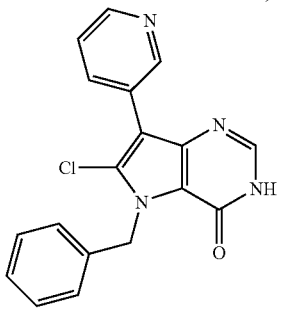

N-chlorosuccinimide (57 mg) was added to a dimethylformamide (2.0 mL) solution of 5-benzyl-7-(3-pyridyl)-3-hydropyrrolo[3,2-d]pyrimidin-4-one (65 mg) and the mixture was stirred at room temperature for 2 hours. N-chlorosuccinimide (57 mg) was added to the reaction mixture and further the mixture was stirred at room temperature for 2 hours. Water (0.2 mL) was added to stop the reaction, and purification by fraction HPLC gave the title compound (33 mg, yield 46%). The HPLC retention time, NMR data and ESI/MS data of the compound are given below.

HPLC retention time=8.0 (min) $^1$H-NMR (400 MHz, DMSO-$d_6$) δ(ppm): 5.82 (s, 2H), 7.22-7.36 (m, 5H), 7.72 (dd, J=5.12, J=8.04, 1H), 8.00 (s, 1H), 8.42 (m, 1H), 8.64 (d, J=5.12, 1H), 9.07 (s, 1H), 12.41 (brs, 1H). ESI/MS m/e: 337.3 (M$^+$+H, $C_{18}H_{13}ClN_4O$

Example 42

Synthesis of 7-(3-pyridyl)-4-oxo-6-cyclopropyl-3-hydropyrrolo[3,2-d]pyrimidine (Compound No. 1178)

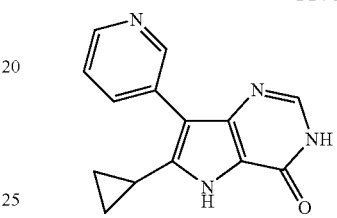

To a 100 mL branched flask was transferred ethyl 3-amino-4-(3-pyridyl)-5-cyclopropyl pyrrole-2-carboxylate (118 mg), and isopropylalcohol (40 mL) and formamidine acetate (1.35 g) were added thereto and heated at 95° C. for 13 hours with stirring. After the completion of the reaction, the solvent was concentrated under reduced pressure. To the concentrated residue were added water (20 mL) and ethyl acetate (20 mL) for separation. The aqueous layer was extracted again with 20 mL ethyl acetate. The organic layer was washed twice with 20 mL water, dehydrated and dried with magnesium sulfate, filtered and concentrated to obtain a crude product (91 g). The crude product was washed 3 times with 1 mL methanol to yield the title compound (49 mg, yield 45%). The ESI/MS data of the compound are given below.

HPLC retention time=4.2 (min) ESI/MS m/e: 253.1 (M$^+$+H, $C_{14}H_{12}N_4O$)

Example 43

Synthesis of (t-butoxy)-N-{2-[6-(3-chloro(2-thienyl))-4-oxo-7-(trifluoromethyl)(3-hydropyrrolo[3,2-d]pyrimidin-5-yl)]ethyl}carboxyamide (Compound No. 947)

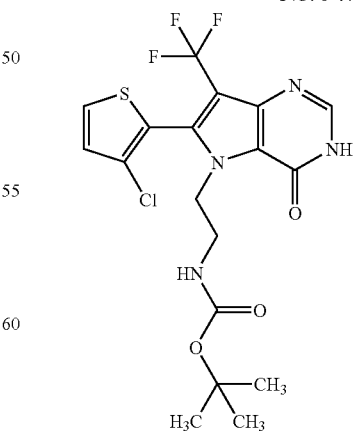

Under nitrogen atmosphere, a dry dimethylformamide suspension (10 mL) of cadmium (2.24 g) was cooled on ice with stirring, and dibromodifluoromethane (1.5 mL) was added thereto, followed by stirring at room temperature for 3 hours. Dry hexamethylphosphoramide (10 mL) was added to the reaction solution and cooled on ice, and copper (I) bromide (1.16 g) was added to the reaction mixture and the mixture was stirred at room temperature for 1 hour to obtain a copper trifluoromethyl compound suspension.

The copper trifluoromethyl compound suspension (10 mL) was added to a dry dimethylformamide solution (3 mL) of (t-butoxy)-N-{2-[6-(3-chloro(2-thienyl))-7-iodo-4-oxo-(3-hydropyrrolo[3,2-d]pyrimidin-5-yl)]ethyl}carboxyamide (115 mg) and the solution was stirred at 65° C. for 6 hours. An aqueous ammonium chloride solution was added to the reaction solution and extracted with ethyl acetate. The organic layer was washed with brine, dried over sodium sulfate, filtered, concentrated, and purified by chromatography on silica gel, to obtain the title compound (35 mg, 34%). The HPLC retention time, NMR data and ESI/MS data of the compound are given below.

HPLC retention time=12.1 (min) $^1$H-NMR (270 MHz, CDCl$_3$)δ(ppm): 1.32 (s, 9H), 3.35-3.60 (m, 2H), 4.00-4.30 (m, 1H), 4.40-4.70 (m, 1H), 7.11 (d, J=5.1 Hz, 1H), 7.61 (d, J=5.4 Hz, 1H), 7.95-8.10 (m, 1H). ESI/MS m/e: 463.2 (M$^+$+H, C$_{18}$H$_{18}$ClF$_3$N$_4$O$_3$S)

Example 44

Synthesis of 6-phenyl-7-(3-pyridyl)-3-hydropyrrolo[3,2-d]pyrimidin-4-one (Compound No. 2445)

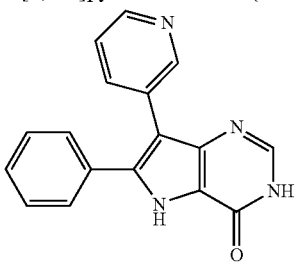

An N,N-dimethylformamide/water (2:1) solution (1.0 mL) of 6-chloro-7-(3-pyridyl)-3-hydropyrrolo[3,2-d]pyrimidin-4-one (40 mg), phenyl boric acid (59 mg), and potassium acetate (78 mg) was subjected to deaeration, and a small amount of [1,1'-bis(diphenylphosphino)ferrocene]palladium (II) chloride dichloro-methane (1:1) complex was added thereto. The reaction mixture was heated at 140° C. for 5 minutes by using microwaves. The solvent was distilled off under reduced pressure and the residue was separated to ethyl acetate and aqueous layers. The organic layer was washed with saturated aqueous sodium hydrogen carbonate solution and brine and dried over sodium sulfate. The sodium sulfate was filtered, and solvent was distilled off under reduced pressure. The residue was purified by chromatography on silica gel (0-5% methanol/ethyl acetate), and further purified by fraction HPLC to obtain the title compound (6.3 mg, yield 10%). The HPLC retention time, NMR data and ESI/MS data of the compound are given below.

HPLC retention time: 4.0 (min) $^1$H-NMR (400 MHz, CD$_3$OD)δ(ppm): 7.50 (m, 5H), 7.86 (dd, J=5.7, J=8.2, 1H), 7.98 (s, 1H), 8.44 (dt, J=1.6, J=8.2, 1H), 8.62 (d, J=5.7, 1H), 8.94 (s, 1H). ESI/MS m/e: 289.1 (M$^+$+H, C$_{17}$H$_{12}$N$_4$O)

Example 45

Synthesis of ethyl 4-(4-oxo-3-hydropyrrolo[3,2-d]pyrimidin-5-yl)butanoate (Compound No. 2501)

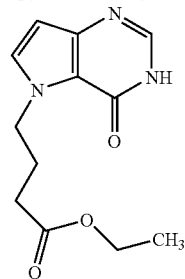

An ethyl 4-[3-amino-2-(ethoxycarbonyl)pyrolyl]butanoate hydrochloride (20.1 g) was dissolved in dichloromethane (400 mL), and saturated aqueous sodium hydrogen carbonate (400 mL) was added thereto. The reaction mixture was vigorously stirred for 30 minutes, and two layers were separated. The aqueous layer was extracted with dichloromethane, and combined organic layer was washed with saturated brine, and dried over magnesium sulfate. The magnesium sulfate was filtered, and the solvent was distilled off under reduced pressure to obtain ethyl 4-[3-amino-2-(ethoxycarbonyl)pyrolyl]butanoate (18.0 g). This compound was dissolved in isopropylalcohol (400 mL), and formamidine acetate (9.78 g) was added thereto. This mixture was heated for 150 minutes to reflux. The solvent was distilled off under reduced pressure and the residue was separated to dichloromethane and aqueous layers. The aqueous layer was extracted with dichloromethane, and the combined organic layer was washed with 10% aqueous citric acid solution, saturated aqueous sodium hydrogen carbonate, and saturated brine, which was dried over magnesium sulfate, and the solvent was distilled off under reduced pressure to obtain the title compound (13.0 mg, yield 78%). The NMR data and ESI/MS data of the compound are given below.

$^1$H-NMR (400 MHz, DMSO-d$_6$)δ(ppm): 1.14 (t, J=7.1, 3H), 2.01 (pent, J=7.0, 2H), 2.21 (t, J=7.5, 2H), 3.99 (q, J=7.1, 2H), 4.38 (t, J=6.7, 2H), 6.33 (d, J=2.9, 1H), 7.41 (d, J=2.9, 1H), 7.76 (s, 1H), 11.86 (brs, 1H). ESI/MS m/e: 250.1 (M$^+$+H, C$_{12}$H$_{15}$N$_3$O$_3$)

Example 46

Synthesis of ethyl 4-(7-iodo-4-oxo-3-hydropyrrolo[3,2-d]pyrimidin-5-yl)butanoate (Compound No. 2502)

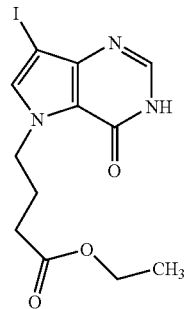

An N-iodosuccinimide (12.8 g) was added to a dichloromethane (350 mL) solution of ethyl 4-(4-oxo-3-hydropyrrolo[3,2-d]pyrimidin-5-yl)butanoate (12.9 g), and stirred at room temperature overnight. A solid was extracted by filtration, washed with diethylether, and then dried under reduced pressure, to obtain the title compound (11.8 g, yield 61%). The filtration solution was concentrated under reduced pressure, ethyl acetate was added to the residue and vigorously stirred. The produced solid was extracted by filtration, washed with ethyl acetate and diethylether, and then dried under reduced pressure, to obtain the title compound (6.63 g, yield 34%). The NMR data and ESI/MS data of the compound are given below.

$^1$H-NMR (400 MHz, DMSO-d$_6$)δ(ppm): 1.13 (t, J=7.1, 3H), 2.02 (pent, J=7.0, 2H), 2.22 (t, J=7.4, 2H), 3.96 (q, j=7.1, 2H), 4.39 (t, J=6.7, 2H), 7.63 (s, 1H), 7.85 (s, 1H), 12.06 (brs, 1H). ESI/MS m/e: 376.0 (M$^+$+H, C$_{17}$H$_{18}$IN$_3$O$_3$)

Example 47

Synthesis of ethyl 4-(4-oxo-7-(3-pyridyl)-3-hydropyrrolo[3,2-d]pyrimidin-5-yl)butanoate (Compound No. 2512)

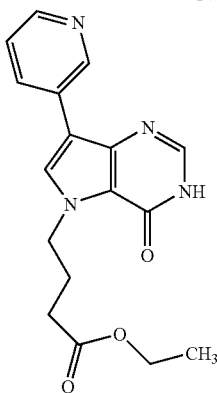

The title compound was obtained by using an ethyl 4-(7-iodo-4-oxo-3-hydropyrrolo[3,2-d]pyrimidin-5-yl)butanoate and 3-pyridyl boric acid in a similar manner to that described in Example 28. The NMR data and ESI/MS data of the compound are given below.

$^1$H-NMR (400 MHz, DMSO-d$_6$)δ(ppm): 1.11 (t, J=7.1, 3H), 2.09 (pent, J=7.0, 2H), 2.29 (t, J=7.4, 2H), 3.96 (q, j=7.1, 2H), 4.45 (t, J=6.7, 2H), 7.41 (m, 1H), 7.93 (s, 1H), 8.06 (s, 1H), 8.40 (m, 2H), 9.21 (m, 1H), 12.10 (s, br, 1H). ESI/MS m/e: 327.0 (M$^+$+H, C$_{17}$H$_{18}$N$_4$O$_3$)

Example 48

Synthesis of 4-(4-oxo-7-(3-pyridyl)-3-hydropyrrolo[3,2-d]pyrimidin-5-yl)butanoic acid (Compound No. 2503)

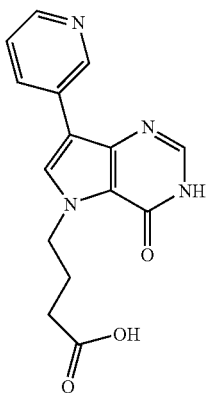

1M of aqueous lithium hydroxide solution (6.3 mL) was added to ethanol (24 mL) and water (3 mL) solution of ethyl-4-(4-oxo-7-(3-pyridyl)-3-hydropyrrolo[3,2-d]pyrimidin-5-yl)butanoate (0.78 g), and stirred at room temperature overnight. The solvent was distilled off under reduced pressure, and water (5 mL) was added to the residue. 1M hydrochloric acid was added thereto to adjust pH to 4, and a produced solid was extracted by filtration, which was dried under reduced pressure, to obtain the title compound (0.75 g, quantitative yield). The NMR data and ESI/MS data of the compound are given below.

$^1$H-NMR (400 MHz, DMSO-d$_6$)δ(ppm): 2.07 (pent, J=7.0, 2H) 2.23 (t, J=7.3, 2H), 4.46 (t, J=6.7, 2H), 7.77 (dd, J=4.3, J=8.2, 1H), 7.98 (s, 1H), 8.24 (s, 1H), 8.58 (d, J=4.3, 1H), 8.79 (d, J=8.2, 1H), 9.39 (s, 1H), 12.12 (brs, 1H), 12.24 (brs, 1H) ESI/MS m/e: 299.1 (M$^+$+H, C$_{15}$H$_{14}$N$_4$O$_3$)

Example 49

Synthesis of 4-(4-oxo-7-(3-pyridyl)-3-hydropyrrolo[3,2-d]pyrimidin-5-yl)-N-benzylbutanamide (Compound No. 2292)

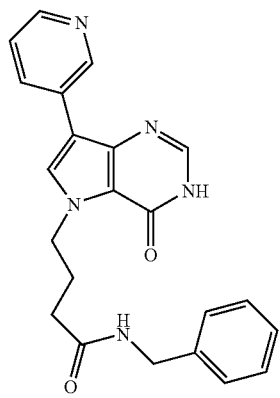

A diisopropylethylamine (91 μL) and benzyl amine (29 μL) were added to solution of N,N-dimethylformamide (4 mL) of 4-(4-oxo-7-(3-pyridyl)-3-hydropyrrolo[3,2-d]pyrimidin-5-yl)butanoate (40 mg). Further, O-(7-azabenzotriazol-1-yl)N,N,N',N'-tetramethyluronium hexafluorophosphate (74 mg) was added thereto, and the mixture solution was stirred at room temperature overnight. The solvent was distilled off under reduced pressure, and hot water was added to the residue. An insoluble portion was filtered off, the filtration solution was concentrated under reduced pressure, purified, to obtain the title compound (11. 6 mg, yield 22%). The HPLC retention time, NMR data and ESI/MS data of the compound are given below.

The HPLC retention time: 5.1 (min) $^1$H-NMR (400 MHz, DMSO-d$_6$)δ(ppm): 2.12 (m, 4H), 4.23 (d, J=6.0, 2H), 4.46 (t, J=6.3, 2H), 7.22 (m, 3H), 7.30 (m, 2H), 7.73 (dd, J=5.0, J=8.2, 1H), 7.98 (s, 1H), 8.19 (s, 1H), 8.33 (t, J=6.0, 1H), 8.56 (d, J=5.0, 1H), 8.74 (d, J=8.2, 1H), 9.37 (brs, 1H), 12.22 (brs, 1H). ESI/MS m/e: 388.1 (M$^+$+H, C$_{22}$H$_{21}$N$_5$O$_2$)

Example 50

Synthesis of ethyl 4-(6-chloro-4-oxo-7-(3-pyridyl)-3-hydropyrrolo[3,2-d]pyrimidin-5-yl)butanoate (Compound No. 2504)

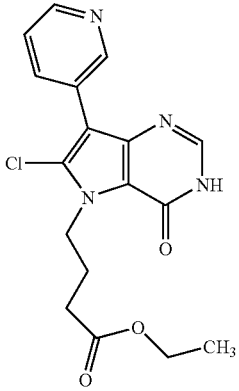

An ethyl 4-(4-oxo-7-(3-pyridyl)-3-hydropyrrolo[3,2-d]pyrimidin-5-yl)butanoate (1.72 g) was dissolved in dichloromethane (63 mL) by heating, and cooled to 0° C. 2 mol/L of surfuryl chloride/dichloromethane solution (7.9 mL) was added dropwise, and stirred at room temperature for 3 hours. The solvent was distilled off under reduced pressure, and dichloromethane and saturated aqueous sodium hydrogen carbonate solution were added, and vigorously stirred. Two layers were separated, and the aqueous layer was extracted with dichloromethane. The combined organic layer was washed with saturated brine, and dried over sodium sulfate. The sodium sulfate was filtered, and the solvent was distilled off under reduced pressure to obtain the title compound (1.89 g, quantitative yield). The NMR data and ESI/MS data of the compound are given below.

$^1$H-NMR (400 MHz, DMSO-$d_6$)δ(ppm) 1.11 (t, J=7.1, 3H), 2.06 (pent, J=7.0, 2H), 2.37 (t, J=7.2, 2H), 3.94 (q, J=7.1, 2H), 4.58 (t, J=6.7, 2H), 7.51 (dd, J=4.7, J=7.9, 1H), 7.93 (d, J=3.0, 1H), 8.13 (dt, J=1.9, J=7.9, 1H), 8.54 (d, J=7, 1H), 8.94 (s, 1H), 12.28 (brs, 1H). ESI/MS m/e: 361.1 (M$^+$+H, $C_{17}H_{17}N_4O_3$)

Example 51

Synthesis of 4-(6-chloro-4-oxo-7-(3-pyridyl)-3-hydropyrrolo[3,2-d]pyrimidin-5-yl)butanoic acid (Compound No. 2505)

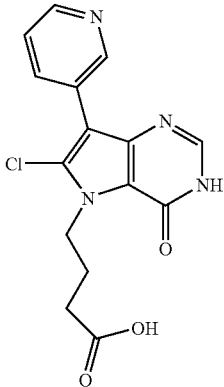

1M of aqueous lithium hydroxide solution (8.6 mL) was added to ethanol (25 mL) solution of ethyl-4-(6-chloro-4-oxo-7-(3-pyridyl)-3-hydropyrrolo[3,2-d]pyrimidin-5-yl)butanoate (1.24 g), and stirred at room temperature overnight. 1M of hydrochloric acid (8.6 mL) was added thereto, the solvent was distilled off under reduced pressure, to obtain the title compound as a mixture (1.73 g) with lithium chloride. The NMR data and ESI/MS data of the compound are given below.

$^1$H-NMR (400 MHz, DMSO-$d_6$)δ(ppm): 2.02 (m, 2H), 2.29 (t, J=7.4, 2H), 4.57 (t, J=6.9, 2H), 7.58 (ddd, J=0.8, J=4.9, J=8.0, 1H), 7.94 (s, 1H), 8.23 (ddd, J=1.5, J=2.3, J=8.0, 1H), 8.57 (dd, J=1.5, J=4.9, 1H), 8.98 (dd, J=0.8, J=2.3, 1H), 12.16 (brs, 1H), 12.39 (brs, 1H). ESI/MS m/e: 333.1 (M$^+$+H, $C_{15}H_{13}ClN_4O_3$ LiCl)

Example 52

Synthesis of 4-(6-chloro-4-oxo-7-(3-pyridyl)-3-hydropyrrolo[3,2-d]pyrimidin-5-yl)-N-(cyclohexylmethyl)butanamide (Compound No. 2264)

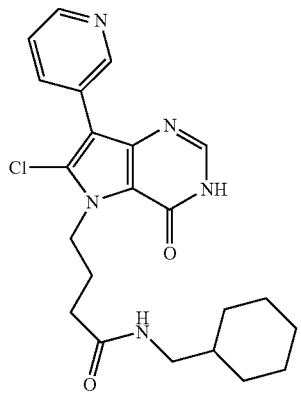

A cyclohexanemethylamine (27 mg) and diisopropyl-ethylamine (84 µL) were added to a solution of N,N-dimethylformamide (1 mL) of 4-(6-chloro-4-oxo-7-(3-pyridyl)-3-hydropyrrolo[3,2-d]pyrimidin-5-yl)butanoate (40 mg). Further, O-(7-azabenzotriazol-1-yl)N,N,N',N'-tetramethyluronium hexafluorophosphate (55 mg) was added thereto, and the mixture solution was stirred at room temperature for 2 hours. The reaction mixture was separated to ethyl acetate and aqueous layers. The organic layer was washed with 1 mol/L of aqueous citric acid solution, saturated aqueous sodium hydrogen carbonate, and saturated brine, which was dried over sodium sulfate. The sodium sulfate was filtered off, and the solvent was distilled off under reduced pressure. The residue was purified by column chromatography on silica gel (5% methanol/ethyl acetate) to obtain the title compound (35 mg, yield 68%). The HPLC retention time, NMR data and ESI/MS data of the compound are given below.

The HPLC retention time: 7.2 (min) $^1$H-NMR (400 MHz, CD$_3$OD)δ(ppm): 0.09 (m, 2H), 1.21 (m, 3H), 1.42 (m, 1H), 1.69 (m, 5H), 2.16 (m, 2H), 2.29 (t, H=7.4, 2H), 2.95 (d, J=7.0, 2H), 4.66 (t, J=6.9, 2H), 7.53 (ddd, J=0.9, J=5.0, J=8.0, 1H), 7.89 (s, 1H), 8.22 (ddd, J=1.6, J=2.2, J=8.0, 1H), 8.49 (dd, J=1.6, J=5.0, 1H), 8.93 (dd, J=0.9, J=2.2, 1H). ESI/MS m/e: 428.2 (M$^+$+H, $C_{22}H_{26}ClN_5O_2$)

Example 53

Synthesis of 4-[6-(3,4-dimethoxyphenyl)-4-oxo-7-(3-pyridyl)(3-hydropyrrolo[3,2-d]pyrimidin-5-yl)]-N-(cyclohexylmethyl)butanamide (Compound No. 2269)

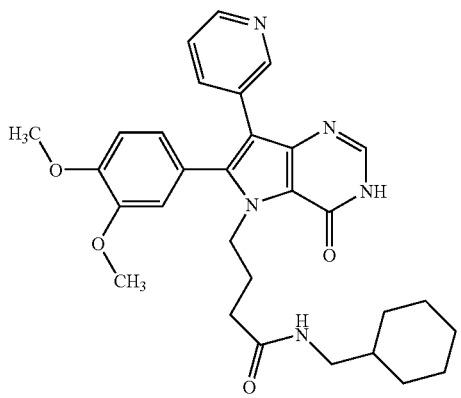

An N,N-dimethylformamide/water (2:1) solution (2 mL) of 4-(6-chloro-4-oxo-7-(3-pyridyl)(3-hydropyrrolo[3,2-d]pyrimidin-5-yl))-N-(cyclohexylmethyl)butanamide (50 mg), 3,4-dimethoxyphenyl boric acid (64 mg), and potassium acetate (57 mg) was subjected to deaeration, followed by flushing with nitrogen gas. A small amount of [1,1'-bis(diphenylphosphino)ferrocene]palladium (II) chloride dichloromethane (1:1) complex body was added thereto. The reaction mixture was heated at 140° C. for 30 minutes by using microwave. The solvent was distilled off under reduced pressure and the residue was purified by column chromatography on silica gel (5-8% methanol/ethyl acetate), and further purified by fraction HPLC to obtain the title compound (12 mg, yield 16%). The HPLC retention time, NMR data and ESI/MS data of the compound are given below.

HPLC retention time: 8.0 (min) $^1$H-NMR (400 MHz, CD$_3$OD)δ(ppm): 0.85 (m, 2H), 1.19 (m, 3H) 1.35 (m, 1H), 1.66 (m, 5H), 2.01 (m, 2H), 2.13 (t, J=7.4, 2H), 2.88 (d, J=6.8, 2H), 3.80 (s, 3H), 3.91 (s, 3H), 4.42 (t, J=7.5, 2H), 7.00 (dd, J=2.0, J=8.1, 1H), 7.03 (d, J=2.0, 1H), 7.13 (d, J=8.1, 1H), 7.81 (dd, J=5.6, J=8.2, 1H), 7.99 (s, 1H), 8.39 (ddd, J=1.4, J=2.1, J=8.2, 1H), 8.52 (d, J=5.6, 1H), 8.90 (d, J=2.1, 1H). ESI/MS m/e: 530.3 (M$^+$+H, C$_{30}$H$_{35}$N$_5$O$_4$)

Example 54

Synthesis of ethyl 4-{7-iodo-4-oxo-3-[(phenylmethoxy)methyl]-3-hydropyrrolo[3,2-d]pyrimidin-5-yl)butanoate

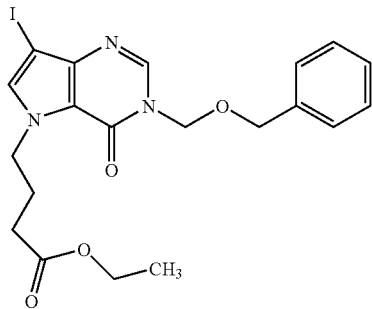

A sodium hydride (521 mg) was added to solution of N,N-dimethylformamide (60 mL) of ethyl 4-(7-iodo-4-oxo-3-hydropyrrolo[3,2-d]pyrimidin-5-yl)butanoate (4.07 g) in a small amount by each, and the mixture solution was stirred at room temperature for 30 minutes. A benzylchloromethylether (2.04 g) was added dropwise, and the mixture solution was further stirred for 2 hours. The solvent was distilled off under reduced pressure to separate the residue to ethyl acetate and aqueous layers. The organic layer was washed with water and saturated brine, and dried over sodium sulfate. The sodium sulfate was filtered off, and the solvent was distilled off under reduced pressure. The residue was purified by column chromatography on silica gel (15-30% ethyl acetate/cyclohexane), to obtain the title compound (3.80 g, yield 71%). The NMR data and ESI/MS data of the compound are given below.

$^1$H-NMR (400 MHz, CDCl$_3$)δ(ppm): 1.25 (t, J=7.1, 3H), 2.18 (pent, J=7.0, 2H), 2.32 (t, J=7.2, 2H), 4.12 (q, J=7.1, 2H), 4.51 (t, J=6.9, 2H), 4.65 (s, 2H), 5.50 (s, 2H), 7.22 (s, 1H), 7.29 (m, 1H), 7.33 (m, 4H), 8.03 (s, 1H). ESI/MS m/e: 496.1 (M$^+$+H, C$_{20}$H$_{22}$IN$_3$O$_4$)

Example 55

Synthesis of ethyl-4-{7-(1-methylpyrazol-4-yl)-4-oxo-3-[(phenylmethoxy)methyl]-3-hydropyrrolo[3,2-d]pyrimidin-5-yl)butanoate

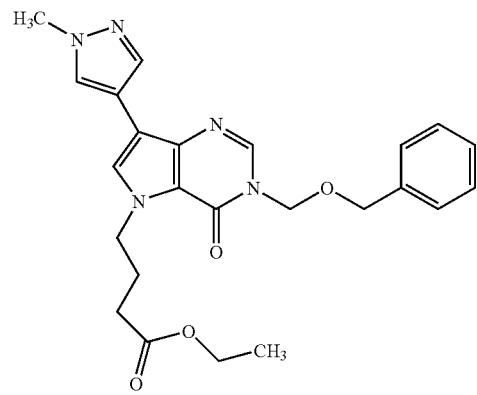

The title compound was obtained by using ethyl 4-{7-iodo-4-oxo-3-[(phenylmethoxy)methyl]-3-hydropyrrolo[3,2-d]pyrimidin-5-yl)butanoate and 1-methyl-4-(4,4,5,5-tetramethyl-1,3,2-dioxaborolane-2-yl)-1H-pyrazol in a similar manner to that in Example 28. The NMR data and ESI/MS data of the compound are given below.

$^1$H-NMR (400 MHz, CD$_3$OD)δ(ppm): 1.16 (t, J=7.1, 3H), 2.16 (pent, J=7.0, 2H), 2.33 (t, J=7.2, 2H), 3.92 (s, 3H), 3.02 (q, J=7.1, 2H), 4.49 (t, J=6.7, 2H), 4.68 (s, 2H), 5.56 (s, 2H), 7.22 (m, 1H), 7.28 (m, 2H), 7.33 (m, 2H), 7.54 (s, 1H), 7.86 (d, J=0.6, 1H), 8.03 (s, 1H), 8.10 (s, 1H). ESI/MS m/e: 450.3 (M$^+$+H, C$_{24}$H$_{27}$N$_5$O$_4$)

Example 56

Synthesis of 4-[6-chloro-7-(1-methylpyrazol-4-yl)-4-oxo-3-hydropyrrolo[3,2-d]pyrimidin-5-yl]butanoic acid (Compound No. 2506)

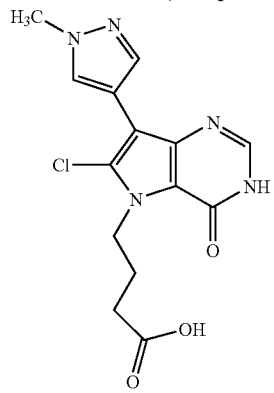

Solution of concentrated hydrochloric acid (3 mL) of ethyl-4-{6-chloro-7-(1-methylpyrazol-4-yl)-4-oxo-3-[(phenylmethoxy)methyl]-3-hydropyrrolo[3,2-d]pyrimidin-5-yl)butanoate was heated for 1 hour to reflux. The solvent was distilled off under reduced pressure, and methanol solution (3 mL) of 2 mol/L ammonia was added to the residue. The solvent was distilled off under reduced pressure, and 1 mol/L of aqueous citric acid solution was added to the residue. A produced solid was extracted by filtration, washed with water and diethylether, and then dried under reduced pressure, to obtain the title compound (133 mg, yield 87%). The NMR data and ESI/MS data of the compound are given below.

$^1$H-NMR (400 MHz, DMSO-$d_6$)δ(ppm): 1.97 (pent, J=7.0, 2H), 2.23 (t, J=7.4, 2H), 3.91 (s, 3H), 4.50 (t, J=6.8, 3H), 7.91 (d, J=3.6, 1H), 8.04 (s, 1H), 8.24 (s, 1H), 12.11 (s, 1H), 12.17 (d, J=3.6, 1H). ESI/MS m/e: 336.2 (M$^+$+H, $C_{14}H_{14}ClN_5O_3$)

Example 57

Synthesis of 4-[6-chloro-7-(1-methylpyrazol-4-yl)-4-oxo-3-hydropyrrolo[3,2-d]pyrimidin-5-yl]]-N-[(4-methylphenyl)methyl]butanamide (Compound No. 2507)

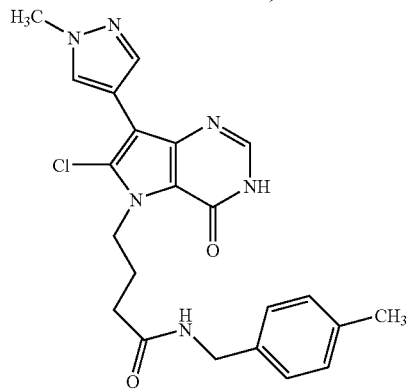

A 4-methylbenzyl amine (29 mg) and a diisopropylethylamine (84 μm) were added to a solution of an N,N-dimethylformamide (1 mL) of 4-[6-chloro-7-(1-methylpyrazol-4-yl)-4-oxo-3-hydropyrrolo[3,2-d]pyrimidin-5-yl)-butanoate (40 mg). An O-(7-azabenzotriazol-1-yl)-N,N,N',N'-tetramethyluronium hexafluorophosphate (55 mg) was further added, and the mixture solution was stirred at room temperature overnight. An ethyl acetate and 1 mol/L of an aqueous citric acid solution were added to the reaction mixture, and separated to two layers. The organic layer was washed with saturated aqueous sodium hydrogen carbonate solution and saturated brine, and dried over sodium sulfate. The sodium sulfate was filtered off, and the solvent was distilled off under reduced pressure, to obtain the title compound (67 mg, quantitative yield). The compound was not further purified, but used for the following reaction. The ESI/MS data of the compound is given below.

ESI/MS m/e: 439.2 (M$^+$+H, $C_{22}H_{23}ClN_6O_2$)

Example 58

Synthesis of 4-[6-(3,4-dimethoxyphenyl)-7-(1-methylpyrazol-4-yl)-4-oxo-7-(3-hydropyrrolo[3,2-d]pyrimidin-5-yl)]-N-[(4-methylphenyl)methyl]butanamide (Compound No. 2345)

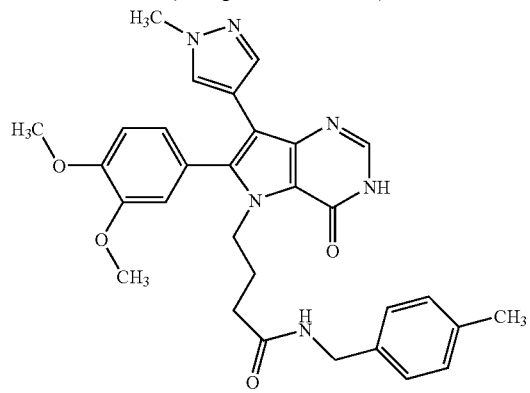

An N,N-dimethylformamide/water (2:1) solution (2 mL) of 4-[6-chloro-7-(1-methylpyrazol-4-yl)-4-oxo (3-hydropyrrolo[3,2-d]pyrimidin-5-yl)]-N-[(4-methylphenyl)methyl]butanamide (65 mg), 3,4-dimethoxyphenyl boric acid (81 mg), and potassium acetate (73 mg) was subjected to deaeration, followed by flushing with nitrogen gas. A small amount of [1,1'-bis(diphenylphosphino)ferrocene]palladium (II) chloride dichloro-methane (1:1) complex body was added thereto. The reaction mixture was heated at 160° C. for 45 minutes by using microwaves. The solvent was distilled off under reduced pressure and the residue was purified by column chromatography on silica gel (5-8% methanol/ethyl acetate), and further purified by fraction HPLC to obtain the title compound (4.4 mg, yield 7%). The HPLC retention time, NMR data and ESI/MS data of the compound are given below.

HPLC retention time: 8.2 (min) $^1$H-NMR (400 MHz, CD$_3$OD)δ(ppm): 1.98 (m, 2H), 2.13 (t, J=7.5, 2H), 2.29 (2, 3H), 3.79 (s, 3H), 3.82 (s, 3H), 3.91 (s, 3H), 4.18 (s, 2H), 4.36 (t, J=7.4, 2H), 6.98 (m, 2H), 7.07 (m, 4H), 7.12 (d, J=7.9, 1H), 7.28 (2, 1H), 7.66 (s, 1H), 7.97 (2, 1H). ESI/MS m/e: 541.1 (M$^+$+H, $C_{30}H_{32}N_6O_4$)

Example 59

Synthesis of ethyl-4-(6-cyclopropyl-4-oxo-3-hydropyrrolo[3,2-d]pyrimidin-5-yl)butanoate (Compound No. 2508)

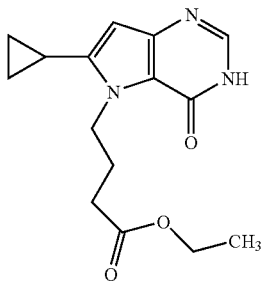

The title compound was obtained by using ethyl-4-[3-amino-5-cyclopropyl-2-(ethoxycarbonyl)pyrolyl]butanoate hydrochloride in a similar manner to that in Example 45. The NMR data and ESI/MS data of the compound are given below.

$^1$H-NMR (400 MHz, DMSO-$d_6$)δ(ppm): 0.74 (m, 2H), 1.00 (m, 2H) 1.13 (t, J=7.2, 3H), 1.93-2.06 (m, 3H), 2.31 (t, J=7.4, 2H), 3.98 (dd, J=7.2, J=14.2, 2H), 4.52 (t, J=7.0, 2H), 6.00 (s, 1H), 7.71 (s, 1H), 11.76 (brs, 1H). ESI/MS m/e: 290.2 (M$^+$+H, $C_{15}H_{19}N_3O_3$)

Example 60

Synthesis of ethyl-4-(6-cyclopropyl-7-iodo-4-oxo-3-hydropyrrolo[3,2-d]pyrimidin-5-yl)butanoate (Compound No. 2509)

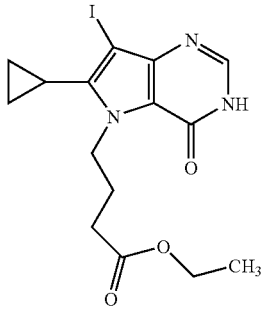

A dichloromethane (40 mL) solution of an ethyl-4-(6-cyclopropyl-4-oxo-3-hydropyrrolo[3,2-d]pyrimidin-5-yl)butanoate (1.58 g) and an N-iodosuccinimide (1.35 g) was stirred at room temperature for 2 hours. Water was added, and the mixture solution was further stirred for 30 minutes. A solid was extracted by filtration, washed by water and ethyl acetate, and dried under reduced pressure, to obtain the title compound (1.82 g, yield 80%). The filtration solution was separated to ethyl acetate and aqueous layers, and the aqueous layer was extracted with ethyl acetate. The combined organic layer was washed with saturated brine, and dried over a magnesium sulfate. The magnesium sulfate was filtered off, and the solvent was distilled off under reduced pressure. A produced solid was extracted by filtration, washed with ethyl acetate, and dried under reduced pressure, to obtain the title compound (0.35 mg, yield 15%). The NMR data and ESI/MS data of the compound are given below.

$^1$H-NMR (400 MHz, DMSO-$d_6$)δ(ppm): 0.89 (m, 2H), 1.08-1.15 (m, 5H), 1.80 (m, 1H), 2.01 (m, 2H), 2.31 (t, J=7.3, 2H), 3.96 (dd, J=7.0, J=14.3, 2H), 4.57 (t, J=7.2, 2H), 7.82 (s, 1H), 12.00 (brs, H). ESI/MS m/e: 416.1 (M$^+$+H, $C_{15}H_{18}IN_3O_3$)

Example 61

Synthesis of ethyl-4-(6-cyclopropyl-4-oxo-7-(3-pyridyl)-3-hydropyrrolo[3,2-d]pyrimidin-5-yl)butanoate (Compound No. 2510)

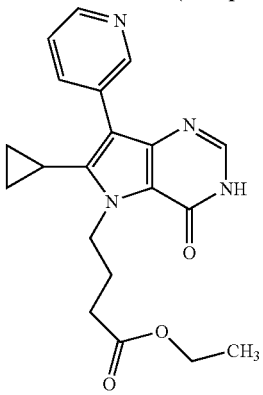

The title compound was obtained by using ethyl-4-(6-cyclopropyl-7-iodo-4-oxo-3-hydropyrrolo[3,2-d]pyrimidin-5-yl)butanoate and 3-pyridyl boric acid in a similar manner to that in Example 28. The NMR data and ESI/MS data of the compound are given below.

$^1$H-NMR (400 MHz, DMSO-$d_6$)δ(ppm): 0.31 (m, 2H), 1.01 (m, 2H) 1.13 (t, J=7.2, 3H), 2.06-2.13 (m, 3H), 2.40 (t, J=7.3, 2H), 3.98 (dd, J=7.2, J=14.2, 2H), 4.61 (t, J=7.2, 2H), 7.43 (ddd, J=0.8, J=4.8, J=7.9, 1H), 7.82 (s, 1H), 8.01 (dt, J=2.0, J=8.1, 1H), 8.46 (dd, J=1.7, J=4.7, 1H), 8.83 (dd, J=0.8, J=2.3, 1H), 11.99 (brs, 1H). ESI/MS m/e: 367.2 (M$^+$+H, $C_{20}H_{22}N_4O_3$)

Example 62

Synthesis of 4-(6-cyclopropyl-4-oxo-7-(3-pyridyl)-3-hydropyrrolo[3,2-d]pyrimidin-5-yl)butanoic acid (Compound No. 2363) hydrochloride

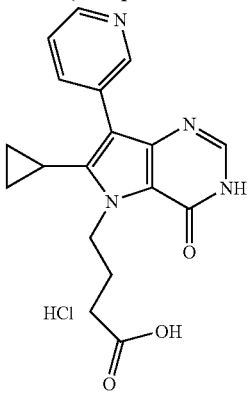

1M of aqueous lithium hydroxide solution (7.3 mL) was added to dioxane (25 mL) and water (10 mL) solution of ethyl-4-(6-cyclopropyl-4-oxo-7-(3-pyridyl)-3-hydropyrrolo[3,2-d]pyrimidin-5-yl)butanoate (1.06 g), and stirred at room temperature for 3 hours. 1M hydrochloric acid (10.2 mL) was added dropwise, and the solvent was distilled off under reduced pressure. An ethanol was added to a residue, a solid was extracted by filtration, washed with ethanol, and dried under reduced pressure, to obtain the title compound (1.10 g, quantitative yield). The NMR data and ESI/MS data of the compound are given below.

$^1$H-NMR (400 MHz, DMSO-$d_6$)δ(ppm): 0.39 (m, 2H), 1.10 (m, 2H) 2.07 (m, 2H), 2.18 (m, 1H), 2.33 (t, J=7.4, 2H), 4.63 (t, J=7.3, 2H), 7.95 (s, 1H), 8.10 (dd, J=5.7, J=8.1, 1H), 8.82 (m, 2H), 9.16 (d, J=1.8, 1H), 12.26 (brs, 1H). ESI/MS m/e: 339.0 (M⁺+H, $C_{18}H_{18}N_4O_3HCl$)

Example 63

Synthesis of 4-(6-cyclopropyl-4-oxo-7-(3-pyridyl)(3-hydropyrrolo[3,2-d]pyrimidin-5-yl))-N-[(4-methylphenyl)methyl]butanamide (Compound No. 2331)

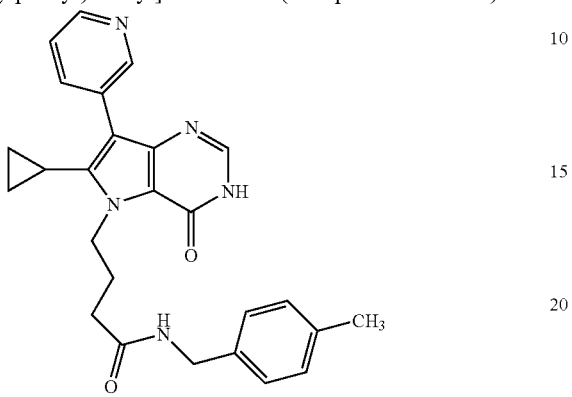

A diisopropylethylamine (70 μL) and a 4-methylbenzyl amine (15 mg) were added to solution of N,N-dimethylformamide (1.5 mL) of 4-(6-cyclopropyl-4-oxo-7-(3-pyridyl)-3-hydropyrrolo[3,2-d]pyrimidin-5-yl)butanoate (30 mg) and O-(7-azabenzotriazol-1-yl)N,N,N',N'-tetramethyluronium hexafluorophosphate (46 mg). The reaction solution was stirred at room temperature for 4 hours. The solvent was distilled off under reduced pressure, and ethyl acetate and water were added to a residue, separated to two layers, and an aqueous layer was extracted with ethyl acetate. The combined organic layer was dried over a sodium sulfate. The sodium sulfate was filtered off, and the solvent was distilled off under reduced pressure. The residue was purified by fraction HPLC, to obtain the title compound (3.1 mg, yield 9%). The HPLC retention time, NMR data and ESI/MS data of the compound are given below.

The HPLC retention time: 7.3 (min) ¹H-NMR (400 MHz, DMSO-d₆)δ(ppm): 0.27 (m, 2H), 0.93 (m, 2H), 2.01-2.11 (m, 3H), 2.21-2.27 (m, 5H), 4.21 (d, J=5.9, 2H), 4.58 (t, J=7.1, 2H), 7.10-7.15 (m, 4H), 7.43 (ddd, J=0.8, J=4.8, J=7.9, 1H), 7.82 (s, 1H), 8.01 (dt, J=2.0, J=8.1, 1H), 8.34 (t, J=5.9, 1H), 8.46 (dd, J=1.8, J=4.8, 1H), 8.84 (dd, J=0.8, J=2.3, 1H). ESI/MS m/e: 442.2 (M⁺+H, $C_{26}H_{27}N_5O_2$)

Example 64

Synthesis of ethyl-4-[6-cyclopropyl-7-(1-methylpyrazol-4-yl)-4-oxo-3-hydropyrrolo[3,2-d]pyrimidin-5-yl)butanoate (Compound No. 2511)

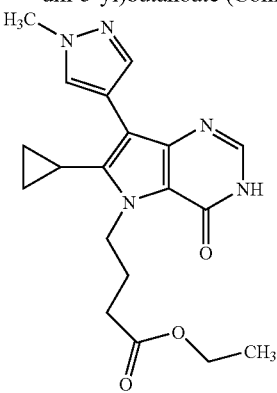

The title compound was obtained by using ethyl-4-(6-cyclopropyl-7-iodo-4-oxo-3-hydropyrrolo[3,2-d]pyrimidin-5-yl)butanoate and 1-methyl-4-(4,4,5,5-tetramethyl-1,3,2-dioxaborolane-2-yl)-1H-pyrazol in a similar manner to that in Example 28. The NMR data and ESI/MS data of the compound are given below.

¹H-NMR (400 MHz, DMSO-d₆)δ(ppm): 0.51 (m, 2H), 1.13 (m, 5H), 1.91 (m, 1H), 2.03 (m, 2H), 2.31 (t, J=7.3, 2H), 3.89 (s, 3H), 3.97 (dd, J=7.2, J=14.2, 2H), 4.58 (t, J=7.0, 2H), 7.80 (d, J=3.3, 1H), 7.83 (d, J=0.7, 1H), 8.03 (s, 1H), 11.87 (brs, 1H). ESI/MS m/e: 370.2 (M⁺+H, $C_{19}H_{23}N_5O_3$)]

Example 65

Synthesis of 4-[6-cyclopropyl-7-(1-methylpyrazol-4-yl)-4-oxo-3-hydropyrrolo[3,2-d]pyrimidin-5-yl]butanoic acid (Compound No. 2364)

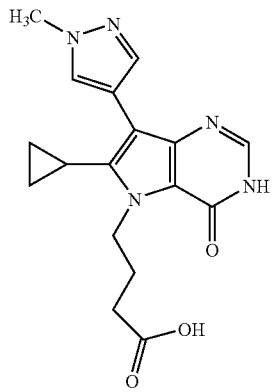

1M of aqueous lithium hydroxide solution (3.5 mL) was added to dioxane/water (4/1) solution (25 mL) of ethyl-4-[6-cyclopropyl-7-(1-methylpyrazol-4-yl)-4-oxo-3-hydropyrrolo[3,2-d]pyrimidin-5-yl)butanoate (0.52 g) dropwise. The reaction solution was stirred at room temperature for 4 hours, and 1M hydrochloric acid (3.5 mL) was added thereto dropwise. The solvent was distilled off under reduced pressure, a residue was purified by column chromatography on silica gel (dichloromethane/methanol/acetate/water=240/30/3/2), a diethylether was added to the obtained solid, and finely pulverized. The solid was extracted by filtration, washed with diethylether, and dried under reduced pressure, to obtain the title compound (0.40 g, yield 84%). The NMR data and ESI/MS data of the compound are given below.

¹H-NMR (400 MHz, DMSO-d₆)δ(ppm): 0.51 (m, 2H), 1.12 (m, 2H), 1.88-2.02 (m, 3H), 2.23 (t, J=7.4, 2H), 3.89 (s, 3H), 4.57 (t, J=7.2, 2H), 7.80 (d, J=3.5, 1H), 7.83 (d, J=0.7, 1H), 8.03 (s, 1H), 11.87 (brs, 1H). ESI/MS m/e: 342.2 (M⁺+H, $C_{17}H_{19}N_5O_3$)

Example 66

Synthesis of 4-[6-cyclopropyl-7-(1-methylpyrazol-4-yl)-4-oxo-(3-hydropyrrolo[3,2-d]pyrimidin-5-yl)]-N-[(4-methylphenyl)methyl]butanamide (Compound No. 2332)

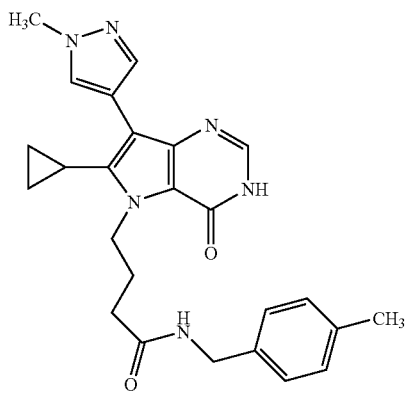

A diisopropylethylamine (78 μL) and a 4-methylbenzyl amine (13 mg) were added to a solution of N,N-dimethylformamide (1.0 mL) of 4-[6-cyclopropyl-7-(1-methylpyrazol-4-yl)-4-oxo-3-hydropyrrolo[3,2-d]pyrimidin-5-yl]butanoate (30 mg) and O-(7-azabenzotriazol-1-yl)N,N,N',N'-tetramethyluronium hexafluorophosphate (40 mg). The reaction solution was stirred at room temperature overnight. The solvent was distilled off under reduced pressure, a residue was purified by fraction HPLC, to obtain the title compound (30 mg, yield 77%). The HPLC retention time and ESI/MS data of the compound are given below.

The HPLC retention time: 8.0 (min) ESI/MS m/e: 445.3 (M$^+$+H, $C_{25}H_{28}N_6O_2$)

Example 67

Synthesis of 5-benzyl-7-(1-oxy(3-pyridyl))-3-hydropyrrolo[3,2-d]pyrimidin-4-one (Compound No. 2499)

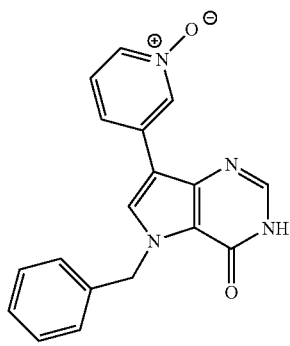

30% aqueous hydrogen peroxide solution (92 mg) was added to an acetic acid (2 mL) solution of 5-benzyl-7-(3-pyridyl)-3-hydropyrrolo[3,2-d]pyrimidin-4-one (31 mg), and the solution mixture was stirred at room temperature overnight. The reaction mixture was cooled to room temperature, purified by fraction HPLC, to obtain the title compound (19 mg, yield 58%). The HPLC retention time, NMR data and ESI/MS data of the compound are given below.

The HPLC retention time: 5.8 (min) $^1$H-NMR (400 MHz, DMSO-d$_6$)δ(ppm): 5.64 (s, 2H), 7.24-7.35 (m, 5H), 7.46 (m, 1H), 8.00 (m, 2H), 8.10 (m, 1H), 8.34 (s, 1H), 9.11 (s, 1H), 12.25 (brs, 1H). ESI/MS m/e: 319.3 (M$^+$+H, $C_{18}H_{14}N_4O_2$)

Example 68

Synthesis of (t-butoxy)-N-{2-[6-(3-chloro(2-thienyl)-7-(5-methyl(1,2,4-oxadiazol-3-yl)-4-oxo-(3-hydropyrrolo[3,2-d]pyrimidin-5-yl)]ethyl}carboxyamide (Compound No. 2126)

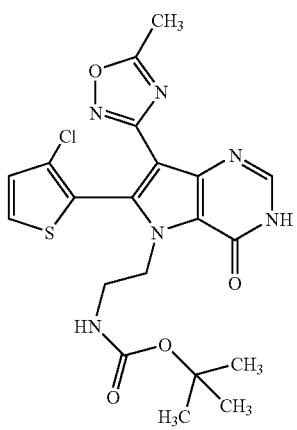

A (t-butoxy)-N-{2-[6-(3-chloro(2-thienyl))-7-cyano-4-oxo(3-hydropyrrolo[3,2-d]pyrimidin-5-yl)]ethyl}carboxyamide (105 mg) was dissolved in ethanol (2.5 mL), 35 mg of a hydroxylamine hydrochloride and a diisopropylethylamine (100 mg) were added thereto, and the solution mixture was stirred overnight under overheat reflux. The solvent was distilled off under reduced pressure, a dichloromethane (2.5 mL) and water (2.5 mL) were added thereto, and an organic layer was fractionally extracted. An aqueous layer was further extracted with dichloromethane (2.5 mL), an organic layer was combined, dried over sodium sulfate, and the solvent was distilled off under reduced pressure, to obtain a residue (113 mg). This residue was dissolved in dichloromethane (2 mL), acetate (18 mg), 1-ethyl-3-(3'-dimethylaminopropyl)carbodiimide hydrochloride (57 mg), and triethylamine (41 μL) were added thereto, and the solution mixture was stirred at 40° C. for 1 hour. The reaction solution was concentrated, and purified by fraction HPLC, to obtain the title compound (7.2 mg, yield 6%). The HPLC retention time and ESI/MS data of the compound are given below.

The HPLC retention time: 9.5 (min) ESI/MS m/e: 476.9 (M$^+$+H, $C_{20}H_{21}ClN_6O_4S$)

Example 69

Synthesis of (t-butoxy)-N-{2-[6-(3-chloro(2-thienyl)-7-(1,2,4-oxadiazol-3-yl)-4-oxo-(3-hydropyrrolo[3,2-d]pyrimidin-5-yl)]ethyl}carboxyamide (Compound No. 2513)

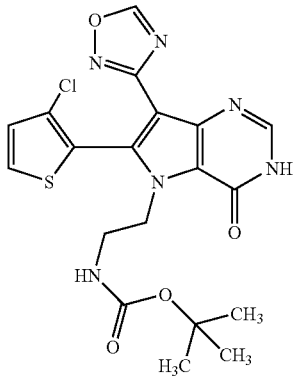

A (t-butoxy)-N-{2-[6-(3-chloro(2-thienyl))-7-cyano-4-oxo(3-hydropyrrolo[3,2-d]pyrimidin-5-yl)]ethyl}carboxyamide (105 mg) was dissolved in ethanol (2.5 mL), 35 mg of a hydroxylamine hydrochloride and a diisopropylethylamine (100 mg) were added thereto, and the solution mixture was stirred overnight under overheat reflux. The solvent was distilled off under reduced pressure, a dichloromethane (2.5 mL) and water (2.5 mL) were added thereto, and an organic layer was fractionally extracted. An aqueous layer was further extracted with dichloromethane (2.5 mL), an organic layer was combined, dried over sodium sulfate, and the solvent was distilled off under reduced pressure, to obtain a residue (113 mg). Meanwhile N,N-dimethylformamide (40 mg) was dissolved in diethylether (1 mL), phosphorus oxychloride (84 mg) was added thereto, and the solution mixture was stirred at room temperature for 1 hour, to obtain an oily compound. The produced oily compound was washed with diethylether (1 mL) twice, and suspended to a solvent mixture (3 mL) of 1,4-dioxane and diethylether. This suspension was added to the residue, and stirred at room temperature for 2 hours. The reaction solution was concentrated, water (5 mL) and ethyl acetate (5 mL) were added thereto, and an organic layer was separated. An aqueous layer was further extracted with ethyl acetate (5 mL), an organic layer was combined and concentrated, and then purified by fraction HPLC, to obtain the title compound (1.9 mg, yield 1.6%). The HPLC retention time and ESI/MS data of the compound are given below.

HPLC retention time: 9.1 (min) ESI/MS m/e: 462.9 ($M^+$+H, $C_{19}H_{19}ClN_6O_4S$)

Example 70

Synthesis of (t-butoxy)-N-{2-[6-(3-hydroxyphenyl)-4-oxo-7-(3-pyridyl)(3-hydropyrrolo[3,2-d]pyrimidin-5-yl)]ethyl}carboxyamide (Compound No. 2121)

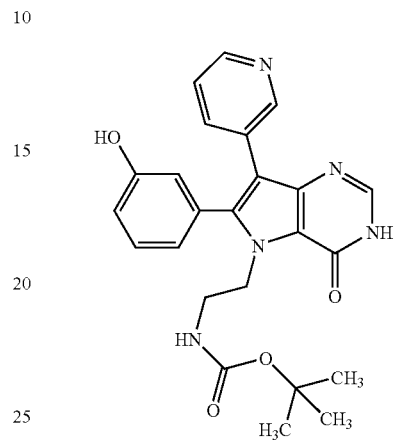

A t-butoxy)-N-(2-{4-oxo-6-[3-(phenylmethoxy)phenyl]-7-(3-pyridyl)(3-hydropyrrolo[3,2-d]pyrimidin-5-yl)}ethyl}carboxyamide (8.0 mg) was dissolved in ethanol, and palladium carbon (20 mg) was added thereto. The reaction system was substituted by hydrogen, and stirred at 60° C. overnight under atmospheric hydrogen pressure. The reaction solution was cooled to room temperature, and the palladium carbon was filtered off. The filtration solution was concentrated, purified by fraction HPLC, to obtain the title compound (4.0 mg, yield 60%). The HPLC retention time and ESI/MS data of the compound are given below.

HPLC retention time: 6.3 (min) ESI/MS m/e: 448.0 ($M^+$+H, $C_{24}H_{25}N_5O_4$)

Examples 71 to 494

The following compounds of the present invention were synthesized according to any method of Example 1 to Example 70 by using corresponding starting materials and reaction agents. The ESI/MS data in the HPLC/mass spectrum analysis, the retention time of the compound in the HPLC analysis and purity under the following analysis conditions of each compound, and compound numbers corresponding to executed syntheses are summarized in Table 2. Compound numbers in the table represent compound numbers of Table 1 listed as the preferred specific examples.

TABLE 2

| Ex. no. | Compound no. | Formula | ESI/MS m/e | HPLC min | Purity (%) | Synthesis |
|---|---|---|---|---|---|---|
| 71 | 19 | $C_{19}H_{21}N_5O_2$ | 352.2 | 5.7 | 96 | Ex. 40 |
| 72 | 27 | $C_{26}H_{25}N_5O_3$ | 456.3 | 7.8 | 99 | Ex. 40 |
| 73 | 29 | $C_{17}H_{17}N_5O_2$ | 324.2 | 3.3 | 99 | Ex. 40 |
| 74 | 40 | $C_{21}H_{15}Cl_2N_7OS$ | 484.2 | 7.7 | 98 | Ex. 38 |
| 75 | 80 | $C_{20}H_{14}BrClN_6OS$ | 503.2 | 6.8 | 100 | Ex. 38 |
| 76 | 83 | $C_{26}H_{19}ClN_6S_2$ | 515.4 | 10.4 | 96 | Ex. 38 |
| 77 | 212 | $C_{19}H_{14}ClN_5OS$ | 395.4 | 11.7 | 86 | Ex. 28 |
| 78 | 219 | $C_{20}H_{18}ClN_5O_2S$ | 428.0 | 5.6 | 95 | Ex. 35 |
| 79 | 230 | $C_{21}H_{20}ClN_5O_2S$ | 442.4 | 6.5 | 100 | Ex. 37 |

TABLE 2-continued

| Ex. no. | Compound no. | Formula | ESI/MS m/e | HPLC min | Purity (%) | Synthesis |
|---|---|---|---|---|---|---|
| 80 | 245 | $C_{21}H_{20}ClN_5O_2S$ | 442.0 | 6.1 | 94 | Ex. 35 |
| 81 | 254 | $C_{22}H_{22}ClN_5O_2S$ | 456.1 | 6.9 | 95 | Ex. 35 |
| 82 | 257 | $C_{21}H_{23}N_5O_2$ | 378.2 | 4.3 | 100 | Ex. 36 |
| 83 | 263 | $C_{20}H_{21}N_5O_2$ | 364.2 | 10.0 | 96 | Ex. 35 |
| 84 | 269 | $C_{21}H_{18}ClN_5O_2S$ | 440.4 | 6.2 | 100 | Ex. 37 |
| 85 | 280 | $C_{22}H_{25}N_5O_2$ | 392.2 | 5.4 | 100 | Ex. 35 |
| 86 | 287 | $C_{23}H_{22}ClN_5O_2S$ | 468.0 | 7.1 | 95 | Ex. 35 |
| 87 | 288 | $C_{22}H_{21}ClN_4O_2S_2$ | 472.9 | 11.8 | 97 | Ex. 35 |
| 88 | 297 | $C_{23}H_{27}N_5O_2$ | 406.2 | 12.9 | 98 | Ex. 35 |
| 89 | 303 | $C_{24}H_{24}ClN_5O_2S$ | 482.4 | 8.8 | 100 | Ex. 37 |
| 90 | 321 | $C_{19}H_{13}ClF_3N_5O_2S$ | 468.4 | 7.3 | 99 | Ex. 37 |
| 91 | 330 | $C_{23}H_{21}N_5O_2$ | 400.5 | 5.0 | 99 | Ex. 35 |
| 92 | 347 | $C_{25}H_{18}ClFN_4OS_2$ | 509.4 | 15.0 | 99 | Ex. 37 |
| 93 | 348 | $C_{24}H_{17}ClFN_5O_2S$ | 494.2 | 8.0 | 100 | Ex. 37 |
| 94 | 361 | $C_{26}H_{20}ClN_5O_4S$ | 534.0 | 9.4 | 78 | Ex. 35 |
| 95 | 370 | $C_{20}H_{13}BrClF_3N_4O_3S$ | 563.1 | 10.4 | 100 | Ex. 35 |
| 96 | 492 | $C_{23}H_{23}ClN_6O_2S$ | 483.1 | 10.8 | 93 | Ex. 33 |
| 97 | 504 | $C_{24}H_{25}ClN_6O_2S$ | 497.5 | 8.6 | 84 | Ex. 33 |
| 98 | 536 | $C_{30}H_{27}ClN_6O_3S$ | 587.4 | 9.0 | 79 | Ex. 33 |
| 99 | 595 | $C_{21}H_{25}N_5O_2$ | 380.2 | 5.2 | 100 | Ex. 35 |
| 100 | 596 | $C_{22}H_{22}ClN_5O_2S$ | 456.1 | 6.9 | 98 | Ex. 35 |
| 101 | 601 | $C_{21}H_{25}N_5O_2$ | 380.2 | 5.3 | 100 | Ex. 35 |
| 102 | 602 | $C_{22}H_{22}ClN_5O_2S$ | 456.1 | 7.1 | 94 | Ex. 35 |
| 103 | 605 | $C_{22}H_{29}N_5O_2$ | 396.3 | 5.1 | 100 | Ex. 35 |
| 104 | 615 | $C_{22}H_{27}N_5O_2$ | 394.1 | 7.5 | 99 | Ex. 35 |
| 105 | 616 | $C_{21}H_{26}N_4O_3$ | 383.2 | 10.3 | 78 | Ex. 28 |
| 106 | 617 | $C_{21}H_{26}N_4O_2S$ | 399.1 | 11.6 | 87 | Ex. 35 |
| 107 | 618 | $C_{20}H_{26}N_6O_2$ | 383.2 | 8.1 | 60 | Ex. 28 |
| 108 | 627 | $C_{22}H_{23}ClN_4O_3S$ | 459.3 | 15.0 | 95 | Ex. 35 |
| 109 | 628 | $C_{22}H_{23}ClN_4O_2S_2$ | 475.2 | 15.7 | 100 | Ex. 35 |
| 110 | 634 | $C_{22}H_{27}N_5O_2$ | 394.2 | 5.7 | 100 | Ex. 53 |
| 111 | 641 | $C_{23}H_{27}N_5O_2$ | 406.2 | 5.9 | 100 | Ex. 35 |
| 112 | 646 | $C_{24}H_{24}ClN_5O_2S$ | 482.0 | 6.9 | 95 | Ex. 35 |
| 113 | 657 | $C_{21}H_{23}N_5O_2$ | 378.3 | 4.3 | 97 | Ex. 35 |
| 114 | 659 | $C_{22}H_{20}ClN_5O_2S$ | 454.1 | 6.5 | 94 | Ex. 35 |
| 115 | 664 | $C_{23}H_{24}ClN_5O_2S$ | 470.2 | 9.1 | 99 | Ex. 35 |
| 116 | 667 | $C_{24}H_{29}N_5O_2$ | 420.2 | 6.3 | 100 | Ex. 36 |
| 117 | 668 | $C_{25}H_{26}ClN_5O_2S$ | 496.0 | 8.3 8.5 | 80 | Ex. 36 |
| 118 | 668 | $C_{25}H_{26}ClN_5O_2S$ | 496.0 | 8.3 | 89 | Ex. 36 |
| 119 | 673 | $C_{25}H_{26}ClN_5O_3S$ | 512.0 | 6.6 6.9 | 98 | Ex. 36 |
| 120 | 678 | $C_{28}H_{32}ClN_5O_2S$ | 538.1 | 11.1 | 97 | Ex. 36 |
| 121 | 689 | $C_{25}H_{25}ClN_6O_3S$ | 525.0 | 5.9 | 78 | Ex. 36 |
| 122 | 694 | $C_{24}H_{29}N_5O_2$ | 420.2 | 6.6 | 100 | Ex. 35 |
| 123 | 696 | $C_{25}H_{26}ClN_5O_2S$ | 496.0 | 8.5 | 98 | Ex. 35 |
| 124 | 702 | $C_{19}H_{21}N_5O_3$ | 368.2 | 9.5 | 82 | Ex. 35 |
| 125 | 704 | $C_{20}H_{18}ClN_5O_3S$ | 444.0 | 5.4 | 87 | Ex. 35 |
| 126 | 709 | $C_{21}H_{21}ClN_6O_2S$ | 457.1 | 4.8 | 94 | Ex. 35 |
| 127 | 713 | $C_{21}H_{19}ClN_6O_3S$ | 471.0 | 5.2 | 85 | Ex. 36 |
| 128 | 718 | $C_{22}H_{20}ClN_5O_4$ | 486.0 | 6.0 | 90 | Ex. 35 |
| 129 | 723 | $C_{24}H_{23}N_5O_2$ | 414.5 | 5.0 | 98 | Ex. 35 |
| 130 | 724 | $C_{25}H_{20}ClN_5O_2S$ | 490.4 | 8.1 | 100 | Ex. 37 |
| 131 | 729 | $C_{25}H_{20}ClN_5O_3S$ | 506.0 | 8.0 | 90 | Ex. 35 |
| 132 | 733 | $C_{25}H_{25}N_5O_2$ | 428.0 | 6.7 | 98 | Ex. 35 |
| 133 | 734 | $C_{26}H_{22}ClN_5O_2S$ | 504.0 | 8.5 | 94 | Ex. 35 |
| 134 | 741 | $C_{22}H_{20}ClN_5O_2S$ | 454.0 | 5.7 | 87 | Ex. 35 |
| 135 | 760 | $C_{20}H_{24}N_6O_2$ | 381.1 | 5.1 | 98 | Ex. 32 |
| 136 | 768 | $C_{21}H_{21}ClN_6O_2S$ | 457.1 | 5.4 | 95 | Ex. 32 |
| 137 | 770 | $C_{20}H_{20}ClN_5O_2S_2$ | 461.9 | 10.9 | 99 | Ex. 32 |
| 138 | 776 | $C_{24}H_{25}ClN_6O_2S$ | 497.0 | 7.7 | 95 | Ex. 32 |
| 139 | 785 | $C_{23}H_{22}N_6O_2$ | 415.0 | 6.9 | 96 | Ex. 32 |
| 140 | 795 | $C_{23}H_{18}ClN_5O_2S_2$ | 495.9 | 12.1 | 99 | Ex. 32 |
| 141 | 801 | $C_{24}H_{18}ClFN_6O_2S$ | 508.9 | 7.9 | 97 | Ex. 32 |
| 142 | 802 | $C_{24}H_{18}ClFN_6O_2S$ | 508.9 | 8.1 | 85 | Ex. 32 |
| 143 | 803 | $C_{24}H_{18}Cl_2N_6O_2S$ | 526.9 | 9.1 | 95 | Ex. 32 |
| 144 | 804 | $C_{25}H_{21}ClN_6O_3S$ | 520.9 | 7.7 | 98 | Ex. 32 |
| 145 | 805 | $C_{25}H_{21}ClN_6O_2S$ | 504.9 | 7.9 | 95 | Ex. 32 |
| 146 | 806 | $C_{25}H_{21}ClN_6O_2S$ | 504.9 | 8.2 | 85 | Ex. 32 |
| 147 | 807 | $C_{25}H_{21}ClN_6O_2S$ | 504.9 | 8.1 | 89 | Ex. 32 |
| 148 | 808 | $C_{24}H_{18}Cl_2N_6O_2S$ | 520.8 | 9.3 | 97 | Ex. 32 |
| 149 | 809 | $C_{24}H_{18}Cl_2N_6O_2S$ | 526.9 | 8.7 | 96 | Ex. 32 |
| 150 | 810 | $C_{24}H_{18}ClFN_6O_2S$ | 508.9 | 7.7 | 96 | Ex. 32 |
| 151 | 811 | $C_{25}H_{21}ClN_6O_3S$ | 520.9 | 8.9 | 93 | Ex. 32 |
| 152 | 812 | $C_{25}H_{21}ClN_6O_3S$ | 520.9 | 7.4 | 99 | Ex. 32 |
| 153 | 912 | $C_{22}H_{26}N_4O_3$ | 349.5 | 9.5 | 91 | Ex. 28 |
| 154 | 915 | $C_{21}H_{25}N_5O_3$ | 396.3 | 5.5 | 98 | Ex. 28 |

TABLE 2-continued

| Ex. no. | Compound no. | Formula | ESI/MS m/e | HPLC min | Purity (%) | Synthesis |
|---|---|---|---|---|---|---|
| 155 | 917 | $C_{20}H_{24}N_4O_4$ | 385.3 | 10.9 | 66 | Ex. 28 |
| 156 | 918 | $C_{20}H_{24}N_4O_3S$ | 401.5 | 12.4 | 93 | Ex. 28 |
| 157 | 948 | $C_{18}H_{21}ClN_4O_3S$ | 409.2 | 11.4 | 82 | Ex. 26 |
| 158 | 956 | $C_{24}H_{25}ClN_4O_3S$ | 485.2 | 13.9 | 91 | Ex. 26 |
| 159 | 968 | $C_{23}H_{29}ClN_4O_3S$ | 477.3 | 12.9 | 95 | Ex. 28 |
| 160 | 970 | $C_{19}H_{19}ClN_4O_3S$ | 419.3 | 10.9 | 98 | Ex. 27 |
| 161 | 972 | $C_{23}H_{27}ClN_4O_3S$ | 475.2 | 11.4 | 83 | Ex. 27 |
| 162 | 973 | $C_{25}H_{30}ClN_5O_3S$ | 499.2 | 7.7 | 81 | Ex. 27 |
| 163 | 974 | $C_{25}H_{23}ClN_4O_3S$ | 495.5 | 10.9 | 98 | Ex. 27 |
| 164 | 975 | $C_{25}H_{22}ClFN_4O_3S$ | 513.2 | 11.1 | 95 | Ex. 27 |
| 165 | 976 | $C_{26}H_{25}ClN_4O_4S$ | 525.2 | 11.0 | 98 | Ex. 27 |
| 166 | 977 | $C_{25}H_{24}ClN_5O_3S$ | 510.2 | 7.9 | 28 | Ex. 27 |
| 167 | 978 | $C_{25}H_{22}Cl_2N_4O_3S$ | 529.2 | 11.5 | 95 | Ex. 27 |
| 168 | 979 | $C_{24}H_{22}ClN_5O_3S$ | 496.2 | 7.9 | 72 | Ex. 27 |
| 169 | 980 | $C_{24}H_{30}ClN_5O_3S$ | 487.3 | 7.5 | 92 | Ex. 27 |
| 170 | 982 | $C_{22}H_{27}ClN_4O_3SSi$ | 491.4 | 12.0 | 87 | Ex. 27 |
| 171 | 983 | $C_{23}H_{23}ClN_4O_3S$ | 471.3 | 10.5 | 92 | Ex. 28 |
| 172 | 984 | $C_{23}H_{22}ClFN_4O_3S$ | 489.2 | 10.9 | 85 | Ex. 28 |
| 173 | 985 | $C_{24}H_{22}ClF_3N_4O_3S$ | 539.2 | 12.1 | 92 | Ex. 28 |
| 174 | 986 | $C_{24}H_{22}ClF_3N_4O_4S$ | 555.3 | 12.2 | 93 | Ex. 28 |
| 175 | 987 | $C_{23}H_{22}Cl_2N_4O_3S$ | 505.1 | 11.6 | 95 | Ex. 28 |
| 176 | 988 | $C_{25}H_{25}ClN_4O_4S$ | 513.3 | 9.8 | 88 | Ex. 28 |
| 177 | 989 | $C_{29}H_{27}ClN_4O_4S$ | 563.3 | 12.5 | 91 | Ex. 28 |
| 178 | 990 | $C_{25}H_{27}ClN_4O_5S$ | 531.3 | 9.5 | 91 | Ex. 28 |
| 179 | 991 | $C_{25}H_{28}ClN_5O_3S$ | 514.2 | 7.3 | 79 | Ex. 28 |
| 180 | 992 | $C_{24}H_{25}ClN_4O_3S$ | 485.3 | 11.1 | 94 | Ex. 28 |
| 181 | 993 | $C_{27}H_{25}ClN_4O_3S$ | 521.6 | — | 81 | Ex. 28 |
| 182 | 994 | $C_{25}H_{27}ClN_4O_3S$ | 499.2 | 11.6 | 96 | Ex. 28 |
| 183 | 995 | $C_{21}H_{21}ClN_6O_3S$ | 473.2 | 8.0 | 22 | Ex. 28 |
| 184 | 996 | $C_{26}H_{28}ClN_5O_4S$ | 542.3 | 8.7 | 90 | Ex. 28 |
| 185 | 997 | $C_{29}H_{33}ClN_4O_3S$ | 553.3 | 14.0 | 88 | Ex. 28 |
| 186 | 998 | $C_{22}H_{22}ClN_5O_3S$ | 472.2 | 6.6 | 78 | Ex. 28 |
| 187 | 999 | $C_{22}H_{22}ClN_5O_3S$ | 472.4 | 8.0 | 97 | Ex. 28 |
| 188 | 1001 | $C_{21}H_{21}ClN_4O_4S$ | 461.1 | 12.5 | 84 | Ex. 28 |
| 189 | 1002 | $C_{21}H_{21}ClN_4O_3S_2$ | 477.1 | 13.1 | 94 | Ex. 28 |
| 190 | 1003 | $C_{23}H_{24}ClN_5O_4S$ | 502.0 | 11.1 | 61 | Ex. 28 |
| 191 | 1004 | $C_{23}H_{24}ClN_5O_4S$ | 502.0 | 11.5 | 71 | Ex. 28 |
| 192 | 1005 | $C_{23}H_{24}ClN_5O_4S$ | 502.1 | 7.7 | 93 | Ex. 28 |
| 193 | 1006 | $C_{22}H_{21}Cl_2N_5O_3S$ | 506.0 | 12.8 | 90 | Ex. 28 |
| 194 | 1007 | $C_{22}H_{21}ClFN_5O_3S$ | 490.1 | 12.1 | 80 | Ex. 28 |
| 195 | 1008 | $C_{22}H_{21}ClFN_5O_3S$ | 490.1 | 12.8 | 94 | Ex. 28 |
| 196 | 1009 | $C_{26}H_{24}ClN_5O_3S$ | 522.0 | 10.4 | 54 | Ex. 28 |
| 197 | 1010 | $C_{24}H_{22}ClN_5O_3S$ | 496.4 | 14.7 | 88 | Ex. 28 |
| 198 | 1011 | $C_{23}H_{22}ClFN_4O_3S$ | 489.3 | 13.0 | 99 | Ex. 28 |
| 199 | 1012 | $C_{23}H_{22}ClFN_4O_3S$ | 489.4 | 13.3 | 96 | Ex. 28 |
| 200 | 1013 | $C_{22}H_{23}ClN_4O_3S_2$ | 491.3 | 12.9 | 99 | Ex. 28 |
| 201 | 1014 | $C_{20}H_{21}ClN_6O_3S$ | 461.4 | 8.9 | 98 | Ex. 28 |
| 202 | 1106 | $C_{18}H_{19}N_5O_2$ | 338.4 | 5.1 | 97 | Ex. 40 |
| 203 | 1131 | $C_{15}H_{15}N_5O_2$ | 298.3 | 2.2 | 99 | Ex. 40 |
| 204 | 1132 | $C_{14}H_{13}N_5O_2$ | 284.2 | 1.7 | 99 | Ex. 40 |
| 205 | 1146 | $C_{16}H_{15}N_5O_2$ | 310.4 | 2.6 | 99 | Ex. 40 |
| 206 | 1161 | $C_{19}H_{15}N_5O_2$ | 346.2 | 5.9 | 96 | Ex. 40 |
| 207 | 1168 | $C_{19}H_{23}N_5O_2$ | 354.3 | 7.1 | 99 | Ex. 40 |
| 208 | 1170 | $C_{15}H_{14}N_4O_3$ | 299.2 | 4.4 | 96 | Ex. 39 |
| 209 | 1174 | $C_{12}H_{10}N_4O$ | 227.2 | 2.4 | 100 | Ex. 28 |
| 210 | 1175 | $C_{12}H_9ClN_4O$ | 261.1 | 4.4 | 95 | Ex. 41 |
| 211 | 1177 | $C_{11}H_8N_4O$ | 213.1 | 5.0 | 99 | Ex. 28 |
| 212 | 1179 | $C_{18}H_{14}N_4O$ | 303.2 | 7.2 | 99 | Ex. 39 |
| 213 | 1181 | $C_{19}H_{15}N_7O$ | 358.1 | 3.6 | 100 | Ex. 38 |
| 214 | 1182 | $C_{23}H_{16}ClN_7OS$ | 474.0 | 6.8 | 67 | Ex. 38 |
| 215 | 1183 | $C_{22}H_{17}ClN_8OS$ | 477.1 | 7.7 | 100 | Ex. 38 |
| 216 | 1184 | $C_{23}H_{19}N_7O$ | 410.3 | 2.3 | 100 | Ex. 38 |
| 217 | 1185 | $C_{24}H_{18}ClN_7OS$ | 487.9 | 6.0 | 90 | Ex. 38 |
| 218 | 1186 | $C_{22}H_{17}ClF_3N_7OS$ | 520.1 | 8.1 | 100 | Ex. 38 |
| 219 | 1206 | $C_{20}H_{19}ClN_6O_2S$ | 443.1 | 6.7 | 97 | Ex. 35 |
| 220 | 1216 | $C_{21}H_{21}ClN_6O_2S$ | 457.0 | 8.6 | 87 | Ex. 8 |
| 221 | 1217 | $C_{22}H_{23}ClN_6O_2S$ | 471.1 | 7.6 | 83 | Ex. 35 |
| 222 | 1228 | $C_{23}H_{25}ClN_6O_2S$ | 485.2 | 8.2 | 96 | Ex. 35 |
| 223 | 1236 | $C_{25}H_{26}ClN_5O_2S$ | 497.9 | 8.4 | 96 | Ex. 36 |
| 224 | 1237 | $C_{24}H_{27}ClN_6O_2S$ | 499.2 | 8.5 | 99 | Ex. 36 |
| 225 | 1243 | $C_{25}H_{22}ClFN_6O_2S$ | 525.2 | 8.5 | 95 | Ex. 35 |
| 226 | 1250 | $C_{21}H_{23}ClN_6O_2S$ | 459.2 | 7.5 | 95 | Ex. 35 |
| 227 | 1257 | $C_{21}H_{23}ClN_6O_2S$ | 459.2 | 7.6 | 98 | Ex. 35 |
| 228 | 1258 | $C_{18}H_{24}N_6O_2$ | 357.2 | 5.9 | 100 | Ex. 53 |
| 229 | 1259 | $C_{18}H_{23}ClN_6O_2$ | 391.2 | 6.7 | 98 | Ex. 50 |
| 230 | 1260 | $C_{21}H_{27}N_5O_2$ | 382.2 | 5.3 | 100 | Ex. 53 |

TABLE 2-continued

| Ex. no. | Compound no. | Formula | ESI/MS m/e | HPLC min | Purity (%) | Synthesis |
|---|---|---|---|---|---|---|
| 231 | 1261 | $C_{20}H_{28}N_6O_2$ | 385.3 | 6.4 | 96 | Ex. 35 |
| 232 | 1262 | $C_{21}H_{30}N_6O_2$ | 399.3 | 6.6 | 100 | Ex. 35 |
| 233 | 1271 | $C_{21}H_{28}N_6O_2$ | 397.2 | 5.8 | 100 | Ex. 35 |
| 234 | 1277 | $C_{23}H_{28}N_6O_3$ | 437.3 | 7.6 | 79 | Ex. 53 |
| 235 | 1278 | $C_{22}H_{26}N_6O_3$ | 423.2 | 7.2 | 100 | Ex. 53 |
| 236 | 1282 | $C_{23}H_{25}N_5O_2S$ | 436.2 | 6.0 | 95 | Ex. 53 |
| 237 | 1284 | $C_{22}H_{26}N_6O_2S$ | 439.2 | 7.5 | 100 | Ex. 53 |
| 238 | 1286 | $C_{23}H_{28}N_6O_2S$ | 453.2 | 8.0 | 100 | Ex. 53 |
| 239 | 1287 | $C_{23}H_{24}ClN_5O_3S$ | 486.3 | 6.7 | 100 | Ex. 67 |
| 240 | 1288 | $C_{22}H_{25}ClN_6O_2S$ | 473.1 | 7.8 | 93 | Ex. 35 |
| 241 | 1293 | $C_{23}H_{27}ClN_6O_2S$ | 487.1 | 8.6 | 100 | Ex. 28 |
| 242 | 1296 | $C_{23}H_{28}N_6O_2S$ | 453.2 | 8.1 | 95 | Ex. 53 |
| 243 | 1297 | $C_{21}H_{25}N_5O_2$ | 380.2 | 5.2 | 96 | Ex. 53 |
| 244 | 1331 | $C_{23}H_{27}N_7O_2$ | 434.2 | 5.2 | 100 | Ex. 53 |
| 245 | 1332 | $C_{22}H_{28}N_8O_2$ | 437.3 | 5.9 | 100 | Ex. 53 |
| 246 | 1333 | $C_{26}H_{32}N_6O_4$ | 493.2 | 7.1 | 81 | Ex. 53 |
| 247 | 1334 | $C_{25}H_{28}N_6O_4$ | 477.2 | 7.5 | 100 | Ex. 53 |
| 248 | 1335 | $C_{23}H_{25}N_5O_3$ | 420.2 | 5.6 | 99 | Ex. 53 |
| 249 | 1337 | $C_{22}H_{26}N_6O_3$ | 423.2 | 7.1 | 100 | Ex. 53 |
| 250 | 1338 | $C_{22}H_{26}N_6O_2S$ | 439.2 | 7.6 | 98 | Ex. 53 |
| 251 | 1341 | $C_{23}H_{28}N_6O_2S$ | 453.2 | 8.3 | 100 | Ex. 53 |
| 252 | 1364 | $C_{21}H_{23}N_5O_2$ | 378.3 | 4.3 | 98 | Ex. 35 |
| 253 | 1374 | $C_{21}H_{21}ClN_6O_2S$ | 457.1 | 7.1 | 96 | Ex. 35 |
| 254 | 1399 | $C_{23}H_{25}ClN_6O_2S$ | 485.2 | 8.0 | 92 | Ex. 36 |
| 255 | 1405 | $C_{24}H_{29}N_5O_2$ | 420.2 | 6.1 | 100 | Ex. 36 |
| 256 | 1413 | $C_{25}H_{26}ClN_5O_2S$ | 497.9 | 8.7 | 96 | Ex. 36 |
| 257 | 1415 | $C_{24}H_{27}ClN_6O_2S$ | 499.1 | 8.6 | 100 | Ex. 36 |
| 258 | 1423 | $C_{25}H_{31}N_5O_2$ | 434.4 | 6.5 | 98 | Ex. 36 |
| 259 | 1427 | $C_{25}H_{29}ClN_6O_2S$ | 513.2 | 9.3 | 96 | Ex. 36 |
| 260 | 1430 | $C_{21}H_{21}ClN_6O_2S$ | 457.1 | 7.1 | 89 | Ex. 35 |
| 261 | 1445 | $C_{24}H_{27}ClN_6O_2S$ | 499.2 | 8.8 | 100 | Ex. 36 |
| 262 | 1482 | $C_{25}H_{31}N_5O_2$ | 434.4 | 6.8 | 96 | Ex. 35 |
| 263 | 1486 | $C_{25}H_{29}ClN_6O_2S$ | 513.2 | 9.5 | 100 | Ex. 36 |
| 264 | 1490 | $C_{22}H_{27}N_5O_2$ | 394.4 | 5.4 | 98 | Ex. 35 |
| 265 | 1494 | $C_{22}H_{25}ClN_6O_2S$ | 473.2 | 8.2 | 98 | Ex. 35 |
| 266 | 1511 | $C_{26}H_{23}ClN_6O_2S$ | 519.1 | 6.5 | 91 | Ex. 33 |
| 267 | 1514 | $C_{21}H_{19}ClN_6O_2S$ | 455.1 | 6.9 | 87 | Ex. 35 |
| 268 | 1519 | $C_{20}H_{23}N_5O_2S$ | 398.2 | 4.9 | 100 | Ex. 36 |
| 269 | 1520 | $C_{21}H_{20}ClN_5O_2S_2$ | 474.0 | 5.3 | 98 | Ex. 35 |
| 270 | 1522 | $C_{24}H_{25}ClN_6O_3S$ | 513.1 | 4.2 | 100 | Ex. 36 |
| 271 | 1530 | $C_{25}H_{27}ClN_6O_2S$ | 512.9 | 5.4 | 92 | Ex. 36 |
| 272 | 1533 | $C_{20}H_{14}ClF_4N_5O_2S$ | 500.0 | 6.3 | 65 | Ex. 35 |
| 273 | 1535 | $C_{21}H_{13}ClF_7N_5O_2S$ | 568.0 | 7.7 | 96 | Ex. 35 |
| 274 | 1549 | $C_{25}H_{31}N_5O_2$ | 434.2 | 6.8 | 100 | Ex. 35 |
| 275 | 1553 | $C_{25}H_{29}ClN_6O_2S$ | 513.2 | 9.5 | 90 | Ex. 35 |
| 276 | 1554 | $C_{26}H_{33}N_5O_2$ | 448.2 | 7.5 | 100 | Ex. 35 |
| 277 | 1558 | $C_{26}H_{31}ClN_6O_2S$ | 527.2 | 10.3 | 95 | Ex. 35 |
| 278 | 1566 | $C_{24}H_{25}ClN_6O_2S$ | 497.2 | 8.3 | 97 | Ex. 36 |
| 279 | 1589 | $C_{23}H_{25}F_2N_5O_2$ | 442.23 | 5.3 | 98 | Ex. 36 |
| 280 | 1600 | $C_{23}H_{23}ClF_2N_6O_2S$ | 521.2 | 7.8 | 98 | Ex. 36 |
| 281 | 1623 | $C_{27}H_{35}N_5O_2$ | 462.2 | 7.5 7.7 | 100 | Ex. 35 |
| 282 | 1647 | $C_{24}H_{26}F_3N_5O_2$ | 474.2 | 6.2 6.5 | 79 | Ex. 36 |
| 283 | 1654 | $C_{24}H_{24}ClF_3N_6O_2S$ | 553.2 | 9.1 | 99 | Ex. 36 |
| 284 | 1660 | $C_{25}H_{31}N_5O_2$ | 434.3 | 6.5 6.6 | 99 | Ex. 36 |
| 285 | 1661 | $C_{25}H_{29}ClN_6O_2S$ | 513.2 | 9.3 9.4 | 98 | Ex. 36 |
| 286 | 1673 | $C_{22}H_{25}N_5O_3$ | 408.2 | 4.5 | 100 | Ex. 36 |
| 287 | 1679 | $C_{22}H_{23}ClN_6O_3S$ | 487.1 | 6.4 | 95 | Ex. 36 |
| 288 | 1682 | $C_{28}H_{31}ClN_6O_4S$ | 583.2 | 6.9 | 96 | Ex. 36 |
| 289 | 1691 | $C_{28}H_{31}ClN_6O_4S$ | 583.2 | 6.9 | 98 | Ex. 36 |
| 290 | 1693 | $C_{27}H_{32}ClN_7O_4S$ | 586.2 | 8.4 | 95 | Ex. 36 |
| 291 | 1695 | $C_{27}H_{32}ClN_7O_4S$ | 586.2 | 8.6 | 95 | Ex. 36 |
| 292 | 1696 | $C_{28}H_{31}ClN_6O_4S$ | 583.1 | 7.0 | 99 | Ex. 36 |
| 293 | 1697 | $C_{27}H_{32}ClN_7O_4S$ | 586.2 | 8.6 | 94 | Ex. 36 |
| 294 | 1698 | $C_{26}H_{30}ClN_7O_4S$ | 572.1 | 7.8 | 93 | Ex. 36 |
| 295 | 1699 | $C_{27}H_{29}ClN_6O_4S$ | 569.1 | 6.2 | 98 | Ex. 36 |
| 296 | 1700 | $C_{26}H_{30}ClN_7O_4S$ | 572.2 | 7.8 | 92 | Ex. 36 |
| 297 | 1715 | $C_{29}H_{33}ClN_6O_3S$ | 581.2 | 6.3 | 93 | Ex. 36 |
| 298 | 1719 | $C_{27}H_{27}ClN_6O_3S$ | 551.1 | 5.2 | 96 | Ex. 36 |
| 299 | 1721 | $C_{28}H_{29}ClN_6O_3S$ | 565.2 | 5.7 | 93 | Ex. 36 |
| 300 | 1739 | $C_{27}H_{31}ClN_6O_2S$ | 539.2 | 4.7 | 90 | Ex. 36 |
| 301 | 1748 | $C_{28}H_{33}ClN_6O_2S$ | 553.2 | 5.1 | 95 | Ex. 36 |
| 302 | 1751 | $C_{28}H_{33}ClN_6O_2S$ | 553.2 | 5.2 | 96 | Ex. 36 |

TABLE 2-continued

| Ex. no. | Compound no. | Formula | ESI/MS m/e | HPLC min | Purity (%) | Synthesis |
|---|---|---|---|---|---|---|
| 303 | 1753 | $C_{29}H_{35}ClN_6O_2S$ | 567.2 | 5.5 | 89 | Ex. 36 |
| 304 | 1758 | $C_{27}H_{29}ClN_6O_2S$ | 537.1 | 4.7 | 96 | Ex. 36 |
| 305 | 1778 | $C_{25}H_{22}F_3N_5O_2$ | 482.3 | 6.5 | 99 | Ex. 36 |
| 306 | 1804 | $C_{27}H_{21}ClN_6O_2S$ | 530.9 | 7.4 | 92 | Ex. 36 |
| 307 | 1805 | $C_{28}H_{23}ClN_6O_2S$ | 543.1 | 8.1 | 89 | Ex. 36 |
| 308 | 1806 | $C_{27}H_{22}ClN_5O_2S$ | 516.1 | 6.8 | 96 | Ex. 35 |
| 309 | 1808 | $C_{27}H_{22}ClN_5O_2S$ | 518.0 | 8.1 | 90 | Ex. 36 |
| 310 | 1823 | $C_{26}H_{23}ClN_6O_2S$ | 519.1 | 5.2 | 94 | Ex. 36 |
| 311 | 1828 | $C_{27}H_{25}ClN_6O_2S$ | 533.1 | 5.2 | 89 | Ex. 36 |
| 312 | 1833 | $C_{26}H_{21}ClN_6O_2S$ | 517.1 | 5.9 | 86 | Ex. 36 |
| 313 | 1843 | $C_{23}H_{25}N_5O_3$ | 419.2 | 4.6 | 86 | Ex. 36 |
| 314 | 1846 | $C_{26}H_{27}N_5O_2$ | 441.2 | 6.1 | 90 | Ex. 36 |
| 315 | 1849 | $C_{28}H_{36}N_6O_4$ | 520.3 | 6.3 | 39 | Ex. 36 |
| 316 | 1852 | $C_{29}H_{38}N_6O_4$ | 534.3 | 6.9 | 43 | Ex. 36 |
| 317 | 1855 | $C_{19}H_{18}F_3N_5O_2$ | 406.2 | 4.4 | 98 | Ex. 36 |
| 318 | 1860 | $C_{19}H_{16}ClF_3N_6O_2S$ | 485.1 | 7.4 | 91 | Ex. 36 |
| 319 | 1861 | $C_{18}H_{16}ClF_2N_5O_2$ | 408.2 | 4.9 | 36 | Ex. 36 |
| 320 | 1865 | $C_{20}H_{22}ClN_5O_2$ | 400.3 | 4.6 | 60 | Ex. 35 |
| 321 | 1868 | $C_{21}H_{23}N_5O_2$ | 378.3 | 4.4 | 97 | Ex. 35 |
| 322 | 1885 | $C_{20}H_{20}F_3N_5O_2$ | 420.1 | 5.0 | 100 | Ex. 36 |
| 323 | 1890 | $C_{20}H_{18}ClF_3N_6O_2S$ | 499.1 | 7.7 | 98 | Ex. 36 |
| 324 | 1891 | $C_{24}H_{29}N_5O_2$ | 420.2 | 6.3 | 100 | Ex. 36 |
| 325 | 1894 | $C_{24}H_{27}ClN_6O_2S$ | 499.2 | 9.0 | 100 | Ex. 35 |
| 326 | 1899 | $C_{21}H_{22}F_3N_5O_2$ | 434.1 | 5.5 | 100 | Ex. 36 |
| 327 | 1900 | $C_{21}H_{20}ClF_3N_6O_2S$ | 513.1 | 8.2 | 98 | Ex. 36 |
| 328 | 1913 | $C_{21}H_{20}N_6O_2$ | 389.1 | 4.1 | 100 | Ex. 36 |
| 329 | 1915 | $C_{21}H_{21}Cl_2N_5O_2$ | 446.1 | 5.5 | 100 | Ex. 36 |
| 330 | 2003 | $C_{24}H_{27}ClN_6O_2$ | 467.2 | 8.6 | 70 | Ex. 53 |
| 331 | 2004 | $C_{26}H_{25}N_5O_2$ | 440.5 | 6.0 | 99 | Ex. 35 |
| 332 | 2005 | $C_{22}H_{23}ClN_6O_2S$ | 471.0 | 7.2 | 97 | Ex. 32 |
| 333 | 2006 | $C_{23}H_{23}ClN_6O_2S$ | 483.0 | 7.4 | 97 | Ex. 32 |
| 334 | 2007 | $C_{24}H_{21}F_3N_6O_2$ | 483.3 | 7.0 | 99 | Ex. 32 |
| 335 | 2008 | $C_{24}H_{21}F_3N_6O_3$ | 499.3 | 7.1 | 96 | Ex. 32 |
| 336 | 2009 | $C_{23}H_{17}Cl_2N_7O_2S$ | 526.0 | 6.5 | 90 | Ex. 33 |
| 337 | 2010 | $C_{25}H_{20}ClFN_6O_2S$ | 523.1 | 6.3 | 97 | Ex. 32 |
| 338 | 2011 | $C_{24}H_{21}ClFN_7O_2S$ | 526.1 | 7.9 | 97 | Ex. 32 |
| 339 | 2012 | $C_{24}H_{20}ClN_7O_2S$ | 506.1 | 4.0 | 81 | Ex. 33 |
| 340 | 2013 | $C_{25}H_{23}F_3N_6O_3$ | 513.1 | 6.8 | 100 | Ex. 32 |
| 341 | 2014 | $C_{25}H_{27}ClN_6O_2S$ | 511.0 | 9.4 | 97 | Ex. 32 |
| 342 | 2015 | $C_{24}H_{28}ClN_7O_2S$ | 514.1 | 8.5 | 100 | Ex. 32 |
| 343 | 2016 | $C_{25}H_{21}ClN_6O_2S$ | 505.0 | 7.7 | 93 | Ex. 32 |
| 344 | 2017 | $C_{24}H_{21}F_3N_6O_2$ | 483.2 | 6.8 | 100 | Ex. 32 |
| 345 | 2018 | $C_{24}H_{21}F_3N_6O_2$ | 483.3 | 6.0 | 99 | Ex. 32 |
| 346 | 2019 | $C_{24}H_{26}ClN_7O_3S$ | 528.1 | 4.4 | 96 | Ex. 33 |
| 347 | 2020 | $C_{25}H_{28}ClN_7O_3S$ | 542.1 | 4.3 | 100 | Ex. 33 |
| 348 | 2021 | $C_{25}H_{28}ClN_7O_2S$ | 526.1 | 4.8 | 98 | Ex. 33 |
| 349 | 2022 | $C_{25}H_{32}N_6O_2$ | 449.2 | 6.7 | 100 | Ex. 32 |
| 350 | 2023 | $C_{26}H_{29}ClN_6O_2S$ | 525.1 | 7.3 | 98 | Ex. 32 |
| 351 | 2024 | $C_{25}H_{30}ClN_7O_2S$ | 528.1 | 8.8 | 98 | Ex. 33 |
| 352 | 2025 | $C_{26}H_{29}ClN_6O_2S$ | 525.2 | 7.2 | 94 | Ex. 33 |
| 353 | 2026 | $C_{25}H_{30}ClN_7O_2S$ | 528.1 | 8.9 | 100 | Ex. 32 |
| 354 | 2027 | $C_{25}H_{27}ClN_6O_3S$ | 527.2 | 5.5 | 96 | Ex. 33 |
| 355 | 2028 | $C_{28}H_{29}ClN_6O_2S$ | 549.0 | 9.7 | 97 | Ex. 32 |
| 356 | 2029 | $C_{25}H_{20}ClFN_6O_2S$ | 523.1 | 5.8 | 97 | Ex. 32 |
| 357 | 2031 | $C_{24}H_{23}FN_6O_2$ | 447.1 | 5.5 | 100 | Ex. 32 |
| 358 | 2032 | $C_{25}H_{20}ClFN_6O_2S$ | 523.1 | 6.3 | 98 | Ex. 32 |
| 359 | 2033 | $C_{24}H_{21}ClFN_7O_2S$ | 526.1 | 7.8 | 94 | Ex. 32 |
| 360 | 2034 | $C_{25}H_{19}ClF_2N_6O_2S$ | 541.0 | 6.7 | 96 | Ex. 32 |
| 361 | 2036 | $C_{24}H_{20}ClF_2N_7O_2S$ | 544.1 | 7.6 | 94 | Ex. 32 |
| 362 | 2040 | $C_{24}H_{22}Cl_2N_6O_2$ | 497.3 | 6.6 | 100 | Ex. 33 |
| 363 | 2042 | $C_{25}H_{23}F_3N_6O_2$ | 497.3 | 6.3 | 97 | Ex. 33 |
| 364 | 2046 | $C_{25}H_{23}F_3N_6O_2$ | 497.3 | 6.6 | 98 | Ex. 33 |
| 365 | 2049 | $C_{25}H_{21}ClF_3N_7O_2S$ | 576.1 | 8.9 | 100 | Ex. 32 |
| 366 | 2052 | $C_{26}H_{20}ClF_3N_6O_3S$ | 589.0 | 7.6 | 98 | Ex. 32 |
| 367 | 2053 | $C_{25}H_{21}ClF_3N_7O_3S$ | 592.1 | 9.0 | 100 | Ex. 32 |
| 368 | 2054 | $C_{24}H_{24}F_3N_7O_3$ | 516.2 | 8.0 | 100 | Ex. 32 |
| 369 | 2056 | $C_{26}H_{20}ClF_3N_6O_3S$ | 589.0 | 7.7 | 98 | Ex. 32 |
| 370 | 2058 | $C_{25}H_{21}ClF_3N_7O_3S$ | 592.1 | 9.1 | 100 | Ex. 32 |
| 371 | 2060 | $C_{26}H_{23}ClN_6O_3S$ | 535.1 | 6.3 | 99 | Ex. 32 |
| 372 | 2062 | $C_{26}H_{23}ClN_6O_3S$ | 535.1 | 6.2 | 96 | Ex. 32 |
| 373 | 2063 | $C_{25}H_{24}ClN_7O_3S$ | 538.1 | 7.7 | 91 | Ex. 32 |
| 374 | 2064 | $C_{25}H_{26}N_6O_3$ | 459.1 | 5.3 | 100 | Ex. 32 |
| 375 | 2065 | $C_{26}H_{23}ClN_6O_3S$ | 535.1 | 6.1 | 99 | Ex. 32 |
| 376 | 2067 | $C_{25}H_{24}ClN_7O_3S$ | 538.1 | 7.7 | 91 | Ex. 32 |
| 377 | 2068 | $C_{27}H_{25}ClN_6O_4S$ | 565.1 | 5.8 | 89 | Ex. 32 |
| 378 | 2069 | $C_{26}H_{26}ClN_7O_4S$ | 568.1 | 7.0 | 63 | Ex. 32 |

TABLE 2-continued

| Ex. no. | Compound no. | Formula | ESI/MS m/e | HPLC min | Purity (%) | Synthesis |
|---|---|---|---|---|---|---|
| 379 | 2070 | $C_{27}H_{25}ClN_6O_4S$ | 565.1 | 6.5 | 87 | Ex. 32 |
| 380 | 2071 | $C_{26}H_{26}ClN_7O_4S$ | 568.1 | 7.7 | 94 | Ex. 32 |
| 381 | 2072 | $C_{26}H_{21}ClN_6O_4S$ | 549.1 | 6.2 | 96 | Ex. 32 |
| 382 | 2073 | $C_{25}H_{22}ClN_7O_4S$ | 552.0 | 7.5 | 90 | Ex. 32 |
| 383 | 2078 | $C_{26}H_{23}ClN_6O_4S_2$ | 583.0 | 5.6 | 78 | Ex. 32 |
| 384 | 2080 | $C_{26}H_{27}ClN_8O_2S$ | 551.0 | 5.8 | 95 | Ex. 33 |
| 385 | 2081 | $C_{24}H_{20}ClN_7O_2S$ | 506.1 | 4.1 | 65 | Ex. 33 |
| 386 | 2083 | $C_{24}H_{20}ClN_7O_2S$ | 506.1 | 4.1 | 75 | Ex. 32 |
| 387 | 2085 | $C_{24}H_{19}Cl_2N_7O_2S$ | 540.0 | 5.0 | 88 | Ex. 32 |
| 388 | 2086 | $C_{23}H_{20}Cl_2N_8O_2S$ | 543.0 | 6.9 | 100 | Ex. 33 |
| 389 | 2087 | $C_{23}H_{19}ClN_6O_3S$ | 495.6 | 5.6 | 90 | Ex. 32 |
| 390 | 2089 | $C_{23}H_{19}ClN_6O_2S_2$ | 511.0 | 5.8 | 94 | Ex. 32 |
| 391 | 2093 | $C_{26}H_{23}ClN_6O_2S$ | 519.1 | 6.5 | 98 | Ex. 32 |
| 392 | 2094 | $C_{26}H_{23}ClN_6O_2S$ | 519.1 | 6.5 | 98 | Ex. 32 |
| 393 | 2095 | $C_{27}H_{25}ClN_6O_3S$ | 549.1 | 6.4 | 100 | Ex. 32 |
| 394 | 2096 | $C_{27}H_{25}ClN_6O_3S$ | 549.1 | 6.4 | 94 | Ex. 32 |
| 395 | 2097 | $C_{26}H_{26}ClN_7O_3S$ | 552.1 | 7.9 | 94 | Ex. 32 |
| 396 | 2098 | $C_{25}H_{23}ClFN_7O_2S$ | 540.1 | 8.2 | 100 | Ex. 32 |
| 397 | 2099 | $C_{25}H_{18}ClF_3N_6O_2S$ | 558.9 | 9.6 | 96 | Ex. 32 |
| 398 | 2100 | $C_{23}H_{17}Cl_2N_7O_2S$ | 526.0 | 6.0 | 93 | Ex. 33 |
| 399 | 2101 | $C_{21}H_{16}ClN_7O_2S_2$ | 497.9 | 6.4 | 85 | Ex. 32 |
| 400 | 2102 | $C_{24}H_{20}ClF_2N_7O_2S$ | 544.1 | 8.1 | 93 | Ex. 33 |
| 401 | 2103 | $C_{25}H_{22}F_4N_6O_2$ | 515.3 | 6.7 | 97 | Ex. 33 |
| 402 | 2105 | $C_{25}H_{22}F_4N_6O_2$ | 515.3 | 6.6 | 100 | Ex. 33 |
| 403 | 2107 | $C_{30}H_{28}N_6O_2$ | 505.4 | 7.0 | 80 | Ex. 33 |
| 404 | 2109 | $C_{25}H_{21}ClN_6O_2S$ | 505.1 | 6.1 | 89 | Ex. 33 |
| 405 | 2110 | $C_{18}H_{21}N_5O_3$ | 356.3 | 4.5 | 91 | Ex. 28 |
| 406 | 2116 | $C_{20}H_{26}N_6O_3$ | 399.1 | 6.7 | 100 | Ex. 28 |
| 407 | 2119 | $C_{23}H_{32}N_6O_3$ | 441.2 | 8.1 | 86 | Ex. 28 |
| 408 | 2120 | $C_{19}H_{22}N_4O_4$ | 371.0 | 7.4 | 33 | Ex. 70 |
| 409 | 2122 | $C_{23}H_{26}N_6O_4$ | 451.0 | 7.7 | 41 | Ex. 70 |
| 410 | 2127 | $C_{18}H_{19}ClN_8O_3S$ | 462.9 | 8.6 | 98 | Ex. 28 |
| 411 | 2141 | $C_{26}H_{28}N_4O_4$ | 461.0 | 11.5 | 99 | Ex. 10 |
| 412 | 2142 | $C_{31}H_{31}N_5O_4$ | 538.0 | 9.3 | 99 | Ex. 28 |
| 413 | 2143 | $C_{30}H_{32}N_6O_4$ | 541.1 | 11.4 | 70 | Ex. 28 |
| 414 | 2146 | $C_{22}H_{22}ClN_5O_3S$ | 472.1 | 6.8 | 99 | Ex. 35 |
| 415 | 2147 | $C_{25}H_{20}ClN_5O_3S$ | 506.1 | 7.1 | 98 | Ex. 35 |
| 416 | 2148 | $C_{22}H_{22}ClN_5O_3S$ | 472.1 | 6.8 | 99 | Ex. 35 |
| 417 | 2158 | $C_{20}H_{23}N_5O_2$ | 366.4 | 4.7 | 100 | Ex. 49 |
| 418 | 2161 | $C_{24}H_{29}N_5O_2$ | 420.3 | 7.1 | 93 | Ex. 63 |
| 419 | 2162 | $C_{23}H_{30}N_6O_2$ | 423.3 | 7.8 | 100 | Ex. 63 |
| 420 | 2164 | $C_{24}H_{28}N_6O_2S$ | 465.3 | 8.6 | 100 | Ex. 53 |
| 421 | 2165 | $C_{29}H_{33}N_5O_4$ | 516.4 | 7.5 | 99 | Ex. 53 |
| 422 | 2165 | $C_{25}H_{27}N_5O_3$ | 446.2 | 7.3 | 98.9 | Ex. 53 |
| 423 | 2166 | $C_{28}H_{34}N_6O_4$ | 519.3 | 8.1 | 100 | Ex. 53 |
| 424 | 2170 | $C_{24}H_{28}N_6O_3$ | 449.3 | 8.3 | 100 | Ex. 53 |
| 425 | 2175 | $C_{30}H_{31}N_5O_3$ | 510.3 | 7.6 | 88 | Ex. 63 |
| 426 | 2176 | $C_{29}H_{32}N_6O_3$ | 513.4 | 8.2 | 100 | Ex. 63 |
| 427 | 2183 | $C_{24}H_{24}FN_5O_2S$ | 466.3 | 6.2 | 98 | Ex. 53 |
| 428 | 2184 | $C_{23}H_{25}FN_6O_2S$ | 469.3 | 7.6 | 100 | Ex. 53 |
| 429 | 2185 | $C_{28}H_{30}FN_5O_4$ | 520.3 | 6.1 | 99 | Ex. 53 |
| 430 | 2186 | $C_{27}H_{31}FN_6O_4$ | 523.3 | 7.7 | 98 | Ex. 53 |
| 431 | 2187 | $C_{24}H_{24}FN_5O_3$ | 450.3 | 5.9 | 98 | Ex. 53 |
| 432 | 2188 | $C_{23}H_{25}FN_6O_3$ | 453.3 | 7.3 | 100 | Ex. 53 |
| 433 | 2202 | $C_{21}H_{25}N_5O_2$ | 380.4 | 5.3 | 100 | Ex. 49 |
| 434 | 2209 | $C_{21}H_{19}N_5O_2$ | 374.3 | 5.1 | 100 | Ex. 49 |
| 435 | 2210 | $C_{24}H_{22}FN_5O_2$ | 432.2 | 7.0 | 93 | Ex. 63 |
| 436 | 2211 | $C_{23}H_{23}FN_6O_2$ | 435.3 | 7.8 | 100 | Ex. 63 |
| 437 | 2212 | $C_{25}H_{22}F_3N_5O_2$ | 482.3 | 7.2 | 79 | Ex. 63 |
| 438 | 2224 | $C_{25}H_{22}F_3N_5O_3$ | 498.3 | 7.5 | 99 | Ex. 63 |
| 439 | 2240 | $C_{25}H_{24}FN_5O_2$ | 446.3 | 7.0 | 96 | Ex. 63 |
| 440 | 2241 | $C_{24}H_{25}FN_6O_2$ | 449.3 | 7.6 | 100 | Ex. 63 |
| 441 | 2265 | $C_{25}H_{31}N_5O_2$ | 434.3 | 7.5 | 98 | Ex. 63 |
| 442 | 2266 | $C_{24}H_{32}N_6O_2$ | 437.4 | 8.3 | 100 | Ex. 63 |
| 443 | 2267 | $C_{26}H_{29}N_5O_2S$ | 476.3 | 7.5 | 98 | Ex. 53 |
| 444 | 2268 | $C_{25}H_{30}N_6O_2S$ | 479.3 | 9.1 | 100 | Ex. 53 |
| 445 | 2270 | $C_{29}H_{31}N_5O_4$ | 514.0 | 8.2 | 100 | Ex. 53 |
| 446 | 2271 | $C_{26}H_{29}N_5O_3$ | 460.3 | 7.4 | 93 | Ex. 53 |
| 447 | 2272 | $C_{25}H_{30}N_6O_3$ | 463.3 | 8.8 | 100 | Ex. 53 |
| 448 | 2275 | $C_{26}H_{33}N_5O_2$ | 448.3 | 8.2 | 83 | Ex. 63 |
| 449 | 2277 | $C_{25}H_{34}N_6O_2$ | 451.4 | 9.0 | 100 | Ex. 63 |
| 450 | 2281 | $C_{27}H_{31}N_5O_2S$ | 490.4 | 7.7 | 100 | Ex. 53 |
| 451 | 2282 | $C_{26}H_{32}N_6O_2S$ | 493.3 | 9.8 | 100 | Ex. 53 |
| 452 | 2287 | $C_{31}H_{37}N_5O_4$ | 544.5 | 7.7 | 100 | Ex. 53 |
| 453 | 2288 | $C_{29}H_{36}N_6O_4$ | 533.3 | 9.0 | 100 | Ex. 53 |
| 454 | 2288 | $C_{30}H_{38}N_6O_4$ | 547.4 | 9.4 | 99 | Ex. 53 |

TABLE 2-continued

| Ex. no. | Compound no. | Formula | ESI/MS m/e | HPLC min | Purity (%) | Synthesis |
|---|---|---|---|---|---|---|
| 455 | 2290 | $C_{27}H_{31}N_5O_3$ | 474.5 | 7.5 | 100 | Ex. 53 |
| 456 | 2291 | $C_{26}H_{32}N_6O_3$ | 477.4 | 9.5 | 100 | Ex. 53 |
| 457 | 2296 | $C_{25}H_{25}N_5O_2$ | 428.3 | 5.9 | 96 | Ex. 63 |
| 458 | 2298 | $C_{24}H_{22}FN_5O_2$ | 432.3 | 5.8 | 95 | Ex. 63 |
| 459 | 2299 | $C_{19}H_{23}N_5O_2$ | 354.4 | 4.6 | 100 | Ex. 49 |
| 460 | 2300 | $C_{18}H_{19}N_5O_4$ | 370.3 | 2.2 | 100 | Ex. 49 |
| 461 | 2301 | $C_{18}H_{21}N_5O_3$ | 356.4 | 2.5 | 100 | Ex. 49 |
| 462 | 2305 | $C_{25}H_{24}FN_5O_2$ | 446.3 | 5.9 | 98 | Ex. 63 |
| 463 | 2311 | $C_{26}H_{24}F_3N_5O_2$ | 496.3 | 7.1 | 98 | Ex. 63 |
| 464 | 2325 | $C_{26}H_{24}F_3N_5O_3$ | 512.3 | 7.3 | 98 | Ex. 63 |
| 465 | 2329 | $C_{26}H_{27}N_5O_2$ | 442.4 | 6.3 | 98 | Ex. 63 |
| 466 | 2336 | $C_{27}H_{25}N_5O_2S$ | 484.3 | 7.3 | 98 | Ex. 53 |
| 467 | 2337 | $C_{26}H_{26}N_6O_2S$ | 487.3 | 8.7 | 100 | Ex. 53 |
| 468 | 2340 | $C_{24}H_{26}N_6O_2$ | 431.4 | 7.4 | 100 | Ex. 53 |
| 469 | 2341 | $C_{26}H_{27}N_5O_2$ | 442.5 | 6.4 6.6 | 100 | Ex. 53 |
| 470 | 2342 | $C_{31}H_{29}N_5O_2$ | 504.4 | 7.7 7.9 | 100 | Ex. 53 |
| 471 | 2343 | $C_{32}H_{29}N_5O_3$ | 532.4 | 8.0 | 100 | Ex. 53 |
| 472 | 2344 | $C_{31}H_{31}N_5O_4$ | 538.5 | 6.9 | 100 | Ex. 53 |
| 473 | 2347 | $C_{27}H_{25}N_5O_3$ | 468.3 | 7.1 | 98 | Ex. 53 |
| 474 | 2348 | $C_{26}H_{26}N_6O_3$ | 471.3 | 8.4 | 100 | Ex. 53 |
| 475 | 2350 | $C_{23}H_{23}N_5O_3$ | 418.3 | 5.1 | 98 | Ex. 63 |
| 476 | 2356 | $C_{26}H_{27}N_5O_2$ | 442.2 | 7.1 | 87 | Ex. 63 |
| 477 | 2357 | $C_{25}H_{28}N_6O_2$ | 445.3 | 7.8 | 100 | Ex. 63 |
| 478 | 2446 | $C_{17}H_{11}ClN_4O$ | 323.2 | 4.5 | 100 | Ex. 53 |
| 479 | 2448 | $C_{17}H_{12}N_4O_2$ | 305.3 | 2.5 | 100 | Ex. 53 |
| 480 | 2452 | $C_{18}H_{14}N_4O_2$ | 319.3 | 4.2 | 100 | Ex. 53 |
| 481 | 2459 | $C_{18}H_{14}N_4O_2$ | 319.3 | 2.9 | 100 | Ex. 53 |
| 482 | 2469 | $C_{16}H_{13}N_5O$ | 292.2 | 2.9 | 100 | Ex. 53 |
| 483 | 2471 | $C_{15}H_{10}N_4OS$ | 295.3 | 3.2 | 100 | Ex. 53 |
| 484 | 2481 | $C_{15}H_{10}N_4O_2$ | 279.3 | 2.5 | 100 | Ex. 53 |
| 485 | 2484 | $C_{17}H_{10}Cl_2N_4O$ | 357.0 | 5.5 | 100 | Ex. 53 |
| 486 | 2486 | $C_{19}H_{16}N_4O_3$ | 349.2 | 4.1 | 100 | Ex. 53 |
| 487 | 2490 | $C_{18}H_{15}N_5O_3S$ | 382.3 | 4.0 | 100 | Ex. 53 |
| 488 | 2492 | $C_{18}H_{12}N_4O_3$ | 333.3 | 2.7 | 100 | Ex. 53 |
| 489 | 2495 | $C_{19}H_{13}N_5O$ | 328.3 | 5.1 | 100 | Ex. 53 |
| 490 | 2500 | $C_{26}H_{22}N_4O_3$ | 439.0 | 7.5 | 94 | Ex. 53 |
| 491 | 1562 | $C_{24}H_{27}N_5O_2$ | 418.5 | 5.7 | 99 | Ex. 36 |
| 492 | 1895 | $C_{25}H_{28}N_6O_2$ | 445.5 | 5.7 | 99 | Ex. 36 |
| 493 | 1875 | $C_{21}H_{19}F_6N_5O_2$ | 488.3 | 6.5 | 99 | Ex. 36 |
| 494 | 2514 | $C_{30}H_{31}N_5O_3$ | 510.5 | 6.6 | 99 | Ex. 36 |

Example 495

$^1$H-NMR (400 MHz, DMSO-$d_6$ or CDCl$_3$) of the compounds according to the present invention were measured.

Data of chemical shift values (δ: ppm) and coupling constant (J: Hz) are shown in Table 3. Compound numbers in Table 3 designate compounds in Table 1 listed as preferred specific examples, and example numbers in the table denote examples of corresponding synthesized compounds

| Ex. no. | Compound no. | NMR data δ(ppm) | Solvent |
|---|---|---|---|
| 72 | 27 | 1.28-1.44(m, 2H), 1.76(m, 2H), 2.76(m, 1H), 2.84-3.01(m, 2H), 3.15(m, 1H), 3.68(m, 1H), 3.87(d, J=12.96, 1H), 4.39(d, J=11.96, 1H), 4.62(m, 2H), 7.52(m, 2H), 7.63(m, 1H), 7.79(dd, J=5.38, J=8.06, 1H), 7.97(m, 3H), 8.24(s, 1H), 8.59(d, J=5.36, 1H), 8.78(d, J=8.32, 1H), 9.37(s, 1H), 12.24(brs, 1H). | DMSO-d6 |
| 73 | 29 | 0.00(m, 2H), 0.25(m, 2H), 2.28(m, 1H), 2.37(t, J=6.70, 2H), 4.34(t, J=6.60, 2H), 7.58(dd, J=5.50, J=7.94, 1H), 7.69(d, J=3.92, 1H), 7.73(s, 1H), 7.86(s, 1H), 8.35(d, J=5.36, 1H), 8.58(d, J=8.28, 1H), 9.14(s, 1H), 12.02(brs, 1H). | DMSO-d6 |
| 75 | 80 | 3.96(m, 2H), 4.49(m, 1H), 4.88(m, 1H), 7.11(m, 1H), 7.73-7.79(m, 2H), 7.83(m, 1H), 7.88(brs, 1H), 8.03(t, J=7.7, 1H), 8.18(d, J=8.5, 1H), 8.64(s, 1H), 10.00(brs, 1H), 12.29(brs, 1H). | DMSO-d6 |

-continued

| Ex. no. | Compound no. | NMR data δ(ppm) | Solvent |
|---|---|---|---|
| 202 | 1106 | 1.44(brs, 2H), 1.62(brs, 4H), 3.45(m, 4H), 5.39(s, 2H), 7.81(dd, J=5.48, J=8.16, 1H), 7.98(s, 1H), 8.09(s, 1H), 8.60(d, J=5.40, 1H), 8.80(d, J=8.04, 1H), 9.39(s, 1H), 12.18(brs, 1H). | DMSO-d6 |
| 206 | 1161 | 5.36(s, 2H), 7.05(m, 1H), 7.31(t, J=7.56, 2H), 7.58(d, J=7.56, 2H), 7.81(dd, J=5.24, J=8.16, 1H), 8.00(s, 1H), 8.18(s, 1H), 8.61(d, J=5.36, 1H), 8.80(d, J=8.04, 1H), 9.41(s, 1H), 10.37(s, 1H), 12.26(brs, 1H). | DMSO-d6 |
| 208 | 1170 | 1.19-1.23(m, 3H), 4.13-4.20(m, 2H), 5.30(s, 2H), 7.79(m, 1H), 8.00(d, J=3.92, 1H), 8.15(d, J=4.16, 1H), 8.60(m, 1H), 8.76(d, J=8.07, 1H), 9.37(s, 1H), 12.28(brs, 1H). | DMSO-d6 |
| 209 | 1174 | 4.06(s, 3H), 7.84(dd, J=5.36, J=8.03, 1H), 7.96(s, 1H), 8.16(s, 1H), 8.61(d, J=5.12, 1H), 8.84(d, J=7.75, 1H), 9.39(s, 1H), 12.21(brs, 1H). | DMSO-d6 |
| 212 | 1179 | 5.67(s, 2H), 7.13-7.36(m, 5H), 7.80(dd, J=5.35, J=8.03, 1H), 8.00(s, 1H), 8.36(s, 1H), 8.60(d, J=5.36, 1H), 8.83(d, J=8.07, 1H), 9.40(s, 1H), 12.29(brs, 1H). | DMSO-d6 |

Example 496

Determination of Inhibition of GSK-3 Activity

The reaction was initiated by adding 25 µL of phospho-glycogen synthase peptide-2 substrate solution [containing 6 µM phospho-glycogen synthase peptide-2, 20 µM ATP, 16 mM MOPS buffer (pH 7.0), 0.2 mM EDTA, 20 mM magnesium acetate, 0.1 µ Ci[γ-$^{33}$P]ATP (relative activity: approximately 110 TBq/mmol)] to 5 µL of each test compound using 5% dimethylsulfoxide as a solvent, and further adding 20 µL of GSK-3β enzyme solution [containing 10 mU recombinant human GSK-3β, 20 mM MOPS buffer (pH 7.0), 1 mM EDTA, 0.1% polyoxyethylene lauryl ether(23 Lauryl Ether; Brij 35), 5% glycerol, and 0.1% β-mercaptoethanol. After 20 minutes at room temperature, the reaction was terminated by the addition of the equivalent amount of 200 mM phosphoric acid solution. 90 µL of the reaction product was spotted onto a multiscreen PH plate (manufactured by Millipore) and washed with 100 mM phosphoric acid solution. The plate was dried, and 30 µL of MicroScint-O (manufactured by Packard BioScience) was added thereto. To evaluate inhibitory activity, cpm was counted using a scintillation counter. Here, Phospho GS Peptide 2 is an amino acid peptide having the following sequence: Tyr-Arg-Arg-Ala-Ala-Val-Pro-Pro-Ser-Pro-Ser-Leu-Ser-Arg-His-Ser-Ser-Pro-His-Gln-Ser(P)-Glu-Asp-Glu-Glu-Glu.

GSK-3 inhibitor activity values ($IC_{50}$ values) of the compounds according to the present invention were measured by the method described above. As a result, an inhibition activity of $IC_{50}$<100 nM was confirmed in compounds of compound numbers 263, 280, 287, 297, 615, 617, 618, 627, 629, 641, 668, 760, 785, 1014, 1183, 1206, 1216, 1217, 1228, 1237, 1243, 1250, 1257, 1271, 1286, 1287, 1288, 1293, 1296, 1374, 1399, 1405, 1415, 1423, 1427, 1430, 1445, 1494, 1514, 1549, 1553, 1566, 1589, 1600, 1647, 1654, 1660, 1661, 1679, 1693, 1695, 1715, 1721, 1890, 1900, 2007, 2008, 2010, 2011, 2012, 2013, 2014, 2015, 2017, 2022, 2026, 2031, 2032, 2033, 2034, 2036, 2040, 2042, 2046, 2049, 2053, 2054, 2058, 2062, 2063, 2064, 2065, 2067, 2068, 2069, 2070, 2071, 2072, 2073, 2078, 2080, 2083, 2085, 2086, 2095, 2097, 2098, 2102, 2103, 2105, 2107, 2212, 2224, 2311.

Also, an inhibition activity of 20 nM<$IC_{50}$<100 nM was confirmed in compounds of compound numbers 40, 217, 219, 230, 245, 269, 288, 303, 595, 596, 601, 602, 616, 626, 628, 634, 646, 657, 659, 664, 667, 668, 673, 689, 694, 696, 723, 733, 734, 741, 768, 770, 776, 793, 795, 801, 802, 803, 804, 805, 806, 807, 809, 810, 812, 915, 1182, 1186, 1236, 1260, 1277, 1278, 1282, 1284, 1335, 1337, 1338, 1341, 1364, 1413, 1482, 1486, 1490, 1519, 1520, 1533, 1554, 1558, 1623, 1673, 1682, 1691, 1696, 1700, 1719, 1739, 1748, 1751, 1753, 1758, 1778, 1806, 1808, 1846, 1849, 1852, 1855, 1865, 1868, 1885, 1894, 1899, 2004, 2005, 2006, 2016, 2018, 2019, 2020, 2021, 2024, 2025, 2027, 2029, 2052, 2056, 2060, 2081, 2087, 2089, 2094, 2099, 2100, 2101, 2146, 2147, 2148, 2161, 2175, 2183, 2184, 2210, 2211, 2240, 2241, 2265, 2266, 2275, 2296, 2298, 2305, 2325, 2329, 2331, 2332, 2336, 2337, 2341, 2342, 2347, 2348, 2350, 2448, 2486, 2492.

Also, an inhibition activity of 100 nM<$IC_{50}$<1 µM was confirmed in compounds of compound numbers 81, 84, 254, 257, 320, 321, 330, 348, 361, 492, 504, 536, 550, 605, 678, 684, 702, 704, 709, 713, 718, 724, 729, 808, 811, 917, 918, 946, 1001, 1002, 1007, 1008, 1178, 1181, 1184, 1185, 1258, 1259, 1261, 1262, 1297, 1331, 1333, 1334, 1511, 1522, 1530, 1535, 1697, 1804, 1805, 1823, 1833, 1843, 1860, 1861, 1891, 1913, 1915, 2003, 2023, 2028, 2093, 2096, 2109, 2116, 2158, 2162, 2164, 2165, 2166, 2170, 2176, 2186, 2187, 2188, 2202, 2209, 2264, 2267, 2268, 2269, 2270, 2271, 2272, 2277, 2281, 2282, 2288, 2290, 2291, 2292, 2299, 2300, 2340, 2344, 2345, 2356, 2357, 2445, 2446, 2452, 2459, 2469, 2471, 2481, 2484, 2490, 2495.

Compound numbers designate compounds in Table 1 listed as preferred specific examples.

As described above, the pyrrolopyrimidine derivatives according to the present invention exhibit strong inhibitory activity against GSK-3. Therefore, the pyrrolopyrimidine derivatives according to the present invention have been found to be inhibitors of GSK-3 activity to be used in prevention and/or treatment of various diseases associated with GSK-3, which are clinically applicable compounds.

Example 493

Preparation of Tablets

Tablets each comprising the following ingredients were prepared.

| | |
|---|---|
| Compound (Example 1) | 50 mg |
| Lactose | 230 mg |
| Potato starch | 80 mg |
| Polyvinylpyrrolidone | 11 mg |
| Magnesium stearate | 5 mg |

The compound of the present invention (the compound prepared in Example 1), lactose, and potato starch were mixed, homogenously wetted with 20% ethanol solution of polyvinylpyrrolidone, passed through a 20 mesh sieve, dried at 45° C., and passed through again a 15 mesh sieve to obtain granules. The thus obtained granules were mixed with magnesium stearate and compressed into tablets.

Reference Example 15

Synthesis of N-{2-[4-chloro-6-(3-chloro(2-thienyl))-7-iodopyrrolo[3,2-d]pyrimidin-5-yl]-ethyl}-2,2,2-trifluoroacetoamide

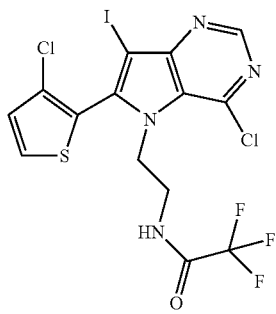

A phosphorus oxychloride (3.0 mL) solution of N-{2-[6-(3-chloro(2-thienyl))-7-iodo-4-oxo(3-hydropyrrolo[3,2-d]pyrimidin-5-yl)]ethyl}-2,2,2-trifluoroacetoamide (333 mg) was stirred at 110° C. for 2 hours. The reaction mixture was cooled to room temperature, and excess phosphorus oxychloride was distilled off under reduced pressure. A residue was dried in vacuo to obtain a crude product of the title compound as a brown oily compound. The product was not purified, but used for the following reaction. The ESI/MS data of the compound is given below.

ESI/MS m/e: 535.2 ($M^+$+H, $C_{14}H_8Cl_2F_3IN_4OS$)

Reference Example 16

Synthesis of N-{2-[7-bromo-4-chloro-6-(3-chloro(2-thienyl))pyrrolo[3,2-d]pyrimidin-5-yl]ethyl}-2,2,2-trifluoroacetoamide

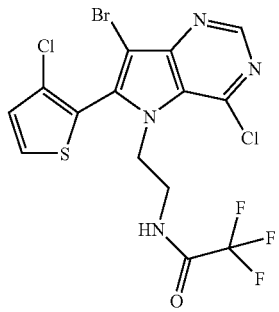

A crude product of the title compound was obtained by using N-{2-[7-promo-6-(3-chloro(2-thienyl))-4-oxo(3-hydropyrrolo[3,2-d]pyrimidin-5-yl)]ethyl}-2,2,2-trifluoroacetoamide (333 mg) in a similar manner to that in Reference Example 15. The ESI/MS data of the compound is given below.

ESI/MS m/e: 489.0 ($M^+$+H, $C_{14}H_8BrCl_2F_3N_4OS$)

Reference Example 17

Synthesis of N-{2-[4,7-dichloro-6-(3-chloro(2-thienyl))pyrrolo[3,2-d]pyrimidin-5-yl]ethyl}-2,2,2-trifluoroacetoamide

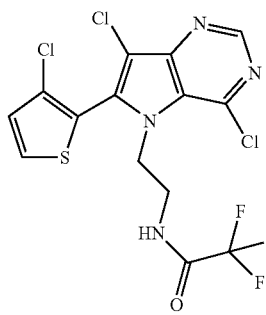

A crude product of the title compound was obtained by using N-{2-[7-chloro-6-(3-chloro(2-thienyl))-4-oxo(3-hydropyrrolo[3,2-d]pyrimidin-5-yl)]ethyl}-2,2,2-trifluoroacetoamide (333 mg) in a similar manner to that in Reference Example 15. The ESI/MS data of the compound is given below.

ESI/MS m/e: 443.4 ($M^+$+H, $C_{14}H_8Cl_3F_3N_4OS$)

INDUSTRIAL APPLICABILITY

The pyrrolopyrimidinone derivatives of Formula (I) according to the present invention and its pharmaceutically acceptable salts have GSK-3 inhibitory activity and are used as effective ingredients of pharmaceutical products. Therefore, pharmaceutical agents containing these compounds as effective ingredients are expected as promising therapeutic drugs or preventive drugs in GSK-3 mediated diseases including diabetes, diabetic complications, Alzheimer's disease, neurodegenerative diseases manic depression, traumatic cerebrospinal injury, alopecia, inflammatory diseases, cancer and immunodeficiency.

The invention claimed is:
1. A compound represented by the formula (I) or its pharmaceutically acceptable salts:

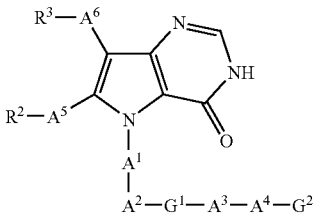

(I)

wherein $A^1$ is —(CH$_2$)$_2$— or —(CH$_2$)$_3$—
$A^2$ represents a group that links $A^1$ with $G^1$ in the form of $A^1$-C(=O)-G$^1$, $A^1$-C(=O)-O-G$^1$, $A^1$-C(=O)—NR$^{101}$-G$^1$, $A^1$-C(=S)—NR$^{102}$-G$^1$, $A^1$-C(=NR$^{103}$)-G$^1$, $A^1$-O-G$^1$, $A^1$-O-C(=O)-G$^1$, $A^1$-NR$^{104}$-G$^1$, $A^1$-NR$^{105}$-C(=O)-G$^1$, $A^1$-NR$^{106}$—S(=O)$_2$-G$^1$, $A^1$-NR$^{107}$—C(=O)O-G$^1$, $A^1$-NR$^{108}$—C(=O)—NR$^{109}$-G$^1$, $A^1$—NR$^{110}$-C(=S)-G$^1$, $A^1$-NR$^{111}$—C(=S)—NR$^{112}$-G$^1$, $A^1$-S-G$^1$, $A^1$-S(=O)-G$^1$, $A^1$-S(=O)$_2$— NR$^{113}$-G$^1$, $A^1$-CR$^{114}$=CH-G$^1$, $A^1$-CR$^{115}$=CF-G$^1$, $A^1$-CH=CR$^{116}$-G$^1$, or $A^1$-CF=CR$^{117}$-G$^1$;
$G^1$ represents a single bond or represents a divalent group which is obtainable by removing two hydrogen atoms from any one of an optionally substituted alicyclic hydrocarbon having 3 to 8 carbon atoms, an optionally substituted aromatic hydrocarbon having 6 to 14 carbon atoms, and an optionally substituted heterocyclic compound having 1 to 4 atoms selected from the group consisting of an oxygen atom, a nitrogen atom and a sulfur atom, in the ring,
$A^3$ represents a single bond or represents an optionally substituted divalent acyclic aliphatic hydrocarbon group having 1 to 6 carbon atoms that links $G^1$ with $A^4$ on the same or different carbon atom;
$A^4$ represents a single bond or represents a group that links $A^3$ with $G^2$ in the form of $A^3$-C(=O)—O-G$^2$, $A^3$-C(=O)—NR$^{121}$-G$^2$, $A^3$-C(=S)—NR$^{122}$-G$^2$, $A^3$-C(=NR$^{123}$)-G$^2$, $A^3$-O-G$^2$, $A^3$-O—C(=O)-G$^2$, $A^3$-NR$^{124}$-G$^2$, $A^3$-NR$^{125}$—C(=O)-G$^2$, $A^3$-NR$^{126}$—S(=O)$_2$-G$^2$, $A^3$-NR$^{127}$—C(=O)—O-G$^2$, $A^3$-NR$^{128}$—C(=O)—NR$^{129}$-G$^2$, $A^3$-NR$^{130}$—C(=S)-G$^2$, $A^3$-NR$^{131}$—C(=S)—NR$^{132}$-G$^2$, $A^3$-S-G$^2$, $A^3$-S(=O_)-G$^2$, $A^3$-S(=O)$_2$-G$^2$, $A^3$-S(=O)$_2$—NR$^{133}$-G$^2$ or $A^3$-S(=O)$_2$—O-G$^2$;
$G^2$ is a hydrogen atom, an optionally substituted acyclic aliphatic hydrocarbon group having 1 to 10 carbon atoms, an optionally substituted alicyclic hydrocarbon group having 3 to 10 carbon atoms, an optionally substituted aromatic hydrocarbon group having 6 to 14 carbon atoms, or an optionally substituted heterocyclic group having 1 to 4 atoms selected from the group consisting of an oxygen atom, a nitrogen atom and a sulfur atom, in the ring;
$A^5$ represents a single bond or —NR$^{201}$—;
$R^2$ is a hydrogen atom, a fluorine atom, a chlorine atom, a bromine atom, an iodine atom, an optionally substituted acyclic aliphatic hydrocarbon group having 1 to 10 carbon atoms, an optionally substituted alicyclic hydrocarbon group having 3 to 8 carbon atoms, an optionally substituted aromatic hydrocarbon group having 6 to 14 carbon atoms, or an optionally substituted heterocyclic group having 1 to 4 atoms selected from the group consisting of an oxygen atom, a nitrogen atom and a sulfur atom, in the ring;
$A^6$ represents a single bond-;
$R^3$ is an optionally substituted aromatic hydrocarbon group having 6 to 14 carbon atoms, or an optionally substituted heterocyclic group having 1 to 4 atoms selected from the group consisting of an oxygen atom, a nitrogen atom and a sulfur atom, in the ring; and
$R^{101}$, $R^{102}$, $R^{103}$, $R^{104}$, $R^{105}$, $R^{106}$, $R^{107}$, $R^{108}$, $R^{109}$, $R^{110}$, $R^{111}$, $R^{112}$, $R^{113}$, $R^{114}$, $R^{115}$, $R^{116}$, $R^{117}$, $R^{121}$, $R^{122}$, $R^{123}$, $R^{124}$, $R^{125}$, $R^{126}$, $R^{127}$, $R^{128}$, $R^{129}$, $R^{130}$, $R^{131}$, $R^{132}$, $R^{133}$, and $R^{201}$ are each independently a hydrogen atom or an aliphatic hydrocarbon group having 1 to 4 carbon atoms.

2. The compound or a pharmaceutically acceptable salt thereof according to claim 1, wherein $A^2$ represents —C(=O)—, —C(=O)—O—, —C(=O)—NH—, —C(=O)—NMe-, —NH—, —NH—C(=O)—, —NH—C(=O)—O—, —NH—C(=O)—NH—, —NH—C(=O)—NMe-, or —NH—C(=S)—.

3. The compound or a pharmaceutically acceptable salt thereof according to claim 1, wherein $A^2$ represents —C(=O)—NH—, —NH—, —NH—C(=O)—, —NH—C(=O)—O—, or —NH—C(=O)—NH—.

4. The compound or a pharmaceutically acceptable salt thereof according to claim 2, wherein combination of $G^1$, $A^3$, $A^4$, and $G^2$ is any of the combinations of 1 to 10 in the following table:

| Combination | $G^1$ | $A^3$ | $A^4$ | $G^2$ |
|---|---|---|---|---|
| 1 | group other than single bond | single bond | single bond | hydrogen atom |
| 2 | single bond | group other than single bond | single bond | hydrogen atom |
| 3 | group other than single bond | single bond | single bond | group other than hydrogen atom |
| 4 | single bond | group other than single bond | single bond | group other than hydrogen atom |
| 5 | group other than single bond | single bond | group other than single bond | group other than hydrogen atom |
| 6 | single bond | group other than single bond | group other than single bond | group other than hydrogen atom |
| 7 | group other than single bond | group other than single bond | single bond | group other than hydrogen atom |
| 8 | group other than single bond | group other than single bond | group other than single bond | group other than hydrogen atom |
| 9 | group other than single bond | group other than single bond | group other than single bond | hydrogen atom |
| 10 | single bond | single bond | single bond | hydrogen atom. |

5. The compound or a pharmaceutically acceptable salt thereof according to claim 2, wherein $G^1$ represents a group other than a single bond, $A^3$ and $A^4$ represent a single bond, and $G^2$ represents a hydrogen atom.

6. The compound or a pharmaceutically acceptable salt thereof according to claim 2, wherein $G^1$ and $A^4$ represent a single bond, $A^3$ represents a group other than a single bond, and $G^2$ represents a hydrogen atom.

7. The compound or a pharmaceutically acceptable salt thereof according to claim 2, wherein $G^1$ represents a group other than a single bond, $A^3$ and $A^4$ represent a single bond, and $G^2$ represents a group other than a hydrogen atom.

8. The compound or a pharmaceutically acceptable salt thereof according claim 2, wherein $G^1$ and $A^4$ represent a single bond, $A^3$ represents a group other than a single bond, and $G^2$ represents a group other than a hydrogen atom.

9. The compound or a pharmaceutically acceptable salt thereof according to claim 8, wherein $A^3$ represent an alkylene group having 1 to 3 carbon atoms.

10. The compound or a pharmaceutically acceptable salt thereof according to claim 2, wherein $G^1$ and $A^4$ represent a group other than a single bond, $A^3$ represents a single bond, and $G^2$ represents a group other than a hydrogen atom.

11. The compound or a pharmaceutically acceptable salt thereof according to claim 10, wherein $A^2$ represents —C(=O)—, —C(=O)—NH—, or —NH—C(=O)—.

12. The compound or a pharmaceutically acceptable salt thereof according to claim 2, wherein $G^1$ represents a single bond, $A^3$ and $A^4$ represent a group other than a single bond, and $G^2$ represents a group other than a hydrogen atom.

13. The compound or a pharmaceutically acceptable salt thereof according to claim 2, wherein $G^1$ and $A^3$ represent a group other than a single bond, $A^4$ represents a single bond, and $G^2$ represents a group other than a hydrogen atom.

14. The compound or a pharmaceutically acceptable salt thereof according to claim 13, wherein $A^3$ represent an alkylene group having 1 to 3 carbon atoms.

15. The compound or a pharmaceutically acceptable salt thereof according to claim 2, wherein $G^1$, $A^3$ and $A^4$ represent a group other than a single bond, and $G^2$ represents a group other than a hydrogen atom.

16. The compound or a pharmaceutically acceptable salt thereof according to claim 1, wherein $A^4$ represents —O—.

17. The compound or a pharmaceutically acceptable salt thereof according to claim 2, wherein $G^1$, $A^3$ and $A^4$ represent a group other than a single bond, and $G^2$ represents a hydrogen atom.

18. The compound or a pharmaceutically acceptable salt thereof according to claim 2, wherein $G^1$, $A^3$ and $A^4$ represent a single bond, and $G^2$ represents a hydrogen atom.

19. The compound or a pharmaceutically acceptable salt thereof according to claim 1, wherein $A^1$ is —(CH$_2$)$_2$— or —(CH$_2$)$_3$—, $A^2$ represents —NH—(C=O)— or —NH—(C=O)—NH—, $G^1$ represents a single bond, and $A^3$ represents a divalent acyclic aliphatic hydrocarbon group having 1 to 6 carbon atoms.

20. The compound or a pharmaceutically acceptable salt thereof according to claim 1, wherein $A^1$ is —(CH$_2$)$_2$— or —(CH$_2$)$_3$—, $A^2$ represents —NH—(C=O)—, —NH—(C=O)—NH—, and $G^1$ represents a group other than a single bond.

21. The compound or a pharmaceutically acceptable salt thereof according to claim 2, wherein $G^1$ represents an optionally substituted aromatic hydrocarbon group, an optionally substituted alicyclic hydrocarbon group having 3 to 8 carbon atoms, or an optionally substituted heterocyclic group, with the proviso that when the aromatic hydrocarbon group of $G^1$ is a phenyl group, or the heterocyclic group of $G^1$ is 5 or 6 membered monocyclic ring, then the phenyl group or the 5 or 6 membered monocyclic heterocyclic group of $G^1$ is substituted, or the $A^3$-$G^2$ portion represents those other than a hydrogen atom.

22. The compound or a pharmaceutically acceptable salt thereof according to claim 2, wherein $G^1$ and $A^4$ represent a single bond, $A^3$ represents an optionally substituted acyclic aliphatic hydrocarbon group having 1 to 6 carbon atoms, $G^2$ represents an optionally substituted alicyclic hydrocarbon group having 5 to 10 carbon atoms, an optionally substituted aromatic hydrocarbon group, or an optionally substituted heterocyclic group.

23. The compound or a pharmaceutically acceptable salt thereof according to claim 2, wherein $G^1$ represents a single bond, $A^3$ represents an optionally substituted acyclic aliphatic hydrocarbon group having 1 to 6 carbon atoms, and $A^4$ represents —C(=O)—, —C(=O)—NR$^{121}$—, —C(=S)—NR$^{122}$—, —C(=NR$^{123}$)—, —O—C(O)—, —NR$^{125}$—C(=O)—, —NR$^{126}$—S(=O)$_2$—, —NR$^{127}$—C(=O)—O—, —NR$^{128}$—C(=O)—NR$^{129}$—, —NR$^{130}$—C(=S)—, —NR$^{131}$—C(=S)—NR$^{132}$—, —S—, —S(=O)—, —S(=O)$_2$—, —S(=O)$_2$—NR$^{133}$—, or —S(=O)$_2$—O—.

24. The compound or a pharmaceutically acceptable salt thereof according to claim 1, wherein $A^5$ represents a single bond.

25. The compound or a pharmaceutically acceptable salt thereof according to claim 24, wherein $R^2$ represents an optionally substituted acyclic aliphatic hydrocarbon group having 1 to 10 carbon atoms, an optionally substituted alicyclic hydrocarbon group having 3 to 8 carbon atoms, an optionally substituted aromatic hydrocarbon group having 6 to 14 carbon atoms, or an optionally substituted heterocyclic group.

26. The compound or a pharmaceutically acceptable salt thereof according to claim 24, wherein $R^2$ represents an acyclic aliphatic hydrocarbon group having 1 to 10 carbon atoms, an alicyclic hydrocarbon group having 3 to 8 carbon atoms, an optionally substituted phenyl group, or an optionally substituted heterocyclic group having 1 or 2 atoms selected from the group consisting of an oxygen atom, a nitrogen atom, or a sulfur atom, in the ring.

27. The compound or a pharmaceutically acceptable salt thereof according to claim 24, wherein $R^2$ represents a cyclopropyl group, cyclobutyl group, cyclopropylmethyl group, methyl group, ethyl group, vinyl group, isopropyl group, or 2-methyl-1-propenyl group.

28. The compound or a pharmaceutically acceptable salt thereof according to claim 24, wherein $R^2$ represents a thienyl group, a pyridyl group, a furyl group, a pyrrolyl group, a pyrazolyl group, or phenyl group; any of which may be further substituted by one or more of an alkyl group having 1 to 4 carbon atoms, an alkoxy group having 1 to 4 carbon atoms, an acyl group having 2 to 4 carbon atoms, a hydroxy group, a carboxyl group, an alkoxycarbonyl group having 2 to 7 carbon atoms, a fluorine atom, or a chlorine atom.

29. The compound or a pharmaceutically acceptable salt thereof according to claim 1 wherein $R^3$ represents a thienyl group, a pyridyl group, a furyl group, a pyrrolyl group, a pyrazolyl group, or phenyl group; any of which may be further substituted by one or more of an alkyl group having 1 to 4 carbon atoms.

30. The compound or a pharmaceutically acceptable salt thereof according to any one of claims 1, 2-3 and 4-5, 7, 10-11, 16, 18, 20, and 24-28, wherein $A^3$ represents a single bond and $R^3$ represents a pyridyl group or a 1-oxypyridyl group, either of which may be further substituted by one alkyl group having 1 to 4 carbon atoms or one halogen atom; a pyrazolyl group; or N-methylpyrazolyl group.

31. The compound or a pharmaceutically acceptable salt thereof according to claim 27, wherein $R^3$ represents a pyridyl group or a 1-oxypyridyl group, either of which may be further substituted by one alkyl group having 1 to 4 carbon atoms or one halogen atom; a pyrazolyl group; or N-methylpyrazolyl group.

32. The compound or a pharmaceutically acceptable salt thereof according to claim 28, $R^3$ represents a pyridyl group or a 1-oxypyridyl group, either of which may be further substituted by one alkyl group having 1 to 4 carbon atoms or one halogen atom; a pyrazolyl group; or N-methylpyrazolyl group.

33. The compound or a pharmaceutically acceptable salt thereof according to any one of claims 19-20 and 21-23, wherein both of $A^5$ represents a single bond.

34. The compound or a pharmaceutically acceptable salt thereof according to claim 33, wherein $R^2$ represents an optionally substituted acyclic aliphatic hydrocarbon group having 1 to 10 carbon atoms, an optionally substituted alicyclic hydrocarbon group having 3 to 8 carbon atoms, an optionally substituted aromatic hydrocarbon group having 6 to 14 carbon atoms, or an optionally substituted heterocyclic group, and $R^3$ represents an optionally substituted aromatic hydrocarbon group having 6 to 14 carbon atoms or an optionally substituted heterocyclic group.

35. The compound or a pharmaceutically acceptable salt thereof according to claim 33, wherein $R^2$ represents an optionally substituted acyclic aliphatic hydrocarbon group having 1 to 10 carbon atoms, an alicyclic hydrocarbon group having 3 to 8 carbon atoms, an optionally substituted phenyl group, or an optionally substituted heterocyclic group having 1 or 2 atoms selected from the group consisting of an oxygen atom, a nitrogen atom, and a sulfur atom, in the ring, and $R^3$ represents a thienyl group, a pyridyl group, a furyl group, a pyrrolyl group, a pyrazolyl group, or a phenyl group, any of which may be further substituted by one or more of a $C_1$-$C_4$ alkyl group.

36. The compound or a pharmaceutically acceptable salt thereof according to claim 33, wherein $R^2$ represents a cyclopropyl group, methyl group, ethyl group, vinyl group, isopropyl group, isobutyl group, or 2-methyl-1-propenyl group, and $R^3$ represents a pyridyl group or a 1-oxypyridyl group, either of which may be further substituted by one alkyl group having 1 to 4 carbon atoms or one halogen atom; pyrazolyl group; or N-methylpyrazolyl group.

37. The compound or a pharmaceutically acceptable salt thereof according to claim 33, wherein $R^2$ represents a thienyl group, a pyridyl group, a furyl group, a pyrrolyl group, a pyrazolyl group, or a phenyl group, any of which may be further substituted by one or more of an alkyl group having 1 to 4 carbon atoms, an alkoxy group having 1 to 4 carbon atoms, or a chlorine atom, and $R^3$ represents a pyridyl group or a 1-oxypyridyl group, either of which may be further substituted by one alkyl group having 1 to 4 carbon atoms or one halogen atom; pyrazolyl group; or N-methylpyrazolyl group.

38. A pharmaceutical composition comprising the compound or a pharmaceutically acceptable salt thereof according to any one of claims 1, 2-3, 4-15, 17-20, 21-28, 29 and 31-32; and a pharmaceutically acceptable carrier.

39. A compound represented by the formula (Ic):

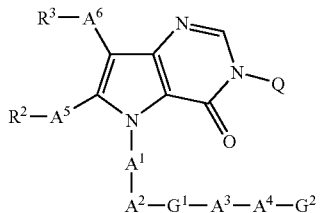

(Ic)

wherein $A^1$ is —$(CH_2)_2$— or —$(CH_2)_3$—;

$A^2$ represents a single bond or represents a group that links $A^1$ with $G^1$ in the form of $A^1$-C(=O)-$G^1$, $A^1$-C(=O)-O-$G^1$, $A^1$-C(=O)—$NR^{101}$-$G^1$, $A^1$-C(=S)—$NR^{102}$-$G^1$, $A^1$-C(=$NR^{103}$)-$G^1$, $A^1$-O-$G^1$, $A^1$-O-C(=O)-$G^1$, $A^1$-$NR^{104}$-$G^1$, $A^1$-$NR^{105}$-C(=O)-$G^1$, $A^1$-$NR^{106}$—S(=O)$_2$-$G^1$, $A^1$-$NR^{107}$—C(=O)O-$G^1$, $A^1$-$NR^{108}$—C(=O)—$NR^{109}$-$G^1$, $A^1$—$NR^{110}$-C(=S)-$G^1$, $A^1$-$NR^{111}$—C(=S)—$NR^{112}$-$G^1$, $A^1$-S-$G^1$, $A^1$-S(=O)-$G^1$, $A^1$-S(=O)$_2$—$NR^{113}$-$G^1$, $A^1$-$CR^{114}$=CH-$G^1$, $A^1$-$CR^{115}$=CF-$G^1$, $A^1$-CH=$CR^{116}$-$G^1$, or $A^1$-CF=$CR^{117}$-$G^1$;

$G^1$ represents a single bond or represents a divalent group which is obtainable by removing two hydrogen atoms from any one of an optionally substituted alicyclic hydrocarbon having 3 to 8 carbon atoms, an optionally substituted aromatic hydrocarbon having 6 to 14 carbon atoms, and an optionally substituted heterocyclic compound having 1 to 4 atoms selected from the group consisting of an oxygen atom, a nitrogen atom and a sulfur atom, in the ring, $A^3$ represents a single bond or represents an optionally substituted divalent acyclic aliphatic hydrocarbon group having 1 to 10 carbon atoms that links $G^1$ with $A^4$ on the same or different carbon atom;

$A^4$ represents a single bond or represents a group that links $A^3$ with $G^2$ in the form of $A^3$—C(=O)—O-$G^2$, $A^3$—C(=O)—$NR^{121}$-$G^2$, $A^3$—C(=S)—$NR^{122}$-$G^2$, $A^3$—C(=$NR^{123}$)-$G^2$, $A^3$-O-$G^2$, $A^3$-O—C(=O)-$G^2$, $A^3$-$NR^{124}$-$G^2$, $A^3$-$NR^{125}$—C(=O)-$G^2$, $A^3$-$NR^{126}$—S(=O)$_2$-$G^2$, $A^3$-$NR^{127}$—C(=O)—O-$G^2$, $A^3$—$NR^{128}$—C(=O)—$NR^{129}$-$G^2$, $A^3$-$NR^{130}$—C(=S)-$G^2$, $A^3$-$NR^{131}$—C(=S)—$NR^{132}$-$G^2$, $A^3$-S-$G^2$, $A^3$-S(=O_)-$G^2$, $A^3$-S(=O)$_2$-$G^2$, $A^3$-S(=O)$_2$—$NR^{133}$-$G^2$ or $A^3$-S(=O)$_2$—O-$G^2$;

$G^2$ is a hydrogen atom, an optionally substituted acyclic aliphatic hydrocarbon group having 1 to 10 carbon atoms, an optionally substituted alicyclic hydrocarbon group having 3 to 10 carbon atoms, an optionally substituted aromatic hydrocarbon group having 6 to 14 carbon atoms, or an optionally substituted heterocyclic group having 1 to 4 atoms selected from the group consisting of an oxygen atom, a nitrogen atom and a sulfur atom, in the ring;

$A^5$ represents a single bond or —$NR^{201}$—;

$R^2$ is a hydrogen atom, a fluorine atom, a chlorine atom, a bromine atom, an iodine atom, an optionally substituted acyclic aliphatic hydrocarbon group having 1 to 10 carbon atoms, an optionally substituted alicyclic hydrocarbon group having 3 to 8 carbon atoms, an optionally substituted aromatic hydrocarbon group having 6 to 14 carbon atoms, or an optionally substituted heterocyclic group having 1 to 4 atoms selected from the group consisting of an oxygen atom, a nitrogen atom and a sulfur atom, in the ring;

$A^6$ represents a single bond;

$R^3$ is an optionally substituted aromatic hydrocarbon group having 6 to 14 carbon atoms, or an optionally substituted heterocyclic group having 1 to 4 atoms selected from the group consisting of an oxygen atom, a nitrogen atom and a sulfur atom, in the ring;

$R^{101}$, $R^{102}$, $R^{103}$, $R^{104}$, $R^{105}$, $R^{106}$, $R^{107}$, $R^{108}$, $R^{109}$, $R^{110}$, $R^{111}$, $R^{112}$, $R^{113}$, $R^{114}$, $R^{115}$, $R^{116}$, $R^{117}$, $R^{121}$, $R^{122}$, $R^{123}$, $R^{124}$, $R^{125}$, $R^{126}$, $R^{127}$, $R^{128}$, $R^{129}$, $R^{130}$, $R^{131}$, $R^{132}$, $R^{133}$, and $R^{201}$ are each independently a hydrogen atom or an aliphatic hydrocarbon group having 1 to 4 carbon atoms;

with the proviso that when both of $A^1$ and $A^3$ represent an acyclic aliphatic hydrocarbon group, then at least either one of $A^2$ or $G^1$ is not a single bond; and Q represents an optionally substitutedacyl group having 2 to 10 carbon atoms, an optionally substituted alkoxymethyl group having 2 to 10 carbon atoms, or an optionally substituted benzyl group.

* * * * *